(12) United States Patent
Chen et al.

(10) Patent No.: US 8,344,137 B2
(45) Date of Patent: Jan. 1, 2013

(54) 3,3-DIMETHYL TETRAHYDROQUINOLINE DERIVATIVES

(75) Inventors: Li Chen, Shanghai (CN); Lichun Feng, Shanghai (CN); Mengwei Huang, Shanghai (CN); Yongfu Liu, Shanghai (CN); Guolong Wu, Shanghai (CN); Jim Zhen Wu, Shanghai (CN); Mingwei Zhou, Shanghai (CN)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 13/081,527

(22) Filed: Apr. 7, 2011

(65) Prior Publication Data
US 2011/0257151 A1 Oct. 20, 2011

(30) Foreign Application Priority Data
Apr. 14, 2010 (WO) ................ PCT/CN2010/071760

(51) Int. Cl.
C07D 215/48 (2006.01)
C07D 401/04 (2006.01)
C07D 401/06 (2006.01)
C07D 401/10 (2006.01)
C07D 401/12 (2006.01)
C07D 413/10 (2006.01)
C07D 413/12 (2006.01)
C07D 413/14 (2006.01)
C07D 471/04 (2006.01)

(52) U.S. Cl. ........ 544/128; 544/279; 544/363; 544/405; 546/165

(58) Field of Classification Search .................. None
See application file for complete search history.

(56) References Cited

FOREIGN PATENT DOCUMENTS
WO WO2011/009523 A1 * 1/2011

OTHER PUBLICATIONS

Richard B. Silverman, The Organic Chemistry of Drug Design and Drug Action, Chapter 2: Drug Discovery, Design, and Development, Academic Press, p. 5-51 (1992).*
Annunziata et al., "European Journal of Organic Chemistry":1184-1190 ( 2002).
Shaw et al., "Science (New York) NY" 310:1642-1646 ( 2005).
Muoio et al., "Diabetes" 46:1360-1363 ( 1997).
Fryer et al., "The Journal of Biological Chem." 277:25226-25232 ( 2002).
Yamauchi et al., "Nature Medicine" 8:1288-1295 ( 2002).
Kahn et al., "Cell Metabolism" 1:15-25 ( 2005).
Minokoshi et al., "Nature" 415:339-343 ( 2002).
Cool et al., "Cell Metabolism, Cell Press" 3:403-416 ( 2006).
"PCT International Search Report PCT/EP2011/055473—dated Jun. 6, 2011".
Bastin et al., "Organic Process Research & Development" 4:427-435 ( 2000).
Zhou et al., "The Journal of Clinical Investigation" 108:1167-1174 ( 2001).
Woods et al., "Molecular & Cellular Biology" 20:6704-6711 ( 2000).
Ansel et al., "Pharmaceutical Dosage Forms & Drug Delivery":456-457 ( 1995).
Yamauchi et al., "Nature Medicine" 7:941-946 ( 2001).
Friedman et al., "Nature" 395:763-770 ( 1998).
Semple et al., "The Journal of Clinical Investigation" 116:581-589 ( 2006).
Pang et al., "The Journal of Biological Chemistry" 283:16051-16060 ( 2008).
Carling et al., "Trends in Biochem. Science" 29:18-24 ( 2004).
Hardie et al., "Annual Review of Pharmacology & Toxicology" 47:185-210 ( 2007).
Kadowaki et al., "The Journal of Clinical Investigation" 116:1784-1792 ( 2006).
Hardie et al., "Nature Reviews in Molecular Cell Biology" 8:774-785 ( 2007).
Owen et al., "The Biochemical Journal" 348:607-614 ( 2000).
Long et al., "The Journal of Clinical Investigation" 116:1776-1783 ( 2006).
El-Mir et al., "The Journal of Biological Chemistry" 275:223-228 ( 2000).

* cited by examiner

*Primary Examiner* — Janet Andres
*Assistant Examiner* — Timothy R Rozof
(74) *Attorney, Agent, or Firm* — George W. Johnston; Patricia S. Rocha-Tramaloni; Gene J. Yao

(57) ABSTRACT

A compound of formula (I)

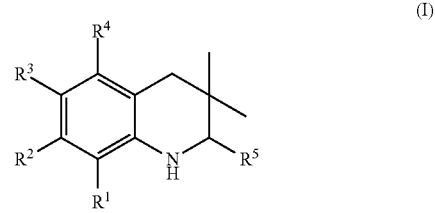

as well as pharmaceutically acceptable salt thereof, wherein $R^1$ to $R^5$ have the significance given in claim 1, can be used as a medicament.

24 Claims, No Drawings

3,3-DIMETHYL TETRAHYDROQUINOLINE DERIVATIVES

PRIORITY TO RELATED APPLICATION(S)

This application claims the benefit of PCT/CN2010/071760, filed Apr. 14, 2010, which is hereby incorporated by reference in its entirety.

FIELD OF THE INVENTION

The invention relates to compounds which are activators of AMP-activated protein kinase (AMPK) and which are useful in the treatment or prophylaxis of diseases that are related to AMPK regulation, such as obesity, dyslipidemia, hyperglycemia, type 1 or type 2 diabetes and cancers.

BACKGROUND OF THE INVENTION

Obesity and type 2 diabetes, hypertension, and cardiovascular disease, are diseases that feature serious disturbances in glucose or lipid metabolism that severely affect the health and quality of life of affected individuals. In addition, cancer metabolism is known to be difference from normal cellular metabolism. The increasing prevalence of these diseases makes finding new drug targets for treating these syndromes an urgent task.

AMP-activated protein kinase (AMPK) acts as a cellular energy sensor and regulator. It is activated by an increase in the cellular AMP:ATP ratio induced by metabolic stress, hormone and nutrient signals, and other cellular mechanisms such as phosphorylation and protein-protein interaction. Once activated, AMPK switches on catabolic pathways that generate ATP and switches off ATP-consuming anabolic pathways by acute regulation of the activity of key enzymes in metabolism and chronic regulation of the expression of pivotal transcription factors (Hardie, D G. *Nature reviews* 8 (2007b), 774-785; Woods, A et al. *Molecular and cellular biology* 20 (2000), 6704-6711). The growing evidence of AMPK regulatory effects on glucose and lipid metabolism makes it a potential drug target for treatment of diabetes, metabolic syndrome and cancer (Carling, D. *Trends Biochem Sci* 29 (2004), 18-24; Hardie, D G. *Annual review of pharmacology and toxicology* 47 (2007a), 185-210; Kahn, B B et al. *Cell metabolism* 1 (2005), 15-25; Long, Y C et al. *The Journal of clinical investigation* 116 (2006), 1776-1783).

At the physiological level, this concept has been supported by two adipokines, leptin and adiponectin, both of which exert excellent effects on glucose and lipid metabolism (Friedman, J M and Halaas, J L. *Nature* 395 (1998), 763-770; Muoio, D M et al. *Diabetes* 46 (1997), 1360-1363; Yamauchi, T et al. *Nature medicine* 7 (2001), 941-946). Recent studies suggest that leptin and adiponectin exert their antidiabetic effects by activating AMPK. Leptin stimulates muscle fatty acid oxidation by activating AMPK directly and through a hypothalamic-adrenergic pathway (Minokoshi, Y et al. *Nature* 415 (2002), 339-343). Adiponectin stimulates glucose uptake and fatty acid oxidation in vitro by activation of AMPK. Furthermore, it exerts its hypoglycemic effect by decreasing PEPCK and G6 Pase expression, whereas the administration of dominant negative α1 adenovirus reverses the effect in vivo (Yamauchi, T et al. *Nature medicine* 8 (2002), 1288-1295).

At the pharmacological level, the concept of AMPK as a potential target for treating metabolic syndrome has been further supported by the discovery of two major classes of existing antidiabetic drugs: thiazolidinediones (rosiglitazone, troglitazone and pioglitazone) and biguanides (metformin and phenformin) activate AMPK in cultured cells and in vivo. Rosiglitazone is traditionally considered to be a PPARγ agonist and exerts its antidiabetic effects through differentiation of adipocytes (Semple, R K et al. *The Journal of clinical investigation* 116 (2006), 581-589). Recent findings indicate that AMPK may be involved in the antidiabetic effects of rosiglitazone (Brunmair, B et al. *The Journal of biological chemistry* 277 (2002), 25226-25232; Kadowaki, T et al. *The Journal of clinical investigation* 116 (2006), 1784-1792). In the case of metformin, an existing antidiabetic agent without a defined mechanism of action, recent studies demonstrate that it could activate AMPK in vitro and in vivo by inhibiting complex I (El-Mir, M Y et al. *The Journal of biological chemistry* 275 (2000), 223-228; Owen, M R et al. *The Biochemical journal* 348 Pt 3 (2000), 607-614; Zhou, G et al. *The Journal of clinical investigation* 108 (2001), 1167-1174), and the hypoglycemic effect could be blocked completely by knockout of its upstream kinase LKB1, confirming the key role of AMPK in mediating the antidiabetic effect of metformin (Shaw, R J et al. *Science* (New York) N.Y. 310 (2005), 1642-1646).

Most recently, Cool and coworkers have identified a small direct AMPK activator, A-769662, which exerts antidiabetic effects in vivo (Cool, B et al. *Cell metabolism* 3 (2006), 403-416). Li's laboratory has also identified a small AMPK activator, PT1, which activates the inactive forms of AMPK α2$_{398}$ and α1$_{394}$ with micromolar activity and exerts some cellular effects (Pang, T et al. *The Journal of biological chemistry* 283 (2008), 16051-16060).

SUMMARY OF THE INVENTION

The present invention relates to a compound of formula (I)

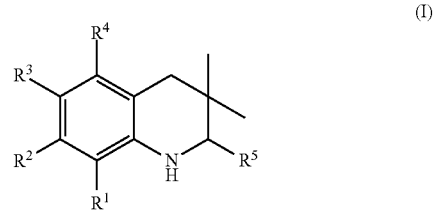

wherein $R^1$ is selected from the group consisting of: hydrogen, halogen, carboxyl, alkoxycarbonyl, alkylsulfonylaminocarbonyl and cycloalkylsulfonylaminocarbonyl;

$R^2$ is selected from the group consisting of: hydrogen, halogen and carboxyl;

$R^3$ is selected from the group consisting of: hydrogen, halogen, carboxyl, haloalkyl, cyano, alkoxycarbonyl, alkylsulfonyl, alkylsulfonylaminocarbonyl, cycloalkylsulfonylaminocarbonyl, carboxylalkylamino(alkyl)carbonyl, alkyl(hydroxy)pyrrolidinylcarbonyl and carboxylpyrrolidinylcarbonyl;

$R^4$ is selected from the group consisting of: hydrogen, carboxyl, alkylsulfonylaminocarbonyl and cycloalkylsulfonylaminocarbonyl; and $R^5$ is selected from the group consisting of: pyridinyl, substituted pyridinyl, morpholinylpyridinyl, phenyl and substituted phenyl wherein substituted pyridinyl and substituted phenyl are pyridinyl and phenyl substituted with one or two substituents independently selected from the group consisting of halogen, halophenyl, alkyl, cycloalkyl, alkoxy, cyano, carboxyl, cycloalkylcarbonylamino, alkylsulfonylamino, phenylsulfonylamino, phenylaminosulfonyl, halophenylsulfonylamino, phenyl, alkylphenyl, alkoxyphenyl, cyanophenyl, alkylaminocarbonylphenyl, alkylsulfonylphenyl, pyrrolidinyl, pyridinylcarbonylamino, morpholinyl, alkylmorpholinyl, piperazinyl, alkylpiperazinyl, alkylcarbonylpiperazinyl, alkylphenylpiperazinyl, halophenylpiperazinyl, oxopyrrolidinyl, dioxoimidazolidinyl, oxoimidazolidinyl, alkyloxoimidazolidinyl, phenyloxoimidazolidinyl, 2-oxo-oxazolidin-3-yl, alkyl-2-oxo-oxazolidin-3-yl, phenylalkyl-2-oxo-oxazolidin-3-yl, dioxopiperazinyl, alkyldioxopiperazinyl, aminocarbonyl, alkylaminocarbonyl, alkoxyalkylaminocarbonyl, alkylaminoalkylaminocarbonyl, cycloalkylaminocarbonyl, alkylpyrrolidinylaminocarbonyl, tetrahydrofuranylaminocarbonyl, alkylpyrrolidinylalkylaminocarbonyl, alkoxycarbonylazetidinylaminocarbonyl, pyrrolidinylcarbonyl, piperidinylcarbonyl, alkylsulfonylaminocarbonyl, cycloaklylsulfonylaminocarbonyl, phenylsulfonylaminocarbonyl, alkylazetidinylaminocarbonyl, haloazetidinyl, alkylpyrrolidinylaminocarbonyl, phenylaminocarbonyl, pyrazinylaminocarbonyl, aminoalkoxyalkyl, aminoalkoxy, carboxylalkoxy, carboxylalkoxyalkyl, alkyltetrazolyl, phenylalkyltetrazolyl, alkylaminosulfonyl, alkylphenylsulfonylamino, alkylcarbonylamino, cycloalkenylcarbonylamino, phenylcarbonylamino, phenylalkylcarbonylamino, alkylaminoalkylamino, 7-benzyl-4-oxo-5,6,7,8-tetrahydro-4H-pyrido[3,4-d]pyrimidin-3-yl, alkylaminophenyl, alkylamino, hydroxyalkylamino, carboxylalkylamino, carboxylcycloalkylamino, alkylaminocarbonylalkylamino, aminocarbonyl(alkyl)amino, morpholinylcarbonylalkylamino, alkylpiperazinylcarbonylalkylamino, alkylaminosulfonylamino, alkylcarbonylaminophenylsulfonylamino, alkylaminocarbonylamino, aminocarbonylamino, morpholinylcarbonylamino, pyrrolidinylcarbonylamino, piperidinylcarbonylamino, alkylpiperazinylcarbonylamino, phenylalkylaminocarbonylamino, halophenylcarbonylamino, halophenylaminocarbonylamino, pyrazinylcarbonylamino, alkylpiperazinyl, pyrrolidinylsulfonyl and alkylpyrrolidinylaminosulfonyl;

or a pharmaceutically acceptable salt or ester thereof.

It has been found that the compounds of the present invention are potent activators of AMP (adenosine monophosphate)-activated protein kinase (AMPK). Activation of AMPK results in lowered blood glucose and lipid levels. The compounds of the invention are therefore useful in the treatment or prophylaxis of diseases that are related to AMPK regulation, such as obesity, dyslipidemia, hyperglycemia, type 1 or type 2 diabetes and cancers.

DETAILED DESCRIPTION OF THE INVENTION

The present invention relates to a compound of formula (I)

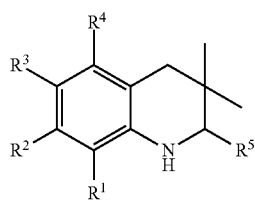

(I)

wherein
$R^1$ is selected from the group consisting of: hydrogen, halogen, carboxyl, alkoxycarbonyl, alkylsulfonylaminocarbonyl and cycloalkylsulfonylaminocarbonyl;
$R^2$ is selected from the group consisting of: hydrogen, halogen and carboxyl;
$R^3$ is selected from the group consisting of: hydrogen, halogen, carboxyl, haloalkyl, cyano, alkoxycarbonyl, alkylsulfonyl, alkylsulfonylaminocarbonyl, cycloalkylsulfonylaminocarbonyl, carboxylalkylamino(alkyl)carbonyl, alkyl(hydroxy)pyrrolidinylcarbonyl and carboxylpyrrolidinylcarbonyl;
$R^4$ is selected from the group consisting of: hydrogen, carboxyl, alkylsulfonylaminocarbonyl and cycloalkylsulfonylaminocarbonyl; and
$R^5$ is selected from the group consisting of: pyridinyl, substituted pyridinyl, morpholinylpyridinyl, phenyl and substituted phenyl wherein substituted pyridinyl and substituted phenyl are pyridinyl and phenyl substituted with one or two substituents independently selected from the group consisting of halogen, halophenyl, alkyl, cycloalkyl, alkoxy, cyano, carboxyl, cycloalkylcarbonylamino, alkylsulfonylamino, phenylsulfonylamino, phenylaminosulfonyl, halophenylsulfonylamino, phenyl, alkylphenyl, alkoxyphenyl, cyanophenyl, alkylaminocarbonylphenyl, alkylsulfonylphenyl, pyrrolidinyl, pyridinylcarbonylamino, morpholinyl, alkylmorpholinyl, piperazinyl, alkylpiperazinyl, alkylcarbonylpiperazinyl, alkylphenylpiperazinyl, halophenylpiperazinyl, oxopyrrolidinyl, dioxoimidazolidinyl, oxoimidazolidinyl, alkyloxoimidazolidinyl, phenyloxoimidazolidinyl, 2-oxo-oxazolidin-3-yl, alkyl-2-oxo-oxazolidin-3-yl, phenylalkyl-2-oxo-oxazolidin-3-yl, dioxopiperazinyl, alkyldioxopiperazinyl, aminocarbonyl, alkylaminocarbonyl, alkoxyalkylaminocarbonyl, alkylaminoalkylaminocarbonyl, cycloalkylaminocarbonyl, alkylpyrrolidinylaminocarbonyl, tetrahydrofuranylaminocarbonyl, alkylpyrrolidinylalkylaminocarbonyl, alkoxycarbonylazetidinylaminocarbonyl, pyrrolidinylcarbonyl, piperidinylcarbonyl, alkylsulfonylaminocarbonyl, cycloaklylsulfonylaminocarbonyl, phenylsulfonylaminocarbonyl, alkylazetidinylaminocarbonyl, haloazetidinyl, alkylpyrrolidinylaminocarbonyl, phenylaminocarbonyl, pyrazinylaminocarbonyl, aminoalkoxyalkyl, aminoalkoxy, carboxylalkoxy, carboxylalkoxyalkyl, alkyltetrazolyl, phenylalkyltetrazolyl, alkylaminosulfonyl, alkylphenylsulfonylamino, alkylcarbonylamino, cycloalkenylcarbonylamino, phenylcarbonylamino, phenylalkylcarbonylamino, alkylaminoalkylamino, 7-benzyl-4-oxo-5,6,7,8-tetrahydro-4H-pyrido[3,4-d]pyrimidin-3-yl, alkylaminophenyl, alkylamino, hydroxyalkylamino, carboxylalkylamino, carboxylcycloalkylamino, alkylaminocarbonylalkylamino, aminocarbonyl(alkyl)amino, morpholinylcarbonylalkylamino, alkylpiperazinylcarbonylalkylamino, alkylaminosulfonylamino, alkylcarbonylaminophenylsulfonylamino, alkylaminocarbonylamino, aminocarbonylamino, morpholinylcarbonylamino, pyrrolidinylcarbonylamino, piperidinylcarbonylamino, alkylpiperazinylcarbonylamino, phenylalkylaminocarbonylamino, halophenylcarbonylamino, halophenylaminocarbonylamino, pyrazinylcarbonylamino, alkylpiperazinyl, pyrrolidinylsulfonyl and alkylpyrrolidinylaminosulfonyl;

or a pharmaceutically acceptable salt or ester thereof.

As used herein, the term "alkyl" alone or in combination signifies a saturated, linear- or branched chain alkyl group containing 1 to 8, preferably 1 to 6, more preferably 1 to 4 carbon atoms, for example methyl, ethyl, propyl, isopropyl, 1-butyl, 2-butyl, tert-butyl and the like. Preferred "alkyl" groups are methyl, ethyl, isopropyl, tert-butyl.

The term "cycloalkenyl" alone or in combination signifies monocyclic alkyl having five, six or seven carbon atoms and one double bond. Preferred cycloalkenyl are cyclopentenyl and cyclohexenyl.

The term "alkoxy" alone or in combination signifies a group alkyl-O—, wherein the "alkyl" is as defined above; for example methoxy, ethoxy, propoxy, isopropoxy, n-butoxy, i-butoxy, 2-butoxy, t-butoxy and the like. Preferred alkoxy groups are methoxy and ethoxy and more preferably methoxy.

The term "cycloalkyl" alone or in combination refers to a saturated carbon ring containing from 3 to 7 carbon atoms, preferably from 3 to 6 carbon atoms, for example, cyclopropyl, cyclobutyl, cyclopentyl, cyclohexyl, cycloheptyl and the like. Preferred cycloalkyl groups are cyclopropyl and cyclopentyl, cyclopropyl being particularly preferred.

The term "halogen" means fluorine, chlorine, bromine or iodine. Halogen is preferably fluorine, chlorine or bromine.

The term "halophenyl" means phenyl substituted by halogen.

The term "carboxyl" alone or in combination refers to the group —COOH.

The term "carbonyl" alone or in combination refers to the group —C(O)—.

The term "amino" alone or in combination refers to primary (—$NH_2$—), secondary (—NH—) or tertiary amino (—N—).

The term "hydroxy" alone or in combination refers to the group —OH.

The term "sulfonyl" alone or in combination refers to the group —$S(O)_2$—.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula (I) and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et. al. organic Process Research & Development 2000, 4, 427-435; or in Ansel, H., et. al., In: Pharmaceutical Dosage Forms and Drug Delivery Systems, 6th ed. (1995), pp. 196 and 1456-1457. Preferred are the sodium salts of the compounds of formula (I).

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention. Preferred are the methyl and ethyl esters of the compounds of formula (I).

In particular, the invention relates to a compound of formula (I) wherein $R^1$ is selected from the group consisting of: hydrogen, carboxyl and alkoxycarbonyl.

The invention relates also in particular is a compound according of formula (I) wherein $R^1$ is selected from the group consisting of: hydrogen, carboxyl and methoxycarbonyl.

The invention relates also to a compound of formula (I) wherein $R^2$ is hydrogen.

A compound of formula (I) wherein $R^3$ is selected from the group consisting of: halogen, carboxyl, haloalkyl, cyano, alkylsulfonyl, alkylsulfonylaminocarbonyl and cycloalkylsulfonylaminocarbonyl is also an object of the invention.

A compound of formula (I) wherein $R^3$ is selected from the group consisting of: fluoro, chloro, carboxyl, trifluoromethyl, cyano, methylsulfonyl, methylsulfonylaminocarbonyl and cyclopropylsulfonylaminocarbonyl is a further object of the invention.

Furthermore, the invention relates to a compound of formula (I) wherein $R^4$ is selected from the group consisting of: hydrogen, carboxyl, methylsulfonylaminocarbonyl and cyclopropylsulfonylaminocarbonyl.

Moreover, the invention is directed in particular to a compound of formula (I) wherein $R^5$ is substituted phenyl wherein substituted phenyl is phenyl substituted with one or two substituents independently selected from the group consisting of: halogen, alkyl, alkylsulfonylamino, phenylsulfonylamino, halophenylsulfonylamino, alkylphenyl, pyrrolidinyl, morpholinyl, alkylpiperazinyl, alkylphenylpiperazinyl, alkyloxoimidazolidinyl, alkyl-2-oxo-oxazolidin-3-yl, aminocarbonyl, alkylaminoalkylaminocarbonyl, alkylpyrrolidinylaminocarbonyl, phenylsulfonylaminocarbonyl, alkylcarbonylamino, alkylaminoalkylamino, alkylamino, carboxylalkylamino, carboxylcycloalkylamino and alkylaminocarbonylalkylamino.

In addition, the invention is also concerned with a compound of formula (I) wherein $R^5$ is substituted phenyl wherein substituted phenyl is phenyl substituted with one or two substituents independently selected from the group consisting of: fluoro, methyl, methylsulfonylamino, phenylsulfonylamino, fluorophenylsulfonylamino, tert-butylphenyl, pyrrolidinyl, morpholinyl, methylpiperazinyl, dimethylphenylpiperazinyl, methylphenylpiperazinyl, methyloxoimidazolidinyl, isoproyl-2-oxo-oxazolidin-3-yl, aminocarbonyl, dimethylaminoethylaminocarbonyl, methylpyrrolidinylaminocarbonyl, phenylsulfonylaminocarbonyl, isopropylcarbonylamino, methylamino(ethyl)(methyl)amino, dimethylamino, carboxylpropylamino, carboxylcyclopropylamino and methylaminocarbonylpropylamino.

Particular compounds of formula (I) according to the invention can be selected from the group consisting of:

2-[3-(3-Benzyl-ureido)-phenyl]-3,3-dimethyl-1,2,3,4-tetrahydro-quinoline-6-carboxylic acid;

Pyrazine-2-carboxylic acid [3-(6-chloro-8-cyclopropanesulfonylaminocarbonyl-3,3-dimethyl-1,2,3,4-tetrahydroquinolin-2-yl)-phenyl]-amide;

3,3-Dimethyl-2-{3-[(pyridine-3-carbonyl)-amino]-phenyl}-1,2,3,4-tetrahydro-quinoline-6-carboxylic acid;

3,3-Dimethyl-2-{3-[(pyridine-2-carbonyl)-amino]-phenyl}-1,2,3,4-tetrahydro-quinoline-6-carboxylic acid;

3,3-Dimethyl-2-{3-[(pyrazine-2-carbonyl)-amino]-phenyl}-1,2,3,4-tetrahydro-quinoline-6-carboxylic acid;

2-[3-(3-Fluoro-benzoylamino)-phenyl]-3,3-dimethyl-1,2,3,4-tetrahydro-quinoline-6-carboxylic acid;
2-(3-Carbonyl-phenyl)-3,3-dimethyl-1,2,3,4-tetrahydro-quinoline-6-carboxylic acid;
N-[3,3-dimethyl-2-(3-morpholin-4-yl-phenyl)-1,2,3,4-tetrahydro-quinoline-6-carbonyl]-methanesulfonamide;
3-(6-Methanesulfonylaminocarbonyl-3,3-dimethyl-1,2,3,4-tetrahydro-quinolin-2-yl)-N-phenyl-benzamide;
Propane-2-sulfonic acid [3,3-dimethyl-2-(3-morpholin-4-yl-phenyl)-1,2,3,4-tetrahydro-quinoline-6-carbonyl]-amide;
Pyrazine-2-carboxylic acid [3-(6-methanesulfonylaminocarbonyl-3,3-dimethyl-1,2,3,4-tetrahydro-quinolin-2-yl)-phenyl]-amide;
2-(3-Benzoylamino-phenyl)-3,3-dimethyl-1,2,3,4-tetrahydro-quinoline-6-carboxylic acid;
2-{3-[3-(3-Fluoro-phenyl)-ureido]-phenyl}-3,3-dimethyl-1,2,3,4-tetrahydro-quinoline-6-carboxylic acid;
3,3-Dimethyl-2-(3-phenylcarbamoyl-phenyl)-1,2,3,4-tetrahydro-quinoline-6-carboxylic acid;
2-[3-(1-Carboxy-1-methyl-ethylamino)-phenyl]-3,3-dimethyl-1,2,3,4-tetrahydro-quinoline-6-carboxylic acid;
3,3-Dimethyl-2-[3-(3-methyl-2-oxo-imidazolidin-1-yl)-phenyl]-1,2,3,4-tetrahydro-quinoline-6-carboxylic acid;
3,3-Dimethyl-2-[3-(2-oxo-imidazolidin-1-yl)-phenyl]-1,2,3,4-tetrahydro-quinoline-6-carboxylic acid;
2-[3-(2,5-Dioxo-piperazin-1-yl)-phenyl]-3,3-dimethyl-1,2,3,4-tetrahydro-quinoline-6-carboxylic acid;
2-[3-(2,4-Dioxo-imidazolidine-1-yl)-phenyl]-3,3-dimethyl-1,2,3,4-tetrahydro-quinoline-6-carboxylic acid;
2-[3-(4-Fluoro-benzoylamino)-phenyl]-3,3-dimethyl-1,2,3,4-tetrahydro-quinoline-6-carboxylic acid;
3,3-Dimethyl-2-{3-[(morpholine-4-carbonyl)-amino]-phenyl}-1,2,3,4-tetrahydro-quinoline-6-carboxylic acid;
3,3-Dimethyl-2-{3-[(piperidine-1-carbonyl)-amino]-phenyl}-1,2,3,4-tetrahydro-quinoline-6-carboxylic acid;
{[3,3-Dimethyl-2-(3-morpholin-4-yl-phenyl)-1,2,3,4-tetrahydro-quinoline-6-carboxyl]-methyl-amino}-acetic acid;
1-[3,3-Dimethyl-2-(3-morpholin-4-yl-phenyl)-1,2,3,4-tetrahydro-quinoline-6-carboxyl]-pyrrolidine-2-carboxylic acid;
2-(3-(N,N-dimethylsulfamoylamino)phenyl)-3,3-dimethyl-1,2,3,4-tetrahydroquinoline-6-carboxylic acid;
3,3-Dimethyl-2-[3-(2-oxo-3-phenyl-imidazolidin-1-yl)-phenyl]-1,2,3,4-tetrahydro-quinoline-6-carboxylic acid;
3,3-Dimethyl-2-{3-[(4-methyl-piperazine-1-carbonyl)-amino]-phenyl}-1,2,3,4-tetrahydro-quinoline-6-carboxylic acid;
2-[3-(6-Methanesulfonylaminocarbonyl-3,3-dimethyl-1,2,3,4-tetrahydro-quinolin-2-yl)-phenylamino]-2-methyl-propionic acid;
2-[3-(2-Hydroxy-1,1-dimethyl-ethylamino)-phenyl]-3,3-dimethyl-1,2,3,4-tetrahydro-quinoline-6-carboxylic acid;
3,3-Dimethyl-2-[3-(trimethyl-ureido)-phenyl]-1,2,3,4-tetrahydro-quinoline-6-carboxylic acid;
3,3-Dimethyl-2-[3-(1-methyl-ureido)-phenyl]-1,2,3,4-tetrahydro-quinoline-6-carboxylic acid;
2-[3-(1-Isopropyl-ureido)-phenyl]-3,3-dimethyl-1,2,3,4-tetrahydro-quinoline-6-carboxylic acid;
2-[3-(2-Amino-1,1-dimethyl-ethoxy)-phenyl]-3,3-dimethyl-1,2,3,4-tetrahydro-quinoline-6-carboxylic acid;
2-[3-(4,4-Dimethyl-2-oxo-oxazolidine-3-yl)-phenyl]-3,3-dimethyl-1,2,3,4-tetrahydro-quinoline-6-carboxylic acid;
3,3-Dimethyl-2-{3-[(pyrrolidine-1-carbonyl)-amino]-phenyl}-1,2,3,4-tetrahydro-quinoline-6-carboxylic acid;
2-[3-(3,3-Diethyl-ureido)-phenyl]-3,3-dimethyl-1,2,3,4-tetrahydro-quinoline-6-carboxylic acid;
2-[3-(6-Chloro-3,3-dimethyl-1,2,3,4-tetrahydro-quinolin-2-yl)-phenylamino]-2-methyl-propionic acid;
2-[3-(6-Cyano-3,3-dimethyl-1,2,3,4-tetrahydro-quinolin-2-yl)-phenylamino]-2-methyl-propionic acid;
2-[3-(6-Methanesulfonylaminocarbonyl-3,3-dimethyl-1,2,3,4-tetrahydro-quinolin-2-yl)-phenylamino]-2,N-dimethyl-propionamide;
2-[3-(1-Dimethylcarbamoyl-1-methyl-ethylamino)-phenyl]-3,3-dimethyl-1,2,3,4-tetrahydro-quinoline-6-carboxylic acid;
2-[3-(1,1-Dimethyl-2-morpholin-4-yl-2-oxo-ethylamino)-phenyl]-3,3-dimethyl-1,2,3,4-tetrahydro-quinoline-6-carboxylic acid;
2-{3-[1,1-Dimethyl-2-(4-methyl-piperazin-1-yl)-2-oxo-ethylamino]-phenyl}-3,3-dimethyl-1,2,3,4-tetrahydro-quinoline-6-carboxylic acid;
N-isopropyl-2-[3-(6-methanesulfonylaminocarbonyl-3,3-dimethyl-1,2,3,4-tetrahydro-quinolin-2-yl)-phenylamino]-2-methyl-propionamide;
2-[3-(1-Carboxy-cyclopropylamino)-phenyl]-3,3-dimethyl-1,2,3,4-tetrahydro-quinoline-6-carboxylic acid;
2-[3-(3,3-Dimethyl-6-trifluoromethyl-1,2,3,4-tetrahydro-quinolin-2-yl)-phenylamino]-2-methyl-propionic acid;
2-[5-(4-tert-Butyl-phenyl)-pyridin-3-yl]-3,3-dimethyl-1,2,3,4-tetrahydro-quinoline-6-carboxylic acid;
2-[3-(6-Cyclopropanesulfonylaminocarbonyl-3,3-dimethyl-1,2,3,4-tetrahydro-quinolin-2-yl)-phenylamino]-2,N-dimethyl-propionamide;
2-[3-(6-Methanesulfonyl-3,3-dimethyl-1,2,3,4-tetrahydro-quinolin-2-yl)-phenylamino]-2-methyl-propionic acid;
N-[2-(4'-tert-Butyl-5-fluoro-biphenyl-3-yl)-3,3-dimethyl-1,2,3,4-tetrahydro-quinoline-6-carbonyl]-methanesulfonamide;
N-[2-(3-Dimethylamino-5-fluoro-phenyl)-3,3-dimethyl-1,2,3,4-tetrahydro-quinoline-6-carbonyl]-methanesulfonamide;
2-(4'-Cyano-5-fluoro-biphenyl-3-yl)-3,3-dimethyl-1,2,3,4-tetrahydro-quinoline-6-carboxylic acid;
Cyclopropanesulfonic acid [2-(3,5-difluoro-phenyl)-3,3-dimethyl-1,2,3,4-tetrahydro-quinoline-6-carbonyl]-amide;
2-(2-Fluoro-5-morpholin-4-yl-phenyl)-3,3-dimethyl-1,2,3,4-tetrahydro-quinoline-6-carboxylic acid;
Cyclopropanesulfonic acid [2-(2-fluoro-5-morpholin-4-yl-phenyl)-3,3-dimethyl-1,2,3,4-tetrahydro-quinoline-6-carbonyl]-amide;
2-(3-Chloro-5-morpholin-4-yl-phenyl)-3,3-dimethyl-1,2,3,4-tetrahydro-quinoline-6-carboxylic acid;
Cyclopropanesulfonic acid [2-(3-chloro-5-morpholin-4-yl-phenyl)-3,3-dimethyl-1,2,3,4-tetrahydro-quinoline-6-carbonyl]-amide;
N-[2-(3-Chloro-5-morpholin-4-yl-phenyl)-3,3-dimethyl-1,2,3,4-tetrahydro-quinoline-6-carbonyl]-methanesulfonamide;
Cyclopropanesulfonic acid [2-(4-fluoro-3-morpholin-4-yl-phenyl)-3,3-dimethyl-1,2,3,4-tetrahydro-quinoline-6-carbonyl]-amide;
N-[2-(4-Fluoro-3-morpholin-4-yl-phenyl)-3,3-dimethyl-1,2,3,4-tetrahydro-quinoline-6-carbonyl]-methanesulfonamide;
Cyclopropanesulfonic acid [2-(5-fluoro-2-methyl-phenyl)-3,3-dimethyl-1,2,3,4-tetrahydro-quinoline-6-carbonyl]-amide;
N-[2-(3-Fluoro-5-pyrrolidin-1-yl-phenyl)-3,3-dimethyl-1,2,3,4-tetrahydro-quinoline-6-carbonyl]-methanesulfonamide;

Cyclopropanesulfonic acid [2-(3-fluoro-5-pyrrolidin-1-yl-phenyl)-3,3-dimethyl-1,2,3,4-tetrahydro-quinoline-6-carbonyl]-amide;
3,3-Dimethyl-2-(3-methyl-5-morpholin-4-yl-phenyl)-1,2,3,4-tetrahydro-quinoline-6-carboxylic acid;
Cyclopropanesulfonic acid [3,3-dimethyl-2-(3-methyl-5-morpholin-4-yl-phenyl)-1,2,3,4-tetrahydro-quinoline-6-carbonyl]-amide;
N-[3,3-Dimethyl-2-(3-methyl-5-morpholin-4-yl-phenyl)-1,2,3,4-tetrahydro-quinoline-6-carbonyl]-methanesulfonamide;
2-(3-Methoxy-5-morpholin-4-yl-phenyl)-3,3-dimethyl-1,2,3,4-tetrahydro-quinoline-6-carboxylic acid;
Cyclopropanesulfonic acid [2-(3-methoxy-5-morpholin-4-yl-phenyl)-3,3-dimethyl-1,2,3,4-tetrahydro-quinoline-6-carbonyl]-amide;
N-[2-(3-Methoxy-5-morpholin-4-yl-phenyl)-3,3-dimethyl-1,2,3,4-tetrahydro-quinoline-6-carbonyl]-methanesulfonamide;
N-[2-(3-Cyano-5-morpholin-4-yl-phenyl)-3,3-dimethyl-1,2,3,4-tetrahydro-quinoline-6-carbonyl]-methanesulfonamide;
Cyclopropanesulfonic acid [2-(3-cyclohexyl-5-fluoro-phenyl)-3,3-dimethyl-1,2,3,4-tetrahydro-quinoline-6-carbonyl]-amide;
2-(3-Fluoro-5-piperazin-1-yl-phenyl)-3,3-dimethyl-1,2,3,4-tetrahydro-quinoline-6-carboxylic acid;
3,3-Dimethyl-2-(4-morpholin-4-yl-phenyl)-1,2,3,4-tetrahydro-quinoline-6-carboxylic acid;
Cyclopropanesulfonic acid [3,3-dimethyl-2-(4-morpholin-4-yl-phenyl)-1,2,3,4-tetrahydro-quinoline-6-carbonyl]-amide;
N-[3,3-Dimethyl-2-(4-morpholin-4-yl-phenyl)-1,2,3,4-tetrahydro-quinoline-6-carbonyl]-methanesulfonamide;
N-{2-[3-Fluoro-5-(4-isopropyl-piperazin-1-yl)-phenyl]-3,3-dimethyl-1,2,3,4-tetrahydro-quinoline-6-carbonyl}-methanesulfonamide;
2-[3-Fluoro-5-(2-oxo-pyrrolidin-1-yl)-phenyl]-3,3-dimethyl-1,2,3,4-tetrahydro-quinoline-6-carboxylic acid;
N-{2-[3-Fluoro-5-(2-oxo-pyrrolidin-1-yl)-phenyl]-3,3-dimethyl-1,2,3,4-tetrahydro-quinoline-6-carbonyl}-methanesulfonamide;
2-[3-(1-Carboxy-1-methyl-ethylamino)-phenyl]-6-chloro-3,3-dimethyl-1,2,3,4-tetrahydro-quinoline-8-carboxylic acid methyl ester;
6-Chloro-3,3-dimethyl-2-[3-(1-methyl-1-methylcarbamoyl-ethylamino)-phenyl]-1,2,3,4-tetrahydro-quinoline-8-carboxylic acid;
2-[3-(1-Carboxy-1-methyl-ethylamino)-phenyl]-6-chloro-3,3-dimethyl-1,2,3,4-tetrahydro-quinoline-8-carboxylic acid;
2-[3-(4-Acetyl-piperazin-1-yl)-phenyl]-6-chloro-3,3-dimethyl-1,2,3,4-tetrahydro-quinoline-8-carboxylic acid;
6-Chloro-3,3-dimethyl-2-[3-(4-o-tolyl-piperazin-1-yl)-phenyl]-1,2,3,4-tetrahydro-quinoline-8-carboxylic acid;
N-[2-(4'-tert-Butyl-biphenyl-3-yl)-3,3-dimethyl-1,2,3,4-tetrahydro-quinoline-6-carbonyl]-methanesulfonamide;
2-(4'-Isopropoxy-biphenyl-3-yl)-3,3-dimethyl-1,2,3,4-tetrahydro-quinoline-6-carboxylic acid;
N-[2-(4'-Isopropoxy-biphenyl-3-yl)-3,3-dimethyl-1,2,3,4-tetrahydro-quinoline-6-carbonyl]-methanesulfonamide;
Cyclopropanesulfonic acid [2-(4'-isopropoxy-biphenyl-3-yl)-3,3-dimethyl-1,2,3,4-tetrahydro-quinoline-6-carbonyl]-amide;
2-{3-[4-(4-Chloro-phenyl)-piperazin-1-yl]-phenyl}-3,3-dimethyl-1,2,3,4-tetrahydro-quinoline-6-carboxylic acid;
N (2-{3-[4 (4 Chloro-phenyl)-piperazin-1-yl]-phenyl}-3,3-dimethyl-1,2,3,4-tetrahydro-quinoline-6-carbonyl)-methanesulfonamide;
2-{3-[4-(2,4-Dimethyl-phenyl)-piperazin-1-yl]-phenyl}-3,3-dimethyl-1,2,3,4-tetrahydro-quinoline-6-carboxylic acid;
N-(2-{3-[4-(2,4-Dimethyl-phenyl)-piperazin-1-yl]-phenyl}-3,3-dimethyl-1,2,3,4-tetrahydro-quinoline-6-carbonyl)-methanesulfonamide;
Cyclopropanesulfonic acid (2-{3-[4-(2,4-dimethyl-phenyl)-piperazin-1-yl]-phenyl}-3,3-dimethyl-1,2,3,4-tetrahydro-quinoline-6-carbonyl)-amide;
6-Fluoro-3,3-dimethyl-2-[3-(4-o-tolyl-piperazin-1-yl)-phenyl]-1,2,3,4-tetrahydro-quinoline-8-carboxylic acid;
N-(6-Chloro-2-{3-[4-(4-chloro-phenyl)-piperazin-1-yl]-phenyl}-3,3-dimethyl-1,2,3,4-tetrahydro-quinoline-8-carbonyl)-methanesulfonamide;
3,3-Dimethyl-2-[3-(4-o-tolyl-piperazin-1-yl)-phenyl]-1,2,3,4-tetrahydro-quinoline-8-carboxylic acid;
6-Chloro-3,3-dimethyl-2-(3-morpholin-4-yl-phenyl)-1,2,3,4-tetrahydro-quinoline-5-carboxylic acid;
N-{3,3-Dimethyl-2-[3-(4-methyl-piperazin-1-yl)-phenyl]-1,2,3,4-tetrahydro-quinoline-6-carbonyl}-methanesulfonamide;
Cyclopropanesulfonic acid [3,3-dimethyl-2-(3-piperazin-1-yl-phenyl)-1,2,3,4-tetrahydro-quinoline-6-carbonyl]-amide;
Ethanesulfonic acid [3,3-dimethyl-2-(3-morpholin-4-yl-phenyl)-1,2,3,4-tetrahydro-quinoline-6-carbonyl]-amide;
3,3-Dimethyl-2-[3-(4-methyl-piperazin-1-yl)-phenyl]-1,2,3,4-tetrahydro-quinoline-6-carboxylic acid;
6-Chloro-3,3-dimethyl-2-(3-morpholin-4-yl-phenyl)-1,2,3,4-tetrahydro-quinoline-8-carboxylic acid;
Cyclopropanesulfonic acid [6-chloro-3,3-dimethyl-2-(3-morpholin-4-yl-phenyl)-1,2,3,4-tetrahydro-quinoline-8-carbonyl]-amide;
3,3-Dimethyl-2-(3-piperazin-1-yl-phenyl)-1,2,3,4-tetrahydro-quinoline-6-carboxylic acid;
N-[3,3-Dimethyl-2-(3-piperazin-1-yl-phenyl)-1,2,3,4-tetrahydro-quinoline-6-carbonyl]-methanesulfonamide;
N-[6-Chloro-3,3-dimethyl-2-(3-morpholin-4-yl-phenyl)-1,2,3,4-tetrahydro-quinoline-8-carbonyl]-methanesulfonamide;
Cyclopropanesulfonic acid {2-[3-(2,6-dimethyl-morpholin-4-yl)-phenyl]-3,3-dimethyl-1,2,3,4-tetrahydro-quinoline-6-carbonyl}-amide;
2-[3-(2,6-Dimethyl-morpholin-4-yl)-phenyl]-3,3-dimethyl-1,2,3,4-tetrahydro-quinoline-6-carboxylic acid;
(3-Hydroxy-3-methyl-pyrrolidin-1-yl)-[2-(3-methoxy-phenyl)-3,3-dimethyl-1,2,3,4-tetrahydro-quinolin-6-yl]-methanone;
3,3-Dimethyl-2-pyridin-3-yl-1,2,3,4-tetrahydro-quinoline-6-carboxylic Acid;
2-(4'-Chloro-biphenyl-3-yl)-3,3-dimethyl-1,2,3,4-tetrahydro-quinoline-6-carboxylic acid;
N-{3,3-Dimethyl-2-[3-(2-oxo-oxazolidin-3-yl)-phenyl]-1,2,3,4-tetrahydro-quinoline-6-carbonyl}-methanesulfonamide;
8-Chloro-3,3-dimethyl-2-(3-morpholin-4-yl-phenyl)-1,2,3,4-tetrahydro-quinoline-5-carboxylic acid;
8-Chloro-3,3-dimethyl-2-(3-morpholin-4-yl-phenyl)-1,2,3,4-tetrahydro-quinoline-6-carboxylic acid;
2-(3-Chloro-4-fluoro-phenyl)-3,3-dimethyl-1,2,3,4-tetrahydro-quinoline-6-carboxylic acid;
Cyclopropanesulfonic acid [3,3-dimethyl-2-(5-morpholin-4-yl-pyridin-3-yl)-1,2,3,4-tetrahydro-quinoline-6-carbonyl]-amide;

N-[8-Chloro-3,3-dimethyl-2-(3-morpholin-4-yl-phenyl)-1,2,3,4-tetrahydro-quinoline-6-carbonyl]-methanesulfonamide;
Cyclopropanesulfonic acid {3,3-dimethyl-2-[3-(2-oxo-oxazolidin-3-yl)-phenyl]-1,2,3,4-tetrahydro-quinoline-6-carbonyl}-amide;
Cyclopropanesulfonic acid [6-fluoro-3,3-dimethyl-2-(3-morpholin-4-yl-phenyl)-1,2,3,4-tetrahydro-quinoline-5-carbonyl]-amide;
N-[6-Fluoro-3,3-dimethyl-2-(3-morpholin-4-yl-phenyl)-1,2,3,4-tetrahydro-quinoline-5-carbonyl]-methanesulfonamide;
2-[3-((S)-4-Isopropyl-2-oxo-oxazolidin-3-yl)-phenyl]-3,3-dimethyl-1,2,3,4-tetrahydro-quinoline-6-carboxylic acid;
3,3-Dimethyl-2-{3-[methyl-(2-methylamino-ethyl)-amino]-phenyl}-1,2,3,4-tetrahydro-quinoline-6-carboxylic acid;
6-Fluoro-3,3-dimethyl-2-(3-morpholin-4-yl-phenyl)-1,2,3,4-tetrahydro-quinoline-5-carboxylic acid;
2-[3-(R)-4-Isopropyl-2-oxo-oxazolidin-3-yl)-phenyl]-3,3-dimethyl-1,2,3,4-tetrahydro-quinoline-6-carboxylic acid;
N-{2-[3-((R)-4-Isopropyl-2-oxo-oxazolidin-3-yl)-phenyl]-3,3-dimethyl-1,2,3,4-tetrahydro-quinoline-6-carbonyl}-methanesulfonamide;
2-[3-((S)-4-Benzyl-2-oxo-oxazolidin-3-yl)-phenyl]-3,3-dimethyl-1,2,3,4-tetrahydro-quinoline-6-carboxylic acid;
Cyclopropanesulfonic acid {2-[3-((R)-4-isopropyl-2-oxo-oxazolidin-3-yl)-phenyl]-3,3-dimethyl-1,2,3,4-tetrahydro-quinoline-6-carbonyl}-amide;
3,3-Dimethyl-2-[3-(4-methyl-2,3-dioxo-piperazin-1-yl)-phenyl]-1,2,3,4-tetrahydro-quinoline-6-carboxylic acid;
2-[3-((R)-4-Benzyl-2-oxo-oxazolidin-3-yl)-phenyl]-3,3-dimethyl-1,2,3,4-tetrahydro-quinoline-6-carboxylic acid;
N-{2-[3-((R)-4-Benzyl-2-oxo-oxazolidin-3-yl)-phenyl]-3,3-dimethyl-1,2,3,4-tetrahydro-quinoline-6-carbonyl}-methanesulfonamide;
Cyclopropanesulfonic acid {3,3-dimethyl-2-[3-(4-methyl-2,3-dioxo-piperazin-1-yl)-phenyl]-1,2,3,4-tetrahydro-quinoline-6-carbonyl}-amide;
Cyclopropanesulfonic acid {2-[3-((R)-4-benzyl-2-oxo-oxazolidin-3-yl)-phenyl]-3,3-dimethyl-1,2,3,4-tetrahydro-quinoline-6-carbonyl}-amide;
N-{3,3-Dimethyl-2-[3-(4-methyl-2,3-dioxo-piperazin-1-yl)-phenyl]-1,2,3,4-tetrahydro-quinoline-6-carbonyl}-methanesulfonamide;
Cyclopropanesulfonic acid {2-[3-((S)-4-benzyl-2-oxo-oxazolidin-3-yl)-phenyl]-3,3-dimethyl-1,2,3,4-tetrahydro-quinoline-6-carbonyl}-amide;
Cyclopropanesulfonic acid [8-chloro-3,3-dimethyl-2-(3-morpholin-4-yl-phenyl)-1,2,3,4-tetrahydro-quinoline-5-carbonyl]-amide;
7-Fluoro-3,3-dimethyl-2-(3-morpholin-4-yl-phenyl)-1,2,3,4-tetrahydro-quinoline-5-carboxylic acid;
N-[7-Fluoro-3,3-dimethyl-2-(3-morpholin-4-yl-phenyl)-1,2,3,4-tetrahydro-quinoline-5-carbonyl]-methanesulfonamide;
2-[3-(7-Benzyl-4-oxo-5,6,7,8-tetrahydro-4H-pyrido[3,4-d]pyrimidin-3-yl)-phenyl]-3,3-dimethyl-1,2,3,4-tetrahydro-quinoline-6-carboxylic acid;
8-Fluoro-3,3-dimethyl-2-(3-morpholin-4-yl-phenyl)-1,2,3,4-tetrahydro-quinoline-7-carboxylic acid;
Cyclopropanesulfonic acid [7-fluoro-3,3-dimethyl-2-(3-morpholin-4-yl-phenyl)-1,2,3,4-tetrahydro-quinoline-5-carbonyl]-amide;
Cyclopropanesulfonic acid {6-chloro-3,3-dimethyl-2-[3-(4-methyl-piperazin-1-yl)-phenyl]-1,2,3,4-tetrahydro-quinoline-8-carbonyl}-amide;
6-Chloro-2-(4'-isopropyl-biphenyl-3-yl)-3,3-dimethyl-1,2,3,4-tetrahydro-quinoline-8-carboxylic acid;
Cyclopropanesulfonic acid [6-chloro-2-(4'-dimethylamino-biphenyl-3-yl)-3,3-dimethyl-1,2,3,4-tetrahydro-quinoline-8-carbonyl]-amide;
2-(4'-tert-Butyl-biphenyl-3-yl)-6-chloro-3,3-dimethyl-1,2,3,4-tetrahydro-quinoline-8-carboxylic acid;
Cyclopropanesulfonic acid [2-(4'-tert-butyl-biphenyl-3-yl)-6-chloro-3,3-dimethyl-1,2,3,4-tetrahydro-quinoline-8-carbonyl]-amide;
N-[2-(4'-tert-Butyl-biphenyl-3-yl)-6-chloro-3,3-dimethyl-1,2,3,4-tetrahydro-quinoline-8-carbonyl]-methanesulfonamide;
Cyclopropanesulfonic acid {2-[3-(5-ethyl-tetrazol-1-yl)-phenyl]-3,3-dimethyl-1,2,3,4-tetrahydro-quinoline-6-carbonyl}-amide;
N-{2-[3-(5-Ethyl-tetrazol-1-yl)-phenyl]-3,3-dimethyl-1,2,3,4-tetrahydro-quinoline-6-carbonyl}-methanesulfonamide;
2-[3-(5-Benzyl-tetrazol-1-yl)-phenyl]-3,3-dimethyl-1,2,3,4-tetrahydro-quinoline-6-carboxylic acid;
2-[3-(5-Ethyl-tetrazol-1-yl)-phenyl]-3,3-dimethyl-1,2,3,4-tetrahydro-quinoline-6-carboxylic acid;
N-[7-Chloro-3,3-dimethyl-2-(3-morpholin-4-yl-phenyl)-1,2,3,4-tetrahydro-quinoline-5-carbonyl]-methanesulfonamide;
Cyclopropanesulfonic acid [8-fluoro-3,3-dimethyl-2-(3-morpholin-4-yl-phenyl)-1,2,3,4-tetrahydro-quinoline-5-carbonyl]-amide;
2-(4'-tert-Butyl-biphenyl-3-yl)-6-fluoro-3,3-dimethyl-1,2,3,4-tetrahydro-quinoline-5-carboxylic acid;
3,3-Dimethyl-2-[3-(4-o-tolyl-piperazin-1-yl)-phenyl]-1,2,3,4-tetrahydroquinoline-6-carboxylic acid;
Cyclopropanesulfonic acid {2-[3-(3-fluoro-azetidin-1-yl)-phenyl]-3,3-dimethyl-1,2,3,4-tetrahydro-quinoline-6-carbonyl}-amide;
N-{2-[3-(3-Fluoro-azetidin-1-yl)-phenyl]-3,3-dimethyl-1,2,3,4-tetrahydro-quinoline-6-carbonyl}-methanesulfonamide;
N-{3,3-Dimethyl-2-[3-(4-o-tolyl-piperazin-1-yl)-phenyl]-1,2,3,4-tetrahydro-quinoline-6-carbonyl}-methanesulfonamide;
Cyclopropanesulfonic acid [2-(4'-tert-butyl-biphenyl-3-yl)-6-fluoro-3,3-dimethyl-1,2,3,4-tetrahydro-quinoline-5-carbonyl]-amide;
N-[2-(4'-tert-Butyl-biphenyl-3-yl)-6-fluoro-3,3-dimethyl-1,2,3,4-tetrahydro-quinoline-5-carbonyl]-methanesulfonamide;
3,3-Dimethyl-2-phenyl-1,2,3,4-tetrahydro-quinoline-6-carboxylic acid;
2-(4'-Isopropylcarbamoyl-biphenyl-3-yl)-3,3-dimethyl-1,2,3,4-tetrahydro-quinoline-6-carboxylic acid;
3'-(6-Methanesulfonylaminocarbonyl-3,3-dimethyl-1,2,3,4-tetrahydro-quinolin-2-yl)-biphenyl-4-carboxylic acid tert-butylamide;
Cyclopropanesulfonic acid [2-(4'-methanesulfonyl-biphenyl-3-yl)-3,3-dimethyl-1,2,3,4-tetrahydro-quinoline-6-carbonyl]-amide;
2-(4'-tert-Butylcarbamoyl-biphenyl-3-yl)-3,3-dimethyl-1,2,3,4-tetrahydro-quinoline-6-carboxylic acid;
2-[2-(1-Carboxy-1-methyl-ethylamino)-phenyl]-3,3-dimethyl-1,2,3,4-tetrahydro-quinoline-6-carboxylic acid;
2-[2-(1-Carboxy-cyclopropylamino)-phenyl]-3,3-dimethyl-1,2,3,4-tetrahydro-quinoline-6-carboxylic acid;
3,3-Dimethyl-2-(3-(1-methylethylsulfonamido)phenyl)-1,2,3,4-tetrahydroquinoline-6-carboxylic acid;

3,3-Dimethyl-2-(3-(1-methylethylsulfonamido)phenyl)-1,2,3,4-tetrahydroquinoline-6-carboxylic acid;
3,3-Dimethyl-2-(3-(tetrahydrofuran-3-ylcarbamoyl)phenyl)-1,2,3,4-tetrahydroquinoline-6-carboxylic acid;
3,3-Dimethyl-2-(4-(phenylsulfonamido)phenyl)-1,2,3,4-tetrahydroquinoline-6-carboxylic acid;
2-(3-(4-Acetamidophenylsulfonamido)phenyl)-3,3-dimethyl-1,2,3,4-tetrahydroquinoline-6-carboxylic acid;
2-(3-(Cyclopropylcarbamoyl)phenyl)-3,3-dimethyl-1,2,3,4-tetrahydroquinoline-6-carboxylic acid;
3,3-Dimethyl-2-(3-(pyrrolidine-1-carbonyl)phenyl)-1,2,3,4-tetrahydroquinoline-6-carboxylic acid;
2-(3-(Cyclobutylcarbamoyl)phenyl)-3,3-dimethyl-1,2,3,4-tetrahydroquinoline-6-carboxylic acid;
2-(3-(Isopropylcarbamoyl)phenyl)-3,3-dimethyl-1,2,3,4-tetrahydroquinoline-6-carboxylic acid;
2-(4-Fluoro-3-isobutyramidophenyl)-3,3-dimethyl-1,2,3,4-tetrahydroquinoline-6-carboxylic acid;
3,3-Dimethyl-2-(3-(phenylsulfonylcarbamoyl)phenyl)-1,2,3,4-tetrahydroquinoline-6-carboxylic acid;
2-(3-Cyclopropylsulfonylcarbamoyl)-phenyl)-3,3-dimethyl-1,2,3,4-tetrahydroquinoline-6-carboxylic acid;
2-(4-Chloro-3-isobutyramidophenyl)-3,3-dimethyl-1,2,3,4-tetrahydroquinoline-6-carboxylic acid;
2-(4-Isobutyramidophenyl)-3,3-dimethyl-1,2,3,4-tetrahydroquinoline-6-carboxylic acid;
3,3-Dimethyl-2-(3-(methylsulfonylcarbamoyl)-phenyl)-1,2,3,4-tetrahydroquinoline-6-carboxylic acid;
2-(4-Fluoro-3-(picolinamido)-phenyl)-3,3-dimethyl-1,2,3,4-tetrahydroquinoline-6-carboxylic acid;
2-(4-(4-Fluorophenylsulfonamido)phenyl)-3,3-dimethyl-1,2,3,4-tetrahydroquinoline-6-carboxylic acid;
2-(4-(4-Fluorobenzamido)phenyl)-3,3-dimethyl-1,2,3,4-tetrahydroquinoline-6-carboxylic acid;
3,3-Dimethyl-2-(4-(4-methylphenylsulfonamido)phenyl)-1,2,3,4-tetrahydroquinoline-6-carboxylic acid;
2-(3-Benzamido-4-fluorophenyl)-3,3-dimethyl-1,2,3,4-tetrahydroquinoline-6-carboxylic acid;
2-(4-Benzamidophenyl)-3,3-dimethyl-1,2,3,4-tetrahydroquinoline-6-carboxylic acid;
3,3-Dimethyl-2-(4-(picolinamido)phenyl)-1,2,3,4-tetrahydroquinoline-6-carboxylic acid;
3,3-Dimethyl-2-(3-(methylcarbamoyl)phenyl)-1,2,3,4-tetrahydroquinoline-6-carboxylic acid;
2-(3-(Cyclopropanecarboxamido)phenyl)-3,3-dimethyl-1,2,3,4-tetrahydroquinoline-6-carboxylic acid;
2-(3-(Cyclopropanecarboxamido)-4-fluorophenyl)-3,3-dimethyl-1,2,3,4-tetrahydroquinoline-6-carboxylic acid;
2-(3-(2-Chloro-4-fluorobenzamido)-4-fluorophenyl)-3,3-dimethyl-1,2,3,4-tetrahydroquinoline-6-carboxylic acid;
3,3-Dimethyl-2-(3-(piperidine-1-carbonyl)phenyl)-1,2,3,4-tetrahydroquinoline-6-carboxylic acid;
2-(3-(2-Methoxyethylcarbamoyl)phenyl)-3,3-dimethyl-1,2,3,4-tetrahydroquinoline-6-carboxylic acid;
3,3-Dimethyl-2-(4-(2-phenylacetamido)phenyl)-1,2,3,4-tetrahydroquinoline-6-carboxylic acid;
2-(3-(Cyclobutanecarboxamido)-4-fluorophenyl)-3,3-dimethyl-1,2,3,4-tetrahydroquinoline-6-carboxylic acid;
2-(4-Chloro-3-(cyclohexanecarboxamido)phenyl)-3,3-dimethyl-1,2,3,4-tetrahydroquinoline-6-carboxylic acid;
2-(3-(Cyclopentanecarboxamido)-4-fluorophenyl)-3,3-dimethyl-1,2,3,4-tetrahydroquinoline-6-carboxylic acid;
Methyl 3,3-dimethyl-2-(3-(pyrazin-2-ylcarbamoyl)-phenyl)-1,2,3,4-tetrahydroquinoline-6-carboxylate;
2-(4-(Cyclohexanecarboxamido)phenyl)-3,3-dimethyl-1,2,3,4-tetrahydroquinoline-6-carboxylic acid;
3,3-Dimethyl-2-(3-(2-phenylacetamido)phenyl)-1,2,3,4-tetrahydroquinoline-6-carboxylic acid;
2-(3-Carbamoylphenyl)-3,3-dimethyl-1,2,3,4-tetrahydroquinoline-6-carboxylic acid;
3,3-Dimethyl-2-(3-(methylsulfonamido)phenyl)-1,2,3,4-tetrahydroquinoline-6-carboxylic acid;
2-(3-Benzamido-5-chlorophenyl)-3,3-dimethyl-1,2,3,4-tetrahydroquinoline-6-carboxylic acid;
2-(3-(2-(Dimethylamino) ethylcarbamoyl)phenyl)-3,3-dimethyl-1,2,3,4-tetrahydroquinoline-6-carboxylic acid;
2-(3-Acetamidophenyl)-3,3-dimethyl-1,2,3,4-tetrahydroquinoline-6-carboxylic acid;
2-(3-((1-Ethylpyrrolidin-2-yl)methylcarbamoyl)phenyl)-3,3-dimethyl-1,2,3,4-tetrahydroquinoline-6-carboxylic acid;
2-(4-Fluoro-3-(3-fluorophenylsulfonamido)phenyl)-3,3-dimethyl-1,2,3,4-tetrahydroquinoline-6-carboxylic acid;
2-(3-(1-(tert-Butoxycarbonyl) azetidin-3-ylcarbamoyl)phenyl)-3,3-dimethyl-1,2,3,4-tetrahydroquinoline-6-carboxylic acid;
3,3-Dimethyl-2-(3-(1-methylazetidin-3-ylcarbamoyl)phenyl)-1,2,3,4-tetrahydroquinoline-6-carboxylic acid;
2-(4-Fluoro-3-(2-fluorophenylsulfonamido)phenyl)-,3-dimethyl-1,2,3,4-tetrahydroquinoline-6-carboxylic acid;
3,3-Dimethyl-2-(3-(3-phenylpropanamido)phenyl)-1,2,3,4-tetrahydroquinoline-6-carboxylic acid;
2-(3-(Cyclohexanecarboxamido)-4-fluorophenyl)-3,3-dimethyl-1,2,3,4-tetrahydroquinoline-6-carboxylic acid;
2-(4-(3-Fluorophenylsulfonamido)phenyl)-3,3-dimethyl-1,2,3,4-tetrahydroquinoline-6-carb oxylic acid;
2-(4-(2-Fluorophenylsulfonamido)phenyl)-3,3-dimethyl-1,2,3,4-tetrahydroquinoline-6-carb oxylic acid;
2-(2-(Cyclopropanecarboxamido)phenyl)-3,3-dimethyl-1,2,3,4-tetrahydroquinoline-6-carboxylic acid;
2-(4-(Cyclobutanecarboxamido)phenyl)-3,3-dimethyl-1,2,3,4-tetrahydroquinoline-6-carboxylic acid;
2-(2-(Cyclobutanecarboxamido)phenyl)-3,3-dimethyl-1,2,3,4-tetrahydroquinoline-6-carboxylic acid;
2-(4-(Cyclohex-1-enecarboxamido)phenyl)-3,3-dimethyl-1,2,3,4-tetrahydroquinoline-6-carboxylic acid;
2-(2-(4-Fluorophenylsulfonamido)phenyl)-3,3-dimethyl-1,2,3,4-tetrahydroquinoline-6-carboxylic acid;
2-(2-(2-Fluorophenylsulfonamido)phenyl)-3,3-dimethyl-1,2,3,4-tetrahydroquinoline-6-carboxylic acid;
3,3-Dimethyl-2-(2-(phenylsulfonamido)phenyl)-1,2,3,4-tetrahydroquinoline-6-carboxylic acid;
2-(3-(N-isopropylsulfamoyl)phenyl)-3,3-dimethyl-1,2,3,4-tetrahydroquinoline-6-carboxylic acid;
2-(2-(3-Fluorophenylsulfonamido)phenyl)-3,3-dimethyl-1,2,3,4-tetrahydroquinoline-6-carboxylic acid;
3,3-Dimethyl-2-(2-(methylsulfonamido)phenyl)-1,2,3,4-tetrahydroquinoline-6-carboxylic acid;
3,3-Dimethyl-2-(3-(1-methylpyrrolidin-3-ylcarbamoyl)phenyl)-1,2,3,4-tetrahydroquinoline-8-carboxylic acid;
3-(6-Chloro-3,3-dimethyl-1,2,3,4-tetrahydroquinolin-2-yl)-N-(1-methylpyrrolidin-3-yl)benzamide;
3,3-Dimethyl-2-(4-(N-methylsulfamoyl)phenyl)-1,2,3,4-tetrahydroquinoline-6-carboxylic acid;
3,3-Dimethyl-2-(3-(pyrrolidin-1-ylsulfonyl)phenyl)-1,2,3,4-tetrahydroquinoline-6-carboxylic acid;
3,3-Dimethyl-2-(3-(N-methylsulfamoyl)phenyl)-1,2,3,4-tetrahydroquinoline-6-carboxylic acid;
3,3-Dimethyl-2-(3-(N-(1-methylpyrrolidin-3-yl)sulfamoyl)phenyl)-1,2,3,4-tetrahydroquinoline-6-carboxylic acid;
3,3-Dimethyl-2-(3-(N-phenylsulfamoyl)phenyl)-1,2,3,4-tetrahydroquinoline-6-carboxylic acid;

2-(3-(N,N-dimethylsulfamoyl)phenyl)-3,3-dimethyl-1,2,3,4-tetrahydroquinoline-6-carboxylic acid;
3,3-Dimethyl-2-(2-(picolinamido)phenyl)-1,2,3,4-tetrahydroquinoline-6-carboxylic acid; and
2-(3-(2-Carboxypropan-2-yloxy)phenyl)-3,3-dimethyl-1,2,3,4-tetrahydroquinoline-6-carboxylic acid.

Further particular compounds of formula (I) can be selected from the group consisting of:
2-[2-(1-Carboxy-1-methyl-ethylamino)-phenyl]-3,3-dimethyl-1,2,3,4-tetrahydro-quinoline-6-carboxylic acid;
2-[3-(1-carboxy-1-methyl-ethylamino)-phenyl]-3,3-dimethyl-1,2,3,4-tetrahydro-quinoline-6-carboxylic acid;
2-[3-(4-Acetyl-piperazin-1-yl)-phenyl]-6-chloro-3,3-dimethyl-1,2,3,4-tetrahydro-quinoline-8-carboxylic acid;
Cyclopropanesulfonic acid [2-(4'-isopropoxy-biphenyl-3-yl)-3,3-dimethyl-1,2,3,4-tetrahydro-quinoline-6-carbonyl]-amide;
2-[3-(1-Carboxy-cyclopropylamino)-phenyl]-3,3-dimethyl-1,2,3,4-tetrahydro-quinoline-6-carboxylic acid;
2-[3-(6-Methanesulfonyl-3,3-dimethyl-1,2,3,4-tetrahydro-quinolin-2-yl)-phenylamino]-2-methyl-propionic acid;
2-(2-(2-Fluorophenylsulfonamido)phenyl)-3,3-dimethyl-1,2,3,4-tetrahydroquinoline-6-carboxylic acid;
2-(2-(4-Fluorophenylsulfonamido)phenyl)-3,3-dimethyl-1,2,3,4-tetrahydroquinoline-6-carboxylic acid;
2-[3-(6-Methanesulfonylaminocarbonyl-3,3-dimethyl-1,2,3,4-tetrahydro-quinolin-2-yl)-phenylamino]-2-methyl-propionic acid;
2-[3-(3,3-Dimethyl-6-trifluoromethyl-1,2,3,4-tetrahydro-quinolin-2-yl)-phenylamino]-2-methyl-propionic acid;
N-[2-(4'-tert-Butyl-5-fluoro-biphenyl-3-yl)-3,3-dimethyl-1,2,3,4-tetrahydro-quinoline-6-carbonyl]-methanesulfonamide;
2-[3-(6-Chloro-3,3-dimethyl-1,2,3,4-tetrahydro-quinolin-2-yl)-phenylamino]-2-methyl-propionic acid;
2-[3-(6-Cyano-3,3-dimethyl-1,2,3,4-tetrahydro-quinolin-2-yl)-phenylamino]-2-methyl-propionic acid;
2-(2-(3-Fluorophenylsulfonamido)phenyl)-3,3-dimethyl-1,2,3,4-tetrahydroquinoline-6-carboxylic acid;
3,3-Dimethyl-2-(2-(methylsulfonamido)phenyl)-1,2,3,4-tetrahydroquinoline-6-carboxylic acid;
3,3-Dimethyl-2-(2-(phenylsulfonamido)phenyl)-1,2,3,4-tetrahydroquinoline-6-carboxylic acid;
2-[3-(1-Carboxy-1-methyl-ethylamino)-phenyl]-6-chloro-3,3-dimethyl-1,2,3,4-tetrahydro-quinoline-8-carboxylic acid methyl ester;
2-[2-(1-Carboxy-cyclopropylamino)-phenyl]-3,3-dimethyl-1,2,3,4-tetrahydro-quinoline-6-carboxylic acid;
2-[3-(1-Carboxy-1-methyl-ethylamino)-phenyl]-6-chloro-3,3-dimethyl-1,2,3,4-tetrahydro-quinoline-8-carboxylic acid;
Cyclopropanesulfonic acid [6-fluoro-3,3-dimethyl-2-(3-morpholin-4-yl-phenyl)-1,2,3,4-tetrahydro-quinoline-5-carbonyl]-amide;
2-(4'-tert-Butyl-biphenyl-3-yl)-6-fluoro-3,3-dimethyl-1,2,3,4-tetrahydro-quinoline-5-carboxylic acid;
Cyclopropanesulfonic acid [2-(4'-tert-butyl-biphenyl-3-yl)-6-fluoro-3,3-dimethyl-1,2,3,4-tetrahydro-quinoline-5-carbonyl]-amide;
3-(6-Chloro-3,3-dimethyl-1,2,3,4-tetrahydroquinolin-2-yl)-N-(1-methylpyrrolidin-3-yl)benzamide;
N-[6-Fluoro-3,3-dimethyl-2-(3-morpholin-4-yl-phenyl)-1,2,3,4-tetrahydro-quinoline-5-carbonyl]-methanesulfonamide;
N-[2-(3-Fluoro-5-pyrrolidin-1-yl-phenyl)-3,3-dimethyl-1,2,3,4-tetrahydro-quinoline-6-carbonyl]-methanesulfonamide;
N-[2-(3-Dimethylamino-5-fluoro-phenyl)-3,3-dimethyl-1,2,3,4-tetrahydro-quinoline-6-carbonyl]-methanesulfonamide;
Cyclopropanesulfonic acid [2-(3-fluoro-5-pyrrolidin-1-yl-phenyl)-3,3-dimethyl-1,2,3,4-tetrahydro-quinoline-6-carbonyl]-amide;
3,3-Dimethyl-2-[3-(3-methyl-2-oxo-imidazolidin-1-yl)-phenyl]-1,2,3,4-tetrahydro-quinoline-6-carboxylic acid;
2-(3-Carbamoylphenyl)-3,3-dimethyl-1,2,3,4-tetrahydroquinoline-6-carboxylic acid;
6-Chloro-3,3-dimethyl-2-(3-morpholin-4-yl-phenyl)-1,2,3,4-tetrahydro-quinoline-5-carboxylic acid;
3,3-Dimethyl-2-(3-methyl-5-morpholin-4-yl-phenyl)-1,2,3,4-tetrahydro-quinoline-6-carboxylic acid;
2-(4'-tert-Butyl-biphenyl-3-yl)-6-chloro-3,3-dimethyl-1,2,3,4-tetrahydro-quinoline-8-carboxylic acid;
2-(4-Fluoro-3-isobutyramidophenyl)-3,3-dimethyl-1,2,3,4-tetrahydroquinoline-6-carboxylic acid;
3,3-Dimethyl-2-(3-(1-methylethylsulfonamido)phenyl)-1,2,3,4-tetrahydroquinoline-6-carboxylic acid;
2-(3-(2-(Dimethylamino)ethylcarbamoyl)phenyl)-3,3-dimethyl-1,2,3,4-tetrahydroquinoline-6-carboxylic acid;
6-Chloro-3,3-dimethyl-2-[3-(4-o-tolyl-piperazin-1-yl)-phenyl]-1,2,3,4-tetrahydro-quinoline-8-carboxylic acid;
2-[3-((S)-4-Isopropyl-2-oxo-oxazolidin-3-yl)-phenyl]-3,3-dimethyl-1,2,3,4-tetrahydro-quinoline-6-carboxylic acid;
3,3-Dimethyl-2-{3-[methyl-(2-methylamino-ethyl)-amino]-phenyl}-1,2,3,4-tetrahydro-quinoline-6-carboxylic acid;
3,3-Dimethyl-2-(3-(phenylsulfonylcarbamoyl)phenyl)-1,2,3,4-tetrahydroquinoline-6-carboxylic acid; and
N-{3,3-Dimethyl-2-[3-(4-methyl-piperazin-1-yl)-phenyl]-1,2,3,4-tetrahydro-quinoline-6-carbonyl}-methanesulfonamide.

The compounds of the present invention can be prepared by any conventional means. Suitable processes for synthesizing these compounds are provided in the examples. Generally, compounds of formula (I) can be prepared according to the schemes illustrated below. $R^6$ to $R^{33}$ are defined respectively in the schemes, and R is methyl or ethyl. Unless otherwise specified in the following schemes, substituted phenyl in schemes 1 to 23 is phenyl substituted with one or two substituents independently selected from the group consisting of: halogen, halophenyl, alkyl, cycloalkyl, alkoxy, cyano, carboxyl, cycloalkylcarbonylamino, alkylsulfonylamino, phenylsulfonylamino, phenylaminosulfonyl, halophenylsulfonylamino, phenyl, alkylphenyl, alkoxyphenyl, cyanophenyl, alkylaminocarbonylphenyl, alkylsulfonylphenyl, pyrrolidinyl, pyridinylcarbonylamino, morpholinyl, alkylmorpholinyl, piperazinyl, alkylpiperazinyl, alkylcarbonylpiperazinyl, alkylphenylpiperazinyl, halophenylpiperazinyl, oxopyrrolidinyl, dioxoimidazolidinyl, oxoimidazolidinyl, alkyloxoimidazolidinyl, phenyloxoimidazolidinyl, 2-oxo-oxazolidin-3-yl, alkyl-2-oxo-oxazolidin-3-yl, phenylalkyl-2-oxo-oxazolidin-3-yl, dioxopiperazinyl, alkyldioxopiperazinyl, aminocarbonyl, alkylaminocarbonyl, alkoxyalkylaminocarbonyl, alkylaminoalkylaminocarbonyl, cycloalkylaminocarbonyl, alkylpyrrolidinylaminocarbonyl, tetrahydrofuranylaminocarbonyl, alkylpyrrolidinylalkylaminocarbonyl, alkoxycarbonylazetidinylaminocarbonyl, pyrrolidinylcarbonyl, piperidinylcarbonyl, alkylsulfonylaminocarbonyl, cycloaklylsulfonylaminocarbonyl, phenylsulfonylaminocarbonyl, alkylazetidinylaminocarbonyl, haloazetidinyl, alkylpyrrolidinylaminocarbonyl, phenylaminocarbonyl, pyrazinylaminocarbonyl, aminoalkoxyalkyl, aminoalkoxy, carboxylalkoxy, carboxylalkoxyalkyl, alkyltetrazolyl, phenylalkyltetrazolyl, alkylaminosulfonyl, alkylphenylsulfonylamino, alkylcarbonylamino, cycloalkenylcarbonylamino, phenylcarbonylamino, phenylalkylcarbonylamino, alkylaminoalkylamino, 7-benzyl-4-oxo-5,6,7,8-tetrahydro-4H-pyrido[3,4-d]pyrimidin-3-yl, alkylaminophenyl, alkylamino, hydroxyalkylamino, carboxylalkylamino, carboxylcycloalkylamino, alkylaminocarbonylalkylamino, aminocarbonyl(alkyl)amino, morpholinylcarbonylalkylamino and alkylpiperazinylcarbonylalkylamino, alkylaminosulfonylamino, alkylcarbonylaminophenylsulfonylamino, alkylaminocarbonylamino, aminocarbonylamino, morpholinylcarbonylamino, pyrrolidinylcarbonylamino, piperidinylcarbonylamino, alkylpiperazinylcarbonylamino, phenylalkylaminocarbonylamino, halophenylcarbonylamino, halophenylaminocarbonylamino, pyrazinylcarbonylamino, alkylpiperazinyl, pyrrolidinylsulfonyl and alkylpyrrolidinylaminosulfonyl.

The following abbreviations are used in the present specification.

ABBREVIATIONS

APCI: atmospheric pressure chemical ionization
d: day or days
DMF: dimethylformamide
DMSO: dimethylsulfoxide
eq. equivalent
g: gram
μg: microgram
h or hr: hour
hrs: hours
HATU: o-(7-azabenzotriazol-1-yl)-N,N,N',N'-tetramethyluronium hexafluorophosphate
HPLC: high performance liquid chromatography
mg: milligram
min: minute or minutes
mL: milliliter
mmol: millimole
mM: millimole per liter
MS (ESI): mass spectroscopy (electron spray ionization)
MW: molecular weight
NMP: N-methylmorpholine
r.t. or R.T.: room temperature
quant.: quantitative
μL: microliter
μM: micro mole per liter Scheme 1

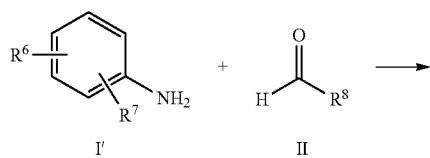

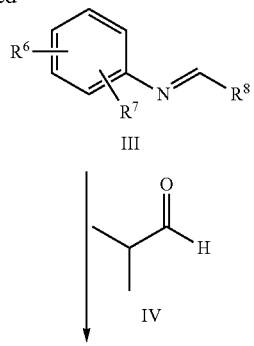

$R^6$ and $R^7$ are independently selected from hydrogen, halogen, trifluoromethyl, alkylsulfonyl, cyano and alkoxycarbonyl; $R^8$ is pyridinyl, phenyl or substituted phenyl.

The compounds of formula Ia can be prepared according to Scheme 1. The aniline I' reacts with the aldehydes II to generate the imine III. The Aza-Diels-Alder reaction between imine III and isobutylaldehyde IV affords the 4-hydroxytetrahydroquinoline V. Removal of hydroxy group the tetrahydroquinoline V affords Ia.

In the method outlined in Scheme 1, the compounds of imine IV can be prepared by a condensation reaction of the substituted aniline I and the substituted aldehydes II in an organic solvent such as toluene, methanol or ethanol and a mixture thereof, at a temperature between 80 and 140° C. for 2 to 16 hours.

The Diels-Alder reaction between the imine III and the isobutylaldehyde IV can be carried out in the presence of a Lewis acid such as ytterbium(III) trifluoromethanesulfonate (Yb(OTf)$_3$), scandium(III) trifluoromethanesulfonate (Sc(OTf)$_3$), lanthanum(III) trifluoromethanesulfonate (La(OTf)$_3$), indium(III) trifluoromethanesulfonate (In(OTf)$_3$), indium trichloride (InCl$_3$) or boron trifluoride diethyl etherate (BF$_3$.Et$_2$O), or a protic acid such as trifluoroacetic acid (TFA) or p-toluenesulfonic acid, in a solvent such as acetonitrile, dichloromethane, tetrahydrofuran, nitromethane, N,N-dimethylformamide, 2,2,2-trifluoroethanol or a mixture thereof, at a temperature between 25 and 100° C. for several hours (reference: Kiselyov, A. S. et al., *Tetrahedron* 54 (1998) 5089).

The reduction of hydroxyl group in compound V can be carried out in the presence of triethylsilane in trifluoroacetic acid at room temperature for several hours to afford the resulting compound Ia.

Scheme 2

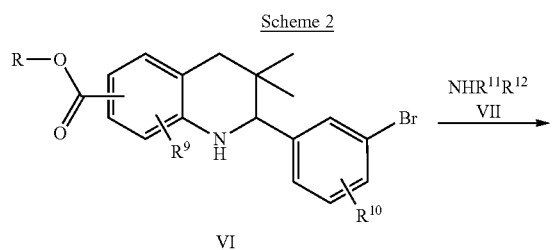

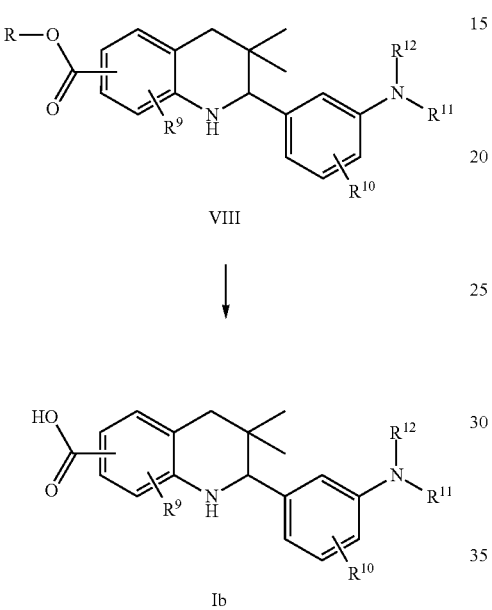

Scheme 3

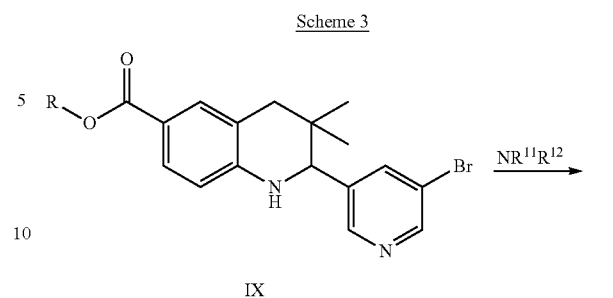

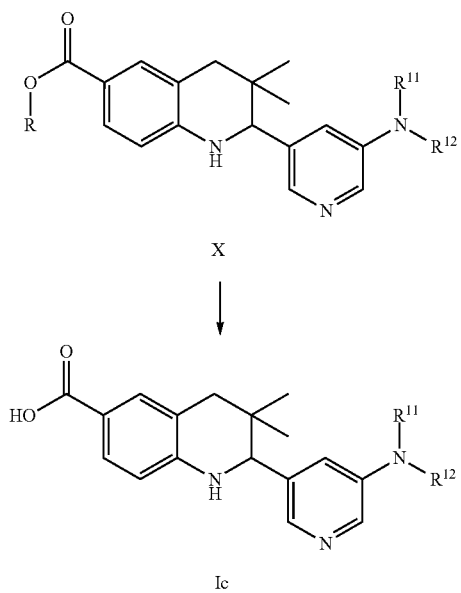

$R^9$ is hydrogen or halogen; $R^{10}$ is hydrogen, halogen, cyano, methyl, alkoxy; $R^{11}$ and $R^{12}$ are alkyl; or $R^{11}$ and $R^{12}$, together with the nitrogen atom to which they are attached, form heterocyclyl.

The compounds of formula Ib can be prepared according to Scheme 2. In this process, the compounds of formula VI can be synthesized as illustrated in Scheme 1. Copper-catalyzed Ullmann coupling reaction followed by hydrolysis of the ester produces the compounds Ib.

The Ullmann coupling reaction as outlined in the Scheme 2 can be carried out in the presence of a copper source such as copper(I) iodide (CuI) or copper(II) trifluoromethanesulfonate and a ligand such as 2,2'-bipyridine, proline, N,N'-dimethyl glycine or ethylene glycol, in the presence of a suitable base such as triethylamine, sodium carbonate, potassium carbonate, cesium carbonate, sodium methoxide, sodium tert-butoxide, potassium tert-butoxide. The reaction can be carried out in a suitable solvent such as 1,4-dioxane, N,N-dimethylformamide, dimethyl sulfoxide or N-methylpyrrolidinone at a temperature between 100 and 130° C. for 10 to 16 hours (reference: Ley, S. V. et al., *Angew. Chem. Int. Ed.* 42 (2003) 5400).

Hydrolysis of the esters VIII to the resulting products Ib can be carried out in the presence of an aqueous inorganic base such as lithium hydroxide, sodium hydroxide or potassium hydroxide in a solvent such as methanol, 1,4-dioxane or tetrahydrofuran at room temperature or refluxed for several hours.

$R^{11}$ and $R^{12}$ are alkyl; or $R^{11}$ and $R^{12}$, together with the nitrogen atom to which they are attached, form a cyclic amine or amide.

The compounds of formula Ic can be prepared according to Scheme 3. In this process, the compounds of formula IX can be synthesized as illustrated in Scheme 1, copper-catalyzed Ullmann coupling reaction followed by hydrolysis of the ester produces the compounds Ic.

The Ullmann coupling reaction as outlined in the Scheme 3 can be carried out in the presence of a copper source such as copper(I) iodide (CuI) or copper(II) trifluoromethanesulfonate and a ligand such as 2,2'-bipyridine, proline, N,N'-dimethyl glycine or ethylene glycol, in the presence of a suitable base such as triethylamine, sodium carbonate, potassium carbonate, cesium carbonate, sodium methoxide, sodium tert-butoxide, potassium tert-butoxide. The reaction can be carried out in a suitable solvent such as 1,4-dioxane, N,N-dimethylformamide, dimethyl sulfoxide or N-methylpyrrolidinone at a temperature between 100 and 130° C. for 10 to 16 hours (reference: Ley, S. V. et al., *Angew. Chem. Int. Ed.* 42 (2003) 5400).

Hydrolysis of the esters X to the resulting products Ic can be carried out in the presence of an aqueous inorganic base such as lithium hydroxide, sodium hydroxide or potassium hydroxide in a solvent such as methanol, 1,4-dioxane or tetrahydrofuran at room temperature or refluxed for several hours.

Scheme 4

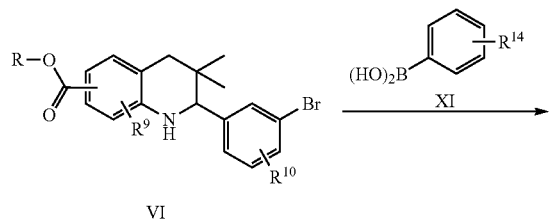

VI

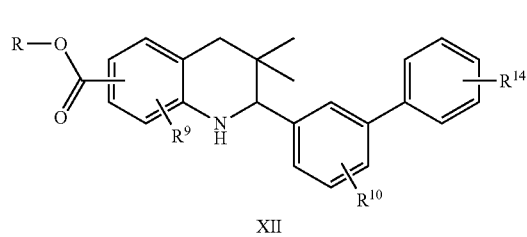

XII

↓

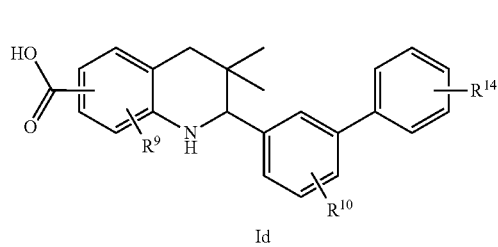

Id $R^9$ is hydrogen or halogen; $R^{10}$ is hydrogen, halogen, cyano, methyl or alkoxy; $R^{14}$ is halogen, alkyl, alkoxy, cyano, alkylsulfonyl, alkylamino or aminocarbonyl.

The compounds of formula Id can be prepared according to Scheme 4. In this process, the compounds of formula VI can be synthesized as illustrated in Scheme 1. Suzuki coupling using a palladium as the catalyst followed by hydrolysis of ester affords the resulting compound Id.

Suzuki coupling reactions can be easily done in the presence of a palladium catalyst such as [1,1'-bis(diphenylphosphino)ferrocene]dichloropalladium(II) (PdCl$_2$(dppf)) or tetrakis(triphenylphosphine)palladium(0), and a base such as potassium tert-butoxide, sodium carbonate, cesium carbonate or sodium hydroxide, in an inert solvent such as N,N-dimethylformamide or dimethyl sulfoxide, at a temperature between 100 and 180° C. for 15 to 30 minutes under microwave irradiation (Lee S. et al., *Bioorg. Med. Chem. Lett.* 15 (2005) 2998). Alternatively, the reactions can be carried out without the use of a microwave at a heated temperature such as 130° C. for a longer reaction time.

Hydrolysis of the esters XII to the resulting products Id can be carried out in the presence of an aqueous inorganic base such as lithium hydroxide, sodium hydroxide or potassium hydroxide in a solvent such as methanol, 1,4-dioxane, tetrahydrofuran or a mixture thereof at room temperature or refluxed for several hours.

Scheme 5

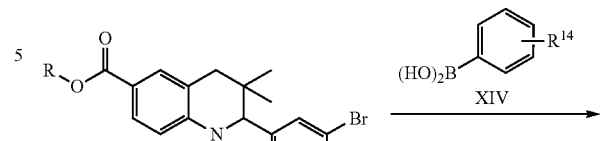

XIII

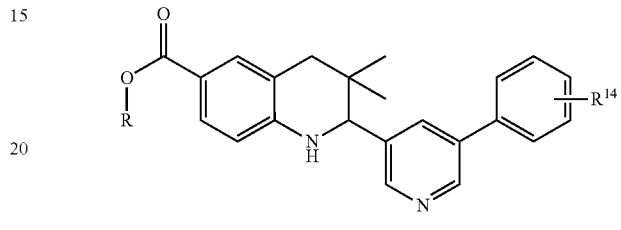

XV

↓

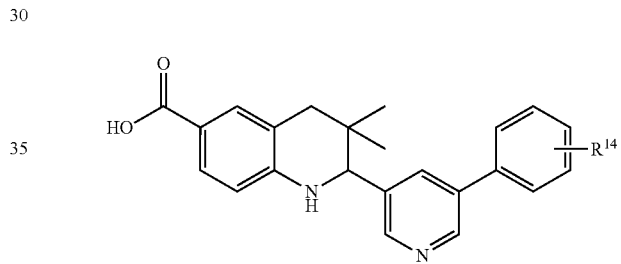

Ie $R^{14}$ is halogen, alkyl, alkoxy, cyano, alkylsulfonyl, alkylamino or aminocarbonyl.

The compounds of formula Ie can be prepared according to Scheme 5. In this process, the compounds of formula XIII can be synthesized as illustrated in Scheme 1. Suzuki coupling using palladium as the catalyst followed by hydrolysis of ester affords the resulting compound Ie.

Suzuki coupling reactions can be easily done in the presence of a palladium catalyst such as [1,1'-bis(diphenylphosphino)ferrocene]dichloropalladium(II) (PdCl$_2$(dppf)) or tetrakis(triphenylphosphine)palladium(0), and a base such as potassium tert-butoxide, sodium carbonate, cesium carbonate or sodium hydroxide, in an inert solvent such as N,N-dimethylformamide or dimethyl sulfoxide, at a temperature between 100 and 180° C. for 15 to 30 minutes under microwave irradiation (Lee S. et al., *Bioorg. Med. Chem. Lett.* 15 (2005) 2998). Alternatively, the reactions can be carried out without the use of a microwave at a heated temperature such as 130° C. for a longer reaction time.

Hydrolysis of the esters XV to the resulting products Ie can be carried out in the presence of an aqueous inorganic base such as lithium hydroxide, sodium hydroxide or potassium hydroxide in a solvent such as methanol, 1,4-dioxane, tetrahydrofuran or a mixture thereof at room temperature or refluxed for several hours.

Scheme 6

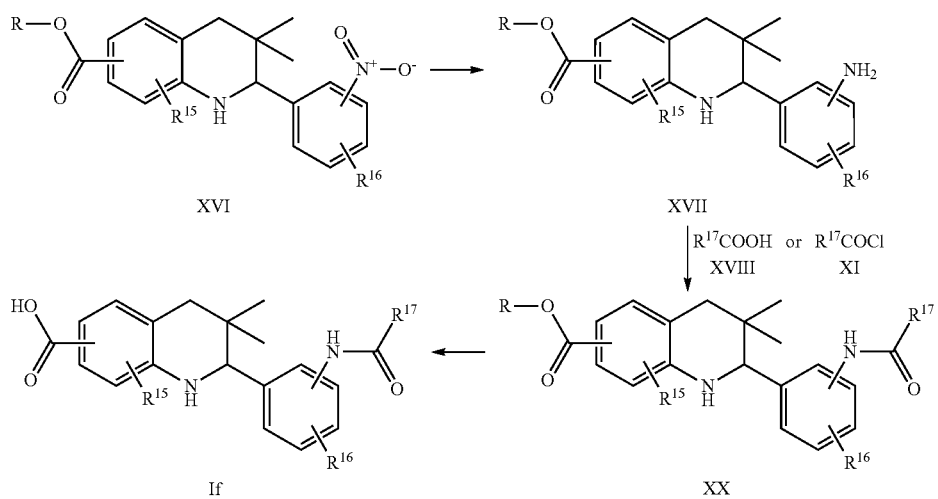

$R^{15}$ is hydrogen or halogen; $R^{16}$ is hydrogen or halogen; $R^{17}$ is alkyl, phenyl, halophenyl or pyridinyl.

The compounds of formula If can be prepared according to Scheme 6. In this process, the compounds of formula XVI can be synthesized as illustrated in Scheme 1. Reduction of nitro group to amine, amide formation in the presence of coupling reagent followed by hydrolysis of ester affords the resulting compound If.

Reduction of the nitro compounds XVI to the corresponding amine derivatives XVII can be accomplished using methods well known to someone skilled in the art. The reaction is typically carried out under acidic conditions by using hydrochloric acid or ammonium chloride in a mixture of ethanol and water at reflux for several hours.

Conversion of the amine XVII to the corresponding amides XIX with suitable carboxylic acid XVIII or carbonyl chloride XIX can be easily accomplished using methods well known to someone skilled in the art. The reaction is typically carried out in the presence of a coupling reagent such as dicyclohexyl carbodiimide (DCC), benzotriazol-1-yl-oxy-tris-pyrrolidinophosphonium hexafluorophosphate (PyBop), o-(7-azabenzotriazol-1-yl)-N,N,N',N'-tetramethyluronium hexafluorophosphate (HATU), o-(1H-benzotriazol-1-yl)-N,N,N',N'-tetramethyluronium hexafluorophosphate (HBTU) or 1-ethyl-3-(3'-dimethylamino)carbodiimide hydrochloride salt (EDCI), in the presence or absence of hydroxybenzotriazole (HOBt), in the presence of a base such as triethylamine or N,N-diisopropyl ethylamine or N,N-dimethylaminopyridine (DMAP). The reaction can be carried out in a solvent such as dichloromethane or N,N-dimethylformamide at room temperature for several hours (reference: Montalbetti, C. A. G. N. et al., *Tetrahedron* 61 (2005) 10827).

Hydrolysis of the esters XX to the resulting products If can be carried out in the presence of an aqueous inorganic base such as lithium hydroxide, sodium hydroxide or potassium hydroxide in a solvent such as methanol, 1,4-dioxane, tetrahydrofuran or a mixture thereof at room temperature or refluxed for several hours.

Scheme 7

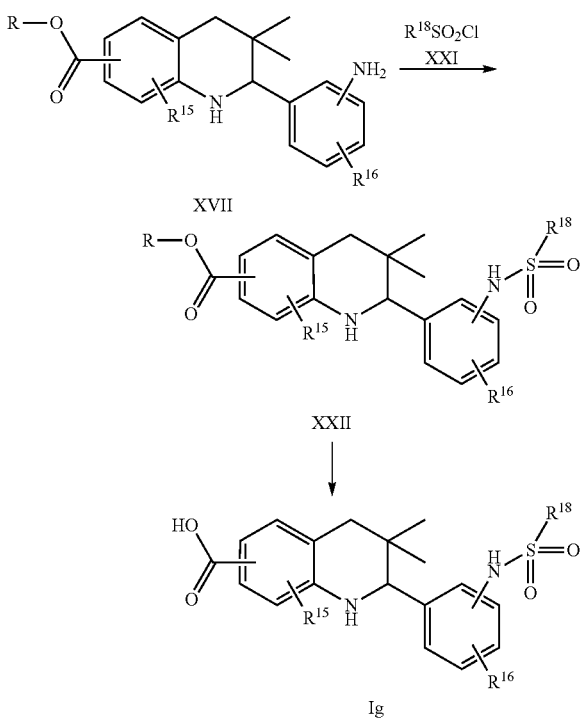

$R^{15}$ is hydrogen or halogen; $R^{16}$ is hydrogen or halogen; $R^{18}$ is alkyl, phenyl or halophenyl.

The compound of formula Ig can be synthesized as illustrated in Scheme 7. Sulfonamide formation followed by hydrolysis of ester affords resulting compound Ig.

The compounds XXII can be easily accomplished using methods well known to someone skilled in the art. The reaction is typically carried out in the presence of a base such as triethylamine, pyridine, sodium methoxide, sodium tert-butoxide, potassium tert-butoxide, sodium hydride or dimethylpyridin-4-yl-amine in a suitable inert solvent such as dichloromethane, acetonitrile, 1,4-dioxane, tetrahydrofuran or a mixture thereof, at room temperature for several hours.

Hydrolysis of the esters XXII to the resulting products Ig can be carried out in the presence of an aqueous inorganic base such as lithium hydroxide, sodium hydroxide or potassium hydroxide in a solvent such as methanol, 1,4-dioxane, tetrahydrofuran or a mixture thereof at room temperature or refluxed for several hours.

romethane or N,N-dimethylformamide at room temperature for several hours (reference: Montalbetti, C. A. G. N. et al., Tetrahedron 61 (2005) 10827).

Hydrolysis of the esters XXVI to the resulting products Ih can be carried out in the presence of an aqueous inorganic base such as lithium hydroxide, sodium hydroxide or potassium hydroxide in a solvent such as methanol, 1,4-dioxane, tetrahydrofuran or a mixture thereof at room temperature or refluxed for several hours.

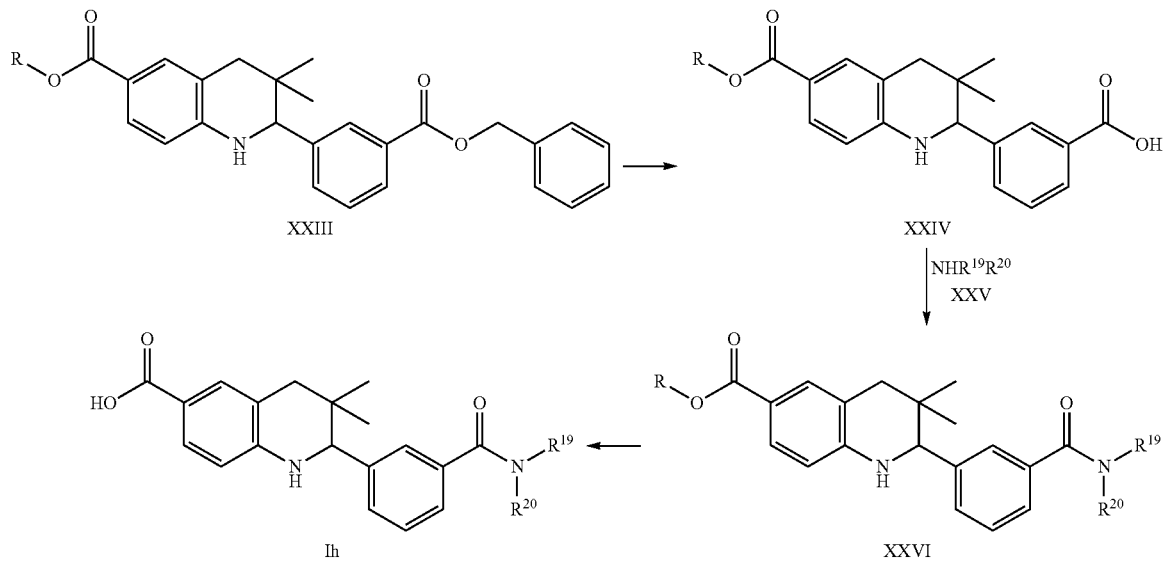

Scheme 8

$R^{19}$ and $R^{20}$ are independently selected from hydrogen, alkyl, aminoalkyl, phenyl halophenyl, pyridinyl and pyrazinyl, provided that $R^{19}$ and $R^{20}$ are not hydrogen simultaneously.

The compounds of formulas Ih can be prepared according to Scheme 8. In this process, the compounds of formula XXIII can be synthesized as illustrated in Scheme 1. Removal of benzyl group, amide formation in the presence of coupling reagent followed by hydrolysis of ester affords the resulting compound Ih.

Removal of the benzyl group in compounds XXIII can be accomplished using methods well known to someone skilled in the art. The reaction is typically carried out in the presence of palladium catalyst under acidic conditions by using acetic acid, hydrochloric acid or ammonium chloride in a suitable solvent such as methanol, ethanol, tetrahydrofuran, water or a mixture thereof, at a temperature between room temperature and reflux temperature of the solvent used for several hours.

Conversion of the carboxylic acid XXIV to the corresponding amides XXV with suitable amines XXVI can be easily accomplished using methods well known to someone skilled in the art. The reaction is typically carried out in the presence of a coupling reagent such as dicyclohexyl carbodiimide (DCC), benzotriazol-1-yl-oxy-tris-pyrrolidinophosphonium hexafluorophosphate (PyBop), o-(7-azabenzotriazol-1-yl)-N,N,N',N'-tetramethyluronium hexafluorophosphate (HATU), o-(1H-benzotriazol-1-yl)-N,N,N',N'-tetramethyluronium hexafluorophosphate (HBTU) or 1-ethyl-3-(3'-dimethylamino)carbodiimide hydrochloride salt (EDCI), in the presence or absence of hydroxybenzotriazole (HOBt), in the presence of a base such as triethylamine or N,N-diisopropyl ethylamine or N,N-dimethylaminopyridine (DMAP). The reaction can be carried out in a solvent such as dichloromethane Scheme 9

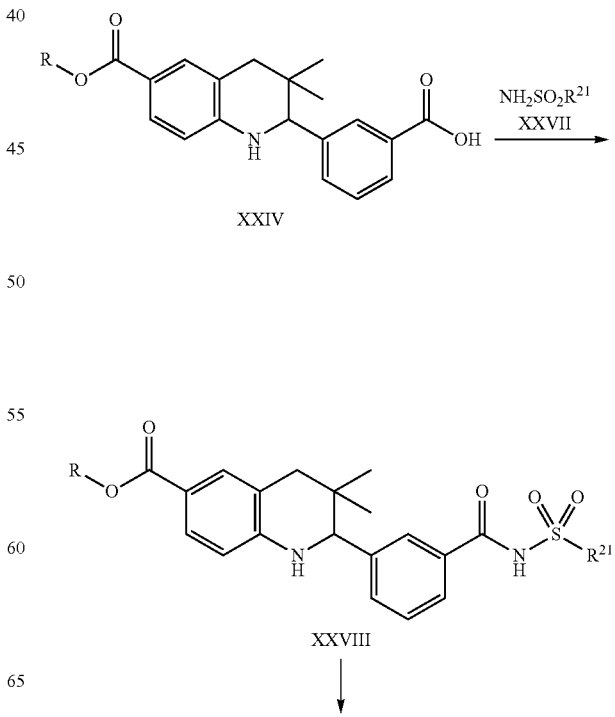

-continued

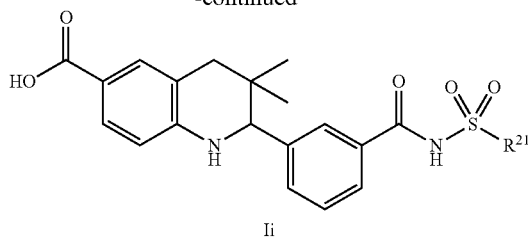

Ii $R^{21}$ is alkyl or phenyl.

The compound of formula II can be synthesized as illustrated in Scheme 9, starting from the compound XXIV. Acetylsulfonamide formation followed by hydrolysis of ester affords the resulting compound II.

The compounds XXVIII can be synthesized by treating acetyl imidazole generated from carboxylic acid XXIV and 1,1'-carbonyldiimidazole with sodium salt generated from sulfonamides and sodium in N,N-dimethylformamide at room temperature for several hours.

Hydrolysis of the esters XXVIII to the resulting products Ii can be carried out in the presence of an aqueous inorganic base such as lithium hydroxide, sodium hydroxide or potassium hydroxide in a solvent such as methanol, 1,4-dioxane, tetrahydrofuran or a mixture thereof at room temperature or refluxed for several hours.

Scheme 10

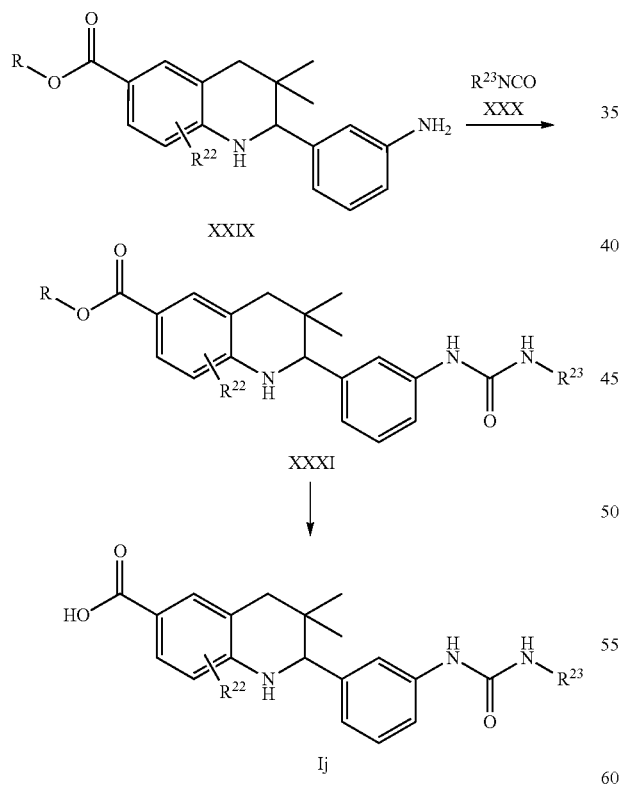

$R^{22}$ is hydrogen or halogen; $R^{23}$ is phenyl.

The compounds of formula Ij can be prepared according to Scheme 10. In this process, the compounds of formula XXVI can be synthesized as illustrated in Scheme 6. Reaction of amine XXIX with isocyanide XXX followed by hydrolysis of ester affords the compounds Ij.

Conversion of amine XXIX to urea XXXI can be carried out in the presence of triethyl amine in tetrahydrofuran at room temperature for several hours.

Hydrolysis of the esters XXXI to the resulting products Ij can be carried out in the presence of an aqueous inorganic base such as lithium hydroxide, sodium hydroxide or potassium hydroxide in a solvent such as methanol, 1,4-dioxane, tetrahydrofuran or a mixture thereof at room temperature or refluxed for several hours.

Scheme 11

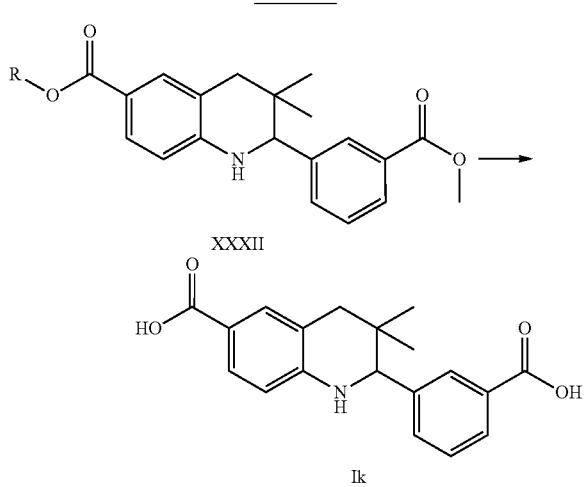

The compounds of formula Ik can be prepared according to Scheme 11. In this process, the compounds of formula XXXII can be synthesized as illustrated in Scheme 1. Hydrolysis of ester affords the compounds Ik.

Hydrolysis of the esters XXXII to the resulting products Ik can be carried out in the presence of an aqueous inorganic base such as lithium hydroxide, sodium hydroxide or potassium hydroxide in a solvent such as methanol, 1,4-dioxane, tetrahydrofuran or a mixture thereof at room temperature or refluxed for several hours.

Scheme 12

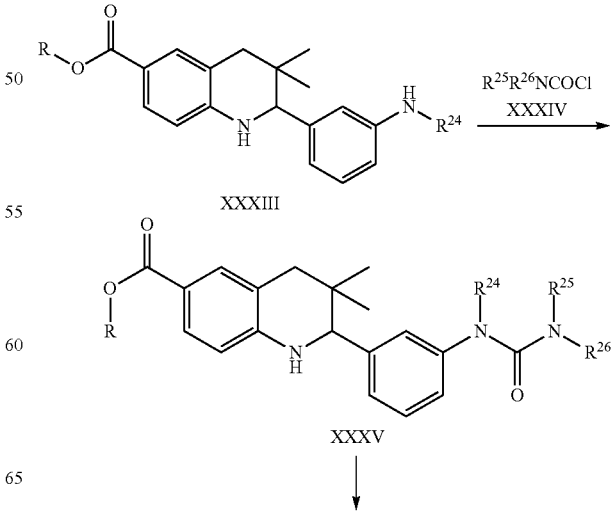

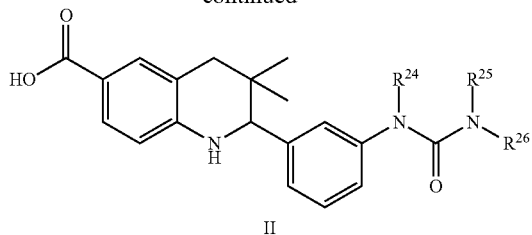

II $R^{24}$ is alkyl; $R^{25}$ and $R^{26}$ are alkyl; or $R^{25}$ and $R^{26}$, together with the nitrogen atom to which they are attached, form heterocycloalkyl.

The compounds of formula Il can be prepared according to Scheme 12. In this process, the compounds of formula XXXIII can be synthesized as illustrated in Scheme 2. Urea formation followed by hydrolysis of ester affords the compounds Il.

Ureas XXXV can be easily synthesized by treating amine XXXIII with carbonyl chloride XXXIV in the presence of pyridine in dichloromethane at room temperature for several hours.

Hydrolysis of the esters XXXV to the resulting products Il can be carried out in the presence of an aqueous inorganic base such as lithium hydroxide, sodium hydroxide or potassium hydroxide in a solvent such as methanol, 1,4-dioxane, tetrahydrofuran or a mixture thereof at room temperature or refluxed for several hours.

The compounds of formula Im can be prepared according to Scheme 13. In this process, the compounds of formula XXXVI can be synthesized as illustrated in Scheme 2. Amide formation followed by hydrolysis of ester affords the compounds Im.

Conversion of the carboxylic acid XXXVI to the corresponding amides XXXVIII with suitable amino esters XXXVII can be easily accomplished using methods well known to someone skilled in the art. The reaction is typically carried out in the presence of a coupling reagent such as dicyclohexyl carbodiimide (DCC), benzotriazol-1-yl-oxy-tris-pyrrolidinophosphonium hexafluorophosphate (PyBop), o-(7-azabenzotriazol-1-yl)-N,N,N',N'-tetramethyluronium hexafluorophosphate (HATU), o-(1H-benzotriazol-1-yl)-N,N,N',N'-tetramethyluronium hexafluorophosphate (HBTU) or 1-ethyl-3-(3'-dimethylamino)carbodiimide hydrochloride salt (EDCI), in the presence or absence of hydroxybenzotriazole (HOBt), in the presence of a base such as triethylamine or N,N-diisopropyl ethylamine or N,N-dimethylaminopyridine (DMAP). The reaction can be carried out in a solvent such as dichloromethane or N,N-dimethylformamide at room temperature for several hours (reference: Montalbetti, C. A. G. N. et al., *Tetrahedron* 61 (2005) 10827).

Hydrolysis of the esters XXXVIII to the resulting products Im can be carried out in the presence of an aqueous inorganic base such as lithium hydroxide, sodium hydroxide or potassium hydroxide in a solvent such as methanol, 1,4-dioxane, tetrahydrofuran or a mixture thereof at room temperature or refluxed for several hours.

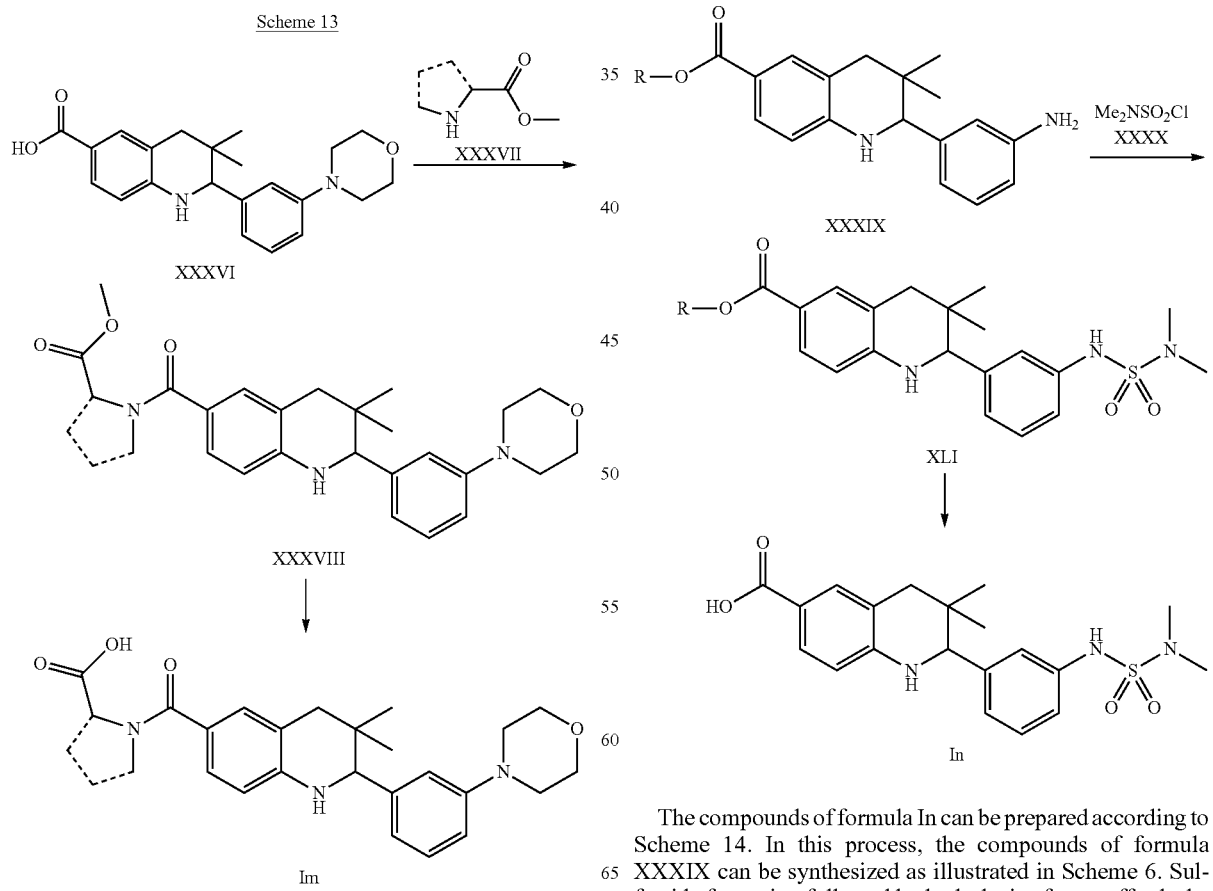

Scheme 13

Scheme 14

The compounds of formula In can be prepared according to Scheme 14. In this process, the compounds of formula XXXIX can be synthesized as illustrated in Scheme 6. Sulfamide formation followed by hydrolysis of ester affords the compounds In.

Sulfamide XLI can be easily synthesized by treating amine XXXIX with dimethylsulfamoyl chloride XL in the presence of pyridine in dichloromethane at room temperature for several hours.

Hydrolysis of the esters XLI to the resulting products In can be carried out in the presence of an aqueous inorganic base such as lithium hydroxide, sodium hydroxide or potassium hydroxide in a solvent such as methanol, 1,4-dioxane, tetrahydrofuran or a mixture thereof at room temperature or refluxed for several hours copper(II) trifluoromethanesulfonate and a ligand such as 2,2'-bipyridine, proline, N,N'-dimethyl glycine or ethylene glycol, in the presence of a suitable base such as triethylamine, sodium carbonate, potassium carbonate, cesium carbonate, sodium methoxide, sodium tert-butoxide, potassium tert-butoxide. The reaction can be carried out in a suitable solvent such as 1,4-dioxane, N,N-dimethylformamide, dimethyl sulfoxide or N-methylpyrrolidinone at a temperature between 100 and 130° C. for 10 to 16 hours (reference: Ley, S. V. et al., *Angew. Chem. Int. Ed.* 42 (2003) 5400).

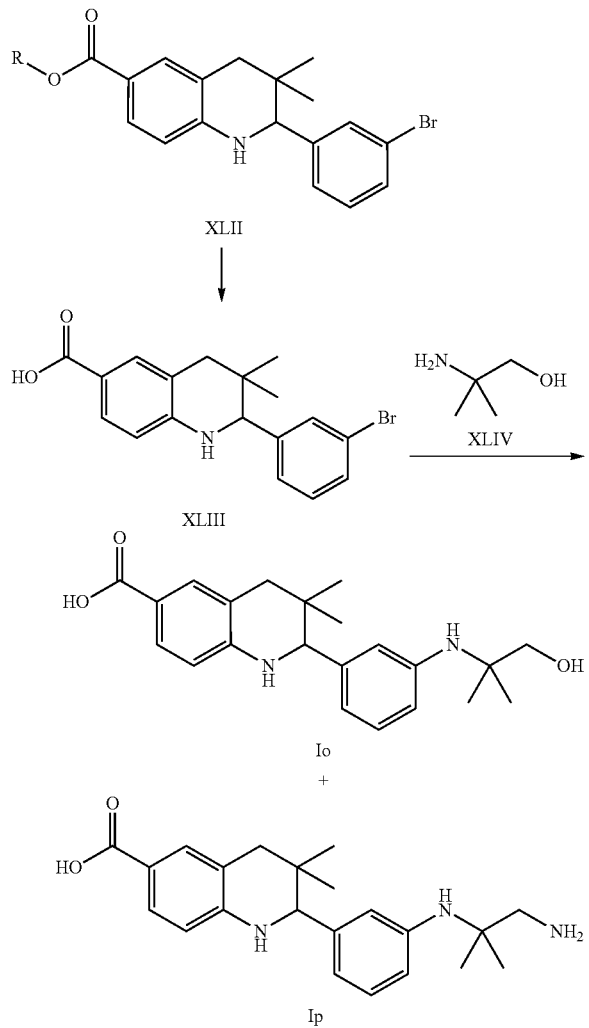

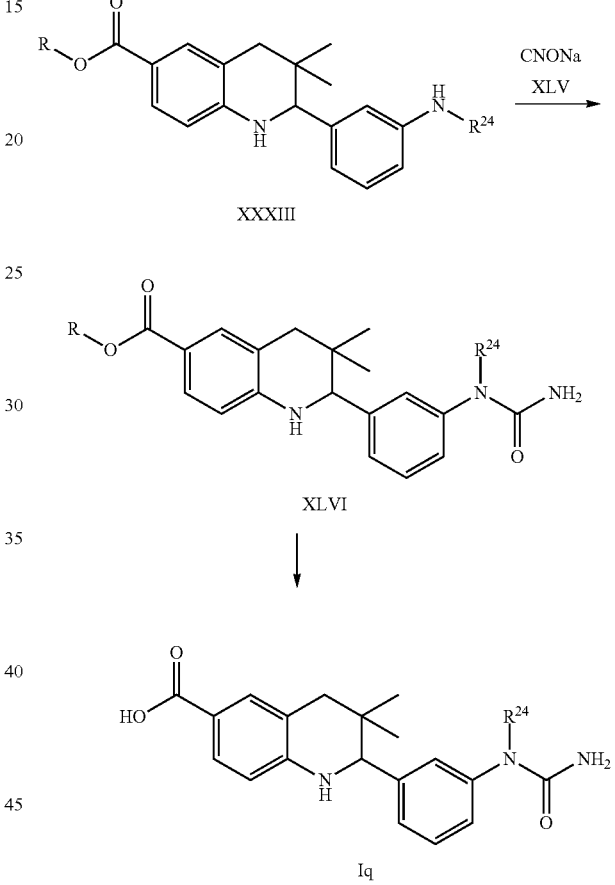

$R^{24}$ is alkyl.

The compounds of formula Iq can be prepared according to Scheme 16. In this process, the compounds of formula XXXIII can be synthesized as illustrated in Scheme 2. Urea formation followed by hydrolysis of ester affords the compounds Iq.

Ureas XLVI can be easily synthesized by treating amine XXXIII with sodium cyanate XLV in the presence of acetic acid in water at a temperature between 30 and 50° C. for several hours.

Hydrolysis of the esters XLVI to the resulting products Iq can be carried out in the presence of an aqueous inorganic base such as lithium hydroxide, sodium hydroxide or potassium hydroxide in a solvent such as methanol, 1,4-dioxane, tetrahydrofuran or a mixture thereof at room temperature or refluxed for several hours The compounds of formula Io and Ip can be prepared according to Scheme 15. In this process, the compounds of formula XLII can be synthesized as illustrated in Scheme 1. Hydrolysis of ester followed by Ullmann coupling affords the compounds Io and Ip.

Hydrolysis of the esters XLII to the resulting products XLIII can be carried out in the presence of an aqueous inorganic base such as lithium hydroxide, sodium hydroxide or potassium hydroxide in a solvent such as methanol, 1,4-dioxane, tetrahydrofuran or a mixture thereof at room temperature or refluxed for several hours The Ullmann coupling reaction can be carried out in the presence of a copper source such as copper(I) iodide (CuI) or Scheme 17

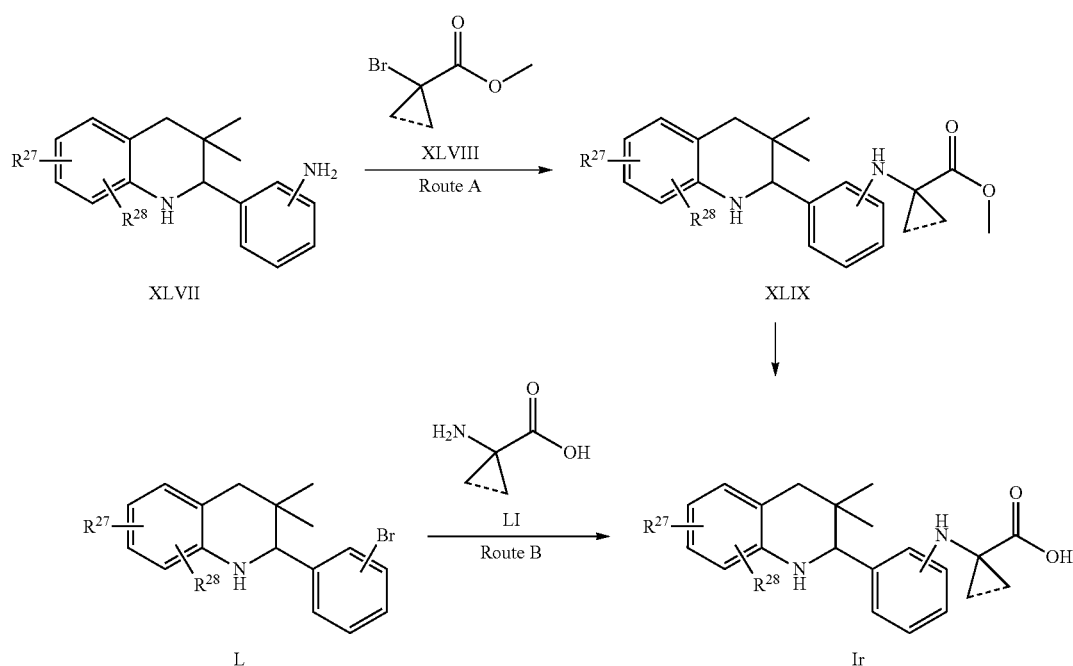

$R^{27}$ and $R^{28}$ are independently selected from halogen, cyano, trifluoromethyl, alkylsulfonyl and alkoxycarbonyl.

The compounds of formula Ir can be prepared according to Scheme 16. Alkylation of compound XLVII followed by hydrolysis of ester affords resulting compound Ir (Route A). Ir can also be synthesized by directly coupling L and amino acids LI. Compounds of formula XLVII can be synthesized as illustrated in Scheme 6. Compounds of formula L can be synthesized as illustrated in Scheme 1.

Alkylation of formula XLVII can be easily accomplished using methods well known to someone skilled in the art. The reaction is typically carried out in the presence of a base such as triethylamine, pyridine, sodium methoxide, sodium tert-butoxide, potassium tert-butoxide, sodium hydride or dimethyl-pyridin-4-yl-amine in a suitable inert solvent such as dichloromethane, acetonitrile, 1,4-dioxane, tetrahydrofuran or a mixture thereof, at room temperature for several hours.

The Ullmann coupling reaction can be carried out in the presence of a copper source such as copper(I) iodide (CuI) or copper(II) trifluoromethanesulfonate and a ligand such as 2,2'-bipyridine, proline, N,N'-dimethyl glycine or ethylene glycol, in the presence of a suitable base such as triethylamine, sodium carbonate, potassium carbonate, cesium carbonate, sodium methoxide, sodium tert-butoxide, potassium tert-butoxide. The reaction can be carried out in a suitable solvent such as 1,4-dioxane, N,N-dimethylformamide, dimethyl sulfoxide or N-methylpyrrolidinone at a temperature between 100 and 130° C. for 10 to 16 hours (reference: Ley, S. V. et al., *Angew. Chem. Int. Ed.* 42 (2003) 5400).

Hydrolysis of the esters XLIX to the resulting products Ir can be carried out in the presence of an aqueous inorganic base such as lithium hydroxide, sodium hydroxide or potassium hydroxide in a solvent such as methanol, 1,4-dioxane, tetrahydrofuran or a mixture thereof at room temperature or refluxed for several hours Scheme 18

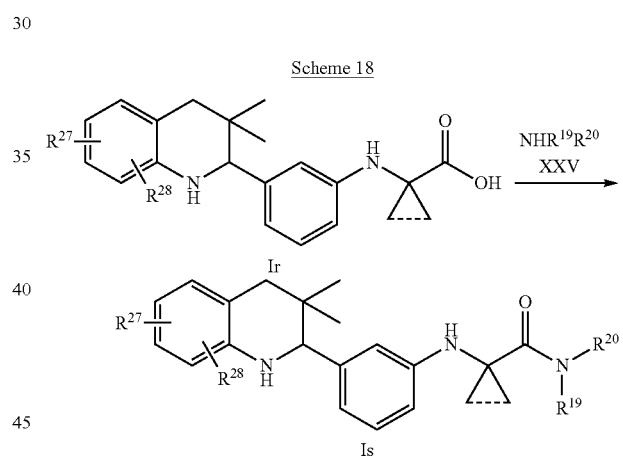

$R^{27}$ and $R^{28}$ are independently selected from halogen, cyano, trifluoromethyl, alkylsulfonyl and alkoxycarbonyl; $R^{19}$ and $R^{20}$ are independently selected from hydrogen, alkyl, aminoalkyl, phenyl, halophenyl, pyridinyl and pyrazinyl, provided that V and $R^{20}$ are not hydrogen simultaneously.

The compounds of formula Is can be prepared by amide formation according to Scheme 18. In this process, the compounds of formula Ir can be synthesized as illustrated in Scheme 17.

Conversion of the carboxylic acid Ir to the corresponding amides Is with suitable amines XXV can be easily accomplished using methods well known to someone skilled in the art. The reaction is typically carried out in the presence of a coupling reagent such as dicyclohexyl carbodiimide (DCC), benzotriazol-1-yl-oxy-tris-pyrrolidinophosphonium hexafluorophosphate (PyBop), o-(7-azabenzotriazol-1-yl)-N,N,N',N'-tetramethyluronium hexafluorophosphate (HATU), o-(1H-benzotriazol-1-yl)-N,N,N',N'-tetramethyluronium hexafluorophosphate (HBTU) or 1-ethyl-3-(3'-dimethylamino)carbodiimide hydrochloride salt (EDCI), in the presence or absence of hydroxybenzotriazole (HOBt), in the presence of a base such as triethylamine or N,N-diisopropyl ethylamine or N,N-dimethylaminopyridine (DMAP). The reaction can be carried out in a solvent such as dichloromethane or N,N-dimethylformamide at room temperature for several hours (reference: Montalbetti, C. A. G. N. et al., *Tetrahedron* 61 (2005) 10827).

Scheme 19

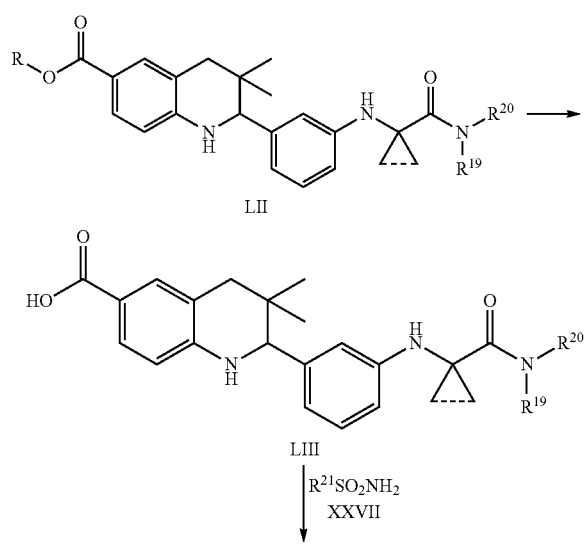

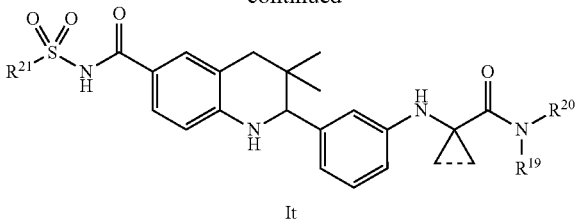

$R^{19}$ and $R^{20}$ are independently selected from hydrogen, alkyl, aminoalkyl, phenyl, halophenyl, pyridinyl and pyrazinyl, provided that $R^{19}$ and $R^{20}$ are not hydrogen simultaneously; $R^{21}$ is alkyl or phenyl.

The compound of formula It can be synthesized as illustrated in Scheme 19. Compounds of formula LII can be synthesized according to Scheme 18. Hydrolysis of ester in compounds LII followed by acetylsulfonamide formation affords the resulting compound It.

Hydrolysis of the esters LII to the resulting products LIII can be carried out in the presence of an aqueous inorganic base such as lithium hydroxide, sodium hydroxide or potassium hydroxide in a solvent such as methanol, 1,4-dioxane, tetrahydrofuran or a mixture thereof at room temperature or refluxed for several hours.

Conversion of carboxylic acids LIII to acetylsulfonamides It can be achieved by treating acetyl imidazoles generated from carboxylic acids LIII and 1,1'-carbonyldiimidazole with sodium salts generated from sulfonamides and sodium hydride in N,N-dimethylformamide at room temperature for several hours.

Scheme 20

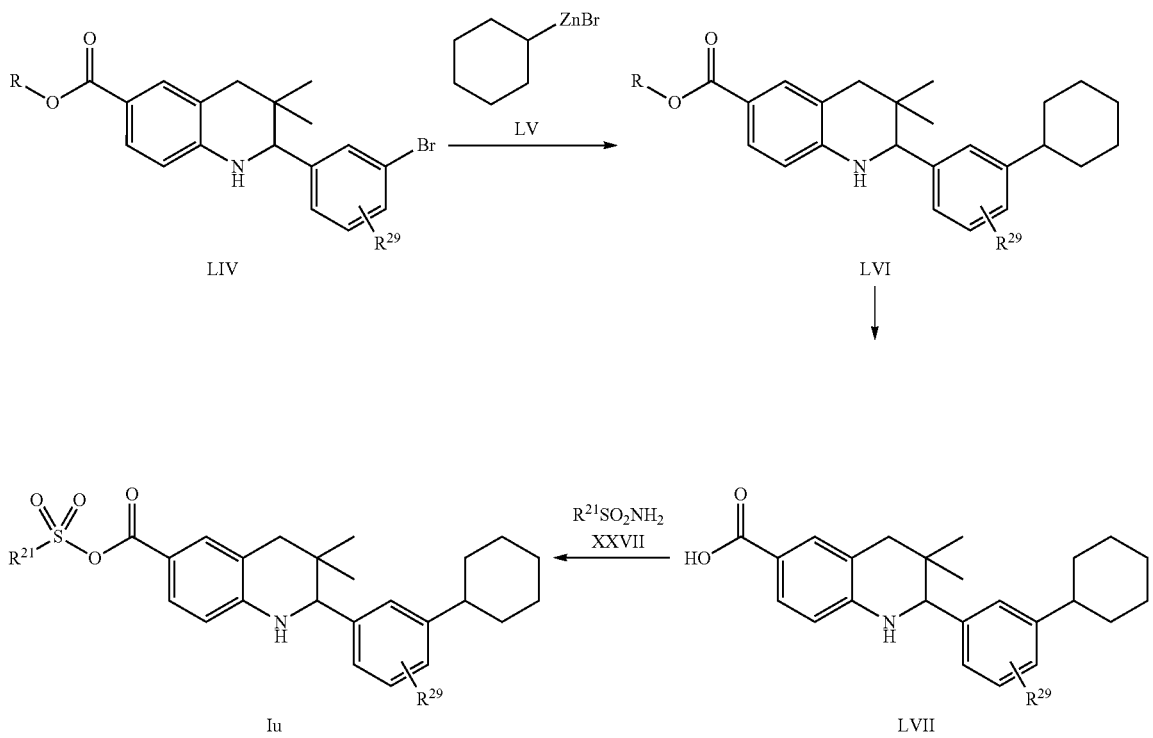

$R^{21}$ is alkyl or phenyl; $R^{29}$ is hydrogen or halogen.

The compound of formula Iu can be synthesized as illustrated in Scheme 20. Compounds of formula LIV can be synthesized according to Scheme 1. Negishi coupling, hydrolysis of ester followed by acetylsulfonamide formation affords the resulting compound Iu.

The Negishi coupling reaction can be carried out in the presence of palladium catalyst such as [1,1'-bis(diphenylphosphino)ferrocene]dichloropalladium(II) (PdCl$_2$(dppf)) or tetrakis(triphenylphosphine)palladium(0), in an inert solvent such as N,N-dimethylformamide or dioxane, at a temperature between 70 and 100° C. for 15 to 30 minutes under microwave irradiation.

Hydrolysis of the esters LVI to the resulting products LVII can be carried out in the presence of an aqueous inorganic base such as lithium hydroxide, sodium hydroxide or potassium hydroxide in a solvent such as methanol, 1,4-dioxane, tetrahydrofuran or a mixture thereof at room temperature or refluxed for several hours.

Conversion of carboxylic acids LVII to acetylsulfonamides Iu can be achieved by treating acetyl imidazoles generated from carboxylic acids LVII and 1,1'-carbonyldiimidazole with sodium salts generated from sulfonamides and sodium hydride in N,N-dimethylformamide at room temperature for several hours.

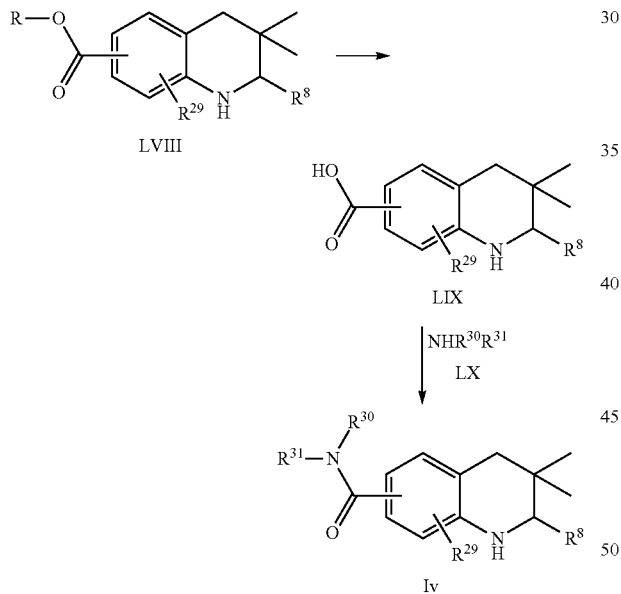

Scheme 21

$R^8$ is pyridinyl, phenyl or substituted phenyl; $R^{29}$ is hydrogen or halogen; $R^{30}$ and $R^{31}$ are independently alkyl; or $R^{30}$ and $R^{31}$, together with the nitrogen atom to which they are attached, form heterocyclyl.

The compound of formula Iv can be synthesized as illustrated in Scheme 21. Compounds of formula LVIII can be synthesized according to Scheme 1. Hydrolysis of esters followed by amide formation affords the resulting compound Iv.

Hydrolysis of the esters LVIII to the resulting products LIX can be carried out in the presence of an aqueous inorganic base such as lithium hydroxide, sodium hydroxide or potassium hydroxide in a solvent such as methanol, 1,4-dioxane, tetrahydrofuran or a mixture thereof at room temperature or refluxed for several hours.

Conversion of the carboxylic acid LIX to the corresponding amides Iv with suitable amines LX can be easily accomplished using methods well known to someone skilled in the art. The reaction is typically carried out in the presence of a coupling reagent such as dicyclohexyl carbodiimide (DCC), benzotriazol-1-yl-oxy-tris-pyrrolidinophosphonium hexafluorophosphate (PyBop), o-(7-azabenzotriazol-1-yl)-N,N,N',N'-tetramethyluronium hexafluorophosphate (HATU), o-(1H-benzotriazol-1-yl)-N,N,N',N'-tetramethyluronium hexafluorophosphate (HBTU) or 1-ethyl-3-(3'-dimethylamino)carbodiimide hydrochloride salt (EDCI), in the presence or absence of hydroxybenzotriazole (HOBt), in the presence of a base such as triethylamine or N,N-diisopropyl ethylamine or N,N-dimethylaminopyridine (DMAP). The reaction can be carried out in a solvent such as dichloromethane or N,N-dimethylformamide at room temperature for several hours (reference: Montalbetti, C. A. G. N. et al., *Tetrahedron* 61 (2005) 10827).

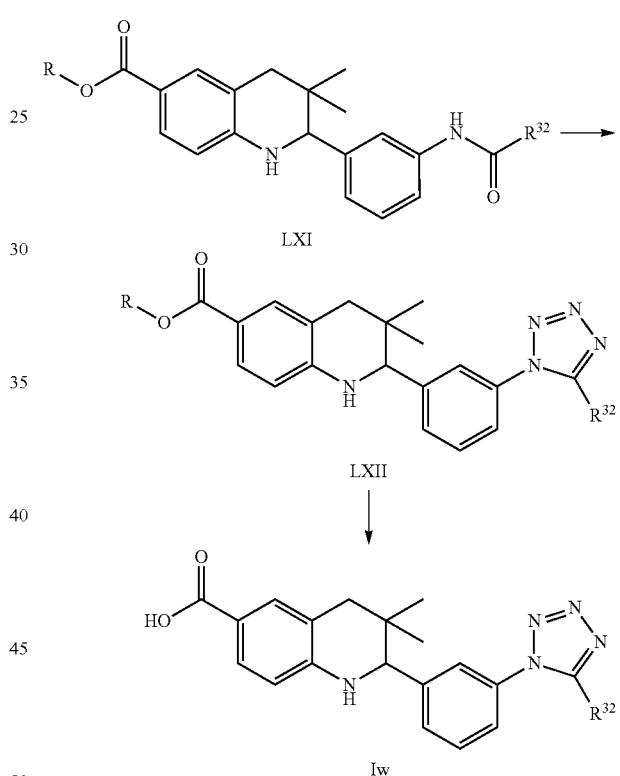

Scheme 22

$R^{32}$ is alkyl or phenylalkyl.

The compound of formula Iw can be synthesized as illustrated in Scheme 22. Compounds of formula LXI can be synthesized according to Scheme 6. Tetrazole formation followed by hydrolysis of esters affords the resulting compound Iw.

Conversion of reverse amides LXI to tetrazoles LXII can be achieved by treating reverse amides with sodium azide and tetrachlorosilane in acetonitrile at room temperature for several hours.

Hydrolysis of the esters LXII to the resulting products Iw can be carried out in the presence of an aqueous inorganic base such as lithium hydroxide, sodium hydroxide or potassium hydroxide in a solvent such as methanol, 1,4-dioxane, tetrahydrofuran or a mixture thereof at room temperature or refluxed for several hours.

Scheme 23

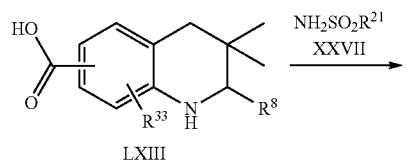

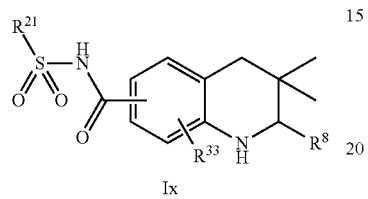

$R^8$ is pyridinyl, phenyl or substituted phenyl; $R^{21}$ is alkyl or phenyl; $R^{33}$ is hydrogen or halogen.

The compound of formula Ix can be synthesized by acetylsulfonamide formation as illustrated in Scheme 23. Compounds of formula LXIII can be synthesized according to Scheme 2, 3, 4, 5, 6, 8, 10, 12 and 22.

Conversion of carboxylic acids LXIII to acetylsulfonamides Ix can be achieved by treating acetyl imidazoles generated from carboxylic acids LXIII and 1,1'-carbonyldiimidazole with sodium salts generated from sulfonamides and sodium hydride in N,N-dimethylformamide at room temperature for several hours.

The invention also relates to a process for the preparation of a compound of formula (I) comprising one of the following steps:

a) the reaction of a compound of formula (A)

(A)

in the presence of triethylsilane and an acid;

b) the reaction of a compound of formula (B)

(B)

in the presence of a base;

c) the reaction of a compound of formula (C)

(C)

in the presence of a base;

d) the reaction of a compound of formula (D)

(D)

in the presence of a base;

e) the reaction of a compound of formula (E)

(E)

in the presence of a base;

f) the reaction of a compound of formula (F)

(F)

in the presence of a base;

g) the reaction of a compound of formula (G)

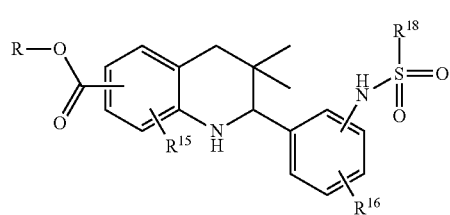

(G)

in the presence of a base;

h) the reaction of a compound of formula (H)

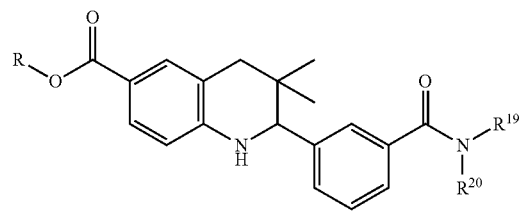

(H)

in the presence of a base;

i) the reaction of a compound of formula (IA)

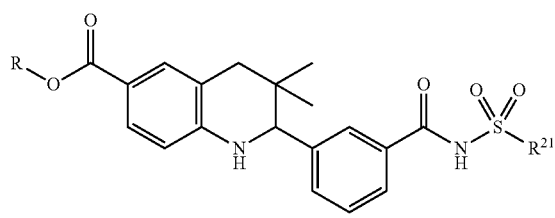

(IA)

in the presence of a base;

j) the reaction of a compound of formula (J)

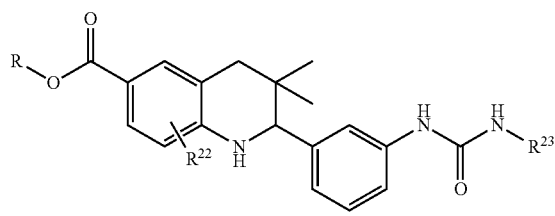

(J)

in the presence of a base;

k) the reaction of a compound of formula (K)

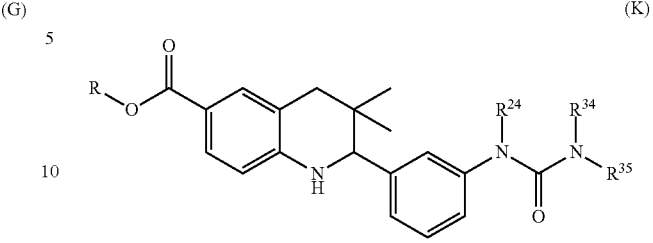

(K)

in the presence of a base;

l) the reaction of a compound of formula (L)

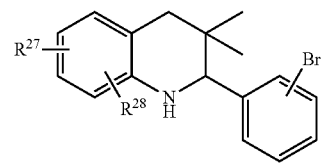

(L)

in the presence of a copper source, a ligand and a base;

m) the reaction of a compound of formula (M1) or (M2)

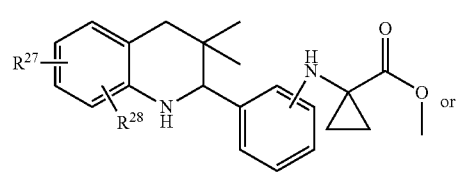

(M1)

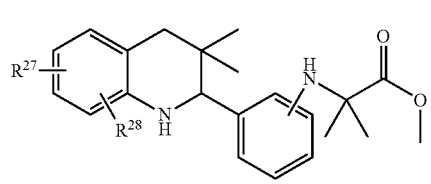

(M2)

in the presence of a base;

n) the reaction of a compound of formula (N1) or (N2)

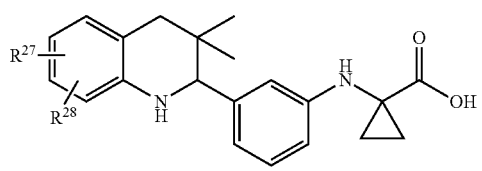

(N1)

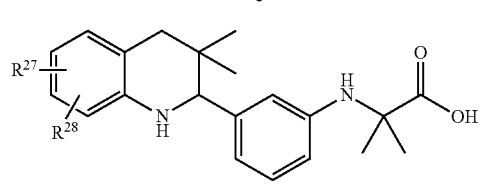

(N2)

in the presence of $NHR^{19}R^{20}$, a coupling reagent and a base;

o) the reaction of a compound of formula (O1) or (O2)

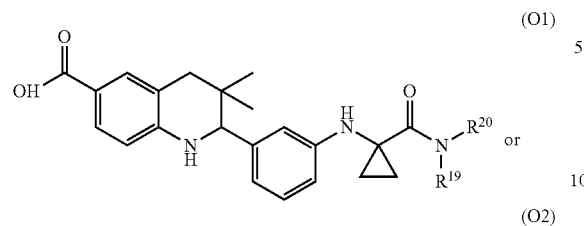
(O1)

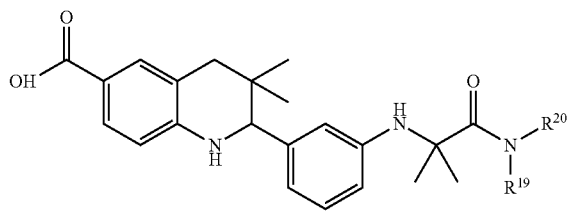
(O2)

with $R^{21}SO_2NH_2$ in the presence of 1,1'-carbonyldiimidazole and a base;

p) the reaction of a compound of formula (P)

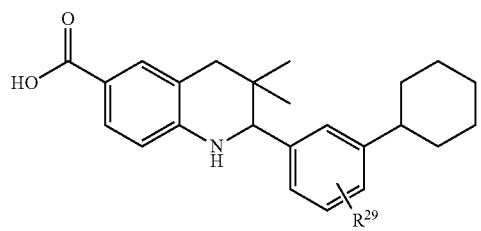
(P)

with $R^{21}SO_2NH_2$ in the presence of 1,1'-carbonyldiimidazole and a base;

q) the reaction of a compound of formula (Q)

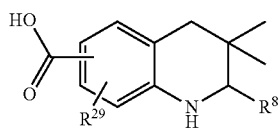
(Q)

with $NHR^{30}R^{31}$ in the presence of a coupling reagent and a base;

r) the reaction of a compound of formula (R)

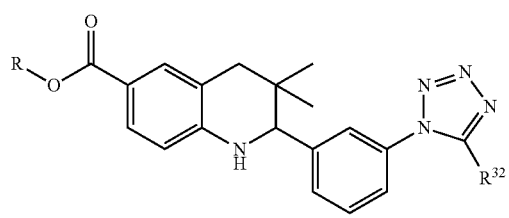
(R)

in the presence of a base;

s) the reaction of a compound of formula (S)

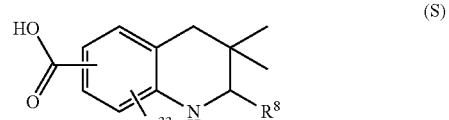
(S)

with $NH_2SO_2R^{21}$ in the presence of 1,1'-carbonyldiimidazole and a base;

t) the reaction of a compound of formula (T)

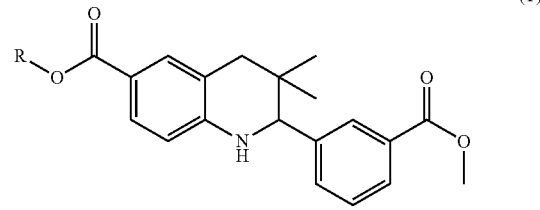
(T)

in the presence of a base;

u) the reaction of a compound of formula (U1) or (U2)

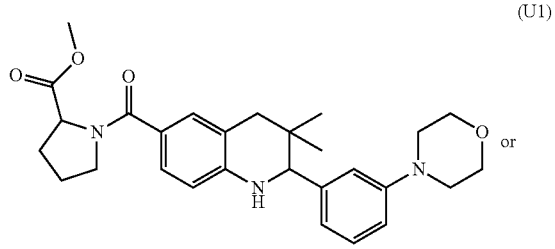
(U1)

(U2)

in the presence of a base;

v) the reaction of a compound of formula (V)

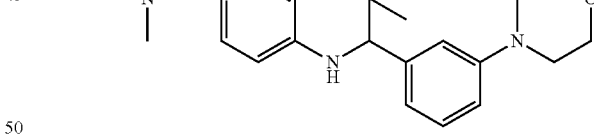
(V)

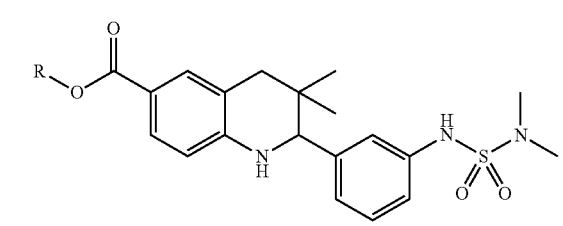

in the presence of a base; or w) the reaction of a compound of formula (W)

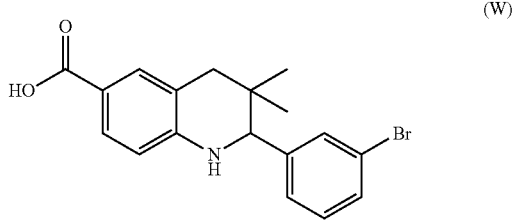 [SMILES: CC1(C)Cc2cc(C(=O)O)ccc2NC1c1cccc(Br)c1]

with H$_2$NC(CH$_3$)$_2$CH$_2$OH in the presence of copper source, a ligand and a base; wherein R$^6$ and R$^7$ are independently selected from hydrogen, halogen, trifluoromethyl, alkylsulfonyl, cyano and alkoxycarbonyl; R$^8$ is pyridinyl, phenyl or substituted phenyl; R$^9$, R$^{15}$, R$^{16}$, R$^{22}$, R$^{29}$ and R$^{33}$ are independently selected from hydrogen and halogen; R$^{10}$ is hydrogen, halogen, cyano, methyl or alkoxy; R$^{11}$ and R$^{12}$ are independently selected from alkyl or R$^{11}$ and R$^{12}$ together with the nitrogen atom to which they are attached form a cyclic amine or amide; R$^{14}$ is halogen, alkyl, alkoxy, cyano, alkylsulfonyl, alkylamino or aminocarbonyl; R$^{17}$ is alkyl, phenyl, phenyl substituted by halogen or pyridinyl; R$^{18}$ is alkyl, phenyl or phenyl substituted by halogen; R$^{19}$ and R$^{20}$ are independently selected from alkyl, aminoalkyl, phenyl halophenyl, pyridinyl and pyrazinyl; R$^{21}$ is alkyl or phenyl; R$^{23}$ is phenyl; R$^{24}$ is alkyl; R$^{27}$ and R$^{28}$ are independently selected from halogen, cyano, trifluoromethyl, alkylsulfonyl and alkoxycarbonyl; R$^{30}$ and R$^{31}$ are independently selected from alkyl or R$^{30}$ and R$^{31}$ together with the nitrogen atom to which they are attached form a cyclic amine; R$^{32}$ is alkyl or phenylalkyl; R$^{34}$ and R$^{35}$ are independently selected from hydrogen and alkyl; R$^{34}$ and R$^{35}$ together with the nitrogen atom to which they are attached form a cyclic amine; and R is methyl or ethyl.

In step (a), the acid can be for example trifluoroacetic acid.

In steps (b)-(k), (m), (r) and (t)-(v) the base can be for example independently selected form lithium hydroxide, sodium hydroxide or potassium hydroxide.

In step (l), the copper source can be for example copper(I) iodide (CuI) or copper(II) trifluoromethanesulfonate. The ligand can be for example 2, 2'-bipyridine, proline, N,N'-dimethyl glycine or ethylene glycol. The reaction can be carried out in solvent such as 1,4-dioxane, N,N-dimethylformamide, dimethyl sulfoxide or N-methylpyrrolidinone at a temperature between 100 and 130° C. for 10 to 16 hours. The base can be for example triethylamine, sodium carbonate, potassium carbonate, etc.

In step (n), the coupling reagent can be for example dicyclohexyl carbodiimide (DCC), benzotriazol-1-yl-oxy-trispyrrolidinophosphonium hexafluorophosphate (PyBop), o-(7-azabenzotriazol-1-yl)-N,N,N',N'-tetramethyluronium hexafluorophosphate (HATU), o-(1H-benzotriazol-1-yl)-N,N,N',N'-tetramethyluronium hexafluorophosphate (HBTU) or 1-ethyl-3-(3'-dimethylamino)carbodiimide hydrochloride salt (EDCI). The reaction can be carried out in a solvent such as dichloromethane or N,N-dimethylformamide at room temperature for several hours. The base can be for example triethylamine or N,N-diisopropyl ethylamine or N,N-dimethylaminopyridine (DMAP).

In step (o), (p), (s), the base can be for example sodium hydride.

In step (q), the coupling reagent can be for example dicyclohexyl carbodiimide (DCC), benzotriazol-1-yl-oxy-trispyrrolidinophosphonium hexafluorophosphate (PyBop), o-(7-azabenzotriazol-1-yl)-N,N,N',N'-tetramethyluronium hexafluorophosphate (HATU), o-(1H-benzotriazol-1-yl)-N,N,N',N'-tetramethyluronium hexafluorophosphate (HBTU) or 1-ethyl-3-(3'-dimethylamino)carbodiimide hydrochloride salt (EDCI). The reaction can be carried out in a solvent such as dichloromethane or N,N-dimethylformamide at room temperature for several hours. The base can be for example triethylamine or N,N-diisopropyl ethylamine or N,N-dimethylaminopyridine (DMAP).

In step (w), the copper source can be for example copper(I) iodide (CuI) or copper(II) trifluoromethanesulfonate. The ligand can be for example 2, 2'-bipyridine, proline, N,N'-dimethyl glycine or ethylene glycol. The reaction can be carried out in solvent such as 1,4-dioxane, N,N-dimethylformamide, dimethyl sulfoxide or N-methylpyrrolidinone at a temperature between 100 and 130° C. for 10 to 16 hours. The base can be for example triethylamine, sodium carbonate, potassium carbonate, etc.

The invention also relates to a compound of formula (I) for use as therapeutically active substance.

The invention also relates to a pharmaceutical composition comprising a compound of formula (I) and a therapeutically inert carrier.

The use of a compound of formula (I) for the preparation of medicaments useful in the treatment or prophylaxis diseases that are related to AMPK regulation is an object of the invention.

The invention relates in particular to the use of a compound of formula (I) for the preparation of a medicament for the treatment or prophylaxis of obesity, dyslipidemia, hyperglycemia, type 1 or type 2 diabetes, in particular type 2 diabetes.

Said medicaments, e.g. in the form of pharmaceutical preparations, can be administered orally, e.g. in the form of tablets, coated tablets, dragées, hard and soft gelatine capsules, solutions, emulsions or suspensions. The administration can, however, also be effected rectally, e.g. in the form of suppositories or parenterally, e.g. in the form of injection solutions with an effective amount of a compound as defined above.

The above-mentioned pharmaceutical composition can be obtained by processing the compounds according to this invention with pharmaceutically inert inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical composition can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage depends on various factors such as manner of administration, species, age and/or individual state of health. The doses to be administered daily are about 5-400 mg/kg, preferably about 10-100 mg/kg, and can be taken singly or distributed over several administrations.

A compound of formula (I) when manufactured according to the above process is also an object of the invention.

Furthermore, the invention also relates to a method for the treatment or prophylaxis of diseases that are related to AMPK regulation, which method comprises administering an effective amount of a compound of formula (I).

The invention further relates to a method for the treatment or prophylaxis of obesity, dyslipidemia, hyperglycemia, type 1 or type 2 diabetes, in particular type 2 diabetes, which method comprises administering an effective amount of a compound of formula (I).

Furthermore, the invention also relates to a compound of formula (I) for the preparation of medicaments useful in the treatment of cancers that are related to AMPK regulation and provides a method for the treatment of cancers that are related to AMPK regulation. The invention will be illustrated by the following examples which have no limiting character. Unless explicitly otherwise stated, all reactions, reaction conditions, abbreviations and symbols have the meanings well known to a person of ordinary skill in organic chemistry.

EXAMPLES

Materials and Instrumentation

Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 µM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp C18 (5 µm, OBD™ 30×100 mm) column or SunFire™ Perp C18 (5 µm, OBD™ 30×100 mm) column.

LC/MS spectra were obtained using a MicroMass Plateform LC (Waters™ alliance 2795-ZQ2000). Standard LC/MS conditions were as follows (running time 6 min):
Acidic condition: A: 0.1% formic acid in H2O; B: 0.1% formic acid in acetonitrile;
Basic condition: A: 0.01% NH3.H2O in H2O; B: acetonitrile;
Neutral condition: A: H2O; B: acetonitrile.

Mass spectra (MS): generally only ions which indicate the parent mass are reported, and unless otherwise stated the mass ion quoted is the positive mass ion-(M+H)+.

The microwave assisted reactions were carried out in a Biotage Initiator Sixty. NMR Spectra were obtained using Bruke Avance 400 MHz.

All reactions involving air-sensitive reagents were performed under an argon atmosphere. Reagents were used as received from commercial suppliers without further purification unless otherwise noted.

Example 1

2-[3-(3-Benzyl-ureido)-phenyl]-3,3-dimethyl-1,2,3,4-tetrahydro-quinoline-6-carboxylic acid

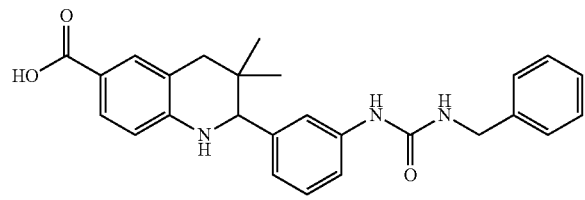 [SMILES: CC1(C)Cc2cc(C(=O)O)ccc2NC1c1cccc(NC(=O)NCc2ccccc2)c1]

A mixture of 4-amino-benzoic acid ethyl ester (16.5 g, 100 mmol), 3-nitro-benzaldehyde (16.6 g, 110 mmol) and p-toluenesulfonic acid (380 mg, 2 mmol) in toluene (300 mL) was heated to reflux for 3 h. Then the reaction mixture was cooled to room temperature. The solvent was removed in vacuo and the residue was washed with ether to afford 4-[(3-nitro-benzylidene)-amino]-benzoc acid ethyl ester (28.4 g, 95%) as a light yellow solid: LC/MS m/e calcd for $C_{16}H_{14}N_2O_4$ (M+H)+: 299.30, observed: 299.0.

To a mixture of 4-[(3-nitro-benzylidene)-amino]-benzoc acid ethyl ester (28.4 g, 95 mmol) and ytterbium(III) triflate hydrate (5.9 g, 9.5 mmol) in dry tetrahydrofuran (200 mL) at 25° C. was added isobutyraldehyde (9.6 mL, 105 mmol) and water (1.7 mL, 95 mmol) dropwise. The reaction mixture was stirred at 25° C. for 16 h. Then the reaction mixture was concentrated in vacuo and the residue was extracted with ethyl acetate (2×200 mL), washed with brine, dried over anhydrous sodium sulfate and concentrated in vacuo to afford 4-hydroxy-3,3-dimethyl-2-(3-nitro-phenyl)-1,2,3,4-tetrahydro-quinoline-6-carboxylic acid ethyl ester (30 g, 85%) as a light yellow oil: LC/MS m/e calcd for $C_{20}H_{22}N_2O_5$ (M+H)+: 371.41, observed: 353.0.

To a mixture of 4-hydroxy-3,3-dimethyl-2-(3-nitro-phenyl)-1,2,3,4-tetrahydro-quinoline-6-carboxylic acid ethyl ester (30 g, 81 mmol) and triethylsilane (60 mL) at 25° C. was added trifluoroacetic acid (30 mL) dropwise. The resulting mixture was stirred at 25° C. for 3 h. Then the reaction mixture was concentrated in vacuo and the residue was extracted with ethyl acetate (2×200 mL), washed with saturated aqueous sodium bicarbonate solution (2×100 mL), dried over anhydrous sodium sulfate and concentrated in vacuo. The residue was triturated with methanol. The resulting precipitate was collected, dried in vacuo to afford 3,3-dimethyl-2-(3-nitro-phenyl)-1,2,3,4-tetrahydro-quinoline-6-carboxylic acid ethyl ester (12 g, 41%) as a white solid: LC/MS m/e calcd for $C_{20}H_{22}N_2O_4$ (M+H)+: 355.41, observed: 355.1.

To a mixture of 3,3-dimethyl-2-(3-nitro-phenyl)-1,2,3,4-tetrahydro-quinoline-6-carboxylic acid ethyl ester (10 g, 28 mmol) in ethanol 95% (150 mL) and 10% hydrochloric acid (20 mL) was added iron (4.74 g, 85 mmol). The reaction mixture was stirred at 95° C. for 4 h. Then the insoluble solid was filtered off and the filtrate was concentrated in vacuo. The residue was extracted with ethyl acetate (2×200 mL), washed with 30% sodium hydroxide in water (2×100 mL), dried over anhydrous sodium sulfate and concentrated in vacuo to afford 2-(3-amino-phenyl)-3,3-dimethyl-1,2,3,4-tetrahydro-quinoline-6-carboxylic acid ethyl ester (8.7 g, 95%) as a light yellow solid: LC/MS m/e calcd for $C_{20}H_{24}N_2O_2$ (M+H)+: 325.43, observed: 325.2.

A mixture of 2-(3-amino-phenyl)-3,3-dimethyl-1,2,3,4-tetrahydro-quinoline-6-carboxylic acid ethyl ester (8.7 g, 26.8 mmol) in methanol (80 mL) and tetrahydrofuran (100 mL), 30% sodium hydroxide in water (50 mL) was stirred at 60° C. for 16 h. The mixture was neutralized with a 3 N aqueous hydrochloric acid solution and extracted with ethyl acetate (2×100 mL), washed with water, dried over anhydrous sodium sulfate and then concentrated in vacuo to afford 2-(3-amino-phenyl)-3,3-dimethyl-1,2,3,4-tetrahydro-quinoline-6-carboxylic acid (7 g, 88%) as a brown solid which was used for next step without further purification: LC/MS m/e calcd for $C_{18}H_{20}N_2O_2$ (M+H)+: 297.37, observed: 297.2.

To a solution of 2-(3-amino-phenyl)-3,3-dimethyl-1,2,3,4-tetrahydro-quinoline-6-carboxylic acid (500 mg, 1.69 mmol) in tetrahydrofuran (5 mL) and triethyl-amine (0.47 mL, 3.38 mmol) was added isocyanatomethyl-benzene (0.25 mL, 2.03 mmol) dropwise. The reaction mixture was stirred at 25° C. for 3 h. Then the reaction mixture was concentrated in vacuo and the residue was extracted with ethyl acetate (2×50 mL), washed with brine, dried over anhydrous sodium sulfate and concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-(3-benzyl-ureido)-phenyl]-3,3-dimethyl-1,2,3,4-tetrahydro-quinoline-6-carboxylic acid (215 mg, 29%) as a white solid: LC/MS m/e calcd for $C_{26}H_{27}N_3O_3$ (M+H)$^+$: 430.52, observed: 430.1.

Example 2

Pyrazine-2-carboxylic acid [3-(6-chloro-8-cyclopropanesulfonylaminocarbonyl-3,3-dimethyl-1,2,3,4-tetrahydro-quinolin-2-yl)-phenyl]-amide

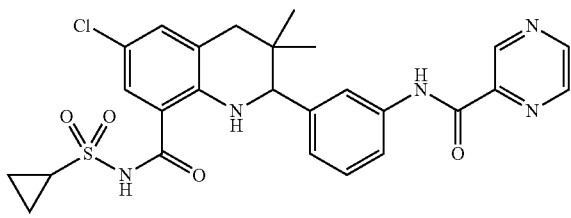 [SMILES: CC1(C)Cc2cc(Cl)cc(C(=O)NS(=O)(=O)C3CC3)c2NC1c1cccc(NC(=O)c2cnccn2)c1]

A mixture of 2-amino-5-chloro-benzoic acid methyl ester (5.55 g, 30 mmol) and 3-nitro-benzaldehyde (4.99 g, 33 mmol) in ethanol (100 mL) was heated to reflux for 2 h. Then the reaction mixture was cooled to room temperature. The solvent was removed in vacuo and the residue was washed with ether to afford 5-chloro-2-[(3-nitro-benzylidene)-amino]-benzoic acid methyl ester (7.2 g, 75%) as a white solid: LC/MS m/e calcd for $C_{15}H_{11}ClN_2O_4$ (M+H)$^+$: 319.72, observed: 319.0.

To a mixture of 5-chloro-2-[(3-nitro-benzylidene)-amino]-benzoic acid methyl ester (7.2 g, 23 mmol) and ytterbium(III) triflate hydrate (1.43 g, 2.3 mmol) in dry tetrahydrofuran (50 mL) at 25° C. was added isobutyraldehyde (2.27 mL, 25 mmol) and water (0.42 mL, 23 mmol) dropwise. The reaction mixture was stirred at 25° C. for 5 h. Then the reaction mixture was concentrated in vacuo and the residue was extracted with ethyl acetate (2×200 mL), washed with brine, dried over anhydrous sodium sulfate and concentrated in vacuo to afford 6-chloro-4-hydroxy-3,3-dimethyl-2-(3-nitrophenyl)-1,2,3,4-tetrahydro-quinoline-8-carboxylic acid methyl ester (7.8 g, 86%) as a light yellow oil: LC/MS m/e calcd for $C_{19}H_{19}ClN_2O_5$ (M+H)$^+$: 391.83, observed: 373.0.

To a mixture of 6-chloro-4-hydroxy-3,3-dimethyl-2-(3-nitro-phenyl)-1,2,3,4-tetrahydro-quinoline-8-carboxylic acid methyl ester (7.8 g, 20 mmol) and triethylsilane (30 mL) at 25° C. was added trifluoroacetic acid (15 mL) dropwise. The resulting mixture was stirred at 25° C. for 1 h. Then the reaction mixture was concentrated in vacuo and the residue was extracted with ethyl acetate (2×200 mL), washed with saturated aqueous sodium bicarbonate solution (2×100 mL), dried over anhydrous sodium sulfate and concentrated in vacuo. Purification on flash silica gel chromatography (silica gel from QingDao, 200-300 mesh, glass column from Shanghai SD company) (10% ethyl acetate/hexanes) afforded 6-chloro-3,3-dimethyl-2-(3-nitro-phenyl)-1,2,3,4-tetrahydro-quinoline-8-carboxylic acid methyl ester (1 g, 13%) as a white solid: LC/MS m/e calcd for $C_{19}H_{19}ClN_2O_4$ (M+H)$^+$: 375.83, observed: 375.1.

To a mixture of 6-chloro-3,3-dimethyl-2-(3-nitro-phenyl)-1,2,3,4-tetrahydro-quinoline-8-carboxylic acid methyl ester (1 g, 2.7 mmol) in ethanol 95% (100 mL) and 10% hydrochloric acid (5 mL) was added iron (0.23 g, 4 mmol). The reaction mixture was stirred at 95° C. for 4 h. Then the insoluble solid was filtered off and the filtrate was concentrated in vacuo and the residue was extracted with ethyl acetate (2×200 mL), washed with 30% sodium hydroxide in water (2×100 mL), dried over anhydrous sodium sulfate and concentrated in vacuo to afford 2-(3-amino-phenyl)-6-chloro-3,3-dimethyl-1,2,3,4-tetrahydro-quinoline-8-carboxylic acid methyl ester (0.8 g, 86%) as a white solid: LC/MS m/e calcd for $C_{19}H_{21}ClN_2O_2$ (M+H)$^+$: 345.84, observed: 345.1.

A mixture of 2-(3-amino-phenyl)-6-chloro-3,3-dimethyl-1,2,3,4-tetrahydro-quinoline-8-carboxylic acid methyl ester (0.8 g, 2.3 mmol) in methanol (50 mL) and tetrahydrofuran (100 mL), 30% sodium hydroxide in water (20 mL) was stirred at 60° C. for 12 h. The mixture was neutralized with a 3 N aqueous hydrochloric acid solution and extracted with ethyl acetate (2×100 mL), washed with water, dried over anhydrous sodium sulfate and then concentrated in vacuo to afford 2-(3-amino-phenyl)-6-chloro-3,3-dimethyl-1,2,3,4-tetrahydro-quinoline-8-carboxylic acid (0.75 g, 65%) as a brown solid which was used for next step without further purification: LC/MS m/e calcd for $C_{18}H_{19}ClN_2O_2$ (M+H)$^+$: 331.82, observed: 331.1.

A solution of pyrazine-2-carboxylic acid (0.412 g, 3.3 mmol) and 1,1'-carbonyldiimidazole (0.7 g, 4.3 mmol) in N,N-dimethylformamide (10 mL) was stirred at 70° C. for 1 h. A solution of 2-(3-amino-phenyl)-6-chloro-3,3-dimethyl-1,2,3,4-tetrahydro-quinoline-8-carboxylic acid (0.75 g, 2.3 mmol) in N,N-dimethylformamide (5 mL) was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% formic acid in water) afforded 6-chloro-3,3-dimethyl-2-{3-[(pyrazine-2-carbonyl)-amino]-phenyl}-1,2,3,4-tetrahydro-quinoline-8-carboxylic acid (228 mg, 15%) as a light yellow solid: LC/MS m/e calcd for $C_{23}H_{21}ClN_4O_3$ (M+H)$^+$: 437.90, observed: 437.1.

To a suspension of cyclopropanesulfonic acid amide (182 mg, 1.5 mmol) in N,N-dimethylformamide (2 mL) was added sodium hydride (57 mg, 1.43 mmol). The resulting mixture was stirred at 25° C. for 1 h. A solution of 6-chloro-3,3-dimethyl-2-{3-[(pyrazine-2-carbonyl)-amino]-phenyl}-1,2,3,4-tetrahydro-quinoline-8-carboxylic acid (65 mg, 0.15 mmol) and 1,1'-carbonyldiimidazole (49 mg, 0.3 mmol) in N,N-dimethylformamide (1.5 mL) was stirred at 70° C. for 1 h, the above suspension of cyclopropanesulfonic acid amide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded pyrazine-2-carboxylic acid [3-(6-chloro-8-cyclopropanesulfonylaminocarbonyl-3,3-dimethyl-1,2,3,4-tetrahydro-quinolin-2-yl)-phenyl]-amide (40 mg, 49%) as a white solid: LC/MS m/e calcd for $C_{26}H_{26}ClN_5O_4S$ (M+H)$^+$: 541.05, observed: 540.0.

Example 3

3,3-Dimethyl-2-{3-[(pyridine-3-carbonyl)-amino]-phenyl}-1,2,3,4-tetrahydro-quinoline-6-carboxylic acid

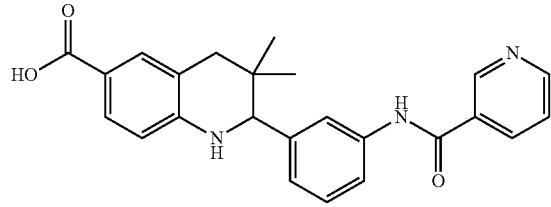 [SMILES: CC1(C)Cc2cc(C(=O)O)ccc2NC1c1cccc(NC(=O)c2cccnc2)c1]

A solution of nicotinic acid (42 mg, 0.34 mmol) and 1,1'-carbonyldiimidazole (72 mg, 0.44 mmol) in N,N-dimethylformamide (1.5 mL) was stirred at 70° C. After stirring at 70° C. for 1 h, a solution of 2-(3-amino-phenyl)-3,3-dimethyl-1,2,3,4-tetrahydro-quinoline-6-carboxylic acid (100 mg, 0.34 mmol) in N,N-dimethylformamide (2 mL) was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% formic acid in water) afforded 3,3-dimethyl-2-{3-[(pyridine-3-carbonyl)-amino]-phenyl}-1,2,3,4-tetrahydro-quinoline-6-carboxylic acid (21 mg, 15%) as a white solid: LC/MS m/e calcd for $C_{24}H_{23}N_3O_3$ (M+H)$^+$: 402.47, observed: 402.1.

Example 4

3,3-Dimethyl-2-{3-[(pyridine-2-carbonyl)-amino]-phenyl}-1,2,3,4-tetrahydro-quinoline-6-carboxylic acid

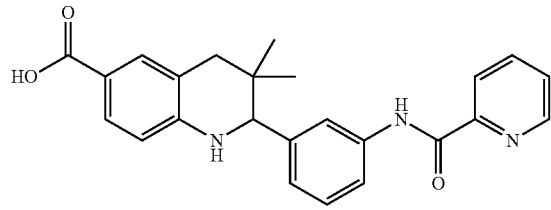

A solution of pyridine-2-carboxylic acid (1.26 g, 10 mmol) and 1,1'-carbonyldiimidazole (2.14 g, 13 mmol) in N,N-dimethylformamide (8 mL) was stirred at 70° C. for 1 h. Then a solution of 2-(3-amino-phenyl)-3,3-dimethyl-1,2,3,4-tetrahydro-quinoline-6-carboxylic acid (2.4 g, 8 mmol) in N,N-dimethylformamide (5 mL) was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% formic acid in water) afforded 3,3-dimethyl-2-{3-[(pyridine-2-carbonyl)-amino]-phenyl}-1,2,3,4-tetrahydro-quinoline-6-carboxylic acid (1.85 g, 57%) as a light yellow solid: LC/MS m/e calcd for $C_{24}H_{23}N_3O_3$ (M+H)$^+$: 402.47, observed: 402.5.

Example 5

3,3-Dimethyl-2-{3-[(pyrazine-2-carbonyl)-amino]-phenyl}-1,2,3,4-tetrahydro-quinoline-6-carboxylic acid

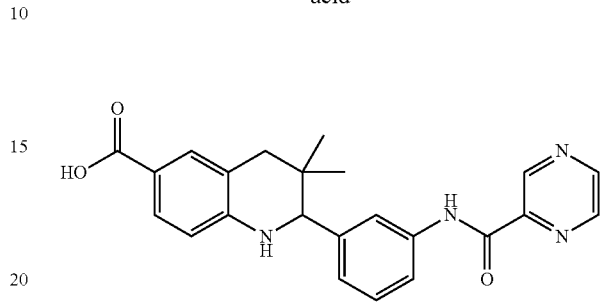

A solution of pyrazine-2-carboxylic acid (1.26 g, 10 mmol) and 1,1'-carbonyldiimidazole (2.14 g, 13 mmol) in N,N-dimethylformamide (8 mL) was stirred at 70° C. for 1 h. Then a solution of 2-(3-amino-phenyl)-3,3-dimethyl-1,2,3,4-tetrahydro-quinoline-6-carboxylic acid (3 g, 10 mmol) in N,N-dimethylformamide (5 mL) was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% formic acid in water) afforded 3,3-dimethyl-2-{3-[(pyrazine-2-carbonyl)-amino]-phenyl}-1,2,3,4-tetrahydro-quinoline-6-carboxylic acid (1.82 g, 45%) as a light yellow solid: LC/MS m/e calcd for $C_{23}H_{22}N_4O_3$ (M+H)$^+$: 403.46, observed: 403.5.

Example 6

2-[3-(3-fluoro-benzoylamino)-phenyl]-3,3-dimethyl-1,2,3,4-tetrahydro-quinoline-6-carboxylic acid

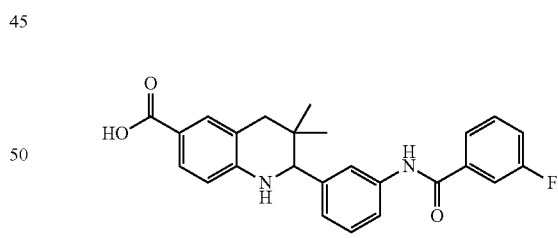

A solution of 3-fluoro-benzoic acid (119 mg, 0.85 mmol) and 1,1'-carbonyldiimidazole (179 mg, 1.1 mmol) in N,N-dimethylformamide (1.5 mL) was stirred at 70° C. for 1 h. Then a solution of 2-(3-amino-phenyl)-3,3-dimethyl-1,2,3,4-tetrahydro-quinoline-6-carboxylic acid (200 mg, 0.68 mmol) in N,N-dimethylformamide (1.5 mL) was added and the mixture was allowed to stir at 50° C. for 3 h. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-(3-fluoro-benzoylamino)-phenyl]-3,3-dimethyl-1,2,3,4-tetrahydro-quinoline-6-carboxylic acid (40 mg, 14%) as a white solid: LC/MS m/e calcd for $C_{25}H_{23}FN_2O_3$ (M+H)$^+$: 419.47, observed: 419.1.

Example 7

2-(3-Carbonyl-phenyl)-3,3-dimethyl-1,2,3,4-tetrahydro-quinoline-6-carboxylic acid

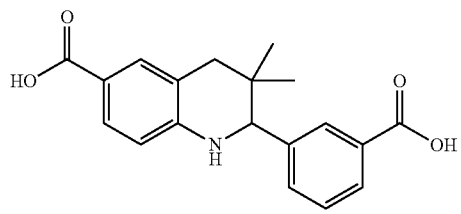 [SMILES: CC1(C)Cc2cc(C(=O)O)ccc2NC1c1cccc(C(=O)O)c1]

A mixture of 4-amino-benzoic acid ethyl ester (16.5 g, 100 mmol), 3-formyl-benzoic acid methyl ester (18 g, 110 mmol) and p-toluenesulfonic acid (380 mg, 2 mmol) in toluene (300 mL). The reaction mixture was heated to reflux for 4 h. Then the reaction mixture was cooled to room temperature. The solvent was removed in vacuo and the residue was washed with ether to afford (E)-methyl-3-((4-(ehoxycarbonyl)phenylimino)methyl)benzoate (26.9 g, 86%) as a white solid: LC/MS m/e calcd for $C_{18}H_{17}NO_4$ (M+H)$^+$: 312.34, observed: 312.0.

To a mixture of (E)-methyl-3-((4-(ehoxycarbonyl)phenylimino)methyl)benzoate (12.44 g, 40 mmol) and ytterbium (III) triflate hydrate (2.48 g, 4 mmol) in dry tetrahydrofuran (60 mL) at 25° C. was added Isobutyraldehyde (3.66 mL, 40 mmol) and water (0.72 mL, 40 mmol) dropwise. The reaction mixture was stirred at 25° C. for 3 h. Then the reaction mixture was concentrated in vacuo and the residue was extracted with ethyl acetate (2×200 mL), washed with brine, dried over anhydrous sodium sulfate and concentrated in vacuo to afford 4-hydroxy-2-(3-methoxycarbonyl-phenyl)-3,3-dimethyl-1,2,3,4-tetrahydro-quinoline-6-carboxylic acid ethyl ester (13 g, 84%) as a light yellow oil which was used for next step without further purification: LC/MS m/e calcd for $C_{22}H_{25}NO_5$ (M+H)$^+$: 384.35, observed: 366.1.

To a mixture of 4-hydroxy-2-(3-methoxycarbonyl-phenyl)-3,3-dimethyl-1,2,3,4-tetrahydro-quinoline-6-carboxylic acid ethyl ester (13 g, 34 mmol) and triethylsilane (20 mL) at 25° C. was added trifluoroacetic acid (10 mL) dropwise. The resulting mixture was stirred at 25° C. for 2 h. Then the reaction mixture was concentrated in vacuo and the residue was extracted with ethyl acetate (2×200 mL), washed with saturated aqueous sodium bicarbonate solution (2×100 mL), dried over anhydrous sodium sulfate and concentrated in vacuo. The residue was triturated with methanol. The resulting precipitate was collected, dried in vacuo to afford 2-(3-methoxycarbonyl-phenyl)-3,3-dimethyl-1,2,3,4-tetrahydro-quinoline-6-carboxylic acid ethyl ester (3.16 g, 25%) as a white solid: LC/MS m/e calcd for $C_{22}H_{25}NO_4$ (M+H)$^+$: 368.45, observed: 368.1.

A mixture of 2-(3-methoxycarbonyl-phenyl)-3,3-dimethyl-1,2,3,4-tetrahydro-quinoline-6-carboxylic acid ethyl ester (2 g, 5.45 mmol) in methanol (20 mL) and tetrahydrofuran (50 mL), 30% sodium hydroxide in water (20 mL) was stirred at 50° C. for 24 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-(3-carbonyl-phenyl)-3,3-dimethyl-1,2,3,4-tetrahydro-quinoline-6-carboxylic acid (500 mg, 28%) as a white solid: LC/MS m/e calcd for $C_{19}H_{19}NO_4$ (M+H)$^+$: 326.27, observed: 326.0.

Example 8

N-[3,3-dimethyl-2-(3-morpholin-4-yl-phenyl)-1,2,3,4-tetrahydro-quinoline-6-carbonyl]-methanesulfonamide

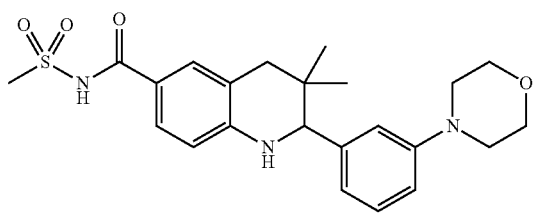 [SMILES: CC1(C)Cc2cc(C(=O)NS(C)(=O)=O)ccc2NC1c1cccc(N2CCOCC2)c1]

A mixture of 4-amino-benzoic acid ethyl ester (33 g, 200 mmol), 3-bromo-benzaldehyde (25.7 mL, 220 mmol) and p-toluenesulfonic acid (760 mg, 4 mmol) in toluene (600 mL) was heated to reflux for 12 h. Then the reaction mixture cooled to room temperature. The solvent was removed in vacuo and the residue was washed with ether to afford 4-[(3-bromo-benzylidene)-amino]-benzoc acid ethyl ester (34 g, 51%) as a light yellow solid: LC/MS m/e calcd for $C_{16}H_{14}BrNO_2$ (M+H)$^+$: 333.20, observed: 332.0.

To a mixture of 4-[(3-bromo-benzylidene)-amino]-benzoc acid ethyl ester (29 g, 87 mmol) and ytterbium(III) triflate hydrate (5.4 g, 8.7 mmol) in dry tetrahydrofuran (200 mL) at 25° C. was added isobutyraldehyde (8.8 mL, 96 mmol) and water (1.6 mL, 87 mmol) dropwise. The reaction mixture was stirred at 25° C. for 16 h. Then the reaction mixture was concentrated in vacuo and the residue was extracted with ethyl acetate (2×200 mL), washed with brine, dried over anhydrous sodium sulfate and concentrated in vacuo to afford 2-(3-bromo-phenyl)-4-hydroxy-3,3-dimethyl-1,2,3,4-tetrahydro-quinoline-6-carboxylic acid ethyl ester (30 g, 85%) as a light yellow oil which was used for next step without further purification: LC/MS m/e calcd for $C_{20}H_{22}BrNO_3$ (M+H)$^+$: 405.31, observed: 388.0.

To a mixture of 2-(3-bromo-phenyl)-4-hydroxy-3,3-dimethyl-1,2,3,4-tetrahydro-quinoline-6-carboxylic acid ethyl ester (30 g, 74 mmol) and triethylsilane (50 mL) at 25° C. was added trifluoroacetic acid (15 mL) dropwise. The resulting mixture was stirred at 25° C. for 4 h. Then the reaction mixture was concentrated in vacuo and the residue was extracted with ethyl acetate (2×200 mL), washed with saturated aqueous sodium bicarbonate solution (2×100 mL), dried over anhydrous sodium sulfate and concentrated in vacuo. The residue was triturated with methanol. The resulting precipitate was collected, dried in vacuo to afford 2-(3-bromo-phenyl)-3,3-dimethyl-1,2,3,4-tetrahydro-quinoline-6-carboxylic acid ethyl ester (15 g, 78%) as a white solid: LC/MS m/e calcd for $C_{20}H_{22}BrNO_2$ (M+H)$^+$: 389.31, observed: 390.0.

A mixture of 2-(3-bromo-phenyl)-3,3-dimethyl-1,2,3,4-tetrahydro-quinoline-6-carboxylic acid ethyl ester (5.7 g, 14.7 mmol), morpholine (12.8 mL, 147 mmol), copper(I)

iodide (1.68 g, 8.8 mmol), N,N-dimethylglycine hydrochloride (1.58 g, 11.8 mmol), and potassium carbonate (6.1 g, 44.1 mmol) in dimethyl sulfoxide (30 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo to afford 3,3-dimethyl-2-(3-morpholin-4-yl-phenyl)-1,2,3,4-tetrahydro-quinoline-6-carboxylic acid ethyl ester (5.6 g, 96%) as a white solid which was used for next step without further purification: LC/MS m/e calcd for $C_{24}H_{30}N_2O_3$ (M+H)$^+$: 395.52, observed: 395.2.

A mixture of 3,3-dimethyl-2-(3-morpholin-4-yl-phenyl)-1,2,3,4-tetrahydro-quinoline-6-carboxylic acid ethyl ester (5.6 g, 14.2 mmol) in methanol (50 mL) and tetrahydrofuran (100 mL), 30% sodium hydroxide in water (30 mL) was stirred at 60° C. for 6 h. The mixture was neutralized with a 3 N aqueous hydrochloric acid solution and extracted with ethyl acetate (2×100 mL), washed with water, dried over anhydrous sodium sulfate and then concentrated in vacuo to afford 3,3-dimethyl-2-(3-morpholin-4-yl-phenyl)-1,2,3,4-tetrahydro-quinoline-6-carboxylic acid (3.6 g, 69%) as a white solid: LC/MS m/e calcd for $C_{22}H_{26}N_2O_3$ (M+H)$^+$: 367.46, observed: 367.1.

To a suspension of methanesulfonamide (4.75 g, 50 mmol) in N,N-dimethylformamide (15 mL) was added sodium hydride (1.98 g, 49.5 mmol). The resulting mixture was stirred at 25° C. for 1 h. A solution of 3,3-dimethyl-2-(3-morpholin-4-yl-phenyl)-1,2,3,4-tetrahydro-quinoline-6-carboxylic acid (3.66 g, 10 mmol) and 1,1'-carbonyldiimidazole (3.24 g, 20 mmol) in N,N-dimethylformamide (7 mL) was stirred at 70° C. for 1 h. Then the above suspension of methanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-[3,3-dimethyl-2-(3-morpholin-4-yl-phenyl)-1,2,3,4-tetrahydro-quinoline-6-carbonyl]-methanesulfonamide (0.99 g, 22%) as a white solid: LC/MS m/e calcd for $C_{23}H_{29}N_3O_4S$ (M+H)$^+$: 444.57, observed: 444.1.

Example 9

3-(6-Methanesulfonylaminocarbonyl-3,3-dimethyl-1,2,3,4-tetrahydro-quinolin-2-yl)-N-phenyl-benzamide

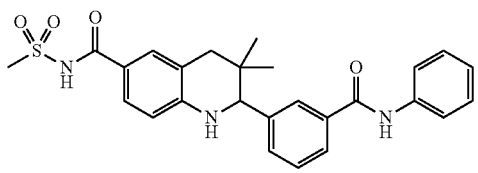 [SMILES: CC1(C)Cc2cc(C(=O)NS(C)(=O)=O)ccc2NC1c1cccc(C(=O)Nc2ccccc2)c1]

To a suspension of methanesulfonamide (237 mg, 2.5 mmol) in N,N-dimethylformamide (1.5 mL) was added sodium hydride (100 mg, 2.48 mmol). The resulting mixture was stirred at 25° C. for 1 h. A solution of 3,3-dimethyl-2-(3-phenylcarbamoyl-phenyl)-1,2,3,4-tetrahydro-quinoline-6-carboxylic acid (200 mg, 0.5 mmol) and 1,1'-carbonyldiimidazole (162 mg, 1 mmol) in N,N-dimethylformamide (1 mL) was stirred at 70° C. for 1 h. Then the above suspension of methanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 3-(6-methanesulfonylaminocarbonyl-3,3-dimethyl-1,2,3,4-tetrahydro-quinolin-2-yl)-N-phenyl-benzamide (100 mg, 18%) as a white solid: LC/MS m/e calcd for $C_{26}H_{27}N_3O_4S$ (M+H)$^+$: 478.59, observed: 478.2.

Example 10

Propane-2-sulfonic acid [3,3-dimethyl-2-(3-morpholin-4-yl-phenyl)-1,2,3,4-tetrahydro-quinoline-6-carbonyl]-amide

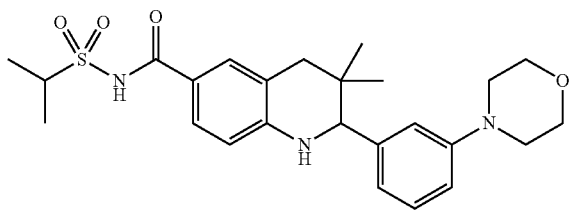 [SMILES: CC(C)S(=O)(=O)NC(=O)c1ccc2c(c1)CC(C)(C)C(c1cccc(N3CCOCC3)c1)N2]

To a suspension of propane-2-sulfonic acid amide (168 mg, 1.37 mmol) in N,N-dimethylformamide (1.5 mL) was added sodium hydride (52 mg, 1.3 mmol). The resulting mixture was stirred at 25° C. for 1 h. A solution of 3,3-dimethyl-2-(3-morpholin-4-yl-phenyl)-1,2,3,4-tetrahydro-quinoline-6-carboxylic acid (100 mg, 0.27 mmol) and 1,1'-carbonyldiimidazole (89 mg, 0.55 mmol) in N,N-dimethylformamide (1 mL) was stirred at 70° C. for 1 h. Then the above suspension of propane-2-sulfonic acid amide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded Propane-2-sulfonic acid [3,3-dimethyl-2-(3-morpholin-4-yl-phenyl)-1,2,3,4-tetrahydro-quinoline-6-carbonyl]-amide (23 mg, 18%) as a white solid: LC/MS m/e calcd for $C_{25}H_{33}N_3O_4S$ (M+H)$^+$: 472.62, observed: 472.1.

Example 11

Pyrazine-2-carboxylic acid [3-(6-methanesulfonylaminocarbonyl-3,3-dimethyl-1,2,3,4-tetrahydro-quinolin-2-yl)-phenyl]-amide

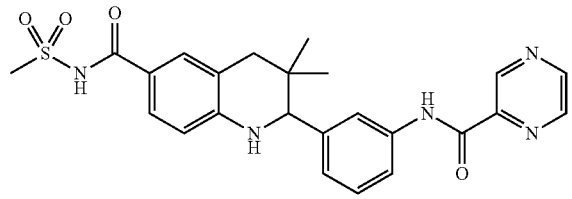 [SMILES: CC1(C)Cc2cc(C(=O)NS(C)(=O)=O)ccc2NC1c1cccc(NC(=O)c2cnccn2)c1]

A mixture of 3,3-dimethyl-2-(3-nitro-phenyl)-1,2,3,4-tetrahydro-quinoline-6-carboxylic acid ethyl ester (2 g, 5.65 mmol) in methanol (15 mL) and tetrahydrofuran (30 mL), 30% sodium hydroxide in water (15 mL) was stirred at 60° C. for 12 h. The mixture was neutralized with a 3 N aqueous hydrochloric acid solution and extracted with ethyl acetate (2×100 mL), washed with water, dried over anhydrous sodium sulfate and then concentrated in vacuo to afford 3,3-dimethyl-2-(3-nitro-phenyl)-1,2,3,4-tetrahydro-quinoline-6-carboxylic acid (1.79 g, 97%) as a brown solid which was used for next step without further purification: LC/MS m/e calcd for $C_{18}H_{18}N_2O_4$ (M+H)$^+$: 327.37, observed: 327.1.

To a suspension of methanesulfonamide (2.6 g, 27.2 mmol) in N,N-dimethylformamide (5 mL) was added sodium hydride (1.1 g, 27.5 mmol). The resulting mixture was stirred at 25° C. for 1 h. A solution of 3,3-dimethyl-2-(3-nitro-phenyl)-1,2,3,4-tetrahydro-quinoline-6-carboxylic acid (1.79 g, 5.5 mmol) and 1,1'-carbonyldiimidazole (1.78 g, 11 mmol) in N,N-dimethylformamide (5 mL) was stirred at 70° C. for 1 h. Then the above suspension of methanesulfonamide and sodium hydride in N,N-dimethylformamide was added and the mixture was allowed to stir at 25° C. for 1 h. The reaction mixture was extracted with ethyl acetate (2×100 mL), washed with water, dried over anhydrous sodium sulfate and then concentrated in vacuo to afford N-[3,3-dimethyl-2-(3-nitro-phenyl)-1,2,3,4-tetrahydro-quinoline-6-carbonyl]-methanesulfonamide (2 g, 90%) as a brown solid which was used for next step without further purification: LC/MS m/e calcd for $C_{19}H_{21}N_3O_5S$ (M+H)$^+$: 404.46, observed: 404.1.

To a mixture of N-[3,3-dimethyl-2-(3-nitro-phenyl)-1,2,3,4-tetrahydro-quinoline-6-carbonyl]-methanesulfonamide (2 g, 5 mmol) in ethanol 95% (100 mL) and 10% hydrochloric acid (20 mL) was added iron (0.84 g, 15 mmol). The reaction mixture was stirred at 95° C. for 1 h. Then the insoluble solid was filtered off and the filtrate was concentrated in vacuo and the residue was extracted with ethyl acetate (2×200 mL), washed with 30% sodium hydroxide in water (2×100 mL), dried over anhydrous sodium sulfate and concentrated in vacuo to afford N-[2-(3-Amino-phenyl)-3,3-dimethyl-1,2,3,4-tetrahydro-quinoline-6-carbonyl]-methanesulfonamide (1.5 g, 80%) as a brown oil which was used for next step without further purification: LC/MS m/e calcd for $C_{19}H_{23}N_3O_3S$ (M+H)$^+$: 374.48, observed: 374.1.

A solution of pyrazine-2-carboxylic acid (42 mg, 0.34 mmol) and 1,1'-carbonyldiimidazole (72 mg, 0.44 mmol) in N,N-dimethylformamide (1.5 mL) was stirred at 70° C. for 1 h. Then a solution of N-[2-(3-Amino-phenyl)-3,3-dimethyl-1,2,3,4-tetrahydro-quinoline-6-carbonyl]-methanesulfonamide (130 mg, 0.34 mmol) in N,N-dimethylformamide (1 mL) was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% formic acid in water) afforded pyrazine-2-carboxylic acid [3-(6-methanesulfonylaminocarbonyl-3,3-dimethyl-1,2,3,4-tetrahydro-quinolin-2-yl)-phenyl]-amide (12 mg, 7%) as a white solid: LC/MS m/e calcd for $C_{24}H_{25}N_5O_4S$ (M+H)$^+$: 480.56, observed: 480.2.

Example 12

2-(3-Benzoylamino-phenyl)-3,3-dimethyl-1,2,3,4-tetrahydro-quinoline-6-carboxylic acid

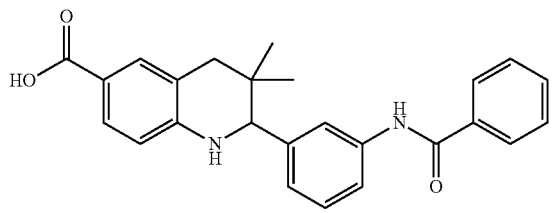 [SMILES: CC1(C)Cc2cc(C(=O)O)ccc2NC1c1cccc(NC(=O)c2ccccc2)c1]

A mixture of 2-(3-amino-phenyl)-3,3-dimethyl-1,2,3,4-tetrahydro-quinoline-6-carboxylic acid ethyl ester (745 mg, 2.3 mmol), benzoic acid (337 mg, 2.76 mmol) and o-(7-azabenzotriazol-1-yl)-N,N,N',N'-tetramethyluronium hexafluorophosphate (1.31 g, 3.45 mmol) in dichloromethane (10 mL) and triethyl-amine (0.8 mL, 5.75 mmol) was stirred at 25° C. for 12 h. Then the reaction mixture was extracted with dichloromethane (2×100 mL), washed with water, dried over anhydrous sodium sulfate and concentrated in vacuo to afford 2-(3-benzoylamino-phenyl)-3,3-dimethyl-1,2,3,4-tetrahydro-quinoline-6-carboxylic acid ethyl ester (984 mg, 100%) as a brown oil which was used for next step without further purification: LC/MS m/e calcd for $C_{27}H_{28}N_2O_3$ (M+H)$^+$: 429.54, observed: 429.1.

A mixture of 2-(3-benzoylamino-phenyl)-3,3-dimethyl-1,2,3,4-tetrahydro-quinoline-6-carboxylic acid ethyl ester (984 mg, 2.3 mmol) in methanol (15 mL) and tetrahydrofuran (20 mL), 30% sodium hydroxide in water (10 mL) was stirred at 50° C. for 12 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-(3-benzoylamino-phenyl)-3,3-dimethyl-1,2,3,4-tetrahydro-quinoline-6-carboxylic acid (494 mg, 44%) as a white solid: LC/MS m/e calcd for $C_{25}H_{24}N_2O_3$ (M+H)$^+$: 401.48, observed: 401.2.

Example 13

2-{3-[3-(3-Fluoro-phenyl)-ureido]-phenyl}-3,3-dimethyl-1,2,3,4-tetrahydro-quinoline-6-carboxylic acid

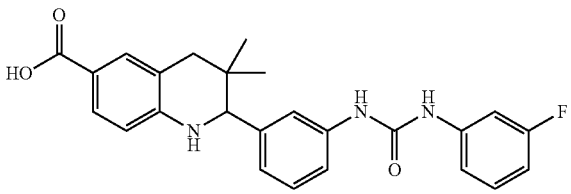 [SMILES: CC1(C)Cc2cc(C(=O)O)ccc2NC1c1cccc(NC(=O)Nc2cccc(F)c2)c1]

To a solution of 2-(3-amino-phenyl)-3,3-dimethyl-1,2,3,4-tetrahydro-quinoline-6-carboxylic acid (220 mg, 0.74 mmol)

in tetrahydrofuran (5 mL) and triethyl-amine (0.2 mL, 1.48 mmol) was added 3-fluorophenyl isocyanate (0.1 mL, 0.89 mmol) dropwise. The reaction mixture was stirred at 25° C. for 1 h. Then the reaction mixture was concentrated in vacuo and the residue was extracted with ethyl acetate (2×30 mL), washed with brine, dried over anhydrous sodium sulfate and concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-{3-[3-(3-fluoro-phenyl)-ureido]-phenyl}-3,3-dimethyl-1,2,3,4-tetrahydro-quinoline-6-carboxylic acid (67 mg, 20%) as a white solid: LC/MS m/e calcd for $C_{25}H_{24}FN_3O_3$ (M+H)$^+$: 434.49, observed: 434.1.

Example 14

3,3-Dimethyl-2-(3-phenylcarbamoyl-phenyl)-1,2,3,4-tetrahydro-quinoline-6-carboxylic acid

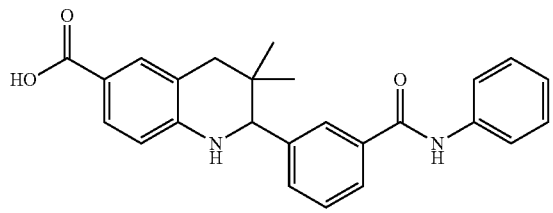 [SMILES: CC1(C)Cc2cc(C(=O)O)ccc2NC1c1cccc(C(=O)Nc2ccccc2)c1]

A mixture of 2-(3-methoxycarbonyl-phenyl)-3,3-dimethyl-1,2,3,4-tetrahydro-quinoline-6-carboxylic acid ethyl ester (1.16 g, 1 mmol) in tetrahydrofuran (40 mL), 2M lithium hydroxide in water (20 mL) was stirred for 48 h at 25° C. The mixture was neutralized with a 3 N aqueous hydrochloric acid solution, diluted with ethyl acetate (100 mL), washed with water, dried over anhydrous sodium sulfate and then concentrated in vacuo to afford 2-(3-carbonyl-phenyl)-3,3-dimethyl-1,2,3,4-tetrahydro-quinoline-6-carboxylic acid ethyl ester (1.1 g, 98%) as a white solid: LC/MS m/e calcd for $C_{21}H_{23}NO_4$ (M+H)$^+$: 354.42, observed: 354.0.

A mixture of 2-(3-carbonyl-phenyl)-3,3-dimethyl-1,2,3,4-tetrahydro-quinoline-6-carboxylic acid ethyl ester (720 mg, 2 mmol), phenylamine (224 mg, 2.4 mmol) and o-(7-azabenzotriazol-1-yl)-N,N,N',N'-tetramethyluronium hexafluorophosphate (1.14 g, 3 mmol) in dichloromethane (5 mL) and triethyl-amine (0.7 mL, 5 mmol) was stirred at 25° C. for 12 h. Then the reaction mixture was extracted with dichloromethane (2×100 mL), washed with water, dried over anhydrous sodium sulfate and concentrated in vacuo to afford 3,3-dimethyl-2-(3-phenylcarbamoyl-phenyl)-1,2,3,4-tetrahydro-quinoline-6-carboxylic acid ethyl ester (0.8 g, 93%) as a brown oil which was used for next step without further purification: LC/MS m/e calcd for C27H28N2O3 (M+H)+: 429.54, observed: 429.1.

A mixture of 3,3-dimethyl-2-(3-phenylcarbamoyl-phenyl)-1,2,3,4-tetrahydro-quinoline-6-carboxylic acid ethyl ester (0.8 g, 1.87 mmol) in methanol (15 mL) and tetrahydrofuran (20 mL), 30% sodium hydroxide in water (10 mL) was stirred at 45° C. for 48 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 3,3-dimethyl-2-(3-phenylcarbamoyl-phenyl)-1,2,3,4-tetrahydro-quinoline-6-carboxylic acid (350 mg, 46%) as a white solid: LC/MS m/e calcd for $C_{25}H_{24}N_2O_3$ (M+H)$^+$: 401.48, observed: 401.1.

Example 15

2-[3-(1-Carboxy-1-methyl-ethylamino)-phenyl]-3,3-dimethyl-1,2,3,4-tetrahydro-quinoline-6-carboxylic acid

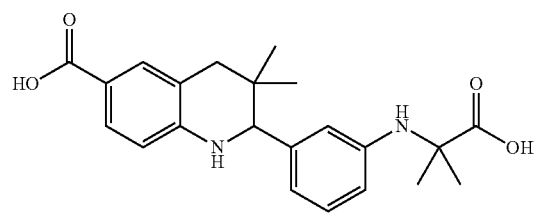 [SMILES: CC(C)(Nc1cccc(C2Nc3ccc(C(=O)O)cc3CC2(C)C)c1)C(=O)O]

A mixture of 2-(3-amino-phenyl)-3,3-dimethyl-1,2,3,4-tetrahydro-quinoline-6-carboxylic acid ethyl ester (0.52 g, 1.6 mmol), 2-bromo-2-methyl-propionic acid methyl ester (0.58 g, 3.2 mmol) and potassium carbonate (1.1 g, 8 mmol) in N,N-dimethylformamide (6 mL) was stirred at 25° C. for 72 h. Then the reaction mixture was extracted with ethyl acetate (2×100 mL), washed with water, dried over anhydrous sodium sulfate and concentrated in vacuo to afford 2-[3-(1-methoxycarbonyl-1-methyl-ethylamino)-phenyl]-3,3-dimethyl-1,2,3,4-tetrahydro-quinoline-6-carboxylic acid ethyl ester (678 mg, 100%) as a brown oil which was used for next step without further purification: LC/MS m/e calcd for $C_{25}H_{32}N_2O_4$ (M+H)$^+$: 425.54, observed: 425.2.

A mixture of 2-[3-(1-methoxycarbonyl-1-methyl-ethylamino)-phenyl]-3,3-dimethyl-1,2,3,4-tetrahydro-quinoline-6-carboxylic acid ethyl ester (678 mg, 1.6 mmol) in methanol (10 mL) and tetrahydrofuran (30 mL), 30% sodium hydroxide in water (10 mL) was stirred at 60° C. for 12 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-(1-carboxy-1-methyl-ethylamino)-phenyl]-3,3-dimethyl-1,2,3,4-tetrahydro-quinoline-6-carboxylic acid (30 mg, 4%) as a white solid: LC/MS m/e calcd for $C_{22}H_{26}N_2O_4$ (M+H)$^+$: 383.46, observed: 383.1.

Example 16

3,3-Dimethyl-2-[3-(3-methyl-2-oxo-imidazolidin-1-yl)-phenyl]-1,2,3,4-tetrahydro-quinoline-6-carboxylic acid

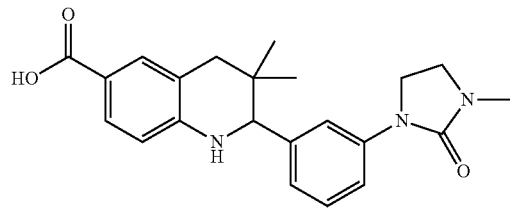 [SMILES: CN1CCN(c2cccc(C3Nc4ccc(C(=O)O)cc4CC3(C)C)c2)C1=O]

A mixture of 2-(3-bromo-phenyl)-3,3-dimethyl-1,2,3,4-tetrahydro-quinoline-6-carboxylic acid ethyl ester (7 g, 18 mmol) in methanol (25 mL) and tetrahydrofuran (100 mL), 30% sodium hydroxide in water (20 mL) was stirred at 60° C. for 56 h. The mixture was neutralized with a 3 N aqueous hydrochloric acid solution and extracted with ethyl acetate (2×100 mL), washed with water, dried over anhydrous sodium sulfate and then concentrated in vacuo to afford 2-(3-bromo-phenyl)-3,3-dimethyl-1,2,3,4-tetrahydro-quinoline-6-carboxylic acid (6.4 g, 88%) as a brown solid which was used for next step without further purification: LC/MS m/e calcd for $C_{18}H_{18}BrNO_2$ (M+H)$^+$: 361.25, observed: 360.2.

A mixture of 2-(3-bromo-phenyl)-3,3-dimethyl-1,2,3,4-tetrahydro-quinoline-6-carboxylic acid (360 mg, 1 mmol), 1-methyl-imidazolidin-2-one (300 mg, 3 mmol), copper(I) iodide (115 mg, 0.6 mmol), N,N-dimethylglycine hydrochloride (112 g, 0.8 mmol) and potassium carbonate (415 mg, 3 mmol) in dimethyl sulfoxide (5 mL) was stirred at 120° C. for 12 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 3,3-dimethyl-2-[3-(3-methyl-2-oxo-imidazolidin-1-yl)-phenyl]-1,2,3,4-tetrahydro-quinoline-6-carboxylic acid (4 mg, 1%) as a white solid: LC/MS m/e calcd for $C_{22}H_{25}N_3O_3$ (M+H)$^+$: 380.46, observed: 380.1.

Example 17

3,3-Dimethyl-2-[3-(2-oxo-imidazolidin-1-yl)-phenyl]-1,2,3,4-tetrahydro-quinoline-6-carboxylic acid

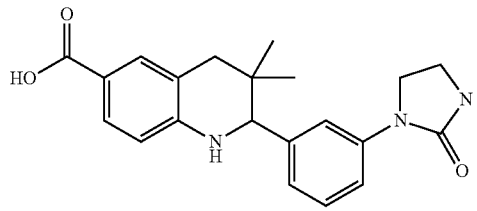 [SMILES: CC1(C)Cc2cc(C(=O)O)ccc2NC1c1cccc(N2CCNC2=O)c1]

A mixture of 2-(3-bromo-phenyl)-3,3-dimethyl-1,2,3,4-tetrahydro-quinoline-6-carboxylic acid (360 mg, 1 mmol), imidazolidin-2-one (430 mg, 5 mmol), copper(I) iodide (115 mg, 0.6 mmol), N,N-dimethylglycine hydrochloride (112 g, 0.8 mmol) and potassium carbonate (415 mg, 3 mmol) in dimethyl sulfoxide (5 mL) was stirred at 120° C. for 12 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 3,3-dimethyl-2-[3-(2-oxo-imidazolidin-1-yl)-phenyl]-1,2,3,4-tetrahydro-quinoline-6-carboxylic acid (22 mg, 6%) as a white solid: LC/MS m/e calcd for $C_{21}H_{23}N_3O_3$ (M+H)$^+$: 366.44, observed: 366.1.

Example 18

2-[3-(2,5-Dioxo-piperazin-1-yl)-phenyl]-3,3-dimethyl-1,2,3,4-tetrahydro-quinoline-6-carboxylic acid

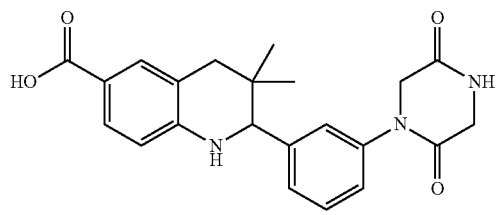 [SMILES: CC1(C)Cc2cc(C(=O)O)ccc2NC1c1cccc(N2CC(=O)NCC2=O)c1]

A mixture of 2-(3-bromo-phenyl)-3,3-dimethyl-1,2,3,4-tetrahydro-quinoline-6-carboxylic acid (360 mg, 1 mmol), piperazine-2,5-dione (570 mg, 5 mmol), copper(I) iodide (115 mg, 0.6 mmol), N,N-dimethylglycine hydrochloride (112 g, 0.8 mmol) and potassium carbonate (415 mg, 3 mmol) in dimethyl sulfoxide (5 mL) was stirred at 120° C. for 12 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-(2,5-dioxo-piperazin-1-yl)-phenyl]-3,3-dimethyl-1,2,3,4-tetrahydro-quinoline-6-carboxylic acid (46 mg, 11%) as a grey solid: LC/MS m/e calcd for $C_{22}H_{23}N_3O_4$ (M+H)$^+$: 394.45, observed: 394.1.

Example 19

2-[3-(2,4-Dioxo-imidazolidine-1-yl)-phenyl]-3,3-dimethyl-1,2,3,4-tetrahydro-quinoline-6-carboxylic acid

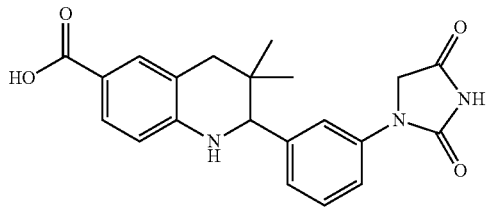 [SMILES: CC1(C)Cc2cc(C(=O)O)ccc2NC1c1cccc(N2CC(=O)NC2=O)c1]

A mixture of 2-(3-bromo-phenyl)-3,3-dimethyl-1,2,3,4-tetrahydro-quinoline-6-carboxylic acid (360 mg, 1 mmol), imidazolidine-2,4-dione (500 mg, 5 mmol), copper(I) iodide (115 mg, 0.6 mmol), N,N-dimethylglycine hydrochloride (112 g, 0.8 mmol) and potassium carbonate (415 mg, 3 mmol) in dimethyl sulfoxide (5 mL) was stirred at 120° C. for 12 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-(2,4-dioxo-imidazolidine-1-yl)-phenyl]-3,3-dimethyl-1,2,3,4-tetrahydro-quinoline-6-carboxylic acid (145 mg, 38%) as a light yellow solid: LC/MS m/e calcd for $C_{21}H_{21}N_3O_4$ (M+H)$^+$: 380.42, observed: 380.0.

Example 20

2-[3-(4-Fluoro-benzoylamino)-phenyl]-3,3-dimethyl-1,2,3,4-tetrahydro-quinoline-6-carboxylic acid

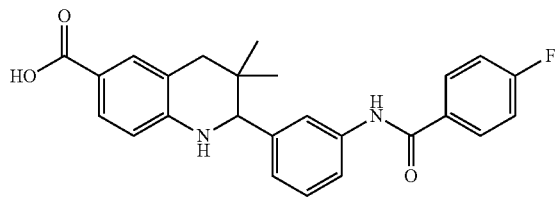 [SMILES: CC1(C)Cc2cc(C(=O)O)ccc2NC1c1cccc(NC(=O)c2ccc(F)cc2)c1]

A solution of 4-fluoro-benzoic acid (119 mg, 0.85 mmol) and 1,1'-carbonyldiimidazole (179 mg, 1.1 mmol) in N,N-dimethylformamide (1.5 mL) was stirred at 70° C. for 1 h. Then a solution of 2-(3-amino-phenyl)-3,3-dimethyl-1,2,3,4-tetrahydro-quinoline-6-carboxylic acid (200 mg, 0.68 mmol) in N,N-dimethylformamide (1.5 mL) was added and the mixture was allowed to stir at 50° C. for 3 h. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-(4-fluoro-benzoylamino)-phenyl]-3,3-dimethyl-1,2,3,4-tetrahydro-quinoline-6-carboxylic acid (44 mg, 15%) as a white solid: LC/MS m/e calcd for $C_{25}H_{23}FN_2O_3$ (M+H)$^+$: 419.47, observed: 419.1.

Example 21

3,3-Dimethyl-2-{3-[(morpholine-4-carbonyl)-amino]-phenyl}-1,2,3,4-tetrahydro-quinoline-6-carboxylic acid

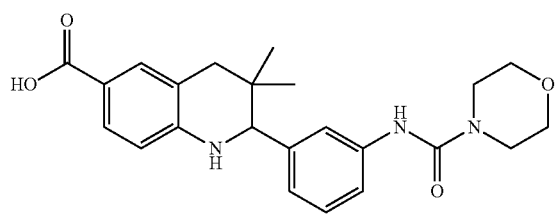 [SMILES: CC1(C)Cc2cc(C(=O)O)ccc2NC1c1cccc(NC(=O)N2CCOCC2)c1]

To a solution of 2-(3-amino-phenyl)-3,3-dimethyl-1,2,3,4-tetrahydro-quinoline-6-carboxylic acid ethyl ester (324 mg, 1 mmol) in dichloromethane (5 mL) and pyridine (0.5 mL, 6 mmol) was added a solution of morpholine-4-carbonyl chloride (0.12 mL, 1 mmol) in dichloromethane (2 mL) dropwise at 0° C. The reaction mixture was stirred at 25° C. for 5 h. Then the reaction mixture was extracted with dichloromethane (2×50 mL), washed with water, dried over anhydrous sodium sulfate and concentrated in vacuo to afford 3,3-dimethyl-2-{3-[(morpholine-4-carbonyl)-amino]-phenyl}-1,2,3,4-tetrahydro-quinoline-6-carboxylic acid ethyl ester (437 mg, 100%) as a brown oil which was used for next step without further purification: LC/MS m/e calcd for $C_{25}H_{31}N_3O_4$ (M+H)$^+$: 438.54, observed: 438.2.

A mixture of 3,3-dimethyl-2-{3-[(morpholine-4-carbonyl)-amino]-phenyl}-1,2,3,4-tetrahydro-quinoline-6-carboxylic acid ethyl ester (437 mg, 1 mmol) in methanol (10 mL) and tetrahydrofuran (20 mL), 30% sodium hydroxide in water (10 mL) was stirred at 55° C. for 32 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 3,3-dimethyl-2-{3-[(morpholine-4-carbonyl)-amino]-phenyl}-1,2,3,4-tetrahydro-quinoline-6-carboxylic acid (90 mg, 22%) as a white solid: LC/MS m/e calcd for $C_{23}H_{27}N_3O_4$ (M+H)$^+$: 410.49, observed: 410.2.

Example 22

3,3-Dimethyl-2-{3-[(piperidine-1-carbonyl)-amino]-phenyl}-1,2,3,4-tetrahydro-quinoline-6-carboxylic acid

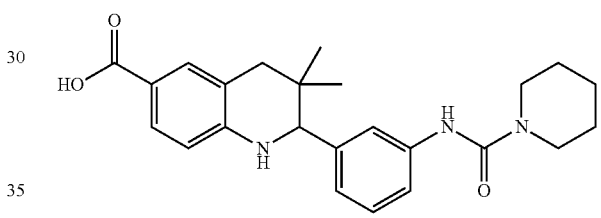

To a solution of 2-(3-amino-phenyl)-3,3-dimethyl-1,2,3,4-tetrahydro-quinoline-6-carboxylic acid ethyl ester (648 mg, 2 mmol) in dichloromethane (5 mL) and pyridine (1 mL, 12 mmol) was added a solution of piperidine-1-carbonyl chloride (0.275 mL, 2.2 mmol) in dichloromethane (2 mL) dropwise at 0° C. The reaction mixture was stirred at 25° C. for 5 h. Then the reaction mixture was extracted with dichloromethane (2×50 mL), washed with water, dried over anhydrous sodium sulfate and concentrated in vacuo to afford 3,3-dimethyl-2-{3-[(piperidine-1-carbonyl)-amino]-phenyl}-1,2,3,4-tetrahydro-quinoline-6-carboxylic acid ethyl ester (870 mg, 100%) as a brown oil which was used for next step without further purification: LC/MS m/e calcd for $C_{26}H_{33}N_3O_3$ (M+H)$^+$: 436.57, observed: 436.2.

A mixture of 3,3-dimethyl-2-{3-[(piperidine-1-carbonyl)-amino]-phenyl}-1,2,3,4-tetrahydro-quinoline-6-carboxylic acid ethyl ester (870 mg, 2 mmol) in methanol (15 mL) and tetrahydrofuran (20 mL), 30% sodium hydroxide in water (10 mL) was stirred at 60° C. for 12 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 3,3-dimethyl-2-{3-[(piperidine-1-carbonyl)-amino]-phenyl}-1,2,3,4-tetrahydro-quinoline-6-carboxylic acid (365 mg, 44%) as a white solid: LC/MS m/e calcd for $C_{24}H_{29}N_3O_3$ (M+H)$^+$: 408.52, observed: 408.2.

Example 23

{[3,3-Dimethyl-2-(3-morpholin-4-yl-phenyl)-1,2,3,4-tetrahydro-quinoline-6-carboxyl]-methyl-amino}-acetic acid

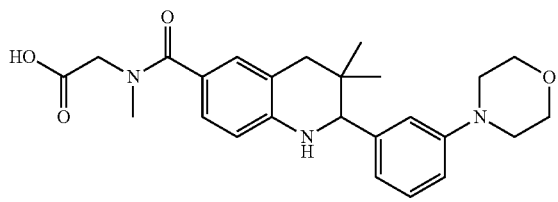 [SMILES: CN(CC(=O)O)C(=O)c1ccc2c(c1)CC(C)(C)C(c1cccc(N3CCOCC3)c1)N2]

A mixture of 3,3-dimethyl-2-(3-morpholin-4-yl-phenyl)-1,2,3,4-tetrahydro-quinoline-6-carboxylic acid (100 mg, 0.27 mmol), methylamino-acetic acid ethyl ester (51 mg, 0.33 mmol) and o-(7-azabenzotriazol-1-yl)-N,N,N',N'-tetramethyluronium hexafluorophosphate (156 mg, 0.41 mmol) in dichloromethane (3 mL) and triethyl-amine (0.12 mL, 0.82 mmol) was stirred at 25° C. for 12 h. Then the reaction mixture was extracted with dichloromethane (2×100 mL), washed with water, dried over anhydrous sodium sulfate and concentrated in vacuo to afford {[3,3-dimethyl-2-(3-morpholin-4-yl-phenyl)-1,2,3,4-tetrahydro-quinoline-6-carboxyl]-methyl-amino}-acetic acid ethyl ester (120 mg, 95%) as a brown oil which was used for next step without further purification: LC/MS m/e calcd for $C_{27}H_{35}N_3O_4$ (M+H)$^+$: 466.60, observed: 466.2.

A mixture of {[3,3-dimethyl-2-(3-morpholin-4-yl-phenyl)-1,2,3,4-tetrahydro-quinoline-6-carboxyl]-methyl-amino}-acetic acid ethyl ester (120 mg, 0.26 mmol) in methanol (2 mL) and tetrahydrofuran (10 mL), 2M lithium hydroxide in water (8 mL) was stirred at 50° C. for 12 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded {[3,3-dimethyl-2-(3-morpholin-4-yl-phenyl)-1,2,3,4-tetrahydro-quinoline-6-carboxyl]-methyl-amino}-acetic acid (45 mg, 39%) as a white solid: LC/MS m/e calcd for $C_{25}H_{31}N_3O_4$ (M+H)$^+$: 438.54, observed: 438.5.

Example 24

1-[3,3-Dimethyl-2-(3-morpholin-4-yl-phenyl)-1,2,3,4-tetrahydro-quinoline-6-carboxyl]-pyrrolidine-2-carboxylic acid

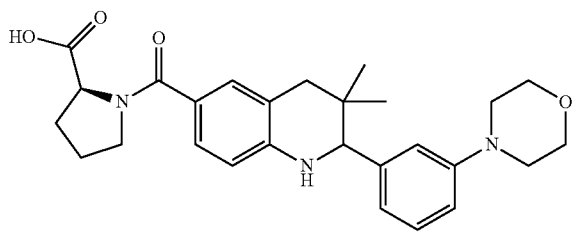 [SMILES: CC1(C)Cc2cc(C(=O)N3CCC[C@H]3C(=O)O)ccc2NC1c1cccc(N2CCOCC2)c1]

A mixture of 3,3-dimethyl-2-(3-morpholin-4-yl-phenyl)-1,2,3,4-tetrahydro-quinoline-6-carboxylic acid (100 mg, 0.27 mmol), pyrrolidine-2-carboxylic acid methyl ester (55 mg, 0.33 mmol) and o-(7-azabenzotriazol-1-yl)-N,N,N',N'-tetramethyluronium hexafluorophosphate (156 mg, 0.41 mmol) in dichloromethane (3 mL) and triethyl-amine (0.12 mL, 0.82 mmol) was prepared. The reaction mixture was stirred at 25° C. for 12 h. Then the reaction mixture was extracted with dichloromethane (2×100 mL), washed with water, dried over anhydrous sodium sulfate and concentrated in vacuo to afford 1-[3,3-dimethyl-2-(3-morpholin-4-yl-phenyl)-1,2,3,4-tetrahydro-quinoline-6-carboxyl]-pyrrolidine-2-carboxylic acid methyl ester (125 mg, 96%) as a brown oil which was used for next step without further purification: LC/MS m/e calcd for $C_{28}H_{35}N_3O_4$ (M+H)$^+$: 478.61, observed: 478.2.

A mixture of 1-[3,3-dimethyl-2-(3-morpholin-4-yl-phenyl)-1,2,3,4-tetrahydro-quinoline-6-carboxyl]-pyrrolidine-2-carboxylic acid methyl ester (125 mg, 0.26 mmol) in tetrahydrofuran (10 mL) and 2M lithium hydroxide in water (8 mL) was stirred at 50° C. for 12 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 1-[3,3-dimethyl-2-(3-morpholin-4-yl-phenyl)-1,2,3,4-tetrahydro-quinoline-6-carboxyl]-pyrrolidine-2-carboxylic acid (65 mg, 54%) as a white solid: LC/MS m/e calcd for $C_{27}H_{33}N_3O_4$ (M+H)$^+$: 464.58, observed: 463.9.

Example 25

2-(3-(N,N-dimethylsulfamoylamino)phenyl)-3,3-dimethyl-1,2,3,4-tetrahydroquinoline-6-carboxylic acid

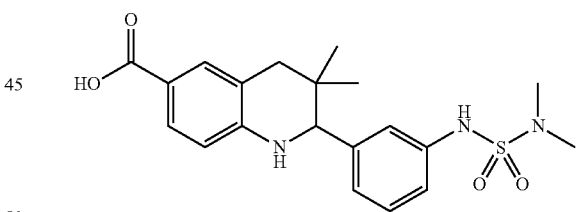

To a solution of 2-(3-amino-phenyl)-3,3-dimethyl-1,2,3,4-tetrahydro-quinoline-6-carboxylic acid ethyl ester (648 mg, 2 mmol) in dichloromethane (5 mL) and pyridine (0.97 mL, 2.2 mmol) was added a solution of dimethylsulfamoylchloride (0.24 mL, 2.2 mmol) in dichloromethane (2 mL) dropwise at 0° C. The reaction mixture was stirred at 25° C. for 16 h. Then the reaction mixture was extracted with dichloromethane (2×50 mL), washed with water, dried over anhydrous sodium sulfate and concentrated in vacuo to afford ethyl 2-(3-(N,N-dimethylsulfamoylamino)phenyl)-3,3-dimethyl-1,2,3,4-tetrahydroquinoline-6-carboxylate (862 mg, 100%) as a brown oil which was used for next step without further purification: LC/MS m/e calcd for $C_{22}H_{29}N_3O_4S$ (M+H)$^+$: 432.56, observed: 432.2.

A mixture of ethyl 2-(3-(N,N-dimethylsulfamoylamino)phenyl)-3,3-dimethyl-1,2,3,4-tetrahydroquinoline-6-carboxylate (862 mg, 2 mmol) in methanol (10 mL) and tetrahydrofuran (20 mL), 30% sodium hydroxide in water (10 mL) was prepared. The reaction mixture was stirred at 60° C. for 5 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-(3-(N,N-dimethylsulfamoylamino)phenyl)-3,3-dimethyl-1,2,3,4-tetrahydroquinoline-6-carboxylic acid (45 mg, 5%) as a white solid: LC/MS m/e calcd for $C_{20}H_{25}N_3O_4S$ (M+H)$^+$: 404.50, observed: 404.1.

Example 26

3,3-Dimethyl-2-[3-(2-oxo-3-phenyl-imidazolidin-1-yl)-phenyl]-1,2,3,4-tetrahydro-quinoline-6-carboxylic acid A mixture of 2-(3-bromo-phenyl)-3,3-dimethyl-1,2,3,4-tetrahydro-quinoline-6-carboxylic acid (720 mg, 2 mmol), imidazolidin-2-one (861 mg, 10 mmol), copper(I) iodide (229 mg, 1.2 mmol), N,N-dimethylglycine hydrochloride (224 g, 1.6 mmol) and potassium carbonate (829 mg, 6 mmol) in dimethyl sulfoxide (5 mL) was stirred at 120° C. for 12 h. Then the reaction mixture cooled to room temperature. Iodobenzene (2.17 mL, 20 mmol), copper(I) iodide (229 mg, 1.2 mmol), N,N-dimethylglycine hydrochloride (224 g, 1.6 mmol) and potassium carbonate (829 mg, 6 mmol) was added. The reaction mixture was stirred at 120° C. for 12 h. Then the reaction mixture cooled to room temperature. The reaction mixture was extracted with ethyl acetate (2×200 mL), washed with water (2×50 mL) and saturated aqueous ammonium chloride solution (2×50 mL), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 3,3-dimethyl-2-[3-(2-oxo-3-phenyl-imidazolidin-1-yl)-phenyl]-1,2,3,4-tetrahydroquinoline-6-carboxylic acid (82 mg, 9%) as a white solid: LC/MS m/e calcd for $C_{27}H_{27}N_3O_3$ (M+H)$^+$: 442.53, observed: 442.1.

Example 27

3,3-Dimethyl-2-{3-[(4-methyl-piperazine-1-carbonyl)-amino]-phenyl}-1,2,3,4-tetrahydro-quinoline-6-carboxylic acid

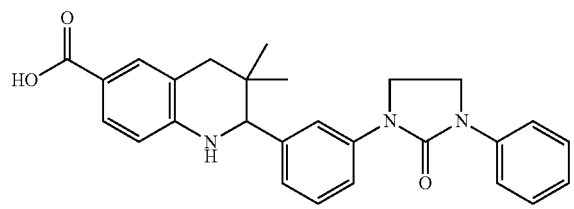 [SMILES: CC1(C)Cc2cc(C(=O)O)ccc2NC1c1cccc(N2CCN(c3ccccc3)C2=O)c1]

To a solution of 2-(3-amino-phenyl)-3,3-dimethyl-1,2,3,4-tetrahydro-quinoline-6-carboxylic acid ethyl ester (441 mg, 1.36 mmol) in dichloromethane (5 mL) and pyridine (1.1 mL, 13.6 mmol) was added 4-methyl-piperazine-1-carbonyl chloride hydrochloride (297 mg, 1.49 mmol) at 0° C. The reaction mixture was stirred at 25° C. for 5 h. Then the reaction mixture was extracted with dichloromethane (2×50 mL), washed with water, dried over anhydrous sodium sulfate and concentrated in vacuo to afford 3,3-dimethyl-2-{3-[(4-methyl-piperazine-1-carbonyl)-amino]-phenyl}-1,2,3,4-tetrahydro-quinoline-6-carboxylic acid ethyl ester (612 mg, 100%) as a brown oil which was used for next step without further purification: LC/MS m/e calcd for $C_{26}H_{34}N_4O_3$ (M+H)$^+$: 451.59, observed: 451.2.

A mixture of 3,3-dimethyl-2-{3-[(4-methyl-piperazine-1-carbonyl)-amino]-phenyl}-1,2,3,4-tetrahydro-quinoline-6-carboxylic acid ethyl ester (612 mg, 1.36 mmol) in methanol (15 mL) and tetrahydrofuran (20 mL), 30% sodium hydroxide in water (10 mL) was stirred at 60° C. for 12 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 3,3-dimethyl-2-{3-[(4-methyl-piperazine-1-carbonyl)-amino]-phenyl}-1,2,3,4-tetrahydro-quinoline-6-carboxylic acid (90 mg, 22%) as a white solid: LC/MS m/e calcd for $C_{24}H_{30}N_4O_3$ (M+H)$^+$: 423.53, observed: 423.2.

Example 28

2-[3-(6-Methanesulfonylaminocarbonyl-3,3-dimethyl-1,2,3,4-tetrahydro-quinolin-2-yl)-phenylamino]-2-methyl-propionic acid

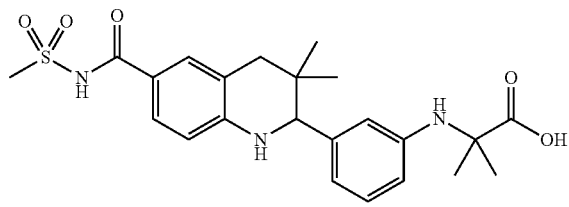 [SMILES: CC(C)(Nc1cccc(C2Nc3ccc(C(=O)NS(C)(=O)=O)cc3CC2(C)C)c1)C(=O)O]

A mixture of N-[2-(3-Amino-phenyl)-3,3-dimethyl-1,2,3,4-tetrahydro-quinoline-6-carbonyl]-methanesulfonamide (0.37 g, 1 mmol), 2-bromo-2-methyl-propionic acid methyl ester (0.39 mL, 3 mmol) and potassium carbonate (690 mg, 5 mmol) in N,N-dimethylformamide (6 mL) was stirred at 25° C. for 96 h. Then the reaction mixture was extracted with ethyl acetate (2×100 mL), washed with water, dried over anhydrous sodium sulfate and concentrated in vacuo to afford 2-[3-(6-methanesulfonylaminocarbonyl-3,3-dimethyl-1,2,3,4-tetrahydro-quinolin-2-yl)-phenylamino]-2-methyl-propionic acid ethyl ester (47 mg, 10%) as a brown oil which was used for next step without further purification: LC/MS m/e calcd for $C_{24}H_{31}N_3O_5S$ (M+H)$^+$: 474.60, observed: 474.1.

A mixture of 2-[3-(6-methanesulfonylaminocarbonyl-3,3-dimethyl-1,2,3,4-tetrahydro-quinolin-2-yl)-phenylamino]-2-methyl-propionic acid ethyl ester (47 mg, 0.1 mmol) in methanol (10 mL) and tetrahydrofuran (30 mL), 30% sodium hydroxide in water (5 mL) was stirred at 50° C. for 5 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-(6-methanesulfonyl-aminocarbonyl-3,3-dimethyl-1,2,3,4-tetrahydro-quinolin-2-yl)-phenylamino]-2-methyl-propionic acid (4 mg, 8%) as a white solid: LC/MS m/e calcd for $C_{23}H_{29}N_3O_5S$ (M+H)$^+$: 460.57, observed: 460.0.

Example 29

2-[3-(2-Hydroxy-1,1-dimethyl-ethylamino)-phenyl]-3,3-dimethyl-1,2,3,4-tetrahydro-quinoline-6-carboxylic acid

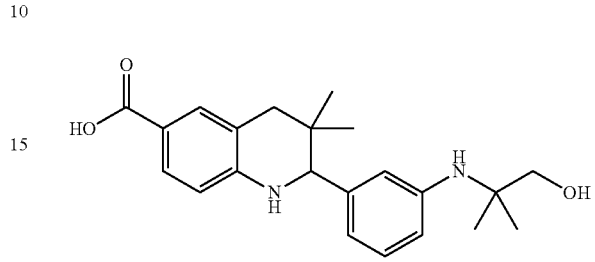

A mixture of 2-(3-bromo-phenyl)-3,3-dimethyl-1,2,3,4-tetrahydro-quinoline-6-carboxylic acid (360 mg, 1 mmol), 2-amino-2-methyl-propan-1-ol (0.48 mL, 5 mmol), copper(I) iodide (115 mg, 0.6 mmol), N,N-dimethylglycine hydrochloride (112 g, 0.8 mmol) and potassium carbonate (415 mg, 3 mmol) in dimethyl sulfoxide (5 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-(2-hydroxy-1,1-dimethyl-ethylamino)-phenyl]-3,3-dimethyl-1,2,3,4-tetrahydro-quinoline-6-carboxylic acid (8 mg, 2%) as a white powder: LC/MS m/e calcd for $C_{22}H_{28}N_2O_3$ (M+H)$^+$: 369.48, observed: 369.1.

Example 30

3,3-Dimethyl-2-[3-(trimethyl-ureido)-phenyl]-1,2,3,4-tetrahydro-quinoline-6-carboxylic acid

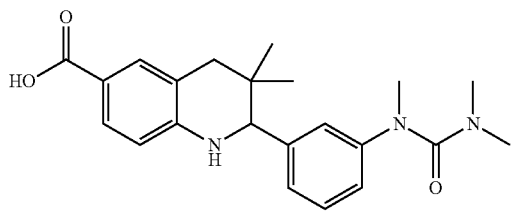 [SMILES: CN(C)C(=O)N(C)c1cccc(C2Nc3ccc(C(=O)O)cc3CC2(C)C)c1]

A mixture of 2-(3-bromo-phenyl)-3,3-dimethyl-1,2,3,4-tetrahydro-quinoline-6-carboxylic acid ethyl ester (970 mg, 2.5 mmol), methylamine hydrochloride (844 mg, 12.5 mmol), copper(I) iodide (285 mg, 1.5 mmol), N,N-dimethylglycine hydrochloride (280 g, 2 mmol) and potassium carbonate (3.455 g, 25 mmol) in dimethyl sulfoxide (15 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo to afford 3,3-dimethyl-2-(3-methylamino-phenyl)-1,2,3,4-tetrahydro-quinoline-6-carboxylic acid ethyl ester (761 mg, 90%) as a light yellow solid which was used for next step without further purification: LC/MS m/e calcd for $C_{21}H_{26}N_2O_2$ (M+H)$^+$: 339.45, observed: 339.2.

To a solution of 3,3-dimethyl-2-(3-methylamino-phenyl)-1,2,3,4-tetrahydro-quinoline-6-carboxylic acid ethyl ester (338 mg, 1 mmol) in dichloromethane (5 mL) and pyridine (0.5 mL, 6 mmol) was added a solution of dimethylcarbamyl chloride (0.1 mL, 1.1 mmol) in dichloromethane (2 mL) dropwise at 0° C. The reaction mixture was stirred at 25° C. for 12 h. Then the reaction mixture was extracted with dichloromethane (2×50 mL), washed with water, dried over anhydrous sodium sulfate and concentrated in vacuo to afford 3,3-dimethyl-2-[3-(trimethyl-ureido)-phenyl]-1,2,3,4-tetrahydro-quinoline-6-carboxylic acid ethyl ester (409 mg, 100%) as a brown oil which was used for next step without further purification: LC/MS m/e calcd for $C_{24}H_{31}N_3O_3$ (M+H)$^+$: 410.53, observed: 410.1.

A mixture of 3,3-dimethyl-2-[3-(trimethyl-ureido)-phenyl]-1,2,3,4-tetrahydro-quinoline-6-carboxylic acid ethyl ester (409 mg, 1 mmol) in methanol (5 mL) and tetrahydrofuran (10 mL), 30% sodium hydroxide in water (5 mL) was stirred at 60° C. for 36 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 3,3-dimethyl-2-[3-(trimethyl-ureido)-phenyl]-1,2,3,4-tetrahydro-quinoline-6-carboxylic acid (100 mg, 26%) as a yellow solid: LC/MS m/e calcd for $C_{22}H_{27}N_3O_3$ (M+H)$^+$: 382.48, observed: 382.1.

Example 31

3,3-Dimethyl-2-[3-(1-methyl-ureido)-phenyl]-1,2,3,4-tetrahydro-quinoline-6-carboxylic acid

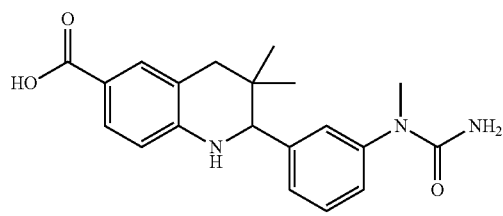 [SMILES: CN(C(N)=O)c1cccc(C2Nc3ccc(C(=O)O)cc3CC2(C)C)c1]

To a solution of 3,3-dimethyl-2-(3-methylamino-phenyl)-1,2,3,4-tetrahydro-quinoline-6-carboxylic acid ethyl ester (169 mg, 0.5 mmol) in acetic acid (2 mL) and water (4 mL) was added a solution of sodium cyanate (65 mg, 1 mmol) in water (2 mL) dropwise at 35° C. The reaction mixture was stirred at 35° C. for 3 h. Then the reaction mixture was extracted with ethyl acetate (2×50 mL), washed with water, dried over anhydrous sodium sulfate and concentrated in vacuo to afford 3,3-dimethyl-2-[3-(1-methyl-ureido)-phenyl]-1,2,3,4-tetrahydro-quinoline-6-carboxylic acid ethyl ester (190 mg, 100%) as a brown oil which was used for next step without further purification: LC/MS m/e calcd for $C_{22}H_{27}N_3O_3$ (M+H)$^+$: 382.48, observed: 382.1.

A mixture of 3,3-dimethyl-2-[3-(1-methyl-ureido)-phenyl]-1,2,3,4-tetrahydro-quinoline-6-carboxylic acid ethyl ester (190 mg, 0.5 mmol) in methanol (5 mL) and tetrahydrofuran (10 mL), 30% sodium hydroxide in water (10 mL) was stirred at 60° C. for 36 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 3,3-dimethyl-2-[3-(1-methyl-ureido)-phenyl]-1,2,3,4-tetrahydro-quinoline-6-carboxylic acid (28 mg, 15%) as a white solid: LC/MS m/e calcd for C20H23N3O3 (M+H)$^+$: 354.42, observed: 354.1.

Example 32

2-[3-(1-Isopropyl-ureido)-phenyl]-3,3-dimethyl-1,2,3,4-tetrahydro-quinoline-6-carboxylic acid

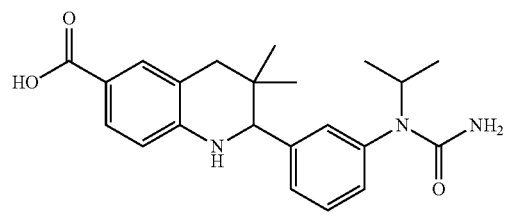 [SMILES: CC(C)N(C(N)=O)c1cccc(C2Nc3ccc(C(=O)O)cc3CC2(C)C)c1]

A mixture of 2-(3-bromo-phenyl)-3,3-dimethyl-1,2,3,4-tetrahydro-quinoline-6-carboxylic acid ethyl ester (970 mg, 2.5 mmol), isopropylamine (1 mL, 12.5 mmol), copper(I) iodide (285 mg, 1.5 mmol), N,N-dimethylglycine hydrochloride (280 g, 2 mmol), and potassium carbonate (3.455 g, 25 mmol) in dimethyl sulfoxide (15 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo to afford 2-(3-isopropylamino-phenyl)-3,3-dimethyl-1,2,3,4-tetrahydro-quinoline-6-carboxylic acid ethyl ester (915 mg, 90%) as a light yellow solid which was used for next step without further purification: LC/MS m/e calcd for $C_{23}H_{30}N_2O_2$ (M+H)$^+$: 367.51, observed: 367.2.

To a solution of 2-(3-isopropylamino-phenyl)-3,3-dimethyl-1,2,3,4-tetrahydro-quinoline-6-carboxylic acid ethyl ester (310 mg, 0.85 mmol) in acetic acid (2 mL) and water (2 mL) was added a solution of sodium cyanate (110 mg, 1.7 mmol) in water (2 mL) dropwise at 40° C. The reaction mixture was stirred at 40° C. for 4 h. Then the reaction mixture was extracted with ethyl acetate (2×50 mL), washed with water, dried over anhydrous sodium sulfate and concentrated in vacuo to afford 2-[3-(1-isopropyl-ureido)-phenyl]-3,3-dimethyl-1,2,3,4-tetrahydro-quinoline-6-carboxylic acid ethyl ester (347 mg, 100%) as a brown oil which was used for next step without further purification: LC/MS m/e calcd for $C_{24}H_{31}N_3O_3$ (M+H)$^+$: 410.53, observed: 410.1.

A mixture of 2-[3-(1-isopropyl-ureido)-phenyl]-3,3-dimethyl-1,2,3,4-tetrahydro-quinoline-6-carboxylic acid ethyl ester (347 mg, 0.85 mmol) in methanol (5 mL) and tetrahydrofuran (10 mL), 30% sodium hydroxide in water (10 mL) was stirred at 60° C. for 12 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-(1-isopropyl-ureido)-phenyl]-3,3-dimethyl-1,2,3,4-tetrahydro-quinoline-6-carboxylic acid (29 mg, 8%) as a white solid: LC/MS m/e calcd for $C_{22}H_{27}N_3O_3$ (M+H)$^+$: 382.48, observed: 382.1.

Example 33

2-[3-(2-Amino-1,1-dimethyl-ethoxy)-phenyl]-3,3-dimethyl-1,2,3,4-tetrahydro-quinoline-6-carboxylic acid

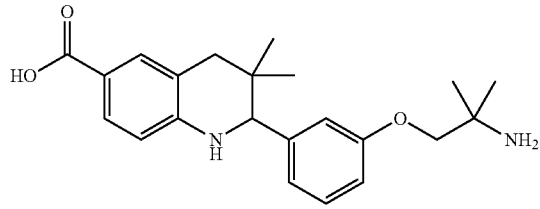 [SMILES: CC(C)(N)COc1cccc(C2Nc3ccc(C(=O)O)cc3CC2(C)C)c1]

A mixture of 2-(3-bromo-phenyl)-3,3-dimethyl-1,2,3,4-tetrahydro-quinoline-6-carboxylic acid (360 mg, 1 mmol), 2-amino-2-methyl-propan-1-ol (0.48 mL, 5 mmol), copper(I) iodide (115 mg, 0.6 mmol), N,N-dimethylglycine hydrochloride (112 g, 0.8 mmol) and potassium carbonate (415 mg, 3 mmol) in dimethyl sulfoxide (5 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-(2-amino-1,1-dimethyl-ethoxy)-phenyl]-3,3-dimethyl-1,2,3,4-tetrahydro-quinoline-6-carboxylic acid (7 mg, 2%) as a white powder: LC/MS m/e calcd for $C_{22}H_{28}N_2O_3$ (M+H)$^+$: 369.48, observed: 369.1.

Example 34

2-[3-(4,4-Dimethyl-2-oxo-oxazolidine-3-yl)-phenyl]-3,3-dimethyl-1,2,3,4-tetrahydro-quinoline-6-carboxylic acid

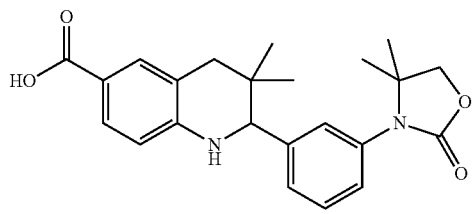 [SMILES: CC1(C)Cc2cc(C(=O)O)ccc2NC1c1cccc(N2C(=O)OCC2(C)C)c1]

A mixture of 2-(3-bromo-phenyl)-3,3-dimethyl-1,2,3,4-tetrahydro-quinoline-6-carboxylic acid (360 mg, 1 mmol), 4,4-dimethyl-oxazolidin-2-one (575 mg, 5 mmol), copper(I) iodide (115 mg, 0.6 mmol), N,N-dimethylglycine hydrochloride (112 g, 0.8 mmol), and potassium carbonate (415 mg, 3 mmol) in dimethyl sulfoxide (5 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-(4,4-dimethyl-2-oxo-oxazolidine-3-yl)-phenyl]-3,3-dimethyl-1,2,3,4-tetrahydro-quinoline-6-carboxylic acid (3 mg, 0.4%) as a light yellow oil: LC/MS m/e calcd for $C_{23}H_{26}N_2O_4$ (M+H)$^+$: 395.47, observed: 395.1.

Example 35

3,3-Dimethyl-2-{3-[(pyrrolidine-1-carbonyl)-amino]-phenyl}-1,2,3,4-tetrahydro-quinoline-6-carboxylic acid

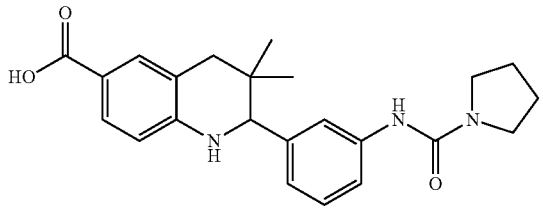 [SMILES: CC1(C)Cc2cc(C(=O)O)ccc2NC1c1cccc(NC(=O)N2CCCC2)c1]

To a solution of 2-(3-amino-phenyl)-3,3-dimethyl-1,2,3,4-tetrahydro-quinoline-6-carboxylic acid ethyl ester (648 mg, 2 mmol) in dichloromethane (5 mL) and pyridine (1 mL, 12 mmol) was added a solution of pyrrolidine-1-carbonyl chloride (0.243 mL, 2.2 mmol) in dichloromethane (2 mL) dropwise at 0° C. The reaction mixture was stirred at 25° C. for 16 h. Then the reaction mixture was extracted with dichloromethane (2×50 mL), washed with water, dried over anhydrous sodium sulfate and concentrated in vacuo to afford 3,3-dimethyl-2-{3-[(pyrrolidine-1-carbonyl)-amino]-phenyl}-1,2,3,4-tetrahydro-quinoline-6-carboxylic acid ethyl ester (842 mg, 100%) as a brown oil which was used for next step without further purification: LC/MS m/e calcd for $C_{25}H_{31}N_3O_3$ (M+H)$^+$: 422.54, observed: 422.2.

A mixture of 3,3-dimethyl-2-{3-[(pyrrolidine-1-carbonyl)-amino]-phenyl}-1,2,3,4-tetrahydro-quinoline-6-carboxylic acid ethyl ester (842 mg, 2 mmol) in methanol (10 mL) and tetrahydrofuran (20 mL), 30% sodium hydroxide in water (10 mL) was stirred at 60° C. for 6 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 3,3-dimethyl-2-{3-[(pyrrolidine-1-carbonyl)-amino]-phenyl}-1,2,3,4-tetrahydro-quinoline-6-carboxylic acid (350 mg, 44%) as a white solid: LC/MS m/e calcd for $C_{23}H_{27}N_3O_3$ (M+H)$^+$: 394.49, observed: 394.2.

Example 36

2-[3-(3,3-Diethyl-ureido)-phenyl}-3,3-dimethyl-1,2,3,4-tetrahydro-quinoline-6-carboxylic acid

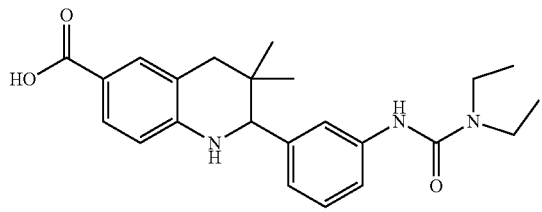

To a solution of 2-(3-amino-phenyl)-3,3-dimethyl-1,2,3,4-tetrahydro-quinoline-6-carboxylic acid ethyl ester (648 mg, 2 mmol) in dichloromethane (5 mL) and pyridine (1 mL, 12 mmol) was added a solution of diethylcarbamyl chloride (0.28 mL, 2.2 mmol) in dichloromethane (2 mL) dropwise at 0° C. The reaction mixture was stirred at 25° C. for 16 h. Then the reaction mixture was extracted with dichloromethane (2×50 mL), washed with water, dried over anhydrous sodium sulfate and concentrated in vacuo to afford 2-[3-(3,3-diethyl-ureido)-phenyl]-3,3-dimethyl-1,2,3,4-tetrahydro-quinoline-6-carboxylic acid ethyl ester (846 mg, 100%) as a brown oil which was used for next step without further purification: LC/MS m/e calcd for $C_{25}H_{33}N_3O_3$ (M+H)$^+$: 424.56, observed: 424.2.

A mixture of 2-[3-(3,3-diethyl-ureido)-phenyl]-3,3-dimethyl-1,2,3,4-tetrahydro-quinoline-6-carboxylic acid ethyl ester (846 mg, 2 mmol) in methanol (10 mL) and tetrahydrofuran (15 mL), 30% sodium hydroxide in water (10 mL) was stirred at 60° C. for 16 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-(3,3-diethyl-ureido)-phenyl}-3,3-dimethyl-1,2,3,4-tetrahydro-quinoline-6-carboxylic acid (80 mg, 10%) as a white solid: LC/MS m/e calcd for $C_{23}H_{29}N_3O_3$ (M+H)$^+$: 396.51, observed: 396.2.

Example 37

2-[3-(6-Chloro-3,3-dimethyl-1,2,3,4-tetrahydro-quinolin-2-yl)-phenylamino]-2-methyl-propionic acid

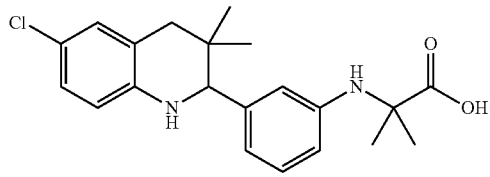 [SMILES: CC(C)(Nc1cccc(C2Nc3ccc(Cl)cc3CC2(C)C)c1)C(=O)O]

A mixture of 4-chloro-phenylamine (6.4 g, 50 mmol) and 3-nitro-benzaldehyde (8.31 g, 55 mmol) in ethanol (100 mL) was prepared. The reaction mixture was heated to reflux for 3 h. Then the reaction mixture cooled to room temperature. The solvent was removed in vacuo and the residue was washed with ether to afford (4-chloro-phenyl)-(3-nitro-benzylidene)-amine (12 g, 92%) as a light yellow oil: LC/MS m/e calcd for $C_{13}H_9ClN_2O_2$ (M+H)$^+$: 261.68, observed: 261.0.

To a mixture of (4-chloro-phenyl)-(3-nitro-benzylidene)-amine (12 g, 46 mmol) and ytterbium(III) triflate hydrate (2.85 g, 4.6 mmol) in dry tetrahydrofuran (100 mL) at 25° C. was added isobutyraldehyde (4.64 mL, 51 mmol) and water (0.83 mL, 46 mmol) dropwise. The reaction mixture was stirred at 25° C. for 3 h. Then the reaction mixture was concentrated in vacuo and the residue was extracted with ethyl acetate (2×200 mL), washed with brine, dried over anhydrous sodium sulfate and concentrated in vacuo to afford 6-chloro-3,3-dimethyl-2-(3-nitro-phenyl)-1,2,3,4-tetrahydro-quinolin-4-ol (14.3 g, 93%) as a light yellow oil: LC/MS m/e calcd for $C_{17}H_{17}ClN_2O_3$ (M+H)$^+$: 333.79, observed: 315.0.

To a mixture of 6-chloro-3,3-dimethyl-2-(3-nitro-phenyl)-1,2,3,4-tetrahydro-quinolin-4-ol (14.3 g, 43 mmol) and triethylsilane (20 mL) at 25° C. was added trifluoroacetic acid (5 mL) dropwise. The resulting mixture was stirred at 25° C. for 1 h. Then the reaction mixture was concentrated in vacuo and the residue was extracted with ethyl acetate (2×200 mL), washed with saturated aqueous sodium bicarbonate solution (2×100 mL), dried over anhydrous sodium sulfate and concentrated in vacuo. Purification on flash silica gel chromatography (silica gel from QingDao, 200-300 mesh, glass column from Shanghai SD company) (10% ethyl acetate/hexanes) to afford 6-chloro-3,3-dimethyl-2-(3-nitro-phenyl)-1,2,3,4-tetrahydro-quinoline (10.5 g, 77%) as a white solid: LC/MS m/e calcd for $C_{17}H_{17}ClN_2O_2$ (M+H)$^+$: 317.79, observed: 317.0.

To a mixture of 6-chloro-3,3-dimethyl-2-(3-nitro-phenyl)-1,2,3,4-tetrahydro-quinoline (10.5 g, 33 mmol) in ethanol 95% (150 mL) and 10% hydrochloric acid (10 mL) was added iron (3.72 g, 66 mmol). The reaction mixture was stirred at 95° C. for 3 h. Then the insoluble solid was filtered off and the filtrate was concentrated in vacuo and the residue was extracted with ethyl acetate (2×200 mL), washed with 30% sodium hydroxide in water (2×100 mL), dried over anhydrous sodium sulfate and concentrated in vacuo to afford 3-(6-chloro-3,3-dimethyl-1,2,3,4-tetrahydro-quinolin-2-yl)-phenylamine (7.8 g, 82%) as a yellow solid: LC/MS m/e calcd for $C_{17}H_{19}ClN_2$ (M+H)$^+$: 287.81, observed: 287.0.

A mixture of 3-(6-chloro-3,3-dimethyl-1,2,3,4-tetrahydro-quinolin-2-yl)-phenylamine (1.5 g, 5.25 mmol), 2-bromo-2-methyl-propionic acid methyl ester (2.85 g, 15.7 mmol) and potassium carbonate (3.62 g, 26.25 mmol) in N,N-dimethyl-formamide (10 mL) was stirred at 25° C. for 5 d. Then the reaction mixture was extracted with ethyl acetate (2×100 mL), washed with water, dried over anhydrous sodium sulfate and concentrated in vacuo. Purification on flash silica gel chromatography (silica gel from QingDao, 200-300 mesh, glass column from Shanghai SD company) (30% ethyl acetate/hexanes) to afford 2-[3-(6-chloro-3,3-dimethyl-1,2,3,4-tetrahydro-quinolin-2-yl)-phenylamino]-2-methyl-propionic acid methyl ester (450 mg, 22%) as a brown oil: LC/MS m/e calcd for $C_{22}H_{27}ClN_2O_2$ (M+H)$^+$: 387.93, observed: 387.1.

A mixture of 2-[3-(6-chloro-3,3-dimethyl-1,2,3,4-tetrahydro-quinolin-2-yl)-phenylamino]-2-methyl-propionic acid methyl ester (450 mg, 1.16 mmol) in tetrahydrofuran (30 mL), 2M lithium hydroxide in water (15 mL) was stirred at 25° C. for 12 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-(6-chloro-3,3-dimethyl-1,2,3,4-tetrahydro-quinolin-2-yl)-phenylamino]-2-methyl-propionic acid (50 mg, 11%) as a white solid: LC/MS m/e calcd for $C_{21}H_{25}ClN_2O_2$ (M+H)$^+$: 373.90, observed: 373.1.

Example 38

2-[3-(6-Cyano-3,3-dimethyl-1,2,3,4-tetrahydro-quinolin-2-yl)-phenylamino]-2-methyl-propionic acid

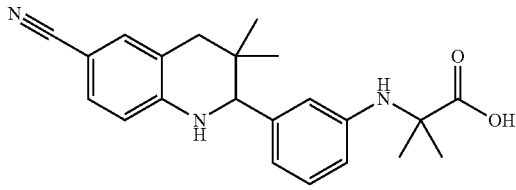 [SMILES: CC(C)(Nc1cccc(C2Nc3ccc(C#N)cc3CC2(C)C)c1)C(=O)O]

A mixture of 4-amino-benzonitrile (11.8 g, 100 mmol) and 3-nitro-benzaldehyde (16.6 g, 110 mmol) in ethanol (100 mL) was prepared. The reaction mixture was heated to reflux for 3 h. Then the reaction mixture cooled to room temperature. The solvent was removed in vacuo and the residue was washed with ether to afford 4-[(3-nitro-benzylidene)-amino]-benzonitrile (21 g, 83%) as a white solid: LC/MS m/e calcd for $C_{14}H_9N_3O_2$ (M+H)$^+$: 252.25, observed: 252.1.

To a mixture of 4-[(3-nitro-benzylidene)-amino]-benzonitrile (21 g, 84 mmol) and ytterbium(III) triflate hydrate (5.21 g, 8.4 mmol) in dry tetrahydrofuran (150 mL) at 25° C. was added isobutyraldehyde (8.4 mL, 92 mmol) and water (1.5 mL, 84 mmol) dropwise. The reaction mixture was stirred at 25° C. for 15 h. Then the reaction mixture was concentrated in vacuo and the residue was extracted with ethyl acetate (2×200 mL), washed with brine, dried over anhydrous sodium sulfate and concentrated in vacuo to afford 4-hydroxy-3,3-dimethyl-2-(3-nitro-phenyl)-1,2,3,4-tetrahydro-quinoline-6-carbonitrile (25 g, 92%) as a light yellow oil: LC/MS m/e calcd for $C_{18}H_{17}N_3O_3$ (M+H)$^+$: 324.35, observed: 324.1.

To a mixture of 4-hydroxy-3,3-dimethyl-2-(3-nitro-phenyl)-1,2,3,4-tetrahydro-quinoline-6-carbonitrile (25 g, 77 mmol) and triethylsilane (50 mL) at 25° C. was added trifluoroacetic acid (25 mL) dropwise. The resulting mixture was stirred at 25° C. for 1 h. Then the reaction mixture was concentrated in vacuo and the residue was extracted with ethyl acetate (2×200 mL), washed with saturated aqueous sodium bicarbonate solution (2×100 mL), dried over anhydrous sodium sulfate and concentrated in vacuo. Purification on flash silica gel chromatography (silica gel from QingDao, 200-300 mesh, glass column from Shanghai SD company) (10% ethyl acetate/hexanes) to afford 3,3-dimethyl-2-(3-nitro-phenyl)-1,2,3,4-tetrahydro-quinoline-6-carbonitrile (4 g, 16%) as a white solid: LC/MS m/e calcd for $C_{18}H_{17}N_3O_2$ (M+H)$^+$: 308.36, observed: 308.1.

To a mixture of 3,3-dimethyl-2-(3-nitro-phenyl)-1,2,3,4-tetrahydro-quinoline-6-carbonitrile (4 g, 13 mmol) in ethanol 95% (150 mL) and 10% hydrochloric acid (10 mL) was added iron (2.18 g, 39.2 mmol). The reaction mixture was stirred at 95° C. for 6 h. Then the insoluble solid was filtered off and the filtrate was concentrated in vacuo and the residue was extracted with ethyl acetate (2×200 mL), washed with 30% sodium hydroxide in water (2×100 mL), dried over anhydrous sodium sulfate and concentrated in vacuo to afford 2-(3-amino-phenyl)-3,3-dimethyl-1,2,3,4-tetrahydro-quinoline-6-carbonitrile (0.9 g, 25%) as a yellow solid: LC/MS m/e calcd for $C_{18}H_{19}N_3$ (M+H)$^+$: 278.37, observed: 278.1.

A mixture of 2-(3-amino-phenyl)-3,3-dimethyl-1,2,3,4-tetrahydro-quinoline-6-carbonitrile (0.64 g, 2.3 mmol), 2-bromo-2-methyl-propionic acid methyl ester (1.25 g, 6.9 mmol) and potassium carbonate (1.59 g, 11.5 mmol) in N,N-dimethylformamide (6 mL) was stirred at 25° C. for 5 d. Then the reaction mixture was extracted with ethyl acetate (2×100 mL), washed with water, dried over anhydrous sodium sulfate and concentrated in vacuo. Purification on flash silica gel chromatography (silica gel from QingDao, 200-300 mesh, glass column from Shanghai SD company) (30% ethyl acetate/hexanes) to afford 2-[3-(6-cyano-3,3-dimethyl-1,2,3,4-tetrahydro-quinolin-2-yl)-phenylamino]-2-methyl-propionic acid methyl ester (500 mg, 43%) as a brown oil: LC/MS m/e calcd for $C_{23}H_{27}N_3O_2$ (M+H)$^+$: 378.49, observed: 378.2.

A mixture of 2-[3-(6-cyano-3,3-dimethyl-1,2,3,4-tetrahydro-quinolin-2-yl)-phenylamino]-2-methyl-propionic acid methyl ester (500 mg, 1.32 mmol) in tetrahydrofuran (30 mL), 2M lithium hydroxide in water (15 mL) was prepared. The reaction mixture was stirred at 25° C. for 36 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-(6-cyano-3,3-dimethyl-1,2,3,4-tetrahydro-quinolin-2-yl)-phenylamino]-2-methyl-propionic acid (36 mg, 7%) as a white solid: LC/MS m/e calcd for $C_{22}H_{25}N_3O_2$ (M+H)$^+$: 364.46, observed: 364.1.

Example 39

2-[3-(6-Methanesulfonylaminocarbonyl-3,3-dimethyl-1,2,3,4-tetrahydro-quinolin-2-yl)-phenylamino]-2,N-dimethyl-propionamide

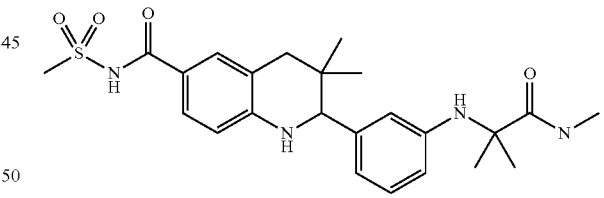

A mixture of 2-(3-bromo-phenyl)-3,3-dimethyl-1,2,3,4-tetrahydro-quinoline-6-carboxylic acid ethyl ester (388 mg, 1 mmol), 2-amino-2-methyl-propionic acid (516 mg, 5 mmol), copper(I) iodide (114 mg, 0.6 mmol), N,N-dimethylglycine hydrochloride (112 mg, 0.8 mmol) and potassium carbonate (415 mg, 3 mmol) in dimethyl sulfoxide (10 mL) was stirred at 120° C. for 12 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo to afford 2-[3-(1-carboxy-1-methyl-ethylamino)-phenyl]-3,3-dimethyl-1,2,3,4-tetrahydro-quinoline-6-carboxylic acid ethyl ester (410 mg, 100%) as a light yellow oil which was used for next step without further purification: LC/MS m/e calcd for $C_{24}H_{30}N_2O_4$ (M+H)$^+$: 411.52, observed: 411.1.

2-[3-(1-carboxy-1-methyl-ethylamino)-phenyl]-3,3-dimethyl-1,2,3,4-tetrahydro-quinoline-6-carboxylic acid ethyl ester (410 mg, 1 mmol), methylamine hydrochloride (203 mg, 3 mmol) and o-(7-azabenzotriazol-1-yl)-N,N,N',N'-tetramethyluronium hexafluorophosphate (570 mg, 1.5 mmol) in dichloromethane (5 mL) and triethyl-amine (0.5 mL, 3 mmol) was stirred at 25° C. for 12 h. Then the reaction mixture was extracted with dichloromethane (2×100 mL), washed with water, dried over anhydrous sodium sulfate and concentrated in vacuo to afford 3,3-dimethyl-2-[3-(1-methyl-1-methylcarbamoyl-ethylamino)-phenyl]-1,2,3,4-tetrahydro-quinoline-6-carboxylic acid ethyl ester (0.4 g, 94%) as a brown oil which was used for next step without further purification: LC/MS m/e calcd for C25H33N3O3 (M+H)+: 424.56, observed: 424.1.

A mixture of 3,3-dimethyl-2-[3-(1-methyl-1-methylcarbamoyl-ethylamino)-phenyl]-1,2,3,4-tetrahydro-quinoline-6-carboxylic acid ethyl ester (0.4 g, 0.95 mmol) in methanol (10 mL) and tetrahydrofuran (20 mL), 30% sodium hydroxide in water (5 mL) was stirred at 50° C. for 16 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 3,3-dimethyl-2-[3-(1-methyl-1-methylcarbamoyl-ethylamino)-phenyl]-1,2,3,4-tetrahydro-quinoline-6-carboxylic acid (130 mg, 34%) as a white solid: LC/MS m/e calcd for C23H29N3O3 (M+H)+: 396.51, observed: 396.2.

To a suspension of methanesulfonamide (85 mg, 0.89 mmol) in N,N-dimethylformamide (2 mL) was added sodium hydride (36 mg, 0.89 mmol). The resulting mixture was stirred at 25° C. for 1 h. A solution of 3,3-dimethyl-2-[3-(1-methyl-1-methylcarbamoyl-ethylamino)-phenyl]-1,2,3,4-tetrahydro-quinoline-6-carboxylic acid (50 mg, 0.127 mmol) and 1,1'-carbonyldiimidazole (41 mg, 0.253 mmol) in N,N-dimethylformamide (1.5 mL) was stirred at 70° C. for 1 h. Then the above suspension of methanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[3-(6-methanesulfonylaminocarbonyl-3,3-dimethyl-1,2,3,4-tetrahydro-quinolin-2-yl)-phenylamino]-2,N-dimethyl-propionamide (15 mg, 25%) as a white solid: LC/MS m/e calcd for $C_{24}H_{32}N_4O_4S$ (M+H)+: 473.61, observed: 473.1.

Example 40

2-[3-(1-Dimethylcarbamoyl-1-methyl-ethylamino)-phenyl]-3,3-dimethyl-1,2,3,4-tetrahydro-quinoline-6-carboxylic acid

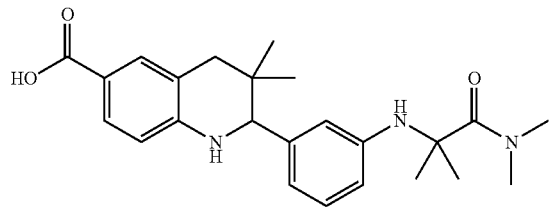 [SMILES: CN(C)C(=O)C(C)(C)Nc1cccc(C2Nc3ccc(C(=O)O)cc3CC2(C)C)c1]

2-[3-(1-carboxy-1-methyl-ethylamino)-phenyl]-3,3-dimethyl-1,2,3,4-tetrahydro-quinoline-6-carboxylic acid ethyl ester (820 mg, 2 mmol), dimethylamine hydrochloride (490 mg, 6 mmol) and o-(7-azabenzotriazol-1-yl)-N,N,N',N'-tetramethyluronium hexafluorophosphate (1140 mg, 3 mmol) in dichloromethane (5 mL) and triethyl-amine (1.7 mL, 12 mmol) was stirred at 25° C. for 12 h. Then the reaction mixture was extracted with dichloromethane (2×100 mL), washed with water, dried over anhydrous sodium sulfate and concentrated in vacuo to afford 2-[3-(1-dimethylcarbamoyl-1-methyl-ethylamino)-phenyl]-3,3-dimethyl-1,2,3,4-tetrahydro-quinoline-6-carboxylic acid ethyl ester (0.8 g, 91%) as a brown oil which was used for next step without further purification: LC/MS m/e calcd for $C_{26}H_{35}N_3O_3$ (M+H)+: 438.59, observed: 438.2.

A mixture of 2-[3-(1-dimethylcarbamoyl-1-methyl-ethylamino)-phenyl]-3,3-dimethyl-1,2,3,4-tetrahydro-quinoline-6-carboxylic acid ethyl ester (0.8 g, 1.8 mmol) in methanol (10 mL) and tetrahydrofuran (20 mL), 30% sodium hydroxide in water (10 mL) was stirred at 50° C. for 12 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-(1-dimethylcarbamoyl-1-methyl-ethylamino)-phenyl]-3,3-dimethyl-1,2,3,4-tetrahydro-quinoline-6-carboxylic acid (45 mg, 6%) as a white solid: LC/MS m/e calcd for $C_{24}H_{31}N_3O_3$ (M+H)+: 410.53, observed: 410.1.

Example 41

2-[3-(1,1-Dimethyl-2-morpholin-4-yl-2-oxo-ethylamino)-phenyl]-3,3-dimethyl-1,2,3,4-tetrahydro-quinoline-6-carboxylic acid

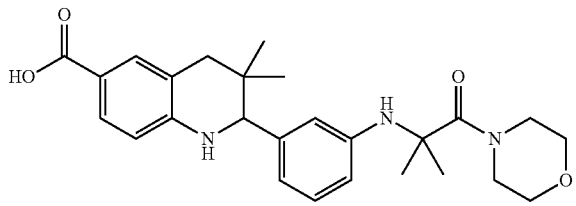 [SMILES: CC(C)(Nc1cccc(C2Nc3ccc(C(=O)O)cc3CC2(C)C)c1)C(=O)N1CCOCC1]

2-[3-(1-carboxy-1-methyl-ethylamino)-phenyl]-3,3-dimethyl-1,2,3,4-tetrahydro-quinoline-6-carboxylic acid ethyl ester (820 mg, 2 mmol), morpholine (0.53 mL, 6 mmol) and o-(7-azabenzotriazol-1-yl)-N,N,N',N'-tetramethyluronium hexafluorophosphate (1140 mg, 3 mmol) in dichloromethane (10 mL) and triethyl-amine (1.7 mL, 12 mmol) was stirred at 25° C. for 36 h. Then the reaction mixture was extracted with dichloromethane (2×100 mL), washed with water, dried over anhydrous sodium sulfate and concentrated in vacuo to afford 2-[3-(1,1-dimethyl-2-morpholin-4-yl-2-oxo-ethylamino)-phenyl]-3,3-dimethyl-1,2,3,4-tetrahydro-quinoline-6-carboxylic acid ethyl ester (0.87 g, 91%) as a brown oil which was used for next step without further purification: LC/MS m/e calcd for C28H37N3O4 (M+H)+: 480.62, observed: 480.1.

A mixture of 2-[3-(1,1-dimethyl-2-morpholin-4-yl-2-oxo-ethylamino)-phenyl]-3,3-dimethyl-1,2,3,4-tetrahydro-quinoline-6-carboxylic acid ethyl ester (0.87 g, 1.8 mmol) in methanol (10 mL) and tetrahydrofuran (20 mL), 30% sodium hydroxide in water (10 mL) was stirred at 50° C. for 12 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-(1,1-dimethyl-2-morpholin-4-yl-2-oxo-ethylamino)-phenyl]-3,3-dimethyl-1,2,3,4-tetrahydro-quinoline-6-carboxylic acid (35 mg, 4%) as a light yellow solid: LC/MS m/e calcd for $C_{26}H_{33}N_3O_4$ (M+H)$^+$: 452.57, observed: 452.1.

Example 42

2-{3-[1,1-Dimethyl-2-(4-methyl-piperazin-1-yl)-2-oxo-ethylamino]-phenyl}-3,3-dimethyl-1,2,3,4-tetrahydro-quinoline-6-carboxylic acid

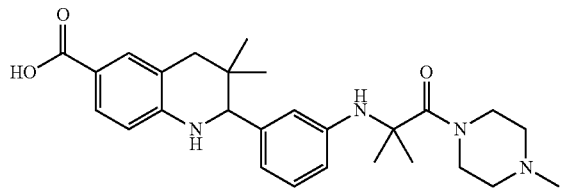 [SMILES: CN1CCN(C(=O)C(C)(C)Nc2cccc(C3Nc4ccc(C(=O)O)cc4CC3(C)C)c2)CC1]

2-[3-(1-carboxy-1-methyl-ethylamino)-phenyl]-3,3-dimethyl-1,2,3,4-tetrahydro-quinoline-6-carboxylic acid ethyl ester (820 mg, 2 mmol), 1-methyl-piperazine (0.67 mL, 6 mmol) and o-(7-azabenzotriazol-1-yl)-N,N,N',N'-tetramethyluronium hexafluorophosphate (1140 mg, 3 mmol) in dichloromethane (10 mL) and triethyl-amine (1.7 mL, 12 mmol) was stirred at 25° C. for 24 h. Then the reaction mixture was extracted with dichloromethane (2×100 mL), washed with water, dried over anhydrous sodium sulfate and concentrated in vacuo to afford 2-{3-[1,1-dimethyl-2-(4-methyl-piperazin-1-yl)-2-oxo-ethylamino]-phenyl}-3,3-dimethyl-1,2,3,4-tetrahydro-quinoline-6-carboxylic acid ethyl ester (0.895 g, 91%) as a brown oil which was used for next step without further purification: LC/MS m/e calcd for $C_{29}H_{40}N_4O_3$ (M+H)$^+$: 493.67, observed: 493.2.

A mixture of 2-{3-[1,1-dimethyl-2-(4-methyl-piperazin-1-yl)-2-oxo-ethylamino]-phenyl}-3,3-dimethyl-1,2,3,4-tetrahydro-quinoline-6-carboxylic acid ethyl ester (0.895 g, 1.8 mmol) in methanol (10 mL) and tetrahydrofuran (20 mL), 30% sodium hydroxide in water (5 mL) was stirred at 50° C. for 12 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-{3-[1,1-dimethyl-2-(4-methyl-piperazin-1-yl)-2-oxo-ethylamino]-phenyl}-3,3-dimethyl-1,2,3,4-tetrahydro-quinoline-6-carboxylic acid (4 mg, 0.4%) as a white solid: LC/MS m/e calcd for $C_{27}H_{36}N_4O_3$ (M+H)$^+$: 465.61, observed: 465.2.

Example 43

N-isopropyl-2-[3-(6-methanesulfonylaminocarbonyl-3,3-dimethyl-1,2,3,4-tetrahydro-quinolin-2-yl)-phenylamino]-2-methyl-propionamide

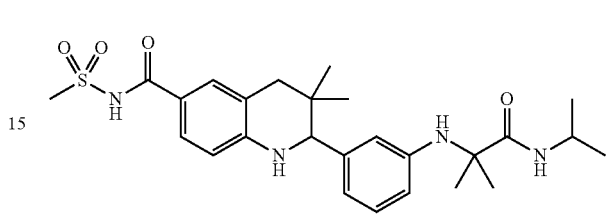

2-[3-(1-carboxy-1-methyl-ethylamino)-phenyl]-3,3-dimethyl-1,2,3,4-tetrahydro-quinoline-6-carboxylic acid ethyl ester (820 mg, 2 mmol), isopropylamine (0.5 mL, 6 mmol) and o-(7-azabenzotriazol-1-yl)-N,N,N',N'-tetramethyluronium hexafluorophosphate (1140 mg, 3 mmol) in dichloromethane (10 mL) and triethyl-amine (0.84 mL, 6 mmol) was stirred at 25° C. for 5 h. Then the reaction mixture was extracted with dichloromethane (2×100 mL), washed with water, dried over anhydrous sodium sulfate and concentrated in vacuo to afford 2-[3-(1-isopropylcarbamoyl-1-methyl-ethylamino)-phenyl]-3,3-dimethyl-1,2,3,4-tetrahydro-quinoline-6-carboxylic acid ethyl ester (0.85 g, 94%) as a brown oil which was used for next step without further purification: LC/MS m/e calcd for $C_{27}H_{37}N_3O_3$ (M+H)$^+$: 452.61, observed: 452.2.

A mixture of 2-[3-(1-isopropylcarbamoyl-1-methyl-ethylamino)-phenyl]-3,3-dimethyl-1,2,3,4-tetrahydro-quinoline-6-carboxylic acid ethyl ester (0.85 g, 1.88 mmol) in methanol (10 mL) and tetrahydrofuran (20 mL), 30% sodium hydroxide in water (10 mL) was stirred at 50° C. for 12 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-(1-isopropylcarbamoyl-1-methyl-ethylamino)-phenyl]-3,3-dimethyl-1,2,3,4-tetrahydro-quinoline-6-carboxylic acid (260 mg, 30%) as a white solid: LC/MS m/e calcd for $C_{25}H_{33}N_3O_3$ (M+H)$^+$: 424.56, observed: 424.1.

To a suspension of methanesulfonamide (158 mg, 1.66 mmol) in N,N-dimethylformamide (2 mL) was added sodium hydride (66 mg, 1.66 mmol). The resulting mixture was stirred at 25° C. for 1 h. A solution of 2-[3-(1-isopropylcarbamoyl-1-methyl-ethylamino)-phenyl]-3,3-dimethyl-1,2,3,4-tetrahydro-quinoline-6-carboxylic acid (100 mg, 0.236 mmol) and 1,1'-carbonyldiimidazole (77 mg, 0.473 mmol) in N,N-dimethylformamide (1.5 mL) was stirred at 70° C. for 1 h. Then the above suspension of methanesulfonamide and sodium hydride in N,N-dimethylformamide was added and the mixture was allowed to stir at 25° C. for 12 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-isopropyl-2-[3-(6-methanesulfonyl aminocarbonyl-3,3-dimethyl-1,2,3,4- tetrahydro-quinolin-2-yl)-phenylamino]-2-methyl-propionamide (25 mg, 21%) as a white solid: LC/MS m/e calcd for $C_{26}H_{36}N_4O_4S$ (M+H)$^+$: 501.67, observed: 501.1.

Example 44

2-[3-(1-Carboxy-cyclopropylamino)-phenyl]-3,3-dimethyl-1,2,3,4-tetrahydro-quinoline-6-carboxylic acid

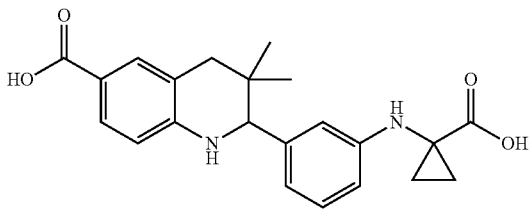 [SMILES: CC1(C)Cc2cc(C(=O)O)ccc2NC1c1cccc(NC2(C(=O)O)CC2)c1]

A mixture of 2-(3-bromo-phenyl)-3,3-dimethyl-1,2,3,4-tetrahydro-quinoline-6-carboxylic acid (500 mg, 1.39 mmol), 1-amino-cyclopropanecarboxylic acid (700 mg, 6.95 mmol), copper(I) iodide (159 mg, 0.85 mmol), N,N-dimethylglycine hydrochloride (155 g, 1.11 mmol) and potassium carbonate (577 mg, 4.17 mmol) in dimethyl sulfoxide (5 mL) was stirred at 120° C. for 12 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-(1-carboxy-cyclopropylamino)-phenyl]-3,3-dimethyl-1,2,3,4-tetrahydro-quinoline-6-carboxylic acid (410 mg, 77%) as a white solid: LC/MS m/e calcd for $C_{22}H_{24}N_2O_4$ (M+H)$^+$: 381.45, observed: 381.2.

Example 45

2-[3-(3,3-Dimethyl-6-trifluoromethyl-1,2,3,4-tetrahydro-quinolin-2-yl)-phenylamino]-2-methyl-propionic acid

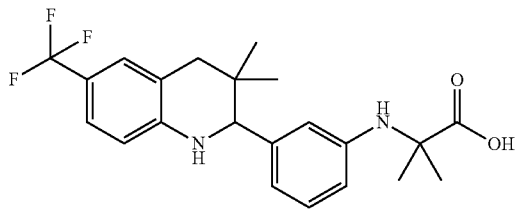 [SMILES: CC(C)(Nc1cccc(C2Nc3ccc(C(F)(F)F)cc3CC2(C)C)c1)C(=O)O]

A mixture of 4-trifluoromethyl-phenylamine (2.6 mL, 21 mmol) and 3-nitro-benzaldehyde (3.44 g, 23 mmol) in ethanol (100 mL) was prepared. The reaction mixture was heated to reflux for 3 h. Then the reaction mixture cooled to room temperature. The solvent was removed in vacuo and the residue was washed with ether to afford (3-nitro-benzylidene)-(4-trifluoromethyl-phenyl)-amine (5.88 g, 95%) as a light yellow oil: LC/MS m/e calcd for $C_{14}H_9F_3N_2O_2$ (M+H)$^+$: 295.24, observed: 295.1.

To a mixture of (3-nitro-benzylidene)-(4-trifluoromethyl-phenyl)-amine (5.88 g, 20 mmol) and ytterbium(III) triflate hydrate (1.24 g, 2 mmol) in dry tetrahydrofuran (50 mL) at 25° C. was added isobutyraldehyde (2 mL, 22 mmol) and water (0.36 mL, 20 mmol) dropwise. The reaction mixture was stirred at 25° C. for 72 h. Then the reaction mixture was concentrated in vacuo and the residue was extracted with ethyl acetate (2×200 mL), washed with brine, dried over anhydrous sodium sulfate and concentrated in vacuo to afford 3,3-dimethyl-2-(3-nitro-phenyl)-6-trifluoromethyl-1,2,3,4-tetrahydro-quinolin-4-ol (7.1 g, 96%) as a light yellow oil: LC/MS m/e calcd for $C_{18}H_{17}F_3N_2O_3$ (M+H)$^+$: 367.34, observed: 349.0.

To a mixture of 3,3-dimethyl-2-(3-nitro-phenyl)-6-trifluoromethyl-1,2,3,4-tetrahydro-quinolin-4-ol (7.1 g, 19 mmol) and triethylsilane (20 mL) at 25° C. was added trifluoroacetic acid (5 mL) dropwise. The resulting mixture was stirred at 25° C. for 1 h. Then the reaction mixture was concentrated in vacuo and the residue was extracted with ethyl acetate (2×200 mL), washed with saturated aqueous sodium bicarbonate solution (2×100 mL), dried over anhydrous sodium sulfate and concentrated in vacuo. Purification on flash silica gel chromatography (silica gel from QingDao, 200-300 mesh, glass column from Shanghai SD company) (10% ethyl acetate/hexanes) to afford 3,3-dimethyl-2-(3-nitro-phenyl)-6-trifluoromethyl-1,2,3,4-tetrahydro-quinoline (2.4 g, 36%) as a white solid: LC/MS m/e calcd for $C_{18}H_{17}F_3N_2O_2$ (M+H)$^+$: 351.34, observed: 351.1.

To a mixture of 3,3-dimethyl-2-(3-nitro-phenyl)-6-trifluoromethyl-1,2,3,4-tetrahydro-quinoline (2.4 g, 6.8 mmol) in ethanol 95% (100 mL) and 10% hydrochloric acid (5 mL) was added iron (1.2 g, 20 mmol). The reaction mixture was stirred at 95° C. for 3 h. Then the insoluble solid was filtered off and the filtrate was concentrated in vacuo and the residue was extracted with ethyl acetate (2×200 mL), washed with 30% sodium hydroxide in water (2×100 mL), dried over anhydrous sodium sulfate and concentrated in vacuo to afford 3-(3,3-dimethyl-6-trifluoromethyl-1,2,3,4-tetrahydro-quinolin-2-yl)-phenylamine (1.8 g, 86%) as a brown solid: LC/MS m/e calcd for $C_{18}H_{19}F_3N_2$ (M+H)$^+$: 321.36, observed: 321.1.

A mixture of 3-(3,3-dimethyl-6-trifluoromethyl-1,2,3,4-tetrahydro-quinolin-2-yl)-phenylamine (1.5 g, 4.7 mmol), 2-bromo-2-methyl-propionic acid methyl ester (2.55 g, 14.1 mmol) and potassium carbonate (3.24 g, 23.5 mmol) in N,N-dimethylformamide (12 mL) was stirred at 25° C. for 5 d. Then the reaction mixture was extracted with ethyl acetate (2×100 mL), washed with water, dried over anhydrous sodium sulfate and concentrated in vacuo. Purification on flash silica gel chromatography (silica gel from QingDao, 200-300 mesh, glass column from Shanghai SD company) (30% ethyl acetate/hexanes) to afford 2-[3-(3,3-dimethyl-6-trifluoromethyl-1,2,3,4-tetrahydro-quinolin-2-yl)-phenylamino]-2-methyl-propionic acid methyl ester (400 mg, 20%) as a brown oil. LC/MS m/e calcd for $C_{23}H_{27}F_3N_2O_2$ (M+H)$^+$: 421.48, observed: 421.1.

A mixture of 2-[3-(3,3-dimethyl-6-trifluoromethyl-1,2,3,4-tetrahydro-quinolin-2-yl)-phenylamino]-2-methyl-propionic acid methyl ester (400 mg, 0.95 mmol) in tetrahydrofuran (30 mL), 2M lithium hydroxide in water (15 mL) was stirred at 25° C. for 12 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-(3,3-dimethyl- 6-trifluoromethyl-1,2,3,4-tetrahydro-quinolin-2-yl)-phenylamino]-2-methyl-propionic acid (3 mg, 0.7%) as a light yellow oil: LC/MS m/e calcd for $C_{22}H_{25}F_3N_2O_2$ (M+H)$^+$: 407.45, observed: 407.2.

Example 46

2-[5-(4-tert-Butyl-phenyl)-pyridin-3-yl]-3,3-dimethyl-1,2,3,4-tetrahydro-quinoline-6-carboxylic acid

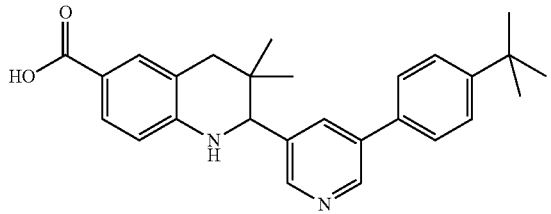 [SMILES: CC(C)(C)c1ccc(-c2cncc(C3Nc4ccc(C(=O)O)cc4CC3(C)C)c2)cc1]

A mixture of 4-amino-benzoic acid ethyl ester (8.06 g, 49 mmol), 5-bromo-pyridine-3-carbaldehyde (10 g, 54 mmol) and p-toluenesulfonic acid (190 mg, 1 mmol) in toluene (300 mL) was heated to reflux for 12 h. Then the reaction mixture cooled to room temperature. The solvent was removed in vacuo and the residue was washed with ether to afford 4-[(5-bromo-pyridin-3-ylmethylene)-amino]-benzoic acid ethyl ester (16.3 g, 100%) as a light yellow solid: LC/MS m/e calcd for $C_{15}H_{13}BrN_2O_2$ (M+H)$^+$: 334.19, observed: 334.1.

To a mixture of 4-[(5-bromo-pyridin-3-ylmethylene)-amino]-benzoic acid ethyl ester (16.3 g, 49 mmol) and ytterbium(III) triflate hydrate (3.1 g, 49 mmol) in dry tetrahydrofuran (100 mL) at 25° C. was added isobutyraldehyde (4.98 mL, 55 mmol) and water (0.89 mL, 49 mmol) dropwise. The reaction mixture was stirred at 25° C. for 12 h. Then the reaction mixture was concentrated in vacuo and the residue was extracted with ethyl acetate (2×200 mL), washed with brine, dried over anhydrous sodium sulfate and concentrated in vacuo to afford 2-(5-bromo-pyridin-3-yl)-4-hydroxy-3,3-dimethyl-1,2,3,4-tetrahydro-quinoline-6-carboxylic acid ethyl ester (16 g, 80%) as a light yellow oil which was used for next step without further purification: LC/MS m/e calcd for $C_{19}H_{21}BrN_2O_3$ (M+H)$^+$: 406.29, observed: 405.1.

To a mixture of 2-(5-bromo-pyridin-3-yl)-4-hydroxy-3,3-dimethyl-1,2,3,4-tetrahydro-quinoline-6-carboxylic acid ethyl ester (16 g, 39.5 mmol) and triethylsilane (40 mL) at 25° C. was added trifluoroacetic acid (20 mL) dropwise. The resulting mixture was stirred at 25° C. for 5 h. Then the reaction mixture was concentrated in vacuo and the residue was extracted with ethyl acetate (2×200 mL), washed with saturated aqueous sodium bicarbonate solution (2×100 mL), dried over anhydrous sodium sulfate and concentrated in vacuo. Purification on flash silica gel chromatography (silica gel from QingDao, 200-300 mesh, glass column from Shanghai SD company) (30% ethyl acetate/hexanes) to afford 2-(5-bromo-pyridin-3-yl)-3,3-dimethyl-1,2,3,4-tetrahydro-quinoline-6-carboxylic acid ethyl ester (4.4 g, 28%) as a yellow solid: LC/MS m/e calcd for $C_{19}H_{21}BrN_2O_2$ (M+H)$^+$: 390.30, observed: 390.9.

To a mixture of 2-(5-bromo-pyridin-3-yl)-3,3-dimethyl-1,2,3,4-tetrahydro-quinoline-6-carboxylic acid ethyl ester (778 mg, 2 mmol), 4-tert-butylphenylboronic acid (358 mg, 2 mmol) and tetrakis(triphenylphosphine)palladium(0) (232 mg, 0.2 mmol) in dioxane (10 mL) was added 2 M sodium carbonate solution in water (2 mL). The resulting mixture was subjected to microwave irradiation for 1 h at 110° C. The mixture was diluted with ethyl acetate (200 mL), washed with saturated aqueous sodium bicarbonate solution (50 mL×2), brine, dried over anhydrous sodium sulfate and then concentrated in vacuo to afford 2-[5-(4-tert-butyl-phenyl)-pyridin-3-yl]-3,3-dimethyl-1,2,3,4-tetrahydro-quinoline-6-carboxylic acid ethyl ester (880 mg, 99%) as a yellow solid: LC/MS m/e calcd for $C_{29}H_{34}N_2O_2$ (M+H)$^+$: 443.61, observed: 443.2.

A mixture of 2-[5-(4-tert-butyl-phenyl)-pyridin-3-yl]-3,3-dimethyl-1,2,3,4-tetrahydro-quinoline-6-carboxylic acid ethyl ester (880 mg, 1.99 mmol) in methanol (20 mL) and tetrahydrofuran (20 mL), 30% sodium hydroxide in water (10 mL) was stirred at 60° C. for 12 h. The mixture was neutralized with a 3 N aqueous hydrochloric acid solution and extracted with ethyl acetate (2×100 mL), washed with water, dried over anhydrous sodium sulfate and then concentrated in vacuo. The residue was re-crystallized from methanol to afford 2-[5-(4-tert-butyl-phenyl)-pyridin-3-yl]-3,3-dimethyl-1,2,3,4-tetrahydro-quinoline-6-carboxylic acid (800 mg, 97%) as a yellow solid: LC/MS m/e calcd for $C_{27}H_{30}N_2O_2$ (M+H)$^+$: 415.55, observed: 415.1.

Example 47

2-[3-(6-Cyclopropanesulfonylaminocarbonyl-3,3-dimethyl-1,2,3,4-tetrahydro-quinolin-2-yl)-phenylamino]-2,N-dimethyl-propionamide

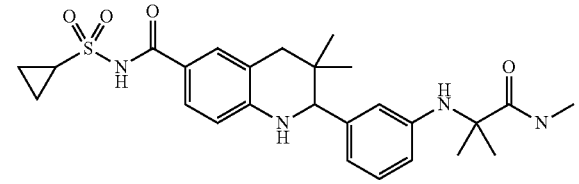 [SMILES: CNC(=O)C(C)(C)Nc1cccc(C2Nc3ccc(C(=O)NS(=O)(=O)C4CC4)cc3CC2(C)C)c1]

To a suspension of cyclopropanesulfonic acid amide (108 mg, 0.89 mmol) in N,N-dimethylformamide (2 mL) was added sodium hydride (36 mg, 0.89 mmol). The resulting mixture was stirred at 25° C. for 1 h. A solution of 3,3-dimethyl-2-[3-(1-methyl-1-methylcarbamoyl-ethylamino)-phenyl]-1,2,3,4-tetrahydro-quinoline-6-carboxylic acid (50 mg, 0.127 mmol) and 1,1'-carbonyldiimidazole (41 mg, 0.253 mmol) in N,N-dimethylformamide (1.5 mL) was stirred at 70° C. for 1 h. Then the above suspension of methanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[3-(6-cyclopropanesulfonylaminocarbonyl-3,3-dimethyl-1,2,3,4-tetrahydro-quinolin-2-yl)-phenylamino]-2,N-dimethyl-propionamide (5 mg, 7%) as a white solid: LC/MS m/e calcd for $C_{26}H_{34}N_4O_4S$ (M+H)$^+$: 499.65, observed: 499.1.

Example 48

2-[3-(6-Methanesulfonyl-3,3-dimethyl-1,2,3,4-tetrahydro-quinolin-2-yl)-phenylamino]-2-methyl-propionic acid

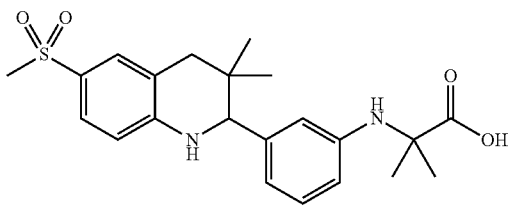 [SMILES: CC(C)(Nc1cccc(C2Nc3ccc(S(C)(=O)=O)cc3CC2(C)C)c1)C(=O)O]

A mixture of 4-methanesulfonyl-phenylamine (5.6 g, 33 mmol) and 3-nitro-benzaldehyde (5.45 g, 36 mmol) in ethanol (100 mL) was prepared. The reaction mixture was heated to reflux for 16 h. Then the reaction mixture cooled to room temperature. The solvent was removed in vacuo and the residue was washed with ether to afford (4-methanesulfonyl-phenyl)-(3-nitro-benzylidene)-amine (10 g, 99%) as a white solid: LC/MS m/e calcd for $C_{14}H_{12}N_2O_4S$ (M+H)$^+$: 305.33, observed: 305.1.

To a mixture of (4-methanesulfonyl-phenyl)-(3-nitro-benzylidene)-amine (10 g, 33 mmol) and ytterbium(III) triflate hydrate (2.05 g, 3.3 mmol) in dry tetrahydrofuran (100 mL) at 25° C. was added isobutyraldehyde (3.3 mL, 36.3 mmol) and water (0.6 mL, 33 mmol) dropwise. The reaction mixture was stirred at 25° C. for 16 h. Then the reaction mixture was concentrated in vacuo and the residue was extracted with ethyl acetate (2×200 mL), washed with brine, dried over anhydrous sodium sulfate and concentrated in vacuo to afford 6-methanesulfonyl-3,3-dimethyl-2-(3-nitro-phenyl)-1,2,3,4-tetrahydro-quinolin-4-ol (10 g, 92%) as a light yellow oil: LC/MS m/e calcd for $C_{18}H_{20}N_2O_5S$ (M+H)$^+$: 377.43, observed: 376.8.

To a mixture of 6-methanesulfonyl-3,3-dimethyl-2-(3-nitro-phenyl)-1,2,3,4-tetrahydro-quinolin-4-ol (10 g, 27 mmol) and triethylsilane (20 mL) at 25° C. was added trifluoroacetic acid (10 mL) dropwise. The resulting mixture was stirred at 25° C. for 1 h. Then the reaction mixture was concentrated in vacuo and the residue was extracted with ethyl acetate (2×200 mL), washed with saturated aqueous sodium bicarbonate solution (2×100 mL), dried over anhydrous sodium sulfate and concentrated in vacuo. Purification on flash silica gel chromatography (silica gel from QingDao, 200-300 mesh, glass column from Shanghai SD company) (50% ethyl acetate/hexanes) to afford 6-methanesulfonyl-3,3-dimethyl-2-(3-nitro-phenyl)-1,2,3,4-tetrahydro-quinoline (6.5 g, 16%) as a yellow solid: LC/MS m/e calcd for $C_{18}H_{20}N_2O_4S$ (M+H)$^+$: 361.44, observed: 360.8.

To a mixture of 6-methanesulfonyl-3,3-dimethyl-2-(3-nitro-phenyl)-1,2,3,4-tetrahydro-quinoline (6.5 g, 18 mmol) in ethanol 95% (100 mL) and 10% hydrochloric acid (10 mL) was added iron (3.04 g, 54 mmol). The reaction mixture was stirred at 95° C. for 5 h. Then the insoluble solid was filtered off and the filtrate was concentrated in vacuo and the residue was extracted with ethyl acetate (2×200 mL), washed with 30% sodium hydroxide in water (2×100 mL), dried over anhydrous sodium sulfate and concentrated in vacuo to afford 3-(6-methanesulfonyl-3,3-dimethyl-1,2,3,4-tetrahydro-quinolin-2-yl)-phenylamine (3.7 g, 25%) as a yellow solid: LC/MS m/e calcd for $C_{18}H_{22}N_2O_2S$ (M+H)$^+$: 331.45, observed: 331.1.

A mixture of 3-(6-methanesulfonyl-3,3-dimethyl-1,2,3,4-tetrahydro-quinolin-2-yl)-phenylamine (1 g, 3 mmol), 2-bromo-2-methyl-propionic acid methyl ester (1.65 g, 9 mmol) and potassium carbonate (2.07 g, 15 mmol) in N,N-dimethylformamide (10 mL) was stirred at 25° C. for 10 d. Then the reaction mixture was extracted with ethyl acetate (2×100 mL), washed with water, dried over anhydrous sodium sulfate and concentrated in vacuo. Purification on flash silica gel chromatography (silica gel from QingDao, 200-300 mesh, glass column from Shanghai SD company) (30% ethyl acetate/hexanes) to afford 2-[3-(6-methanesulfonyl-3,3-dimethyl-1,2,3,4-tetrahydro-quinolin-2-yl)-phenylamino]-2-methyl-propionic acid methyl ester (100 mg, 7%) as a brown oil: LC/MS m/e calcd for $C_{23}H_{30}N_2O_4S$ (M+H)$^+$: 431.57, observed: 431.1.

A mixture of 2-[3-(6-methanesulfonyl-3,3-dimethyl-1,2,3,4-tetrahydro-quinolin-2-yl)-phenylamino]-2-methyl-propionic acid methyl ester (100 mg, 0.23 mmol) in tetrahydrofuran (20 mL), 2M lithium hydroxide in water (10 mL) was stirred at 25° C. for 12 h. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-(6-methanesulfonyl-3,3-dimethyl-1,2,3,4-tetrahydro-quinolin-2-yl)-phenylamino]-2-methyl-propionic acid (19 mg, 7%) as a white solid: LC/MS m/e calcd for $C_{22}H_{28}N_2O_4S$ (M+H)$^+$: 417.54, observed: 417.0.

Example 49

N-[2-(4'-tert-Butyl-5-fluoro-biphenyl-3-yl)-3,3-dimethyl-1,2,3,4-tetrahydro-quinoline-6-carbonyl]-methanesulfonamide

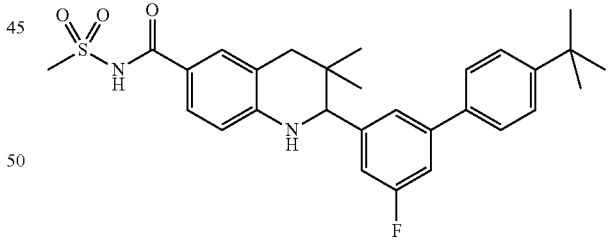

A mixture of 4-amino-benzoic acid ethyl ester (1.65 g, 10 mmol) and 3-bromo-5-fluoro-benzaldehyde (2.03 g, 10 mmol) in ethanol (20 mL) was heated to reflux for 2 h. Then the reaction mixture cooled to room temperature. The solvent was removed in vacuo and the residue was washed with ether to afford 4-{[1-(3-bromo-5-fluoro-phenyl)-methylidene]-amino}-benzoic acid ethyl ester (2.25 g, 64%) as a white solid: LC/MS m/e calcd for $C_{16}H_{13}BrFNO_2$ M$^+$: 350.2, observed: 350.2, 352.2.

To a mixture of 4-{[1-(3-bromo-5-fluoro-phenyl)-methylidene]-amino}-benzoic acid ethyl ester (2.25 g, 6.43 mmol) and ytterbium(III) triflate hydrate (0.40 g, 0.64 mmol) in dry tetrahydrofuran (10 mL) at 25° C. was added isobutyraldehyde (0.59 mL, 6.43 mmol) and water (0.12 mL, 6.43 mmol) dropwise. The reaction mixture was stirred at 25° C. for 5 h. Then the reaction mixture was concentrated in vacuo and the residue was extracted with ethyl acetate (2×100 mL), washed with brine, dried over anhydrous sodium sulfate and concentrated in vacuo to afford 2-(3-bromo-5-fluoro-phenyl)-4-hydroxy-3,3-dimethyl-1,2,3,4-tetrahydro-quinoline-6-carboxylic acid ethyl ester (2.33 g, 86%) as a light yellow oil: LC/MS m/e calcd for $C_{20}H_{21}BrFNO_3$ M+: 422.3, observed: 404.3, 406.3.

To a mixture of 2-(3-bromo-5-fluoro-phenyl)-4-hydroxy-3,3-dimethyl-1,2,3,4-tetrahydro-quinoline-6-carboxylic acid ethyl ester (3.3 g, 7.9 mmol) and triethylsilane (5 mL) at 25° C. was added trifluoroacetic acid (5 mL) dropwise. The resulting mixture was stirred at 25° C. for 1 h. Then the reaction mixture was concentrated in vacuo and the residue was extracted with ethyl acetate (2×20 mL), washed with saturated aqueous sodium bicarbonate solution (2×10 mL), dried over anhydrous sodium sulfate and concentrated in vacuo. Purification on flash silica gel chromatography (silica gel from QingDao, 200-300 mesh, glass column from Shanghai SD company) (10% ethyl acetate/hexanes) to afford 2-(3-bromo-5-fluoro-phenyl)-3,3-dimethyl-1,2,3,4-tetrahydro-quinoline-6-carboxylic acid ethyl ester (1.2 g, 16%) as a white solid: LC/MS m/e calcd for $C_{20}H_{21}BrFNO_2$ M+: 406.3, observed: 406.2, 408.2.

A mixture of 2-(3-bromo-5-fluoro-phenyl)-3,3-dimethyl-1,2,3,4-tetrahydro-quinoline-6-carboxylic acid ethyl ester (0.41 g, 1.0 mmol), 4-tert-butylbenzeneboronic acid (0.36 g, 2.0 mmol), bis(triphenylphosphine)palladium (II) chloride (70.2 mg, 0.1 mmol) and 2 M sodium carbonate (1.5 mL, 3.0 mmol) in dioxane (5 mL) was heated for 3 hours at 120° C. After cooling to room temperature, the mixture was treated with ethyl acetate (50 mL) and washed with water (20 mL). The organic layer was dried over anhydrous sodium sulfate and concentrated in vacuo. Purification on flash silica gel chromatography (silica gel from QingDao, 200-300 mesh, glass column from Shanghai SD company) (10% ethyl acetate/hexanes) to afford 2-(4'-tert-butyl-5-fluoro-biphenyl-3-yl)-3,3-dimethyl-1,2,3,4-tetrahydro-quinoline-6-carboxylic acid ethyl ester (0.17 g, 37%) as a white solid: LC/MS m/e calcd for $C_{30}H_{34}FNO_2$ (M+H)+: 460.6, observed: 460.3.

A mixture of 2-(4'-tert-butyl-5-fluoro-biphenyl-3-yl)-3,3-dimethyl-1,2,3,4-tetrahydro-quinoline-6-carboxylic acid ethyl ester (0.17 g, 0.37 mmol) in ethanol (3 mL) and tetrahydrofuran (5 mL), 30% sodium hydroxide in water (1 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford 2-(4'-tert-butyl-5-fluoro-biphenyl-3-yl)-3,3-dimethyl-1,2,3,4-tetrahydro-quinoline-6-carboxylic acid (0.13 g, 80%) as a white solid which was used for next step without further purification: LC/MS m/e calcd for $C_{28}H_{30}FNO_2$ (M+H)+: 432.6, observed: 432.3;

A mixture of 2-(4'-tert-butyl-5-fluoro-biphenyl-3-yl)-3,3-dimethyl-1,2,3,4-tetrahydro-quinoline-6-carboxylic acid (30 mg, 0.07 mmol), 1-3-dimethylaminopropyl-3-ethylcarbodiimide hydrochloride (20 mg, 0.10 mmol), 4-dimethylaminopyridine (12.2 mg, 0.10 mmol), methane sulfonamide (20 mg, 0.21 mmol) in dichloromethane (10 mL) was refluxed for 12 hours. Removal of the solvent afforded an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded N-[2-(4'-tert-butyl-5-fluoro-biphenyl-3-yl)-3,3-dimethyl-1,2,3,4-tetrahydro-quinoline-6-carbonyl]-methanesulfonamide (11 mg, 30%) as a light yellow solid: LC/MS m/e calcd for $C_{29}H_{33}FN_2O_3S$ (M+H)+: 509.66, observed: 509.2.

Example 50

N-[2-(3-Dimethylamino-5-fluoro-phenyl)-3,3-dimethyl-1,2,3,4-tetrahydro-quinoline-6-carbonyl]-methanesulfonamide

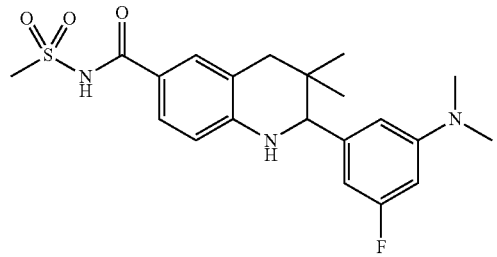

A mixture of 2-(3-bromo-5-fluoro-phenyl)-3,3-dimethyl-1,2,3,4-tetrahydro-quinoline-6-carboxylic acid ethyl ester (0.41 g, 1.0 mmol), dimethylamine hydrochloride (0.41 g, 5 mmol), copper (I) iodide (0.12 g, 0.6 mmol) and potassium hydroxide (0.34, 6.0 mmol) in DMSO (5 mL) was heated for 3 hours at 120° C. After cooling to room temperature, the mixture was treated with ethyl acetate (50 mL) and washed with water (20 mL). The organic layer was dried over anhydrous sodium sulfate and concentrated in vacuo. Purification on flash silica gel chromatography (silica gel from QingDao, 200-300 mesh, glass column from Shanghai SD company) (20% ethyl acetate/hexanes) to afford 2-(3-dimethylamino-5-fluoro-phenyl)-3,3-dimethyl-1,2,3,4-tetrahydro-quinoline-6-carboxylic acid ethyl ester (0.11 g, 30%) as a white solid: LC/MS m/e calcd for $C_{22}H_{27}FN_2O_2$ (M+H)+: 371.47, observed: 371.3.

A mixture of 2-(3-dimethylamino-5-fluoro-phenyl)-3,3-dimethyl-1,2,3,4-tetrahydro-quinoline-6-carboxylic acid ethyl ester (0.11 g, 0.3 mmol), lithium hydroxide hydrate (0.12 g, 3.0 mmol), water (2 mL) in methanol (3 mL) and tetrahydrofuran (10 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford 2-(3-dimethylamino-5-fluoro-phenyl)-3,3-dimethyl-1,2,3,4-tetrahydro-quinoline-6-carboxylic acid (35 mg, 30%) as a white solid which was used for next step without further purification: LC/MS m/e calcd for $C_{20}H_{23}FN_2O_2$ (M+H)+: 343.2, observed: 343.1.

A mixture of 2-(3-dimethylamino-5-fluoro-phenyl)-3,3-dimethyl-1,2,3,4-tetrahydro-quinoline-6-carboxylic acid (10 mg, 0.03 mmol), 1-(3-dimethylaminopropyl)-3-ethylcarbodiimide hydrochloride (8.4 mg, 0.044 mmol), 4-dimethylaminopyridine (5.4 mg, 0.044 mmol), methane sulfonamide (8.3 mg, 0.09 mmol) in dichloromethane (3 mL) was refluxed for 12 hours. Removal of the solvent afforded an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded N-[2-(3-dimethylamino-5-fluoro-phenyl)-3,3-dimethyl-1,2,3,4-tetrahydro-quinoline-6-carbonyl]-methanesulfonamide (5 mg, 42%) as a light yellow solid: LC/MS m/e calcd for $C_{21}H_{26}FN_3O_3S$ (M+H)+: 420.5, observed: 420.1.

Example 51

2-(4'-Cyano-5-fluoro-biphenyl-3-yl)-3,3-dimethyl-1,2,3,4-tetrahydro-quinoline-6-carboxylic acid

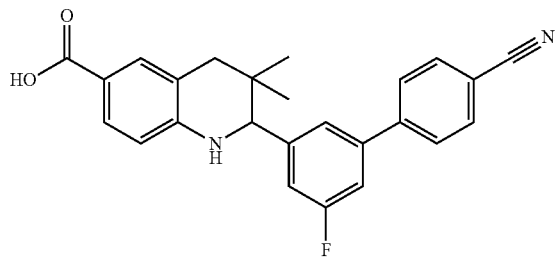 [SMILES: CC1(C)Cc2cc(C(=O)O)ccc2NC1c1cc(F)cc(-c2ccc(C#N)cc2)c1]

A mixture of 2-(3-bromo-5-fluoro-phenyl)-3,3-dimethyl-1,2,3,4-tetrahydro-quinoline-6-carboxylic acid ethyl ester (0.41 g, 1.0 mmol), 4-cyanobenzeneboronic acid (0.29 g, 2.0 mmol), bis(triphenylphosphine)palladium (II) chloride (70.2 mg, 0.1 mmol) and 2 M sodium carbonate (1.5 mL, 3.0 mmol) in dioxane (4 mL) was heated for 3 hours at 120° C. After cooling to room temperature, the mixture was treated with ethyl acetate (50 mL) and washed with water (20 mL). The organic layer was dried over anhydrous sodium sulfate and concentrated in vacuo. Purification on flash silica gel chromatography (silica gel from QingDao, 200-300 mesh, glass column from Shanghai SD company) (10% ethyl acetate/hexanes) to afford 2-(4'-cyano-5-fluoro-biphenyl-3-yl)-3,3-dimethyl-1,2,3,4-tetrahydro-quinoline-6-carboxylic acid ethyl ester (0.15 g, 35%) as a white solid: LC/MS m/e calcd for $C_{27}H_{25}FN_2O_2$ (M+H)$^+$: 429.5, observed: 429.3.

A mixture of 2-(4'-cyano-5-fluoro-biphenyl-3-yl)-3,3-dimethyl-1,2,3,4-tetrahydro-quinoline-6-carboxylic acid ethyl ester (0.15 g, 0.35 mmol), lithium hydroxide hydrate (0.15 g, 3.5 mmol), water (1 mL) in methanol (3 mL) and tetrahydrofuran (10 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 244'-cyano-5-fluoro-biphenyl-3-yl)-3,3-dimethyl-1,2,3,4-tetrahydro-quinoline-6-carboxylic acid (50 mg, 36%) as a white solid: LC/MS m/e calcd for $C_{25}H_{21}FN_2O_2$ (M+H)$^+$: 401.5, observed: 401.3.

Example 52

Cyclopropanesulfonic acid [2-(3,5-difluoro-phenyl)-3,3-dimethyl-1,2,3,4-tetrahydro-quinoline-6-carbonyl]-amide

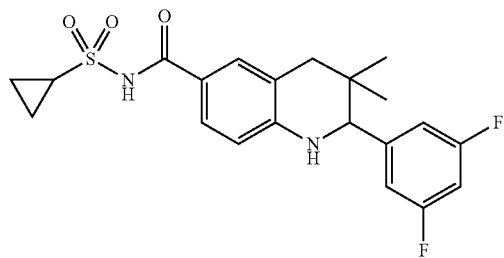 [SMILES: CC1(C)Cc2cc(C(=O)NS(=O)(=O)C3CC3)ccc2NC1c1cc(F)cc(F)c1]

A mixture of 4-amino-benzoic acid ethyl ester (3.3 g, 20 mmol) and 3,5-difluoro-benzaldehyde (2.84 g, 20 mmol) in ethanol (50 mL) was heated to reflux for 2 h. Then the reaction mixture cooled to room temperature. The solvent was removed in vacuo and the residue was washed with ether to afford 4-{[1-(3,5-difluoro-phenyl)-methylidene]-amino}-benzoic acid ethyl ester (4.27 g, 74%) as a white solid: LC/MS m/e calcd for $C_{16}H_{13}F_2NO_2$ (M+H)$^+$: 290.3, observed: 290.2.

To a mixture of 4-{[1-(3,5-difluoro-phenyl)-methylidene]-amino}-benzoic acid ethyl ester (4.27 g, 14.8 mmol) and ytterbium(III) triflate hydrate (0.92 g, 1.48 mmol) in dry tetrahydrofuran (50 mL) at 25° C. was added isobutyraldehyde (1.34 mL, 14.8 mmol) and water (0.27 mL, 14.8 mmol) dropwise. The reaction mixture was stirred at 25° C. for 5 h. Then the reaction mixture was concentrated in vacuo and the residue was extracted with ethyl acetate (2×100 mL), washed with brine, dried over anhydrous sodium sulfate and concentrated in vacuo to afford 2-(3,5-difluoro-phenyl)-4-hydroxy-3,3-dimethyl-1,2,3,4-tetrahydro-quinoline-6-carboxylic acid ethyl ester (5.34 g, 100%) as a light yellow oil: LC/MS m/e calcd for $C_{20}H_{21}F_2NO_3$ M$^+$: 361.4, observed: 344.2.

To a mixture of 2-(3,5-difluoro-phenyl)-4-hydroxy-3,3-dimethyl-1,2,3,4-tetrahydro-quinoline-6-carboxylic acid ethyl ester (5.34 g, 14.8 mmol) and triethylsilane (20 mL) at 25° C. was added trifluoroacetic acid (5 mL) dropwise. The resulting mixture was stirred at 25° C. for 1 h. Then the reaction mixture was concentrated in vacuo and the residue was extracted with ethyl acetate (2×200 mL), washed with saturated aqueous sodium bicarbonate solution (2×100 mL), dried over anhydrous sodium sulfate and concentrated in vacuo. Purification on flash silica gel chromatography (silica gel from QingDao, 200-300 mesh, glass column from Shanghai SD company) (10% ethyl acetate/hexanes) to afford 2-(3,5-difluoro-phenyl)-3,3-dimethyl-1,2,3,4-tetrahydro-quinoline-6-carboxylic acid ethyl ester (2.0 g, 41%) as a white solid: LC/MS m/e calcd for $C_{20}H_{21}F_2NO_2$ (M+H)$^+$: 346.4, observed: 346.1.

A mixture of 2-(3,5-difluoro-phenyl)-3,3-dimethyl-1,2,3,4-tetrahydro-quinoline-6-carboxylic acid ethyl ester (2.0 g, 6.1 mmol), lithium hydroxide hydrate (2.57 g, 61 mmol), water (5 mL) in methanol (10 mL) and tetrahydrofuran (20 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford 2-(3,5-difluoro-phenyl)-3,3-dimethyl-1,2,3,4-tetrahydro-quinoline-6-carboxylic acid (0.84 g, 44%) as a white solid which was used for next step without further purification: LC/MS m/e calcd for $C_{18}H_{17}F_2NO_2$ (M+H)$^+$: 318.3, observed: 318.2.

To a suspension of cyclopropanesulfonic acid amide (650 mg, 5.36 mmol) in N,N-dimethylformamide (4 mL) was added sodium hydride (210 mg, 5.36 mmol). The resulting mixture was stirred at 25° C. for 1 h. A solution of 2-(3,5-difluoro-phenyl)-3,3-dimethyl-1,2,3,4-tetrahydro-quinoline-6-carboxylic acid (210 mg, 0.67 mmol) and 1,1'-carbonyldiimidazole (220 mg, 1.34 mmol) in N,N-dimethylformamide (3 mL) was stirred at 70° C. for 1 h. Then the above suspension of cyclopropanesulfonic acid amide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [2-(3,5-difluoro-phenyl)-3,3-dimethyl-1,2,3,4- tetrahydro-quinoline-6-carbonyl]-amide (40 mg, 15%) as a white solid: LC/MS m/e calcd for $C_{21}H_{22}F_2N_2O_3S$ (M+H)$^+$: 421.5, observed: 421.2.

Example 53

2-(2-Fluoro-5-morpholin-4-yl-phenyl)-3,3-dimethyl-1,2,3,4-tetrahydro-quinoline-6-carboxylic acid

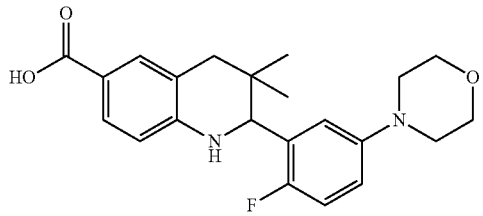 [SMILES: CC1(C)Cc2cc(C(=O)O)ccc2NC1c1cc(N2CCOCC2)ccc1F]

A mixture of 4-amino-benzoic acid ethyl ester (1.65 g, 10 mmol) and 5-bromo-2-fluoro-benzaldehyde (2.03 g, 10 mmol) in ethanol (20 mL) was heated to reflux for 2 h. Then the reaction mixture cooled to room temperature. The solvent was removed in vacuo and the residue was washed with ether to afford 4-{[1-(5-bromo-2-fluoro-phenyl)-methylidene]-amino}-benzoic acid ethyl ester (2.76 g, 79%) as a white solid: LC/MS m/e calcd for $C_{16}H_{13}BrFNO_2$ M$^+$: 350.2, observed: 350.1, 352.1.

To a mixture of 4-{[1-(5-bromo-2-fluoro-phenyl)-methylidene]-amino}-benzoic acid ethyl ester (2.76 g, 7.9 mmol) and ytterbium(III) triflate hydrate (0.49 g, 0.79 mmol) in dry tetrahydrofuran (10 mL) at 25° C. was added isobutyraldehyde (0.72 mL, 7.9 mmol) and water (0.14 mL, 7.9 mmol) dropwise. The reaction mixture was stirred at 25° C. for 5 h. Then the reaction mixture was concentrated in vacuo and the residue was extracted with ethyl acetate (2×100 mL), washed with brine, dried over anhydrous sodium sulfate and concentrated in vacuo to afford 2-(5-bromo-2-fluoro-phenyl)-4-hydroxy-3,3-dimethyl-1,2,3,4-tetrahydro-quinoline-6-carboxylic acid ethyl ester (3.33 g, 100%) as a light yellow oil: LC/MS m/e calcd for $C_{20}H_{21}BrFNO_3$ M$^+$: 422.3, observed: 404.2, 406.2.

To a mixture of 2-(5-bromo-2-fluoro-phenyl)-4-hydroxy-3,3-dimethyl-1,2,3,4-tetrahydro-quinoline-6-carboxylic acid ethyl ester (3.33 g, 7.9 mmol) and triethylsilane (5 mL) at 25° C. was added trifluoroacetic acid (1 mL) dropwise. The resulting mixture was stirred at 25° C. for 1 h. Then the reaction mixture was concentrated in vacuo and the residue was extracted with ethyl acetate (2×20 mL), washed with saturated aqueous sodium bicarbonate solution (2×10 mL), dried over anhydrous sodium sulfate and concentrated in vacuo. Purification on flash silica gel chromatography (silica gel from QingDao, 200-300 mesh, glass column from Shanghai SD company) (10% ethyl acetate/hexanes) to afford 2-(5-bromo-2-fluoro-phenyl)-3,3-dimethyl-1,2,3,4-tetrahydro-quinoline-6-carboxylic acid ethyl ester (0.76 g, 24%) as a white solid: LC/MS m/e calcd for $C_{20}H_{21}BrFNO_2$ M$^+$: 406.3, observed: 406.3, 408.2.

A mixture of 2-(5-bromo-2-fluoro-phenyl)-3,3-dimethyl-1,2,3,4-tetrahydro-quinoline-6-carboxylic acid ethyl ester (0.76 g, 1.87 mmol), morpholine (1.63 g, 18.7 mmol), copper (I) iodide (0.21 g, 1.1 mmol), L-proline (0.11 g, 0.94 mmol) and potassium carbonate (0.78, 5.61 mmol) in DMSO (3 mL) was heated for 4 hours at 120° C. After cooling to room temperature, the mixture was treated with ethyl acetate (50 mL) and washed with water (20 mL). The organic layer was dried over anhydrous sodium sulfate and concentrated in vacuo. Purification on flash silica gel chromatography (silica gel from QingDao, 200-300 mesh, glass column from Shanghai SD company) (20% ethyl acetate/hexanes) to afford 2-(2-fluoro-5-morpholin-4-yl-phenyl)-3,3-dimethyl-1,2,3,4-tetrahydro-quinoline-6-carboxylic acid ethyl ester (0.12 g, 16%) as a white solid: LC/MS m/e calcd for $C_{24}H_{29}FN_2O_3$ (M+H)$^+$: 413.5, observed: 413.4.

A mixture of 2-(2-fluoro-5-morpholin-4-yl-phenyl)-3,3-dimethyl-1,2,3,4-tetrahydro-quinoline-6-carboxylic acid ethyl ester (0.12 g, 0.29 mmol), lithium hydroxide hydrate (0.12 g, 0.29 mmol), water (2 mL) in methanol (3 mL) and tetrahydrofuran (10 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-(2-fluoro-5-morpholin-4-yl-phenyl)-3,3-dimethyl-1,2,3,4-tetrahydro-quinoline-6-carboxylic acid (40 mg, 36%) as a white solid: LC/MS m/e calcd for $C_{22}H_{25}FN_2O_3$ (M+H)$^+$: 385.5, observed: 385.3.

Example 54

Cyclopropanesulfonic acid [2-(2-fluoro-5-morpholin-4-yl-phenyl)-3,3-dimethyl-1,2,3,4-tetrahydro-quinoline-6-carbonyl]-amide

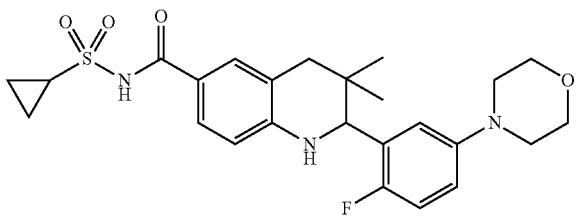 [SMILES: CC1(C)Cc2cc(C(=O)NS(=O)(=O)C3CC3)ccc2NC1c1cc(N2CCOCC2)ccc1F]

To a suspension of cyclopropanesulfonic acid amide (78.7 mg, 0.65 mmol) in N,N-dimethylformamide (3 mL) was added sodium hydride (26 mg, 0.65 mmol). The resulting mixture was stirred at 25° C. for 1 h. A solution of 2-(2-fluoro-5-morpholin-4-yl-phenyl)-3,3-dimethyl-1,2,3,4-tetrahydro-quinoline-6-carboxylic acid (50 mg, 0.13 mmol) and 1,1'-carbonyldiimidazole (42 mg, 0.26 mmol) in N,N-dimethylformamide (2 mL) was stirred at 70° C. for 1 h. Then the above suspension of cyclopropanesulfonic acid amide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [2-(2-fluoro-5-morpholin-4-yl-phenyl)-3,3-dimethyl-1,2,3,4-tetrahydro-quinoline-6-carbonyl]-amide

Example 55

2-(3-Chloro-5-morpholin-4-yl-phenyl)-3,3-dimethyl-1,2,3,4-tetrahydro-quinoline-6-carboxylic acid

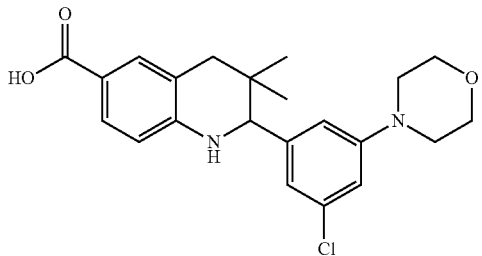 [SMILES: CC1(C)Cc2cc(C(=O)O)ccc2NC1c1cc(Cl)cc(N2CCOCC2)c1]

A mixture of 4-amino-benzoic acid ethyl ester (8.3 g, 50.3 mmol) and 3-bromo-5-chloro-benzaldehyde (11.0 g, 50.3 mmol) in ethanol (100 mL) was heated to reflux for 2 hours. Then the reaction mixture cooled to room temperature. The solvent was removed in vacuo and the residue was washed with ether to afford 4-{[1-(3-bromo-5-chloro-phenyl)-methylidene]-amino}-benzoic acid ethyl ester (6.4 g, 35%) as a white solid: LC/MS m/e calcd for $C_{16}H_{13}BrClNO_2$ M+: 366.6, observed: 366.6.

To a mixture of 4-{[1-(3-bromo-5-chloro-phenyl)-methylidene]-amino}-benzoic acid ethyl ester (6.4 g, 17.5 mmol) and ytterbium(III) triflate hydrate (1.08 g, 1.75 mmol) in dry tetrahydrofuran (50 mL) at 25° C. was added isobutyraldehyde (1.59 mL, 17.5 mmol) and water (0.32 mL, 17.5 mmol) dropwise. The reaction mixture was stirred at 25° C. for 5 h. Then the reaction mixture was concentrated in vacuo and the residue was extracted with ethyl acetate (2×100 mL), washed with brine, dried over anhydrous sodium sulfate and concentrated in vacuo to afford 2-(3-bromo-5-chloro-phenyl)-4-hydroxy-3,3-dimethyl-1,2,3,4-tetrahydro-quinoline-6-carboxylic acid ethyl ester (7.67 g, 100%) as a light yellow oil: LC/MS m/e calcd for $C_{20}H_{21}BrClNO_3$ M+: 438.8, observed: 438.8, 440.8.

To a mixture of 2-(3-bromo-5-chloro-phenyl)-4-hydroxy-3,3-dimethyl-1,2,3,4-tetrahydro-quinoline-6-carboxylic acid ethyl ester (7.67 g, 17.5 mmol) and triethylsilane (10 mL) at 25° C. was added trifluoroacetic acid (5 mL) dropwise. The resulting mixture was stirred at 25° C. for 1 h. Then the reaction mixture was concentrated in vacuo and the residue was extracted with ethyl acetate (2×100 mL), washed with saturated aqueous sodium bicarbonate solution (2×50 mL), dried over anhydrous sodium sulfate and concentrated in vacuo. Purification on flash silica gel chromatography (silica gel from QingDao, 200-300 mesh, glass column from Shanghai SD company) (10% ethyl acetate/hexanes) to afford 2-(3-bromo-5-chloro-phenyl)-3,3-dimethyl-1,2,3,4-tetrahydro-quinoline-6-carboxylic acid ethyl ester (3.12 g, 42%) as a white solid: LC/MS m/e calcd for $C_{20}H_{21}BrClNO_2$ M+: 422.8, observed: 422.0, 424.0.

A mixture of 2-(3-bromo-5-chloro-phenyl)-3,3-dimethyl-1,2,3,4-tetrahydro-quinoline-6-carboxylic acid ethyl ester (1.56 g, 3.7 mmol), morpholine (1.60 g, 18.5 mmol), copper (I) iodide (0.42 g, 2.2 mmol), L-proline (0.25 g, 2.2 mmol) and potassium hydroxide (0.12, 2.2 mmol) in DMSO (20 mL) was heated for 4 hours at 120° C. After cooling to room temperature, the mixture was treated with ethyl acetate (50 mL) and washed with water (20 mL). The organic layer was dried over anhydrous sodium sulfate and concentrated in vacuo. Purification on flash silica gel chromatography (silica gel from QingDao, 200-300 mesh, glass column from Shanghai SD company) (20% ethyl acetate/hexanes) to afford 2-(3-chloro-5-morpholin-4-yl-phenyl)-3,3-dimethyl-1,2,3,4-tetrahydro-quinoline-6-carboxylic acid ethyl ester (0.70 g, 44%) as a white solid: LC/MS m/e calcd for $C_{24}H_{29}ClN_2O_3$ (M+H)+: 430.0, observed: 429.3.

A mixture of 2-(3-chloro-5-morpholin-4-yl-phenyl)-3,3-dimethyl-1,2,3,4-tetrahydro-quinoline-6-carboxylic acid ethyl ester (0.7 g, 1.63 mmol), lithium hydroxide hydrate (0.69 g, 16.3 mmol), water (5 mL) in ethanol (20 mL) and tetrahydrofuran (20 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-(3-chloro-5-morpholin-4-yl-phenyl)-3,3-dimethyl-1,2,3,4-tetrahydro-quinoline-6-carboxylic acid (200 mg, 31%) as a white solid: LC/MS m/e calcd for $C_{22}H_{25}ClN_2O_3$ M+: 400.9, observed: 401.2.

Example 56

Cyclopropanesulfonic acid [2-(3-chloro-5-morpholin-4-yl-phenyl)-3,3-dimethyl-1,2,3,4-tetrahydro-quinoline-6-carbonyl]-amide

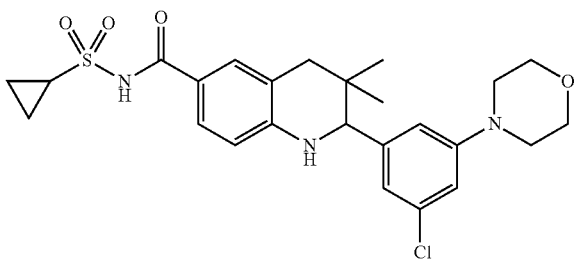 [SMILES: CC1(C)Cc2cc(C(=O)NS(=O)(=O)C3CC3)ccc2NC1c1cc(Cl)cc(N2CCOCC2)c1]

A mixture of 2-(3-chloro-5-morpholin-4-yl-phenyl)-3,3-dimethyl-1,2,3,4-tetrahydro-quinoline-6-carboxylic acid (100 mg, 0.25 mmol), 1-(3-dimethylaminopropyl)-3-ethyl-carbodiimide hydrochloride (72 mg, 0.38 mmol), 4-dimethylaminopyridine (46 mg, 0.38 mmol), cyclopropane sulfonamide (91 mg, 0.75 mmol) in dichloromethane (3 mL) was heated for at 65° C. for 12 hours. Removal of the solvent afforded an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded cyclopropanesulfonic acid [2-(3-chloro-5-morpholin-4-yl-phenyl)-3,3-dimethyl-1,2,3,4-tetrahydro-quinoline- 6-carbonyl]-amide (37.8 mg, 30%) as a light yellow solid: LC/MS m/e calcd for $C_{25}H_{30}ClN_3O_4S$ (M+H)$^+$: 504.1, observed: 504.2.

Example 57

N-[2-(3-Chloro-5-morpholin-4-yl-phenyl)-3,3-dimethyl-1,2,3,4-tetrahydro-quinoline-6-carbonyl]-methanesulfonamide

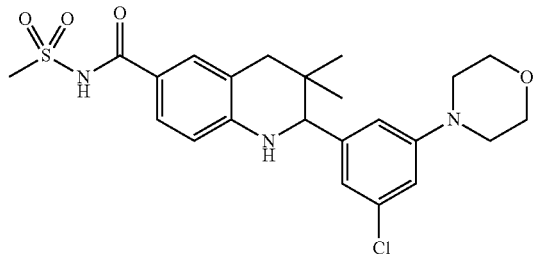 [SMILES: CC1(C)Cc2cc(C(=O)NS(C)(=O)=O)ccc2NC1c1cc(Cl)cc(N2CCOCC2)c1]

A mixture of 2-(3-chloro-5-morpholin-4-yl-phenyl)-3,3-dimethyl-1,2,3,4-tetrahydro-quinoline-6-carboxylic acid (100 mg, 0.25 mmol), 1-(3-dimethylaminopropyl)-3-ethyl-carbodiimide hydrochloride (72 mg, 0.38 mmol), 4-dimethylaminopyridine (46 mg, 0.38 mmol), methane sulfonamide (47.5 mg, 0.50 mmol) in dichloromethane (4 mL) was heated for at 65° C. for 12 hours. Removal of the solvent to afforded an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded N-[2-(3-chloro-5-morpholin-4-yl-phenyl)-3,3-dimethyl-1,2,3,4-tetrahydro-quinoline-6-carbonyl]-methanesulfonamide (35.8 mg, 30%) as a light yellow solid: LC/MS m/e calcd for $C_{23}H_{28}ClN_3O_4S$ (M+H)$^+$: 479.1, observed: 478.2.

Example 58

Cyclopropanesulfonic acid [2-(4-fluoro-3-morpholin-4-yl-phenyl)-3,3-dimethyl-1,2,3,4-tetrahydro-quinoline-6-carbonyl]-amide

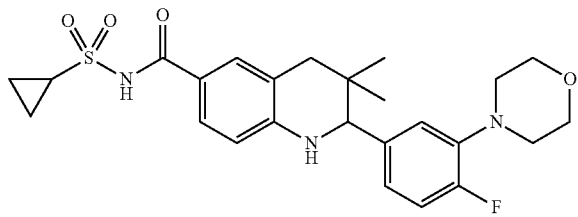 [SMILES: CC1(C)Cc2cc(C(=O)NS(=O)(=O)C3CC3)ccc2NC1c1ccc(F)c(N2CCOCC2)c1]

A mixture of 4-amino-benzoic acid ethyl ester (1.65 g, 10 mmol) and 3-bromo-4-fluoro-benzaldehyde (2.03 g, 10 mmol) in ethanol (100 mL) was heated to reflux for 2 hours. Then the reaction mixture cooled to room temperature. The solvent was removed in vacuo and the residue was washed with ether to afford 4-{[1-(3-bromo-4-fluoro-phenyl)-methylidene]-amino}-benzoic acid ethyl ester (1.6 g, 46%) as a white solid: LC/MS m/e calcd for $C_{16}H_{13}BrCFNO_2$ M$^+$: 350.2, observed: 350.2, 352.2.

To a mixture of 4-{[1-(3-bromo-4-fluoro-phenyl)-methylidene]-amino}-benzoic acid ethyl ester (1.6 g, 4.57 mmol) and ytterbium(III) triflate hydrate (0.28 g, 0.457 mmol) in dry tetrahydrofuran (10 mL) at 25° C. was added isobutyraldehyde (0.42 mL, 4.57 mmol) and water (82 mg, 4.57 mmol) dropwise. The reaction mixture was stirred at 25° C. for 5 h. Then the reaction mixture was concentrated in vacuo and the residue was extracted with ethyl acetate (2×50 mL), washed with brine, dried over anhydrous sodium sulfate and concentrated in vacuo to afford 2-(3-bromo-4-fluoro-phenyl)-4-hydroxy-3,3-dimethyl-1,2,3,4-tetrahydro-quinoline-6-carboxylic acid ethyl ester (1.93 g, 100%) as a light yellow oil: LC/MS m/e calcd for $C_{20}H_{21}BrFNO_3$ M$^+$: 422.3, observed: 404.2.

To a mixture of 2-(3-bromo-4-fluoro-phenyl)-4-hydroxy-3,3-dimethyl-1,2,3,4-tetrahydro-quinoline-6-carboxylic acid ethyl ester (1.93 g, 4.57 mmol) and triethylsilane (5 mL) at 25° C. was added trifluoroacetic acid (1 mL) dropwise. The resulting mixture was stirred at 25° C. for 1 h. Then the reaction mixture was concentrated in vacuo and the residue was extracted with ethyl acetate (2×50 mL), washed with saturated aqueous sodium bicarbonate solution (2×20 mL), dried over anhydrous sodium sulfate and concentrated in vacuo. Purification on flash silica gel chromatography (silica gel from QingDao, 200-300 mesh, glass column from Shanghai SD company) (10% ethyl acetate/hexanes) to afford 2-(3-bromo-4-fluoro-phenyl)-3,3-dimethyl-1,2,3,4-tetrahydro-quinoline-6-carboxylic acid ethyl ester (0.63 g, 34%) as a white solid: LC/MS m/e calcd for $C_{20}H_{21}BrFNO_2$ M$^+$: 406.3, observed: 406.2, 408.2.

A mixture of 2-(3-bromo-4-fluoro-phenyl)-3,3-dimethyl-1,2,3,4-tetrahydro-quinoline-6-carboxylic acid ethyl ester (0.63 g, 1.55 mmol), morpholine (1.35 g, 15.5 mmol), copper (I) iodide (0.18 g, 0.93 mmol), L-proline (89 mg, 0.78 mmol) and potassium carbonate (0.64, 4.65 mmol) in DMSO (3 mL) was heated for 4 hours at 120° C. After cooling to room temperature, the mixture was treated with ethyl acetate (50 mL) and washed with water (20 mL). The organic layer was dried over anhydrous sodium sulfate and concentrated in vacuo. Purification on flash silica gel chromatography (silica gel from QingDao, 200-300 mesh, glass column from Shanghai SD company) (20% ethyl acetate/hexanes) to afford 2-(4-fluoro-5-morpholin-4-yl-phenyl)-3,3-dimethyl-1,2,3,4-tetrahydro-quinoline-6-carboxylic acid ethyl ester (0.11 g, 17%) as a white solid: LC/MS m/e calcd for $C_{24}H_{29}FN_2O_3$ (M+H)$^+$: 413.5, observed: 413.4.

A mixture of 2-(4-fluoro-5-morpholin-4-yl-phenyl)-3,3-dimethyl-1,2,3,4-tetrahydro-quinoline-6-carboxylic acid ethyl ester (0.11 g, 0.27 mmol), lithium hydroxide hydrate (0.11 g, 2.7 mmol), water (2 mL) in tetrahydrofuran (10 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-(4-fluoro-3-morpholin-4-yl-phenyl)-3,3-dimethyl-1,2,3,4-tetrahydro-quinoline-6-carboxylic acid (60 mg, 57%) as a white solid: LC/MS m/e calcd for $C_{22}H_{25}FN_2O_3$ (M+H)$^+$: 385.5, observed: 385.3.

To a suspension of cyclopropanesulfonic acid amide (190 mg, 1.55 mmol) in N,N-dimethylformamide (3 mL) was added sodium hydride (62 mg, 1.55 mmol). The resulting mixture was stirred at 25° C. for 1 h. A solution of 2-(4-fluoro-3-morpholin-4-yl-phenyl)-3,3-dimethyl-1,2,3,4-tetrahydroquinoline-6-carboxylic acid (120 mg, 0.31 mmol) and 1,1'-carbonyldiimidazole (100 mg, 0.62 mmol) in N,N-dimethylformamide (3 mL) was stirred at 70° C. for 1 h. Then the above suspension of cyclopropanesulfonic acid amide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [2-(4-fluoro-3-morpholin-4-yl-phenyl)-3,3-dimethyl-1,2,3,4-tetrahydro-quinoline-6-carbonyl]-amide (38 mg, 25%) as a white solid: LC/MS m/e calcd for $C_{25}H_{30}FN_3O_4S$ (M+H)$^+$: 488.6, observed: 488.5.

Example 59

N-[2-(4-Fluoro-3-morpholin-4-yl-phenyl)-3,3-dimethyl-1,2,3,4-tetrahydro-quinoline-6-carbonyl]-methanesulfonamide

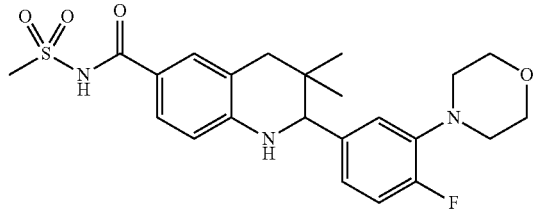 [SMILES: CC1(C)Cc2cc(C(=O)NS(C)(=O)=O)ccc2NC1c1ccc(F)c(N2CCOCC2)c1]

To a suspension of methanesulfonamide (150 mg, 1.55 mmol) in N,N-dimethylformamide (3 mL) was added sodium hydride (62 mg, 1.55 mmol). The resulting mixture was stirred at 25° C. for 1 h. A solution of 2-(4-fluoro-3-morpholin-4-yl-phenyl)-3,3-dimethyl-1,2,3,4-tetrahydro-quinoline-6-carboxylic acid (120 mg, 0.31 mmol) and 1,1'-carbonyldiimidazole (100 mg, 0.62 mmol) in N,N-dimethylformamide (3 mL) was stirred at 70° C. for 1 h. Then the above suspension of methanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-[2-(4-fluoro-3-morpholin-4-yl-phenyl)-3,3-dimethyl-1,2,3,4-tetrahydro-quinoline-6-carbonyl]-methanesulfonamide (36 mg, 25%) as a white solid: LC/MS m/e calcd for $C_{23}H_{28}FN_3O_4S$ (M+H)$^+$: 462.6, observed: 462.4.

Example 60

Cyclopropanesulfonic acid [2-(5-fluoro-2-methyl-phenyl)-3,3-dimethyl-1,2,3,4-tetrahydro-quinoline-6-carbonyl]-amide

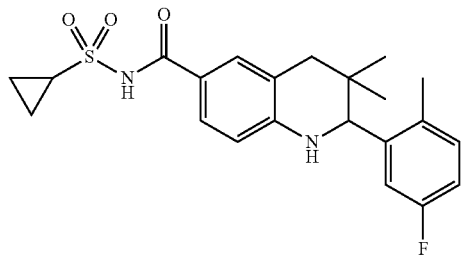 [SMILES: Cc1ccc(F)cc1C1Nc2ccc(C(=O)NS(=O)(=O)C3CC3)cc2CC1(C)C]

A mixture of 4-amino-benzoic acid ethyl ester (1.65 g, 10 mmol) and 5-fluoro-2-methyl-benzaldehyde (1.38 g, 10 mmol) in ethanol (10 mL) was heated to reflux for 2 hours. Then the reaction mixture cooled to room temperature. The solvent was removed in vacuo and the residue was washed with ether to afford 4-{[1-(5-fluoro-2-methyl-phenyl)-methylidene]-amino}-benzoic acid ethyl ester (2.0 g, 70%) as a white solid: LC/MS m/e calcd for $C_{17}H_{16}FNO_2$ (M+H)$^+$: 285.3, observed: 286.3.

To a mixture of 4-{[1-(5-fluoro-2-methyl-phenyl)-methylidene]-amino}-benzoic acid ethyl ester (3.01 g, 10.6 mmol) and ytterbium(III) triflate hydrate (0.66 g, 1.06 mmol) in dry tetrahydrofuran (10 mL) at 25° C. was added isobutyraldehyde (0.96 mL, 10.6 mmol) and water (190 mg, 10.6 mmol) dropwise. The reaction mixture was stirred at 25° C. for 5 h. Then the reaction mixture was concentrated in vacuo and the residue was extracted with ethyl acetate (2×50 mL), washed with brine, dried over anhydrous sodium sulfate and concentrated in vacuo to afford 2-(5-fluoro-2-methyl-phenyl)-4-hydroxy-3,3-dimethyl-1,2,3,4-tetrahydro-quinoline-6-carboxylic acid ethylester (3.78 g, 100%) as a light yellow oil: LC/MS m/e calcd for $C_{21}H_{24}FNO_3$ M$^+$: 357.4, observed: 340.3.

To a mixture of 2-(5-fluoro-2-methyl-phenyl)-4-hydroxy-3,3-dimethyl-1,2,3,4-tetrahydro-quinoline-6-carboxylic acid ethylester (3.78 g, 10.6 mmol) and triethylsilane (10 mL) at 25° C. was added trifluoroacetic acid (2 mL) dropwise. The resulting mixture was stirred at 25° C. for 1 h. Then the reaction mixture was concentrated in vacuo and the residue was extracted with ethyl acetate (2×50 mL), washed with saturated aqueous sodium bicarbonate solution (2×20 mL), dried over anhydrous sodium sulfate and concentrated in vacuo. Purification on flash silica gel chromatography (silica gel from QingDao, 200-300 mesh, glass column from Shanghai SD company) (10% ethyl acetate/hexanes) to afford 2-(5-fluoro-2-methyl-phenyl)-3,3-dimethyl-1,2,3,4-tetrahydro-quinoline-6-carboxylic acid ethyl ester (0.70 g, 19%) as a white solid: LC/MS m/e calcd for $C_{21}H_{24}FNO_2$ (M+H)$^+$: 342.4, observed: 342.3.

A mixture of 2-(5-fluoro-2-methyl-phenyl)-3,3-dimethyl-1,2,3,4-tetrahydro-quinoline-6-carboxylic acid ethyl ester (0.70 g, 2.05 mmol), lithium hydroxide hydrate (0.86 g, 20.5 mmol), water (3 mL) in tetrahydrofuran (30 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-(5-fluoro-2-methyl-phenyl)-3,3-dimethyl-1,2,3,4-tetrahydro-quinoline-6-carboxylic acid (260 mg, 40%) as a white solid: LC/MS m/e calcd for $C_{19}H_{20}FNO_2$ $(M+H)^+$: 314.4, observed: 314.3.

To a suspension of cyclopropanesulfonic acid amide (250 mg, 2.1 mmol) in N,N-dimethylformamide (3 mL) was added sodium hydride (84 mg, 2.1 mmol). The resulting mixture was stirred at 25° C. for 1 hour. A solution of 2-(5-fluoro-2-methyl-phenyl)-3,3-dimethyl-1,2,3,4-tetrahydro-quinoline-6-carboxylic acid (130 mg, 0.42 mmol) and 1,1'-carbonyldiimidazole (130 mg, 0.84 mmol) in N,N-dimethylformamide (3 mL) was stirred at 70° C. for 1 h. Then the above suspension of cyclopropanesulfonic acid amide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [2-(5-fluoro-2-methyl-phenyl)-3,3-dimethyl-1,2,3,4-tetrahydro-quinoline-6-carbonyl]-amide (40 mg, 23%) as a white solid: LC/MS m/e calcd for $C_{22}H_{25}FN_2O_3S$ $(M+H)^+$: 417.5, observed: 417.3.

Example 61

N-[2-(3-Fluoro-5-pyrrolidin-1-yl-phenyl)-3,3-dimethyl-1,2,3,4-tetrahydro-quinoline-6-carbonyl]-methanesulfonamide

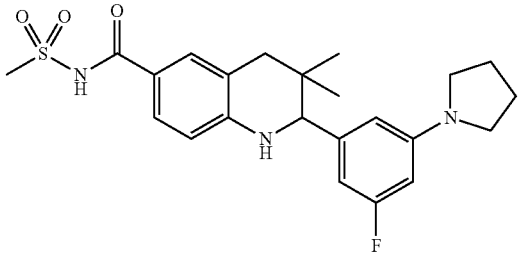 [SMILES: CC1(C)Cc2cc(C(=O)NS(C)(=O)=O)ccc2NC1c1cc(F)cc(N2CCCC2)c1]

A mixture of 2-(3-bromo-5-fluoro-phenyl)-3,3-dimethyl-1,2,3,4-tetrahydro-quinoline-6-carboxylic acid ethyl ester (0.41 g, 1.0 mmol), pyrrolidine (0.21 g, 3.0 mmol), copper (I) iodide (0.11 g, 0.6 mmol) and potassium hydroxide (33.6 mg, 0.6 mmol) in DMSO (2 mL) was heated for 3 hours at 120° C. After cooling to room temperature, the mixture was treated with ethyl acetate (50 mL) and washed with water (20 mL). The organic layer was dried over anhydrous sodium sulfate and concentrated in vacuo. Purification on flash silica gel chromatography (silica gel from QingDao, 200-300 mesh, glass column from Shanghai SD company) (20% ethyl acetate/hexanes) to afford 2-(3-fluoro-5-pyrrolidin-1-yl-phenyl)-3,3-dimethyl-1,2,3,4-tetrahydro-quinoline-6-carboxylic acid ethyl ester (0.18 g, 45%) as a white solid: LC/MS m/e calcd for $C_{24}H_{29}FN_2O_2$ $(M+H)^+$: 397.5, observed: 397.3.

A mixture of 2-(3-fluoro-5-pyrrolidin-1-yl-phenyl)-3,3-dimethyl-1,2,3,4-tetrahydro-quinoline-6-carboxylic acid ethyl ester (0.18 g, 0.45 mmol), lithium hydroxide hydrate (0.19 g, 4.5 mmol), water (1 mL) in methanol (3 mL) and tetrahydrofuran (10 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford 2-(3-fluoro-5-pyrrolidin-1-yl-phenyl)-3,3-dimethyl-1,2,3,4-tetrahydro-quinoline-6-carboxylic acid (100 mg, 60%) as a white solid which was used for next step without further purification: LC/MS m/e calcd for $C_{22}H_{25}FN_2O_2$ $(M+H)^+$: 369.5, observed: 369.2.

A mixture of 2-(3-fluoro-5-pyrrolidin-1-yl-phenyl)-3,3-dimethyl-1,2,3,4-tetrahydro-quinoline-6-carboxylic acid (50 mg, 0.14 mmol), 1-3-dimethylaminopropyl-3-ethylcarbodiimide hydrochloride (39 mg, 0.20 mmol), 4-dimethylaminopyridine (24.4 mg, 0.20 mmol), methane sulfonamide (40 mg, 0.42 mmol) in dichloromethane (3 mL) was heated for 12 hours at 60° C. Removal of the solvent afforded an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded N-[2-(3-fluoro-5-pyrrolidin-1-yl-phenyl)-3,3-dimethyl-1,2,3,4-tetrahydro-quinoline-6-carbonyl]-methanesulfonamide (22 mg, 35%) as a light yellow solid: LC/MS m/e calcd for $C_{23}H_{28}FN_3O_3S$ $(M+H)^+$: 446.6, observed: 446.2.

Example 62

Cyclopropanesulfonic acid [2-(3-fluoro-5-pyrrolidin-1-yl-phenyl)-3,3-dimethyl-1,2,3,4-tetrahydro-quinoline-6-carbonyl]-amide

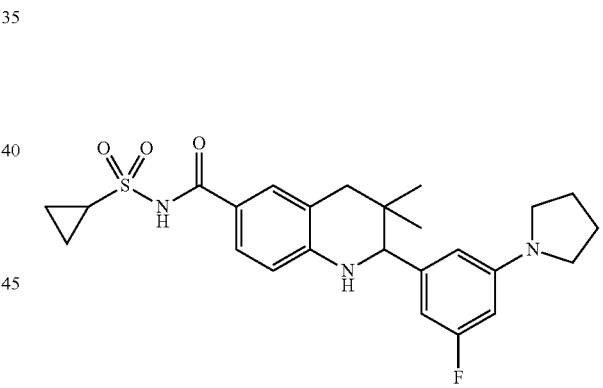

A mixture of 2-(3-fluoro-5-pyrrolidin-1-yl-phenyl)-3,3-dimethyl-1,2,3,4-tetrahydro-quinoline-6-carboxylic acid (50 mg, 0.14 mmol), 1-3-dimethylaminopropyl-3-ethylcarbodiimide hydrochloride (39 mg, 0.20 mmol), 4-dimethylaminopyridine (24.4 mg, 0.20 mmol), cyclopropanesulfonic acid amide (51 mg, 0.42 mmol) in dichloromethane (3 mL) was heated for 12 hours at 60° C. Removal of the solvent afforded an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded cyclopropanesulfonic acid [2-(3-fluoro-5-pyrrolidin-1-yl-phenyl)-3,3-dimethyl-1,2,3,4-tetrahydro-quinoline-6-carbonyl]- amide (13 mg, 20%) as a light yellow solid: LC/MS m/e calcd for $C_{25}H_{30}FN_3O_3S$ (M+H)$^+$: 472.6, observed: 472.2.

Example 63

3,3-Dimethyl-2-(3-methyl-5-morpholin-4-yl-phenyl)-1,2,3,4-tetrahydro-quinoline-6-carboxylic acid

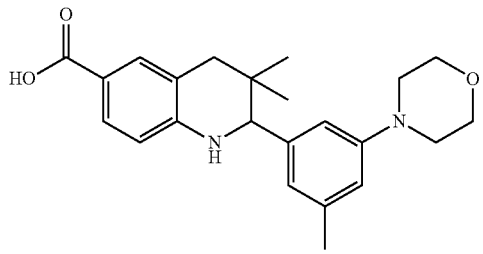 [SMILES: Cc1cc(C2Nc3ccc(C(=O)O)cc3CC2(C)C)cc(N2CCOCC2)c1]

A mixture of 4-amino-benzoic acid ethyl ester (8.3 g, 50.3 mmol) and 3-bromo-5-methyl-benzaldehyde (11.0 g, 50.3 mmol) in ethanol (100 mL) was prepared. The reaction mixture was heated to reflux for 2 hours. Then the reaction mixture cooled to room temperature. The solvent was removed in vacuo and the residue was washed with ether to afford 4-{[1-(3-bromo-5-methyl-phenyl)-methylidene]-amino}-benzoic acid ethyl ester (7.3 g, 50%) as a white solid: LC/MS m/e calcd for $C_{17}H_{16}BrNO_2$ M$^+$: 346.2, observed: 346.1.

To a mixture of 4-{[1-(3-bromo-5-methyl-phenyl)-methylidene]-amino}-benzoic acid ethyl ester (2.5 g, 7.3 mmol) and ytterbium(III) triflate hydrate (0.45 g, 0.73 mmol) in dry tetrahydrofuran (15 mL) at 25° C. was added isobutyraldehyde (0.53 g, 7.3 mmol) and water (0.13 mL, 7.3 mmol) dropwise. The reaction mixture was stirred at 25° C. for 5 h. Then the reaction mixture was concentrated in vacuo and the residue was extracted with ethyl acetate (2×100 mL), washed with brine, dried over anhydrous sodium sulfate and concentrated in vacuo to afford 2-(3-bromo-5-methyl-phenyl)-4-hydroxy-3,3-dimethyl-1,2,3,4-tetrahydro-quinoline-6-carboxylic acid ethyl ester (3.1 g, 100%) as a light yellow oil: LC/MS m/e calcd for $C_{21}H_{24}BrNO_3$ M$^+$: 418.3, observed: 400.1.

To a mixture of 2-(3-bromo-5-methyl-phenyl)-4-hydroxy-3,3-dimethyl-1,2,3,4-tetrahydro-quinoline-6-carboxylic acid ethyl ester (6.1 g, 14.6 mmol) and triethylsilane (20 mL) at 25° C. was added trifluoroacetic acid (10 mL) dropwise. The resulting mixture was stirred at 25° C. for 1 h. Then the reaction mixture was concentrated in vacuo and the residue was extracted with ethyl acetate (2×100 mL), washed with saturated aqueous sodium bicarbonate solution (2×50 mL), dried over anhydrous sodium sulfate and concentrated in vacuo. Purification on flash silica gel chromatography (silica gel from QingDao, 200-300 mesh, glass column from Shanghai SD company) (10% ethyl acetate/hexanes) to afford 2-(3-bromo-5-methyl-phenyl)-3,3-dimethyl-1,2,3,4-tetrahydro-quinoline-6-carboxylic acid ethyl ester (3.12 g, 42%) as a white solid: LC/MS m/e calcd for $C_{21}H_{24}BrNO_2$ M$^+$: 402.3, observed: 402.1, 404.1.

A mixture of 2-(3-bromo-5-methyl-phenyl)-3,3-dimethyl-1,2,3,4-tetrahydro-quinoline-6-carboxylic acid ethyl ester (1.0 g, 2.5 mmol), morpholine (2.2 g, 25 mmol), copper (I) iodide (0.29 g, 1.5 mmol), N,N-dimethylglycine (0.28 g, 2.0 mmol) and potassium carbonate (1.04 g, 7.5 mmol) in DMSO (6 mL) was heated for 4 hours at 120° C. After cooling to room temperature, the mixture was treated with ethyl acetate (50 mL) and washed with water (20 mL). The organic layer was dried over anhydrous sodium sulfate and concentrated in vacuo. Purification on flash silica gel chromatography (silica gel from QingDao, 200-300 mesh, glass column from Shanghai SD company) (20% ethyl acetate/hexanes) to afford 3,3-dimethyl-2-(3-methyl-5-morpholin-4-yl-phenyl)-1,2,3,4-tetrahydro-quinoline-6-carboxylic acid ethyl ester (0.52 g, 51%) as a white solid: LC/MS m/e calcd for $C_{25}H_{32}N_2O_3$ (M+H)$^+$: 409.6, observed: 409.2.

A mixture of 3,3-dimethyl-2-(3-methyl-5-morpholin-4-yl-phenyl)-1,2,3,4-tetrahydro-quinoline-6-carboxylic acid ethyl ester (0.52 g, 1.3 mmol), lithium hydroxide hydrate (0.54 g, 13 mmol), water (1 mL) in methanol (2 mL) and tetrahydrofuran (10 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded 3,3-dimethyl-2-(3-methyl-5-morpholin-4-yl-phenyl)-1,2,3,4-tetrahydro-quinoline-6-carboxylic acid (200 mg, 31%) as a white solid: LC/MS m/e calcd for $C_{23}H_{28}N_2O_3$ (M+H)$^+$: 381.5, observed: 381.2.

Example 64

Cyclopropanesulfonic acid [3,3-dimethyl-2-(3-methyl-5-morpholin-4-yl-phenyl)-1,2,3,4-tetrahydro-quinoline-6-carbonyl]-amide

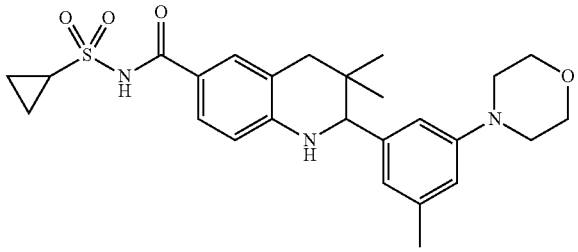 [SMILES: Cc1cc(C2Nc3ccc(C(=O)NS(=O)(=O)C4CC4)cc3CC2(C)C)cc(N2CCOCC2)c1]

A mixture of 3,3-dimethyl-2-(3-methyl-5-morpholin-4-yl-phenyl)-1,2,3,4-tetrahydro-quinoline-6-carboxylic acid (150 mg, 0.39 mmol), 1-3-dimethylaminopropyl-3-ethylcarbodiimide hydrochloride (110 mg, 0.59 mmol), 4-dimethylaminopyridine (72 mg, 0.59 mmol), cyclopropane sulfonamide (140 mg, 1.17 mmol) in dichloromethane (5 mL) was heated for at 65° C. for 12 hours. Removal of the solvent afforded an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded cyclopropanesulfonic acid [3,3-dimethyl-2-(3-methyl-5-morpholin-4-yl-phenyl)-1,2,3,4-tetrahydro-quinoline-6-carbonyl]- amide (45 mg, 25%) as a light yellow solid: LC/MS m/e calcd for $C_{26}H_{33}N_3O_4S$ $(M+H)^+$: 484.6, observed: 484.2.

Example 65

N-[3,3-Dimethyl-2-(3-methyl-5-morpholin-4-yl-phenyl)-1,2,3,4-tetrahydro-quinoline-6-carbonyl]-methanesulfonamide

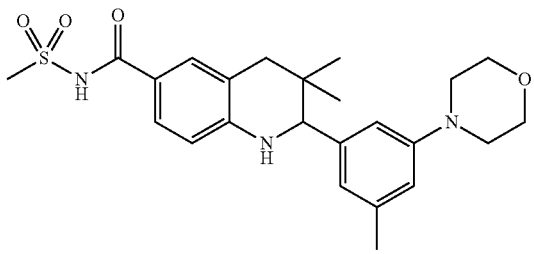 [SMILES: Cc1cc(C2Nc3ccc(C(=O)NS(C)(=O)=O)cc3CC2(C)C)cc(N2CCOCC2)c1]

A mixture of 3,3-dimethyl-2-(3-methyl-5-morpholin-4-yl-phenyl)-1,2,3,4-tetrahydro-quinoline-6-carboxylic acid (150 mg, 0.39 mmol), 1-3-dimethylaminopropyl-3-ethylcarbodi-imide hydrochloride (110 mg, 0.59 mmol), 4-dimethylami-nopyridine (72 mg, 0.59 mmol), methane sulfonamide (110 mg, 1.17 mmol) in dichloromethane (5 mL) was heated for at 65° C. for 12 hours. Removal of the solvent afforded an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded N-[3,3-dimethyl-2-(3-methyl-5-morpholin-4-yl-phenyl)-1,2,3,4-tetrahydro-quinoline-6-carbonyl]-methanesulfonamide (71 mg, 40%) as a light yellow solid: LC/MS m/e calcd for $C_{24}H_{31}N_3O_4S$ $(M+H)^+$: 458.6, observed: 458.2.

Example 66

2-(3-Methoxy-5-morpholin-4-yl-phenyl)-3,3-dim-ethyl-1,2,3,4-tetrahydro-quinoline-6-carboxylic acid

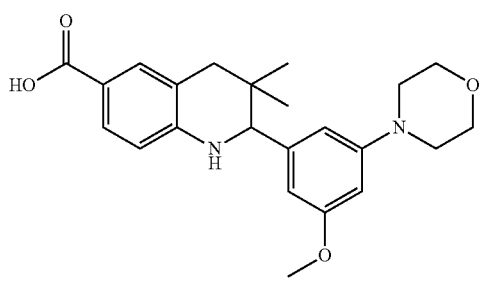 [SMILES: COc1cc(C2Nc3ccc(C(=O)O)cc3CC2(C)C)cc(N2CCOCC2)c1]

A mixture of 4-amino-benzoic acid ethyl ester (6.1 g, 36.9 mmol) and 3-bromo-5-methoxy-benzaldehyde (8.0 g, 36.9 mmol) in ethanol (100 mL) was prepared. The reaction mixture was heated to reflux for 2 hours. Then the reaction mixture cooled to room temperature. The solvent was removed in vacuo and the residue was washed with ether to afford 4-{[1-(3-bromo-5-methoxy-phenyl)-methylidene]-amino}-benzoic acid ethyl ester (4.5 g, 34%) as a white solid: LC/MS m/e calcd for $C_{17}H_{16}BrNO_3$ $M^+$: 362.2, observed: 362.1.

To a mixture of 4-{[1-(3-bromo-5-methoxy-phenyl)-methylidene]-amino}-benzoic acid ethyl ester (4.5 g, 12.4 mmol) and ytterbium(III) triflate hydrate (0.77 g, 1.24 mmol) in dry tetrahydrofuran (20 mL) at 25° C. was added isobutyralde-hyde (0.89 g, 12.4 mmol) and water (0.22 mL, 12.4 mmol) dropwise. The reaction mixture was stirred at 25° C. for 5 h. Then the reaction mixture was concentrated in vacuo and the residue was extracted with ethyl acetate (2×100 mL), washed with brine, dried over anhydrous sodium sulfate and concentrated in vacuo to afford 2-(3-bromo-5-methoxy-phenyl)-4-hydroxy-3,3-dimethyl-1,2,3,4-tetrahydro-quinoline-6-carboxylic acid ethyl ester (5.4 g, 100%) as a light yellow oil: LC/MS m/e calcd for $C_{21}H_{24}BrNO_4$ $M^+$: 434.3, observed: 418.1.

To a mixture of 2-(3-bromo-5-methoxy-phenyl)-4-hydroxy-3,3-dimethyl-1,2,3,4-tetrahydro-quinoline-6-carboxylic acid ethyl ester (5.4 g, 12.4 mmol) and triethylsilane (10 mL) at 25° C. was added trifluoroacetic acid (10 mL) dropwise. The resulting mixture was stirred at 25° C. for 1 h. Then the reaction mixture was concentrated in vacuo and the residue was extracted with ethyl acetate (2×100 mL), washed with saturated aqueous sodium bicarbonate solution (2×50 mL), dried over anhydrous sodium sulfate and concentrated in vacuo. Purification on flash silica gel chromatography (silica gel from QingDao, 200-300 mesh, glass column from Shanghai SD company) (10% ethyl acetate/hexanes) to afford 2-(3-bromo-5-methoxy-phenyl)-3,3-dimethyl-1,2,3,4-tet-rahydro-quinoline-6-carboxylic acid ethyl ester (2.7 g, 52%) as a white solid: LC/MS m/e calcd for $C_{21}H_{24}BrNO_3$ $M^+$: 418.3, observed: 418.1, 420.1.

A mixture of 2-(3-bromo-5-methoxy-phenyl)-3,3-dim-ethyl-1,2,3,4-tetrahydro-quinoline-6-carboxylic acid ethyl ester (0.85 g, 2.0 mmol), morpholine (1.77 g, 20 mmol), copper (I) iodide (0.23 g, 1.2 mmol), N,N-dimethylglycine hydrochloride (0.22 g, 1.6 mmol) and potassium carbonate (0.83 g, 6.0 mmol) in DMSO (5 mL) was heated for 4 hours at 120° C. After cooling to room temperature, the mixture was treated with ethyl acetate (50 mL) and washed with water (20 mL). The organic layer was dried over anhydrous sodium sulfate and concentrated in vacuo. Purification on flash silica gel chromatography (silica gel from QingDao, 200-300 mesh, glass column from Shanghai SD company) (20% ethyl acetate/hexanes) to afford 3,3-dimethyl-2-(3-methoxy-5-morpholin-4-yl-phenyl)-1,2,3,4-tetrahydro-quinoline-6-car-boxylic acid ethyl ester (0.30 g, 36%) as a white solid: LC/MS m/e calcd for $C_{25}H_{32}N_2O_4$ $(M+H)^+$: 425.5, observed: 425.3.

A mixture of 3,3-dimethyl-2-(3-methoxy-5-morpholin-4-yl-phenyl)-1,2,3,4-tetrahydro-quinoline-6-carboxylic acid ethyl ester (0.30 g, 0.71 mmol), lithium hydroxide hydrate (0.30 g, 7.1 mmol), water (1 mL) in methanol (2 mL) and tetrahydrofuran (10 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded 3,3-dimethyl-2-(3-methoxy-5-mor-pholin-4-yl-phenyl)-1,2,3,4-tetrahydro-quinoline-6-carboxylic acid (200 mg, 31%) as a white solid: LC/MS m/e calcd for $C_{23}H_{28}N_2O_4$ (M+H)+: 397.5, observed: 397.3.

Example 67

Cyclopropanesulfonic acid [2-(3-methoxy-5-morpholin-4-yl-phenyl)-3,3-dimethyl-1,2,3,4-tetrahydro-quinoline-6-carbonyl]-amide

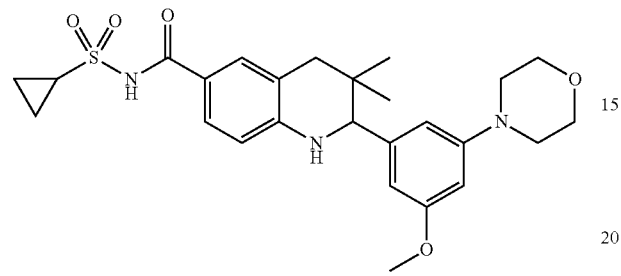

A mixture of 3,3-dimethyl-2-(3-methoxy-5-morpholin-4-yl-phenyl)-1,2,3,4-tetrahydro-quinoline-6-carboxylic acid (120 mg, 0.3 mmol), 1-3-dimethylaminopropyl-3-ethylcarbodiimide hydrochloride (87 mg, 0.45 mmol), 4-dimethylaminopyridine (55 mg, 0.45 mmol), cyclopropane sulfonamide (109 mg, 0.9 mmol) in dichloromethane (10 mL) was heated for at 65° C. for 12 hours. Removal of the solvent afforded an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded cyclopropanesulfonic acid [3,3-dimethyl-2-(3-methoxy-5-morpholin-4-yl-phenyl)-1,2,3,4-tetrahydro-quinoline-6-carbonyl]-amide (52 mg, 35%) as a light yellow solid: LC/MS m/e calcd for $C_{26}H_{33}N_3O_5S$ (M+H)+: 500.6, observed: 500.2.

Example 68

N-[2-(3-Methoxy-5-morpholin-4-yl-phenyl)-3,3-dimethyl-1,2,3,4-tetrahydro-quinoline-6-carbonyl]-methanesulfonamide

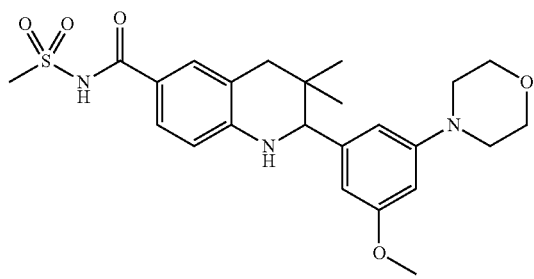 [SMILES: COc1cc(C2Nc3ccc(C(=O)NS(C)(=O)=O)cc3CC2(C)C)cc(N2CCOCC2)c1]

A mixture of 3,3-dimethyl-2-(3-methoxy-5-morpholin-4-yl-phenyl)-1,2,3,4-tetrahydro-quinoline-6-carboxylic acid (120 mg, 0.3 mmol), 1-3-dimethylaminopropyl-3-ethylcarbodiimide hydrochloride (87 mg, 0.45 mmol), 4-dimethylaminopyridine (55 mg, 0.45 mmol), methane sulfonamide (86 mg, 0.9 mmol) in dichloromethane (10 mL) was heated for at 65° C. for 12 hours. Removal of the solvent afforded an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded N-[3,3-dimethyl-2-(3-methoxy-5-morpholin-4-yl-phenyl)-1,2,3,4-tetrahydro-quinoline-6-carbonyl]-methanesulfonamide (57 mg, 40%) as a light yellow solid: LC/MS m/e calcd for $C_{24}H_{31}N_3O_5S$ (M+H)+: 474.6, observed: 474.0.

Example 69

N-[2-(3-Cyano-5-morpholin-4-yl-phenyl)-3,3-dimethyl-1,2,3,4-tetrahydro-quinoline-6-carbonyl]-methanesulfonamide

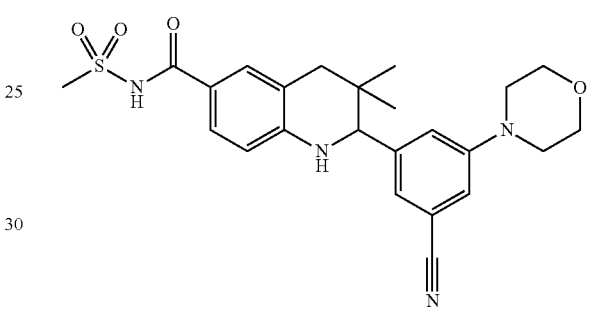

A mixture of 2-(3-chloro-5-morpholin-4-yl-phenyl)-3,3-dimethyl-1,2,3,4-tetrahydro-quinoline-6-carboxylic acid (100 mg, 0.25 mmol), sodium cyanide (24.5 mg, 0.5 mmol), nickel(II) bromide (54.6 mg, 0.25 mmol) in NMP (0.5 mL) was stirred for 10 minutes at 200° C. with microwave. After removal of the solid, the rediue was purificated by Waters automated flash system (column: Xterra 30 mm×100 mm, sample manager 2767, pump 2525, detector: ZQ mass and UV 2487, solvent system: acetonitrile and 0.1% formic acid in water) afforded 2-(3-cyano-5-morpholin-4-yl-phenyl)-3,3-dimethyl-1,2,3,4-tetrahydro-quinoline-6-carboxylic acid (39 mg, 40%) as a white solid: LC/MS m/e calcd for $C_{23}H_{25}N_3O_3$ (M+H)+: 392.5, observed: 392.2.

A mixture of 2-(3-cyano-5-morpholin-4-yl-phenyl)-3,3-dimethyl-1,2,3,4-tetrahydro-quinoline-6-carboxylic acid (60 mg, 0.15 mmol), 1-(3-dimethylaminopropyl)-3-ethylcarbodiimide hydrochloride (44 mg, 0.23 mmol), 4-dimethylaminopyridine (28 mg, 0.23 mmol), methane sulfonamide (43 mg, 0.45 mmol) in dichloromethane (10 mL) was heated at 65° C. for 12 hours. Removal of the solvent afforded an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded N-[2-(3-cyano-5-morpholin-4-yl-phenyl)-3,3-dimethyl-1,2,3,4-tetrahydro-quinoline-6-carbonyl]-methanesulfonamide (21 mg, 30%) as a light yellow solid: LC/MS m/e calcd for $C_{24}H_{28}N_4O_4S$ (M+H)$^+$: 469.6, observed: 469.2.

Example 70

Cyclopropanesulfonic acid [2-(3-cyclohexyl-5-fluoro-phenyl)-3,3-dimethyl-1,2,3,4-tetrahydro-quinoline-6-carbonyl]-amide

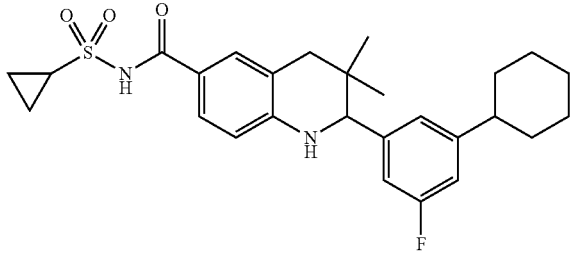 [SMILES: CC1(C)Cc2cc(C(=O)NS(=O)(=O)C3CC3)ccc2NC1c1cc(F)cc(C2CCCCC2)c1]

A mixture of 2-(3-bromo-5-fluoro-phenyl)-3,3-dimethyl-1,2,3,4-tetrahydro-quinoline-6-carboxylic acid ethyl ester (0.41 g, 1.0 mmol), cyclohexylzinc bromide solution 0.5 M in tetrahydrofuran (3.0 mL, 1.5 mmol), 1,1'-bis(diphenylphosphino) ferrocenedichloropalladium (II) (41 mg, 0.05 mmol), and DMF (0.5 mL) in dioxane (3 mL) was stirred at 70° C. for 2 hours. Then treated with saturated ammonium chloride (20 mL), extracted with ether (100 mL). After removal of solvent, the residue was purified on flash silica gel chromatography (silica gel from QingDao, 200-300 mesh, glass column from Shanghai SD company) (10% ethyl acetate/hexanes) to afford 2-(3-cyclohexyl-5-fluoro-phenyl)-3,3-dimethyl-1,2,3,4-tetrahydro-quinoline-6-carboxylic acid ethyl ester (0.21 g, 51%) as a white solid: LC/MS m/e calcd for $C_{26}H_{32}FNO_2$ M$^+$: 410.6, observed: 410.1.

A mixture of 2-(3-cyclohexyl-5-fluoro-phenyl)-3,3-dimethyl-1,2,3,4-tetrahydro-quinoline-6-carboxylic acid ethyl ester (0.21 g, 0.51 mmol), lithium hydroxide hydrate (0.22 g, 5.1 mmol), water (1 mL) in methanol (2 mL) and tetrahydrofuran (10 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-(3-cyclohexyl-5-fluoro-phenyl)-3,3-dimethyl-1,2,3,4-tetrahydro-quinoline-6-carboxylic acid (120 mg, 62%) as a white solid: LC/MS m/e calcd for $C_{24}H_{28}FNO_2$ (M+H)$^+$: 382.5, observed: 382.2.

A mixture of 2-(3-cyclohexyl-5-fluoro-phenyl)-3,3-dimethyl-1,2,3,4-tetrahydro-quinoline-6-carboxylic acid (60 mg, 0.16 mmol), 1-3-dimethylaminopropyl-3-ethylcarbodiimide hydrochloride (45 mg, 0.24 mmol), 4-dimethylaminopyridine (29 mg, 0.24 mmol), cyclopropane sulfonamide (58 mg, 0.48 mmol) in dichloromethane (10 mL) was heated at 65° C. for 12 hours. Removal of the solvent afforded an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded cyclopropane-sulfonic acid [2-(3-cyclohexyl-5-fluoro-phenyl)-3,3-dimethyl-1,2,3,4-tetrahydro-quinoline-6-carbonyl]-amide (16 mg, 20%) as a light yellow solid: LC/MS m/e calcd for $C_{27}H_{33}FN_2O_3S$ (M+H)$^+$: 485.6, observed: 485.3.

Example 71

2-(3-Fluoro-5-piperazin-1-yl-phenyl)-3,3-dimethyl-1,2,3,4-tetrahydro-quinoline-6-carboxylic acid

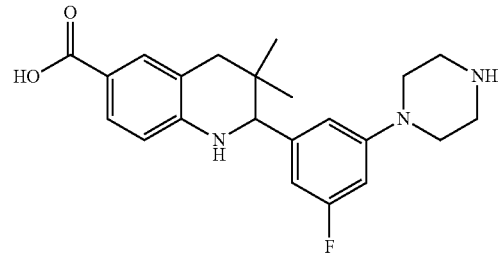 [SMILES: CC1(C)Cc2cc(C(=O)O)ccc2NC1c1cc(F)cc(N2CCNCC2)c1]

A mixture of 2-(3-bromo-5-fluoro-phenyl)-3,3-dimethyl-1,2,3,4-tetrahydro-quinoline-6-carboxylic acid methyl ester (0.41 g, 1.0 mmol), piperazine (0.26 g, 3.0 mmol), copper (I) iodidie (110 mg, 0.6 mmol), L-proline (69 mg, 0.6 mmol) and potassium hydroxide (33.6 mg, 0.6 mmol) in DMSO (2 mL) was stirred at 120° C. for 2 hours. Then treated with saturated ammonium chloride (20 mL), extracted with ether (100 mL). After removal of solvent, the residue was purified on flash silica gel chromatography (silica gel from QingDao, 200-300 mesh, glass column from Shanghai SD company) (40% ethyl acetate/hexanes) to afford 2-(3-fluoro-5-piperazin-1-yl-phenyl)-3,3-dimethyl-1,2,3,4-tetrahydro-quinoline-6-carboxylic acid ethyl ester (0.18 g, 43%) as a white solid: LC/MS m/e calcd for $C_{24}H_{30}FN_3O_2$ (M+H)$^+$: 412.5, observed: 412.3.

A mixture of 2-(3-fluoro-5-piperazin-1-yl-phenyl)-3,3-dimethyl-1,2,3,4-tetrahydro-quinoline-6-carboxylic acid ethyl ester (0.18 g, 0.43 mmol), lithium hydroxide hydrate (0.18 g, 4.3 mmol), water (2 mL) in methanol (5 mL) and tetrahydrofuran (5 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-(3-fluoro-5-piperazin-1-yl-phenyl)-3,3-dimethyl-1,2,3,4-tetrahydro-quinoline-6-carboxylic acid (49 mg, 30%) as a white solid: LC/MS m/e calcd for $C_{22}H_{26}FN_3O_2$ (M+H)$^+$: 384.5, observed: 384.1.

Example 72

3,3-Dimethyl-2-(4-morpholin-4-yl-phenyl)-1,2,3,4-tetrahydro-quinoline-6-carboxylic acid

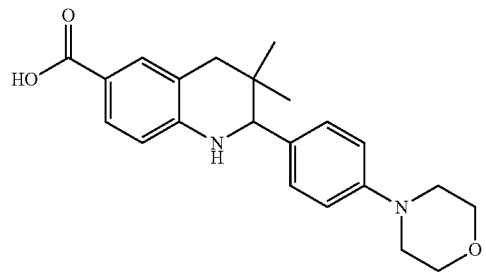 [SMILES: CC1(C)Cc2cc(C(=O)O)ccc2NC1c1ccc(N2CCOCC2)cc1]

A mixture of 4-amino-benzoic acid ethyl ester (4.5 g, 27 mmol) and 4-bromo-benzaldehyde (5.0 g, 27 mmol) in ethanol (150 mL) was prepared. The reaction mixture was heated to reflux for 2 h. Then the reaction mixture cooled to room temperature. The solvent was removed in vacuo and the residue was washed with ether to afford 4-{[1-(4-bromo-phenyl)-methylidene]-amino}-benzoic acid ethyl ester (6.3 g, 70%) as a white solid: LC/MS m/e calcd for $C_{16}H_{14}BrNO_2$ M+: 332.2, observed: 332.2, 334.2.

To a mixture of 4-{[1-(4-bromo-phenyl)-methylidene]-amino}-benzoic acid ethyl ester (9.8 g, 29.5 mmol) and ytterbium(III) triflate hydrate (1.83 g, 2.95 mmol) in dry tetrahydrofuran (20 mL) at 25° C. was added isobutyraldehyde (2.1 g, 29.5 mmol) and water (0.53 mL, 29.5 mmol) dropwise. The reaction mixture was stirred at 25° C. for 5 h. Then the reaction mixture was concentrated in vacuo and the residue was extracted with ethyl acetate (2×100 mL), washed with brine, dried over anhydrous sodium sulfate and concentrated in vacuo to afford 2-(4-bromo-phenyl)-4-hydroxy-3,3-dimethyl-1,2,3,4-tetrahydro-quinoline-6-carboxylic acid ethyl ester (11.9 g, 100%) as a light yellow oil: LC/MS m/e calcd for $C_{20}H_{22}BrNO_3$ M+: 404.3, observed: 404.1, 406.1.

To a mixture of 2-(4-bromo-phenyl)-4-hydroxy-3,3-dimethyl-1,2,3,4-tetrahydro-quinoline-6-carboxylic acid ethyl ester (11.9 g, 29.5 mmol) and triethylsilane (10 mL) at 25° C. was added trifluoroacetic acid (10 mL) dropwise. The resulting mixture was stirred at 25° C. for 1 h. Then the reaction mixture was concentrated in vacuo and the residue was extracted with ethyl acetate (2×200 mL), washed with saturated aqueous sodium bicarbonate solution (2×100 mL), dried over anhydrous sodium sulfate and concentrated in vacuo. Purification on flash silica gel chromatography (silica gel from QingDao, 200-300 mesh, glass column from Shanghai SD company) (10% ethyl acetate/hexanes) to 2-(4-bromo-phenyl)-3,3-dimethyl-1,2,3,4-tetrahydro-quinoline-6-carboxylic acid ethyl ester (6.9 g, 60%) as a white solid: LC/MS m/e calcd for $C_{20}H_{22}BrNO_2$ M+: 388.3, observed: 388.1, 390.1.

A mixture of 2-(4-bromo-phenyl)-3,3-dimethyl-1,2,3,4-tetrahydro-quinoline-6-carboxylic acid ethyl ester (1.0 g, 2.6 mmol), morpholine (2.24 g, 25.8 mmol), copper (I) iodide (0.29 g, 1.55 mmol), N,N-dimethylglycine hydrochloride (0.29 g, 2.06 mmol) and potassium carbonate (1.07, 7.74 mmol) in DMSO (10 mL) was heated for 3 hours at 120° C. After cooling to room temperature, the mixture was treated with ethyl acetate (50 mL) and washed with water (20 mL). The organic layer was dried over anhydrous sodium sulfate and concentrated in vacuo. Purification on flash silica gel chromatography (silica gel from QingDao, 200-300 mesh, glass column from Shanghai SD company) (20% ethyl acetate/hexanes) to afford 3,3-dimethyl-2-(4-morpholin-4-yl-phenyl)-1,2,3,4-tetrahydro-quinoline-6-carboxylic acid ethyl ester (0.20 g, 20%) as a white solid: LC/MS m/e calcd for $C_{24}H_{30}N_2O_3$ (M+H)+: 395.5, observed: 395.2.

A mixture of 3,3-dimethyl-2-(4-morpholin-4-yl-phenyl)-1,2,3,4-tetrahydro-quinoline-6-carboxylic acid ethyl ester (0.20 g, 0.51 mmol), lithium hydroxide hydrate (0.21 g, 5.1 mmol), water (1 mL) in methanol (2 mL) and tetrahydrofuran (10 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded 3,3-dimethyl-2-(4-morpholin-4-yl-phenyl)-1,2,3,4-tetrahydro-quinoline-6-carboxylic acid (56 mg, 30%) as a white solid: LC/MS m/e calcd for $C_{22}H_{26}N_2O_3$ (M+H)+: 367.5, observed: 367.1.

Example 73

Cyclopropanesulfonic acid [3,3-dimethyl-2-(4-morpholin-4-yl-phenyl)-1,2,3,4-tetrahydro-quinoline-6-carbonyl]-amide

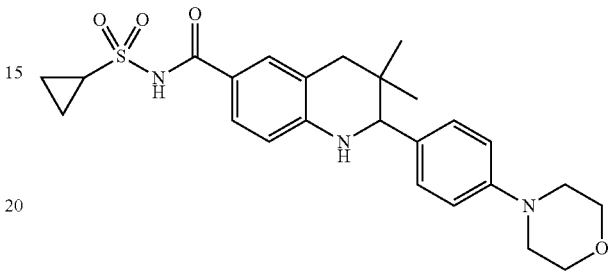

A mixture of 3,3-dimethyl-2-(4-morpholin-4-yl-phenyl)-1,2,3,4-tetrahydro-quinoline-6-carboxylic acid (70 mg, 0.19 mmol), 1-3-dimethylaminopropyl-3-ethylcarbodiimide hydrochloride (55 mg, 0.29 mmol), 4-dimethylaminopyridine (35 mg, 0.29 mmol), cyclopropane sulfonamide (69 mg, 0.57 mmol) in dichloromethane (10 mL) was heated for at 65° C. for 12 hours. Removal of the solvent afforded an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded cyclopropanesulfonic acid [3,3-dimethyl-2-(4-morpholin-4-yl-phenyl)-1,2,3,4-tetrahydro-quinoline-6-carbonyl]-amide (24 mg, 27%) as a light yellow solid: LC/MS m/e calcd for $C_{25}H_{31}N_3O_4S$ (M+H)+: 470.6, observed: 470.3.

Example 74

N-[3,3-Dimethyl-2-(4-morpholin-4-yl-phenyl)-1,2,3,4-tetrahydro-quinoline-6-carbonyl]-methanesulfonamide

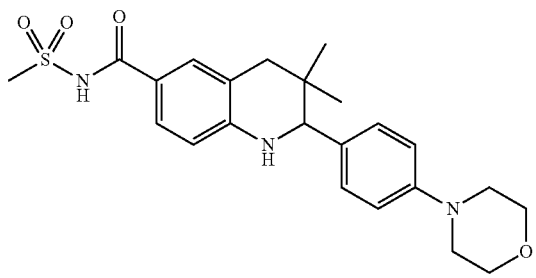 [SMILES: CC1(C)Cc2cc(C(=O)NS(C)(=O)=O)ccc2NC1c1ccc(N2CCOCC2)cc1]

A mixture of 3,3-dimethyl-2-(4-morpholin-4-yl-phenyl)-1,2,3,4-tetrahydro-quinoline-6-carboxylic acid (70 mg, 0.19 mmol), 1-3-dimethylaminopropyl-3-ethylcarbodiimide hydrochloride (55 mg, 0.29 mmol), 4-dimethylaminopyridine (35 mg, 0.29 mmol), methane sulfonamide (54 mg, 0.57 mmol) in dichloromethane (10 mL) was heated for at 65° C. for 12 hours. Removal of the solvent to affored an oil residue. Purification by Waters automated flash system (column:

Example 75

N-{2-[3-Fluoro-5-(4-isopropyl-piperazin-1-yl)-phenyl]-3,3-dimethyl-1,2,3,4-tetrahydro-quinoline-6-carbonyl}-methanesulfonamide

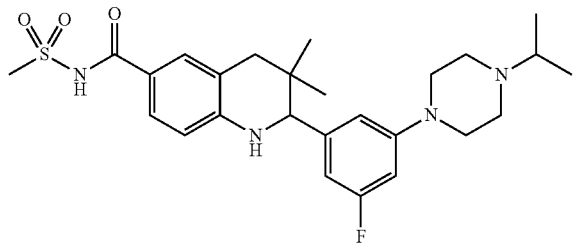 [SMILES: CC(C)N1CCN(c2cc(F)cc(C3Nc4ccc(C(=O)NS(C)(=O)=O)cc4CC3(C)C)c2)CC1]

A mixture of 2-(3-bromo-5-fluoro-phenyl)-3,3-dimethyl-1,2,3,4-tetrahydro-quinoline-6-carboxylic acid methyl ester (0.41 g, 1.0 mmol), 1-isopropyl piperazine (0.64 g, 5.0 mmol), copper (I) iodidie (120 mg, 0.6 mmol), L-proline (69 mg, 0.6 mmol) and potassium hydroxide (33.6 mg, 0.6 mmol) in DMSO (2 mL) was stirred at 120° C. for 2 hours. Then treated with saturated ammonium chloride (20 mL), extracted with ether (100 mL). After removal of solvent, the residue was purified on flash silica gel chromatography (silica gel from QingDao, 200-300 mesh, glass column from Shanghai SD company) (40% ethyl acetate/hexanes) to afford 2-[3-fluoro-5-(4-isopropyl-piperazin-1-yl)-phenyl]-3,3-dimethyl-1,2,3,4-tetrahydro-quinoline-6-carboxylic acid ethyl ester (0.27 g, 60%) as a white solid: LC/MS m/e calcd for $C_{27}H_{36}FN_3O_2$ (M+H)$^+$: 454.6, observed: 454.3.

A mixture of 2-[3-fluoro-5-(4-isopropyl-piperazin-1-yl)-phenyl]-3,3-dimethyl-1,2,3,4-tetrahydro-quinoline-6-carboxylic acid ethyl ester (0.27 g, 0.60 mmol), lithium hydroxide hydrate (0.25 g, 6.0 mmol), water (2 mL) in methanol (3 mL) and tetrahydrofuran (10 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-fluoro-5-(4-isopropyl-piperazin-1-yl)-phenyl]-3,3-dimethyl-1,2,3,4-tetrahydro-quinoline-6-carboxylic acid (89 mg, 35%) as a white solid: LC/MS m/e calcd for $C_{25}H_{32}FN_3O_2$ (M+H)$^+$: 426.6, observed: 426.3.

To a suspension of methanesulfonic acid amide (266 mg, 2.8 mmol) in N,N-dimethylformamide (3 mL) was added sodium hydride (112 mg, 2.8 mmol). The resulting mixture was stirred at 25° C. for 1 h. A solution of 2-[3-fluoro-5-(4-isopropyl-piperazin-1-yl)-phenyl]-3,3-dimethyl-1,2,3,4-tetrahydro-quinoline-6-carboxylic acid (120 mg, 0.28 mmol), and 1,1'-carbonyldiimidazole (91.5 mg, 0.56 mmol) in N,N-dimethylformamide (2 mL) was stirred at 70° C. for 1 h. The above suspension of methanesulfonic acid amide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-{2-[3-Fluoro-5-(4-isopropyl-piperazin-1-yl)-phenyl]-3,3-dimethyl-1,2,3,4-tetrahydro-quinoline-6-carbonyl}methanesulfonamide (20 mg, 14%) as a white solid: LC/MS m/e calcd for $C_{26}H_{35}FN_4O_3S$ (M+H)$^+$: 503.7, observed: 503.3.

Example 76

2-[3-Fluoro-5-(2-oxo-pyrrolidin-1-yl)-phenyl]-3,3-dimethyl-1,2,3,4-tetrahydro-quinoline-6-carboxylic acid

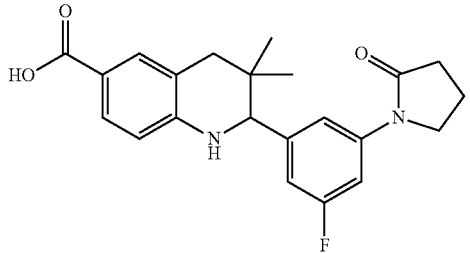 [SMILES: CC1(C)Cc2cc(C(=O)O)ccc2NC1c1cc(F)cc(N2CCCC2=O)c1]

A mixture of 2-(3-bromo-5-fluoro-phenyl)-3,3-dimethyl-1,2,3,4-tetrahydro-quinoline-6-carboxylic acid methyl ester (0.41 g, 1.0 mmol), pyrrolidin-2-one (0.24 g, 3.0 mmol), copper (I) iodidie (110 mg, 0.6 mmol), L-proline (69 mg, 0.6 mmol) and potassium hydroxide (33.6 mg, 0.6 mmol) in DMSO (2 mL) was stirred at 120° C. for 2 hours. Then treated with saturated ammonium chloride (20 mL), extracted with ether (100 mL). After removal of solvent, the residue was purified on flash silica gel chromatography (silica gel from QingDao, 200-300 mesh, glass column from Shanghai SD company) (20% ethyl acetate/hexanes) to afford 2-[3-fluoro-5-(2-oxo-pyrrolidin-1-yl)-phenyl]-3,3-dimethyl-1,2,3,4-tetrahydro-quinoline-6-carboxylic acid ethyl ester (0.25 g, 61%) as a white solid: LC/MS m/e calcd for $C_{24}H_{27}FN_2O_3$ (M+H)$^+$: 411.5, observed: 411.3.

A mixture of 2-[3-fluoro-5-(2-oxo-pyrrolidin-1-yl)-phenyl]-3,3-dimethyl-1,2,3,4-tetrahydro-quinoline-6-carboxylic acid ethyl ester (0.25 g, 0.61 mmol), lithium hydroxide hydrate (0.26 g, 6.1 mmol), water (2 mL) in methanol (3 mL) and tetrahydrofuran (10 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-fluoro-5-(2-oxo-pyrrolidin-1-yl)-phenyl]-3,3-dimethyl-1,2,3,4-tetrahydro-quinoline-6-carboxylic acid (77 mg, 33%) as a white solid: LC/MS m/e calcd for $C_{22}H_{23}FN_2O_3$ (M+H)$^+$: 383.4, observed: 383.2.

Example 77

N-{2-[3-Fluoro-5-(2-oxo-pyrrolidin-1-yl)-phenyl]-3,3-dimethyl-1,2,3,4-tetrahydro-quinoline-6-carbonyl}-methanesulfonamide

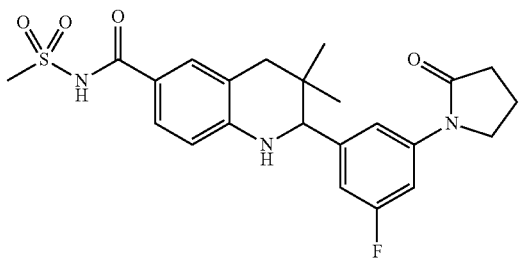 [SMILES: CC1(C)Cc2cc(C(=O)NS(C)(=O)=O)ccc2NC1c1cc(F)cc(N2CCCC2=O)c1]

A mixture of 2-[3-fluoro-5-(2-oxo-pyrrolidin-1-yl)-phenyl]-3,3-dimethyl-1,2,3,4-tetrahydro-quinoline-6-carboxylic acid (130 mg, 0.34 mmol), 1-3-dimethylaminopropyl-3-ethylcarbodiimide hydrochloride (98 mg, 0.51 mmol), 4-dimethylaminopyridine (62 mg, 0.51 mmol), methane sulfonamide (97 mg, 1.02 mmol) in dichloromethane (10 mL) was heated for at 65° C. for 12 hours. Removal of the solvent afforded an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded N-{2-[3-fluoro-5-(2-oxo-pyrrolidin-1-yl)-phenyl]-3,3-dimethyl-1,2,3,4-tetrahydro-quinoline-6-carbonyl}-methanesulfonamide (45 mg, 29%) as a light yellow solid: LC/MS m/e calcd for $C_{23}H_{26}FN_3O_4S$ (M+H)$^+$: 460.5, observed: 460.2.

Example 78

2-[3-(1-Carboxy-1-methyl-ethylamino)-phenyl]-6-chloro-3,3-dimethyl-1,2,3,4-tetrahydro-quinoline-8-carboxylic acid methyl ester

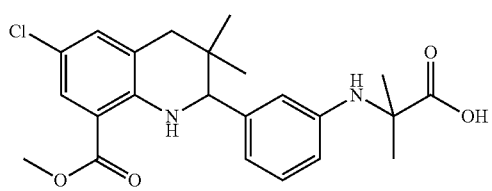 [SMILES: COC(=O)c1cc(Cl)cc2c1NC(c1cccc(NC(C)(C)C(=O)O)c1)C(C)(C)C2]

A mixture of 2-amino-5-chloro-benzoic acid methyl ester (11.7 g, 63 mmol) and 3-bromo-benzaldehyde (11.7 g, 63 mmol) in ethanol (200 mL). The reaction mixture was heated to reflux for 2 hours. Then the reaction mixture cooled to room temperature. The solvent was removed in vacuo and the residue was washed with ether to afford 2-{[1-(3-bromo-phenyl)-methylidene]-amino}-5-chloro-benzoic acid methyl ester (5.3 g, 24%) as a white solid: LC/MS m/e calcd for $C_{15}H_{11}BrClNO_2$ M$^+$: 353.6, observed: 353.6.

To a mixture of 2-{[1-(3-bromo-phenyl)-methylidene]-amino}-5-chloro-benzoic acid methyl ester (5.3 g, 15 mmol) and ytterbium(III) triflate hydrate (0.93 g, 1.5 mmol) in dry tetrahydrofuran (10 mL) at 25° C. was added isobutyraldehyde (1.08 g, 15 mmol) and water (0.27 mL, 15 mmol) dropwise. The reaction mixture was stirred at 25° C. for 5 h. Then the reaction mixture was concentrated in vacuo and the residue was extracted with ethyl acetate (2×100 mL), washed with brine, dried over anhydrous sodium sulfate and concentrated in vacuo to afford 2-(3-bromo-phenyl)-6-chloro-4-hydroxy-3,3-dimethyl-1,2,3,4-tetrahydro-quinoline-8-carboxylic acid methyl ester (6.4 g, 100%) as a light yellow oil: LC/MS m/e calcd for $C_{19}H_{19}BrClNO_3$ M$^+$: 424.7, observed: 408.0.

To a mixture of 2-(3-bromo-phenyl)-6-chloro-4-hydroxy-3,3-dimethyl-1,2,3,4-tetrahydro-quinoline-8-carboxylic acid methyl ester (6.4 g, 15 mmol) and triethylsilane (10 mL) at 25° C. was added trifluoroacetic acid (10 mL) dropwise. The resulting mixture was stirred at 25° C. for 1 h. Then the reaction mixture was concentrated in vacuo and the residue was extracted with ethyl acetate (2×100 mL), washed with saturated aqueous sodium bicarbonate solution (2×50 mL), dried over anhydrous sodium sulfate and concentrated in vacuo. Purification on flash silica gel chromatography (silica gel from QingDao, 200-300 mesh, glass column from Shanghai SD company) (5% ethyl acetate/hexanes) to afford 2-(3-bromo-phenyl)-6-chloro-3,3-dimethyl-1,2,3,4-tetrahydro-quinoline-8-carboxylic acid methyl ester (2.51 g, 41%) as a white solid: LC/MS m/e calcd for $C_{19}H_{19}BrClNO_2$ M$^+$: 408.7, observed: 408.8.

A mixture of 2-(3-bromo-phenyl)-6-chloro-3,3-dimethyl-1,2,3,4-tetrahydro-quinoline-8-carboxylic acid methyl ester (1.2 g, 2.94 mmol), 2-aminoisobutyric acid (1.20 g, 12 mmol), copper (I) iodide (0.34 g, 1.76 mmol), N,N-dimethylglycine hydrochloride (0.33 g, 2.35 mmol) and potassium carbonate (1.22, 8.82 mmol) in DMSO (10 mL) was heated for 4 hours at 120° C. After cooling to room temperature, the mixture was treated with ethyl acetate (50 mL) and washed with water (20 mL). The organic layer was dried over anhydrous sodium sulfate and concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-(1-carboxy-1-methyl-ethylamino)-phenyl]-6-chloro-3,3-dimethyl-1,2,3,4-tetrahydro-quinoline-8-carboxylic acid methyl ester (300 mg, 24%) as a white solid: LC/MS m/e calcd for $C_{23}H_{27}ClN_2O_4$ (M+H)$^+$: 431.9, observed: 431.1.

Example 79

6-Chloro-3,3-dimethyl-2-[3-(1-methyl-1-methylcarbamoyl-ethylamino)-phenyl]-1,2,3,4-tetrahydro-quinoline-8-carboxylic acid

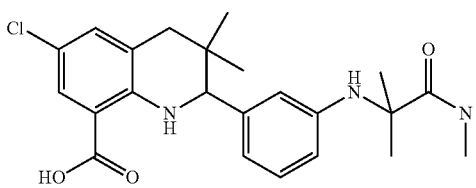 [SMILES: CNC(=O)C(C)(C)Nc1cccc(C2Nc3c(cc(Cl)cc3C(=O)O)CC2(C)C)c1]

A mixture of 2-[3-(1-carboxy-1-methyl-ethylamino)-phenyl]-6-chloro-3,3-dimethyl-1,2,3,4-tetrahydro-quinoline-8-carboxylic acid methyl ester (73 mg, 0.17 mmol), 1-(3-dimethylaminopropyl)-3-ethylcarbodiimide hydrochloride (65 mg, 0.34 mmol), 4-dimethylaminopyridine (41.5 mg, 0.34 mmol), methaneamine (0.26 mL, 0.52 mmol) in tetrahydrofuran and triethylamine (34 mg, 0.34 mmol) in dichloromethane (10 mL) was stirred for 48 hours. Removal of the solvent to afford the crude product 6-chloro-3,3-dimethyl-2-[3-(1-methyl-1-methylcarbamoyl-ethylamino)-phenyl]-1,2,3,4-tetrahydro-quinoline-8-carboxylic acid methyl ester (75 mg, 100%) which was used in next step without purification: LC/MS m/e calcd for $C_{24}H_{30}ClN_3O_3$ $(M+H)^+$: 444.98, observed: 444.1.

A mixture of 6-chloro-3,3-dimethyl-2-[3-(1-methyl-1-methylcarbamoyl-ethylamino)-phenyl]-1,2,3,4-tetrahydro-quinoline-8-carboxylic acid methyl ester (75 mg, 0.17 mmol), lithium hydroxide hydrate (71 mg, 1.7 mmol), water (0.5 mL) in methanol (1 mL) and tetrahydrofuran (5 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded 6-chloro-3,3-dimethyl-2-[3-(1-methyl-1-methylcarbamoyl-ethylamino)-phenyl]-1,2,3,4-tetrahydro-quinoline-8-carboxylic acid (24 mg, 33%) as a white solid: LC/MS m/e calcd for $C_{23}H_{28}ClN_3O_3$ $(M+H)^+$: 430.95, observed: 430.1.

Example 80

2-[3-(1-Carboxy-1-methyl-ethylamino)-phenyl]-6-chloro-3,3-dimethyl-1,2,3,4-tetrahydro-quinoline-8-carboxylic acid

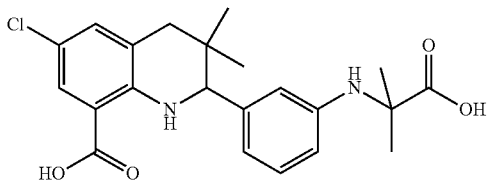 [SMILES: CC(C)(Nc1cccc(C2Nc3c(cc(Cl)cc3C(=O)O)CC2(C)C)c1)C(=O)O]

A mixture of 2-[3-(1-carboxy-1-methyl-ethylamino)-phenyl]-6-chloro-3,3-dimethyl-1,2,3,4-tetrahydro-quinoline-8-carboxylic acid methyl ester (100 mg, 0.23 mmol), lithium hydroxide hydrate (98 mg, 2.3 mmol), water (0.5 mL) in methanol (1 mL) and tetrahydrofuran (5 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-(1-carboxy-1-methyl-ethylamino)-phenyl]-6-chloro-3,3-dimethyl-1,2,3,4-tetrahydro-quinoline-8-carboxylic acid (24 mg, 25%) as a white solid: LC/MS m/e calcd for $C_{22}H_{25}ClN_2O_4$ $(M+H)^+$: 417.91, observed: 417.0.

Example 81

2-[3-(4-Acetyl-piperazin-1-yl)-phenyl]-6-chloro-3,3-dimethyl-1,2,3,4-tetrahydro-quinoline-8-carboxylic acid

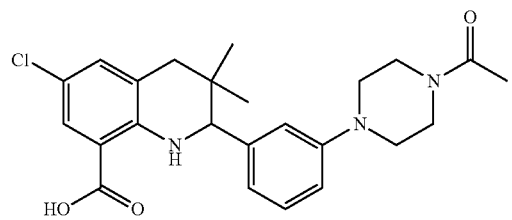 [SMILES: CC(=O)N1CCN(c2cccc(C3Nc4c(cc(Cl)cc4C(=O)O)CC3(C)C)c2)CC1]

To a mixture of 2-(3-bromo-phenyl)-6-chloro-3,3-dimethyl-1,2,3,4-tetrahydro-quinoline-8-carboxylic acid methyl ester (410 mg, 1 mmol), palladium acetate (6.73 mg, 0.03 mmol), cesium carbonate (0.65 g, 2 mmol), xantphos (23 mg, 0.04 mmol) and N-acetylpiperazine (192 mg, 1.5 mmol) in toluene (10 mL) was stirred at 120° C. for 12 hours. Then the reaction mixture was concentrated in vacuo and the residue was extracted with ethyl acetate (2×100 mL), washed with saturated aqueous sodium chloride (2×50 mL), dried over anhydrous sodium sulfate and concentrated in vacuo. Purification on flash silica gel chromatography (silica gel from QingDao, 200-300 mesh, glass column from Shanghai SD company) (20% ethyl acetate/hexanes) to afford 2-[3-(4-acetyl-piperazin-1-yl)-phenyl]-6-chloro-3,3-dimethyl-1,2,3,4-tetrahydro-quinoline-8-carboxylic acid methyl ester (0.25 g, 54%) as a white solid: LC/MS m/e calcd for $C_{25}H_{30}ClN_3O_3$ $M^+$: 455.99, observed: 456.1.

A mixture of 2-[3-(4-acetyl-piperazin-1-yl)-phenyl]-6-chloro-3,3-dimethyl-1,2,3,4-tetrahydro-quinoline-8-carboxylic acid methyl ester (247 mg, 0.54 mmol), lithium hydroxide hydrate (230 mg, 5.4 mmol), water (1.0 mL) in methanol (2 mL) and tetrahydrofuran (10 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-[3-(4-acetyl-piperazin-1-yl)-phenyl]-6-chloro-3,3-dimethyl-1,2,3,4-tetrahydro-quinoline-8-carboxylic acid (62 mg, 26%) as a white solid: LC/MS m/e calcd for $C_{24}H_{28}ClN_3O_3$ $M^+$: 441.96, observed: 442.0.

Example 82

6-Chloro-3,3-dimethyl-2-[3-(4-o-tolyl-piperazin-1-yl)-phenyl]-1,2,3,4-tetrahydro-quinoline-8-carboxylic acid

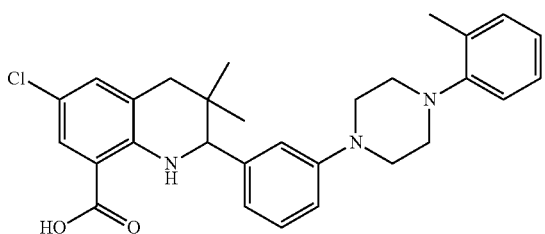 [SMILES: Cc1ccccc1N1CCN(c2cccc(C3Nc4c(cc(Cl)cc4C(=O)O)CC3(C)C)c2)CC1]

To a mixture of 2-(3-bromo-phenyl)-6-chloro-3,3-dimethyl-1,2,3,4-tetrahydro-quinoline-8-carboxylic acid methyl ester (410 mg, 1 mmol), palladium acetate (6.73 mg, 0.03 mmol), cesium carbonate (0.65 g, 2 mmol), xantphos (23 mg, 0.04 mmol) and 1-(ortho-tolyl)piperazine hydrochloride (320 mg, 1.5 mmol) in toluene (10 mL) was stirred at 120° C. for 12 hours. Then the reaction mixture was concentrated in vacuo and the residue was extracted with ethyl acetate (2×100 mL), washed with saturated aqueous sodium chloride (2×50 mL), dried over anhydrous sodium sulfate and concentrated in vacuo. Purification on flash silica gel chromatography (silica gel from QingDao, 200-300 mesh, glass column from Shanghai SD company) (20% ethyl acetate/hexanes) to afford 6-chloro-3,3-dimethyl-2-[3-(4-o-tolyl-piperazin-1-yl)-phenyl]-1,2,3,4-tetrahydro-quinoline-8-carboxylic acid methyl ester (0.36 g, 73%) as a white solid: LC/MS m/e calcd for $C_{30}H_{34}ClN_3O_2$ M$^+$: 505.08, observed: 504.2.

A mixture of 6-chloro-3,3-dimethyl-2-[3-(4-o-tolyl-piperazin-1-yl)-phenyl]-1,2,3,4-tetrahydro-quinoline-8-carboxylic acid methyl ester (0.36 g, 0.73 mmol), lithium hydroxide hydrate (310 mg, 7.3 mmol), water (2.0 mL) in methanol (3 mL) and tetrahydrofuran (10 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded 6-chloro-3,3-dimethyl-2-[3-(4-o-tolyl-piperazin-1-yl)-phenyl]-1,2,3,4-tetrahydro-quinoline-8-carboxylic acid (150 mg, 42%) as a white solid: LC/MS m/e calcd for $C_{29}H_{32}ClN_3O_2$ M$^+$: 490.05, observed: 490.1.

Example 83

N-[2-(4'-tert-Butyl-biphenyl-3-yl)-3,3-dimethyl-1,2,3,4-tetrahydro-quinoline-6-carbonyl]-methanesulfonamide

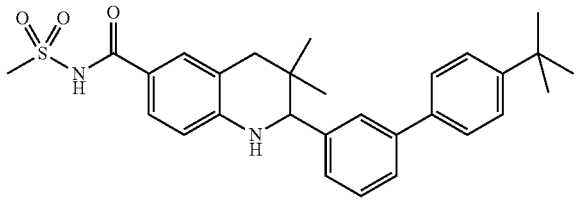 [SMILES: CC(C)(C)c1ccc(-c2cccc(C3Nc4ccc(C(=O)NS(C)(=O)=O)cc4CC3(C)C)c2)cc1]

A mixture of 4-amino-benzoic acid ethyl ester (16.5 g, 100 mmol) and 3-bromo-benzaldehyde (18.5 g, 100 mmol) in ethanol (100 mL) was heated to reflux for 2 h. Then the reaction mixture cooled to room temperature. The solvent was removed in vacuo and the residue was washed with ether to afford 4-{[1-(3-bromo-phenyl)-methylidene]-amino}-benzoic acid ethyl ester (20 g, 60%) as a white solid: LC/MS m/e calcd for $C_{16}H_{14}BrNO_2$ M$^+$: 332.2, observed: 332.0, 334.0.

To a mixture of 4-{[1-(3-bromo-phenyl)-methylidene]-amino}-benzoic acid ethyl ester (6.7 g, 20.1 mmol) and ytterbium(III) triflate hydrate (1.25 g, 2.01 mmol) in dry tetrahydrofuran (15 mL) at 25° C. was added isobutyraldehyde (1.45 g, 20.1 mmol) and water (0.36 mL, 20.1 mmol) dropwise. The reaction mixture was stirred at 25° C. for 5 h. Then the reaction mixture was concentrated in vacuo and the residue was extracted with ethyl acetate (2×100 mL), washed with brine, dried over anhydrous sodium sulfate and concentrated in vacuo to afford 2-(3-bromo-phenyl)-4-hydroxy-3,3-dimethyl-1,2,3,4-tetrahydro-quinoline-6-carboxylic acid ethyl ester (8.12 g, 100%) as a light yellow oil: LC/MS m/e calcd for $C_{20}H_{22}BrNO_3$ M$^+$: 404.3, observed: 404.0, 406.0.

To a mixture of 2-(3-bromo-phenyl)-4-hydroxy-3,3-dimethyl-1,2,3,4-tetrahydro-quinoline-6-carboxylic acid ethyl ester (8.12 g, 20.1 mmol) and triethylsilane (10 mL) at 25° C. was added trifluoroacetic acid (10 mL) dropwise. The resulting mixture was stirred at 25° C. for 1 h. Then the reaction mixture was concentrated in vacuo and the residue was extracted with ethyl acetate (2×200 mL), washed with saturated aqueous sodium bicarbonate solution (2×100 mL), dried over anhydrous sodium sulfate and concentrated in vacuo. Purification on flash silica gel chromatography (silica gel from QingDao, 200-300 mesh, glass column from Shanghai SD company) (10% ethyl acetate/hexanes) to afford 2-(3-bromo-phenyl)-3,3-dimethyl-1,2,3,4-tetrahydro-quinoline-6-carboxylic acid ethyl ester (2.9 g, 37%) as a white solid: LC/MS m/e calcd for $C_{20}H_{22}BrNO_2$ M$^+$: 388.3, observed: 388.0, 390.0.

A mixture of 2-(3-bromo-phenyl)-3,3-dimethyl-1,2,3,4-tetrahydro-quinoline-6-carboxylic acid ethyl ester (0.50 g, 1.29 mmol), 4-tert-butylbenzeneboronic acid (0.46 g, 2.58 mmol), bis(triphenylphosphine)palladium (II) chloride (91 mg, 0.13 mmol) and 2 M sodium carbonate (1.3 mL, 2.6 mmol) in dioxane (5 mL) was heated for 3 hours at 120° C. After cooling to room temperature, the mixture was treated with ethyl acetate (50 mL) and washed with water (20 mL). The organic layer was dried over anhydrous sodium sulfate and concentrated in vacuo. Purification on flash silica gel chromatography (silica gel from QingDao, 200-300 mesh, glass column from Shanghai SD company) (10% ethyl acetate/hexanes) to afford 2-(4'-tert-butyl-biphenyl-3-yl)-3,3-dimethyl-1,2,3,4-tetrahydro-quinoline-6-carboxylic acid ethyl ester (0.28 g, 49%) as a white solid: LC/MS m/e calcd for $C_{30}H_{35}NO_2$ (M+H)$^+$: 442.6, observed: 442.2.

A mixture of 2-(4'-tert-butyl-biphenyl-3-yl)-3,3-dimethyl-1,2,3,4-tetrahydro-quinoline-6-carboxylic acid ethyl ester (0.28 g, 0.63 mmol) in methanol (7 mL) and tetrahydrofuran (5 mL), lithium hydroxide hydrate (0.27 g, 6.3 mmol) in water (0.5 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford 2-(4'-tert-butyl-biphenyl-3-yl)-3,3-dimethyl-1,2,3,4-tetrahydro-quinoline-6-carboxylic acid (0.18 g, 70%) as a white solid which was used for next step without further purification: LC/MS m/e calcd for $C_{28}H_{31}NO_2$ (M+H)$^+$: 414.6, observed: 414.1;

A mixture of 2-(4'-tert-butyl-biphenyl-3-yl)-3,3-dimethyl-1,2,3,4-tetrahydro-quinoline-6-carboxylic acid (90 mg, 0.22 mmol), 1-3-dimethylaminopropyl-3-ethylcarbodiimide hydrochloride (63 mg, 0.33 mmol), 4-dimethylaminopyridine (40 mg, 0.33 mmol), methane sulfonamide (63 mg, 0.66 mmol) in dichloromethane (10 mL) was refluxed for 12 hours. Removal of the solvent afforded an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded N-[2-(4'-tert-butyl-biphenyl-3-yl)-3,3-dimethyl-1,2,3,4-tetrahydro-quinoline-6-carbonyl]-methanesulfonamide (30 mg, 28%) as a light yellow solid: LC/MS m/e calcd for $C_{29}H_{34}N_2O_3S$ (M+H)$^+$: 491.67, observed: 491.2.

Example 84

2-(4'-Isopropoxy-biphenyl-3-yl)-3,3-dimethyl-1,2,3,4-tetrahydro-quinoline-6-carboxylic acid

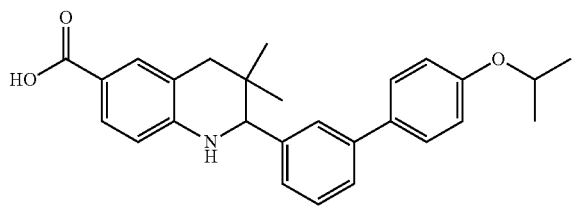 [SMILES: CC(C)Oc1ccc(-c2cccc(C3Nc4ccc(C(=O)O)cc4CC3(C)C)c2)cc1]

A mixture of 2-(3-bromo-phenyl)-3,3-dimethyl-1,2,3,4-tetrahydro-quinoline-6-carboxylic acid ethyl ester (0.43 g, 1.1 mmol), 4-isopropoxy benzeneboronic acid (0.40 g, 2.2 mmol), bis(triphenylphosphine)palladium (II) chloride (77 mg, 0.11 mmol) and 2 M sodium carbonate (1.6 mL, 3.2 mmol) in dioxane (10 mL) was heated for 3 hours at 120° C. After cooling to room temperature, the mixture was treated with ethyl acetate (50 mL) and washed with water (20 mL). The organic layer was dried over anhydrous sodium sulfate and concentrated in vacuo. Purification on flash silica gel chromatography (silica gel from QingDao, 200-300 mesh, glass column from Shanghai SD company) (10% ethyl acetate/hexanes) to afford 2-(4'-isopropoxy-biphenyl-3-yl)-3,3-dimethyl-1,2,3,4-tetrahydro-quinoline-6-carboxylic acid ethyl ester (0.30 g, 62%) as a white solid: LC/MS m/e calcd for $C_{29}H_{33}NO_3$ (M+H)$^+$: 444.6, observed: 444.1.

A mixture of 2-(4'-isopropoxy-biphenyl-3-yl)-3,3-dimethyl-1,2,3,4-tetrahydro-quinoline-6-carboxylic acid ethyl ester (0.30 g, 0.68 mmol) in methanol (2 mL) and tetrahydrofuran (15 mL), lithium hydroxide hydrate (0.28 g, 6.8 mmol) in water (1.0 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-(4'-isopropoxy-biphenyl-3-yl)-3,3-dimethyl-1,2,3,4-tetrahydro-quinoline-6-carboxylic acid (0.18 g, 65%) as a white solid which was used for next step without further purification: LC/MS m/e calcd for $C_{27}H_{29}NO_3$ (M+H)$^+$: 416.5, observed: 416.1.

Example 85

N-[2-(4'-Isopropoxy-biphenyl-3-yl)-3,3-dimethyl-1,2,3,4-tetrahydro-quinoline-6-carbonyl]-methanesulfonamide

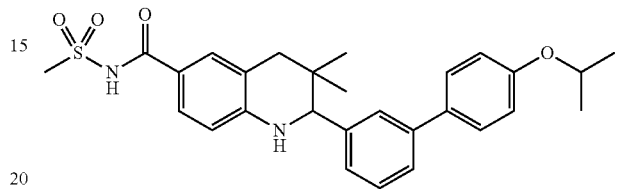

A mixture of 2-(4'-isopropoxy-biphenyl-3-yl)-3,3-dimethyl-1,2,3,4-tetrahydro-quinoline-6-carboxylic acid (90 mg, 0.22 mmol), 1-3-dimethylaminopropyl-3-ethylcarbodiimide hydrochloride (63 mg, 0.33 mmol), 4-dimethylaminopyridine (40 mg, 0.33 mmol), methane sulfonamide (63 mg, 0.66 mmol) in dichloromethane (10 mL) was refluxed for 12 hours. Removal of the solvent afforded an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded N-[2-(4'-isopropoxy-biphenyl-3-yl)-3,3-dimethyl-1,2,3,4-tetrahydro-quinoline-6-carbonyl]-methanesulfonamide (30 mg, 28%) as a light yellow solid: LC/MS m/e calcd for $C_{28}H_{32}N_2O_4S$ (M+H)$^+$: 493.64, observed: 493.5.

Example 86

Cyclopropanesulfonic acid [2-(4'-isopropoxy-biphenyl-3-yl)-3,3-dimethyl-1,2,3,4-tetrahydro-quinoline-6-carbonyl]-amide

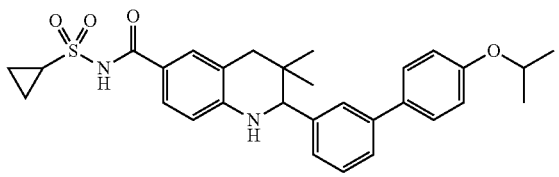 [SMILES: CC(C)Oc1ccc(-c2cccc(C3Nc4ccc(C(=O)NS(=O)(=O)C5CC5)cc4CC3(C)C)c2)cc1]

A mixture of 2-(4'-isopropoxy-biphenyl-3-yl)-3,3-dimethyl-1,2,3,4-tetrahydro-quinoline-6-carboxylic acid (90 mg, 0.22 mmol), 1-3-dimethylaminopropyl-3-ethylcarbodiimide hydrochloride (63 mg, 0.33 mmol), 4-dimethylaminopyridine (40 mg, 0.33 mmol), cyclopropane sulfonamide (80 mg, 0.66 mmol) in dichloromethane (10 mL) was refluxed for 12 hours. Removal of the solvent afforded an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded cyclopropanesulfonic acid [2-(4'-isopropoxy-biphenyl-3-yl)-3,3-dimethyl-1,2,3,4-tetrahydro-quinoline-6-carbonyl]-amide (25 mg, 22%) as a light yellow solid: LC/MS m/e calcd for $C_{30}H_{34}N_2O_4S$ (M+H)$^+$: 519.68, observed: 519.4.

Example 87

2-{3-[4-(4-Chloro-phenyl)-piperazin-1-yl]-phenyl}-3,3-dimethyl-1,2,3,4-tetrahydro-quinoline-6-carboxylic acid

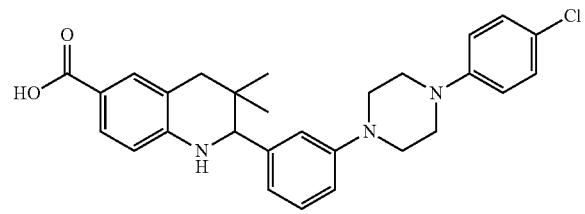 [SMILES: CC1(C)Cc2cc(C(=O)O)ccc2NC1c1cccc(N2CCN(c3ccc(Cl)cc3)CC2)c1]

To a mixture of 2-(3-bromo-phenyl)-3,3-dimethyl-1,2,3,4-tetrahydro-quinoline-6-carboxylic acid ethyl ester (388 mg, 1 mmol), palladium acetate (6.73 mg, 0.03 mmol), cesium carbonate (0.65 g, 2 mmol), xantphos (23 mg, 0.04 mmol) and 1-(4-chloro-phenyl)-piperazine hydrochloride (350 mg, 1.5 mmol) in toluene (10 mL) was stirred at 120° C. for 12 hours. Then the reaction mixture was concentrated in vacuo and the residue was extracted with ethyl acetate (2×100 mL), washed with saturated aqueous sodium chloride (2×50 mL), dried over anhydrous sodium sulfate and concentrated in vacuo. Purification on flash silica gel chromatography (silica gel from QingDao, 200-300 mesh, glass column from Shanghai SD company) (20% ethyl acetate/hexanes) to afford 2-{3-[4-(4-chloro-phenyl)-piperazin-1-yl]-phenyl}-3,3-dimethyl-1,2,3,4-tetrahydro-quinoline-6-carboxylic acid ethyl ester (0.20 g, 40%) as a white solid: LC/MS m/e calcd for $C_{30}H_{34}ClN_3O_2$ M$^+$: 504.08, observed: 504.2.

A mixture of 2-{3-[4-(4-chloro-phenyl)-piperazin-1-yl]-phenyl}-3,3-dimethyl-1,2,3,4-tetrahydro-quinoline-6-carboxylic acid ethyl ester (0.20 g, 0.40 mmol), lithium hydroxide hydrate (167 mg, 4.0 mmol), water (0.5 mL) in methanol (1 mL) and tetrahydrofuran (10 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-{3-[4-(4-chloro-phenyl)-piperazin-1-yl]-phenyl}-3,3-dimethyl-1,2,3,4-tetrahydro-quinoline-6-carboxylic acid (100 mg, 53%) as a white solid: LC/MS m/e calcd for $C_{28}H_{30}ClN_3O_2$ M$^+$: 476.02, observed: 476.3.

Example 88

N-(2-{3-[4-(4-Chloro-phenyl)-piperazin-1-yl]-phenyl}-3,3-dimethyl-1,2,3,4-tetrahydro-quinoline-6-carbonyl)-methanesulfonamide

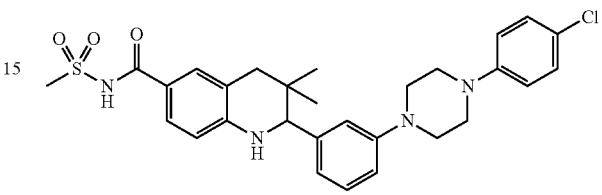

A mixture of 2-{3-[4-(4-chloro-phenyl)-piperazin-1-yl]-phenyl}-3,3-dimethyl-1,2,3,4-tetrahydro-quinoline-6-carboxylic acid (100 mg, 0.21 mmol), 1-3-dimethylaminopropyl-3-ethylcarbodiimide hydrochloride (60.5 mg, 0.32 mmol), 4-dimethylaminopyridine (39 mg, 0.32 mmol), methane sulfonamide (60 mg, 0.63 mmol) in dichloromethane (10 mL) was refluxed for 12 hours. Removal of the solvent afforded an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded N-(2-{3-[4-(4-chloro-phenyl)-piperazin-1-yl]-phenyl}-3,3-dimethyl-1,2,3,4-tetrahydroquinoline-6-carbonyl)-methanesulfonamide (30 mg, 26%) as a light yellow solid: LC/MS m/e calcd for $C_{29}H_{33}ClN_4O_3S$ M$^+$: 553.13, observed: 553.2.

Example 89

2-{3-[4-(2,4-Dimethyl-phenyl)-piperazin-1-yl]-phenyl}-3,3-dimethyl-1,2,3,4-tetrahydro-quinoline-6-carboxylic acid

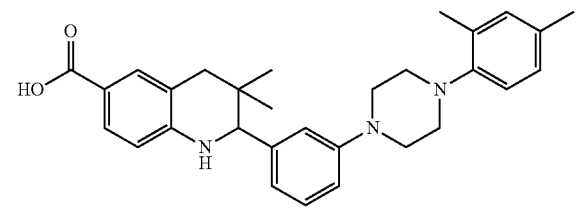 [SMILES: Cc1ccc(N2CCN(c3cccc(C4Nc5ccc(C(=O)O)cc5CC4(C)C)c3)CC2)c(C)c1]

To a mixture of 2-(3-bromo-phenyl)-3,3-dimethyl-1,2,3,4-tetrahydro-quinoline-6-carboxylic acid ethyl ester (388 mg, 1 mmol), palladium acetate (6.73 mg, 0.03 mmol), cesium carbonate (0.65 g, 2 mmol), xantphos (23 mg, 0.04 mmol) and 1-(2,4-dimethyl-phenyl)-piperazine hydrochloride (285 mg, 1.5 mmol) in toluene (10 mL) was stirred at 120° C. for 12 hours. Then the reaction mixture was concentrated in vacuo and the residue was extracted with ethyl acetate (2×100 mL), washed with saturated aqueous sodium chloride (2×50 mL), dried over anhydrous sodium sulfate and concentrated in vacuo. Purification on flash silica gel chromatography (silica gel from QingDao, 200-300 mesh, glass column from Shanghai SD company) (20% ethyl acetate/hexanes) to afford 2-{3-[4-(2,4-dimethyl-phenyl)-piperazin-1-yl]-phenyl}-3,3-dimethyl-1,2,3,4-tetrahydro-quinoline-6-carboxylic acid ethyl ester (0.20 g, 40%) as a white solid: LC/MS m/e calcd for $C_{32}H_{39}N_3O_2$ (M+H)$^+$: 498.7, observed: 498.9.

A mixture of 2-{3-[4-(2,4-dimethyl-phenyl)-piperazin-1-yl]-phenyl}-3,3-dimethyl-1,2,3,4-tetrahydro-quinoline-6-carboxylic acid ethyl ester (0.20 g, 0.40 mmol), lithium hydroxide hydrate (167 mg, 4.0 mmol), water (0.5 mL) in methanol (1 mL) and tetrahydrofuran (10 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded 2-{3-[4-(2,4-dimethyl-phenyl)-piperazin-1-yl]-phenyl}-3,3-dimethyl-1,2,3,4-tetrahydro-quinoline-6-carboxylic acid (150 mg, 80%) as a white solid: LC/MS m/e calcd for $C_{30}H_{35}N_3O_2$ (M+H)$^+$: 470.6, observed: 470.4.

Example 90

N-(2-{3-[4-(2,4-Dimethyl-phenyl)-piperazin-1-yl]-phenyl}-3,3-dimethyl-1,2,3,4-tetrahydro-quinoline-6-carbonyl)-methanesulfonamide

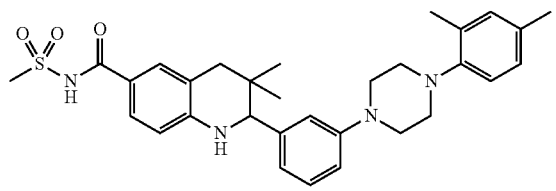

A mixture of 2-{3-[4-(2,4-dimethyl-phenyl)-piperazin-1-yl]-phenyl}-3,3-dimethyl-1,2,3,4-tetrahydro-quinoline-6-carboxylic acid (100 mg, 0.21 mmol), 1-3-dimethylaminopropyl-3-ethylcarbodiimide hydrochloride (61 mg, 0.32 mmol), 4-dimethylaminopyridine (39 mg, 0.32 mmol), methane sulfonamide (60 mg, 0.63 mmol) in dichloromethane (10 mL) was refluxed for 12 hours. Removal of the solvent afforded an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded N-(2-{3-[4-(2,4-Dimethyl-phenyl)-piperazin-1-yl]-phenyl}-3,3-dimethyl-1,2,3,4tetrahydro-quinoline-6-carbonyl)-methanesulfonamide (34 mg, 30%) as a light yellow solid: LC/MS m/e calcd for $C_{31}H_{38}N_4O_3S$ (M+H)$^+$: 547.7, observed: 547.2.

Example 91

Cyclopropanesulfonic acid (2-{3-[4-(2,4-dimethyl-phenyl)-piperazin-1-yl]-phenyl}-3,3-dimethyl-1,2,3,4-tetrahydro-quinoline-6-carbonyl)-amide

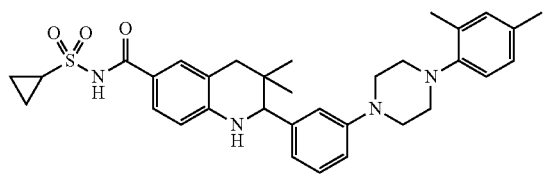 [SMILES: Cc1ccc(N2CCN(c3cccc(C4Nc5ccc(C(=O)NS(=O)(=O)C6CC6)cc5CC4(C)C)c3)CC2)c(C)c1]

A mixture of 2-{3-[4-(2,4-dimethyl-phenyl)-piperazin-1-yl]-phenyl}-3,3-dimethyl-1,2,3,4-tetrahydro-quinoline-6-carboxylic acid (100 mg, 0.21 mmol), 1-3-dimethylaminopropyl-3-ethylcarbodiimide hydrochloride (61 mg, 0.32 mmol), 4-dimethylaminopyridine (39 mg, 0.32 mmol), cyclopropane sulfonamide (76 mg, 0.63 mmol) in dichloromethane (10 mL) was refluxed for 12 hours. Removal of the solvent afforded an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded cyclopropanesulfonic acid (2-{3-[4-(2,4-dimethyl-phenyl)-piperazin-1-yl]-phenyl}-3,3-dimethyl-1,2,3,4-tetrahydro-quinoline-6-carbonyl)-amide (30 mg, 25%) as a light yellow solid: LC/MS m/e calcd for $C_{33}H_{40}N_4O_3S$ (M+H)$^+$: 573.8, observed: 573.3.

Example 92

6-Fluoro-3,3-dimethyl-2-[3-(4-o-tolyl-piperazin-1-yl)-phenyl]-1,2,3,4-tetrahydro-quinoline-8-carboxylic acid

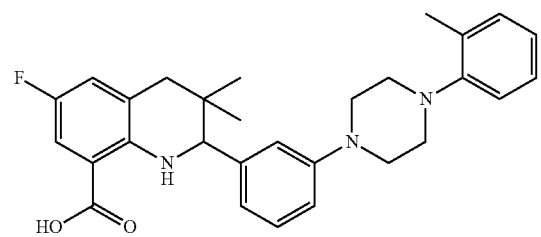 [SMILES: Cc1ccccc1N1CCN(c2cccc(C3Nc4c(cc(F)cc4C(=O)O)CC3(C)C)c2)CC1]

A mixture of 2-amino-5-fluoro-benzoic acid methyl ester (15 g, 89 mmol) and 3-bromo-benzaldehyde (16.4 g, 89 mmol) in ethanol (200 mL) was heated to reflux for 2 hours. Then the reaction mixture cooled to room temperature. The solvent was removed in vacuo and the residue was washed with ether to afford 2-{[1-(3-bromo-phenyl)-methylidene]-amino}-5-fluoro-benzoic acid methyl ester (15.3 g, 52%) as a white solid: LC/MS m/e calcd for $C_{15}H_{11}BrFNO_2$ M$^+$: 336.2, observed: 336.2.

To a mixture of 2-{[1-(3-bromo-phenyl)-methylidene]-amino}-5-fluoro-benzoic acid methyl ester (50 g, 59.8 mmol) and ytterbium(III) triflate hydrate (3.7 g, 5.95 mmol) in dry tetrahydrofuran (30 mL) at 25° C. was added isobutyraldehyde (4.3 g, 59.5 mmol) and water (1.1 mL, 59.5 mmol) dropwise. The reaction mixture was stirred at 25° C. for 5 h. Then the reaction mixture was concentrated in vacuo and the residue was extracted with ethyl acetate (2×100 mL), washed with brine, dried over anhydrous sodium sulfate and concentrated in vacuo to afford 2-(3-bromo-phenyl)-6-fluoro-4-hydroxy-3,3-dimethyl-1,2,3,4-tetrahydro-quinoline-8-carboxylic acid methyl ester (24.3 g, 100%) as a light yellow oil: LC/MS m/e calcd for $C_{19}H_{19}BrFNO_3$ M+: 408.3, observed: 408.1.

To a mixture of 2-(3-bromo-phenyl)-6-fluoro-4-hydroxy-3,3-dimethyl-1,2,3,4-tetrahydro-quinoline-8-carboxylic acid methyl ester (24.3 g, 59.5 mmol) and triethylsilane (20 mL) at 25° C. was added trifluoroacetic acid (20 mL) dropwise. The resulting mixture was stirred at 25° C. for 1 h. Then the reaction mixture was concentrated in vacuo and the residue was extracted with ethyl acetate (2×100 mL), washed with saturated aqueous sodium bicarbonate solution (2×50 mL), dried over anhydrous sodium sulfate and concentrated in vacuo. Purification on flash silica gel chromatography (silica gel from QingDao, 200-300 mesh, glass column from Shanghai SD company) (5% ethyl acetate/hexanes) to afford 2-(3-bromo-phenyl)-6-fluoro-3,3-dimethyl-1,2,3,4-tetrahydro-quinoline-8-carboxylic acid methyl ester (10 g, 43%) as a white solid: LC/MS m/e calcd for $C_{19}H_{19}BrFNO_2$ M+: 392.3, observed: 391.9, 393.9.

To a mixture of 2-(3-bromo-phenyl)-6-fluoro-3,3-dimethyl-1,2,3,4-tetrahydro-quinoline-8-carboxylic acid methyl ester (1.0 g, 2.6 mmol), palladium acetate (17.5 mg, 0.078 mmol), cesium carbonate (1.7 g, 5.2 mmol), xantphos (60.2 mg, 0.10 mmol) and 1-(ortho-tolyl)piperazine hydrochloride (830 mg, 3.9 mmol) in toluene (30 mL) was stirred at 120° C. for 12 hours. Then the reaction mixture was concentrated in vacuo and the residue was extracted with ethyl acetate (2×100 mL), washed with saturated aqueous sodium chloride (2×50 mL), dried over anhydrous sodium sulfate and concentrated in vacuo. Purification on flash silica gel chromatography (silica gel from QingDao, 200-300 mesh, glass column from Shanghai SD company) (20% ethyl acetate/hexanes) to afford 6-fluoro-3,3-dimethyl-2-[3-(4-o-tolyl-piperazin-1-yl)-phenyl]-1,2,3,4-tetrahydro-quinoline-8-carboxylic acid methyl ester (0.80 g, 63%) as a white solid: LC/MS m/e calcd for $C_{30}H_{34}FN_3O_2$ (M+H)+: 488.6, observed: 488.3.

A mixture of 6-fluoro-3,3-dimethyl-2-[3-(4-o-tolyl-piperazin-1-yl)-phenyl]-1,2,3,4-tetrahydro-quinoline-8-carboxylic acid methyl ester (0.80 g, 1.64 mmol), lithium hydroxide hydrate (690 mg, 16.4 mmol), water (1.0 mL) in methanol (5 mL) and tetrahydrofuran (20 mL) was stirred at 60° C. for 12 h. The mixture was neutralized with a 3N aqueous hydrochloric acid solution and extracted with ethyl acetate (2×50 mL), washed with water, dried over anhydrous sodium sulfate and then concentrated in vacuo to afford an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded 6-fluoro-3,3-dimethyl-2-[3-(4-o-tolyl-piperazin-1-yl)-phenyl]-1,2,3,4-tetrahydro-quinoline-8-carboxylic acid (400 mg, 52%) as a white solid: LC/MS m/e calcd for $C_{29}H_{32}FN_3O_2$ (M+H)+: 474.6, observed: 474.3.

Example 93

N-(6-Chloro-2-{3-[4-(4-chloro-phenyl)-piperazin-1-yl]-phenyl}-3,3-dimethyl-1,2,3,4-tetrahydro-quinoline-8-carbonyl)-methanesulfonamide

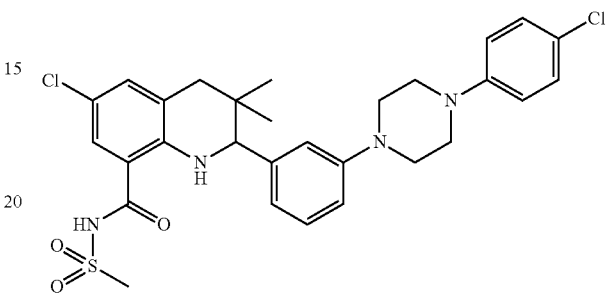

To a mixture of 2-(3-bromo-phenyl)-6-chloro-3,3-dimethyl-1,2,3,4-tetrahydro-quinoline-8-carboxylic acid methyl ester (410 mg, 1 mmol), palladium acetate (6.73 mg, 0.03 mmol), cesium carbonate (0.65 g, 2 mmol), xantphos (23 mg, 0.04 mmol) and 1-(4-chloro-phenyl)piperazine hydrochloride (350 mg, 1.5 mmol) in toluene (10 mL) was stirred at 120° C. for 12 hours. Then the reaction mixture was concentrated in vacuo and the residue was extracted with ethyl acetate (2×100 mL), washed with saturated aqueous sodium chloride (2×50 mL), dried over anhydrous sodium sulfate and concentrated in vacuo. Purification on flash silica gel chromatography (silica gel from QingDao, 200-300 mesh, glass column from Shanghai SD company) (20% ethyl acetate/hexanes) to afford 6-chloro-2-{3-[4-(4-chloro-phenyl)-piperazin-1-yl]-phenyl}-3,3-dimethyl-1,2,3,4-tetrahydro-quinoline-8-carboxylic acid methyl ester (0.13 g, 25%) as a white solid: LC/MS m/e calcd for $C_{29}H_{31}Cl_2N_3O_2$ M+: 524.5, observed: 524.0.

A mixture of 6-chloro-2-{3-[4-(4-chloro-phenyl)-piperazin-1-yl]-phenyl}-3,3-dimethyl-1,2,3,4-tetrahydro-quinoline-8-carboxylic acid methyl ester (0.13 g, 0.25 mmol), lithium hydroxide hydrate (104 mg, 2.5 mmol), water (0.5 mL) in methanol (1 mL) and tetrahydrofuran (5 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded 6-chloro-2-{3-[4-(4-chloro-phenyl)-piperazin-1-yl]-phenyl}-3,3-dimethyl-1,2,3,4-tetrahydro-quinoline-8-carboxylic acid (100 mg, 80%) as a white solid: LC/MS m/e calcd for $C_{28}H_{29}Cl_2N_3O_2$ M+: 510.5, observed: 510.0;

A mixture of 2-{3-[4-(4-chloro-phenyl)-piperazin-1-yl]-phenyl}-3,3-dimethyl-1,2,3,4-tetrahydro-quinoline-6-carboxylic acid (100 mg, 0.2 mmol), 1-3-dimethylaminopropyl-3-ethylcarbodiimide hydrochloride (56 mg, 0.3 mmol), 4-dimethylaminopyridine (37 mg, 0.3 mmol), methane sulfonamide (57 mg, 0.6 mmol) in dichloromethane (10 mL) was refluxed for 12 hours. Removal of the solvent afforded an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded N-(6-chloro-2-{3-[4-(4-chloro-phenyl)-piperazin-1-yl]-phenyl}-3,3-dimethyl-1,2,3,4-tetrahydro-quinoline-8-carbonyl)-methanesulfonamide (44 mg, 37%) as a light yellow solid: LC/MS m/e calcd for $C_{29}H_{32}Cl_2N_4O_3S$ (M+H)$^+$: 588.6, observed: 589.2.

Example 94

3,3-Dimethyl-2-[3-(4-o-tolyl-piperazin-1-yl)-phenyl]-1,2,3,4-tetrahydro-quinoline-8-carboxylic acid

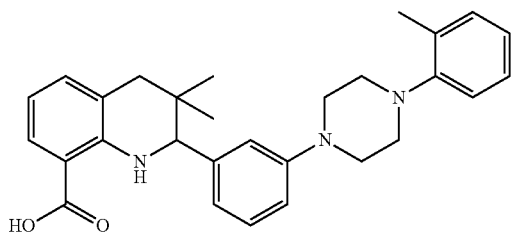 [SMILES: Cc1ccccc1N1CCN(c2cccc(C3Nc4c(cccc4C(=O)O)CC3(C)C)c2)CC1]

To a mixture of 2-(3-bromo-phenyl)-6-chloro-3,3-dimethyl-1,2,3,4-tetrahydro-quinoline-8-carboxylic acid methyl ester (410 mg, 1 mmol), palladium acetate (6.73 mg, 0.03 mmol), cesium carbonate (0.65 g, 2 mmol), xantphos (23 mg, 0.04 mmol) and 1-(ortho-tolyl)piperazine hydrochloride (320 mg, 1.5 mmol) in toluene (10 mL) was stirred at 120° C. for 12 hours. Then the reaction mixture was concentrated in vacuo and the residue was extracted with ethyl acetate (2×100 mL), washed with saturated aqueous sodium chloride (2×50 mL), dried over anhydrous sodium sulfate and concentrated in vacuo. Purification on flash silica gel chromatography (silica gel from QingDao, 200-300 mesh, glass column from Shanghai SD company) (20% ethyl acetate/hexanes) to afford 3,3-dimethyl-2-[3-(4-o-tolyl-piperazin-1-yl)-phenyl]-1,2,3, 4-tetrahydro-quinoline-8-carboxylic acid methyl ester (0.10 g, 21%) as a white solid: LC/MS m/e calcd for $C_{30}H_{35}N_3O_2$ (M+H)$^+$: 470.6, observed: 470.6.

A mixture of 3,3-dimethyl-2-[3-(4-o-tolyl-piperazin-1-yl)-phenyl]-1,2,3,4-tetrahydro-quinoline-8-carboxylic acid methyl ester (0.10 g, 0.21 mmol), lithium hydroxide hydrate (88 mg, 2.1 mmol), water (0.5 mL) in methanol (1 mL) and tetrahydrofuran (5 mL) was stirred at 60° C. for 12 h. The mixture was neutralized with a 3N aqueous hydrochloric acid solution and extracted with ethyl acetate (2×20 mL), washed with water, dried over anhydrous sodium sulfate and then concentrated in vacuo to afford an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded 3,3-dimethyl-2-[3-(4-o-tolyl-piperazin-1-yl)-phenyl]-1,2,3,4-tetrahydro-quinoline-8-carboxylic acid (30 mg, 31%) as a white solid: LC/MS m/e calcd for $C_{29}H_{33}N_3O_2$ (M+H)$^+$: 456.6, observed: 456.3.

Example 95

6-Chloro-3,3-dimethyl-2-(3-morpholin-4-yl-phenyl)-1,2,3,4-tetrahydro-quinoline-5-carboxylic acid

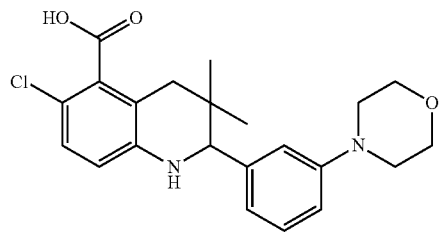 [SMILES: CC1(C)Cc2c(ccc(Cl)c2C(=O)O)NC1c1cccc(N2CCOCC2)c1]

To a stirred solution of 5-amino-2-chloro-benzoic acid (50 g, 291 mmol) in methanol (300 mL) was added thionyl chloride (45 mL, 605 mmol) dropwise at 0° C. Then the mixture solution was refluxed for 12 hours before cooling to room temperature. Then the reaction mixture was concentrated in vacuo and the residue was dissolved in ethyl acetate (500 mL), washed with saturated aqueous sodium bicarbonate solution (3×100 mL), dried over anhydrous sodium sulfate and concentrated in vacuo to afford 5-amino-2-chloro-benzoic acid methyl ester (54 g, quant.) as a pale-white solid: LC/MS m/e calcd for $C_8H_8ClNO_2$ (M+H)$^+$: 186.61, observed: 185.9.

A mixture solution of 5-amino-2-chloro-benzoic acid methyl ester (21 g, 113.2 mmol), 3-bromo-benzaldehyde (21 g, 113.2 mmol) and p-toluenesulfonic acid (431 mg, 2.2 mmol) in toluene (200 mL) was heated to reflux for 12 hours. Then the reaction mixture was cooled to room temperature. The solvent was removed in vacuo and the residue was washed with ether to afford 5-[(3-bromo-benzylidene)-amino]-2-chloro-benzoic acid methyl ester (39.8 g, quant.) as a pale-white solid: MS calcd. for $C_{15}H_{11}BrClNO_2$ 353.62, obsd. (ESI$^+$) [(M+H)$^+$] 351.9 & 353.9.

To a stirred mixture solution of 5-[(3-bromo-benzylidene)-amino]-2-chloro-benzoic acid methyl ester (39.8 g, 113.2 mmol) and ytterbium(III) triflate hydrate (10.5 g, 16.9 mmol) in dry tetrahydrofuran (100 mL) at 25° C. was added isobutyraldehyde (10.4 mL, 113.2 mmol) and water (2.1 mL, 113.2 mmol) dropwise. The reaction mixture was stirred at 25° C. for 16 h. Then the reaction mixture was concentrated in vacuo and the residue was extracted with ethyl acetate (2×200 mL), washed with brine, dried over anhydrous sodium sulfate and concentrated in vacuo to afford 2-(3-bromo-phenyl)-6-chloro-4-hydroxy-3,3-dimethyl-1,2,3,4-tetrahydro-quinoline-5-carboxylic acid methyl ester (48 g, quant.) as a light yellow oil which was used for next step without further purification: LC/MS m/e calcd for $C_{19}H_{19}BrClNO_3$ (M+H)$^+$: 425.73, observed: 405.9 & 407.9.

To a stirred mixture solution of 2-(3-bromo-phenyl)-6-chloro-4-hydroxy-3,3-dimethyl-1,2,3,4-tetrahydro-quinoline-5-carboxylic acid methyl ester (48 g, 113.2 mmol) and triethylsilane (60 mL) at 25° C. was added trifluoroacetic acid (30 mL) dropwise. The resulting mixture solution was stirred at 25° C. for 3 hours. Then the reaction mixture was concentrated in vacuo and the residue was extracted with ethyl acetate (2×200 mL), washed with saturated aqueous sodium bicarbonate solution (4×100 mL), dried over anhydrous sodium sulfate and concentrated in vacuo. The residue was triturated with methanol. The resulting precipitate was collected, dried in vacuo to afford 2-(3-bromo-phenyl)-6-chloro-3,3-dimethyl-1,2,3,4-tetrahydro-quinoline-5-carboxylic acid methyl ester (15 g, 32.6%) as a white solid: LC/MS m/e calcd for $C_{19}H_{19}BrClNO_2$ (M+H)$^+$: 409.73, observed: 407.9 & 409.9.

A mixture of 2-(3-bromo-phenyl)-6-chloro-3,3-dimethyl-1,2,3,4-tetrahydro-quinoline-5-carboxylic acid methyl ester (1.2 g, 2.94 mmol), morpholine (1.3 mL, 14.7 mmol), copper (I) iodide (140 mg, 0.7 mmol), N,N-dimethylglycine hydrochloride (206 mg, 1.5 mmol) and potassium carbonate (1.2 g, 8.8 mmol) in dimethyl sulfoxide (15 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo to afford 6-chloro-3,3-dimethyl-2-(3-morpholin-4-yl-phenyl)-1,2,3,4-tetrahydro-quinoline-5-carboxylic acid methyl ester (973 mg, 80%) as a white solid which was used for next step without further purification: LC/MS m/e calcd for $C_{23}H_{27}ClN_2O_3$ (M+H)$^+$: 415.94, observed: 415.1.

To a stirred mixture solution of 6-chloro-3,3-dimethyl-2-(3-morpholin-4-yl-phenyl)-1,2,3,4-tetrahydro-quinoline-5-carboxylic acid methyl ester (200 mg, 0.5 mmol) in methanol (5.0 mL) and tetrahydrofuran (5.0 mL) was added 50% sodium hydroxide in water (1.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 6-chloro-3,3-dimethyl-2-(3-morpholin-4-yl-phenyl)-1,2,3,4-tetrahydro-quinoline-5-carboxylic acid (180 mg, 90%) as a light yellow solid: LC/MS m/e calcd for $C_{22}H_{25}ClN_2O_3$ (M+H)$^+$: 401.91, observed: 401.1.

Example 96

N-{3,3-Dimethyl-2-[3-(4-methyl-piperazin-1-yl)-phenyl]-1,2,3,4-tetrahydro-quinoline-6-carbonyl}-methanesulfonamide

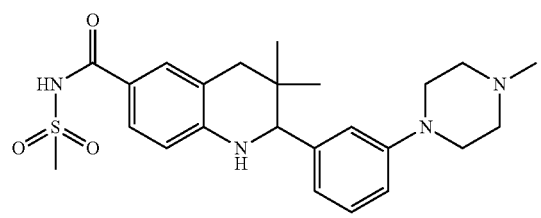 [SMILES: CN1CCN(c2cccc(C3Nc4ccc(C(=O)NS(C)(=O)=O)cc4CC3(C)C)c2)CC1]

To a suspension of 60% sodium hydride (187 mg, 4.7 mmol) in N,N-dimethylformamide (1.5 mL) was added methanesulfonamide (451 mg, 4.8 mmol) at room temperature. The resulting mixture was stirred at 25° C. for 1 h. A solution of 3,3-dimethyl-2-[3-(4-methyl-piperazin-1-yl)-phenyl]-1,2,3,4-tetrahydro-quinoline-6-carboxylic acid (180 mg, 0.47 mmol) and 1,1'-carbonyldiimidazole (155 mg, 1.0 mmol) in N,N-dimethylformamide (2.0 mL) was stirred at 70° C. After stirring at 70° C. for 1 h, the above suspension of methanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-{3,3-dimethyl-2-[3-(4-methyl-piperazin-1-yl)-phenyl]-1,2,3,4-tetrahydro-quinoline-6-carbonyl}-methanesulfonamide (68 mg, 32%) as a white solid: LC/MS m/e calcd for $C_{24}H_{32}N_4O_3S$ (M+H)$^+$: 457.61, observed: 456.9.

Example 97

Cyclopropanesulfonic acid [3,3-dimethyl-2-(3-piperazin-1-yl-phenyl)-1,2,3,4-tetrahydro-quinoline-6-carbonyl]-amide

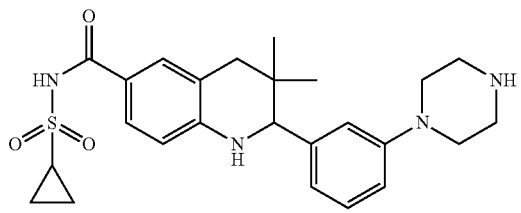 [SMILES: CC1(C)Cc2cc(C(=O)NS(=O)(=O)C3CC3)ccc2NC1c1cccc(N2CCNCC2)c1]

To a suspension of 60% sodium hydride (196 mg, 4.9 mmol) in N,N-dimethylformamide (1.5 mL) was added cyclopropanesulfonamide (605 mg, 5.0 mmol) at room temperature. The resulting mixture was stirred at 25° C. for 1 h. A solution of 3,3-dimethyl-2-(3-piperazin-1-yl-phenyl)-1,2,3, 4-tetrahydro-quinoline-6-carboxylic acid (180 mg, 0.5 mmol) and 1,1'-carbonyldiimidazole (162 mg, 1.0 mmol) in N,N-dimethylformamide (2.0 mL) was stirred at 70° C. After stirring at 70° C. for 1 h, the above suspension of cyclopropanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [3,3-dimethyl-2-(3-piperazin-1-yl-phenyl)-1,2,3,4-tetrahydro-quinoline-6-carbonyl]-amide (74 mg, 32%) as a light yellow solid: LC/MS m/e calcd for $C_{25}H_{32}N_4O_3S$ (M+H)$^+$: 469.61, observed: 469.0.

Example 98

Ethanesulfonic acid [3,3-dimethyl-2-(3-morpholin-4-yl-phenyl)-1,2,3,4-tetrahydro-quinoline-6-carbonyl]-amide

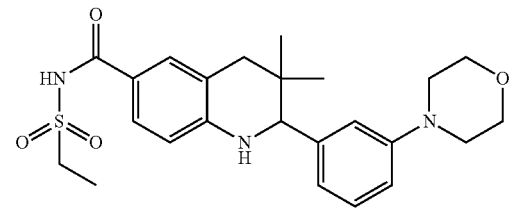

To a suspension of 60% sodium hydride (745 mg, 18.6 mmol) in N,N-dimethylformamide (2.5 mL) was added ethanesulfonamide (2.3 g, 19 mmol) at room temperature.

The resulting mixture was stirred at 25° C. for 1 h. A solution of 3,3-dimethyl-2-(3-morpholin-4-yl-phenyl)-1,2,3,4-tetrahydro-quinoline-6-carboxylic acid (690 mg, 1.9 mmol) and 1,1'-carbonyldiimidazole (650 mg, 3.8 mmol) in N,N-dimethylformamide (2.0 mL) was stirred at 70° C. After stirring at 70° C. for 1 h, the above suspension of ethanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded ethanesulfonic acid [3,3-dimethyl-2-(3-morpholin-4-yl-phenyl)-1,2,3,4-tetrahydro-quinoline-6-carbonyl]-amide (347 mg, 40%) as a white solid: LC/MS m/e calcd for $C_{24}H_{31}N_3O_4S$ (M+H)$^+$: 458.61, observed: 458.0.

Example 99

3,3-Dimethyl-2-[3-(4-methyl-piperazin-1-yl)-phenyl]-1,2,3,4-tetrahydro-quinoline-6-carboxylic acid

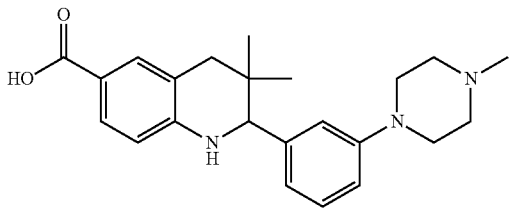 [SMILES: CN1CCN(c2cccc(C3Nc4ccc(C(=O)O)cc4CC3(C)C)c2)CC1]

A mixture of 4-amino-benzoic acid ethyl ester (33 g, 200 mmol), 3-bromo-benzaldehyde (25.7 mL, 220 mmol) and p-toluenesulfonic acid (760 mg, 4 mmol) in toluene (600 mL) was heated to reflux for 12 h. Then the reaction mixture cooled to room temperature. The solvent was removed in vacuo and the residue was washed with ether to afford 4-[(3-bromo-benzylidene)-amino]-benzoc acid ethyl ester (34 g, 51%) as a light yellow solid: LC/MS m/e calcd for $C_{16}H_{14}BrNO_2$ (M+H)$^+$: 333.20, observed: 332.0 & 334.0.

To a mixture of 4-[(3-bromo-benzylidene)-amino]-benzoc acid ethyl ester (29 g, 87 mmol) and Ytterbium(III) triflate hydrate (5.4 g, 8.7 mmol) in dry tetrahydrofuran (200 mL) at 25° C. was added Isobutyraldehyde (8.8 mL, 96 mmol) and water (1.6 mL, 87 mmol) dropwise. The reaction mixture was stirred at 25° C. for 16 h. Then the reaction mixture was concentrated in vacuo and the residue was extracted with ethyl acetate (2×200 mL), washed with brine, dried over anhydrous sodium sulfate and concentrated in vacuo to afford 2-(3-bromo-phenyl)-4-hydroxy-3,3-dimethyl-1,2,3,4-tetrahydro-quinoline-6-carboxylic acid ethyl ester (30 g, 85%) as a light yellow oil which was used for next step without further purification: LC/MS m/e calcd for $C_{20}H_{22}BrNO_3$ (M+H)$^+$: 405.31, observed: 386.0 & 388.0.

To a mixture of 2-(3-bromo-phenyl)-4-hydroxy-3,3-dimethyl-1,2,3,4-tetrahydro-quinoline-6-carboxylic acid ethyl ester (30 g, 74 mmol) and triethylsilane (50 mL) at 25° C. was added trifluoroacetic acid (15 mL) dropwise. The resulting mixture was stirred at 25° C. for 4 h. Then the reaction mixture was concentrated in vacuo and the residue was extracted with ethyl acetate (2×200 mL), washed with saturated aqueous sodium bicarbonate solution (2×100 mL), dried over anhydrous sodium sulfate and concentrated in vacuo. The residue was triturated with methanol. The resulting precipitate was collected, dried in vacuo to afford 2-(3-bromo-phenyl)-3,3-dimethyl-1,2,3,4-tetrahydro-quinoline-6-carboxylic acid ethyl ester (15 g, 78%) as a white solid: LC/MS m/e calcd for $C_{20}H_{22}BrNO_2$ (M+H)$^+$: 389.31, observed: 388.0 & 390.0.

A mixture of 2-(3-bromo-phenyl)-3,3-dimethyl-1,2,3,4-tetrahydro-quinoline-6-carboxylic acid ethyl ester (4.0 g, 10.3 mmol), 1-methyl-piperazine (3.5 mL, 30.9 mmol), copper(I) iodide (785 mg, 4.1 mmol), N,N-dimethylglycine hydrochloride (1.2 g, 8.2 mmol) and potassium carbonate (6.1 g, 44.1 mmol) in dimethyl sulfoxide (30 mL) was stirred at 120° C. for 16 hours. Then the reaction mixture cooled to room temperature. The reaction mixture was extracted with ethyl acetate (2×200 mL), washed with water (2×50 mL) and saturated aqueous ammonium chloride solution (2×50 mL), dried over anhydrous sodium sulfate and then concentrated in vacuo to afford 3,3-dimethyl-2-[3-(4-methyl-piperazin-1-yl)-phenyl]-1,2,3,4-tetrahydro-quinoline-6-carboxylic acid ethyl ester (3.4 g, 80%) as a light yellow oil which was used for next step without further purification: LC/MS m/e calcd for $C_{25}H_{33}N_3O_2$ (M+H)$^+$: 408.56, observed: 408.2.

To a stirred mixture solution of 3,3-dimethyl-2-[3-(4-methyl-piperazin-1-yl)-phenyl]-1,2,3,4-tetrahydro-quinoline-6-carboxylic acid ethyl ester (1.0 g, 2.5 mmol) in methanol (5.0 mL) and tetrahydrofuran (6.0 mL) was added 50% sodium hydroxide in water (2.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 3,3-dimethyl-2-[3-(4-methyl-piperazin-1-yl)-phenyl]-1,2,3,4-tetrahydro-quinoline-6-carboxylic acid (840 mg, 90%) as a white solid: LC/MS m/e calcd for $C_{23}H_{29}N_3O_2$ (M+H)$^+$: 380.51, observed: 380.0.

Example 100

6-Chloro-3,3-dimethyl-2-(3-morpholin-4-yl-phenyl)-1,2,3,4-tetrahydro-quinoline-8-carboxylic acid

To a stirred solution of 2-amino-5-chloro-benzoic acid (50 g, 291 mmol) in methanol (300 mL) was added thionyl chloride (45 mL, 605 mmol) dropwise at 0° C. Then the mixture solution was refluxed for 12 hours before cooling to room temperature. Then the reaction mixture was concentrated in vacuo and the residue was dissolved in ethyl acetate (500 mL), washed with saturated aqueous sodium bicarbonate solution (3×100 mL), dried over anhydrous sodium sulfate and concentrated in vacuo to afford 2-amino-5-chloro-benzoic acid methyl ester (54 g, quant.) as a pale-white solid: LC/MS m/e calcd for $C_8H_8ClNO_2$ (M+H)$^+$: 186.61, observed: 185.9.

A mixture solution of 2-amino-5-chloro-benzoic acid methyl ester (21 g, 113.2 mmol), 3-bromo-benzaldehyde (21 g, 113.2 mmol) and p-toluenesulfonic acid (431 mg, 2.2 mmol) in toluene (200 mL) was heated to reflux for 12 hours. Then the reaction mixture was cooled to room temperature. The solvent was removed in vacuo and the residue was washed with ether to afford 2-[(3-bromo-benzylidene)-amino]-5-chloro-benzoic acid methyl ester (39.8 g, quant.) as a pale-white solid: MS calcd. for $C_{15}H_{11}BrClNO_{2}$ 353.62, obsd. (ESI$^+$) [(M+H)$^+$] 351.9 & 353.9.

To a stirred mixture solution of 2-[(3-bromo-benzylidene)-amino]-5-chloro-benzoic acid methyl ester (39.8 g, 113.2 mmol) and ytterbium(III) triflate hydrate (10.5 g, 16.9 mmol) in dry tetrahydrofuran (100 mL) at 25° C. was added isobutyraldehyde (10.4 mL, 113.2 mmol) and water (2.1 mL, 113.2 mmol) dropwise. The reaction mixture was stirred at 25° C. for 16 h. Then the reaction mixture was concentrated in vacuo and the residue was extracted with ethyl acetate (2×200 mL), washed with brine, dried over anhydrous sodium sulfate and concentrated in vacuo to afford 2-(3-bromo-phenyl)-6-chloro-4-hydroxy-3,3-dimethyl-1,2,3,4-tetrahydro-quinoline-8-carboxylic acid methyl ester (48 g, quant.) as a light yellow oil which was used for next step without further purification: LC/MS m/e calcd for $C_{19}H_{19}BrClNO_3$ (M+H)$^+$: 425.73, observed: 405.9 & 407.9.

To a stirred mixture solution of 2-(3-bromo-phenyl)-6-chloro-4-hydroxy-3,3-dimethyl-1,2,3,4-tetrahydro-quinoline-8-carboxylic acid methyl ester (48 g, 113.2 mmol) and triethylsilane (60 mL) at 25° C. was added trifluoroacetic acid (30 mL) dropwise. The resulting mixture solution was stirred at 25° C. for 3 hours. Then the reaction mixture was concentrated in vacuo and the residue was extracted with ethyl acetate (2×200 mL), washed with saturated aqueous sodium bicarbonate solution (4×100 mL), dried over anhydrous sodium sulfate and concentrated in vacuo. The residue was triturated with methanol. The resulting precipitate was collected, dried in vacuo to afford 2-(3-bromo-phenyl)-6-chloro-3,3-dimethyl-1,2,3,4-tetrahydro-quinoline-8-carboxylic acid methyl ester (23.1 g, 50%) as a white solid: LC/MS m/e calcd for $C_{19}H_{19}BrClNO_2$ (M+H)$^+$: 409.73, observed: 407.9 & 409.9.

A mixture of 2-(3-bromo-phenyl)-6-chloro-3,3-dimethyl-1,2,3,4-tetrahydro-quinoline-8-carboxylic acid methyl ester (5.6 g, 13.7 mmol), morpholine (12 mL, 137 mmol), copper (I) iodide (1.1 g, 5.4 mmol), N,N-dimethylglycine hydrochloride (1.5 g, 10.9 mmol) and potassium carbonate (5.7 g, 41.1 mmol) in dimethyl sulfoxide (35 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo to afford 6-chloro-3,3-dimethyl-2-(3-morpholin-4-yl-phenyl)-1,2,3,4-tetrahydro-quinoline-8-carboxylic acid methyl ester (4.5 g, 80%) as a yellow solid which was used for next step without further purification: LC/MS m/e calcd for $C_{23}H_{27}ClN_2O_3$ (M+H)$^+$: 415.94, observed: 415.1.

To a stirred mixture solution of 6-chloro-3,3-dimethyl-2-(3-morpholin-4-yl-phenyl)-1,2,3,4-tetrahydro-quinoline-8-carboxylic acid methyl ester (400 mg, 1.0 mmol) in methanol (15.0 mL) and tetrahydrofuran (15.0 mL) was added 50% sodium hydroxide in water (2.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 6-chloro-3,3-dimethyl-2-(3-morpholin-4-yl-phenyl)-1,2,3,4-tetrahydro-quinoline-8-carboxylic acid (360 mg, 90%) as a light yellow solid: LC/MS m/e calcd for $C_{22}H_{25}ClN_2O_3$ (M+H)$^+$: 401.91, observed: 401.1.

Example 101

Cyclopropanesulfonic acid [6-chloro-3,3-dimethyl-2-(3-morpholin-4-yl-phenyl)-1,2,3,4-tetrahydro-quinoline-8-carbonyl]-amide

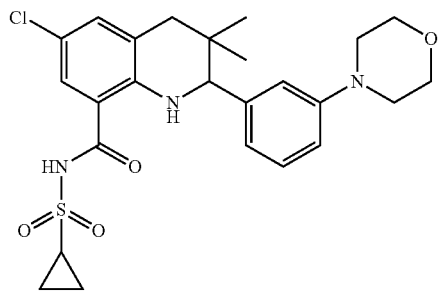 [SMILES: CC1(C)Cc2cc(Cl)cc(C(=O)NS(=O)(=O)C3CC3)c2NC1c1cccc(N2CCOCC2)c1]

To a suspension of 60% sodium hydride (294 mg, 7.4 mmol) in N,N-dimethylformamide (2.5 mL) was added cyclopropanesulfonamide (908 mg, 7.5 mmol) at room temperature. The resulting mixture was stirred at 25° C. for 1 h. A solution of 6-chloro-3,3-dimethyl-2-(3-morpholin-4-yl-phenyl)-1,2,3,4-tetrahydro-quinoline-8-carboxylic acid (300 mg, 0.75 mmol) and 1,1'-carbonyldiimidazole (244 mg, 1.5 mmol) in N,N-dimethylformamide (2.0 mL) was stirred at 70° C. After stirring at 70° C. for 1 h, the above suspension of cyclopropanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [6-chloro-3,3-dimethyl-2-(3-morpholin-4-yl-phenyl)-1,2,3,4-tetrahydro-quinoline-8-carbonyl]-amide (113 mg, 30%) as a white solid: LC/MS m/e calcd for $C_{25}H_{30}ClN_3O_4S$ (M+H)$^+$: 505.05, observed: 504.0.

Example 102

3,3-Dimethyl-2-(3-piperazin-1-yl-phenyl)-1,2,3,4-tetrahydro-quinoline-6-carboxylic acid

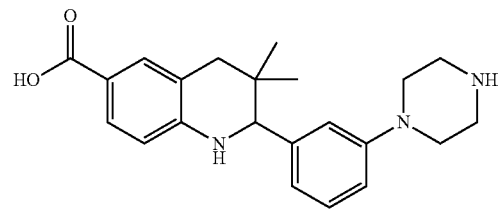 [SMILES: CC1(C)Cc2cc(C(=O)O)ccc2NC1c1cccc(N2CCNCC2)c1]

A mixture of 2-(3-bromo-phenyl)-3,3-dimethyl-1,2,3,4-tetrahydro-quinoline-6-carboxylic acid ethyl ester (4.0 g, 10.3 mmol), piperazine (4.5 g, 51.6 mmol), copper(I) iodide (785 mg, 4.1 mmol), N,N-dimethylglycine hydrochloride (1.2 g, 8.2 mmol) and potassium carbonate (4.3 g, 30.9 mmol) in dimethyl sulfoxide (20 mL) was stirred at 120° C. for 16 hours. Then the reaction mixture cooled to room temperature. The reaction mixture was extracted with ethyl acetate (2×200 mL), washed with water (2×50 mL) and saturated aqueous ammonium chloride solution (2×50 mL), dried over anhydrous sodium sulfate and then concentrated in vacuo to afford 3,3-dimethyl-2-(3-piperazin-1-yl-phenyl)-1,2,3,4-tetrahydro-quinoline-6-carboxylic acid ethyl ester (3.2 g, 80%) as a light yellow solid which was used for next step without further purification: LC/MS m/e calcd for $C_{24}H_{31}N_3O_2$ (M+H)$^+$: 394.53, observed: 394.1.

To a stirred mixture solution of 3,3-dimethyl-2-(3-piperazin-1-yl-phenyl)-1,2,3,4-tetrahydro-quinoline-6-carboxylic acid ethyl ester (1.0 g, 2.5 mmol) in methanol (5.0 mL) and tetrahydrofuran (6.0 mL) was added 50% sodium hydroxide in water (2.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 3,3-dimethyl-2-(3-piperazin-1-yl-phenyl)-1,2,3,4-tetrahydro-quinoline-6-carboxylic acid (820 mg, 90%) as a white solid: LC/MS m/e calcd for $C_{22}H_{27}N_3O_2$ (M+H)$^+$: 366.48, observed: 366.0.

Example 103

N-[3,3-Dimethyl-2-(3-piperazin-1-yl-phenyl)-1,2,3,4-tetrahydro-quinoline-6-carbonyl]-methanesulfonamide

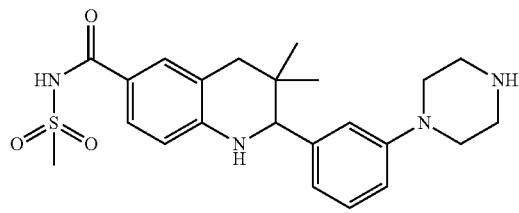 [SMILES: CC1(C)Cc2cc(C(=O)NS(C)(=O)=O)ccc2NC1c1cccc(N2CCNCC2)c1]

To a suspension of 60% sodium hydride (196 mg, 4.9 mmol) in N,N-dimethylformamide (2.5 mL) was added methanesulfonamide (475 mg, 5 mmol) at room temperature. The resulting mixture was stirred at 25° C. for 1 h. A solution of 3,3-dimethyl-2-(3-piperazin-1-yl-phenyl)-1,2,3,4-tetrahydro-quinoline-6-carboxylic acid (180 mg, 0.5 mmol) and 1,1'-carbonyldiimidazole (162 mg, 1.0 mmol) in N,N-dimethylformamide (1.0 mL) was stirred at 70° C. After stirring at 70° C. for 1 h, the above suspension of methanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-[3,3-dimethyl-2-(3-piperazin-1-yl-phenyl)-1,2,3,4-tetrahydro-quinoline-6-carbonyl]-methanesulfonamide (66 mg, 30%) as a white solid: LC/MS m/e calcd for $C_{23}H_{30}N_4O_3S$ (M+H)$^+$: 443.58, observed: 442.9.

Example 104

N-[6-Chloro-3,3-dimethyl-2-(3-morpholin-4-yl-phenyl)-1,2,3,4-tetrahydro-quinoline-8-carbonyl]-methanesulfonamide

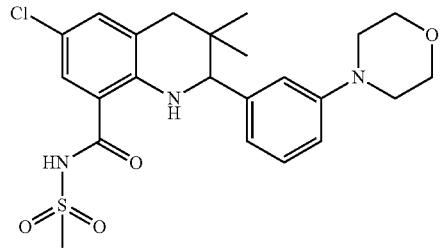 [SMILES: CC1(C)Cc2cc(Cl)cc(C(=O)NS(C)(=O)=O)c2NC1c1cccc(N2CCOCC2)c1]

To a suspension of 60% sodium hydride (294 mg, 7.4 mmol) in N,N-dimethylformamide (2.5 mL) was added methanesulfonamide (713 mg, 7.5 mmol) at room temperature. The resulting mixture was stirred at 25° C. for 1 h. A solution of 6-chloro-3,3-dimethyl-2-(3-morpholin-4-yl-phenyl)-1,2,3,4-tetrahydro-quinoline-8-carboxylic acid (300 mg, 0.75 mmol) and 1,1'-carbonyldiimidazole (244 mg, 1.5 mmol) in N,N-dimethylformamide (2.0 mL) was stirred at 70° C. After stirring at 70° C. for 1 h, the above suspension of methanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-[6-chloro-3,3-dimethyl-2-(3-morpholin-4-yl-phenyl)-1,2,3,4-tetrahydro-quinoline-8-carbonyl]-methanesulfonamide (107 mg, 30%) as a white solid: LC/MS m/e calcd for $C_{25}H_{30}ClN_3O_4S$ (M+H)$^+$: 505.05, observed: 504.0.

Example 105

Cyclopropanesulfonic acid {2-[3-(2,6-dimethyl-morpholin-4-yl)-phenyl]-3,3-dimethyl-1,2,3,4-tetrahydro-quinoline-6-carbonyl}-amide

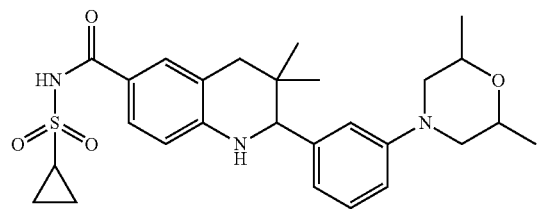 [SMILES: CC1CN(c2cccc(C3Nc4ccc(C(=O)NS(=O)(=O)C5CC5)cc4CC3(C)C)c2)CC(C)O1]

To a suspension of 60% sodium hydride (149 mg, 3.7 mmol) in N,N-dimethylformamide (2.5 mL) was added cyclopropanesulfonamide (460 mg, 3.8 mmol) at room temperature. The resulting mixture was stirred at 25° C. for 1 h. A solution of 2-[3-(2,6-dimethyl-morpholin-4-yl)-phenyl]-3,3-dimethyl-1,2,3,4-tetrahydro-quinoline-6-carboxylic acid (150 mg, 0.38 mmol) and 1,1'-carbonyldiimidazole (125 mg, 0.76 mmol) in N,N-dimethylformamide (1.0 mL) was stirred at 70° C. After stirring at 70° C. for 1 h, the above suspension of cyclopropanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid {2-[3-(2,6-dimethyl-morpholin-4-yl)-phenyl]-3,3-dimethyl-1,2,3,4-tetrahydro-quinoline-6-carbonyl}-amide (56 mg, 30%) as a white solid: LC/MS m/e calcd for $C_{27}H_{35}N_3O_4S$ (M+H)$^+$: 498.66, observed: 498.0.

Example 106

2-[3-(2,6-Dimethyl-morpholin-4-yl)-phenyl]-3,3-dimethyl-1,2,3,4-tetrahydro-quinoline-6-carboxylic acid

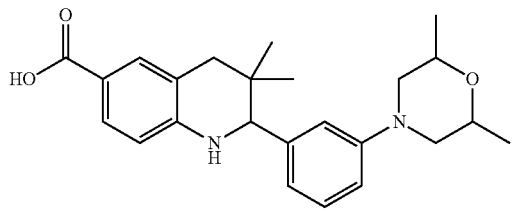 [SMILES: CC1CN(c2cccc(C3Nc4ccc(C(=O)O)cc4CC3(C)C)c2)CC(C)O1]

A mixture of 2-(3-bromo-phenyl)-3,3-dimethyl-1,2,3,4-tetrahydro-quinoline-6-carboxylic acid ethyl ester (4.0 g, 10.3 mmol), 2,6-dimethyl-morpholine (6.4 mL, 51.6 mmol), copper(I) iodide (785 mg, 4.1 mmol), N,N-dimethylglycine hydrochloride (1.2 g, 8.2 mmol) and potassium carbonate (4.3 g, 30.9 mmol) in dimethyl sulfoxide (20 mL) was stirred at 120° C. for 16 hours. Then the reaction mixture cooled to room temperature. The reaction mixture was extracted with ethyl acetate (2×200 mL), washed with water (2×50 mL) and saturated aqueous ammonium chloride solution (2×50 mL), dried over anhydrous sodium sulfate and then concentrated in vacuo to afford 2-[3-(2,6-dimethyl-morpholin-4-yl)-phenyl]-3,3-dimethyl-1,2,3,4-tetrahydro-quinoline-6-carboxylic acid ethyl ester (3.5 g, 80%) as a white solid which was used for next step without further purification: LC/MS m/e calcd for $C_{26}H_{34}N_2O_3$ (M+H)$^+$: 423.57, observed: 423.0.

To a stirred mixture solution of 2-[3-(2,6-dimethyl-morpholin-4-yl)-phenyl]-3,3-dimethyl-1,2,3,4-tetrahydro-quinoline-6-carboxylic acid ethyl ester (0.9 g, 2.1 mmol) in methanol (5.0 mL) and tetrahydrofuran (6.0 mL) was added 50% sodium hydroxide in water (2.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[3-(2,6-dimethyl-morpholin-4-yl)-phenyl]-3,3-dimethyl-1,2,3,4-tetrahydro-quinoline-6-carboxylic acid (745 mg, 90%) as a white solid: LC/MS m/e calcd for $C_{24}H_{30}N_2O_3$ (M+H)$^+$: 395.52, observed: 395.0.

Example 107

(3-Hydroxy-3-methyl-pyrrolidin-1-yl)-[2-(3-methoxy-phenyl)-3,3-dimethyl-1,2,3,4-tetrahydro-quinolin-6-yl]-methanone

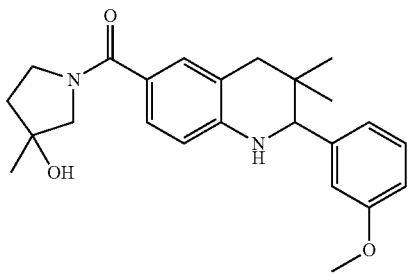 [SMILES: COc1cccc(C2Nc3ccc(C(=O)N4CCC(C)(O)C4)cc3CC2(C)C)c1]

A mixture solution of 4-amino-benzoic acid methyl ester (10.0 g, 66.2 mmol), 3-methoxy-benzaldehyde (10.1 g, 72.7 mmol) and p-toluenesulfonic acid (225 mg, 1.32 mmol) in toluene (200 mL) was heated to reflux for 12 hours. Then the reaction mixture was cooled to room temperature. The solvent was removed in vacuo and the residue was washed with ether to afford 4-[(3-methoxy-benzylidene)-amino]-benzoic acid methyl ester (17.8 g, quant.) as a pale-white solid: MS calcd. for $C_{16}H_{15}NO_3$ (M+H)$^+$: 270.3, obsd. (ESI$^+$) [(M+H)$^+$] 270.1.

To a stirred mixture solution of 4-[(3-methoxy-benzylidene)-amino]-benzoic acid methyl ester (2.7 g, 10.0 mmol) and ytterbium(III) triflate hydrate (620.3 mg, 1.0 mmol) in dry tetrahydrofuran (10 mL) at 25° C. was added isobutyraldehyde (0.93 mL, 10.2 mmol) and water (0.2 mL, 10.2 mmol) dropwise. The reaction mixture was stirred at 25° C. for 16 h. Then the reaction mixture was concentrated in vacuo and the residue was extracted with ethyl acetate (2×200 mL), washed with brine, dried over anhydrous sodium sulfate and concentrated in vacuo to afford 4-hydroxy-2-(3-methoxy-phenyl)-3,3-dimethyl-1,2,3,4-tetrahydro-quinoline-6-carboxylic acid methyl ester (3.4 g, quant.) as a light yellow oil which was used for next step without further purification: LC/MS m/e calcd for $C_{20}H_{23}NO_4$ (M+H)$^+$: 342.41, observed: 324.2 & 342.2.

To a stirred mixture solution of 4-hydroxy-2-(3-methoxy-phenyl)-3,3-dimethyl-1,2,3,4-tetrahydro-quinoline-6-carboxylic acid methyl ester (3.4 g, 10.2 mmol) and triethylsilane (6.0 mL) at 25° C. was added trifluoroacetic acid (3.0 mL) dropwise. The resulting mixture solution was stirred at 25° C. for 3 hours. Then the reaction mixture was concentrated in vacuo and the residue was extracted with ethyl acetate (2×200 mL), washed with saturated aqueous sodium bicarbonate solution (4×100 mL), dried over anhydrous sodium sulfate and concentrated in vacuo. The residue was triturated with methanol. The resulting precipitate was collected, dried in vacuo to afford 2-(3-methoxy-phenyl)-3,3-dimethyl-1,2,3,4-tetrahydro-quinoline-6-carboxylic acid methyl ester (1.6 g, 50%) as a white solid: LC/MS m/e calcd for $C_{20}H_{23}NO_3$ (M+H)$^+$: 326.41, observed: 326.2.

To a stirred mixture solution of 2-(3-methoxy-phenyl)-3,3-dimethyl-1,2,3,4-tetrahydro-quinoline-6-carboxylic acid methyl ester (1.5, 4.6 mmol) in methanol (5.0 mL) and tetrahydrofuran (5.0 mL) was added 50% sodium hydroxide in water (1.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-(3-methoxy-phenyl)-3,3-dimethyl-1,2,3,4-tetrahydro-quinoline-6-carboxylic acid (1.2 g, 90%) as a white foam: LC/MS m/e calcd for $C_{19}H_{21}NO_3$ (M+H)$^+$: 312.38, observed: 312.2.

To a stirred solution of 2-(3-methoxy-phenyl)-3,3-dimethyl-1,2,3,4-tetrahydro-quinoline-6-carboxylic acid (100 mg, 0.32 mmol), 2-(1H-7-azabenzotriazol-1-yl)-1,1,3,3-tetramethyl uronium hexafluorophosphate methanaminium (HATU) (243 mg, 0.64 mmol) and triethyl amine (0.36 mL, 1.28 mmol) in dichloromethane was added 3-methyl-pyrrolidin-3-ol (66 mg, 0.38 mmol) at room temperature and stirred at room temperature for overnight. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded (3-hydroxy-3-methyl-pyrrolidin-1-yl)-[2-(3-methoxy-phenyl)-3,3-dimethyl-1,2,3,4-tetrahydro-quinolin-6-yl]-methanone (63 mg, 50%) as a white foam: LC/MS m/e calcd for $C_{24}H_{30}N_2O_3$ (M+H)$^+$: 395.52, observed: 395.2.

Example 108

3,3-Dimethyl-2-pyridin-3-yl-1,2,3,4-tetrahydro-quinoline-6-carboxylic Acid

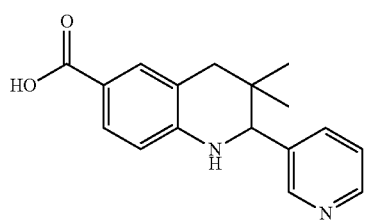 [SMILES: CC1(C)Cc2cc(C(=O)O)ccc2NC1c1cccnc1]

A mixture of 4-amino-benzoic acid ethyl ester (33 g, 200 mmol), pyridine-3-carbaldehyde (24.0 g, 220 mmol) and p-toluenesulfonic acid (760 mg, 4 mmol) in toluene (600 mL) was heated to reflux for 12 h. Then the reaction mixture cooled to room temperature. The solvent was removed in vacuo and the residue was washed with ether to afford 4-[(pyridin-3-ylmethylene)-amino]-benzoic acid ethyl ester (51 g, quant.) as a light yellow solid: LC/MS m/e calcd for $C_{15}H_{14}N_2O_2$ (M+H)$^+$: 255.29, observed: 255.4.

To a mixture of 4-[(pyridin-3-ylmethylene)-amino]-benzoic acid ethyl ester (51 g, 200 mmol) and Ytterbium(III) triflate hydrate (12.4 g, 20 mmol) in dry tetrahydrofuran (200 mL) at 25° C. was added isobutyraldehyde (18.2 mL, 200 mmol) and water (3.6 mL, 200 mmol) dropwise. The reaction mixture was stirred at 25° C. for 16 h. Then the reaction mixture was concentrated in vacuo and the residue was extracted with ethyl acetate (2×200 mL), washed with brine, dried over anhydrous sodium sulfate and concentrated in vacuo to afford 4-hydroxy-3,3-dimethyl-2-pyridin-3-yl-1,2,3,4-tetrahydro-quinoline-6-carboxylic acid ethyl ester (65.2 g, quant.) as a light yellow oil which was used for next step without further purification: LC/MS m/e calcd for $C_{19}H_{22}N_2O_3$ (M+H)$^+$: 327.40, observed: 309.0.

To a mixture of 4-hydroxy-3,3-dimethyl-2-pyridin-3-yl-1,2,3,4-tetrahydro-quinoline-6-carboxylic acid ethyl ester (62.5 g, 200 mmol) and triethylsilane (50 mL) at 25° C. was added trifluoroacetic acid (25 mL) dropwise. The resulting mixture was stirred at 25° C. for 4 h. Then the reaction mixture was concentrated in vacuo and the residue was extracted with ethyl acetate (2×200 mL), washed with saturated aqueous sodium bicarbonate solution (2×100 mL), dried over anhydrous sodium sulfate and concentrated in vacuo. The residue was triturated with methanol. The resulting precipitate was collected, dried in vacuo to afford 3,3-dimethyl-2-pyridin-3-yl-1,2,3,4-tetrahydro-quinoline-6-carboxylic acid ethyl ester (15 g, 24%) as a white solid: LC/MS m/e calcd for $C_{19}H_{22}N_2O_2$ (M+H)$^+$: 311.40, observed: 311.1.

To a stirred mixture solution of 3,3-dimethyl-2-[3-(4-methyl-piperazin-1-yl)-phenyl]-1,2,3,4-tetrahydro-quinoline-6-carboxylic acid ethyl ester (2.3 g, 7.5 mmol) in methanol (15.0 mL) and tetrahydrofuran (16.0 mL) was added 50% sodium hydroxide in water (2.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 3,3-dimethyl-2-pyridin-3-yl-1,2,3,4-tetrahydro-quinoline-6-carboxylic acid (1.9 g, 90%) as a white solid: LC/MS m/e calcd for $C_{17}H_{18}N_2O_2$ (M+H)$^+$: 283.35, observed: 283.1.

Example 109

2-(4'-Chloro-biphenyl-3-yl)-3,3-dimethyl-1,2,3,4-tetrahydro-quinoline-6-carboxylic acid

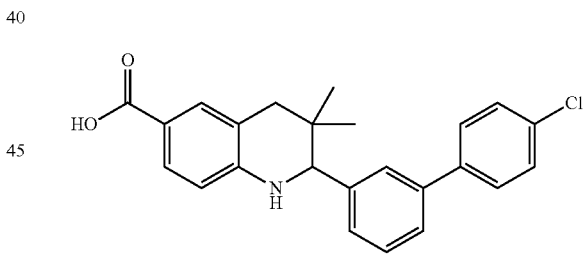

To a mixture of 2-(3-bromo-phenyl)-3,3-dimethyl-1,2,3,4-tetrahydro-quinoline-6-carboxylic acid ethyl ester (4.0 g, 10.3 mmol), 4-chlorophenylboronic acid (2.1 g, 13.4 mmol) and tetrakis(triphenylphosphine)palladium(0) (1.2 g, 1.1 mmol) in dioxane (10 mL) was added 2 M sodium carbonate solution in water (10 mL, 20 mmol). The resulting mixture was subjected to microwave irradiation for 60 min at 110° C. The mixture was diluted with ethyl acetate (150 mL), washed with saturated aqueous sodium bicarbonate solution (30 mL×2), brine, dried over anhydrous sodium sulfate and then concentrated in vacuo. Purification by flash silica gel chromatography (silica gel from QingDao, 200-300 mesh, glass column from Shanghai SD company) (10% ethyl acetate/hexanes) afforded 2-(4'-chloro-biphenyl-3-yl)-3,3-dimethyl-1,2,3,4-tetrahydro-quinoline-6-carboxylic acid ethyl ester (3.4 g, 80%) as a white solid: LC/MS m/e calcd for $C_{26}H_{26}ClNO_2$ (M+H)$^+$: 420.96, observed: 420.5.

To a stirred mixture solution of 2-(4'-chloro-biphenyl-3-yl)-3,3-dimethyl-1,2,3,4-tetrahydro-quinoline-6-carboxylic acid ethyl ester (1.5 g, 3.6 mmol) in methanol (15.0 mL) and tetrahydrofuran (16.0 mL) was added 50% sodium hydroxide in water (2.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-(4'-chloro-biphenyl-3-yl)-3,3-dimethyl-1,2,3,4-tetrahydro-quinoline-6-carboxylic acid (1.3 g, 90%) as a white solid: LC/MS m/e calcd for $C_{24}H_{22}ClNO_2$ (M+H)$^+$: 392.9, observed: 392.2.

Example 110

N-{3,3-Dimethyl-2-[3-(2-oxo-oxazolidin-3-yl)-phenyl]-1,2,3,4-tetrahydro-quinoline-6-carbonyl}-methanesulfonamide

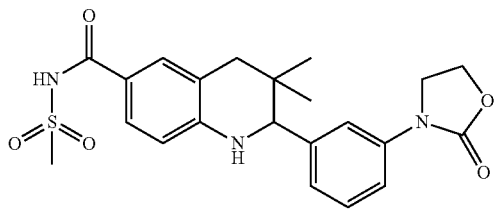 [SMILES: CC1(C)Cc2cc(C(=O)NS(C)(=O)=O)ccc2NC1c1cccc(N2CCOC2=O)c1]

To a stirred mixture solution of 2-(3-bromo-phenyl)-3,3-dimethyl-1,2,3,4-tetrahydro-quinoline-6-carboxylic acid ethyl ester (15 g, 38.7 mmol) in methanol (50.0 mL) and tetrahydrofuran (50.0 mL) was added 50% sodium hydroxide in water (8.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo to afford 2-(3-bromo-phenyl)-3,3-dimethyl-1,2,3,4-tetrahydro-quinoline-6-carboxylic acid (12.5 g, 90%) as a light yellow solid: LC/MS m/e calcd for $C_{18}H_{18}BrNO_2$ (M+H)$^+$: 361.25, observed: 360.0 & 362.0.

A mixture of 2-(3-bromo-phenyl)-3,3-dimethyl-1,2,3,4-tetrahydro-quinoline-6-carboxylic acid (600 mg, 1.7 mmol), oxazolidin-2-one (322 mg, 2.5 mmol), copper(I) iodide (96 mg, 0.5 mmol), N,N-dimethylglycine hydrochloride (140 mg, 1.0 mmol) and potassium carbonate (923 mg, 6.7 mmol) in dimethyl sulfoxide (5 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 3,3-dimethyl-2-[3-(2-oxo-oxazolidin-3-yl)-phenyl]-1,2,3,4-tetrahydro-quinoline-6-carboxylic acid (498 mg, 80%) as a white solid: LC/MS m/e calcd for $C_{21}H_{22}N_2O_4$ (M+H)$^+$: 367.42, observed: 367.1.

To a suspension of 60% sodium hydride (106 mg, 2.6 mmol) in N,N-dimethylformamide (2.5 mL) was added methanesulfonamide (257 mg, 2.7 mmol) at room temperature. The resulting mixture was stirred at 25° C. for 1 h. A solution of 3,3-dimethyl-2-[3-(2-oxo-oxazolidin-3-yl)-phenyl]-1,2,3,4-tetrahydro-quinoline-6-carboxylic acid (100 mg, 0.27 mmol) and 1,1'-carbonyldiimidazole (87 mg, 0.55 mmol) in N,N-dimethylformamide (2.0 mL) was stirred at 70° C. After stirring at 70° C. for 1 h, the above suspension of methanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-{3,3-dimethyl-2-[3-(2-oxo-oxazolidin-3-yl)-phenyl]-1,2,3,4-tetrahydro-quinoline-6-carbonyl}-methanesulfonamide (24 mg, 20%) as a white solid: LC/MS m/e calcd for $C_{22}H_{25}N_3O_5S$ (M+H)$^+$: 444.53, observed: 444.1.

Example 111

8-Chloro-3,3-dimethyl-2-(3-morpholin-4-yl-phenyl)-1,2,3,4-tetrahydro-quinoline-5-carboxylic acid

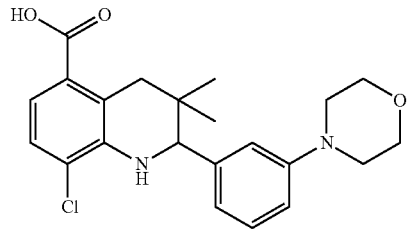 [SMILES: CC1(C)Cc2c(C(=O)O)ccc(Cl)c2NC1c1cccc(N2CCOCC2)c1]

To a stirred solution of 3-amino-4-chloro-benzoic acid (50 g, 291 mmol) in methanol (300 mL) was added thionyl chloride (45 mL, 605 mmol) dropewise at 0° C. Then the mixture solution was refluxed for 12 hours before cooling to room temperature. Then the reaction mixture was concentrated in vacuo and the residue was dissolved in ethyl acetate (500 mL), washed with saturated aqueous sodium bicarbonate solution (3×100 mL), dried over anhydrous sodium sulfate and concentrated in vacuo to afford 3-amino-4-chloro-benzoic acid methyl ester (54 g, quant.) as a pale-white solid: LC/MS m/e calcd for $C_8H_8ClNO_2$ (M+H)$^+$: 186.61, observed: 185.9.

A mixture solution of 3-amino-4-chloro-benzoic acid methyl ester (21 g, 113.2 mmol), 3-bromo-benzaldehyde (21 g, 113.2 mmol) and p-toluenesulfonic acid (431 mg, 2.2 mmol) in toluene (200 mL) was heated to reflux for 12 hours. Then the reaction mixture was cooled to room temperature. The solvent was removed in vacuo and the residue was washed with ether to afford 3-[(3-bromo-benzylidene)-amino]-4-chloro-benzoic acid methyl ester (39.8 g, quant.) as a pale-white solid: MS calcd. for $C_{15}H_{11}BrClNO_2$ 353.62, obsd. (ESI$^+$) [(M+H)$^+$] 351.9 & 353.9.

To a stirred mixture solution of 3-[(3-bromo-benzylidene)-amino]-4-chloro-benzoic acid methyl ester (39.8 g, 113.2 mmol) and ytterbium(III) triflate hydrate (10.5 g, 16.9 mmol) in dry tetrahydrofuran (100 mL) at 25° C. was added isobutyraldehyde (10.4 mL, 113.2 mmol) and water (2.1 mL, 113.2 mmol) dropwise. The reaction mixture was stirred at 25° C. for 16 h. Then the reaction mixture was concentrated in vacuo and the residue was extracted with ethyl acetate (2×200 mL), washed with brine, dried over anhydrous sodium sulfate and concentrated in vacuo to afford 2-(3-bromo-phenyl)-8-chloro-4-hydroxy-3,3-dimethyl-1,2,3,4-tetrahydro-quinoline-5-carboxylic acid methyl ester (48 g, quant.) as a light yellow oil which was used for next step without further purification: LC/MS m/e calcd for $C_{19}H_{19}BrClNO_3$ (M+H)$^+$: 425.73, observed: 405.9 & 407.9.

To a stirred mixture solution of 2-(3-bromo-phenyl)-8-chloro-4-hydroxy-3,3-dimethyl-1,2,3,4-tetrahydro-quinoline-5-carboxylic acid methyl ester (48 g, 113.2 mmol) and triethylsilane (60 mL) at 25° C. was added trifluoroacetic acid (30 mL) dropwise. The resulting mixture solution was stirred at 25° C. for 3 hours. Then the reaction mixture was concentrated in vacuo and the residue was extracted with ethyl acetate (2×200 mL), washed with saturated aqueous sodium bicarbonate solution (4×100 mL), dried over anhydrous sodium sulfate and concentrated in vacuo. The residue was triturated with methanol. The resulting precipitate was collected, dried in vacuo to afford 2-(3-bromo-phenyl)-8-chloro-3,3-dimethyl-1,2,3,4-tetrahydro-quinoline-5-carboxylic acid methyl ester (23.1 g, 50%) as a white solid: LC/MS m/e calcd for $C_{19}H_{19}BrClNO_2$ (M+H)$^+$: 409.73, observed: 407.9 & 409.9.

A mixture of 2-(3-bromo-phenyl)-8-chloro-3,3-dimethyl-1,2,3,4-tetrahydro-quinoline-5-carboxylic acid methyl ester (1.2 g, 2.94 mmol), morpholine (1.3 mL, 14.7 mmol), copper (I) iodide (140 mg, 0.7 mmol), N,N-dimethylglycine hydrochloride (206 mg, 1.5 mmol) and potassium carbonate (1.2 g, 8.8 mmol) in dimethyl sulfoxide (15 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo to afford 8-chloro-3,3-dimethyl-2-(3-morpholin-4-yl-phenyl)-1,2,3,4-tetrahydro-quinoline-5-carboxylic acid methyl ester (973 mg, 80%) as a white solid which was used for next step without further purification: LC/MS m/e calcd for $C_{23}H_{27}ClN_2O_3$ (M+H)$^+$: 415.94, observed: 415.1.

To a stirred mixture solution of 8-chloro-3,3-dimethyl-2-(3-morpholin-4-yl-phenyl)-1,2,3,4-tetrahydro-quinoline-5-carboxylic acid methyl ester (200 mg, 0.5 mmol) in methanol (5.0 mL) and tetrahydrofuran (5.0 mL) was added 50% sodium hydroxide in water (1.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 8-chloro-3,3-dimethyl-2-(3-morpholin-4-yl-phenyl)-1,2,3,4-tetrahydro-quinoline-5-carboxylic acid (180 mg, 90%) as a light yellow solid: LC/MS m/e calcd for $C_{22}H_{25}ClN_2O_3$ (M+H)$^+$: 401.91, observed: 401.1.

Example 112

8-Chloro-3,3-dimethyl-2-(3-morpholin-4-yl-phenyl)-1,2,3,4-tetrahydro-quinoline-6-carboxylic acid

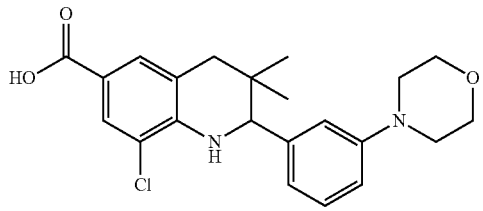 [SMILES: CC1(C)Cc2cc(C(=O)O)cc(Cl)c2NC1c1cccc(N2CCOCC2)c1]

To a stirred solution of 4-amino-3-chloro-benzoic acid (50 g, 291 mmol) in methanol (300 mL) was added thionyl chloride (45 mL, 605 mmol) dropewise at 0° C. Then the mixture solution was refluxed for 12 hours before cooling to room temperature. Then the reaction mixture was concentrated in vacuo and the residue was dissolved in ethyl acetate (500 mL), washed with saturated aqueous sodium bicarbonate solution (3×100 mL), dried over anhydrous sodium sulfate and concentrated in vacuo to afford 4-amino-3-chloro-benzoic acid methyl ester (54 g, quant.) as a pale-white solid: LC/MS m/e calcd for $C_8H_8ClNO_2$ (M+H)$^+$: 186.61, observed: 185.9.

A mixture solution of 4-amino-3-chloro-benzoic acid methyl ester (21 g, 113.2 mmol), 3-bromo-benzaldehyde (21 g, 113.2 mmol) and p-toluenesulfonic acid (431 mg, 2.2 mmol) in toluene (200 mL) was heated to reflux for 12 hours. Then the reaction mixture was cooled to room temperature. The solvent was removed in vacuo and the residue was washed with ether to afford 4-[(3-bromo-benzylidene)-amino]-3-chloro-benzoic acid methyl ester (39.8 g, quant.) as a pale-white solid: MS calcd. for $C_{15}H_{11}BrClNO_2$ 353.62, obsd. (ESI$^+$) [(M+H)$^+$] 351.9 & 353.9.

To a stirred mixture solution of 4-[(3-bromo-benzylidene)-amino]-3-chloro-benzoic acid methyl ester (39.8 g, 113.2 mmol) and ytterbium(III) triflate hydrate (10.5 g, 16.9 mmol) in dry tetrahydrofuran (100 mL) at 25° C. was added isobutyraldehyde (10.4 mL, 113.2 mmol) and water (2.1 mL, 113.2 mmol) dropwise. The reaction mixture was stirred at 25° C. for 16 h. Then the reaction mixture was concentrated in vacuo and the residue was extracted with ethyl acetate (2×200 mL), washed with brine, dried over anhydrous sodium sulfate and concentrated in vacuo to afford 2-(3-bromo-phenyl)-8-chloro-4-hydroxy-3,3-dimethyl-1,2,3,4-tetrahydro-quinoline-6-carboxylic acid methyl ester (48 g, quant.) as a light yellow oil which was used for next step without further purification: LC/MS m/e calcd for $C_{19}H_{19}BrClNO_3$ (M+H)$^+$: 425.73, observed: 405.9 & 407.9.

To a stirred mixture solution of 2-(3-bromo-phenyl)-8-chloro-4-hydroxy-3,3-dimethyl-1,2,3,4-tetrahydro-quinoline-6-carboxylic acid methyl ester (48 g, 113.2 mmol) and triethylsilane (60 mL) at 25° C. was added trifluoroacetic acid (30 mL) dropwise. The resulting mixture solution was stirred at 25° C. for 3 hours. Then the reaction mixture was concentrated in vacuo and the residue was extracted with ethyl acetate (2×200 mL), washed with saturated aqueous sodium bicarbonate solution (4×100 mL), dried over anhydrous sodium sulfate and concentrated in vacuo. The residue was triturated with methanol. The resulting precipitate was collected, dried in vacuo to afford 2-(3-bromo-phenyl)-8-chloro-3,3-dimethyl-1,2,3,4-tetrahydro-quinoline-6-carboxylic acid methyl ester (23.1 g, 50%) as a white solid: LC/MS m/e calcd for $C_{19}H_{19}BrClNO_2$ (M+H)$^+$: 409.73, observed: 407.9 & 409.9.

A mixture of 2-(3-bromo-phenyl)-8-chloro-3,3-dimethyl-1,2,3,4-tetrahydro-quinoline-6-carboxylic acid methyl ester (1.2 g, 2.94 mmol), morpholine (1.3 mL, 14.7 mmol), copper (I) iodide (140 mg, 0.7 mmol), N,N-dimethylglycine hydrochloride (206 mg, 1.5 mmol) and potassium carbonate (1.2 g, 8.8 mmol) in dimethyl sulfoxide (15 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo to afford 8-chloro-3,3-dimethyl-2-(3-morpholin-4-yl-phenyl)-1,2,3,4-tetrahydro-quinoline-6-carboxylic acid methyl ester (973 mg, 80%) as a white solid which was used for next step without further purification: LC/MS m/e calcd for $C_{23}H_{27}ClN_2O_3$ (M+H)$^+$: 415.94, observed: 415.1.

To a stirred mixture solution of 8-chloro-3,3-dimethyl-2-(3-morpholin-4-yl-phenyl)-1,2,3,4-tetrahydro-quinoline-6-carboxylic acid methyl ester (700 mg, 1.8 mmol) in methanol (5.0 mL) and tetrahydrofuran (5.0 mL) was added 50% sodium hydroxide in water (1.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 8-chloro-3,3-dimethyl-2-(3-morpholin-4-yl-phenyl)-1,2,3,4-tetrahydro-quinoline-6-carboxylic acid (630 mg, 90%) as a light yellow solid: LC/MS m/e calcd for $C_{22}H_{25}ClN_2O_3$ $(M+H)^+$: 401.91, observed: 401.1.

Example 113

2-(3-Chloro-4-fluoro-phenyl)-3,3-dimethyl-1,2,3,4-tetrahydro-quinoline-6-carboxylic acid

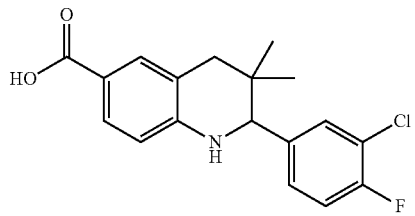 [SMILES: CC1(C)Cc2cc(C(=O)O)ccc2NC1c1ccc(F)c(Cl)c1]

A mixture solution of 4-amino-benzoic acid ethyl ester (16.5 g, 100 mmol), 3-chloro-4-fluoro-benzaldehyde (16.1 g, 100 mmol) and p-toluenesulfonic acid (384 mg, 2.0 mmol) in toluene (200 mL) was heated to reflux for 12 hours. Then the reaction mixture was cooled to room temperature. The solvent was removed in vacuo and the residue was washed with ether to afford 4-[(3-chloro-4-fluoro-benzylidene)-amino]-benzoic acid ethyl ester (30.8 g, quant.) as a pale-white solid: MS calcd. for $C_{16}H_{13}ClFNO_2$ 306.74, obsd. (ESI$^+$) $[(M+H)^+]$ 306.1.

To a stirred mixture solution of 4-[(3-chloro-4-fluoro-benzylidene)-amino]-benzoic acid ethyl ester (3.1 g, 10.2 mmol) and ytterbium(III) triflate hydrate (944 mg, 1.5 mmol) in dry tetrahydrofuran (10 mL) at 25° C. was added isobutyraldehyde (0.93 mL, 10.2 mmol) and water (0.2 mL, 10.2 mmol) dropwise. The reaction mixture was stirred at 25° C. for 16 h. Then the reaction mixture was concentrated in vacuo and the residue was extracted with ethyl acetate (2×200 mL), washed with brine, dried over anhydrous sodium sulfate and concentrated in vacuo to afford 2-(3-chloro-4-fluoro-phenyl)-4-hydroxy-3,3-dimethyl-1,2,3,4-tetrahydroquinoline-6-carboxylic acid ethyl ester (3.8 g, quant.) as a light yellow oil which was used for next step without further purification: LC/MS m/e calcd for $C_{20}H_{21}ClFNO_3$ $(M+H)^+$: 378.85, observed: 360.1 & 378.1.

To a stirred mixture solution of 2-(3-chloro-4-fluoro-phenyl)-4-hydroxy-3,3-dimethyl-1,2,3,4-tetrahydroquinoline-6-carboxylic acid ethyl ester (3.8 g, 10.2 mmol) and triethylsilane (6.0 mL) at 25° C. was added trifluoroacetic acid (3.0 mL) dropwise. The resulting mixture solution was stirred at 25° C. for 3 hours. Then the reaction mixture was concentrated in vacuo and the residue was extracted with ethyl acetate (2×200 mL), washed with saturated aqueous sodium bicarbonate solution (4×100 mL), dried over anhydrous sodium sulfate and concentrated in vacuo. The residue was triturated with methanol. The resulting precipitate was collected, dried in vacuo to afford 2-(3-chloro-4-fluoro-phenyl)-3,3-dimethyl-1,2,3,4-tetrahydro-quinoline-6-carboxylic acid ethyl ester (1.8 g, 50%) as a white solid: LC/MS m/e calcd for $C_{20}H_{21}ClFNO_2$ $(M+H)^+$: 362.85, observed: 362.2.

To a stirred mixture solution of 2-(3-chloro-4-fluoro-phenyl)-3,3-dimethyl-1,2,3,4-tetrahydro-quinoline-6-carboxylic acid ethyl ester (1.0, 2.8 mmol) in methanol (5.0 mL) and tetrahydrofuran (5.0 mL) was added 50% sodium hydroxide in water (1.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-(3-chloro-4-fluoro-phenyl)-3,3-dimethyl-1,2,3,4-tetrahydro-quinoline-6-carboxylic acid (840 mg, 90%) as a white foam: LC/MS m/e calcd for $C_{18}H_{17}ClFNO_2$ $(M+H)^+$: 334.79, observed: 334.1.

Example 114

Cyclopropanesulfonic acid [3,3-dimethyl-2-(5-morpholin-4-yl-pyridin-3-yl)-1,2,3,4-tetrahydro-quinoline-6-carbonyl]-amide

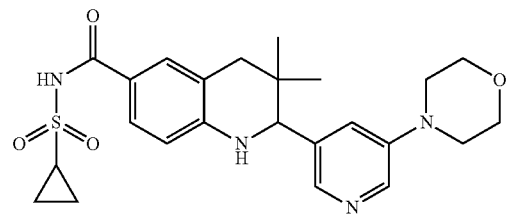 [SMILES: CC1(C)Cc2cc(C(=O)NS(=O)(=O)C3CC3)ccc2NC1c1cncc(N2CCOCC2)c1]

A mixture of 4-amino-benzoic acid ethyl ester (16.5 g, 100 mmol), 5-bromo-pyridine-3-carbaldehyde (18.6 g, 100 mmol) and p-toluenesulfonic acid (380 mg, 2 mmol) in toluene (200 mL) was heated to reflux for 12 h. Then the reaction mixture cooled to room temperature. The solvent was removed in vacuo and the residue was washed with ether to afford 4-[(5-bromo-pyridin-3-ylmethylene)-amino]-benzoic acid ethyl ester (33.8 g, quant.) as a light yellow solid: LC/MS m/e calcd for $C_{15}H_{13}BrN_2O_2$ $(M+H)^+$: 334.19, observed: 332.9 & 335.0.

To a mixture of 4-[(5-bromo-pyridin-3-ylmethylene)-amino]-benzoic acid ethyl ester (33.8 g, 100 mmol) and Ytterbium(III) triflate hydrate (6.2 g, 10 mmol) in dry tetrahydrofuran (100 mL) at 25° C. was added isobutyraldehyde (9.2 mL, 100 mmol) and water (1.8 mL, 100 mmol) dropwise. The reaction mixture was stirred at 25° C. for 16 h. Then the reaction mixture was concentrated in vacuo and the residue was extracted with ethyl acetate (2×200 mL), washed with brine, dried over anhydrous sodium sulfate and concentrated in vacuo to afford 2-(5-bromo-pyridin-3-yl)-4-hydroxy-3,3-dimethyl-1,2,3,4-tetrahydro-quinoline-6-carboxylic acid ethyl ester (42.2 g, quant.) as a light yellow oil which was used for next step without further purification: LC/MS m/e calcd for $C_{19}H_{21}BrN_2O_3$ $(M+H)^+$: 406.29, observed: 405.0 & 406.9.

To a mixture of 2-(5-bromo-pyridin-3-yl)-4-hydroxy-3,3-dimethyl-1,2,3,4-tetrahydro-quinoline-6-carboxylic acid ethyl ester (42.2 g, 100 mmol) and triethylsilane (30 mL) at 25° C. was added trifluoroacetic acid (15 mL) dropwise. The resulting mixture was stirred at 25° C. for 4 h. Then the reaction mixture was concentrated in vacuo and the residue was extracted with ethyl acetate (2×200 mL), washed with saturated aqueous sodium bicarbonate solution (2×100 mL), dried over anhydrous sodium sulfate and concentrated in vacuo. The residue was triturated with methanol. The resulting precipitate was collected, dried in vacuo to afford 2-(5-bromo-pyridin-3-yl)-3,3-dimethyl-1,2,3,4-tetrahydro-quinoline-6-carboxylic acid ethyl ester (11 g, 28.3%) as a white solid: LC/MS m/e calcd for $C_{19}H_{21}BrN_2O_2$ (M+H)$^+$: 390.40, observed: 389.0 & 391.0.

A mixture of 2-(5-bromo-pyridin-3-yl)-3,3-dimethyl-1,2,3,4-tetrahydro-quinoline-6-carboxylic acid ethyl ester (8.5 g, 21.94 mmol), morpholine (19.1 mL, 219.3 mmol), copper(I) iodide (1.7 g, 8.8 mmol), N,N-dimethylglycine hydrochloride (2.5 g, 17.5 mmol) and potassium carbonate (9.1 g, 65.8 mmol) in dimethyl sulfoxide (35 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo to afford 3,3-dimethyl-2-(5-morpholin-4-yl-pyridin-3-yl)-1,2,3,4-tetrahydro-quinoline-6-carboxylic acid ethyl ester (3.5 g, 40.4%) as a white solid which was used for next step without further purification: LC/MS m/e calcd for $C_{23}H_{29}N_3O_3$ (M+H)$^+$: 396.53, observed: 396.1.

To a stirred mixture solution of 3,3-dimethyl-2-(5-morpholin-4-yl-pyridin-3-yl)-1,2,3,4-tetrahydro-quinoline-6-carboxylic acid ethyl ester (2.5 g, 6.5 mmol) in methanol (15.0 mL) and tetrahydrofuran (16.0 mL) was added 50% sodium hydroxide in water (2.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 3,3-dimethyl-2-(5-morpholin-4-yl-pyridin-3-yl)-1,2,3,4-tetrahydro-quinoline-6-carboxylic acid (2.1 g, 90%) as a white solid: LC/MS m/e calcd for $C_{21}H_{25}N_3O_3$ (M+H)$^+$: 368.45, observed: 368.1.

To a suspension of 60% sodium hydride (535 mg, 13.7 mmol) in N,N-dimethylformamide (2.5 mL) was added cyclopropanesulfonamide (1.65 g, 13.8 mmol) at room temperature. The resulting mixture was stirred at 25° C. for 1 h. A solution of 3,3-dimethyl-2-(5-morpholin-4-yl-pyridin-3-yl)-1,2,3,4-tetrahydro-quinoline-6-carboxylic acid (500 mg, 1.38 mmol) and 1,1'-carbonyldiimidazole (442 mg, 2.76 mmol) in N,N-dimethylformamide (2.0 mL) was stirred at 70° C. After stirring at 70° C. for 1 h, the above suspension of cyclopropanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [3,3-dimethyl-2-(5-morpholin-4-yl-pyridin-3-yl)-1,2,3,4-tetrahydro-quinoline-6-carbonyl]-amide (256 mg, 40%) as a white solid: LC/MS m/e calcd for $C_{24}H_{30}N_4O_4S$ (M+H)$^+$: 471.6, observed: 471.1.

Example 115

N-[8-Chloro-3,3-dimethyl-2-(3-morpholin-4-yl-phenyl)-1,2,3,4-tetrahydro-quinoline-6-carbonyl]-methanesulfonamide

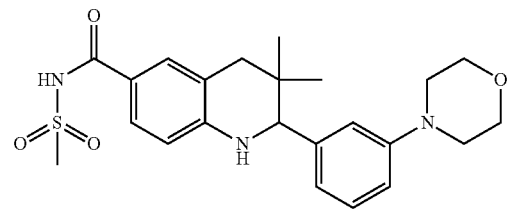 [SMILES: CC1(C)Cc2cc(C(=O)NS(C)(=O)=O)ccc2NC1c1cccc(N2CCOCC2)c1]

To a suspension of 60% sodium hydride (118 mg, 2.9 mmol) in N,N-dimethylformamide (2.5 mL) was added methanesulfonamide (285 mg, 3.0 mmol) at room temperature. The resulting mixture was stirred at 25° C. for 1 h. A solution of 8-chloro-3,3-dimethyl-2-(3-morpholin-4-yl-phenyl)-1,2,3,4-tetrahydro-quinoline-6-carboxylic acid (120 mg, 0.3 mmol) and 1,1'-carbonyldiimidazole (98 mg, 0.6 mmol) in N,N-dimethylformamide (2.0 mL) was stirred at 70° C. After stirring at 70° C. for 1 h, the above suspension of methanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-[8-chloro-3,3-dimethyl-2-(3-morpholin-4-yl-phenyl)-1,2,3,4-tetrahydro-quinoline-6-carbonyl]-methanesulfonamide (43 mg, 30%) as a white solid: LC/MS m/e calcd for $C_{23}H_{28}ClN_3O_4S$ (M+H)$^+$: 479.05, observed: 478.1.

Example 116

Cyclopropanesulfonic acid {3,3-dimethyl-2-[3-(2-oxo-oxazolidin-3-yl)-phenyl]-1,2,3,4-tetrahydro-quinoline-6-carbonyl}-amide

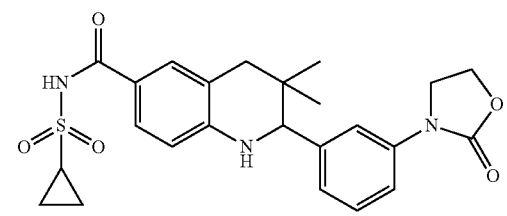 [SMILES: CC1(C)Cc2cc(C(=O)NS(=O)(=O)C3CC3)ccc2NC1c1cccc(N2CCOC2=O)c1]

To a suspension of 60% sodium hydride (106 mg, 2.6 mmol) in N,N-dimethylformamide (2.5 mL) was added cyclopropanesulfonamide (327 mg, 2.7 mmol) at room temperature. The resulting mixture was stirred at 25° C. for 1 h. A solution of 3,3-dimethyl-2-[3-(2-oxo-oxazolidin-3-yl)-phenyl]-1,2,3,4-tetrahydro-quinoline-6-carboxylic acid (100 mg, 0.27 mmol) and 1,1'-carbonyldiimidazole (87 mg, 0.55 mmol) in N,N-dimethylformamide (2.0 mL) was stirred at 70° C. After stirring at 70° C. for 1 h, the above suspension of cyclopropanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid {3,3-dimethyl-2-[3-(2-oxo-oxazolidin-3-yl)-phenyl]-1,2,3,4-tetrahydro-quinoline-6-carbonyl}-amide (25 mg, 20%) as a white solid: LC/MS m/e calcd for $C_{24}H_{27}N_3O_5S$ (M+H)$^+$: 470.53, observed: 470.4.

Example 117

Cyclopropanesulfonic acid [6-fluoro-3,3-dimethyl-2-(3-morpholin-4-yl-phenyl)-1,2,3,4-tetrahydro-quinoline-5-carbonyl]-amide

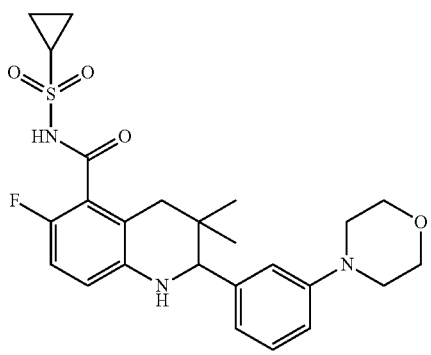 [SMILES: CC1(C)Cc2c(ccc(F)c2C(=O)NS(=O)(=O)C2CC2)NC1c1cccc(N2CCOCC2)c1]

To a suspension of 60% sodium hydride (102 mg, 2.5 mmol) in N,N-dimethylformamide (2.5 mL) was added cyclopropanesulfonamide (315 mg, 2.6 mmol) at room temperature. The resulting mixture was stirred at 25° C. for 1 h. A solution of 6-fluoro-3,3-dimethyl-2-(3-morpholin-4-yl-phenyl)-1,2,3,4-tetrahydro-quinoline-5-carboxylic acid (100 mg, 0.26 mmol) and 1,1'-carbonyldiimidazole (106 mg, 0.65 mmol) in N,N-dimethylformamide (2.0 mL) was stirred at 70° C. After stirring at 70° C. for 1 h, the above suspension of cyclopropanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [6-fluoro-3,3-dimethyl-2-(3-morpholin-4-yl-phenyl)-1,2,3,4-tetrahydro-quinoline-5-carbonyl]-amide (25.3 mg, 20%) as a white solid: LC/MS m/e calcd for $C_{25}H_{30}FN_3O_4S$ (M+H)$^+$: 488.60, observed: 488.1.

Example 118

N-[6-Fluoro-3,3-dimethyl-2-(3-morpholin-4-yl-phenyl)-1,2,3,4-tetrahydro-quinoline-5-carbonyl]-methanesulfonamide

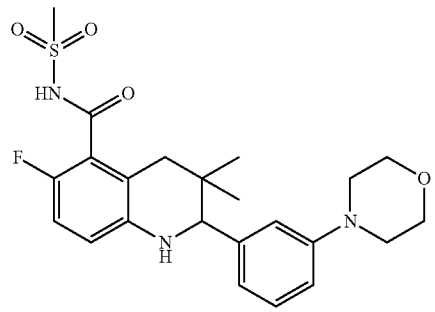 [SMILES: CC1(C)Cc2c(ccc(F)c2C(=O)NS(C)(=O)=O)NC1c1cccc(N2CCOCC2)c1]

To a suspension of 60% sodium hydride (102 mg, 2.5 mmol) in N,N-dimethylformamide (2.5 mL) was added methanesulfonamide (247 mg, 2.6 mmol) at room temperature. The resulting mixture was stirred at 25° C. for 1 h. A solution of 6-fluoro-3,3-dimethyl-2-(3-morpholin-4-yl-phenyl)-1,2,3,4-tetrahydro-quinoline-5-carboxylic acid (100 mg, 0.26 mmol) and 1,1'-carbonyldiimidazole (106 mg, 0.65 mmol) in N,N-dimethylformamide (2.0 mL) was stirred at 70° C. After stirring at 70° C. for 1 h, the above suspension of methanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-[6-fluoro-3,3-dimethyl-2-(3-morpholin-4-yl-phenyl)-1,2,3,4-tetrahydro-quinoline-5-carbonyl]-methanesulfonamide (36 mg, 30%) as a white solid: LC/MS m/e calcd for $C_{23}H_{28}FN_3O_4S$ (M+H)$^+$: 462.56, observed: 462.1.

Example 119

2-[3-((S)-4-Isopropyl-2-oxo-oxazolidin-3-yl)-phenyl]-3,3-dimethyl-1,2,3,4-tetrahydro-quinoline-6-carboxylic acid

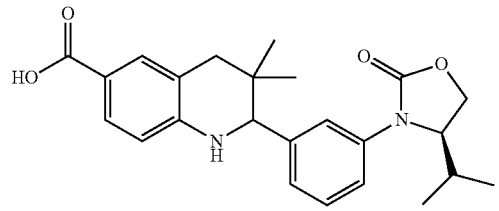 [SMILES: CC(C)[C@@H]1COC(=O)N1c1cccc(C2Nc3ccc(C(=O)O)cc3CC2(C)C)c1]

To a stirred mixture solution of 2-(3-bromo-phenyl)-3,3-dimethyl-1,2,3,4-tetrahydro-quinoline-6-carboxylic acid ethyl ester (15 g, 38.7 mmol) in methanol (50.0 mL) and tetrahydrofuran (50.0 mL) was added 50% sodium hydroxide in water (8.0 mL). The reaction mixture was stirred at 70° C.

for 6 hours. The mixture was neutralized with a 3 N aqueous hydrochloric acid solution and extracted with ethyl acetate (2×100 mL), washed with water, dried over anhydrous sodium sulfate and then concentrated in vacuo to afford 2-(3-bromo-phenyl)-3,3-dimethyl-1,2,3,4-tetrahydro-quinoline-6-carboxylic acid (12.5 g, 90%) as a light yellow solid: LC/MS m/e calcd for $C_{18}H_{18}BrNO_2$ (M+H)$^+$: 361.25, observed: 360.0 & 362.0.

A mixture of 2-(3-bromo-phenyl)-3,3-dimethyl-1,2,3,4-tetrahydro-quinoline-6-carboxylic acid (600 mg, 1.7 mmol), (S)-4-isopropyl-2-oxazolidinone (322 mg, 2.5 mmol), copper (I) iodide (96 mg, 0.5 mmol), N,N-dimethylglycine hydrochloride (140 mg, 1.0 mmol) and potassium carbonate (923 mg, 6.7 mmol) in dimethyl sulfoxide (5 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[3-((S)-4-isopropyl-2-oxo-oxazolidin-3-yl)-phenyl]-3,3-dimethyl-1,2,3,4-tetrahydro-quinoline-6-carboxylic acid (555 mg, 80%) as a white solid: LC/MS m/e calcd for $C_{24}H_{28}N_2O_4$ (M+H)$^+$: 409.50, observed: 409.1.

Example 120

3,3-Dimethyl-2-{3-[methyl-(2-methylamino-ethyl)-amino]-phenyl}-1,2,3,4-tetrahydro-quinoline-6-carboxylic acid

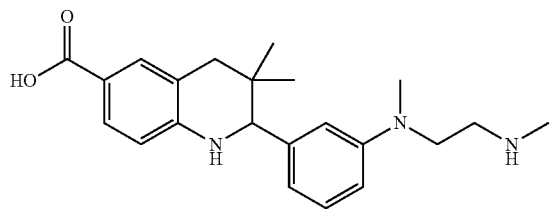 [SMILES: CNCCN(C)c1cccc(C2Nc3ccc(C(=O)O)cc3CC2(C)C)c1]

A mixture of 2-(3-bromo-phenyl)-3,3-dimethyl-1,2,3,4-tetrahydro-quinoline-6-carboxylic acid (600 mg, 1.7 mmol), N,N'-dimethyl-ethane-1,2-diamine (0.37 mL, 3.4 mmol), copper(I) iodide (96 mg, 0.5 mmol), N,N-dimethylglycine hydrochloride (140 mg, 1.0 mmol) and potassium carbonate (923 mg, 6.7 mmol) in dimethyl sulfoxide (5 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 3,3-dimethyl-2-{3-[methyl-(2-methylamino-ethyl)-amino]-phenyl}-1,2,3,4-tetrahydro-quinoline-6-carboxylic acid (500 mg, 80%) as a white solid: LC/MS m/e calcd for $C_{22}H_{29}N_3O_2$ (M+H)$^+$: 368.50, observed: 368.1.

Example 121

6-Fluoro-3,3-dimethyl-2-(3-morpholin-4-yl-phenyl)-1,2,3,4-tetrahydro-quinoline-5-carboxylic acid

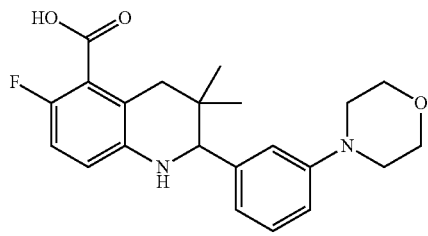 [SMILES: CC1(C)Cc2c(ccc(F)c2C(=O)O)NC1c1cccc(N2CCOCC2)c1]

To a stirred solution of 5-amino-2-fluoro-benzoic acid (25 g, 161 mmol) in methanol (300 mL) was added thionyl chloride (30 mL, 403 mmol) dropwise at 0° C. Then the mixture solution was refluxed for 12 hours before cooling to room temperature. Then the reaction mixture was concentrated in vacuo and the residue was dissolved in ethyl acetate (500 mL), washed with saturated aqueous sodium bicarbonate solution (3×100 mL), dried over anhydrous sodium sulfate and concentrated in vacuo to afford 5-amino-2-fluoro-benzoic acid methyl ester (27.5 g, quant.) as a pale-white solid: LC/MS m/e calcd for $C_8H_8FNO_2$ (M+H)$^+$: 170.16, observed: 169.9.

A mixture solution of 5-amino-2-fluoro-benzoic acid methyl ester (26 g, 153.8 mmol), 3-bromo-benzaldehyde (28.5 g, 153.8 mmol) and p-toluenesulfonic acid (590 mg, 3.2 mmol) in toluene (200 mL) was heated to reflux for 12 hours. Then the reaction mixture was cooled to room temperature. The solvent was removed in vacuo and the residue was washed with ether to afford 5-[(3-bromo-benzylidene)-amino]-2-fluoro-benzoic acid methyl ester (51.7 g, quant.) as a pale-white solid: MS calcd. for $C_{15}H_{11}BrFNO_2$ 337.16, obsd. (ESI$^+$) [(M+H)$^+$] 336.0 & 338.0.

To a stirred mixture solution of 5-[(3-bromo-benzylidene)-amino]-2-fluoro-benzoic acid methyl ester (51.7 g, 153.8 mmol) and ytterbium(III) triflate hydrate (14.3 g, 23.1 mmol) in dry tetrahydrofuran (100 mL) at 25° C. was added isobutyraldehyde (14 mL, 153.8 mmol) and water (2.8 mL, 153.8 mmol) dropwise. The reaction mixture was stirred at 25° C. for 16 h. Then the reaction mixture was concentrated in vacuo and the residue was extracted with ethyl acetate (2×200 mL), washed with brine, dried over anhydrous sodium sulfate and concentrated in vacuo to afford 2-(3-bromo-phenyl)-6-fluoro-4-hydroxy-3,3-dimethyl-1,2,3,4-tetrahydro-quinoline-5-carboxylic acid methyl ester (63.0 g, quant.) as a light yellow oil which was used for next step without further purification: LC/MS m/e calcd for $C_{19}H_{19}BrFNO_3$ (M+H)$^+$: 409.27, observed: 390.0 & 392.0.

To a stirred mixture solution of 2-(3-bromo-phenyl)-6-fluoro-4-hydroxy-3,3-dimethyl-1,2,3,4-tetrahydro-quinoline-5-carboxylic acid methyl ester (63.0 g, 154 mmol) and triethylsilane (60 mL) at 25° C. was added trifluoroacetic acid (30 mL) dropwise. The resulting mixture solution was stirred at 25° C. for 3 hours. Then the reaction mixture was concentrated in vacuo and the residue was extracted with ethyl acetate (2×200 mL), washed with saturated aqueous sodium bicarbonate solution (4×100 mL), dried over anhydrous sodium sulfate and concentrated in vacuo. The residue was triturated with methanol. The resulting precipitate was collected, dried in vacuo to afford 2-(3-bromo-phenyl)-6-fluoro-3,3-dimethyl-1,2,3,4-tetrahydro-quinoline-5-carboxylic acid methyl ester (30.2 g, 50%) as a yellow oil: LC/MS m/e calcd for $C_{19}H_{19}BrFNO_2$ (M+H)$^+$: 393.27, observed: 392.0 & 394.0.

A mixture of 2-(3-bromo-phenyl)-6-fluoro-3,3-dimethyl-1,2,3,4-tetrahydro-quinoline-5-carboxylic acid methyl ester (6.0 g, 15.3 mmol), morpholine (13.3 mL, 153 mmol), copper (I) iodide (874 mg, 4.6 mmol), N,N-dimethylglycine hydrochloride (1.3 g, 9.2 mmol) and potassium carbonate (8.5 g, 61.2 mmol) in dimethyl sulfoxide (15 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo to afford 6-fluoro-3,3-dimethyl-2-(3-morpholin-4-yl-phenyl)-1,2,3,4-tetrahydro-quinoline-5-carboxylic acid methyl ester (4.8 g, 80%) as a white solid which was used for next step without further purification: LC/MS m/e calcd for $C_{23}H_{27}FN_2O_3$ (M+H)$^+$: 399.48, observed: 399.1.

To a stirred mixture solution of 6-fluoro-3,3-dimethyl-2-(3-morpholin-4-yl-phenyl)-1,2,3,4-tetrahydro-quinoline-5-carboxylic acid methyl ester (400 mg, 1.0 mmol) in methanol (5.0 mL) and tetrahydrofuran (5.0 mL) was added 50% sodium hydroxide in water (1.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 6-fluoro-3,3-dimethyl-2-(3-morpholin-4-yl-phenyl)-1,2,3,4-tetrahydro-quinoline-5-carboxylic acid (345 mg, 90%) as a light yellow solid: LC/MS m/e calcd for $C_{22}H_{25}FN_2O_3$ (M+H)$^+$: 385.45, observed: 385.1.

Example 122

2-[3-(R)-4-Isopropyl-2-oxo-oxazolidin-3-yl)-phenyl]-3,3-dimethyl-1,2,3,4-tetrahydro-quinoline-6-carboxylic acid

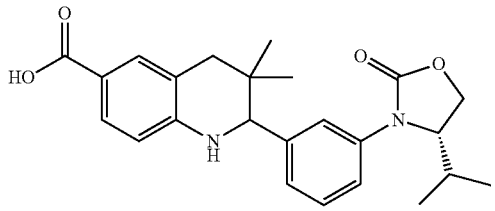 [SMILES: CC(C)[C@H]1COC(=O)N1c1cccc(C2Nc3ccc(C(=O)O)cc3CC2(C)C)c1]

To a stirred mixture solution of 2-(3-bromo-phenyl)-3,3-dimethyl-1,2,3,4-tetrahydro-quinoline-6-carboxylic acid ethyl ester (15 g, 38.7 mmol) in methanol (50.0 mL) and tetrahydrofuran (50.0 mL) was added 50% sodium hydroxide in water (8.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo to afford 2-(3-bromo-phenyl)-3,3-dimethyl-1,2,3,4-tetrahydro-quinoline-6-carboxylic acid (12.5 g, 90%) as a light yellow solid: LC/MS m/e calcd for $C_{18}H_{18}BrNO_2$ (M+H)$^+$: 361.25, observed: 360.0 & 362.0.

A mixture of 2-(3-bromo-phenyl)-3,3-dimethyl-1,2,3,4-tetrahydro-quinoline-6-carboxylic acid (600 mg, 1.7 mmol), (R)-4-isopropyl-2-oxazolidinone (322 mg, 2.5 mmol), copper(I) iodide (96 mg, 0.5 mmol), N,N-dimethylglycine hydrochloride (140 mg, 1.0 mmol) and potassium carbonate (923 mg, 6.7 mmol) in dimethyl sulfoxide (5 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[3-((R)-4-isopropyl-2-oxo-oxazolidin-3-yl)-phenyl]-3,3-dimethyl-1,2,3,4-tetrahydro-quinoline-6-carboxylic acid (555 mg, 80%) as a white solid: LC/MS m/e calcd for $C_{24}H_{28}N_2O_4$ (M+H)$^+$: 409.50, observed: 409.1.

Example 123

N-{2-[3-((R)-4-Isopropyl-2-oxo-oxazolidin-3-yl)-phenyl]-3,3-dimethyl-1,2,3,4-tetrahydro-quinoline-6-carbonyl}-methanesulfonamide

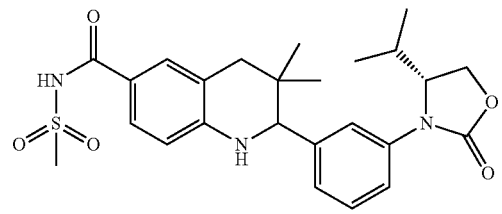 [SMILES: CC(C)[C@@H]1COC(=O)N1c1cccc(C2Nc3ccc(C(=O)NS(C)(=O)=O)cc3CC2(C)C)c1]

To a suspension of 60% sodium hydride (290 mg, 7.3 mmol) in N,N-dimethylformamide (2.5 mL) was added methanesulfonamide (703 mg, 7.4 mmol) at room temperature. The resulting mixture was stirred at 25° C. for 1 h. A solution of 2-[3-((R)-4-isopropyl-2-oxo-oxazolidin-3-yl)-phenyl]-3,3-dimethyl-1,2,3,4-tetrahydro-quinoline-6-carboxylic acid (300 mg, 0.74 mmol) and 1,1'-carbonyldiimidazole (300 mg, 1.84 mmol) in N,N-dimethylformamide (2.0 mL) was stirred at 70° C. After stirring at 70° C. for 1 h, the above suspension of methanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-{2-[3-((R)-4-isopropyl-2-oxo-oxazolidin-3-yl)-phenyl]-3,3-dimethyl-1,2,3,4-tetrahydro-quinoline-6-carbonyl}-methanesulfonamide (71 mg, 20%) as a white solid: LC/MS m/e calcd for $C_{25}H_{31}N_3O_5S$ (M+H)$^+$: 486.61, observed: 486.1.

Example 124

2-[3-((S)-4-Benzyl-2-oxo-oxazolidin-3-yl)-phenyl]-3,3-dimethyl-1,2,3,4-tetrahydro-quinoline-6-carboxylic acid

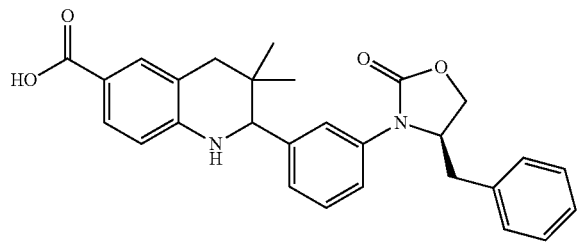 [SMILES: CC1(C)Cc2cc(C(=O)O)ccc2NC1c1cccc(N2C(=O)OC[C@H]2Cc2ccccc2)c1]

A mixture of 2-(3-bromo-phenyl)-3,3-dimethyl-1,2,3,4-tetrahydro-quinoline-6-carboxylic acid (600 mg, 1.7 mmol), (S)-4-benzyl-oxazolidin-2-one (592 mg, 3.34 mmol), copper (I) iodide (96 mg, 0.5 mmol), N,N-dimethylglycine hydrochloride (140 mg, 1.0 mmol) and potassium carbonate (923 mg, 6.7 mmol) in dimethyl sulfoxide (5 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[3-((S)-4-benzyl-2-oxo-oxazolidin-3-yl)-phenyl]-3,3-dimethyl-1,2,3,4-tetrahydro-quinoline-6-carboxylic acid (609 mg, 80%) as a white solid: LC/MS m/e calcd for $C_{28}H_{28}N_2O_4$ (M+H)$^+$: 457.55, observed: 457.1.

Example 125

Cyclopropanesulfonic acid {2-[3-((R)-4-isopropyl-2-oxo-oxazolidin-3-yl)-phenyl]-3,3-dimethyl-1,2,3,4-tetrahydro-quinoline-6-carbonyl}-amide

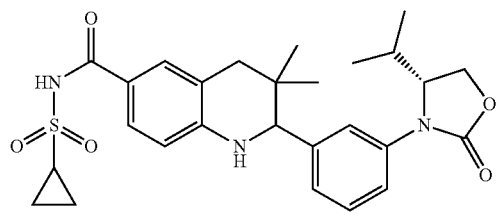 [SMILES: CC(C)[C@@H]1COC(=O)N1c1cccc(C2Nc3ccc(C(=O)NS(=O)(=O)C4CC4)cc3CC2(C)C)c1]

To a suspension of 60% sodium hydride (290 mg, 7.3 mmol) in N,N-dimethylformamide (2.5 mL) was added cyclopropanesulfonamide (895 mg, 7.4 mmol) at room temperature. The resulting mixture was stirred at 25° C. for 1 h. A solution of 2-[3-((R)-4-isopropyl-2-oxo-oxazolidin-3-yl)-phenyl]-3,3-dimethyl-1,2,3,4-tetrahydro-quinoline-6-carboxylic acid (300 mg, 0.74 mmol) and 1,1'-carbonyldiimidazole (300 mg, 1.84 mmol) in N,N-dimethylformamide (2.0 mL) was stirred at 70° C. After stirring at 70° C. for 1 h, the above suspension of cyclopropanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid {2-[3-((R)-4-isopropyl-2-oxo-oxazolidin-3-yl)-phenyl]-3,3-dimethyl-1,2,3,4-tetrahydro-quinoline-6-carbonyl}-amide (75 mg, 20%) as a white solid: LC/MS m/e calcd for $C_{27}H_{33}N_3O_5S$ (M+H)$^+$: 512.65, observed: 512.1.

Example 126

3,3-Dimethyl-2-[3-(4-methyl-2,3-dioxo-piperazin-1-yl)-phenyl]-1,2,3,4-tetrahydro-quinoline-6-carboxylic acid

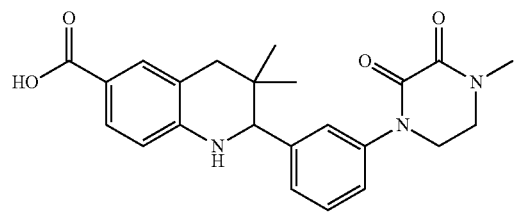 [SMILES: CN1CCN(c2cccc(C3Nc4ccc(C(=O)O)cc4CC3(C)C)c2)C(=O)C1=O]

A mixture of 2-(3-bromo-phenyl)-3,3-dimethyl-1,2,3,4-tetrahydro-quinoline-6-carboxylic acid (500 mg, 1.4 mmol), 1-methyl-piperazine-2,3-dione (267 mg, 2.1 mmol), copper (I) iodide (80 mg, 0.4 mmol), N,N-dimethylglycine hydrochloride (117 mg, 0.8 mmol) and potassium carbonate (769 mg, 5.6 mmol) in dimethyl sulfoxide (5 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 3,3-dimethyl-2-[3-(4-methyl-2,3-dioxo-piperazin-1-yl)-phenyl]-1,2,3,4-tetrahydro-quinoline-6-carboxylic acid (456 mg, 80%) as a white solid: LC/MS m/e calcd for $C_{23}H_{25}N_3O_4$ (M+H)$^+$: 408.47, observed: 408.1.

Example 127

2-[3-((R)-4-Benzyl-2-oxo-oxazolidin-3-yl)-phenyl]-3,3-dimethyl-1,2,3,4-tetrahydro-quinoline-6-carboxylic acid

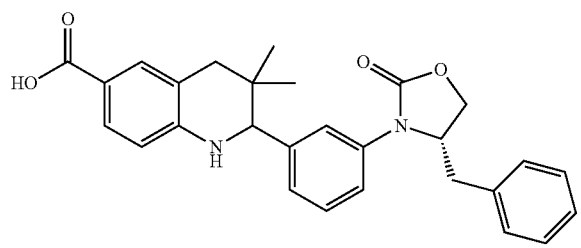 [SMILES: CC1(C)Cc2cc(C(=O)O)ccc2NC1c1cccc(N2C(=O)OC[C@@H]2Cc2ccccc2)c1]

A mixture of 2-(3-bromo-phenyl)-3,3-dimethyl-1,2,3,4-tetrahydro-quinoline-6-carboxylic acid (600 mg, 1.7 mmol), (R)-4-benzyl-oxazolidin-2-one (592 mg, 3.34 mmol), copper (I) iodide (96 mg, 0.5 mmol), N,N-dimethylglycine hydrochloride (140 mg, 1.0 mmol) and potassium carbonate (923 mg, 6.7 mmol) in dimethyl sulfoxide (5 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[3-((R)-4-benzyl-2-oxo-oxazolidin-3-yl)-phenyl]-3,3-dimethyl-1,2,3,4-tetrahydro-quinoline-6-carboxylic acid (609 mg, 80%) as a white solid: LC/MS m/e calcd for $C_{28}H_{28}N_2O_4$ (M+H)$^+$: 457.55, observed: 457.1.

Example 128

N-{2-[3-((R)-4-Benzyl-2-oxo-oxazolidin-3-yl)-phenyl]-3,3-dimethyl-1,2,3,4-tetrahydro-quinoline-6-carbonyl}-methanesulfonamide

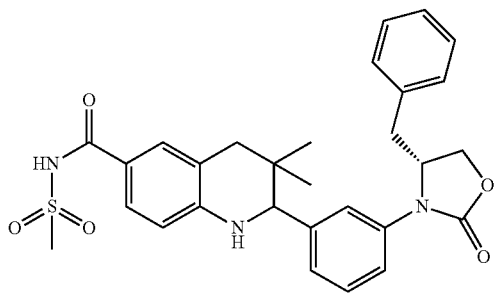 [SMILES: CC1(C)Cc2cc(C(=O)NS(C)(=O)=O)ccc2NC1c1cccc(N2C(=O)OC[C@H]2Cc2ccccc2)c1]

To a suspension of 60% sodium hydride (301 mg, 7.5 mmol) in N,N-dimethylformamide (2.5 mL) was added methanesulfonamide (730 mg, 7.7 mmol) at room temperature. The resulting mixture was stirred at 25° C. for 1 h. A solution of 2-[3-((R)-4-benzyl-2-oxo-oxazolidin-3-yl)-phenyl]-3,3-dimethyl-1,2,3,4-tetrahydro-quinoline-6-carboxylic acid (350 mg, 0.77 mmol) and 1,1'-carbonyldiimidazole (310 mg, 1.9 mmol) in N,N-dimethylformamide (2.0 mL) was stirred at 70° C. After stirring at 70° C. for 1 h, the above suspension of methanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-{2-[3-((R)4-Benzyl-2-oxo-oxazolidin-3-yl)-phenyl]-3,3-dimethyl-1,2,3,4-tetrahydro-quinoline-6-carbonyl}-methanesulfonamide (82 mg, 20%) as a white solid: LC/MS m/e calcd for $C_{29}H_{31}N_3O_5S$ (M+H)$^+$: 534.65, observed: 534.1.

Example 129

Cyclopropanesulfonic acid {3,3-dimethyl-2-[3-(4-methyl-2,3-dioxo-piperazin-1-yl)-phenyl]-1,2,3,4-tetrahydro-quinoline-6-carbonyl}-amide

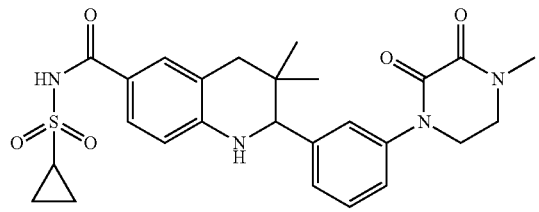 [SMILES: CN1CCN(c2cccc(C3Nc4ccc(C(=O)NS(=O)(=O)C5CC5)cc4CC3(C)C)c2)C(=O)C1=O]

To a suspension of 60% sodium hydride (192 mg, 4.8 mmol) in N,N-dimethylformamide (2.5 mL) was added cyclopropanesulfonamide (593 mg, 4.9 mmol) at room temperature. The resulting mixture was stirred at 25° C. for 1 h. A solution of 3,3-dimethyl-2-[3-(4-methyl-2,3-dioxo-piperazin-1-yl)-phenyl]-1,2,3,4-tetrahydro-quinoline-6-carboxylic acid (200 mg, 0.5 mmol) and 1,1'-carbonyldiimidazole (200 mg, 1.2 mmol) in N,N-dimethylformamide (2.0 mL) was stirred at 70° C. After stirring at 70° C. for 1 h, the above suspension of cyclopropanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid {3,3-dimethyl-2-[3-(4-methyl-2,3-dioxo-piperazin-1-yl)-phenyl]-1,2,3,4-tetrahydro-quinoline-6-carbonyl}-amide (51 mg, 20%) as a white solid: LC/MS m/e calcd for $C_{26}H_{30}N_4O_5S$ (M+H)$^+$: 511.62, observed: 511.2.

Example 130

Cyclopropanesulfonic acid {2-[3-((R)-4-benzyl-2-oxo-oxazolidin-3-yl)-phenyl]-3,3-dimethyl-1,2,3,4-tetrahydro-quinoline-6-carbonyl}-amide

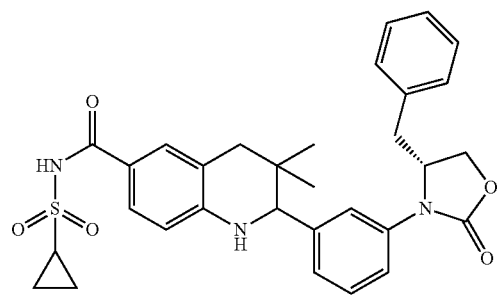 [SMILES: CC1(C)Cc2cc(C(=O)NS(=O)(=O)C3CC3)ccc2NC1c1cccc(N2C(=O)OC[C@H]2Cc2ccccc2)c1]

To a suspension of 60% sodium hydride (301 mg, 7.5 mmol) in N,N-dimethylformamide (2.5 mL) was added cyclopropanesulfonamide (930 mg, 7.7 mmol) at room temperature. The resulting mixture was stirred at 25° C. for 1 h. A solution of 2-[3-((R)-4-benzyl-2-oxo-oxazolidin-3-yl)-phenyl]-3,3-dimethyl-1,2,3,4-tetrahydro-quinoline-6-carboxylic acid (350 mg, 0.77 mmol) and 1,1'-carbonyldiimidazole (310 mg, 1.9 mmol) in N,N-dimethylformamide (2.0 mL) was stirred at 70° C. After stirring at 70° C. for 1 h, the above suspension of methanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid {2-[3-((R)-4-benzyl-2-oxo-oxazolidin-3-yl)-phenyl]-3,3-dimethyl-1,2,3,4-tetrahydro-quinoline-6-carbonyl}-amide (86 mg, 20%) as a white solid: LC/MS m/e calcd for $C_{31}H_{33}N_3O_5S$ (M+H)$^+$: 560.65, observed: 560.1.

Example 131

N-{3,3-Dimethyl-2-[3-(4-methyl-2,3-dioxo-piperazin-1-yl)-phenyl]-1,2,3,4-tetrahydro-quinoline-6-carbonyl}-methanesulfonamide

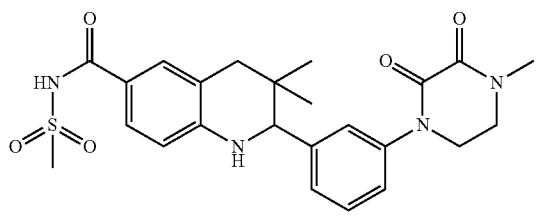 [SMILES: CN1CCN(c2cccc(C3Nc4ccc(C(=O)NS(C)(=O)=O)cc4CC3(C)C)c2)C(=O)C1=O]

To a suspension of 60% sodium hydride (192 mg, 4.8 mmol) in N,N-dimethylformamide (2.5 mL) was added methanesulfonamide (466 mg, 4.9 mmol) at room temperature. The resulting mixture was stirred at 25° C. for 1 h. A solution of 3,3-dimethyl-2-[3-(4-methyl-2,3-dioxo-piperazin-1-yl)-phenyl]-1,2,3,4-tetrahydro-quinoline-6-carboxylic acid (200 mg, 0.5 mmol) and 1,1'-carbonyldiimidazole (200 mg, 1.2 mmol) in N,N-dimethylformamide (2.0 mL) was stirred at 70° C. After stirring at 70° C. for 1 h, the above suspension of methanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-{3,3-dimethyl-2-[3-(4-methyl-2,3-dioxo-piperazin-1-yl)-phenyl]-1,2,3,4-tetrahydro-quinoline-6-carbonyl}-methanesulfonamide (51 mg, 20%) as a white solid: LC/MS m/e calcd for $C_{24}H_{28}N_4O_5S$ (M+H)$^+$: 485.58, observed: 485.2.

Example 132

Cyclopropanesulfonic acid {2-[3-((S)-4-benzyl-2-oxo-oxazolidin-3-yl)-phenyl]-3,3-dimethyl-1,2,3,4-tetrahydro-quinoline-6-carbonyl}-amide

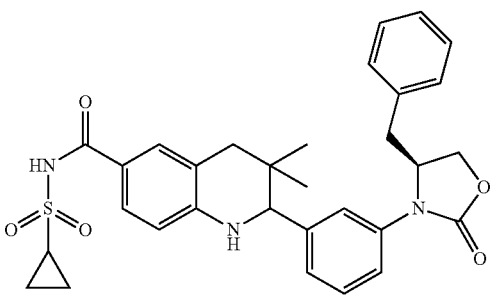 [SMILES: CC1(C)Cc2cc(C(=O)NS(=O)(=O)C3CC3)ccc2NC1c1cccc(N2C(=O)OC[C@@H]2Cc2ccccc2)c1]

To a suspension of 60% sodium hydride (301 mg, 7.5 mmol) in N,N-dimethylformamide (2.5 mL) was added cyclopropanesulfonamide (930 mg, 7.7 mmol) at room temperature. The resulting mixture was stirred at 25° C. for 1 h. A solution of 2-[3-((S)-4-benzyl-2-oxo-oxazolidin-3-yl)-phenyl]-3,3-dimethyl-1,2,3,4-tetrahydro-quinoline-6-carboxylic acid (350 mg, 0.77 mmol) and 1,1'-carbonyldiimidazole (310 mg, 1.9 mmol) in N,N-dimethylformamide (2.0 mL) was stirred at 70° C. After stirring at 70° C. for 1 h, the above suspension of methanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid {2-[3-((S)-4-benzyl-2-oxo-oxazolidin-3-yl)-phenyl]-3,3-dimethyl-1,2,3,4-tetrahydro-quinoline-6-carbonyl}-amide (86 mg, 20%) as a white solid: LC/MS m/e calcd for $C_{31}H_{33}N_3O_5S$ (M+H)$^+$: 560.65, observed: 560.1.

Example 133

Cyclopropanesulfonic acid [8-chloro-3,3-dimethyl-2-(3-morpholin-4-yl-phenyl)-1,2,3,4-tetrahydro-quinoline-5-carbonyl]-amide

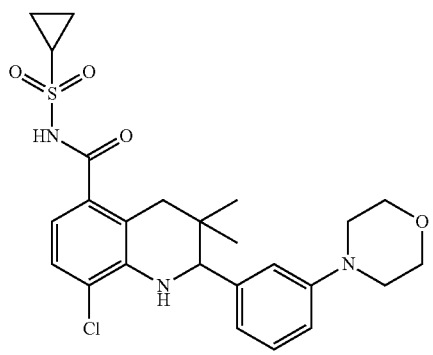 [SMILES: CC1(C)Cc2c(C(=O)NS(=O)(=O)C3CC3)ccc(Cl)c2NC1c1cccc(N2CCOCC2)c1]

To a suspension of 60% sodium hydride (50 mg, 1.2 mmol) in N,N-dimethylformamide (1.5 mL) was added cyclopropanesulfonamide (151 mg, 1.3 mmol) at room temperature. The resulting mixture was stirred at 25° C. for 1 h. A solution of 8-chloro-3,3-dimethyl-2-(3-morpholin-4-yl-phenyl)-1,2,3,4-tetrahydro-quinoline-5-carboxylic acid (50 mg, 0.13 mmol) and 1,1'-carbonyldiimidazole (41 mg, 0.25 mmol) in N,N-dimethylformamide (2.0 mL) was stirred at 70° C. After stirring at 70° C. for 1 h, the above suspension of cyclopropanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid-[8-chloro-3,3-dimethyl-2-(3-morpholin-4-yl-phenyl)-1,2,3,4-tetrahydro-quinoline-5-carbonyl]-amide (13 mg, 20%) as a white solid: LC/MS m/e calcd for $C_{25}H_{30}ClN_3O_4S$ (M+H)$^+$: 505.05, observed: 504.1.

Example 134

7-Fluoro-3,3-dimethyl-2-(3-morpholin-4-yl-phenyl)-1,2,3,4-tetrahydro-quinoline-5-carboxylic acid

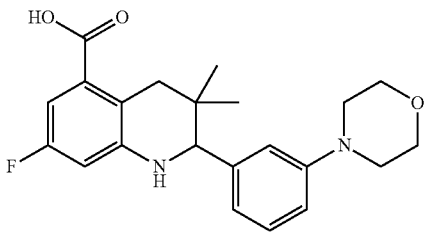 [SMILES: CC1(C)Cc2c(cc(F)cc2C(=O)O)NC1c1cccc(N2CCOCC2)c1]

To a stirred solution of 3-amino-5-fluoro-benzoic acid (25 g, 161 mmol) in methanol (300 mL) was added thionyl chloride (30 mL, 403 mmol) dropewise at 0° C. Then the mixture solution was refluxed for 12 hours before cooling to room temperature. Then the reaction mixture was concentrated in vacuo and the residue was dissolved in ethyl acetate (500 mL), washed with saturated aqueous sodium bicarbonate solution (3×100 mL), dried over anhydrous sodium sulfate and concentrated in vacuo to afford 3-amino-5-fluoro-benzoic acid methyl ester (27.5 g, quant.) as a pale-white solid: LC/MS m/e calcd for $C_8H_8FNO_2$ (M+H)$^+$: 170.16, observed: 169.9.

A mixture solution of 3-amino-5-fluoro-benzoic acid methyl ester (26 g, 153.8 mmol), 3-bromo-benzaldehyde (28.5 g, 153.8 mmol) and p-toluenesulfonic acid (590 mg, 3.2 mmol) in toluene (200 mL) was heated to reflux for 12 hours. Then the reaction mixture was cooled to room temperature. The solvent was removed in vacuo and the residue was washed with ether to afford 3-[(3-bromo-benzylidene)-amino]-5-fluoro-benzoic acid methyl ester (51.7 g, quant.) as a pale-white solid: MS calcd. for $C_{15}H_{11}BrFNO_2$ 337.16, obsd. (ESI$^+$) [(M+H)$^+$] 336.0 & 338.0.

To a stirred mixture solution of 3-[(3-bromo-benzylidene)-amino]-5-fluoro-benzoic acid methyl ester (51.7 g, 153.8 mmol) and ytterbium(III) triflate hydrate (14.3 g, 23.1 mmol) in dry tetrahydrofuran (100 mL) at 25° C. was added isobutyraldehyde (14 mL, 153.8 mmol) and water (2.8 mL, 153.8 mmol) dropwise. The reaction mixture was stirred at 25° C. for 16 h. Then the reaction mixture was concentrated in vacuo and the residue was extracted with ethyl acetate (2×200 mL), washed with brine, dried over anhydrous sodium sulfate and concentrated in vacuo to afford 2-(3-bromo-phenyl)-7-fluoro-4-hydroxy-3,3-dimethyl-1,2,3,4-tetrahydro-quinoline-5-carboxylic acid methyl ester (63.0 g, quant.) as a light yellow oil which was used for next step without further purification: LC/MS m/e calcd for $C_{19}H_{19}BrFNO_3$ (M+H)$^+$: 409.27, observed: 390.0 & 392.0.

To a stirred mixture solution of 2-(3-bromo-phenyl)-7-fluoro-4-hydroxy-3,3-dimethyl-1,2,3,4-tetrahydro-quinoline-5-carboxylic acid methyl ester (63.0 g, 154 mmol) and triethylsilane (60 mL) at 25° C. was added trifluoroacetic acid (30 mL) dropwise. The resulting mixture solution was stirred at 25° C. for 3 hours. Then the reaction mixture was concentrated in vacuo and the residue was extracted with ethyl acetate (2×200 mL), washed with saturated aqueous sodium bicarbonate solution (4×100 mL), dried over anhydrous sodium sulfate and concentrated in vacuo. The residue was triturated with methanol. The resulting precipitate was collected, dried in vacuo to afford 2-(3-bromo-phenyl)-7-fluoro-3,3-dimethyl-1,2,3,4-tetrahydro-quinoline-5-carboxylic acid methyl ester (30.2 g, 50%) as a yellow oil: LC/MS m/e calcd for $C_{19}H_{19}BrFNO_2$ (M+H)$^+$: 393.27, observed: 392.0 & 394.0.

A mixture of 2-(3-bromo-phenyl)-7-fluoro-3,3-dimethyl-1,2,3,4-tetrahydro-quinoline-5-carboxylic acid methyl ester (6.0 g, 15.3 mmol), morpholine (13.3 mL, 153 mmol), copper (I) iodide (874 mg, 4.6 mmol), N,N-dimethylglycine hydrochloride (1.3 g, 9.2 mmol) and potassium carbonate (8.5 g, 61.2 mmol) in dimethyl sulfoxide (15 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo to afford 7-fluoro-3,3-dimethyl-2-(3-morpholin-4-yl-phenyl)-1,2,3,4-tetrahydro-quinoline-5-carboxylic acid methyl ester (4.8 g, 80%) as a white solid which was used for next step without further purification: LC/MS m/e calcd for $C_{23}H_{27}FN_2O_3$ (M+H)$^+$: 399.48, observed: 399.1.

To a stirred mixture solution of 7-fluoro-3,3-dimethyl-2-(3-morpholin-4-yl-phenyl)-1,2,3,4-tetrahydro-quinoline-5-carboxylic acid methyl ester (400 mg, 1.0 mmol) in methanol (5.0 mL) and tetrahydrofuran (5.0 mL) was added 50% sodium hydroxide in water (1.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 7-fluoro-3,3-dimethyl-2-(3-morpholin-4-yl-phenyl)-1,2,3,4-tetrahy-

Example 135

N-[7-Fluoro-3,3-dimethyl-2-(3-morpholin-4-yl-phenyl)-1,2,3,4-tetrahydro-quinoline-5-carbonyl]-methanesulfonamide

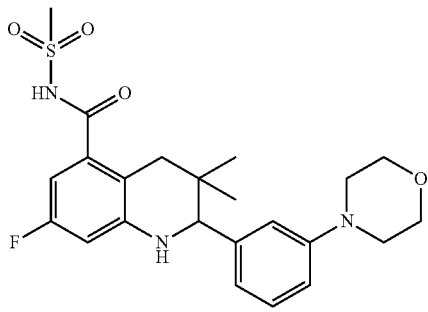 [SMILES: CC1(C)Cc2c(cc(F)cc2C(=O)NS(C)(=O)=O)NC1c1cccc(N2CCOCC2)c1]

To a suspension of 60% sodium hydride (200 mg, 5.0 mmol) in N,N-dimethylformamide (1.5 mL) was added methanesulfonamide (494 mg, 5.2 mmol) at room temperature. The resulting mixture was stirred at 25° C. for 1 h. A solution of 7-fluoro-3,3-dimethyl-2-(3-morpholin-4-yl-phenyl)-1,2,3,4-tetrahydro-quinoline-5-carboxylic acid (200 mg, 0.52 mmol) and 1,1'-carbonyldiimidazole (170 mg, 1.04 mmol) in N,N-dimethylformamide (2.0 mL) was stirred at 70° C. After stirring at 70° C. for 1 h, the above suspension of methanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-[7-fluoro-3,3-dimethyl-2-(3-morpholin-4-yl-phenyl)-1,2,3,4-tetrahydro-quinoline-5-carbonyl]-methanesulfonamide (48 mg, 20%) as a white solid: LC/MS m/e calcd for $C_{23}H_{28}FN_3O_4S$ (M+H)$^+$: 462.56, observed: 462.1.

Example 136

2-[3-(7-Benzyl-4-oxo-5,6,7,8-tetrahydro-4H-pyrido[3,4-d]pyrimidin-3-yl)-phenyl]-3,3-dimethyl-1,2,3,4-tetrahydro-quinoline-6-carboxylic acid

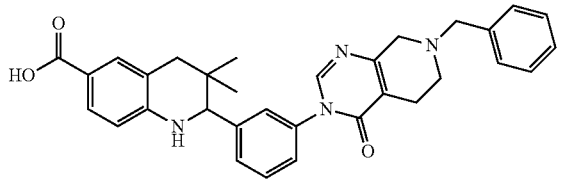 [SMILES: CC1(C)Cc2cc(C(=O)O)ccc2NC1c1cccc(-n2cnc3c(c2=O)CCN(Cc2ccccc2)C3)c1]

A mixture of 2-(3-bromo-phenyl)-3,3-dimethyl-1,2,3,4-tetrahydro-quinoline-6-carboxylic acid (360 mg, 1.0 mmol), 7-benzyl-5,6,7,8-tetrahydro-3H-pyrido[3,4-d]pyrimidin-4-one (300 mg, 1.3 mmol), copper(I) iodide (80 mg, 0.4 mmol), N,N-dimethylglycine hydrochloride (117 mg, 0.8 mmol) and potassium carbonate (769 mg, 5.6 mmol) in dimethyl sulfoxide (5 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[3-(7-benzyl-4-oxo-5,6,7,8-tetrahydro-4H-pyrido[3,4-d]pyrimidin-3-yl)-phenyl]-3,3-dimethyl-1,2,3,4-tetrahydro-quinoline-6-carboxylic acid (320 mg, 61%) as a white solid: LC/MS m/e calcd for $C_{32}H_{32}N_4O_3$ (M+H)$^+$: 521.64, observed: 521.2.

Example 137

8-Fluoro-3,3-dimethyl-2-(3-morpholin-4-yl-phenyl)-1,2,3,4-tetrahydro-quinoline-7-carboxylic acid

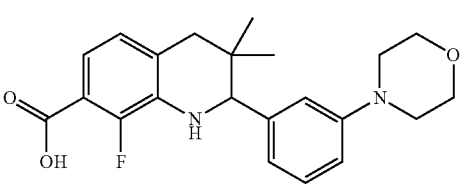 [SMILES: CC1(C)Cc2ccc(C(=O)O)c(F)c2NC1c1cccc(N2CCOCC2)c1]

To a stirred solution of 3-amino-2-fluoro-benzoic acid (25 g, 161 mmol) in methanol (300 mL) was added thionyl chloride (30 mL, 403 mmol) dropwise at 0° C. Then the mixture solution was refluxed for 12 hours before cooling to room temperature. Then the reaction mixture was concentrated in vacuo and the residue was dissolved in ethyl acetate (500 mL), washed with saturated aqueous sodium bicarbonate solution (3×100 mL), dried over anhydrous sodium sulfate and concentrated in vacuo to afford 3-amino-2-fluoro-benzoic acid methyl ester (27.5 g, quant.) as a pale-white solid: LC/MS m/e calcd for $C_8H_8FNO_2$ (M+H)$^+$: 170.16, observed: 169.9. A mixture solution of 3-amino-2-fluoro-benzoic acid methyl ester (26 g, 153.8 mmol), 3-bromo-benzaldehyde (28.5 g, 153.8 mmol) and p-toluenesulfonic acid (590 mg, 3.2 mmol) in toluene (200 mL) was heated to reflux for 12 hours. Then the reaction mixture was cooled to room temperature. The solvent was removed in vacuo and the residue was washed with ether to afford 3-[(3-bromo-benzylidene)-amino]-2-fluoro-benzoic acid methyl ester (51.7 g, quant.) as a pale-white solid: MS calcd. for $C_{15}H_{11}BrFNO_2$ 337.16, obsd. (ESI$^+$) [(M+H)$^+$] 336.0 & 338.0.

To a stirred mixture solution of 3-[(3-bromo-benzylidene)-amino]-2-fluoro-benzoic acid methyl ester (51.7 g, 153.8 mmol) and ytterbium(III) triflate hydrate (14.3 g, 23.1 mmol) in dry tetrahydrofuran (100 mL) at 25° C. was added isobutyraldehyde (14 mL, 153.8 mmol) and water (2.8 mL, 153.8 mmol) dropwise. The reaction mixture was stirred at 25° C. for 16 h. Then the reaction mixture was concentrated in vacuo and the residue was extracted with ethyl acetate (2×200 mL), washed with brine, dried over anhydrous sodium sulfate and concentrated in vacuo to afford 2-(3-bromo-phenyl)-8-fluoro-4-hydroxy-3,3-dimethyl-1,2,3,4-tetrahydro-quinoline-7-carboxylic acid methyl ester (63.0 g, quant.) as a light yellow oil which was used for next step without further purification: LC/MS m/e calcd for $C_{19}H_{19}BrFNO_3$ (M+H)$^+$: 409.27, observed: 390.0 & 392.0.

To a stirred mixture solution of 2-(3-bromo-phenyl)-8-fluoro-4-hydroxy-3,3-dimethyl-1,2,3,4-tetrahydro-quinoline-7-carboxylic acid methyl ester (63.0 g, 154 mmol) and triethylsilane (60 mL) at 25° C. was added trifluoroacetic acid (30 mL) dropwise. The resulting mixture solution was stirred at 25° C. for 3 hours. Then the reaction mixture was concentrated in vacuo and the residue was extracted with ethyl acetate (2×200 mL), washed with saturated aqueous sodium bicarbonate solution (4×100 mL), dried over anhydrous sodium sulfate and concentrated in vacuo. The residue was triturated with methanol. The resulting precipitate was collected, dried in vacuo to afford 2-(3-bromo-phenyl)-8-fluoro-3,3-dimethyl-1,2,3,4-tetrahydro-quinoline-7-carboxylic acid methyl ester (30.2 g, 50%) as a yellow oil: LC/MS m/e calcd for $C_{19}H_{19}BrFNO_2$ $(M+H)^+$: 393.27, observed: 392.0 & 394.0. A mixture of 2-(3-bromo-phenyl)-8-fluoro-3,3-dimethyl-1,2,3,4-tetrahydro-quinoline-7-carboxylic acid methyl ester (6.0 g, 15.3 mmol), morpholine (13.3 mL, 153 mmol), copper(I) iodide (874 mg, 4.6 mmol), N,N-dimethylglycine hydrochloride (1.3 g, 9.2 mmol) and potassium carbonate (8.5 g, 61.2 mmol) in dimethyl sulfoxide (15 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo to afford 8-fluoro-3,3-dimethyl-2-(3-morpholin-4-yl-phenyl)-1,2,3,4-tetrahydro-quinoline-7-carboxylic acid methyl ester (4.8 g, 80%) as a white solid which was used for next step without further purification: LC/MS m/e calcd for $C_{23}H_{27}FN_2O_3$ $(M+H)^+$: 399.48, observed: 399.1.

To a stirred mixture solution of 8-fluoro-3,3-dimethyl-2-(3-morpholin-4-yl-phenyl)-1,2,3,4-tetrahydro-quinoline-7-carboxylic acid methyl ester (400 mg, 1.0 mmol) in methanol (5.0 mL) and tetrahydrofuran (5.0 mL) was added 50% sodium hydroxide in water (1.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 8-fluoro-3,3-dimethyl-2-(3-morpholin-4-yl-phenyl)-1,2,3,4-tetrahydro-quinoline-7-carboxylic acid (345 mg, 90%) as a light yellow solid: LC/MS m/e calcd for $C_{22}H_{25}FN_2O_3$ $(M+H)^+$: 385.45, observed: 385.1.

Example 138

Cyclopropanesulfonic acid [7-fluoro-3,3-dimethyl-2-(3-morpholin-4-yl-phenyl)-1,2,3,4-tetrahydro-quinoline-5-carbonyl]-amide

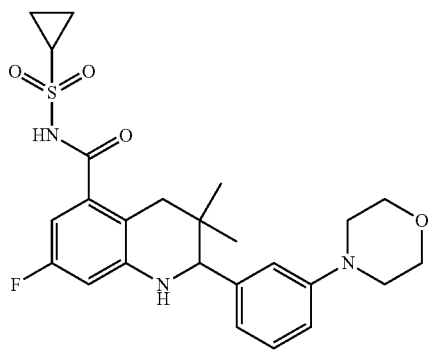 [SMILES: CC1(C)Cc2c(cc(F)cc2C(=O)NS(=O)(=O)C2CC2)NC1c1cccc(N2CCOCC2)c1]

To a suspension of 60% sodium hydride (200 mg, 5.0 mmol) in N,N-dimethylformamide (1.5 mL) was added cyclopropanesulfonamide (630 mg, 5.2 mmol) at room temperature. The resulting mixture was stirred at 25° C. for 1 h. A solution of 7-fluoro-3,3-dimethyl-2-(3-morpholin-4-yl-phenyl)-1,2,3,4-tetrahydro-quinoline-5-carboxylic acid (200 mg, 0.52 mmol) and 1,1'-carbonyldiimidazole (170 mg, 1.04 mmol) in N,N-dimethylformamide (2.0 mL) was stirred at 70° C. After stirring at 70° C. for 1 h, the above suspension of cyclopropanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [7-fluoro-3,3-dimethyl-2-(3-morpholin-4-yl-phenyl)-1,2,3,4-tetrahydro-quinoline-5-carbonyl]-amide (100 mg, 40%) as a white solid: LC/MS m/e calcd for $C_{25}H_{30}FN_3O_4S$ $(M+H)^+$: 488.60, observed: 488.1.

Example 139

Cyclopropanesulfonic acid {6-chloro-3,3-dimethyl-2-[3-(4-methyl-piperazin-1-yl)-phenyl]-1,2,3,4-tetrahydro-quinoline-8-carbonyl}-amide

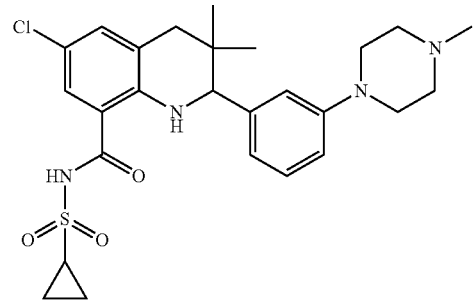 [SMILES: CN1CCN(c2cccc(C3Nc4c(cc(Cl)cc4C(=O)NS(=O)(=O)C4CC4)CC3(C)C)c2)CC1]

A mixture solution of 2-(3-bromo-phenyl)-6-chloro-3,3-dimethyl-1,2,3,4-tetrahydro-quinoline-8-carboxylic acid methyl ester (1.5 g, 3.7 mmol), 1-methyl-piperazine (2.5 g, 14.7 mmol), copper(I) iodide (282 mg, 1.48 mmol), N,N-dimethylglycine hydrochloride (413 mg, 2.96 mmol) and potassium carbonate (5.6 g, 40.7 mmol) in dimethyl sulfoxide (8.0 mL) was stirred at 120° C. for 16 hours. Then the reaction mixture cooled to room temperature. The reaction mixture was extracted with ethyl acetate (2×200 mL), washed with water (2×50 mL) and saturated aqueous ammonium chloride solution (2×50 mL), dried over anhydrous sodium sulfate and then concentrated in vacuo to afford 6-chloro-3,3-dimethyl-2-[3-(4-methyl-piperazin-1-yl)-phenyl]-1,2,3,4-tetrahydro-quinoline-8-carboxylic acid methyl ester (1.3 g, 80%) as a light yellow oil which was used for next step without further purification: LC/MS m/e calcd for $C_{24}H_{30}ClN_3O_2$ $(M+H)^+$: 428.98, observed: 428.1.

To a stirred mixture solution of 6-chloro-3,3-dimethyl-2-[3-(4-methyl-piperazin-1-yl)-phenyl]-1,2,3,4-tetrahydro-quinoline-8-carboxylic acid methyl ester (1.0 g, 2.4 mmol) in methanol (5.0 mL) and tetrahydrofuran (6.0 mL) was added 50% sodium hydroxide in water (2.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 6-chloro-3,3-dimethyl-2-[3-(4-methyl-piperazin-1-yl)-phenyl]-1,2,3,4-tetrahydro-quinoline-8-carboxylic acid (892 mg, 90%) as a white solid: LC/MS m/e calcd for $C_{23}H_{28}ClN_3O_2$ (M+H)$^+$: 414.95, observed: 414.1.

To a suspension of 60% sodium hydride (114 mg, 2.8 mmol) in N,N-dimethylformamide (1.5 mL) was added cyclopropanesulfonamide (350 mg, 2.9 mmol) at room temperature. The resulting mixture was stirred at 25° C. for 1 h. A solution of 6-chloro-3,3-dimethyl-2-[3-(4-methyl-piperazin-1-yl)-phenyl]-1,2,3,4-tetrahydro-quinoline-8-carboxylic acid (120 mg, 0.3 mmol) and 1,1'-carbonyldiimidazole (118 mg, 0.8 mmol) in N,N-dimethylformamide (2.0 mL) was stirred at 70° C. After stirring at 70° C. for 1 h, the above suspension of cyclopropanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid {6-chloro-3,3-dimethyl-2-[3-(4-methyl-piperazin-1-yl)-phenyl]-1,2,3,4-tetrahydro-quinoline-8-carbonyl}-amide (62 mg, 40%) as a white solid: LC/MS m/e calcd for $C_{26}H_{33}ClN_4O_3S$ (M+H)$^+$: 517.0, observed: 517.1.

Example 140

6-Chloro-2-(4'-isopropyl-biphenyl-3-yl)-3,3-dimethyl-1,2,3,4-tetrahydro-quinoline-8-carboxylic acid

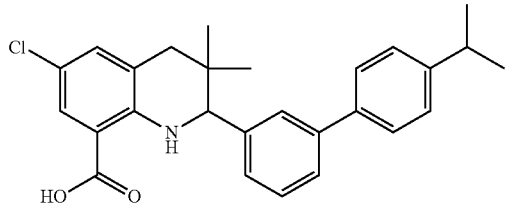 [SMILES: CC(C)c1ccc(-c2cccc(C3Nc4c(cc(Cl)cc4C(=O)O)CC3(C)C)c2)cc1]

To a mixture of 2-(3-bromo-phenyl)-6-chloro-3,3-dimethyl-1,2,3,4-tetrahydro-quinoline-8-carboxylic acid methyl ester (680 mg, 1.67 mmol), 4-isopropylphenylboronic acid (320 mg, 2.0 mmol) and tetrakis(triphenylphosphine)palladium(0) (193 mg, 0.17 mmol) in dioxane (5.0 mL) was added 2 M sodium carbonate solution in water (1.7 mL). The resulting mixture was subjected to microwave irradiation for 2 h at 110° C. The mixture was diluted with ethyl acetate (200 mL), washed with saturated aqueous sodium bicarbonate solution (50 mL×2), brine, dried over anhydrous sodium sulfate and then concentrated in vacuo. Purification by flash silica gel chromatography (silica gel from QingDao, 200-300 mesh, glass column from Shanghai SD company) (10% ethyl acetate/hexanes) afforded 6-chloro-2-(4'-isopropyl-biphenyl-3-yl)-3,3-dimethyl-1,2,3,4-tetrahydro-quinoline-8-carboxylic acid methyl ester (400 mg, 53.4%) as a white solid: LC/MS m/e calcd for $C_{28}H_{30}ClNO_2$ (M+H)$^+$: 449.01, observed: 448.1.

To a stirred mixture solution of 6-chloro-2-(4'-isopropyl-biphenyl-3-yl)-3,3-dimethyl-1,2,3,4-tetrahydro-quinoline-8-carboxylic acid methyl ester (400 mg, 0.9 mmol) in methanol (5.0 mL) and tetrahydrofuran (6.0 mL) was added 50% sodium hydroxide in water (2.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 6-chloro-2-(4'-isopropyl-biphenyl-3-yl)-3,3-dimethyl-1,2,3,4-tetrahydro-quinoline-8-carboxylic acid (351 mg, 90%) as a white solid: LC/MS m/e calcd for $C_{27}H_{28}ClNO_2$ (M+H)$^+$: 434.98, observed: 434.0.

Example 141

Cyclopropanesulfonic acid [6-chloro-2-(4'-dimethylamino-biphenyl-3-yl)-3,3-dimethyl-1,2,3,4-tetrahydro-quinoline-8-carbonyl]-amide

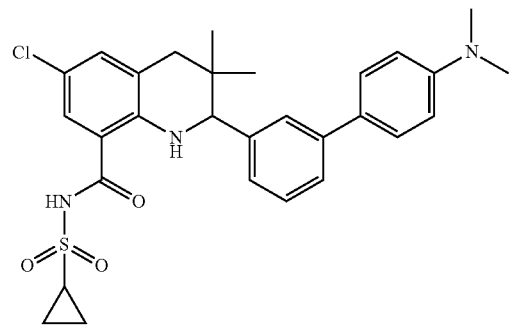 [SMILES: CN(C)c1ccc(-c2cccc(C3Nc4c(cc(Cl)cc4C(=O)NS(=O)(=O)C4CC4)CC3(C)C)c2)cc1]

To a mixture of 2-(3-bromo-phenyl)-6-chloro-3,3-dimethyl-1,2,3,4-tetrahydro-quinoline-8-carboxylic acid methyl ester (680 mg, 1.67 mmol), 4-dimethylaminophenylboronic acid (358 mg, 1.3 mmol) and tetrakis(triphenylphosphine)palladium(0) (193 mg, 0.17 mmol) in dioxane (5.0 mL) was added 2 M sodium carbonate solution in water (1.7 mL). The resulting mixture was subjected to microwave irradiation for 2 h at 110° C. The mixture was diluted with ethyl acetate (200 mL), washed with saturated aqueous sodium bicarbonate solution (50 mL×2), brine, dried over anhydrous sodium sulfate and then concentrated in vacuo. Purification by flash silica gel chromatography (silica gel from QingDao, 200-300 mesh, glass column from Shanghai SD company) (10% ethyl acetate/hexanes) afforded 6-chloro-2-(4'-dimethylamino-biphenyl-3-yl)-3,3-dimethyl-1,2,3,4-tetrahydro-quinoline-8-carboxylic acid methyl ester (524 mg, 70.0%) as a white solid: LC/MS m/e calcd for $C_{27}H_{29}ClN_2O_2$ (M+H)$^+$: 450.01, observed: 449.1.

To a stirred mixture solution of 6-chloro-2-(4'-dimethylamino-biphenyl-3-yl)-3,3-dimethyl-1,2,3,4-tetrahydro-quinoline-8-carboxylic acid methyl ester (400 mg, 0.9 mmol) in methanol (5.0 mL) and tetrahydrofuran (6.0 mL) was added 50% sodium hydroxide in water (2.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 6-chloro-2-(4'-dimethylamino-biphenyl-3-yl)-3,3-dimethyl-1,2,3,4-tetrahydro-quinoline-8-carboxylic acid (351 mg, 90%) as a white solid: LC/MS m/e calcd for $C_{26}H_{27}ClN_2O_2$ (M+H)$^+$: 435.98, observed: 435.0.

To a suspension of 60% sodium hydride (91 mg, 2.2 mmol) in N,N-dimethylformamide (1.5 mL) was added cyclopropanesulfonamide (280 mg, 2.3 mmol) at room temperature. The resulting mixture was stirred at 25° C. for 1 h. A solution of 6-chloro-2-(4'-dimethylamino-biphenyl-3-yl)-3,3-dimethyl-1,2,3,4-tetrahydro-quinoline-8-carboxylic acid (100 mg, 0.23 mmol) and 1,1'-carbonyldiimidazole (94 mg, 0.58 mmol) in N,N-dimethylformamide (2.0 mL) was stirred at 70° C. After stirring at 70° C. for 1 h, the above suspension of cyclopropanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [6-chloro-2-(4'-dimethylamino-biphenyl-3-yl)-3,3-dimethyl-1,2,3,4-tetrahydro-quinoline-8-carbonyl]-amide (49 mg, 40%) as a white solid: LC/MS m/e calcd for $C_{29}H_{32}ClN_3O_3S$ (M+H)$^+$: 539.11, observed: 538.1.

Example 142

2-(4'-tert-Butyl-biphenyl-3-yl)-6-chloro-3,3-dimethyl-1,2,3,4-tetrahydro-quinoline-8-carboxylic acid

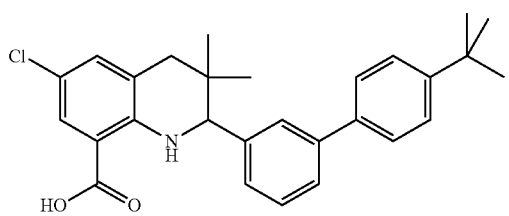 [SMILES: CC(C)(C)c1ccc(-c2cccc(C3Nc4c(cc(Cl)cc4C(=O)O)CC3(C)C)c2)cc1]

To a mixture solution of 2-(3-bromo-phenyl)-6-chloro-3,3-dimethyl-1,2,3,4-tetrahydro-quinoline-8-carboxylic acid methyl ester (1.0 g, 2.5 mmol), 4-tert-butylphenylboronic acid (582 mg, 3.3 mmol) and tetrakis(triphenylphosphine)palladium(0) (289 mg, 0.25 mmol) in dioxane (5.0 mL) was added 2 M sodium carbonate solution in water (2.5 mL). The resulting mixture was subjected to microwave irradiation for 2 h at 110° C. The mixture was diluted with ethyl acetate (200 mL), washed with saturated aqueous sodium bicarbonate solution (50 mL×2), brine, dried over anhydrous sodium sulfate and then concentrated in vacuo. Purification by flash silica gel chromatography (silica gel from QingDao, 200-300 mesh, glass column from Shanghai SD company) (10% ethyl acetate/hexanes) afforded 2-(4'-tert-butyl-biphenyl-3-yl)-6-chloro-3,3-dimethyl-1,2,3,4-tetrahydro-quinoline-8-carboxylic acid methyl ester (924 mg, 80%) as a white solid: LC/MS m/e calcd for $C_{29}H_{32}ClNO_2$ (M+H)$^+$: 463.04, observed: 463.1.

To a stirred mixture solution of 2-(4'-tert-butyl-biphenyl-3-yl)-6-chloro-3,3-dimethyl-1,2,3,4-tetrahydro-quinoline-8-carboxylic acid methyl ester (600 mg, 1.3 mmol) in methanol (5.0 mL) and tetrahydrofuran (6.0 mL) was added 50% sodium hydroxide in water (2.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-(4'-tert-butyl-biphenyl-3-yl)-6-chloro-3,3-dimethyl-1,2,3,4-tetrahydro-quinoline-8-carboxylic acid (524 mg, 90%) as a white solid: LC/MS m/e calcd for $C_{28}H_{30}ClNO_2$ (M+H)$^+$: 449.01, observed: 448.1.

Example 143

Cyclopropanesulfonic acid [2-(4'-tert-butyl-biphenyl-3-yl)-6-chloro-3,3-dimethyl-1,2,3,4-tetrahydro-quinoline-8-carbonyl]-amide

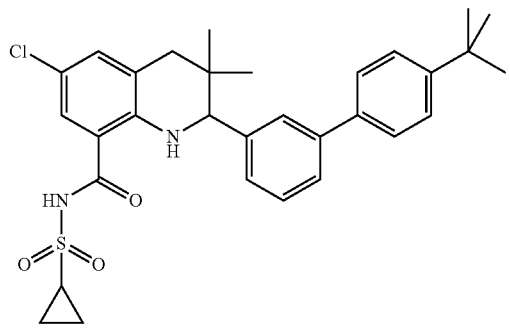 [SMILES: CC(C)(C)c1ccc(-c2cccc(C3Nc4c(cc(Cl)cc4C(=O)NS(=O)(=O)C4CC4)CC3(C)C)c2)cc1]

To a suspension of 60% sodium hydride (128 mg, 3.2 mmol) in N,N-dimethylformamide (1.5 mL) was added cyclopropanesulfonamide (400 mg, 3.3 mmol) at room temperature. The resulting mixture was stirred at 25° C. for 1 h. A solution of 2-(4'-tert-butyl-biphenyl-3-yl)-6-chloro-3,3-dimethyl-1,2,3,4-tetrahydro-quinoline-8-carboxylic acid (150 mg, 0.33 mmol)) and 1,1'-carbonyldiimidazole (136 mg, 0.84 mmol) in N,N-dimethylformamide (2.0 mL) was stirred at 70° C. After stirring at 70° C. for 1 h, the above suspension of cyclopropanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [2-(4'-tert-butyl-biphenyl-3-yl)-6-chloro-3,3-dimethyl-1,2,3,4-tetrahydro-quinoline-8-carbonyl]-amide (72 mg, 40%) as a white solid: LC/MS m/e calcd for $C_{31}H_{35}ClN_2O_3S$ (M+H)$^+$: 552.11, observed: 551.1.

Example 144

N-[2-(4'-tert-Butyl-biphenyl-3-yl)-6-chloro-3,3-dimethyl-1,2,3,4-tetrahydro-quinoline-8-carbonyl]-methanesulfonamide

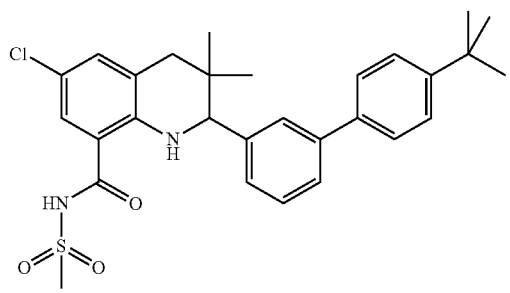 [SMILES: CC(C)(C)c1ccc(-c2cccc(C3Nc4c(cc(Cl)cc4C(=O)NS(C)(=O)=O)CC3(C)C)c2)cc1]

To a suspension of 60% sodium hydride (128 mg, 3.2 mmol) in N,N-dimethylformamide (1.5 mL) was added methanesulfonamide (314 mg, 3.3 mmol) at room temperature. The resulting mixture was stirred at 25° C. for 1 h. A solution of 2-(4'-tert-butyl-biphenyl-3-yl)-6-chloro-3,3-dimethyl-1,2,3,4-tetrahydro-quinoline-8-carboxylic acid (150 mg, 0.33 mmol) and 1,1'-carbonyldiimidazole (136 mg, 0.84 mmol) in N,N-dimethylformamide (2.0 mL) was stirred at 70° C. After stirring at 70° C. for 1 h, the above suspension of methanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-[2-(4'-tert-butyl-biphenyl-3-yl)-6-chloro-3,3-dimethyl-1,2,3,4-tetrahydro-quinoline-8-carbonyl]-methanesulfonamide (69 mg, 40%) as a white solid: LC/MS m/e calcd for $C_{29}H_{33}ClN_2O_3S$ (M+H)$^+$: 526.11, observed: 525.1.

Example 145

Cyclopropanesulfonic acid {2-[3-(5-ethyl-tetrazol-1-yl)-phenyl]-3,3-dimethyl-1,2,3,4-tetrahydro-quinoline-6-carbonyl}-amide

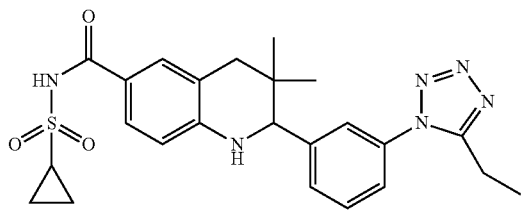 [SMILES: CCc1nnnn1-c1cccc(C2Nc3ccc(C(=O)NS(=O)(=O)C4CC4)cc3CC2(C)C)c1]

To a suspension of 60% sodium hydride (160 mg, 3.9 mmol) in N,N-dimethylformamide (1.5 mL) was added cyclopropanesulfonamide (484 mg, 4.0 mmol) at room temperature. The resulting mixture was stirred at 25° C. for 1 h. A solution of 2-[3-(5-ethyl-tetrazol-1-yl)-phenyl]-3,3-dimethyl-1,2,3,4-tetrahydro-quinoline-6-carboxylic acid (150 mg, 0.4 mmol) and 1,1'-carbonyldiimidazole (136 mg, 0.84 mmol) in N,N-dimethylformamide (2.0 mL) was stirred at 70° C. After stirring at 70° C. for 1 h, the above suspension of cyclopropanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid {2-[3-(5-ethyl-tetrazol-1-yl)-phenyl]-3,3-dimethyl-1,2,3,4-tetrahydro-quinoline-6-carbonyl}-amide (77 mg, 40%) as a white solid: LC/MS m/e calcd for $C_{24}H_{28}N_6O_3S$ (M+H)$^+$: 481.59, observed: 481.1.

Example 146

N-{2-[3-(5-Ethyl-tetrazol-1-yl)-phenyl]-3,3-dimethyl-1,2,3,4-tetrahydro-quinoline-6-carbonyl}-methanesulfonamide

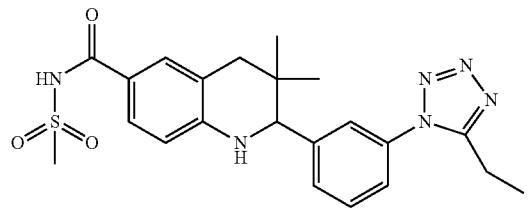 [SMILES: CCc1nnnn1-c1cccc(C2Nc3ccc(C(=O)NS(C)(=O)=O)cc3CC2(C)C)c1]

To a suspension of 60% sodium hydride (160 mg, 3.9 mmol) in N,N-dimethylformamide (1.5 mL) was added methanesulfonamide (380 mg, 4.0 mmol) at room temperature. The resulting mixture was stirred at 25° C. for 1 h. A solution of 2-[3-(5-ethyl-tetrazol-1-yl)-phenyl]-3,3-dimethyl-1,2,3,4-tetrahydro-quinoline-6-carboxylic acid (150 mg, 0.4 mmol) and 1,1'-carbonyldiimidazole (136 mg, 0.84 mmol) in N,N-dimethylformamide (2.0 mL) was stirred at 70° C. After stirring at 70° C. for 1 h, the above suspension of methanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-{2-[3-(5-ethyl-tetrazol-1-yl)-phenyl]-3,3-dimethyl-1,2,3,4-tetrahydro-quinoline-6-carbonyl}-methanesulfonamide (72 mg, 40%) as a white solid: LC/MS m/e calcd for $C_{22}H_{26}N_6O_3S$ (M+H)$^+$: 455.55, observed: 455.2.

Example 147

2-[3-(5-Benzyl-tetrazol-1-yl)-phenyl]-3,3-dimethyl-1,2,3,4-tetrahydro-quinoline-6-carboxylic acid

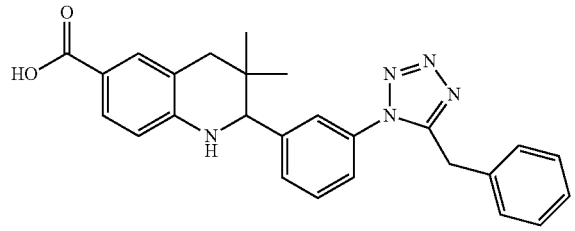 [SMILES: CC1(C)Cc2cc(C(=O)O)ccc2NC1c1cccc(-n2nnnc2Cc2ccccc2)c1]

To a stirred solution of phenylacetic acid (850 mg, 6.2 mmol), 2-(1H-7-Azabenzotriazol-1-yl)-1,1,3,3-tetramethyl uronium hexafluorophosphate Methanaminium (HATU) (3.5 g, 9.3 mmol) and triethyl amine (2.6 mL, 18.6 mmol) in dichloromethane (20 mL) was added 2-(3-amino-phenyl)-3,3-dimethyl-1,2,3,4-tetrahydro-quinoline-6-carboxylic acid ethyl ester (2.0 g, 6.2 mmol) at room temperature and stirred at room temperature for overnight. Then the reaction mixture was concentrated in vacuo and the residue was extracted with ethyl acetate (2×200 mL), washed with brine, dried over anhydrous sodium sulfate and concentrated in vacuo to afford 3,3-dimethyl-2-(3-phenylacetylamino-phenyl)-1,2,3,4-tetrahydro-quinoline-6-carboxylic acid ethyl ester (2.7 g, quant.) as a light yellow solid which was used for next step without further purification: LC/MS m/e calcd for $C_{28}H_{30}N_2O_3$ (M+H)$^+$: 443.56, observed: 443.1.

To a stirred solution of tetrachlorosilane (6.0 mL, 52 mmol), sodium azide (5.1 g, 78.1 mmol) in dry acetonitrile (20 mL) was added 3,3-dimethyl-2-(3-phenylacetylamino-phenyl)-1,2,3,4-tetrahydro-quinoline-6-carboxylic acid ethyl ester (2.3 g, 5.2 mmol) at room temperature. Then the mixture solution was stirred at room temperature for over night. LC/MS showed that reaction finished completely. The reaction mixture was poured into ice-cold saturated aqueous sodium bicarbonate solution and extracted with ethyl acetate (2×200 mL), washed with brine, dried over anhydrous sodium sulfate and concentrated in vacuo. Purification by flash silica gel chromatography (silica gel from QingDao, 200-300 mesh, glass column from Shanghai SD company) (40% ethyl acetate/hexanes) afforded 2-[3-(5-benzyl-tetrazol-1-yl)-phenyl]-3,3-dimethyl-1,2,3,4-tetrahydro-quinoline-6-carboxylic acid ethyl ester (1.4 g, 58.3%) as a white solid: LC/MS m/e calcd for $C_{28}H_{29}N_5O_2$ (M+H)$^+$: 468.58, observed: 468.1.

To a stirred mixture solution of 2-[3-(5-benzyl-tetrazol-1-yl)-phenyl]-3,3-dimethyl-1,2,3,4-tetrahydro-quinoline-6-carboxylic acid ethyl ester (1.4 g, 3.0 mmol) in methanol (10.0 mL) and tetrahydrofuran (10.0 mL) was added 50% sodium hydroxide in water (2.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[3-(5-benzyl-tetrazol-1-yl)-phenyl]-3,3-dimethyl-1,2,3,4-tetrahydro-quinoline-6-carboxylic acid (1.2 g, 90%) as a white solid: LC/MS m/e calcd for $C_{26}H_{25}N_5O_2$ (M+H)$^+$: 440.52, observed: 440.2.

ture was extracted with ethyl acetate and orderly washed with copper(II) sulfate solution, and brine, dried over anhydrous sodium sulfate and concentrated in vacuo to afford 3,3-dimethyl-2-(3-propionylamino-phenyl)-1,2,3,4-tetrahydro-quinoline-6-carboxylic acid ethyl ester (2.7 g, quant.) as a light yellow solid which was used for next step without further purification: LC/MS m/e calcd for $C_{23}H_{28}N_2O_3$ (M+H)$^+$: 381.49, observed: 381.2.

To a stirred solution of tetrachlorosilane (5.3 mL, 46.3 mmol), sodium azide (5.6 g, 87 mmol) in dry acetonitrile (20 mL) was added 3,3-dimethyl-2-(3-propionylamino-phenyl)-1,2,3,4-tetrahydro-quinoline-6-carboxylic acid ethyl ester (2.2 g, 5.8 mmol) at room temperature. Then the mixture solution was stirred at room temperature for over night. LC/MS showed that reaction finished completely. The reaction mixture was poured into ice-cold saturated aqueous sodium bicarbonate solution and extracted with ethyl acetate (2×200 mL), washed with brine, dried over anhydrous sodium sulfate and concentrated in vacuo. Purification by flash silica gel chromatography (silica gel from QingDao, 200-300 mesh, glass column from Shanghai SD company) (30% ethyl acetate/hexanes) afforded 2-[3-(5-ethyl-tetrazol-1-yl)-phenyl]-3,3-dimethyl-1,2,3,4-tetrahydro-quinoline-6-carboxylic acid ethyl ester (1.5 g, 66%) as a white solid: LC/MS m/e calcd for $C_{23}H_{27}N_5O_2$ (M+H)$^+$: 406.50, observed: 406.2.

To a stirred mixture solution of 243-(5-ethyl-tetrazol-1-yl)-phenyl]-3,3-dimethyl-1,2,3,4-tetrahydro-quinoline-6-carboxylic acid ethyl ester (1.5 g, 3.7 mmol) in methanol (10.0 mL) and tetrahydrofuran (10.0 mL) was added 50% sodium hydroxide in water (2.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[3-(5-ethyl-tetrazol-1-yl)-phenyl]-3,3-dimethyl-1,2,3,4-tetrahydro-quinoline-6-carboxylic acid (1.3 g, 90%) as a off-yellow solid: LC/MS m/e calcd for $C_{21}H_{23}N_5O_2$ (M+H)$^+$: 378.45, observed: 378.2.

Example 148

2-[3-(5-Ethyl-tetrazol-1-yl)-phenyl]-3,3-dimethyl-1,2,3,4-tetrahydro-quinoline-6-carboxylic acid

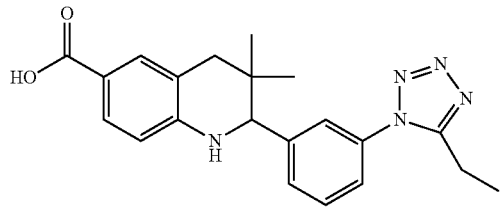 [SMILES: CCc1nnnn1-c1cccc(C2Nc3ccc(C(=O)O)cc3CC2(C)C)c1]

To a stirred solution of 2-(3-amino-phenyl)-3,3-dimethyl-1,2,3,4-tetrahydro-quinoline-6-carboxylic acid ethyl ester (2.3 g, 7.1 mmol) and pyridine (0.86 mL, 10.7 mmol) dissolved in dry dichloromethane (20 mL) was added propionic anhydride (1.1 mL, 7.8 mmol) at 0° C. Then the mixture solution stirred at room temperature for 1 hour, LC/MS showed that reaction finished completely. The reaction mix- Example 149

N-[7-Chloro-3,3-dimethyl-2-(3-morpholin-4-yl-phenyl)-1,2,3,4-tetrahydro-quinoline-5-carbonyl]-methanesulfonamide

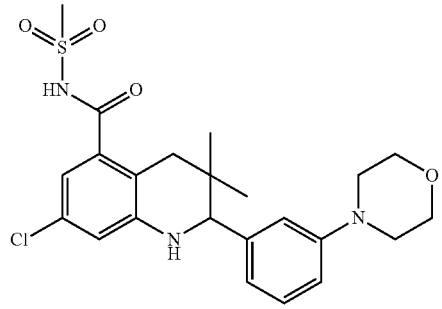 [SMILES: CC1(C)Cc2c(cc(Cl)cc2C(=O)NS(C)(=O)=O)NC1c1cccc(N2CCOCC2)c1]

To a stirred solution of 3-amino-5-chloro-benzoic acid (50 g, 291 mmol) in methanol (300 mL) was added thionyl chloride (45 mL, 605 mmol) dropewise at 0° C. Then the mixture solution was refluxed for 12 hours before cooling to room temperature. Then the reaction mixture was concentrated in vacuo and the residue was dissolved in ethyl acetate (500 mL), washed with saturated aqueous sodium bicarbonate solution (3×100 mL), dried over anhydrous sodium sulfate and concentrated in vacuo to afford 3-amino-5-chloro-benzoic acid methyl ester (54 g, quant.) as a pale-white solid: LC/MS m/e calcd for $C_8H_8ClNO_2$ (M+H)$^+$: 186.61, observed: 185.9.

A mixture solution of 3-amino-5-chloro-benzoic acid methyl ester (21 g, 113.2 mmol), 3-bromo-benzaldehyde (21 g, 113.2 mmol) and p-toluenesulfonic acid (431 mg, 2.2 mmol) in toluene (200 mL) was heated to reflux for 12 hours. Then the reaction mixture was cooled to room temperature. The solvent was removed in vacuo and the residue was washed with ether to afford 3-[(3-bromo-benzylidene)-amino]-5-chloro-benzoic acid methyl ester (39.8 g, quant.) as a pale-white solid: MS calcd. for $C_{15}H_{11}BrClNO_2$ 353.62, obsd. (ESI$^+$) [(M+H)$^+$] 351.9 & 353.9.

To a stirred mixture solution of 3-[(3-bromo-benzylidene)-amino]-5-chloro-benzoic acid methyl ester (39.8 g, 113.2 mmol) and ytterbium(III) triflate hydrate (10.5 g, 16.9 mmol) in dry tetrahydrofuran (100 mL) at 25° C. was added isobutyraldehyde (10.4 mL, 113.2 mmol) and water (2.1 mL, 113.2 mmol) dropwise. The reaction mixture was stirred at 25° C. for 16 h. Then the reaction mixture was concentrated in vacuo and the residue was extracted with ethyl acetate (2×200 mL), washed with brine, dried over anhydrous sodium sulfate and concentrated in vacuo to afford 2-(3-bromo-phenyl)-7-chloro-4-hydroxy-3,3-dimethyl-1,2,3,4-tetrahydro-quinoline-5-carboxylic acid methyl ester (48 g, quant.) as a light yellow oil which was used for next step without further purification: LC/MS m/e calcd for $C_{19}H_{19}BrClNO_3$ (M+H)$^+$: 425.73, observed: 405.9 & 407.9.

To a stirred mixture solution of 2-(3-bromo-phenyl)-7-chloro-4-hydroxy-3,3-dimethyl-1,2,3,4-tetrahydro-quinoline-5-carboxylic acid methyl ester (48 g, 113.2 mmol) and triethylsilane (60 mL) at 25° C. was added trifluoroacetic acid (30 mL) dropwise. The resulting mixture solution was stirred at 25° C. for 3 hours. Then the reaction mixture was concentrated in vacuo and the residue was extracted with ethyl acetate (2×200 mL), washed with saturated aqueous sodium bicarbonate solution (4×100 mL), dried over anhydrous sodium sulfate and concentrated in vacuo. The residue was triturated with methanol. The resulting precipitate was collected, dried in vacuo to afford 2-(3-bromo-phenyl)-7-chloro-3,3-dimethyl-1,2,3,4-tetrahydro-quinoline-5-carboxylic acid methyl ester (15 g, 32.6%) as a white solid: LC/MS m/e calcd for $C_{19}H_{19}BrClNO_2$ (M+H)$^+$: 409.73, observed: 407.9 & 409.9.

A mixture of 2-(3-bromo-phenyl)-7-chloro-3,3-dimethyl-1,2,3,4-tetrahydro-quinoline-5-carboxylic acid methyl ester (1.2 g, 2.94 mmol), morpholine (1.3 mL, 14.7 mmol), copper (I) iodide (140 mg, 0.7 mmol), N,N-dimethylglycine hydrochloride (206 mg, 1.5 mmol) and potassium carbonate (1.2 g, 8.8 mmol) in dimethyl sulfoxide (15 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo to afford 7-chloro-3,3-dimethyl-2-(3-morpholin-4-yl-phenyl)-1,2,3,4-tetrahydro-quinoline-5-carboxylic acid methyl ester (973 mg, 80%) as a white solid which was used for next step without further purification: LC/MS m/e calcd for $C_{23}H_{27}ClN_2O_3$ (M+H)$^+$: 415.94, observed: 415.1.

To a stirred mixture solution of 7-chloro-3,3-dimethyl-2-(3-morpholin-4-yl-phenyl)-1,2,3,4-tetrahydro-quinoline-5-carboxylic acid methyl ester (800 mg, 0.5 mmol) in methanol (5.0 mL) and tetrahydrofuran (5.0 mL) was added 50% sodium hydroxide in water (1.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 7-chloro-3,3-dimethyl-2-(3-morpholin-4-yl-phenyl)-1,2,3,4-tetrahydro-quinoline-5-carboxylic acid (720 mg, 90%) as a light yellow solid: LC/MS m/e calcd for $C_{22}H_{25}ClN_2O_3$ (M+H)$^+$: 401.91, observed: 401.1.

To a suspension of 60% sodium hydride (200 mg, 5.0 mmol) in N,N-dimethylformamide (1.5 mL) was added methanesulfonamide (494 mg, 5.2 mmol) at room temperature. The resulting mixture was stirred at 25° C. for 1 h. A solution of 7-chloro-3,3-dimethyl-2-(3-morpholin-4-yl-phenyl)-1,2,3,4-tetrahydro-quinoline-5-carboxylic acid (200 mg, 0.5 mmol) and 1,1'-carbonyldiimidazole (170 mg, 1.04 mmol) in N,N-dimethylformamide (2.0 mL) was stirred at 70° C. After stirring at 70° C. for 1 h, the above suspension of methanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-[7-chloro-3,3-dimethyl-2-(3-morpholin-4-yl-phenyl)-1,2,3,4-tetrahydro-quinoline-5-carbonyl]-methanesulfonamide (48 mg, 20%) as a white solid: LC/MS m/e calcd for $C_{23}H_{28}ClN_3O_4S$ (M+H)$^+$: 478.01, observed: 478.1.

Example 150

Cyclopropanesulfonic acid [8-fluoro-3,3-dimethyl-2-(3-morpholin-4-yl-phenyl)-1,2,3,4-tetrahydro-quinoline-5-carbonyl]-amide

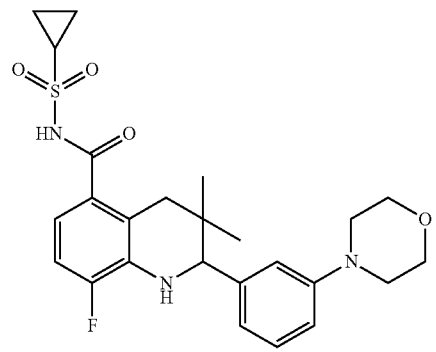 [SMILES: CC1(C)Cc2c(C(=O)NS(=O)(=O)C3CC3)ccc(F)c2NC1c1cccc(N2CCOCC2)c1]

To a stirred solution of 3-amino-4-fluoro-benzoic acid (25 g, 161 mmol) in methanol (300 mL) was added thionyl chloride (30 mL, 403 mmol) dropwise at 0° C. Then the mixture solution was refluxed for 12 hours before cooling to room temperature. Then the reaction mixture was concentrated in vacuo and the residue was dissolved in ethyl acetate (500 mL), washed with saturated aqueous sodium bicarbonate solution (3×100 mL), dried over anhydrous sodium sulfate and concentrated in vacuo to afford 3-amino-4-fluoro-benzoic acid methyl ester (27.5 g, quant.) as a pale-white solid: LC/MS m/e calcd for $C_8H_8FNO_2$ (M+H)$^+$: 170.16, observed: 169.9.

A mixture solution of 3-amino-4-fluoro-benzoic acid methyl ester (26 g, 153.8 mmol), 3-bromo-benzaldehyde (28.5 g, 153.8 mmol) and p-toluenesulfonic acid (590 mg, 3.2 mmol) in toluene (200 mL) was heated to reflux for 12 hours. Then the reaction mixture was cooled to room temperature. The solvent was removed in vacuo and the residue was washed with ether to afford 3-[(3-bromo-benzylidene)-amino]-4-fluoro-benzoic acid methyl ester (51.7 g, quant.) as a pale-white solid: MS calcd. for $C_{15}H_{11}BrFlNO_2$ 337.16, obsd. (ESI$^+$) [(M+H)$^+$] 336.0 & 338.0.

To a stirred mixture solution of 3-[(3-bromo-benzylidene)-amino]-4-fluoro-benzoic acid methyl ester (51.7 g, 153.8 mmol) and ytterbium(III) triflate hydrate (14.3 g, 23.1 mmol) in dry tetrahydrofuran (100 mL) at 25° C. was added isobutyraldehyde (14 mL, 153.8 mmol) and water (2.8 mL, 153.8 mmol) dropwise. The reaction mixture was stirred at 25° C. for 16 h. Then the reaction mixture was concentrated in vacuo and the residue was extracted with ethyl acetate (2×200 mL), washed with brine, dried over anhydrous sodium sulfate and concentrated in vacuo to afford 2-(3-bromo-phenyl)-8-fluoro-4-hydroxy-3,3-dimethyl-1,2,3,4-tetrahydro-quinoline-5-carboxylic acid methyl ester (63.0 g, quant.) as a light yellow oil which was used for next step without further purification: LC/MS m/e calcd for $C_{19}H_{19}BrFNO_3$ (M+H)$^+$: 409.27, observed: 390.0 & 392.0.

To a stirred mixture solution of 2-(3-bromo-phenyl)-8-fluoro-4-hydroxy-3,3-dimethyl-1,2,3,4-tetrahydro-quinoline-5-carboxylic acid methyl ester (63.0 g, 154 mmol) and triethylsilane (60 mL) at 25° C. was added trifluoroacetic acid (30 mL) dropwise. The resulting mixture solution was stirred at 25° C. for 3 hours. Then the reaction mixture was concentrated in vacuo and the residue was extracted with ethyl acetate (2×200 mL), washed with saturated aqueous sodium bicarbonate solution (4×100 mL), dried over anhydrous sodium sulfate and concentrated in vacuo. The residue was triturated with methanol. The resulting precipitate was collected, dried in vacuo to afford 2-(3-bromo-phenyl)-8-fluoro-3,3-dimethyl-1,2,3,4-tetrahydro-quinoline-5-carboxylic acid methyl ester (30.2 g, 50%) as a yellow oil: LC/MS m/e calcd for $C_{19}H_{19}BrFNO_2$ (M+H)$^+$: 393.27, observed: 392.0 & 394.0.

A mixture of 2-(3-bromo-phenyl)-8-fluoro-3,3-dimethyl-1,2,3,4-tetrahydro-quinoline-5-carboxylic acid methyl ester (6.0 g, 15.3 mmol), morpholine (13.3 mL, 153 mmol), copper (I) iodide (874 mg, 4.6 mmol), N,N-dimethylglycine hydrochloride (1.3 g, 9.2 mmol) and potassium carbonate (8.5 g, 61.2 mmol) in dimethyl sulfoxide (15 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo to afford 8-fluoro-3,3-dimethyl-2-(3-morpholin-4-yl-phenyl)-1,2,3,4-tetrahydro-quinoline-5-carboxylic acid methyl ester (4.8 g, 80%) as a white solid which was used for next step without further purification: LC/MS m/e calcd for $C_{23}H_{27}FN_2O_3$ (M+H)$^+$: 399.48, observed: 399.1.

To a stirred mixture solution of 8-fluoro-3,3-dimethyl-2-(3-morpholin-4-yl-phenyl)-1,2,3,4-tetrahydro-quinoline-5-carboxylic acid methyl ester (400 mg, 1.0 mmol) in methanol (5.0 mL) and tetrahydrofuran (5.0 mL) was added 50% sodium hydroxide in water (1.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 8-fluoro-3,3-dimethyl-2-(3-morpholin-4-yl-phenyl)-1,2,3,4-tetrahydro-quinoline-5-carboxylic acid (345 mg, 90%) as a light yellow solid: LC/MS m/e calcd for $C_{22}H_{25}FN_2O_3$ (M+H)$^+$: 385.45, observed: 385.1.

To a suspension of 60% sodium hydride (200 mg, 5.0 mmol) in N,N-dimethylformamide (1.5 mL) was added cyclopropanesulfonamide (630 mg, 5.2 mmol) at room temperature. The resulting mixture was stirred at 25° C. for 1 h. A solution of 8-fluoro-3,3-dimethyl-2-(3-morpholin-4-yl-phenyl)-1,2,3,4-tetrahydro-quinoline-5-carboxylic acid (200 mg, 0.52 mmol) and 1,1'-carbonyldiimidazole (170 mg, 1.04 mmol) in N,N-dimethylformamide (2.0 mL) was stirred at 70° C. After stirring at 70° C. for 1 h, the above suspension of cyclopropanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [8-fluoro-3,3-dimethyl-2-(3-morpholin-4-yl-phenyl)-1,2,3,4-tetrahydro-quinoline-5-carbonyl]-amide (100 mg, 40%) as a white solid: LC/MS m/e calcd for $C_{25}H_{30}FN_3O_4S$ (M+H)$^+$: 488.60, observed: 488.1.

Example 151

2-(4'-tert-Butyl-biphenyl-3-yl)-6-fluoro-3,3-dimethyl-1,2,3,4-tetrahydro-quinoline-5-carboxylic acid

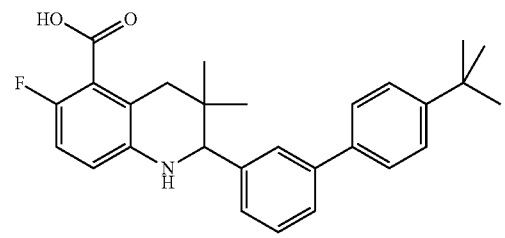 [SMILES: CC(C)(C)c1ccc(-c2cccc(C3Nc4ccc(F)c(C(=O)O)c4CC3(C)C)c2)cc1]

To a mixture solution of 2-(3-bromo-phenyl)-6-fluoro-3,3-dimethyl-1,2,3,4-tetrahydro-quinoline-5-carboxylic acid methyl ester (1.0 g, 2.6 mmol), 4-tert-butylphenylboronic acid (590 mg, 3.3 mmol) and tetrakis(triphenylphosphine)palladium(0) (289 mg, 0.25 mmol) in dioxane (5.0 mL) was added 2 M sodium carbonate solution in water (2.5 mL). The resulting mixture was subjected to microwave irradiation for 2 h at 110° C. The mixture was diluted with ethyl acetate (200 mL), washed with saturated aqueous sodium bicarbonate solution (50 mL×2), brine, dried over anhydrous sodium sulfate and then concentrated in vacuo. Purification by flash silica gel chromatography (silica gel from QingDao, 200-300 mesh, glass column from Shanghai SD company) (10% ethyl acetate/hexanes) afforded 2-(4'-tert-butyl-biphenyl-3-yl)-6-fluoro-3,3-dimethyl-1,2,3,4-tetrahydro-quinoline-8-carboxylic acid methyl ester (926 mg, 80%) as a white solid: LC/MS m/e calcd for $C_{29}H_{32}FNO_2$ (M+H)$^+$: 446.58, observed: 446.1.

To a stirred mixture solution of 2-(4'-tert-butyl-biphenyl-3-yl)-6-fluoro-3,3-dimethyl-1,2,3,4-tetrahydro-quinoline-8-carboxylic acid methyl ester (600 mg, 1.3 mmol) in methanol (5.0 mL) and tetrahydrofuran (6.0 mL) was added 50% sodium hydroxide in water (2.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-(4'-tert-butyl-biphenyl-3-yl)-6-fluoro-3,3-dimethyl-1,2,3,4-tetrahydro-quinoline-8-carboxylic acid (524 mg, 90%) as a white solid: LC/MS m/e calcd for $C_{28}H_{30}FNO_2$ (M+H)$^+$: 432.56, observed: 432.1.

Example 152

3,3-Dimethyl-2-[3-(4-o-tolyl-piperazin-1-yl)-phenyl]-1,2,3,4-tetrahydroquinoline-6-carboxylic acid

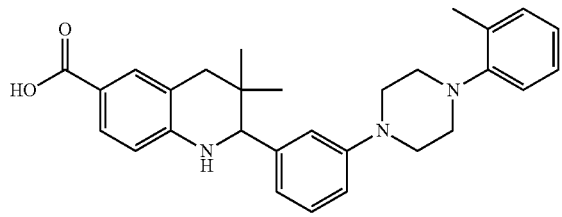 [SMILES: Cc1ccccc1N1CCN(c2cccc(C3Nc4ccc(C(=O)O)cc4CC3(C)C)c2)CC1]

A mixture of 2-(3-bromo-phenyl)-3,3-dimethyl-1,2,3,4-tetrahydro-quinoline-6-carboxylic acid ethyl ester (1.2 g, 3.1 mmol), 1-o-tolyl-piperazine (987 mg, 4.6 mmol), copper(I) iodide (180 mg, 0.93 mmol), N,N-dimethylglycine hydrochloride (260 mg, 1.86 mmol) and potassium carbonate (1.3 g, 9.3 mmol) in dimethyl sulfoxide (10 mL) was stirred at 120° C. for 16 hours. Then the reaction mixture cooled to room temperature. The reaction mixture was extracted with ethyl acetate (2×200 mL), washed with water (2×50 mL) and saturated aqueous ammonium chloride solution (2×50 mL), dried over anhydrous sodium sulfate and then concentrated in vacuo to afford 3,3-dimethyl-2-[3-(4-o-tolyl-piperazin-1-yl)-phenyl]-1,2,3,4-tetrahydro-quinoline-6-carboxylic acid ethyl ester (1.2 g, 80%) as a light yellow oil which was used for next step without further purification: LC/MS m/e calcd for $C_{31}H_{37}N_3O_2$ (M+H)$^+$: 484.56, observed: 484.2.

To a stirred mixture solution 3,3-dimethyl-2-[3-(4-o-tolyl-piperazin-1-yl)-phenyl]-1,2,3,4-tetrahydro-quinoline-6-carboxylic acid ethyl ester (1.0 g, 2.1 mmol) in methanol (5.0 mL) and tetrahydrofuran (6.0 mL) was added 50% sodium hydroxide in water (2.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 3,3-dimethyl-2-[3-(4-o-tolyl-piperazin-1-yl)-phenyl]-1,2,3,4-tetrahydro-quinoline-6-carboxylic acid (850 mg, 90%) as a white solid: LC/MS m/e calcd for $C_{29}H_{33}N_3O_2$ (M+H)$^+$: 456.61, observed: 456.2.

Example 153

Cyclopropanesulfonic acid {2-[3-(3-fluoro-azetidin-1-yl)-phenyl]-3,3-dimethyl-1,2,3,4-tetrahydro-quinoline-6-carbonyl}-amide

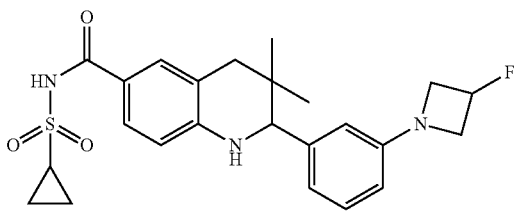 [SMILES: CC1(C)Cc2cc(C(=O)NS(=O)(=O)C3CC3)ccc2NC1c1cccc(N2CC(F)C2)c1]

A mixture of 2-(3-bromo-phenyl)-3,3-dimethyl-1,2,3,4-tetrahydro-quinoline-6-carboxylic acid (1.2 g, 3.3 mmol), 3-fluoro-azetidine (740 mg, 6.6 mmol), copper(I) iodide (190 mg, 1.0 mmol), N,N-dimethylglycine hydrochloride (280 mg, 2.0 mmol) and potassium carbonate (1.8 g, 13.2 mmol) in dimethyl sulfoxide (10 mL) was stirred at 120° C. for 16 hours. Then the reaction mixture cooled to room temperature. The reaction mixture was extracted with ethyl acetate (2×200 mL), washed with water (2×50 mL) and saturated aqueous ammonium chloride solution (2×50 mL), dried over anhydrous sodium sulfate and then concentrated in vacuo to afford 2-[3-(3-fluoro-azetidin-1-yl)-phenyl]-3,3-dimethyl-1,2,3,4-tetrahydro-quinoline-6-carboxylic acid (934 mg, 80%) as a light yellow oil which was used for next step without further purification: LC/MS m/e calcd for $C_{21}H_{23}FN_2O_2$ (M+H)$^+$: 355.43, observed: 355.1.

To a suspension of 60% sodium hydride (165 mg, 4.1 mmol) in N,N-dimethylformamide (1.5 mL) was added cyclopropanesulfonamide (510 mg, 4.2 mmol) at room temperature. The resulting mixture was stirred at 25° C. for 1 h. A solution of 2-[3-(3-fluoro-azetidin-1-yl)-phenyl]-3,3-dimethyl-1,2,3,4-tetrahydro-quinoline-6-carboxylic acid (150 mg, 0.42 mmol) and 1,1'-carbonyldiimidazole (170 mg, 1.04 mmol) in N,N-dimethylformamide (2.0 mL) was stirred at 70° C. After stirring at 70° C. for 1 h, the above suspension of cyclopropanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid {2-[3-(3-fluoro-azetidin-1-yl)-phenyl]-3,3-dimethyl-1,2,3,4-tetrahydroquinoline-6-carbonyl}-amide (38 mg, 20%) as a white solid: LC/MS m/e calcd for $C_{24}H_{28}FN_3O_3S$ (M+H)$^+$: 458.57, observed: 458.1.

Example 154

N-{2-[3-(3-Fluoro-azetidin-1-yl)-phenyl]-3,3-dimethyl-1,2,3,4-tetrahydro-quinoline-6-carbonyl}-methanesulfonamide

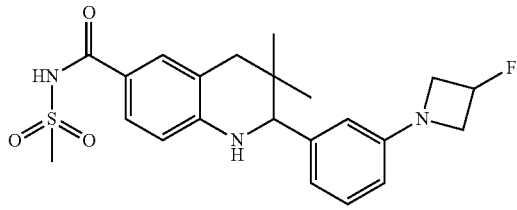 [SMILES: CC1(C)Cc2cc(C(=O)NS(C)(=O)=O)ccc2NC1c1cccc(N2CC(F)C2)c1]

To a suspension of 60% sodium hydride (165 mg, 4.1 mmol) in N,N-dimethylformamide (1.5 mL) was added methanesulfonamide (400 mg, 4.2 mmol) at room temperature. The resulting mixture was stirred at 25° C. for 1 h. A solution of 2-[3-(3-fluoro-azetidin-1-yl)-phenyl]-3,3-dimethyl-1,2,3,4-tetrahydro-quinoline-6-carboxylic acid (150 mg, 0.42 mmol), and 1,1'-carbonyldiimidazole (170 mg, 1.04 mmol) in N,N-dimethylformamide (2.0 mL) was stirred at 70° C. After stirring at 70° C. for 1 h, the above suspension of methanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-{2-[3-(3-fluoro-azetidin-1-yl)-phenyl]-3,3-dimethyl-1,2,3,4-tetrahydro-quinoline-6-carbonyl}-methanesulfonamide (36 mg, 20%) as a white solid: LC/MS m/e calcd for $C_{22}H_{26}FN_3O_3S$ (M+H)$^+$: 432.51, observed: 432.1.

Example 155

N-{3,3-Dimethyl-2-[3-(4-o-tolyl-piperazin-1-yl)-phenyl]-1,2,3,4-tetrahydro-quinoline-6-carbonyl}-methanesulfonamide

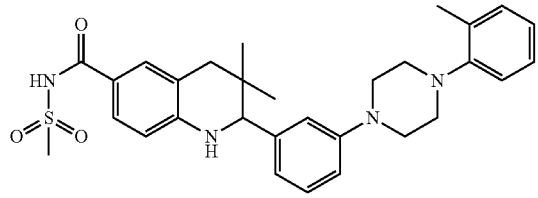 [SMILES: Cc1ccccc1N1CCN(c2cccc(C3Nc4ccc(C(=O)NS(C)(=O)=O)cc4CC3(C)C)c2)CC1]

To a suspension of 60% sodium hydride (172 mg, 4.3 mmol) in N,N-dimethylformamide (1.5 mL) was added methanesulfonamide (418 mg, 4.4 mmol) at room temperature. The resulting mixture was stirred at 25° C. for 1 h. A solution of 3,3-dimethyl-2-[3-(4-o-tolyl-piperazin-1-yl)-phenyl]-1,2,3,4-tetrahydro-quinoline-6-carboxylic acid (200 mg, 0.44 mmol), and 1,1'-carbonyldiimidazole (170 mg, 1.04 mmol) in N,N-dimethylformamide (2.0 mL) was stirred at 70° C. After stirring at 70° C. for 1 h, the above suspension of methanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-{3,3-dimethyl-2-[3-(4-o-tolyl-piperazin-1-yl)-phenyl]-1,2,3,4-tetrahydro-quinoline-6-carbonyl}methanesulfonamide (46 mg, 20%) as a white solid: LC/MS m/e calcd for $C_{30}H_{36}N_4O_3S$ (M+H)$^+$: 533.71, observed: 533.2.

Example 156

Cyclopropanesulfonic acid [2-(4'-tert-butyl-biphenyl-3-yl)-6-fluoro-3,3-dimethyl-1,2,3,4-tetrahydro-quinoline-5-carbonyl]-amide

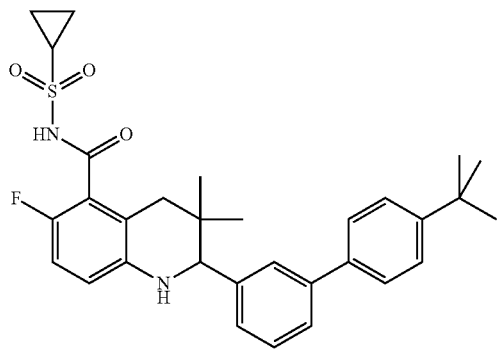 [SMILES: CC(C)(C)c1ccc(-c2cccc(C3Nc4ccc(F)c(C(=O)NS(=O)(=O)C5CC5)c4CC3(C)C)c2)cc1]

To a suspension of 60% sodium hydride (75 mg, 1.86 mmol) in N,N-dimethylformamide (1.5 mL) was added cyclopropanesulfonamide (242 mg, 1.9 mmol) at room temperature. The resulting mixture was stirred at 25° C. for 1 h. A solution of 2-(4'-tert-butyl-biphenyl-3-yl)-6-fluoro-3,3-dimethyl-1,2,3,4-tetrahydro-quinoline-5-carboxylic acid (80 mg, 0.19 mmol) and 1,1'-carbonyldiimidazole (65 mg, 0.38 mmol) in N,N-dimethylformamide (2.0 mL) was stirred at 70° C. After stirring at 70° C. for 1 h, the above suspension of cyclopropanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [2-(4'-tert-butyl-biphenyl-3-yl)-6-fluoro-3,3-dimethyl-1,2,3,4-tetrahydroquinoline-5-carbonyl]-amide (21 mg, 20%) as a white solid: LC/MS m/e calcd for $C_{31}H_{35}FN_2O_3S$ (M+H)$^+$: 535.70, observed: 535.1.

Example 157

N-[2-(4'-tert-Butyl-biphenyl-3-yl)-6-fluoro-3,3-dimethyl-1,2,3,4-tetrahydro-quinoline-5-carbonyl]-methanesulfonamide

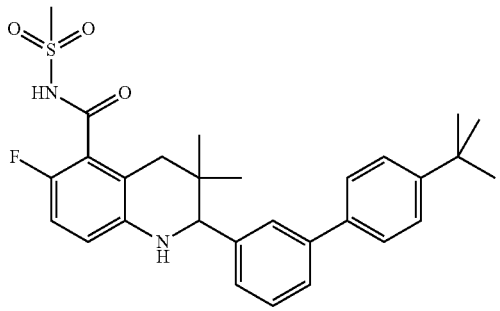 [SMILES: CC(C)(C)c1ccc(-c2cccc(C3Nc4ccc(F)c(C(=O)NS(C)(=O)=O)c4CC3(C)C)c2)cc1]

To a suspension of 60% sodium hydride (75 mg, 1.86 mmol) in N,N-dimethylformamide (1.5 mL) was added methanesulfonamide (181 mg, 1.9 mmol) at room temperature. The resulting mixture was stirred at 25° C. for 1 h. A solution of 2-(4'-tert-butyl-biphenyl-3-yl)-6-fluoro-3,3-dimethyl-1,2,3,4-tetrahydro-quinoline-5-carboxylic acid (80 mg, 0.19 mmol) and 1,1'-carbonyldiimidazole (65 mg, 0.38 mmol) in N,N-dimethylformamide (2.0 mL) was stirred at 70° C. After stirring at 70° C. for 1 h, the above suspension of methanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-[2-(4'-tert-butyl-biphenyl-3-yl)-6-fluoro-3,3-dimethyl-1,2,3,4-tetrahydro-quinoline-5-carbonyl]-methanesulfonamide (19 mg, 20%) as a white solid: LC/MS m/e calcd for $C_{29}H_{33}FN_2O_3S$ (M+H)$^+$: 509.66, observed: 509.1.

Example 158

3,3-Dimethyl-2-phenyl-1,2,3,4-tetrahydro-quinoline-6-carboxylic acid

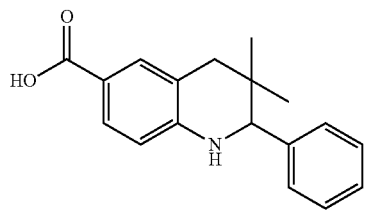 [SMILES: CC1(C)Cc2cc(C(=O)O)ccc2NC1c1ccccc1]

A mixture of 4-amino-benzoic acid ethyl ester (3.3 g, 20.0 mmol), benzaldehyde (2.4 g, 22.0 mmol) and p-toluenesulfonic acid (76 mg, 0.4 mmol) in toluene (60.0 mL) was heated to reflux for 12 h. Then the reaction mixture cooled to room temperature. The solvent was removed in vacuo and the residue was washed with ether to afford 4-(benzylidene-amino)-benzoic acid ethyl ester (5.1 g, quant.) as a light yellow solid: LC/MS m/e calcd for $C_{16}H_{15}NO_2$ (M+H)$^+$: 254.3, observed: 254.1.

To a mixture of 4-(benzylidene-amino)-benzoic acid ethyl ester (5.1 g, 20.0 mmol) and ytterbium(III) triflate hydrate (1.3 g, 2.0 mmol) in dry tetrahydrofuran (20.0 mL) at 25° C. was added isobutyraldehyde (18.2 mL, 200 mmol) and water (0.36 mL, 20.0 mmol) dropwise. The reaction mixture was stirred at 25° C. for 16 h. Then the reaction mixture was concentrated in vacuo and the residue was extracted with ethyl acetate (2×200 mL), washed with brine, dried over anhydrous sodium sulfate and concentrated in vacuo to afford 4-hydroxy-3,3-dimethyl-2-phenyl-1,2,3,4-tetrahydro-quinoline-6-carboxylic acid ethyl ester (6.6 g, quant.) as a light yellow oil which was used for next step without further purification: LC/MS m/e calcd for $C_{20}H_{23}NO_3$ (M+H)$^+$: 326.40, observed: 308.0.

To a mixture of 4-hydroxy-3,3-dimethyl-2-phenyl-1,2,3,4-tetrahydro-quinoline-6-carboxylic acid ethyl ester (6.5 g, 20.0 mmol) and triethylsilane (5.0 mL) at 25° C. was added trifluoroacetic acid (2.5 mL) dropwise. The resulting mixture was stirred at 25° C. for 4 h. Then the reaction mixture was concentrated in vacuo and the residue was extracted with ethyl acetate (2×200 mL), washed with saturated aqueous sodium bicarbonate solution (2×100 mL), dried over anhydrous sodium sulfate and concentrated in vacuo. The residue was triturated with methanol. The resulting precipitate was collected, dried in vacuo to afford 3,3-dimethyl-2-phenyl-1,2,3,4-tetrahydro-quinoline-6-carboxylic acid ethyl ester (1.5 g, 24%) as a white solid: LC/MS m/e calcd for $C_{20}H_{23}NO_2$ (M+H)$^+$: 310.40, observed: 310.1.

To a stirred mixture solution of 3,3-dimethyl-2-phenyl-1,2,3,4-tetrahydro-quinoline-6-carboxylic acid ethyl ester (230 mg, 0.75 mmol) in methanol (2.5 mL) and tetrahydrofuran (3.0 mL) was added 50% sodium hydroxide in water (2.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 3,3-dimethyl-2-phenyl-1,2,3,4-tetrahydro-quinoline-6-carboxylic acid (190 mg, 90%) as a white solid: LC/MS m/e calcd for $C_{18}H_{19}NO_2$ (M+H)$^+$: 282.35, observed: 282.1.

Example 159

2-(4'-Isopropylcarbamoyl-biphenyl-3-yl)-3,3-dimethyl-1,2,3,4-tetrahydro-quinoline-6-carboxylic acid

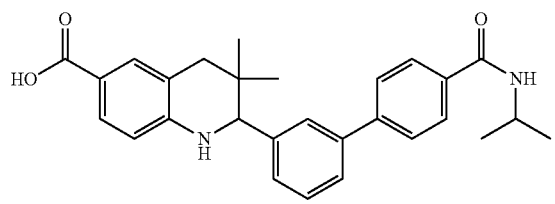 [SMILES: CC(C)NC(=O)c1ccc(-c2cccc(C3Nc4ccc(C(=O)O)cc4CC3(C)C)c2)cc1]

To a mixture of 2-(3-bromo-phenyl)-3,3-dimethyl-1,2,3,4-tetrahydro-quinoline-6-carboxylic acid ethyl ester (4.0 g, 10.3 mmol), 4-carboxyphenylboronic acid (2.5 g, 15.4 mmol)

and tetrakis(triphenylphosphine)palladium(0) (1.2 g, 1.1 mmol) in dioxane (10 mL) was added 2 M sodium carbonate solution in water (10 mL, 20 mmol). The resulting mixture was subjected to microwave irradiation for 60 min at 110° C. The mixture was diluted with ethyl acetate (150 mL), washed with saturated aqueous sodium bicarbonate solution (30 mL×2), brine, dried over anhydrous sodium sulfate and then concentrated in vacuo. Purification by flash silica gel chromatography (silica gel from QingDao, 200-300 mesh, glass column from Shanghai SD company) (10% ethyl acetate/hexanes) afforded 2-(4'-carboxy-biphenyl-3-yl)-3,3-dimethyl-1,2,3,4-tetrahydro-quinoline-6-carboxylic acid ethyl ester (3.4 g, 80%) as a white solid: LC/MS m/e calcd for $C_{27}H_{27}NO_4$ (M+H)+: 430.52, observed: 430.1.

To a stirred solution of 2-(4'-carboxy-biphenyl-3-yl)-3,3-dimethyl-1,2,3,4-tetrahydro-quinoline-6-carboxylic acid ethyl ester (860 mg, 2 mmol), 2-(1H-7-azabenzotriazol-1-yl)-1,1,3,3-tetramethyl uronium hexafluorophosphate methanaminium (HATU) (1.2 g, 3 mmol) and triethyl amine (0.86 mL, 6 mmol) in dichloromethane was added isopropylamine (0.66 mL, 8 mmol) at room temperature and stirred at room temperature for overnight. Then the reaction mixture was concentrated in vacuo and the residue was extracted with ethyl acetate (2×200 mL), washed with brine, dried over anhydrous sodium sulfate and concentrated in vacuo to afford 2-(4'-isopropylcarbamoyl-biphenyl-3-yl)-3,3-dimethyl-1,2,3,4-tetrahydro-quinoline-6-carboxylic acid ethyl ester (940 mg, quant.) as a light yellow solid which was used for next step without further purification: LC/MS m/e calcd for $C_{30}H_{34}N_2O_3$ (M+H)+: 471.62, observed: 471.2.

To a stirred mixture solution of 2-(4'-isopropylcarbamoyl-biphenyl-3-yl)-3,3-dimethyl-1,2,3,4-tetrahydro-quinoline-6-carboxylic acid ethyl ester (940 mg, 2 mmol) in methanol (15.0 mL) and tetrahydrofuran (16.0 mL) was added 50% sodium hydroxide in water (2.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-(4'-isopropylcarbamoyl-biphenyl-3-yl)-3,3-dimethyl-1,2,3,4-tetrahydro-quinoline-6-carboxylic acid (795 mg, 90%) as a white solid: LC/MS m/e calcd for $C_{28}H_{30}N_2O_3$ (M+H)+: 443.56, observed: 443.1.

Example 160

3'-(6-Methanesulfonylaminocarbonyl-3,3-dimethyl-1,2,3,4-tetrahydro-quinolin-2-yl)-biphenyl-4-carboxylic acid tert-butylamide

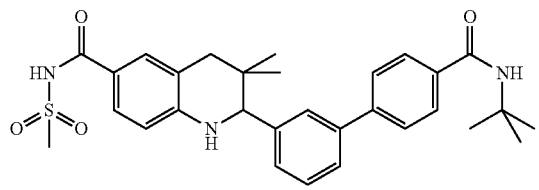 [SMILES: CC(C)(C)NC(=O)c1ccc(-c2cccc(C3Nc4ccc(C(=O)NS(C)(=O)=O)cc4CC3(C)C)c2)cc1]

To a suspension of 60% sodium hydride (87 mg, 2.1 mmol) in N,N-dimethylformamide (1.5 mL) was added methanesulfonamide (210 mg, 2.2 mmol) at room temperature. The resulting mixture was stirred at 25° C. for 1 h. A solution of 2-(4'-tert-butylcarbamoyl-biphenyl-3-yl)-3,3-dimethyl-1,2,3,4-tetrahydro-quinoline-6-carboxylic acid (100 mg, 0.22 mmol) and 1,1'-carbonyldiimidazole (72 mg, 0.44 mmol) in N,N-dimethylformamide (2.0 mL) was stirred at 70° C. After stirring at 70° C. for 1 h, the above suspension of methanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 3'-(6-methanesulfonylaminocarbonyl-3,3-dimethyl-1,2,3,4-tetrahydro-quinolin-2-yl)-biphenyl-4-carboxylic acid tert-butylamide (23 mg, 20%) as a white solid: LC/MS m/e calcd for $C_{30}H_{35}N_3O_4S$ (M+H)+: 534.70, observed: 534.1.

Example 161

Cyclopropanesulfonic acid [2-(4'-methanesulfonyl-biphenyl-3-yl)-3,3-dimethyl-1,2,3,4-tetrahydro-quinoline-6-carbonyl]-amide

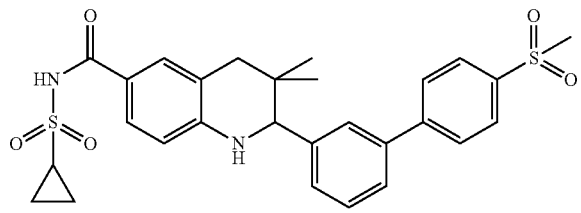 [SMILES: CC1(C)Cc2cc(C(=O)NS(=O)(=O)C3CC3)ccc2NC1c1cccc(-c2ccc(S(C)(=O)=O)cc2)c1]

To a mixture of 2-(3-bromo-phenyl)-3,3-dimethyl-1,2,3,4-tetrahydro-quinoline-6-carboxylic acid (720 mg, 2.0 mmol), 4-(methanesulfonyl)phenylboronic acid (600 mg, 3.0 mmol) and tetrakis(triphenylphosphine)palladium(0) (347 mg, 0.3 mmol) in dioxane (6 mL) was added 2 M sodium carbonate solution in water (4 mL, 8 mmol). The resulting mixture was subjected to microwave irradiation for 60 min at 110° C. The mixture was diluted with ethyl acetate (150 mL), washed with saturated aqueous sodium bicarbonate solution (30 mL×2), brine, dried over anhydrous sodium sulfate and then concentrated in vacuo. Purification by flash silica gel chromatography (silica gel from QingDao, 200-300 mesh, glass column from Shanghai SD company) (10% ethyl acetate/hexanes) afforded 2-(4'-methanesulfonyl-biphenyl-3-yl)-3,3-dimethyl-1,2,3,4-tetrahydro-quinoline-6-carboxylic acid (696 mg, 80%) as a white solid: LC/MS m/e calcd for $C_{25}H_{25}NO_4S$ (M+H)+: 436.55, observed: 436.1.

To a suspension of 60% sodium hydride (91 mg, 2.2 mmol) in N,N-dimethylformamide (1.5 mL) was added cyclopropanesulfonamide (278 mg, 2.3 mmol) at room temperature. The resulting mixture was stirred at 25° C. for 1 h. A solution of 2-(4'-methanesulfonyl-biphenyl-3-yl)-3,3-dimethyl-1,2,3,4-tetrahydro-quinoline-6-carboxylic acid (100 mg, 0.23 mmol) and 1,1'-carbonyldiimidazole (75 mg, 0.46 mmol) in N,N-dimethylformamide (2.0 mL) was stirred at 70° C. After stirring at 70° C. for 1 h, the above suspension of cyclopropanesulfonamide and sodium hydride in N,N-dimethylformamide was added and the mixture was allowed to stir at 25° C. for 1 h. Purification by Waters automated flash system (column: Xterra 30 mm×100 mm, sample manager 2767, pump 2525, detector: ZQ mass and UV 2487, solvent system:

acetonitrile and 0.1% ammonium hydroxide in water) afforded cyclopropanesulfonic acid [2-(4'-methanesulfonyl-biphenyl-3-yl)-3,3-dimethyl-1,2,3,4-tetrahydro-quinoline-6-carbonyl]-amide (25 mg, 20%) as a white solid: LC/MS m/e calcd for $C_{28}H_{30}N_2O_5S_2$ (M+H)$^+$: 539.69, observed: 539.1.

Example 162

2-(4'-tert-Butylcarbamoyl-biphenyl-3-yl)-3,3-dimethyl-1,2,3,4-tetrahydro-quinoline-6-carboxylic acid

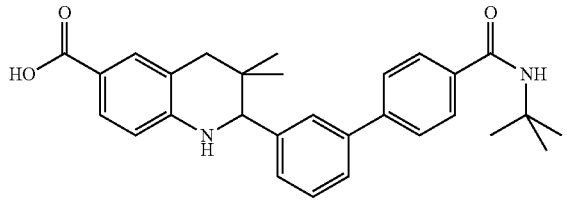 [SMILES: CC(C)(C)NC(=O)c1ccc(-c2cccc(C3Nc4ccc(C(=O)O)cc4CC3(C)C)c2)cc1]

To a stirred solution of 2-(4'-carboxy-biphenyl-3-yl)-3,3-dimethyl-1,2,3,4-tetrahydro-quinoline-6-carboxylic acid ethyl ester (860 mg, 2 mmol), 2-(1H-7-azabenzotriazol-1-yl)-1,1,3,3-tetramethyl uronium hexafluorophosphate methanaminium (HATU) (1.2 g, 3 mmol) and triethyl amine (0.86 mL, 6 mmol) in dichloromethane was added tert-butylamine (0.86 mL, 8 mmol) at room temperature and stirred at room temperature for overnight. Then the reaction mixture was concentrated in vacuo and the residue was extracted with ethyl acetate (2×200 mL), washed with brine, dried over anhydrous sodium sulfate and concentrated in vacuo to afford 2-(4'-tert-butylcarbamoyl-biphenyl-3-yl)-3,3-dimethyl-1,2,3,4-tetrahydro-quinoline-6-carboxylic acid ethyl ester (968 mg, quant.) as a light yellow solid which was used for next step without further purification: LC/MS m/e calcd for $C_{31}H_{36}N_2O_3$ (M+H)$^+$: 485.62, observed: 485.2.

To a stirred mixture solution of 2-(4'-tert-butylcarbamoyl-biphenyl-3-yl)-3,3-dimethyl-1,2,3,4-tetrahydro-quinoline-6-carboxylic acid ethyl ester (968 mg, 2 mmol) in methanol (15.0 mL) and tetrahydrofuran (16.0 mL) was added 50% sodium hydroxide in water (2.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-(4'-tert-butylcarbamoyl-biphenyl-3-yl)-3,3-dimethyl-1,2,3,4-tet-rahydro-quinoline-6-carboxylic acid (820 mg, 90%) as a white solid: LC/MS m/e calcd for $C_{29}H_{32}N_2O_3$ (M+H)$^+$: 457.56, observed: 457.1.

Example 163

2-[2-(1-Carboxy-1-methyl-ethylamino)-phenyl]-3,3-dimethyl-1,2,3,4-tetrahydro-quinoline-6-carboxylic acid

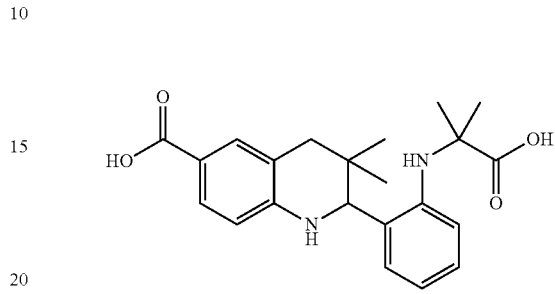

A mixture of 4-amino-benzoic acid ethyl ester (33 g, 200 mmol), 2-bromo-benzaldehyde (25.7 mL, 220 mmol) and p-toluenesulfonic acid (760 mg, 4 mmol) in toluene (600 mL) was heated to reflux for 12 h. Then the reaction mixture cooled to room temperature. The solvent was removed in vacuo and the residue was washed with ether to afford 4-[(2-bromo-benzylidene)-amino]-benzoc acid ethyl ester (34 g, 51%) as a light yellow solid: LC/MS m/e calcd for $C_{16}H_{14}BrNO_2$ (M+H)$^+$: 333.20, observed: 332.0 & 334.0.

To a mixture of 4-[(2-bromo-benzylidene)-amino]-benzoc acid ethyl ester (29 g, 87 mmol) and Ytterbium(III) triflate hydrate (5.4 g, 8.7 mmol) in dry tetrahydrofuran (200 mL) at 25° C. was added Isobutyraldehyde (8.8 mL, 96 mmol) and water (1.6 mL, 87 mmol) dropwise. The reaction mixture was stirred at 25° C. for 16 h. Then the reaction mixture was concentrated in vacuo and the residue was extracted with ethyl acetate (2×200 mL), washed with brine, dried over anhydrous sodium sulfate and concentrated in vacuo to afford 2-(2-bromo-phenyl)-4-hydroxy-3,3-dimethyl-1,2,3,4-tet-rahydro-quinoline-6-carboxylic acid ethyl ester (30 g, 85%) as a light yellow oil which was used for next step without further purification: LC/MS m/e calcd for $C_{20}H_{22}BrNO_3$ (M+H)$^+$: 405.31, observed: 386.0 & 388.0.

To a mixture of 2-(2-bromo-phenyl)-4-hydroxy-3,3-dimethyl-1,2,3,4-tetrahydro-quinoline-6-carboxylic acid ethyl ester (30 g, 74 mmol) and triethylsilane (50 mL) at 25° C. was added trifluoroacetic acid (15 mL) dropwise. The resulting mixture was stirred at 25° C. for 4 h. Then the reaction mixture was concentrated in vacuo and the residue was extracted with ethyl acetate (2×200 mL), washed with saturated aqueous sodium bicarbonate solution (2×100 mL), dried over anhydrous sodium sulfate and concentrated in vacuo. The residue was triturated with methanol. The resulting precipitate was collected, dried in vacuo to afford 2-(2-bromo-phenyl)-3,3-dimethyl-1,2,3,4-tetrahydro-quinoline-6-carboxylic acid ethyl ester (15 g, 78%) as a white solid: LC/MS m/e calcd for $C_{20}H_{22}BrNO_2$ (M+H)$^+$: 389.31, observed: 388.0 & 390.0.

To a stirred mixture solution of 2-(2-bromo-phenyl)-3,3-dimethyl-1,2,3,4-tetrahydro-quinoline-6-carboxylic acid ethyl ester (1.5 g, 3.8 mmol) in methanol (5.0 mL) and tetrahydrofuran (5.0 mL) was added 50% sodium hydroxide in water (1.0 mL). The reaction mixture was stirred at 70° C. for 6 hours. The mixture was neutralized with a 3 N aqueous hydrochloric acid solution and extracted with ethyl acetate (2×100 mL), washed with water, dried over anhydrous sodium sulfate and then concentrated in vacuo to afford 2-(2-bromo-phenyl)-3,3-dimethyl-1,2,3,4-tetrahydro-quinoline-6-carboxylic acid (1.3 g, 90%) as a light yellow solid: LC/MS m/e calcd for $C_{18}H_{18}BrNO_2$ $(M+H)^+$: 361.25, observed: 360.0 & 362.0.

A mixture of 2-(2-bromo-phenyl)-3,3-dimethyl-1,2,3,4-tetrahydro-quinoline-6-carboxylic acid (150 mg, 0.42 mmol), copper(I) iodide (24 mg, 0.13 mmol), 2-methylalanine (170 mg, 1.7 mmol), and potassium carbonate (174 mg, 1.26 mmol) in dimethyl sulfoxide (3 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[2-(1-carboxy-1-methyl-ethylamino)-phenyl]-3,3-dimethyl-1,2,3,4-tetrahydro-quinoline-6-carboxylic acid (128 mg, 80%) as a white solid: LC/MS m/e calcd for $C_{22}H_{26}N_2O_4$ $(M+H)^+$: 383.46, observed: 383.0.

Example 164

2-[2-(1-Carboxy-cyclopropylamino)-phenyl]-3,3-dimethyl-1,2,3,4-tetrahydro-quinoline-6-carboxylic acid

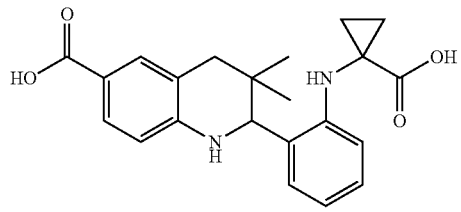 [SMILES: CC1(C)Cc2cc(C(=O)O)ccc2NC1c1ccccc1NC1(C(=O)O)CC1]

A mixture of 2-(2-bromo-phenyl)-3,3-dimethyl-1,2,3,4-tetrahydro-quinoline-6-carboxylic acid (150 mg, 0.42 mmol), copper(I) iodide (24 mg, 0.13 mmol), 1-amino-cyclopropane-1-carboxylate (170 mg, 1.7 mmol) and potassium carbonate (174 mg, 1.26 mmol) in dimethyl sulfoxide (3 mL) was stirred at 120° C. for 16 h. Then the reaction mixture cooled to room temperature. The reaction mixture was extracted with ethyl acetate (2×150 mL), washed with water (2×50 mL) and saturated aqueous ammonium chloride solution (2×50 mL), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[2-(1-carboxy-cyclopropylamino)-phenyl]-3,3-dimethyl-1,2,3,4-tetrahydro-quinoline-6-carboxylic acid (128 mg, 80%) as a white solid: LC/MS m/e calcd for $C_{22}H_{24}N_2O_4$ $(M+H)^+$: 381.46, observed: 381.1.

Example 165

3,3-Dimethyl-2-(3-(1-methylethylsulfonamido)phenyl)-1,2,3,4-tetrahydroquinoline-6-carboxylic acid

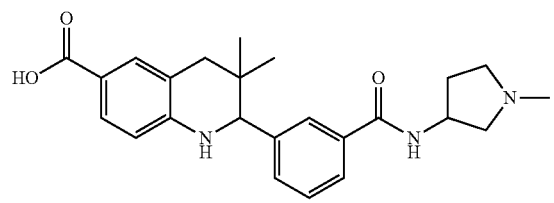 [SMILES: CN1CCC(NC(=O)c2cccc(C3Nc4ccc(C(=O)O)cc4CC3(C)C)c2)C1]

A mixture of methyl 3-formylbenzoate (6.15 g, 37.46 mmol) in methanol (61.5 mL) and 2 M sodium hydroxide aqueous solution (37.5 mL, 75 mmol) was stirred at r.t. for 1 h, Thin layer chromatography (Petroleum ether:ethyl acetate=1:1) showed the reaction was complete. The reaction mixture was acidified with 80 mL of 1 M hydrochloric acid aqueous solution to pH=2 and the resulting mixture was concentrated in vacuo. The residue was extracted with ethyl acetate for 3 times and the combined organic layers were washed with brine, dried over anhydrous sodium sulfate. Removal of the solvent in vacuo gave 5.59 g of 3-formylbenzoic acid as a white solid. Yield: 99.5%.

To a suspension of 3-formylbenzoic acid (8.15 g, 54.3 mmol, 1.0 eq.), 4-Dimethylaminopyridine (0.66 g, 5.43 mmol, 0.1 eq.) in dichloromethane (122.5 mL) was added dicyclohexylcarbodiimide (12.3 g, 59.71 mmol, 1.1 eq.) in dichloromethane (81.5 mL), which was placed in a drop funnel, at room temperature under nitrogen. Upon completion of addition, the resulting white suspension was stirred for an addition 1 h. Thin layer chromatography (Petroleum ether: ethyl acetate=2:1) showed the reaction was complete. The reaction mixture was cooled to 0° C. and filtered. The filtrate was washed with water, 10% glacial acetic acid/water aqueous solution (once) and water (4 times). The combined organic layers were dried over anhydrous sodium sulfate. The solvent was removed in vacuo and the residual was purified by column chromatography (petroleum ether: ethyl acetate=10:1) to give 10.63 g of benzyl 3-formylbenzoate as a colorless oil, yield: 81.5%.

To a solution of methyl 4-aminobenzoate (7.94 g, 52.5 mmol) in ethanol (100 mL) was added benzyl 3-formylbenzoate in ethanol (50 mL) and the resulting mixture was stirred at room temperature for 2 h. The white solid precipitated was collected by filtration and washed with ethanol, dried in vacuo (50° C.) to give 15.6 g of (E)-benzyl 3-((4-(methoxycarbonyl)phenylimino)methyl)benzoate as a white solid.

To a solution of (E)-benzyl 3-((4-(methoxycarbonyl)phenylimino)methyl)benzoate (15.0 g, 40.1 mmol, 1.0 eq.), yttrium(III) trifluoromethanesulfonate (0.5 g, 0.8 mmol, 0.02 eq.) in Tetrahydrofuran (85 mL) in a four-necked flask was added Isobutyl aldehyde (3.18 g, 44.2 mmol, 1.1 eq.) via syringe. The reaction mixture was stirred at room temperature under nitrogen overnight. Thin layer chromatography (Petroleum ether:ethyl acetate=6:1) showed the reaction was complete. The reaction mixture was washed with water and the aqueous layer was extracted with ethyl acetate (twice). The organic layers were washed with brine, dried over anhydrous sodium sulfate. The solvent was removed in vacuo and the residue was purified by column chromatography (Petroleum ether: ethyl acetate=5:1, then 2:1) to afford 14.2 g of methyl 2-(3-(benzyl oxycarbonyl)phenyl)-4-hydroxy-3,3-dimethyl-1,2,3,4-tetrahydroquinoline-6-carboxylate as a yellow solid, which was used in next step without further purification. Yield: 78.9%. MS (ESI+APCI) M−17=428.1.

To a solution of methyl 2-(3-(benzyloxycarbonyl)phenyl)-4-hydroxy-3,3-dimethyl-1,2,3,4-tetrahydroquinoline-6-carboxylate (14.0 g, 31.4 mmol, 1.0 eq.), triethylsilane (10.6 g, 91.4 mmol, 2.91 eq.) in dichloromethane (240 mL), which was placed in a drop funnel, under nitrogen below 0° C. over 1 h. colorless solution turned yellow gradually. The resulting mixture was allowed to warm back to room temperature naturally overnight. Thin layer chromatography (Petroleum ether: ethyl acetate=3:1) showed the reaction was complete. The reaction mixture was basified with solid sodium carbonate to pH=7 and filtered. The filtrate was concentrated in vacuo and the residue was purified by column chromatography (Petroleum ether: ethyl acetate=10:1) to give 10.2 g of methyl 2-(3-(benzyloxycarbonyl)phenyl)-3,3-dimethyl-1,2,3,4-tetrahydroquinoline-6-carboxylate as a yellow oil, yield: 75.6%. MS (ESI+APCI) M+1=430.2.

A mixture of methyl 2-(3-(benzyloxycarbonyl)-phenyl)-3,3-dimethyl-1,2,3,4-tetrahydroquinoline-6-carboxylate (10.2 g, 23.7 mmol, 1.0 eq.), 2.04 g Pd/C in methanol/tetrahydrofuran (V/V=1/1, 102 mL) was treated with H$_2$ at room temperature overnight. Thin layer chromatography (petroleum ether: ethyl acetate=3:1) showed the reaction was complete. The mixture was separated by filtration and the filtrate was concentrated in vacuo to give 7.35 g of 3-(6-(methoxycarbonyl)-3,3-dimethyl-1,2,3,4-tetrahydroquinolin-2-yl)benzoic acid as a white solid, yield: 91.2%. MS (ESI+APCI) M+1=340.1.

To a suspension of 3-(6-(methoxycarbonyl)-3,3-dimethyl-1,2,3,4-tetrahydroquinolin-2-yl)benzoic acid (150 mg, 0.44 mmol.) in dichloromethane (10 mL) was added N-hydroxybenzotriazole (89.2 mg, 0.66 mmol) and 1-(3-Dimethylaminopropyl)-3-Ethylcarbodiimide hydrochloride (253 mg, 1.32 mmol), followed by 4-methylmorpholine (133.5 mg, 1.32 mmol) and the resultant mixture was stirred at room temperature for 1 h. Then 1-methyl-pyrrolidin-3-amine (66.1 mg, 0.66 mmol) was added to the flask and the reaction mixture was stirred under nitrogen overnight. Thin layer chromatography (petroleum ether:ethyl acetate=1:1) and LC-MS showed the reaction was complete. The reaction was quenched with water and extracted with dichloromethane (twice). The combined organic layers were washed with 2% sodium hydroxide aqueous solution (twice) and water (3 times), dried over anhydrous sodium sulfate. Removal of the solvent in vacuo gave 224 mg white solid, which was dissolved in methanol and treated with sodium borohydride (24 mg, 0.63 mmol) for an additional 3 h. LC-MS showed the reaction was complete. The reaction was quenched with water and extracted with ethyl acetate/tetrahydrofuran, dried over anhydrous sodium sulfate. The solvent was removed under reduced pressure to afford 163 mg of methyl 3,3-dimethyl-2-(3-(1-methylpyrrolidin-3-ylcarbamoyl)phenyl)-1,2,3,4-tetrahydroquinoline-6-carboxylate as a white solid, which was pure enough for next step without further purification.

A mixture of methyl 3,3-dimethyl-2-(3-(1-methylpyrrolidin-3-ylcarbamoyl)phenyl)-1,2,3,4-tetrahydroquinoline-6-carboxylate (150 mg, 0.36 mmol) in methanol (6 mL) and 1N sodium hydroxide aqueous solution (5.3 mL, 5.3 mmol) was heated to reflux for 4 h, LC-MS showed the reaction was complete. The solvent was removed in vacuo and the residual was acidified with 1N hydrochloric acid solution to pH=6. The precipitated white solid was collected by filtration and washed with acetone, dichloromethane and ether sequentially to afford 78 mg of 3,3-dimethyl-2-(3-(1-methylpyrrolidin-3-ylcarbamoyl)phenyl)-1,2,3,4-tetrahydroquinoline-6-carboxylic acid as a white solid. Yield: 53.8%, LC-MS (M+1) =408.2.

Example 166

3,3-Dimethyl-2-(3-(1-methylethylsulfonamido)phenyl)-1,2,3,4-tetrahydroquinoline-6-carboxylic acid

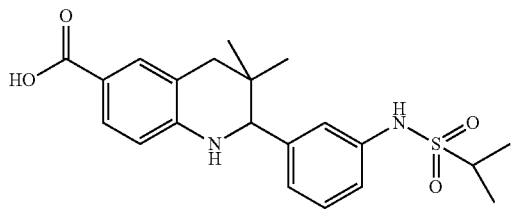 [SMILES: CC(C)S(=O)(=O)Nc1cccc(C2Nc3ccc(C(=O)O)cc3CC2(C)C)c1]

Methyl 2-(3-aminophenyl)-3,3-dimethyl-1,2,3,4-tetrahydroquinoline-6-carboxylate (100 mg, 0.32 mmol) and sodium hydroxide (0.2 g, 5 mmol) was dissolved in methanol/water (10 mL/2 mL) and the reaction mixture was allowed to reflux for 1.5 h. Thin layer chromatography (petroleum ether: ethyl acetate=3:1, Rf=0.1) showed the reaction was complete. The solvent was removed in vacuo and the residue was acidified with 1 M hydrochloric acid solution to pH=6. The precipitated off-white solid was collected by filtration and dissolved in 50 ml of acetone, dried over sodium sulfate. Filtered and concentrated, the residue was recrystallization from dichloromethane/hexane to afford 78 mg of 2-(3-aminophenyl)-3,3-dimethyl-1,2,3,4-tetrahydroquinoline-6-carboxylic acid, Yield: 82.1%, MS (ES+APCI) M+1=297.1.

2-(3-Aminophenyl)-3,3-dimethyl-1,2,3,4-tetrahydroquinoline-6-carboxylic acid (100 mg, 0.34 mmol) was dissolved in 2 mL of dry pyridine under nitrogen. Then propane-2-sulfonyl chloride (0.1 mL, 0.89 mmol) was added drop wise to the reaction mixture. The reaction mixture was allowed to stir overnight. Thin layer chromatography (petroleum ether: ethyl acetate=1:1, Rf=0.5) showed the reaction was complete. Pyridine was removed in vacuo and the residue was purified by column chromatography (petroleum ether:ethyl acetate=1:1) to afford 50 mg of 3,3-dimethyl-2-(3-(1-methylethylsulfonamido)phenyl)-1,2,3,4-tetrahydroquinoline-6-carboxylic acid. Yield: 36.8%. MS (ES+APCI) M+1=403.1.

Example 167

3,3-Dimethyl-2-(3-(tetrahydrofuran-3-ylcarbamoyl)phenyl)-1,2,3,4-tetrahydroquinoline-6-carboxylic acid

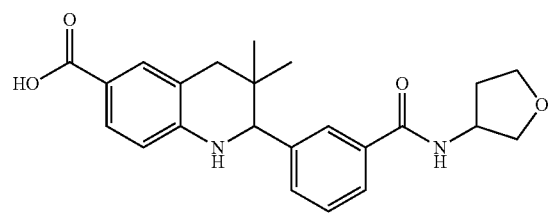 [SMILES: CC1(C)Cc2cc(C(=O)O)ccc2NC1c1cccc(C(=O)NC2CCOC2)c1]

To a suspension of 3-(6-(methoxycarbonyl)-3,3-dimethyl-1,2,3,4-tetrahydroquinolin-2-yl)benzoic acid (150 mg, 0.44 mmol.) in dichloromethane (10 mL) was added N-hydroxybenzotriazole (89.2 mg, 0.66 mmol) and 1-(3-dimethylaminopropyl)-3-ethylcarbodiimide.hydrochloric acid (253 mg, 1.32 mmol.), followed by 4-methylmorpholine (133.5 mg, 1.32 mmol) and the resultant mixture was stirred at room temperature for 1 h. Then tetrahydrofuran-3-amine (57.5 mg, 0.66 mmol) was added to the flask and the reaction mixture was stirred under nitrogen overnight. Thin layer chromatography (petroleum ether:ethyl acetate=1:1) and LC-MS showed the reaction was complete. The reaction was quenched with water and extracted with dichloromethane (twice). The combined organic layers were washed with 2% sodium hydroxide aqueous solution (twice) and water (3 times), dried over anhydrous sodium sulfate. Removal of the solvent in vacuo gave 236 mg methyl 3,3-dimethyl-2-(3-(tetrahydrofuran-3-ylcarbamoyl)phenyl)-1,2,3,4-tetrahydroquinoline-6-carboxylate of as a white solid, which was dissolved in methanol and treated with sodium borohydride (24 mg, 0.63 mmol) for an additional 2 h. LC-MS showed the reaction was complete. The reaction was quenched with water and extracted with ethyl acetate/tetrahydrofuran, dried over anhydrous sodium sulfate. The solvent was removed under reduced pressure to afford 192 mg of desired product as a white solid, which was pure enough for next step without further purification.

A mixture of methyl 3,3-dimethyl-2-(3-(tetrahydrofuran-3-ylcarbamoyl)phenyl)-1,2,3,4-tetrahydroquinoline-6-carboxylate (185 mg, 0.44 mmol) in methanol (7.4 mL) and 1N sodium hydroxide aqueous solution (6.6 mL, 6.6 mmol) was heated to reflux for 1 h, LC-MS showed the reaction was complete. The solvent was removed in vacuo and the residue was acidified with 1N hydrochloric acid solution to pH=6. The precipitated white solid was collected by filtration and washed with dichloromethane/ether to afford 125 mg of 3,3-dimethyl-2-(3-(tetrahydrofuran-3-ylcarbamoyl)phenyl)-1,2,3,4-tetrahydroquinoline-6-carboxylic acid as a white solid. Yield: 70%. LC-MS (M+1)=395.2.

Example 168

3,3-Dimethyl-2-(4-(phenylsulfonamido)phenyl)-1,2,3,4-tetrahydroquinoline-6-carboxylic acid

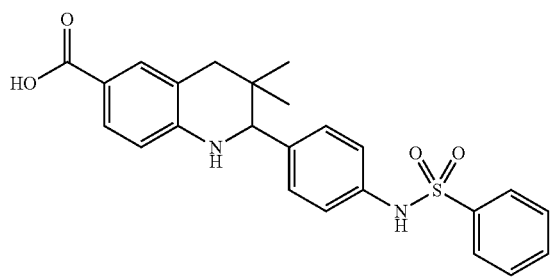 [SMILES: CC1(C)Cc2cc(C(=O)O)ccc2NC1c1ccc(NS(=O)(=O)c2ccccc2)cc1]

To a mixture of methyl 2-(4-aminophenyl)-3,3-dimethyl-1,2,3,4-tetrahydroquinoline-6-carboxy late (500 mg, 1.61 mmol) in methanol (10 mL) and water (5 mL) was added a solution of sodium hydroxide (1100 mg, 27.4 mmol) in water (15 mL). The resultant mixture was heated for reflux until the complete of the reaction (monitored by thin layer chromatography). The methanol was removed under vacuum. The residue was acidified with 2 M hydrochloric acid to pH=1. The precipitates were collected by filtration to afford 2-(4-aminophenyl)-3,3-dimethyl-1,2,3,4-tetrahydroquinoline-6-carboxylic acid as a yellow solid, 430 mg, Yield 94%.

To a solution of 2-(4-aminophenyl)-3,3-dimethyl-1,2,3,4-tetrahydroquinoline-6-carboxylic acid (100 mg, 0.34 mmol) in pyridine (5 mL) was added benzenesulfonyl chloride (0.05 mL, 0.38 mmol) via syringe with ice cooling. Upon completion of the addition, the resultant mixture was allowed to warm back to room temperature and stir for 24 h. LC-MS showed the reaction was complete. Pyridine was removed in vacuo and the residue was purified by preparative thin layer chromatography to afford 81 mg of 3,3-dimethyl-2-(4-(phenylsulfonamido)phenyl)-1,2,3,4-tetrahydroquinoline-6-carboxylic acid as a white solid. Yield: 65%; MS (ESI+APCI) M+1=437.54.

Example 169

2-(3-(4-Acetamidophenylsulfonamido)phenyl)-3,3-dimethyl-1,2,3,4-tetrahydroquinoline-6-carboxylic acid

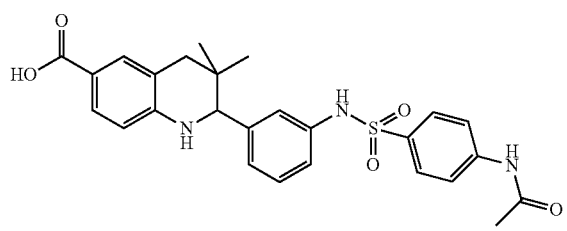 [SMILES: CC(=O)Nc1ccc(S(=O)(=O)Nc2cccc(C3Nc4ccc(C(=O)O)cc4CC3(C)C)c2)cc1]

2-(3-aminophenyl)-3,3-dimethyl-1,2,3,4-tetrahydroquinoline-6-carboxylic acid (100 mg, 0.34 mmol) was dissolved in 2 mL of dry pyridine under nitrogen. Then 4-acetamid obenzene-1-sulfonyl chloride (209 mg, 0.85 mmol) was added drop wise to the reaction mixture. The reaction mixture was allowed to stir for 20 h. Thin layer chromatography (petroleum ether:ethyl acetate=1:1, Rf=0.5) showed the reaction was complete. Pyridine was removed in vacuo and the residue was purified by column chromatography (petroleum ether:ethyl acetate=1:1) to afford 85 mg of 2-(3-(4-acetamidophenylsulfonamido)phenyl)-3,3-dimethyl-1,2,3,4-tetrahydroquinoline-6-carboxylic acid. Yield: 51%. MS (ES+APCI) M+1=494.2.

Example 170

2-(3-(Cyclopropylcarbamoyl)phenyl)-3,3-dimethyl-1,2,3,4-tetrahydroquinoline-6-carboxylic acid

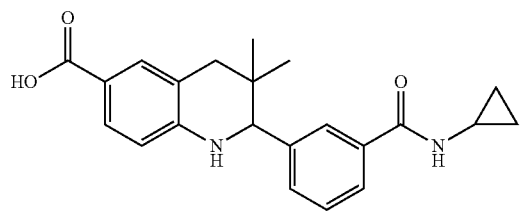 [SMILES: CC1(C)Cc2cc(C(=O)O)ccc2NC1c1cccc(C(=O)NC2CC2)c1]

To a suspension of 3-(6-(methoxycarbonyl)-3,3-dimethyl-1,2,3,4-tetrahydroquinolin-2-yl)benzoic acid (150 mg, 0.44 mmol.) in dichloromethane (10 mL) was added N-hydroxybenzotriazole (89.2 mg, 0.66 mmol) and 1-(3-dimethylaminopropyl)-3-ethylcarbodiimide.hydrochloric acid (253 mg, 1.32 mmol.), followed by 4-methylmorpholine (133.5 mg, 1.32 mmol) and the resultant mixture was stirred at room temperature for 1 h. Then cyclopropanamine (57.5 mg, 0.66 mmol) was added to the flask and the reaction mixture was stirred under nitrogen overnight. Thin layer chromatography (petroleum ether:ethyl acetate=1:1) and LC-MS showed the reaction was complete. The reaction was quenched with water and extracted with dichloromethane (twice). The combined organic layers were washed with 2% sodium hydroxide aqueous solution (twice) and water (3 times), dried over anhydrous sodium sulfate. Removal of the solvent in vacuo gave yellow oil, which was purified by recrystallization from dichloromethane/Hexane/Ether to afford 118 mg of methyl 2-(3-(cyclopropylcarbamoyl)phenyl)-3,3-dimethyl-1,2,3,4-tetrahydroquinoline-6-carboxylate as a white crystal. Yield: 70.5%.

A mixture of methyl 2-(3-(cyclopropylcarbamoyl)phenyl)-3,3-dimethyl-1,2,3,4-tetrahydroquinoline-6-carboxylate (115 mg, 0.30 mmol) in methanol (4.6 mL) and 1N sodium hydroxide aqueous solution (4.5 mL, 4.5 mmol) was heated to reflux for 1.5 h, LC-MS showed the reaction was complete. The solvent was removed in vacuo and the residual was acidified with 1N hydrochloric acid solution to pH=6, extracted with ethyl acetate/tetrahydrofuran. The combined organic layers were washed with brine and dried over anhydrous sodium sulfate. Removal of the solvent in vacuo gave 110 mg of white solid, which was washed with dichloromethane to afford 70 mg of 2-(3-(cyclopropylcarbamoyl)phenyl)-3,3-dimethyl-1,2,3,4-tetrahydroquinoline-6-carboxylic acid as a white powder. Yield: 63.2%. LC-MS (M+1)=365.2.

Example 171

3,3-Dimethyl-2-(3-(pyrrolidine-1-carbonyl)phenyl)-1,2,3,4-tetrahydroquinoline-6-carboxylic acid

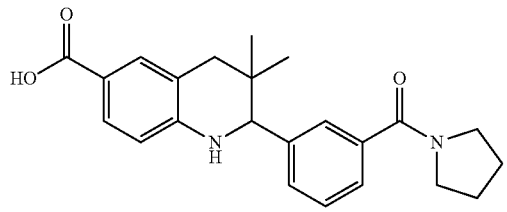 [SMILES: CC1(C)Cc2cc(C(=O)O)ccc2NC1c1cccc(C(=O)N2CCCC2)c1]

To a suspension of 3-(6-(methoxycarbonyl)-3,3-dimethyl-1,2,3,4-tetrahydroquinolin-2-yl)benzoic acid (150 mg, 0.44 mmol.) in dichloromethane (10 mL) was added N-hydroxybenzotriazole (89.2 mg, 0.66 mmol) and 1-(3-dimethylaminopropyl)-3-ethylcarbodiimide.hydrochloric acid (253 mg, 1.32 mmol.), followed by 4-methylmorpholine (133.5 mg, 1.32 mmol) and the resultant mixture was stirred at room temperature for 1 h. Then pyrrolidine (46.9 mg, 0.66 mmol) was added to the flask and the reaction mixture was stirred under nitrogen overnight. Thin layer chromatography (petroleum ether:ethyl acetate=1:1) and LC-MS showed the reaction was complete. The reaction was quenched with water and extracted with dichloromethane (twice). The combined organic layers were washed with 2% sodium hydroxide aqueous solution (twice) and water (3 times), dried over anhydrous sodium sulfate. Removal of the solvent in vacuo gave 196 mg yellow oil, which was dissolved in methanol (3 mL) and treated with sodium borohydride (24 mg, 0.63 mmol) for an additional 3 h. LC-MS showed the reaction was complete. The reaction was quenched with water and extracted with ethyl acetate/tetrahydrofuran, dried over anhydrous sodium sulfate. The solvent was removed under reduced pressure to afford 153 mg of white solid, which was recrystallized from dichloromethane/Hexane/Ether to give 125 mg of methyl-3,3-dimethyl-2-(3-(pyrrolidine-1-carbonyl)phenyl)-1,2,3,4-tetrahydroquinoline-6-carboxylate. Yield: 69.4%.MS (ESI+APCI) M+1=393.2.

A mixture of methyl 3,3-dimethyl-2-(3-(pyrrolidine-1-carbonyl)-phenyl)-1,2,3,4-tetrahydroquinoline-6-carboxylate (120 mg, 0.31 mmol) in methanol (4.8 mL) and 1N sodium hydroxide aqueous solution (4.58 mL, 4.58 mmol) was heated to reflux for 2 h, LC-MS showed the reaction was complete. The solvent was removed in vacuo and the residual was acidified with 1N hydrochloric acid solution to pH=6. The precipitated white solid was collected by filtration and washed with dichloromethane to afford 70 mg of 3,3-dimethyl-2-(3-(pyrrolidine-1-carbonyl)-phenyl)-1,2,3,4-tetrahydroquinoline-6-carboxylic acid as a white powder. Yield: 60.5%. LC-MS (M+1)=379.2.

Example 172

2-(3-(Cyclobutylcarbamoyl)phenyl)-3,3-dimethyl-1,2,3,4-tetrahydroquinoline-6-carboxylic acid

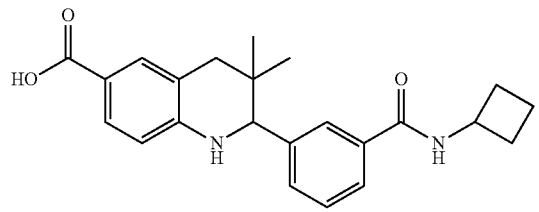 [SMILES: CC1(C)Cc2cc(C(=O)O)ccc2NC1c1cccc(C(=O)NC2CCC2)c1]

To a suspension of 3-(6-(methoxycarbonyl)-3,3-dimethyl-1,2,3,4-tetrahydroquinolin-2-yl)benzoic acid (150 mg, 0.44 mmol.) in dichloromethane (10 mL) was added N-hydroxybenzotriazole (89.2 mg, 0.66 mmol) and 1-(3-dimethylaminopropyl)-3-ethylcarbodiimide.hydrochloric acid (253 mg, 1.32 mmol.), followed by 4-methylmorpholine (133.5 mg, 1.32 mmol) and the resultant mixture was stirred at room temperature for 1 h. Then cyclobutanamine (47 mg, 0.66 mmol) was added to the flask and the reaction mixture was stirred under nitrogen overnight. Thin layer chromatography (petroleum ether:ethyl acetate=1:1) and LC-MS showed the reaction was complete. The reaction was quenched with water and extracted with dichloromethane (twice). The combined organic layers were washed with 2% sodium hydroxide aqueous solution (twice) and water (3 times), dried over anhydrous sodium sulfate. Removal of the solvent in vacuo gave 290 mg of yellow oil, which was dissolved in methanol (3 mL) and treated with sodium borohydride (24 mg, 0.63 mmol) for an additional 3 h. LC-MS showed the reaction was complete. The reaction was quenched with water and extracted with ethyl acetate/tetrahydrofuran, dried over anhydrous sodium sulfate. The solvent was removed under reduced pressure to afford 186 mg of methyl-2-(3-(cyclobutylcarbamoyl)phenyl)-3,3-dimethyl-1,2,3,4-tetrahydroquinoline-6-carboxylate, which was used in next step without further purification. Yield: quantitative. MS (ESI+APCI) M+1=393.2, 2M+1=785.3.

A mixture of methyl 2-(3-(cyclobutylcarbamoyl)phenyl)-3,3-dimethyl-1,2,3,4-tetrahydroquinoline-6-carboxylate (173 mg, 0.44 mmol) in methanol (6.9 mL) and 1N sodium hydroxide aqueous solution (8.8 mL, 8.8 mmol) was heated to reflux for 2 h, LC-MS showed the reaction was complete. The solvent was removed in vacuo and the residual was acidified with 1N hydrochloric acid solution to pH=6, extracted with ethyl acetate/tetrahydrofuran. The combined organic layers were washed with brine and dried over anhydrous sodium sulfate. Removal of the solvent in vacuo gave 159 mg of white solid, which was washed with dichloromethane/Ether to afford 85 mg of 2-(3-(cyclobutylcarbamoyl)phenyl)-3,3-dimethyl-1,2,3,4-tetrahydroquinoline-6-carboxylic acid as a white powder. MS (ESI+APCI) M+1=379.2.

Example 173

2-(3-(Isopropylcarbamoyl)phenyl)-3,3-dimethyl-1,2,3,4-tetrahydroquinoline-6-carboxylic acid

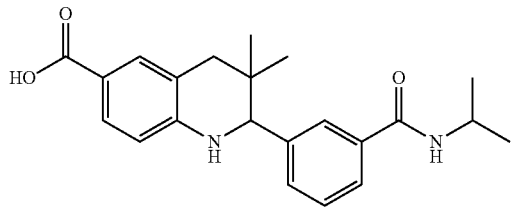 [SMILES: CC(C)NC(=O)c1cccc(C2Nc3ccc(C(=O)O)cc3CC2(C)C)c1]

To a suspension of 3-(6-(methoxycarbonyl)-3,3-dimethyl-1,2,3,4-tetrahydroquinolin-2-yl)-benzoic acid (150 mg, 0.44 mmol.) in dichloromethane (10 mL) was added N-hydroxybenzotriazole (89.2 mg, 0.66 mmol) and 1-(3-dimethylaminopropyl)-3-ethyl-carbodiimide.hydrochloric acid (253 mg, 1.32 mmol.), followed by 4-methylmorpholine (133.5 mg, 1.32 mmol) and the resultant mixture was stirred at room temperature for 1 h. Then propan-2-amine (39 mg, 0.66 mmol) was added to the flask and the reaction mixture was stirred under nitrogen overnight. Thin layer chromatography (petroleum ether:ethyl acetate=3:1) and LC-MS showed the reaction was complete. The reaction was quenched with water and extracted with dichloromethane (twice). The combined organic layers were washed with 2% sodium hydroxide aqueous solution (twice) and water (3 times), dried over anhydrous sodium sulfate. Removal of the solvent in vacuo gave 230 mg of yellow oil, which was dissolved in methanol (3 mL) and treated with sodium borohydride (23 mg, 0.6 mmol) for an additional 1 h. LC-MS showed the reaction was complete. The reaction was quenched with water and extracted with ethyl acetate, dried over anhydrous sodium sulfate. The solvent was removed under reduced pressure to afford 175 mg of white solid, which was recrystallized from Ether/hexane to afford 137 mg of methyl 2-(3-(isopropylcarbamoyl)phenyl)-3,3-dimethyl-1,2,3,4-tetrahydroquinoline-6-carboxylate as a white crystal. Yield: 81.4% (2 steps). MS (ESI+APCI) M+1=381.2.

A mixture of methyl 2-(3-(isopropylcarbamoyl)phenyl)-3,3-dimethyl-1,2,3,4-tetrahydroquinoline-6-carboxylate (120 mg, 0.315 mmol) in methanol (4.8 mL) and 2N sodium hydroxide aqueous solution (3.2 mL, 6.4 mmol) was heated to reflux for 2 h. Thin layer chromatography (petroleum ether: ethyl acetate=3:1) and LC-MS showed the reaction was complete. The solvent was removed in vacuo to give white solid, which was dissolved in water and acidified with 1N hydrochloric acid solution to pH=6, extracted with ethyl acetate/tetrahydrofuran, washed with brine and dried over anhydrous sodium sulfate. Removal of the solvent in vacuo gave 92 mg of 2-(3-(isopropylcarbamoyl)phenyl)-3,3-dimethyl-1,2,3,4-tetrahydroquinoline-6-carboxylic acid as a white solid. Yield: 80%. LC-MS (M+1)=367.2.

Example 174

2-(4-Fluoro-3-isobutyramidophenyl)-3,3-dimethyl-1,2,3,4-tetrahydroquinoline-6-carboxylic acid

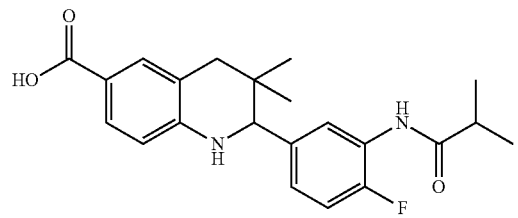 [SMILES: CC(C)C(=O)Nc1cc(C2Nc3ccc(C(=O)O)cc3CC2(C)C)ccc1F]

To a solution of methyl 2-(4-fluoro-3-nitrophenyl)-3,3-dimethyl-1,2,3,4-tetrahydroquinoline-6-carboxylate (150 mg, 0.46 mmol) and N,N-diisopropylethylamine (0.15 mL, 0.91 mmol) in dichloromethane (10 mL) was added isobutyryl chloride (0.053 mL, 0.50 mmol) via syringe with ice cooling. The resultant mixture was stirred for an additional 20 h. The solvent was removed in vacuo and the residue was purified by column chromatography (petroleum ether:ethyl acetate=3:1) to afford 183 mg of methyl-2-(4-fluoro-3-isobutyramidophenyl)-3,3-dimethyl-1,2,3,4-tetrahydroquinoline-6-carboxylate. Yield: 97%.

A mixture of methyl-2-(4-fluoro-3-isobutyramidophenyl)-3,3-dimethyl-1,2,3,4-tetrahydroquinoline-6-carboxylate (183 mg, 0.46 mmol), sodium hydroxide (312 mg, 7.8 mmol) in methanol/water (10 mL/4 mL) was heated to reflux for 1.5 h. LC-MS indicated that the starting material was consumed completely. The solvent was removed in vacuo and the residue was acidified with 2M hydrochloric acid solution to Ph=5. The precipitated white solid was collected by filtration and dissolved in acetone, dried over anhydrous magnesium sulfate. The solvent was removed in vacuo to give 2-(4-fluoro-3-isobutyramidophenyl)-3,3-dimethyl-1,2,3,4-tetrahydroquinoline-6-carboxylic acid, which was purified by recrystallization from dichloromethane/methanol/Hexant to afford 140 mg of off-white crystal. Yield: 79.3%. LC-MS (M+1)=385.

Example 175

3,3-Dimethyl-2-(3-(phenylsulfonylcarbamoyl)phenyl)-1,2,3,4-tetrahydroquinoline-6-carboxylic acid

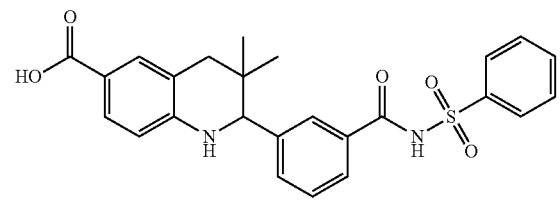 [SMILES: CC1(C)Cc2cc(C(=O)O)ccc2NC1c1cccc(C(=O)NS(=O)(=O)c2ccccc2)c1]

A solution of 3-(6-(methoxycarbonyl)-3,3-dimethyl-1,2,3,4-tetrahydroquinolin-2-yl)-benzoic acid (150 mg, 0.44 mmol, 1.0 eq.) and 1,1'-carbonyldiimidazole (214 mg, 1.32 mmol, 3.0 eq.) in tetrahydrofuran (3 mL) was heated to 60° C. for 2 h, then was cooled to room temperature and treated with benzenesulfonamide (89.6 mg, 0.57 mmol, 1.3 eq.). After stirring for 10 min, the reaction mixture was treated with dropwise addition of a solution of 1,8-diazabicyclo[5.4.0]undec-7-ene (221 mg, 1.45 mmol, 3.3 eq.) in tetrahydrofuran (1 mL). Upon completion of addition, the resultant mixture was stirred overnight. Thin layer chromatography (petroleum ether:ethyl acetate=1:1) showed the reaction was complete. The reaction mixture was quenched with brine and acidified with 1N hydrochloric acid solution to pH=6, extracted with ethyl acetate (twice). The combined organic layers were washed with brine for 3 times, dried over anhydrous magnesium sulfate. Removal of the solvent in vacuo gave 252 mg of methyl 3,3-dimethyl-2-(3-(phenylsulfonylcarbamoyl)phenyl)-1,2,3,4-tetrahydroquinoline-6-carboxylate as a white solid, which was pure enough for next step without further purification. MS (ESI+APCI) M+1=479.2.

A mixture of methyl 3,3-dimethyl-2-(3-(phenylsulfonylcarbamoyl)phenyl)-1,2,3,4-tetrahydroquinoline-6-carboxylate (250 mg, 0.44 mmol, 1.0 eq.) in methanol (8 mL) and 1N sodium hydroxide aqueous solution (6.6 mL, 6.6 mmol, 15.0 eq.) was heated to reflux for 1 h, Thin layer chromatography (petroleum ether:ethyl acetate=1:1) and LC-MS showed the reaction was completed. The reaction mixture was concentrated under reduced pressure and the residual was acidified with 1 M hydrochloric acid solution to pH=3. The white solid precipitated was collected by filtration and washed with acetone to give 100 mg of 3,3-dimethyl-2-(3-(phenylsulfonylcarbamoyl)phenyl)-1,2,3,4-tetrahydroquinoline-6-carboxylic acid as a off-white solid, yield: 50.4%. LC-MS (M+1)=465.1.

Example 176

2-(3-(Cyclopropylsulfonylcarbamoyl)-phenyl)-3,3-dimethyl-1,2,3,4-tetrahydroquinoline-6-carboxylic acid

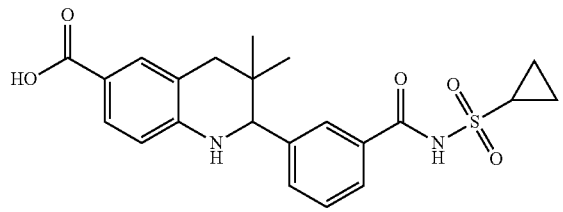 [SMILES: CC1(C)Cc2cc(C(=O)O)ccc2NC1c1cccc(C(=O)NS(=O)(=O)C2CC2)c1]

A solution of 3-(6-(methoxycarbonyl)-3,3-dimethyl-1,2,3,4-tetrahydroquinolin-2-yl)benzoic acid (150 mg, 0.44 mmol) and 1,1'-carbonyldiimidazole (214 mg, 1.32 mmol) in tetrahydrofuran (3 mL) was heated to 60° C. for 1.5 h, then was cooled to room temperature and treated with cyclopropanesulfonamide (69.1 mg, 0.57 mmol). After stirring for 10 min, the reaction mixture was treated with dropwise addition of a solution of 1,8-diazabicyclo[5.4.0]undec-7-ene (221 mg, 1.45 mmol) in tetrahydrofuran (1 mL). Upon completion of addition, the resultant mixture was stirred for an additional 3 h, Thin layer chromatography (petroleum ether:ethyl acetate=1:1) showed the reaction was complete. The reaction mixture was quenched with brine and acidified with 1N hydrochloric acid solution to pH=6, extracted with ethyl acetate (twice). The combined organic layers were washed with brine for 3 times, dried over anhydrous magnesium sulfate. Removal of the solvent in vacuo gave 216 mg of methyl 2-(3-(cyclopropylsulfonylcarbamoyl)phenyl)-3,3-dimethyl-1,2,3,4-tetrahydroquinoline-6-carboxylate as a white solid, which was pure enough for next step without further purification. MS (ESI+APCI) M+1=443.2.

A mixture of methyl 2-(3-(cyclopropylsulfonylcarbamoyl)-phenyl)-3,3-dimethyl-1,2,3,4-tetrahydroquinoline-6-carboxylate (209 mg, 0.44 mmol of theory) in methanol (8 mL) and 1N sodium hydroxide aqueous solution (6.6 mL, 6.6 mmol) was heated to reflux for 1 h. Thin layer chromatography (petroleum ether:ethyl acetate=1:1) and LC-MS showed the reaction was complete. The reaction mixture was concentrated under reduced pressure and the residual was acidified with 1 M hydrochloric acid solution to pH=3. The white solid precipitated was obtained by filtration and dissolved in dichloromethane, filtered. The filtrate was concentrated in vacuo to give 175 mg product as a white solid, washed with acetone to afford 65 mg of 2-(3-(cyclopropylsulfonylcarbamoyl)-phenyl)-3,3-dimethyl-1,2,3,4-tetrahydroquinoline-6-carboxylic acid, yield: 34.5%. MS (ESI+APCI) M+1=429.1.

Example 177

2-(4-Chloro-3-isobutyramidophenyl)-3,3-dimethyl-1,2,3,4-tetrahydroquinoline-6-carboxylic acid

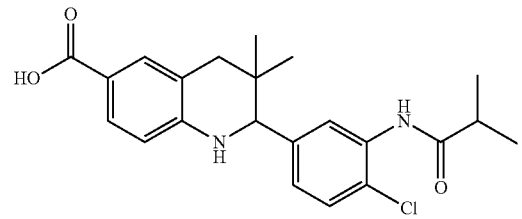 [SMILES: CC(C)C(=O)Nc1cc(C2Nc3ccc(C(=O)O)cc3CC2(C)C)ccc1Cl]

To a solution of 4-chloro-3-nitrobenzaldehyde (5.0 g, 27 mmol) in 42 mL of ethonal was added methyl 4-aminobenzoate (4.07 g, 27 mmol), and the reaction mixture was stirred over weekend. The yellow precipitates were filtered, and 8.47 g of (E)-methyl 4-(4-chloro-3-nitrobenzylidenamino)benzoate a yellow solid was obtained. (Yield=98%). (E)-methyl 4-(4-chloro-3-nitrobenzylideneamino)benzoate (8.47 g, 26.6 mmol) and yttrium(III) trifluoromethanesulfonate (800 mg, 1.33 mmol) was dissolved in dry tetrahydrofuran (100 mL), and then cooled below 0° C. Isobutyl aldehyde (2.30 g, 31.9 mmol) was added below 0° C. The reaction mixture was stirred at room temperature overnight. Thin layer chromatography showed most of starting material was consumed. 50 mL of ethyl acetate and 50 mL of water were added to the mixture, and the separated organic layer was washed with brine again. The organic layer was dried over sodium sulfate and purified on silica gel to afford 4.9 g of methyl 2-(4-chloro-3-nitrophenyl)-4-hydroxy-3,3-dimethyl-1,2,3,4-tetrahydroquinoline-6-carboxylate. (Yield=47%). MS (ESI+APCI) M+1=373.

To a solution of methyl 2-(4-chloro-3-nitrophenyl)-4-hydroxy-3,3-dimethyl-1,2,3,4-tetrahydroquinoline-6-carboxylate (8.2 g, 21 mmol) in dichloromethane (150 mL), which was cooled to −10° C. under a nitrogen atmosphere, was added triethylsilane (7.08 g, 60.9 mmol) and trifluoroacetic acid (9.82 g, 86.1 mmol). The resulting reaction mixture was stirred overnight at room temperature. The mixture was neutralized with 20 g of Sodium bicarbonate. The solid was filtered and the filtrate was evaporated to remove the solvent.

The residue was dissolved in methanol, and insoluble solid was the crude product (3.0 g). The filtrate was purified on silica gel to afford 170 mg of methyl 2-(4-chloro-3-nitrophenyl)-3,3-dimethyl-1,2,3,4-tetrahydroquinoline-6-carboxylate.

To a solution of methyl 2-(4-chloro-3-nitrophenyl)-3,3-dimethyl-1,2,3,4-tetrahydroquinoline-6-carboxylate (2.82 g, 7.53 mmol) in ethanol/water (30 mL/7.5 mL) was added 0.5 mL of concentrated hydrochloric acid solution and iron powder (4.21 g, 75.3 mmol). The resultant mixture was stirred and heated to reflux for 4 h. LC-MS showed the reaction was complete. The reaction mixture was cooled to room temperature and filtered. The filtrate was evaporated and the residue was purified by column chromatography on silica gel to afford 400 mg of methyl 2-(3-amino-4-chlorophenyl)-3,3-dimethyl-1,2,3,4-tetrahydroquinoline-6-carboxylate as a solid. Yield: 15%.

To a solution of methyl 2-(3-amino-4-chlorophenyl)-3,3-dimethyl-1,2,3,4-tetrahydroquinoline-6-carboxylate (182 mg, 0.53 mmol) in dichloromethane (5 mL) was added N,N-diisopropylethylamine (136 mg, 1.06 mmol) with ice cooling, followed by the addition of isobutyryl chloride (84 mg, 0.8 mmol) in dichloromethane (2 mL) via syringe. The resultant mixture was stirred at room temperature overnight. Thin layer chromatography (petroleum ether: ethyl acetate=10:1) showed the reaction was complete. The mixture was separated by Preparative Thin layer chromatography to afford 240 mg of methyl 2-(4-chloro-3-isobutyramidophenyl)-3,3-dimethyl-1,2,3,4-tetrahydroquinoline-6-carboxylate, which was used in next step without further purification.

A mixture of methyl 2-(4-chloro-3-isobutyramidophenyl)-3,3-dimethyl-1,2,3,4-tetrahydroquinoline-6-carboxylate (216 mg, 0.52 mmol) in methanol (8 mL) and 4.2 mL of aqueous solution of sodium hydroxide (1 M, 4.2 mmol) was stirred at reflux for 2 h. Thin layer chromatography indicated that the starting material was consumed completely. Methanol was removed under reduced pressure and the residue was acidified to pH=6 with 1 M hydrochloric acid solution. The precipitated white solid were collected by filtration and dissolved in Ethyl acetate, dried over anhydrous sodium sulfate. The solvent was removed in vacuo to afford 120 mg of 2-(4-chloro-3-isobutyramidophenyl)-3,3-dimethyl-1,2,3,4-tetrahydroquinoline-6-carboxylic acid as a white solid. LC-MS (M+1)=383.

Example 178

2-(4-Isobutyramidophenyl)-3,3-dimethyl-1,2,3,4-tetrahydroquinoline-6-carboxylic acid

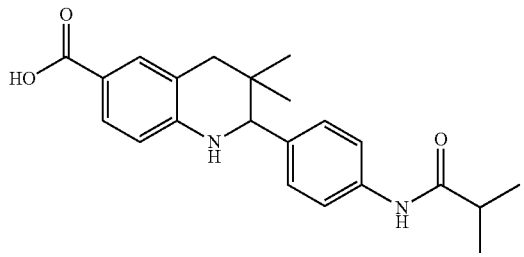 [SMILES: CC(C)C(=O)Nc1ccc(C2Nc3ccc(C(=O)O)cc3CC2(C)C)cc1]

To a solution of methyl 2-(4-aminophenyl)-3,3-dimethyl-1,2,3,4-tetrahydroquinoline-6-carboxylate (70 mg, 0.23 mmol) and N,N-diisopropylethylamine (0.09 mL, 0.52 mmol,) in dichloromethane (5 mL) was added isobutyryl chloride (0.04 mL, 0.34 mmol). The resultant mixture was stirred at room temperature for 16 hrs under nitrogen. The solvent was removed and the residue was washed with dichloromethane/petroleum ether, the precipitate was collected to afford methyl 2-(4-isobutyramidophenyl)-3,3-dimethyl-1,2,3,4-tetrahydroquinoline-6-carboxylate as a yellow solid, 61 mg, yield: 68%.

To a mixture of methyl 2-(4-isobutyramidophenyl)-3,3-dimethyl-1,2,3,4-tetrahydroquinoline-6-carboxylate (46 mg, 0.12 mmol) in methanol (3 mL) and water (1.5 mL) was added a solution of sodium hydroxide (82 mg, 2.06 mmol.) in water (1.5 mL). The resultant mixture was heated to reflux until the completion of the reaction (monitored by thin layer chromatography). Methanol was removed under vacuum. The residue was acidified with 2 M hydrochloric acid to pH=1. The precipitates were collected by filtration to afford 2-(4-isobutyramidophenyl)-3,3-dimethyl-1,2,3,4-tetrahydroquinoline-6-carboxylic acid as a yellow solid, 40 mg, 92% yield; MS (ESI+APCI) M+1=367.6.

Example 179

3,3-Dimethyl-2-(3-(methylsulfonylcarbamoyl)-phenyl)-1,2,3,4-tetrahydroquinoline-6-carboxylic acid

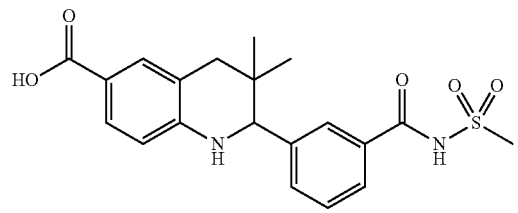 [SMILES: CC1(C)Cc2cc(C(=O)O)ccc2NC1c1cccc(C(=O)NS(C)(=O)=O)c1]

A solution of 3-(6-(methoxycarbonyl)-3,3-dimethyl-1,2,3,4-tetrahydroquinolin-2-yl)benzoic acid (150 mg, 0.44 mmol) and 1,1'-carbonyldiimidazole (214 mg, 1.32 mmol) in tetrahydrofuran (3 mL) was heated to 60° C. for 2 h, then was cooled to room temperature and treated with methanesulfonamide (54.2 mg, 0.57 mmol, 1.3 eq.). After stirring for 10 min, the reaction mixture was treated with dropwise addition of a solution of 1,8-diazabicyclo[5.4.0]undec-7-ene (221 mg, 1.45 mmol) in tetrahydrofuran (1 mL). Upon completion of addition, the resultant mixture was stirred overnight. Thin layer chromatography (petroleum ether:ethyl acetate=1:1) showed the reaction was complete. The reaction mixture was quenched with brine and acidified with 1N hydrochloric acid solution to pH=5, extracted with ethyl acetate (twice). The combined organic layers were washed with brine for 3 times, dried over anhydrous sodium sulfate. Removal of the solvent in vacuo gave 205 mg of methyl 3,3-dimethyl-2-(3-(methylsulfonylcarbamoyl)phenyl)-1,2,3,4-tetrahydroquinoline-6-carboxylate as a white solid, which was purified by column chromatography (petroleum ether:ethyl acetate=2:1 to 1:1) to afford 58 mg of white solid, which was used in next step.

A mixture of methyl 3,3-dimethyl-2-(3-(methylsulfonylcarbamoyl)phenyl)-1,2,3,4-tetrahydroquinoline-6-carboxylate (58 mg, 0.14 mmol, 1.0 eq.) in methanol (2.5 mL) and 1N sodium hydroxide aqueous solution (2.1 mL, 2.1 mmol, 15.0 eq.) was heated to reflux for 1 h. Thin layer chromatography (petroleum ether:ethyl acetate=1:1) and LC-MS showed the reaction was complete. The reaction mixture was concentrated under reduced pressure and the residual was acidified with 1N hydrochloric acid solution to pH=5. The white solid precipitated was dissolved in ethyl acetate and separated. The aqueous layer was extracted with ethyl acetate and the combined organic layers were washed with brine, dried over anhydrous sodium sulfate Removal of the solvent in vacuo gave 56 mg of 3,3-dimethyl-2-(3-(methylsulfonylcarbamoyl)-phenyl)-1,2,3,4-tetrahydroquinoline-6-carboxylic acid as a yellow solid in quantitative yield. MS (ESI+APCI) M+1=403.1.

Example 180

2-(4-Fluoro-3-(picolinamido)-phenyl)-3,3-dimethyl-1,2,3,4-tetrahydroquinoline-6-carboxylic acid

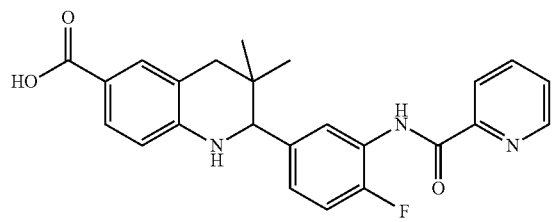 [SMILES: CC1(C)Cc2cc(C(=O)O)ccc2NC1c1ccc(F)c(NC(=O)c2ccccn2)c1]

To s solution of 2-(4-fluoro-3-nitrophenyl)-3,3-dimethyl-1,2,3,4-tetrahydroquinoline-6-carboxy late (150 mg, 0.46 mmol) and N,N-diisopropylethylamine (0.15 mL, 0.91 mmol) in dichloro methane (10 mL) was added picolinoyl chloride (77 mg, 0.54 mmol) with ice cooling. Upon completion of addition, the resultant mixture was allowed to stir for 20 h. Solvent was removed in vacuo and the residue was purified by column chromatography (petroleum ether:ethyl acetate=3:1) to afford 84 mg of methyl2-(4-fluoro-3-(picolinamido)phenyl)-3,3-dimethyl-1,2,3,4-tetrahydroquinoline-6-carboxylate. Yield: 42.4%.

A mixture of methyl 2-(4-fluoro-3-(picolinamido)phenyl)-3,3-dimethyl-1,2,3,4-tetrahydroquinoline-6-carboxylate (84 mg, 0.19 mmol) and sodium hydroxide (62 mg, 1.55 mmol) in tetrahydrofuran (10 mL), water (2 mL) was heated to reflux for 20 h. LC-MS showed the reaction was complete. The solvent was removed in vacuo and the residue was acidified by 1 M hydrochloric acid solution to pH=5-6. The precipitated white solid was collected by filtration and dissolved in acetone, dried over anhydrous magnesium sulfate. Removal of the solvent in vacuo gave crude product, which was purified by recrystallization from dichloromethane/Hexane/tetrahydrofuran to afford 30 mg of 2-(4-fluoro-3-(picolinamido)-phenyl)-3,3-dimethyl-1,2,3,4-tetrahydroquinoline-6-carboxylic acid. Yield: 42.1%. MS (ES+APCI) M+1=420.1.

Example 181

2-(4-(4-Fluorophenylsulfonamido)phenyl)-3,3-dimethyl-1,2,3,4-tetrahydroquinoline-6-carboxylic acid

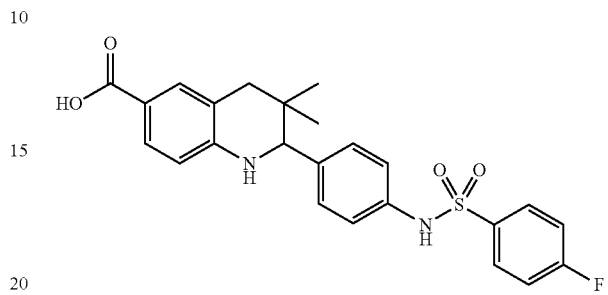

To a solution of 2-(4-aminophenyl)-3,3-dimethyl-1,2,3,4-tetrahydroquinoline-6-carboxylic acid (80 mg, 0.27 mmol) in pyridine (5 mL) was added 4-fluorobenzene-1-sulfonyl chloride (57 mg, 0.30 mmol) with ice cooling. Upon completion of the addition, the resultant mixture was allowed to warm back to room temperature and stir overnight. LC-MS showed the reaction was complete. Pyridine was removed in vacuo and the residue was purified by preparative Thin layer chromatography to afford 74 mg of 2-(4-(4-fluorophenyl-sulfonamido)phenyl)-3,3-dimethyl-1,2,3,4-tetrahydroquinoline-6-carboxylic acid as a yellow powder. Yield: 63%; MS (ESI+APCI) M+1=455.46.

Example 182

2-(4-(4-Fluorobenzamido)phenyl)-3,3-dimethyl-1,2,3,4-tetrahydroquinoline-6-carboxylic acid

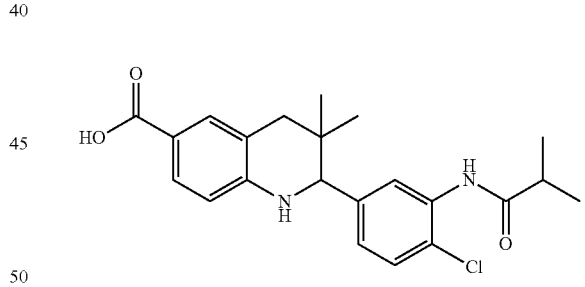

A mixture of methyl 4-aminobenzoate (1.51 g, 10 mmol) and 4-nitrobenzaldehyde (1.51 g, 10 mmol) in ethanol (30 mL) was stirred overnight to give the yellow slurry. The precipitated off-white solid was collected and dried in vacuo to give (E)-methyl 4-(4-nitrobenzylideneamino)benzoate (2.93 g, 95% yield).

To a solution of (E)-methyl 4-(4-nitrobenzylideneamino) benzoate (284 mg 1 mmol) and yttrium(III) trifluoromethanesulfonate (62 mg, 0.1 mmol) in tetrahydrofuran (5 mL) was added isobutyraldehyde (72 mg, 1.5 mmol). The resultant mixture was stirred at room temperature for 16 h. Thin layer chromatography showed the starting material was completely consumed. The reaction mixture was quenched with water and separated. The aqueous solution was extracted with dichloromethane and the combined organic layers were dried over anhydrous sodium sulfate. Solvent was removed in vacuo to give the crude product, which was purified by column chromatography (petroleum ether/ethyl acetate=3:1) to afford 70 mg of methyl 4-hydroxy-3,3-dimethyl-2-(4-nitrophenyl)-1,2,3,4-tetrahydroquinoline-6-carboxylate as a yellow solid. Yield: 20%.

To a solution of methyl 4-hydroxy-3,3-dimethyl-2-(4-nitrophenyl)-1,2,3,4-tetrahydroquinoline-6-carboxylate (61 mg 0.18 mmol) and triethylsilane (0.06 mL, 0.34 mmol) in dichloromethane (10 mL) was added dropwise a solution of trifluoroacetic acid (0.04 mL, 0.51 mol) in dichloromethane (5 mL) below 0° C. Upon completion of addition, the resultant mixture was stirred at room temperature for 24 h, then was quenched with sodium bicarbonate solution and separated. The organic layer was dried over anhydrous sodium sulfate and concentrated. The residue was purified by column chromatography to afford 50 mg of methyl 3,3-dimethyl-2-(4-nitrophenyl)-1,2,3,4-tetrahydroquinoline-6-carboxylate as a yellow solid Yield: 78%. Methyl-3,3-dimethyl-2-(4-nitrophenyl)-1,2,3,4-tetrahydroquinoline-6-carboxylate (110 mg, 0.32 mmol) was dissolved in methanol/water Solution, iron powder (25 mg, 3.2 mmol) was added. The reaction mixture was heated to reflux for 2 hrs The mixture was filtered, the filtration was concentrated and purified by column chromatography on silica gel (petroleum ether/ethyl acetate=4:1) to afford 95 mg of methyl 2-(4-aminophenyl)-3,3-dimethyl-1,2,3,4-tetrahydroquinoline-6-carboxylate as a yellow solid. (yield: 96%). MS (ESI+APCI) M+1=311.5.

To a solution of methyl 2-(4-aminophenyl)-3,3-dimethyl-1,2,3,4-tetrahydroquinoline-6-carboxylate (70 mg, 0.23 mmol) and N,N-diisopropylethylamine (0.09 mL, 0.52 mmol,) in dichloro methane (5 mL) was added 4-fluorobenzoyl chloride (54 mg, 0.34 mmol). The resultant mixture was stirred at room temperature for 16 hrs under nitrogen. The solvent was removed in vacuo and the residue was washed with dichloromethane/petroleum ether, the precipitate was collected to afford methyl 2-(4-(4-fluorobenzamido)phenyl)-3,3-dimethyl-1,2,3,4-tetrahydroquinoline-6-carboxylate as a yellow solid, 43 mg, yield: 37%.

To a mixture of methyl 2-(4-(4-fluorobenzamido)phenyl)-3,3-dimethyl-1,2,3,4-tetrahydroquinoline-6-carboxylate (43 mg, 0.01 mmol) in methanol (3 mL) and water (1.5 mL) was add a solution of sodium hydroxide (68 mg, 0.17 mmol.) in water (1.5 mL). The resultant mixture was heated to reflux until the completion of the reaction (monitored by thin layer chromatography). The methanol was removed under vacuum. The residue was acidified with 2 M hydrochloric acid to pH=1. The precipitates were collected by filtration to afford 2-(4-(4-fluorobenzamido)phenyl)-3,3-dimethyl-1,2,3,4-tetrahydroquinoline-6-carboxylic acid as a yellow solid, 40 mg, Yield 95% MS (ESI+APCI) M+1=419.6.

Example 183

3,3-Dimethyl-2-(4-(4-methylphenylsulfonamido) phenyl)-1,2,3,4-tetrahydroquinoline-6-carboxylic acid

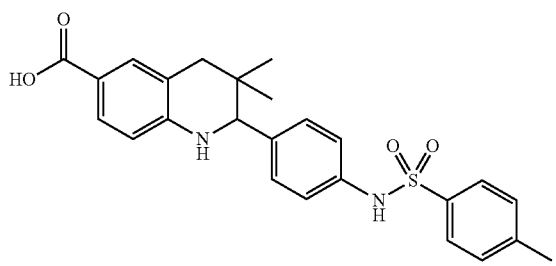 [SMILES: Cc1ccc(S(=O)(=O)Nc2ccc(C3Nc4ccc(C(=O)O)cc4CC3(C)C)cc2)cc1]

To a solution of 2-(4-aminophenyl)-3,3-dimethyl-1,2,3,4-tetrahydroquinoline-6-carboxylic acid (80 mg, 0.27 mmol) in pyridine (5 mL) was added 4-methylbenzene-1-sulfonyl chloride (57 mg, 0.30 mmol) with ice cooling. Upon completion of the addition, the resultant mixture was allowed to warm back to room temperature and stir overnight. LC-MS showed the reaction was complete. Pyridine was removed in vacuo and the residue was purified by preparative Thin layer chromatography to afford 70 mg of 3,3-dimethyl-2-(4-(4-methylphenylsulfonamido)phenyl)-1,2,3,4-tetrahydroquinoline-6-carboxylic acid as a yellow powder. Yield: 69%; MS (ESI+APCI) M+1=451.20.

Example 184

2-(3-Benzamido-4-fluorophenyl)-3,3-dimethyl-1,2,3, 4-tetrahydroquinoline-6-carboxylic acid

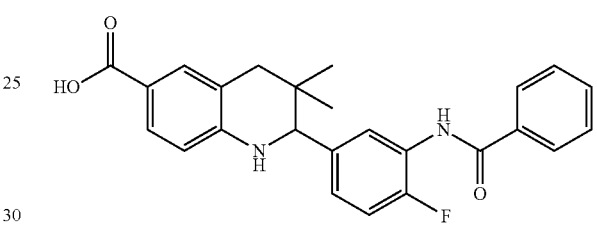

A mixture of methyl 4-aminobenzoate (4.57 g, 30.2 mmol) and 4-fluoro-3-nitrobenzaldehyde (5.00 g, 29.6 mmol) in ethanol (30 mL) was stirred at room temperature for 16 hours (precipitates formed within 30 min). The solid product was collected by filtration and the trace amount of solvent was removed under vacuum. 8.32 g (83%) of (E)-methyl 4-(4-fluoro-3-nitrobenzylideneamino)benzoate was obtained as a yellow solid.

To a suspension of (E)-methyl 4-(4-fluoro-3-nitrobenzylideneamino)benzoate (3.62 g, 12.0 mmol) in tetrahydrofuran (24 mL), yttrium(III) trifluoromethanesulfonate (75 mg, 0.12 mmol) and isobutyraldehyde (0.87 g, 12.0 mmol) were added under nitrogen at room temperature The resultant mixture was stirred at room temperature for 20 hours (turned into clear in 10 min). Water was added to the reaction mixture and extracted with Ethyl acetate. The combined organic layers were washed with brine, dried over anhydrous sodium sulfate. Solvent was removed and the residue was purified by column (petroleum ether/ethyl acetate=3:1, silica gel) to afford methyl 2-(4-fluoro-3-nitrophenyl)-4-hydroxy-3,3-dimethyl-1,2,3,4-tetrahydroquinoline-6-carboxylate 3.15 g (70%) as a yellow solid.

To an ice-cooled mixture of methyl 2-(4-fluoro-3-nitrophenyl)-4-hydroxy-3,3-dimethyl-1,2,3,4-tetrahydroquinoline-6-carboxylate (3.39 g, 9.06 mmol) and triethylsilane (3.06 g, 26.3 mmol) in dichloromethane (180 mL) was added a solution of trifluoroacetic acid (4.24 g, 37.1 mmol) in dichloromethane (90 mL) dropwise during 3 hours. After addition, ice-bath was removed and the reaction mixture was stirred at room temperature for 44 hours. Solid sodium carbonate was added and stirred for 15 minutes, filtered, and concentrated. The oil residue was purified by column (silica gel, petroleum ether/ethyl acetate=10:1 to 1:1 due to bad solubility) to afford methyl 2-(4-fluoro-3-nitrophenyl)-3,3-dimethyl-1,2,3,4-tetrahydroquinoline-6-carboxylate 2.44 mg (75%) as a yellow solid.

A flask fitted with a reflux condenser was charged with methyl 2-(4-fluoro-3-nitrophenyl)-3,3-dimethyl-1,2,3,4-tetrahydroquinoline-6-carboxylate (2.44 g, 6.81 mmol), reduced iron (4.09 g), ethanol (50 mL), water (10 mL), and three drops of conc. hydrochloric acid. The mixture was heated for reflux for 2 hours. The iron was removed by filtration. The filtrate was concentrated, extracted with Ethyl acetate, dried over anhydrous sodium sulfate. Solvent was removed and the residue was purified by column (silica gel, petroleum ether/ethyl acetate=5:1) to afford methyl 2-(4-fluoro-3-nitrophenyl)-3,3-dimethyl-1,2,3,4-tetrahydroquinoline-6-carboxylate 1.90 g (85%) as a yellow solid.

To a solution of methyl 2-(4-fluoro-3-nitrophenyl)-3,3-dimethyl-1,2,3,4-tetrahydroquinoline-6-carboxylate (105 mg, 0.32 mmol) in dichloromethane (5 mL) was added N,N-diisopropylethylamine (83 mg, 0.64 mmol) followed by benzoyl chloride (49 mg, 0.35 mmol) at 0° C. under nitrogen. The reaction mixture was then stirred at room temperature for 16 hours. The solvent was removed and the residue was purified by preparative Thin layer chromatography (silica gel, petroleum ether/ethyl acetate=3:1) to afford methyl 2-(3-benzamido-4-fluorophenyl)-3,3-dimethyl-1,2,3,4-tetrahydroquinoline-6-carboxylate 130 mg (94%) as a pale yellow solid. MS (ESI+APCI) M+1=433.

To a round bottom flask, a mixture of methyl 2-(3-benzamido-4-fluorophenyl)-3,3-dimethyl-1,2,3,4-tetrahydroquinoline-6-carboxylate (130 mg, 0.30 mmol) in methanol (3 mL) and water (0.6 mL) was treated with a solution of sodium hydroxide (204 mg, 5.1 mmol) in water (0.6 mL). The resultant mixture was heated for reflux for 1 h. The methanol was removed under vacuum. The residue was acidified with 1 M hydrochloric acid to pH=5. The precipitates were collected by filtration, purified by preparative Thin layer chromatography (silica gel, petroleum ether/ethyl acetate=2:1, 5% methanol) to afford 55 mg (44%) of 2-(3-benzamido-4-fluorophenyl)-3,3-dimethyl-1,2,3,4-tetrahydroquinoline-6-carboxylic acid as a colorless solid. MS (ESI+APCI) M+1=419.

Example 185

2-(4-Benzamidophenyl)-3,3-dimethyl-1,2,3,4-tetrahydroquinoline-6-carboxylic acid

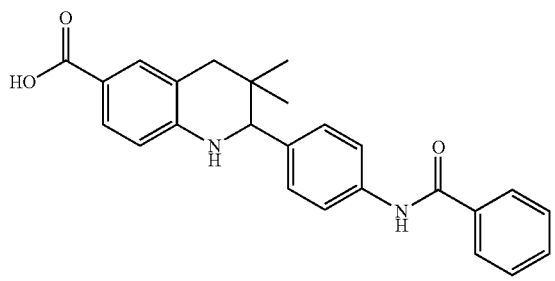 [SMILES: CC1(C)Cc2cc(C(=O)O)ccc2NC1c1ccc(NC(=O)c2ccccc2)cc1]

To a solution of methyl 2-(4-aminophenyl)-3,3-dimethyl-1,2,3,4-tetrahydroquinoline-6-carboxy late (100 mg, 0.32 mmol) and N,N-diisopropylethylamine (0.11 mL, 0.64 mmol) in dichloro methane (5 mL) was added benzoyl chloride (0.04 mL, 0.35 mmol) with ice cooling. Upon completion of addition, the resultant solution was allowed to warm back to room temperature and stir overnight. LC-MS showed the reaction was complete. Solvent was removed in vacuo and the residue was purified by preparative Thin layer chromatography to afford 70 mg of methyl 2-(4-benzamidophenyl)-3,3-dimethyl-1,2,3,4-tetrahydroquinoline-6-carboxylate as a white solid. Yield: 53%. MS (ESI+APCI) M+1=415.20.

A mixture of methyl 2-(4-benzamidophenyl)-3,3-dimethyl-1,2,3,4-tetrahydroquinoline-6-carboxylate (67 mg, 0.16 mmol) in methanol (8 mL) and aqueous sodium hydroxide solution (1 M, 1.2 mL, 1.2 mmol) was heated to reflux for 5 h, LC-MS showed the reaction was complete. The solvent was removed in vacuo and the residue was acidified with 2 M hydrochloric acid solution until lots of yellow solid precipitated, which was collected by filtration to afford 51 mg of 2-(4-benzamidophenyl)-3,3-dimethyl-1,2,3,4-tetrahydroquinoline-6-carboxylic acid in 80% yield. MS (ESI+APCI) M+1=401.

Example 186

3,3-Dimethyl-2-(4-(picolinamido)phenyl)-1,2,3,4-tetrahydroquinoline-6-carboxylic acid

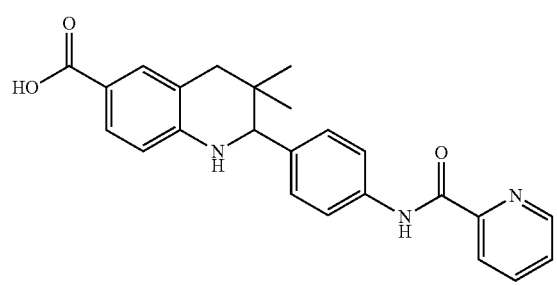 [SMILES: CC1(C)Cc2cc(C(=O)O)ccc2NC1c1ccc(NC(=O)c2ccccn2)cc1]

To a solution of methyl 2-(4-aminophenyl)-3,3-dimethyl-1,2,3,4-tetrahydroquinoline-6-carboxylate (100 mg, 0.32 mmol) and N,N-diisopropylethylamine (0.11 mL, 0.64 mmol) in dichloromethane (5 mL) was added freshly prepared picolinoyl chloride (56 mg, 0.35 mmol) with ice cooling. Upon completion of addition, the resultant deep blue solution was allowed to warm back to room temperature and stir overnight. LC-MS showed the reaction was complete. Solvent was removed in vacuo and the residue was purified by preparative Thin layer chromatography to afford 70 mg of methyl 3,3-dimethyl-2-(4-(picolinamido)phenyl)-1,2,3,4-tetrahydroquinoline-6-carboxylate as a white solid. Yield: 52%. MS (ESI+APCI) M+1=416.20.

A mixture of methyl 3,3-dimethyl-2-(4-(picolinamido)phenyl)-1,2,3,4-tetrahydroquinoline-6-carboxylate (67 mg, 0.16 mmol) in methanol (8 mL) and aqueous sodium hydroxide solution (1 M, 1.2 mL, 1.2 mmol) was heated to reflux for 5 h, LC-MS showed the reaction was complete. The solvent was removed in vacuo and the residue was acidified with 2 M hydrochloric acid solution until lots of yellow solid precipitated, which was collected by filtration to afford 51 mg of 3,3-dimethyl-2-(4-(picolinamido)phenyl)-1,2,3,4-tetrahydroquinoline-6-carboxylic acid. Yield: 80%. MS (ESI+APCI) M+1=402.

Example 187

3,3-Dimethyl-2-(3-(methylcarbamoyl)phenyl)-1,2,3,4-tetrahydroquinoline-6-carboxylic acid

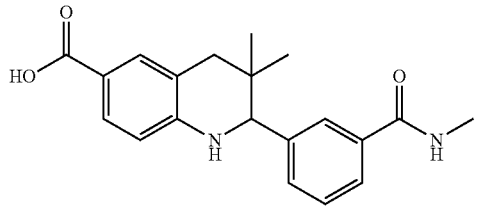 [SMILES: CNC(=O)c1cccc(C2Nc3ccc(C(=O)O)cc3CC2(C)C)c1]

To a suspension of 3-(6-(methoxycarbonyl)-3,3-dimethyl-1,2,3,4-tetrahydroquinolin-2-yl)benzoic acid (100 mg, 0.30 mmol.) in dichloromethane (6.7 mL) was added N-hydroxybenzotriazole (59.7 mg, 0.44 mmol) and 1-(3-dimethylaminopropyl)-3-ethylcarbodiimide.hydrochloric acid (169.7 mg, 0.44 mmol.), followed by 4-methylmorpholine (89.5 mg, 0.89 mmol) and the resultant mixture was stirred at room temperature for 1 h. Then methylamine hydrochloride (29.7 mg, 0.44 mmol) was added to the flask and the reaction mixture was stirred under nitrogen overnight. Thin layer chromatography (petroleum ether: ethyl acetate=1:1) and LC-MS showed the reaction was complete. The reaction was quenched with water and extracted with dichloromethane (twice). The combined organic layers were washed with 2% sodium hydroxide aqueous solution (twice) and water (3 times), dried over anhydrous sodium sulfate. Removal of the solvent in vacuo gave 122 mg of crude product as a off-white solid, which was dissolved in methanol (3 mL) and treated with sodium borohydride (37.8 mg, 1.0 mmol) for an additional 19 h. LC-MS showed the reaction was complete. The reaction was quenched with water and extracted with ethyl acetate, dried over anhydrous sodium sulfate. The solvent was removed under reduced pressure to afford 105 mg of white solid, which was further purified by Prep. Thin layer chromatography (petroleum ether:ethyl acetate=1:1) to afford 87 mg of methyl 3,3-dimethyl-2-(3-(methylcarbamoyl)phenyl)-1,2,3,4-tetrahydroquinoline-6-carboxylate as a white crystal. Yield: 83.8%.

A mixture of methyl 3,3-dimethyl-2-(3-(methylcarbamoyl)phenyl)-1,2,3,4-tetrahydroquinoline-6-carboxylate (85 mg, 0.24 mmol) in methanol (4.6 mL) and 1N sodium hydroxide aqueous solution (3.6 mL, 3.6 mmol) was heated to reflux for 1 h. LC-MS showed the reaction was complete. The solvent was removed in vacuo to give white solid, which was dissolved in water and acidified with 1N hydrochloric acid solution to pH=2. The precipitated white solid was collected by filtration and back-dissolved in aqueous sodium hydroxide solution, then was acidified with 1 M hydrochloric acid solution again to pH=7. The white precipitated solid was collected by filtration and dried in vacuo to afford 35 mg of 3,3-dimethyl-2-(3-(methyl carbamoyl)phenyl)-1,2,3,4-tetrahydroquinoline-6-carboxylic acid. Yield: 42.9%. LC-MS (M+1)=339.2.

Example 188

2-(3-(Cyclopropanecarboxamido)phenyl)-3,3-dimethyl-1,2,3,4-tetrahydroquinoline-6-carboxylic acid

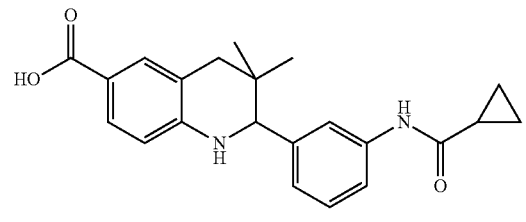 [SMILES: CC1(C)Cc2cc(C(=O)O)ccc2NC1c1cccc(NC(=O)C2CC2)c1]

To an ice-cold mixture of 2-(3-aminophenyl)-3,3-dimethyl-1,2,3,4-tetrahydroquinoline-6-carboxylate (150 mg, 0.48 mmol), cyclopropanecarboxylic acid (86.1 mg, 0.73 mmol), N,N-diisopropyl ethylamine (0.16 mL, 0.96 mmol) in dichloromethane (10 mL) was added a solution of phosphorus oxychloride (0.08 mL, 0.82 mmol). Then the reaction mixture was stirred at room temperature for 2.5 h. LC-MS indicated that the starting material was consumed completely. Solvent was removed in vacuo and the residue was purified by Prep. thin layer chromatography (petroleum ether/ethyl acetate=2:1) to afford 109 mg of methyl 2-(3-(cyclopropanecarboxamido)phenyl)-3,3-dimethyl-1,2,3,4-tetrahydroquinoline-6-carboxylate as a pale yellow solid; Yield: 59.8%;

In a round bottom flask, to a mixture of methyl 2-(3-(cyclopropane-carboxamido) phenyl)-3,3-dimethyl-1,2,3,4-tetrahydroquinoline-6-carboxylate (109 mg, 0.29 mmol) in methanol (5 mL) and water (2.5 mL) was added a solution of sodium hydroxide (196 mg, 4.90 mmol) in water (2.5 mL). The resultant mixture was heated for reflux for 1.5 hours. The methanol was removed under vacuum. The residue was acidified with 2 M hydrochloric acid to pH=5-6. The precipitates were collected by filtration, purified by preparative Thin layer chromatography (silica gel, petroleum ether/ethyl acetate=3:1) to afford 2-(3-(cyclopropanecarboxamido)phenyl)-3,3-dimethyl-1,2,3,4-tetrahydroquinoline-6-carboxylic acid as a solid product. (61 mg, yield: 58.2%). MS (ESI+APCI) M+1=347.2.

Example 189

2-(3-(Cyclopropanecarboxamido)-4-fluorophenyl)-3,3-dimethyl-1,2,3,4-tetrahydroquinoline-6-carboxylic acid

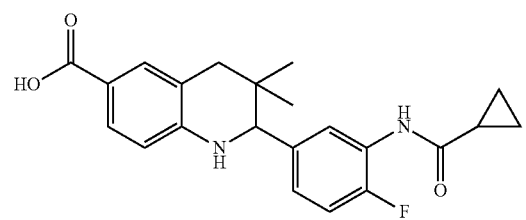 [SMILES: CC1(C)Cc2cc(C(=O)O)ccc2NC1c1ccc(F)c(NC(=O)C2CC2)c1]

To an ice-cold mixture of methyl 2-(4-fluoro-3-nitrophenyl)-3,3-dimethyl-1,2,3,4-tetrahydroquinoline-6-carboxylate (0.3 mmol, 1.0 eq.), cyclopropanecarboxylic acid (0.46 mmol, 1.5 eq.), N,N-diisopropylethylamine (0.6 mmol, 2.0 eq.) in dichloromethane (5 mL) was added a solution of phosphorus oxychloride (0.36 mmol, 1.2 eq.). Then the reaction mixture was stirred at room temperature for 2.5 hours. LC-MS indicated that the starting material was consumed completely. The reaction was quenched by 20 mL water extracted with ethyl acetate (20 mL×2). The combined organic layer was concentrated and the residue was purified by column chromatography (petroleum ether/ethyl acetate=3:1) to afford 105 mg of methyl 2-(3-(cyclopropanecarboxamido)-4-fluorophenyl)-3,3-dimethyl-1,2,3,4-tetrahydroquinoline-6-carboxylate as a pale yellow solid; yield: 89%. MS (ESI+APCI) M+1=397.2.

A mixture of methyl 2-(3-(cyclopropanecarboxamido)-4-fluorophenyl)-3,3-dimethyl-1,2,3,4-tetrahydroquinoline-6-carboxylate (0.26 mmol, 1.0 eq) and 4.5 mL sodium hydroxide (1 mol/L) in 3 mL methanol was stirred at reflux for 1-2 h. LC-MS indicated that the starting material was consumed completely. The methanol was removed by reduced pressure. The residue was acidified pH to 5-6 with 1 M hydrochloric acid. A lot of precipitates were formed and collected by filtration to afford 71 mg of 2-(3-(cyclopropanecarboxamido)-4-fluorophenyl)-3,3-dimethyl-1,2,3,4-tetrahydroquinoline-6-carboxylic acid as a white solid; yield: 72%. MS (ESI+APCI) M+1=383.

Example 190

2-(3-(2-Chloro-4-fluorobenzamido)-4-fluorophenyl)-3,3-dimethyl-1,2,3,4-tetrahydroquinoline-6-carboxylic acid

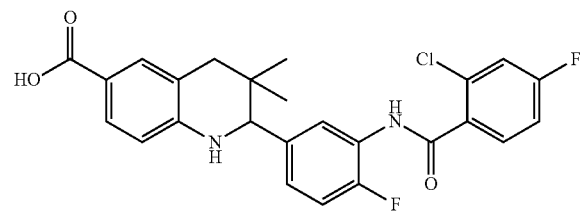 [SMILES: CC1(C)Cc2cc(C(=O)O)ccc2NC1c1ccc(F)c(NC(=O)c2ccc(F)cc2Cl)c1]

To an ice-cold mixture of methyl 2-(4-fluoro-3-nitrophenyl)-3,3-dimethyl-1,2,3,4-tetrahydroquinoline-6-carboxylate (170 mg, 0.52 mmol) and N,N-diisopropylethylamine (140 mg, 1.03 mmol) in 5 mL of dichloromethane was dropwise added a solution of 2-chloro-4-fluorobenzoyl chloride (120 mg, 0.62 mmol) in 3 mL dichloromethane under nitrogen. Then the resulted mixture was stirred at R.T. for overnight. Thin layer chromatography and LC-MS indicated that the starting material was consumed completely. The solvent was removed by rotary evaporation. The residue was purified by silica gel (petroleum ether/ethyl acetate=3:1) to afford 189 mg of methyl 2-(3-(2-chloro-4-fluorobenzamido)-4-fluorophenyl)-3,3-dimethyl-1,2,3,4-tetrahydroquinoline-6-carboxylate as a yellow solid; yield: 76%. MS (ESI+APCI) M+1=485.

A mixture of methyl 2-(3-(2-chloro-4-fluorobenzamido)-4-fluorophenyl)-3,3-dimethyl-1,2,3,4-tetrahydroquinoline-6-carboxylate (100 mg, 0.2 mmol), 3.1 mL aqueous solution of sodium hydroxide (124 mg, 3.1 mmol) in 5 mL methanol was stirred at reflux for 1 h. LC-MS indicated that the starting material was consumed completely. The solvent was removed by reduced pressure. The residue was purified by column chromatography (petroleum ether/ethyl acetate=1:1) to afford 68 mg of 2-(3-(2-chloro-4-fluorobenzamido)-4-fluorophenyl)-3,3-dimethyl-1,2,3,4-tetrahydroquinoline-6-carboxylic acid as a pale yellow solid; yield: 72.3%. MS (ESI+APCI) M+1=471.

Example 191

3,3-Dimethyl-2-(3-(piperidine-1-carbonyl)phenyl)-1,2,3,4-tetrahydroquinoline-6-carboxylic acid

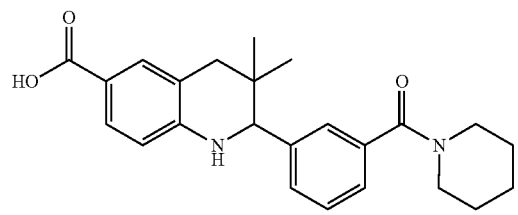 [SMILES: CC1(C)Cc2cc(C(=O)O)ccc2NC1c1cccc(C(=O)N2CCCCC2)c1]

To a suspension of 3-(6-(methoxycarbonyl)-3,3-dimethyl-1,2,3,4-tetrahydroquinolin-2-yl)benzoic acid (100 mg, 0.30 mmol.) in dichloromethane (6.7 mL) was added N-hydroxybenzotriazole (59.7 mg, 0.44 mmol) and 1-(3-dimethylaminopropyl)-3-ethylcarbodiimide.hydrochloric acid (169.7 mg, 0.44 mmol.), followed by 4-methylmorpholine (89.5 mg, 0.89 mmol) and the resultant mixture was stirred at room temperature for 1 h. Then piperidine (30.1 mg, 0.44 mmol) was added to the flask and the reaction mixture was stirred under nitrogen overnight. Thin layer chromatography (petroleum ether:ethyl acetate=1:1) and LC-MS showed the reaction was complete. The reaction was quenched with water and extracted with dichloromethane (twice). The combined organic layers were washed with 2% sodium hydroxide aqueous solution (twice) and water (3 times), dried over anhydrous sodium sulfate. Removal of the solvent in vacuo gave 147 mg of crude product as a off-white solid, which was dissolved in methanol (3 mL) and treated with sodium borohydride (37.8 mg, 1.0 mmol) for an additional 27 h. LC-MS showed the reaction was complete. The reaction was quenched with water and extracted with ethyl acetate, dried over anhydrous sodium sulfate. The solvent was removed under reduced pressure to afford 105 mg of white solid, which was further purified by recrystallization from methanol to afford 69 mg of methyl-3,3-dimethyl-2-(3-(piperidine-1-carbonyl)phenyl)-1,2,3,4-tetrahydroquinoline-6-carboxylate as a white crystal. Yield: 57.5%.

A mixture of methyl 3,3-dimethyl-2-(3-(piperidine-1-carbonyl)phenyl)-1,2,3,4-tetrahydroquinoline-6-carboxylate (68 mg, 0.24 mmol) in methanol (6 mL) and 1N sodium hydroxide aqueous solution (2.5 mL, 2.5 mmol) was heated to reflux for 1 h. LC-MS showed the reaction was complete. The solvent was removed in vacuo to give white solid, which was dissolved in water and acidified with 1N hydrochloric acid solution to pH=2. The precipitated white solid was collected by filtration and back-dissolved in aqueous sodium hydroxide solution, then was acidified with 1 M hydrochloric acid solution again to pH=7. The white precipitated solid was collected by filtration and dried in vacuo to afford 55 mg of 3,3-dimethyl-2-(3-(piperidine-1-carbonyl)phenyl)-1,2,3,4-tetrahydroquinoline-6-carboxylic acid. Yield: 83.8%. LC-MS (M+1)=393.2.

Example 192

2-(3-(2-Methoxyethylcarbamoyl)phenyl)-3,3-dimethyl-1,2,3,4-tetrahydroquinoline-6-carboxylic acid

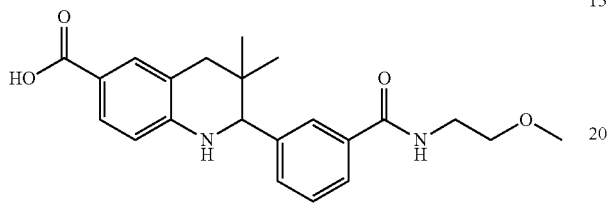

To a suspension of 3-(6-(methoxycarbonyl)-3,3-dimethyl-1,2,3,4-tetrahydroquinolin-2-yl)benzoic acid (100 mg, 0.30 mmol.) in dichloromethane (6.7 mL) was added N-hydroxybenzotriazole (59.7 mg, 0.44 mmol) and 1-(3-dimethylaminopropyl)-3-ethylcarbodiimide.hydrochloric acid (169.7 mg, 0.44 mmol.), followed by 4-methylmorpholine (89.5 mg, 0.89 mmol) and the resultant mixture was stirred at room temperature for 1 h. Then 2-methoxyethanamine (26.6 mg, 0.44 mmol) was added to the flask and the reaction mixture was stirred under nitrogen overnight. Thin layer chromatography (petroleum ether:ethyl acetate=1:1) and LC-MS showed the reaction was complete. The reaction was quenched with water and extracted with dichloromethane (twice). The combined organic layers were washed with 2% sodium hydroxide aqueous solution (twice) and water (3 times), dried over anhydrous sodium sulfate. Removal of the solvent in vacuo gave 130 mg of crude product as a yellow oil, which was dissolved in methanol (3 mL) and treated with sodium borohydride (20 mg, 0.53 mmol) for an additional 3 h. LC-MS showed the reaction was complete. The reaction was quenched with water and extracted with ethyl acetate, dried over anhydrous sodium sulfate. The solvent was removed under reduced pressure to afford crude product, which was further purified by column chromatography (petroleum ether:ethyl acetate=1:1) from methanol to give 100 mg of methyl 2-(3-(2-methoxy ethylcarbamoyl)phenyl)-3,3-dimethyl-1,2,3,4-tetrahydroquinoline-6-carboxylate as a white crystal. Yield: 85.6%.

A mixture of methyl 2-(3-(2-methoxyethylcarbamoyl)phenyl)-3,3-dimethyl-1,2,3,4-tetrahydroquinoline-6-carboxylate (100 mg, 0.25 mmol) in methanol (4.5 mL) and 1N sodium hydroxide aqueous solution (3.7 mL, 3.7 mmol) was heated to reflux for 1 h. LC-MS showed the reaction was complete. The solvent was removed in vacuo to give white solid, which was dissolved in water and acidified with 1N hydrochloric acid solution to pH=2. The precipitated white solid was collected by filtration and washed with water, dried in vacuo to afford 69 mg of 2-(3-(2-methoxyethylcarbamoyl) phenyl)-3,3-dimethyl-1,2,3,4-tetrahydroquinoline-6-carboxylic acid. Yield: 71.9%. LC-MS (M+1)=383.2.

Example 193

3,3-Dimethyl-2-(4-(2-phenylacetamido)phenyl)-1,2,3,4-tetrahydroquinoline-6-carboxylic acid

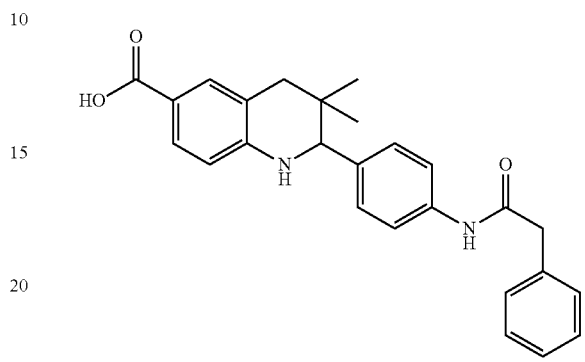

To a solution of methyl 2-(4-aminophenyl)-3,3-dimethyl-1,2,3,4-tetrahydroquinoline-6-carboxylate (80 mg, 0.26 mmol) and N,N-diisopropylethylamine (0.09 mL, 0.52 mmol) in dichloromethane (5 mL) was added 2-phenylacetyl chloride (0.05 mL, 0.34 mmol). The resultant mixture was stirred at room temperature for 16 hrs under nitrogen. The solvent was removed and the residue was washed with dichloromethane/petroleum ether, the precipitate was collected to afford methyl 3,3-dimethyl-2-(4-(2-phenylacetamido)phenyl)-1,2,3,4-tetrahydroquinoline-6-carboxylate as a yellow solid, 90 mg, yield: 81%.

To a mixture of methyl 3,3-dimethyl-2-(4-(2-phenylacetamido)phenyl)-1,2,3,4-tetrahydroquinoline-6-carboxylate (90 mg, 0.21 mmol) in methanol (3 mL) and water (1.5 mL) was added a solution of sodium hydroxide (143 mg, 3.57 mmol.) in water (1.5 mL). The resultant mixture was heated to reflux until the completion of the reaction (monitored by Thin layer chromatography). The methanol was removed under vacuum. The residue was acidified with 2 M hydrochloric acid to pH=1. The precipitates were collected by filtration to afford 3,3-dimethyl-2-(4-(2-phenylacetamido)phenyl)-1,2,3,4-tetrahydroquinoline-6-carboxylic acid as a yellow solid, 75 mg, Yield 85% MS (ESI+APCI) M+1=415.6.

Example 194

2-(3-(Cyclobutanecarboxamido)-4-fluorophenyl)-3,3-dimethyl-1,2,3,4-tetrahydroquinoline-6-carboxylic acid

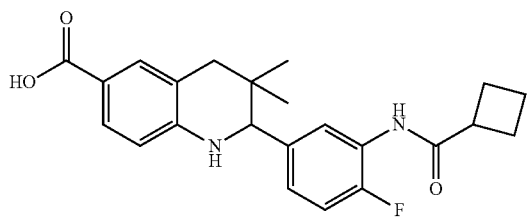 [SMILES: CC1(C)Cc2cc(C(=O)O)ccc2NC1c1ccc(F)c(NC(=O)C2CCC2)c1]

To an ice-cold mixture of methyl 2-(4-fluoro-3-nitrophenyl)-3,3-dimethyl-1,2,3,4-tetrahydroquinoline-6-carboxylate (0.3 mmol, 1.0 eq.), cyclobutanecarboxylic acid (0.46 mmol, 1.5 eq.), N,N-diisopropylethylamine (0.6 mmol, 2.0 eq.) in dichloromethane (5 mL) was added a solution of phosphorus oxychloride (0.36 mmol, 1.2 eq.). Then the reaction mixture was stirred at room temperature for 2.5 hours. LC-MS indicated that the starting material was consumed completely. The reaction was quenched by 20 mL water extracted with ethyl acetate (20 mL×2). The combined organic layer was concentrated and the residue was purified by column chromatography (petroleum ether/ethyl acetate=3:1) to afford methyl 2-(3-(cyclobutanecarboxamido)-4-fluorophenyl)-3,3-dimethyl-1,2,3,4-tetrahydroquinoline-6-carboxylate as a pale yellow solid; Yield: 89%; MS (ESI+APCI) M+1=411.

A mixture of methyl 2-(3-(cyclobutanecarboxamido)-4-fluorophenyl)-3,3-dimethyl-1,2,3,4-tetrahydroquinoline-6-carboxylate (0.26 mmol, 1.0 eq.) and 4.5 mL sodium hydroxide (1 mol/L) in 3 mL methanol was stirred at reflux for 1-2 h. LC-MS indicated that the starting material was consumed completely. The methanol was removed by reduced pressure. The residue was acidified pH to 5-6 with 1 M hydrochloric acid. A lot of precipitates were formed and collected by filtration to afford 2-(3-(cyclobutanecarboxamido)-4-fluorophenyl)-3,3-dimethyl-1,2,3,4-tetrahydroquinoline-6-carboxylic acid as a white solid; Yield: 80%; MS (ESI+APCI) M+1=397.

Example 195

2-(4-Chloro-3-(cyclohexanecarboxamido)phenyl)-3,3-dimethyl-1,2,3,4-tetrahydroquinoline-6-carboxylic acid

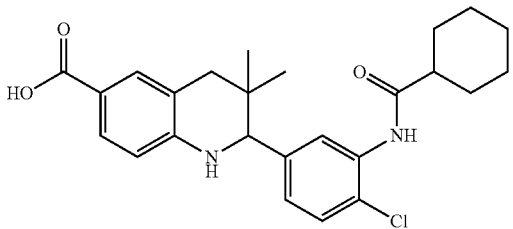 [SMILES: CC1(C)Cc2cc(C(=O)O)ccc2NC1c1ccc(Cl)c(NC(=O)C2CCCCC2)c1]

To a solution of methyl 2-(3-amino-4-chlorophenyl)-3,3-dimethyl-1,2,3,4-tetrahydroquinoline-6-carboxylate (200 mg, 0.58 mmol) in 8 mL of dichloromethane, was added N,N-diisopropylethylamine (150 mg, 1.16 mmol) under nitrogen atmosphere. Then a solution of cyclohexanecarbonyl chloride (127 mg, 0.87 mmol) was added via syringe with an ice bath. The mixture was stirred for 1.5 h. The mixture was purified by column chromatography to afford 250 mg of methyl 2-(4-chloro-3-(cyclohexanecarboxamido)phenyl)-3,3-dimethyl-1,2,3,4-tetrahydroquinoline-6-carboxylate as a crude product. (Yield: 95%).

To a solution of methyl 2-(4-chloro-3-(cyclohexanecarboxamido)phenyl)-3,3-dimethyl-1,2,3,4-tetrahydroquinoline-6-carboxylate (380 mg, 0.835 mmol) in methanol (15 mL) was added a solution of sodium hydroxide (270 mg, 6.68 mmol) in water (6.8 mL). The mixture was stirred and heated to reflux for 5 h. The mixture was evaporated, and the residue was dissolved in 15 mL of water. The aqueous solution was acidified to pH=3 with 1M hydrochloric acid. The precipitated solid was collected by filtration, and dissolved in ethyl acetate. The organic layer was dried over sodium sulfate. After evaporation, the mixture was purified on silica gel to afford 50 mg of 2-(4-chloro-3-(cyclohexanecarboxamido)phenyl)-3,3-dimethyl-1,2,3,4-tetrahydroquinoline-6-carboxylic acid as an off white solid. (Yield: 14%) MS (ESI+APCI) M+1=423.2, M−1=441.0.

Example 196

2-(3-(Cyclopentanecarboxamido)-4-fluorophenyl)-3,3-dimethyl-1,2,3,4-tetrahydroquinoline-6-carboxylic acid

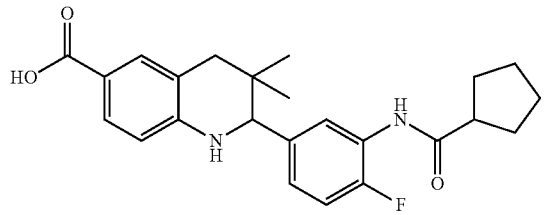 [SMILES: CC1(C)Cc2cc(C(=O)O)ccc2NC1c1ccc(F)c(NC(=O)C2CCCC2)c1]

To an ice-cold mixture of 2-(4-fluoro-3-nitrophenyl)-3,3-dimethyl-1,2,3,4-tetrahydroquinoline-6-carboxylate (0.3 mmol, 1.0 eq.), cyclopentanecarboxylic acid (0.46 mmol, 1.5 eq.), N,N-diisopropyl ethylamine (0.6 mmol, 2.0 eq.) in dichloromethane (5 mL) was added a solution of phosphorus oxychloride (0.36 mmol, 1.2 eq.). Then the reaction mixture was stirred at room temperature for 2.5 hours. LC-MS indicated that the starting material was consumed completely. The reaction was quenched by 20 mL water extracted with ethyl acetate (20 mL×2). The combined organic layer was concentrated and the residue was purified by column chromatography (petroleum ether/ethyl acetate=3:1) to afford methyl 2-(3-(cyclopentanecarboxamido)-4-fluorophenyl)-3,3-dimethyl-1,2,3,4-tetrahydroquinoline-6-carboxylate as a pale yellow solid; Yield: 90%; MS (ESI+APCI) M+1=425.

A mixture of methyl 2-(3-(cyclopentanecarboxamido)-4-fluorophenyl)-3,3-dimethyl-1,2,3,4-tetrahydroquinoline-6-carboxylate (0.26 mmol, 1.0 eq.) and 4.5 mL sodium hydroxide (1 mol/L) in 3 mL methanol was stirred at reflux for 1-2 h. LC-MS indicated that the starting material was consumed completely. The methanol was removed by reduced pressure. The residue was acidified pH to 5-6 with 1 M hydrochloric acid. A lot of precipitates were formed and collected by filtration to afford 2-(3-(cyclopentanecarboxamido)-4-fluorophenyl)-3,3-dimethyl-1,2,3,4-tetrahydroquinoline-6-carboxylic acid as a white solid; Yield: 70%; MS (ESI+APCI) M+1=411.

Example 197

Methyl 3,3-dimethyl-2-(3-(pyrazin-2-ylcarbamoyl)-phenyl)-1,2,3,4-tetrahydroquinoline-6-carboxylate

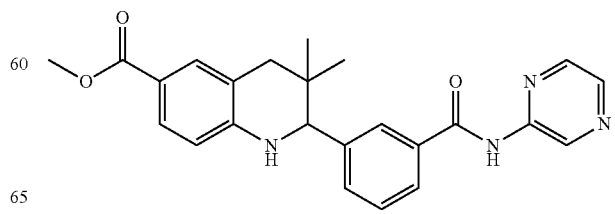

A solution of 3-(6-(methoxycarbonyl)-3,3-dimethyl-1,2,3,4-tetrahydroquinolin-2-yl)benzoic acid (330 mg, 0.88 mmol) and 1,1'-carbonyldiimidazole (500 mg, 3.08 mmol) in tetrahydrofuran (6 mL) was heated to 60° C. for 2 h, then was cooled to room temperature and treated with pyrazin-2-amine (92.2 mg, 0.97 mmol,). After stirring for 20 min, the reaction mixture was treated with dropwise addition of a solution of 1,8-diazabicyclo[5.4.0]undec-7-ene (670 mg, 4.4 mmol) in tetrahydrofuran (2 mL). Upon completion of addition, the resultant mixture was stirred overnight. Thin layer chromatography (dichloromethane:ethyl acetate=5:1) showed the reaction was nearly complete. The reaction mixture was quenched with brine and acidified with 1N hydrochloric acid solution to pH=6, extracted with ethyl acetate (twice). The combined organic layers were washed with brine for 3 times, dried over anhydrous magnesium sulfate. Removal of the solvent in vacuo gave crude product, which was purified by column chromatography (dichloromethane:ethyl acetate=5:1) to afford 175 mg of methyl 3,3-dimethyl-2-(3-(pyrazin-2-ylcarbamoyl)-phenyl)-1,2,3,4-tetrahydroquinoline-6-carboxylate as a white solid. Yield: 47.5%. MS (ESI+APCI) M+1=417.2.

Example 198

2-(4-(Cyclohexanecarboxamido)phenyl)-3,3-dimethyl-1,2,3,4-tetrahydroquinoline-6-carboxylic acid

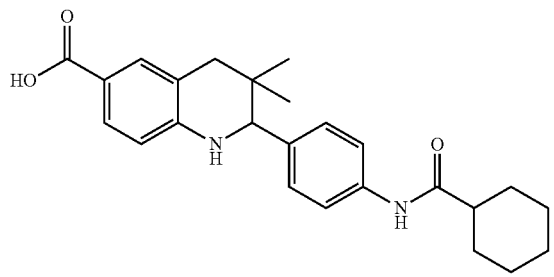 [SMILES: CC1(C)Cc2cc(C(=O)O)ccc2NC1c1ccc(NC(=O)C2CCCCC2)cc1]

To a solution of methyl 2-(4-aminophenyl)-3,3-dimethyl-1,2,3,4-tetrahydroquinoline-6-carboxy late (50 mg, 0.16 mmol), cyclohexanecarboxylic acid (0.03 mL, 0.24 mmol) and N,N-diisopropylethylamine (0.05 mL, 0.32 mmol,) in dichloromethane (5 mL) was added phosphorus oxychloride (0.02 mL, 0.24 mmol) via syringe below 0° C. The mixture was stirred at room temperature for 16 h under nitrogen. The solvent was removed and the residue was washed with dichloromethane/petroleum ether, the precipitate was collected to afford methyl 2-(4-(cyclohexane carboxamido)phenyl)-3,3-dimethyl-1,2,3,4-tetrahydroquinoline-6-carboxylate as a yellow solid, 42 mg, yield: 53%.

To a mixture of methyl 2-(4-(cyclohexanecarboxamido)phenyl)-3,3-dimethyl-1,2,3,4-tetrahydroquinoline-6-carboxylate (53 mg, 0.11 mmol) in methanol (3 mL) and water (1.5 mL) was added a solution of sodium hydroxide (123 mg, 2.83 mmol.) in water (1.5 mL). The resultant mixture was heated for reflux until the complete of the reaction (monitored by thin layer chromatography). The methanol was removed under vacuum. The residue was acidified with 2 M hydrochloric acid to pH=1. The precipitates were collected by filtration to afford 2-(4-(cyclohexanecarboxamido)phenyl)-3,3-dimethyl-1,2,3,4-tetrahydroquinoline-6-carboxylic acid as a yellow solid, yellow solid, 50 mg, 95% Yield; MS (ESI+APCI) M+1=429.11.

Example 199

3,3-Dimethyl-2-(3-(2-phenylacetamido)phenyl)-1,2,3,4-tetrahydroquinoline-6-carboxylic acid

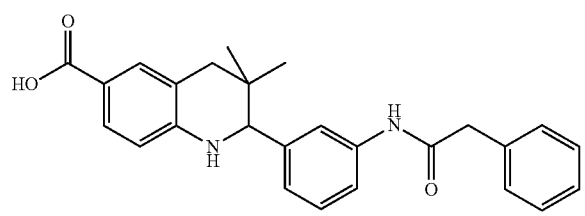 [SMILES: CC1(C)Cc2cc(C(=O)O)ccc2NC1c1cccc(NC(=O)Cc2ccccc2)c1]

To a solution of 2-(3-aminophenyl)-3,3-dimethyl-1,2,3,4-tetrahydroquinoline-6-carboxylate (150 mg, 0.48 mmol) and N,N-diisopropylethylamine (0.16 mL, 0.97 mmol) in dichloromethane (10 mL) was added 2-phenylacetyl chloride (0.1 mL, 0.63 mmol) with ice cooling. The resultant mixture was kept 0° C. for 10 h. Thin layer chromatography (petroleum ether:ethyl acetate=3:1, Rf=0.4) showed the reaction was complete. Solvent was removed in vacuo and the residue was purified by Prep. Thin layer chromatography (petroleum ether:ethyl acetate=3:1) to afford 139 mg of methyl-3,3-dimethyl-2-(3-(2-phenylacetamido)phenyl)-1,2,3,4-tetrahydroquinoline-6-carboxy late as a off-white solid. Yield: 67.1%. MS (ES+APCI) M+1-CH$_3$O=397.1.

To a mixture of methyl 3,3-dimethyl-2-(3-(2-phenylacetamido)phenyl)-1,2,3,4-tetrahydroquinoline-6-carboxylate (139 mg, 0.32 mmol) in methanol (5 mL) and water (2.5 mL) was added a solution of sodium hydroxide (220 mg, 5.50 mmol) in water (2.5 mL). The resultant mixture was heated for reflux for 1.5 hours. The methanol was removed under vacuum. The residue was acidified with 2 M hydrochloric acid to pH=5. The precipitates were collected by filtration, purified by preparative thin layer chromatography (silica gel, petroleum ether/ethyl acetate=3:1) to afford 3,3-dimethyl-2-(3-(2-phenylacetamido)phenyl)-1,2,3,4-tetrahydroquinoline-6-carboxylic acid as a solid. (70 mg, yield: 52.2%). MS (ESI+APCI) M+1-OH=397.2.

Example 200

2-(3-Carbamoylphenyl)-3,3-dimethyl-1,2,3,4-tetrahydroquinoline-6-carboxylic acid

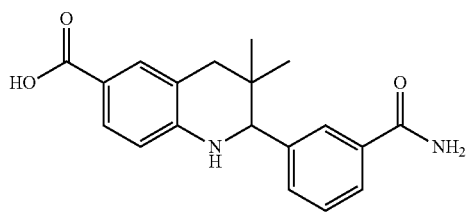 [SMILES: CC1(C)Cc2cc(C(=O)O)ccc2NC1c1cccc(C(N)=O)c1]

To a suspension of 3-(6-(methoxycarbonyl)-3,3-dimethyl-1,2,3,4-tetrahydroquinolin-2-yl)benzoic acid (100 mg, 0.29 mmol, 1.0 eq.) in dichloromethane (6.7 ml) was added N-hydroxybenzotriazole (59.7 mg, 0.44 mmol, 1.5 eq.) and 1-(3- dimethylaminopropyl)-3-ethyl carbo diimide hydrochloric acid (169.7 mg, 0.88 mmol, 3.0 eq.), followed by 4-methylmorpholine (89.5 mg, 0.88 mmol) and the resultant mixture was stirred at room temperature for 30 min. Then ammonium hydroxide (40 mg, 0.59 mmol, 2.0 eq.) was added to the flask and the reaction mixture was stirred for an additional 30 min, LC-MS showed only little product formed, so additional 1.0 mL of ammonium aqueous solution (1.0 mL, 14.7 mmol, 50.0 eq.) was added to the flask and the resultant mixture was stirred for an additional 7 h, LC-MS showed the reaction was complete. The reaction was quenched with water, separated, and the aqueous layer was extracted with dichloromethane (twice). The combined organic layers were washed with 2% sodium hydroxide aqueous solution (twice) and brine (3 times), dried over anhydrous magnesium sulfate. Removal of the solvent in vacuo gave crude product, which was recrystallized from dichloromethane/hexane to afford 85 mg of methyl 2-(3-carbamoylphenyl)-3,3-dimethyl-1,2,3,4-tetrahydroquinoline-6-carboxylate as a white crystal. Yield: 85.1%.

A mixture of methyl 2-(3-carbamoylphenyl)-3,3-dimethyl-1,2,3,4-tetrahydroquinoline-6-carboxy late (84 mg, 0.25 mmol) in methanol (4.5 mL) and 1 M sodium hydroxide aqueous solution (3.2 mL, 3.2 mmol, 13.0 eq.) was heated to reflux for 30 min, LC-MS showed the reaction was complete and only the desired product formed. The solvent was concentrated in vacuo and the residue was dissolved in water and acidified with 1 M hydrochloric acid solution to pH=6. The white precipitated solid was collected by filtration and dried in vacuo to afford 50 mg of 2-(3-carbamoylphenyl)-3,3-dimethyl-1,2,3,4-tetrahydroquinoline-6-carboxylic acid as a white solid. Yield: 62.1%. MS (ESI+APCI) M+1=325.1.

Example 201

3,3-Dimethyl-2-(3-(methylsulfonamido)phenyl)-1,2, 3,4-tetrahydroquinoline-6-carboxylic acid

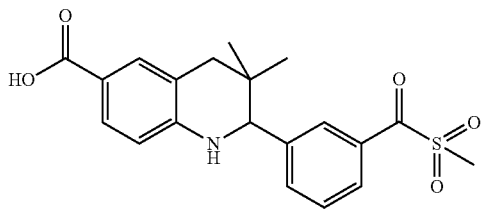 [SMILES: CC1(C)Cc2cc(C(=O)O)ccc2NC1c1cccc(C(=O)S(C)(=O)=O)c1]

In a round-bottomed flask, methanesulfonyl chloride (0.07 mL, 0.84 mmol) was added dropwise to a solution of 2-(3-aminophenyl)-3,3-dimethyl-1,2,3,4-tetrahydroquinoline-6-carboxylic acid (0.1 g, 0.34 mmol) in dry pyridine (2 mL) was allowed to stir at room temperature for 1 h. The pyridine was removed under vacuum. The residue was purified by column chromatography (silica gel, petroleum ether:ethyl acetate=1:1) to afford 3,3-dimethyl-2-(3-(methylsulfonamido)phenyl)-1,2,3,4-tetrahydroquinoline-6-carboxylic acid as a white solid (27 mg, yield: 21.3%); MS (ES+APCI) M+1=375.1.

Example 202

2-(3-Benzamido-5-chlorophenyl)-3,3-dimethyl-1,2, 3,4-tetrahydroquinoline-6-carboxylic acid

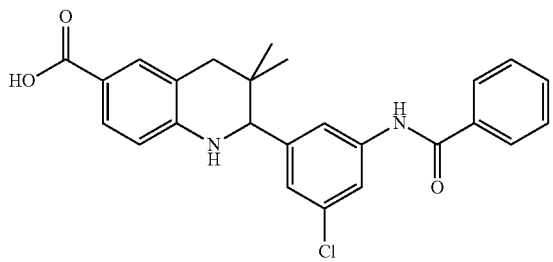 [SMILES: CC1(C)Cc2cc(C(=O)O)ccc2NC1c1cc(Cl)cc(NC(=O)c2ccccc2)c1]

To a solution of 3-chloro-5-nitrobenzaldehyde (371 mg, 0.1 mmol) in ethanol (6 mL) was added methyl 4-aminobenzoate (302 mg, 2.0 mmol). After a while, solids precipitated from the resulting clear yellow solution. The precipitated solid was filtered and 346 mg of (E)-methyl 4-(3-chloro-5-nitrobenzylideneamino)benzoate as a yellow solid was obtained. Yield=54%.

To a solution of (E)-methyl 4-(3-chloro-5-nitrobenzylideneamino)benzoate (346 mg, 1.09 mmol) in dry tetrahydrofuran (4 mL) was added yttrium(III) trifluoromethanesulfonate (34 mg, 0.054 mmol). The mixture was stirred under a nitrogen atmosphere. Then a solution of isobutyl aldehyde (95 mg, 1.30 mmol) in tetrahydrofuran (1 mL) was added via syringe. The mixture was stirred overnight. The reaction mixture was purified by column chromatography (petroleum ether: ethyl acetate=10:1) to afford 250 mg of methyl 2-(3-chloro-5-nitrophenyl)-4-hydroxy-3,3-dimethyl-1,2,3,4-tetrahydroquinoline-6-carboxylate as a crude product. (Yield=59%). MS (ESI+APCI) M+1-water=373.

To a solution of methyl 2-(3-chloro-5-nitrophenyl)-4-hydroxy-3,3-dimethyl-1,2,3,4-tetrahydroquinoline-6-carboxylate (250 mg, 0.64 mmol) in dichloromethane (5 mL) was added a solution of trifluoroacetic acid (300 mg, 0.8 mmol) in dichloromethane (5 mL) under a nitrogen atmosphere with an ice bath slowly (1.5-2 h). The resultant mixture was stirred at room temperature for 3 h. The mixture was treated with 1 g of Sodium bicarbonate and filtered. The filtrate was concentrated, and purified on preparative Thin layer chromatography to afford 125 mg of methyl 2-(3-chloro-5-nitrophenyl)-3,3-dimethyl-1,2,3,4-tetrahydroquinoline-6-carboxylate as a yellow solid. Yield=52%.

To a solution of methyl 2-(3-chloro-5-nitrophenyl)-3,3-dimethyl-1,2,3,4-tetrahydroquinoline-6-carboxylate (124 mg, 0.33 mmol) in ethanol/water (2 mL/0.5 mL) was added 2 drops of conc. hydrochloric acid and iron (370 mg, 6.62 mmol). The mixture was stirred and heated to reflux for 4 h. LC-MS showed most of SM was consumed. The mixture was dried over silica gel and washed through a short column with petroleum ether:ethyl acetate=3:1 to afford 95 mg of methyl 2-(3-amino-5-chlorophenyl)-3,3-dimethyl-1,2,3,4-tetrahydroquinoline-6-carboxylate as a brown solid. (Yield=83%). MS (ESI+APCI) M+1=345.

To a solution of methyl 2-(3-amino-5-chlorophenyl)-3,3-dimethyl-1,2,3,4-tetrahydroquinoline-6-carboxylate (100 mg, 0.29 mmol) and N,N-diisopropylethylamine (75 mg, 0.58 mmol) in dichloro methane (4 mL) was added benzoyl chloride (49 mg, 0.35 mmol) slowly via syringe under nitrogen. The mixture was stirred at room temperature for 1 h. Solid precipitated and was collected by filtration to afford 65 mg of methyl 2-(3-benzamido-5-chlorophenyl)-3,3-dimethyl-1,2,3,4-tetrahydroquinoline-6-carboxylate as a white solid. Yield: 50%; MS (ESI+APCI) M+1-water=431.

To a solution of methyl 2-(3-benzamido-5-chlorophenyl)-3,3-dimethyl-1,2,3,4-tetrahydroquinoline-6-carboxylate (61 mg, 0.14 mmol) in methanol (4 mL) was added a 1 M solution of sodium hydroxide (1.63 mL, 1.63 mmol). The mixture was stirred and heated to reflux for 3 h. The mixture was concentrated, dissolved in water and acidified to pH=5-6. The precipitated solid was collected by filtration, dissolved in tetrahydrofuran, and dried over anhydrous magnesium sulfate. After evaporation of the organic solvent, the residue was purified by column chromatography (silica gel, petroleum ether:ethyl acetate=3:1) to afford 54 mg of 2-(3-benzamido-5-chloro phenyl)-3,3-dimethyl-1,2,3,4-tetrahydroquinoline-6-carboxylic acid as a white solid. Yield: 91%; MS (ESI+APCI) M+1=417.

Example 203

2-(3-(2-(Dimethylamino)ethylcarbamoyl)phenyl)-3,3-dimethyl-1,2,3,4-tetrahydroquinoline-6-carboxylic acid

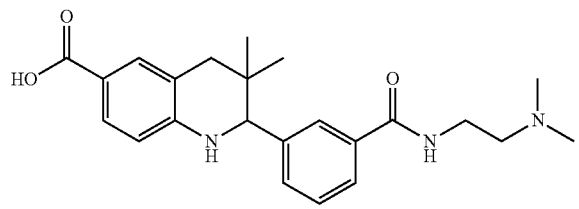 [SMILES: CN(C)CCNC(=O)c1cccc(C2Nc3ccc(C(=O)O)cc3CC2(C)C)c1]

To a suspension of 3-(6-(methoxycarbonyl)-3,3-dimethyl-1,2,3,4-tetrahydroquinolin-2-yl)benzoic acid (150 mg, 0.44 mmol, 1.0 eq.) in dichloromethane (10.0 ml) was added N-hydroxy benzotriazole (89.2 mg, 0.66 mmol, 1.5 eq.) and 1-(3-dimethylaminopropyl)-3-ethylcarbodiimide.hydrochloric acid (253.0 mg, 1.32 mmol, 3.0 eq.), followed by 4-methylmorpholine (133.5 mg, 1.32 mmol) and the resultant mixture was stirred at room temperature for 40 min. Then $N_1$, $N_1$-dimethylethane-1,2-diamine (42.7 mg, 0.48 mmol, 1.1 eq.) was added to the flask and the reaction mixture was stirred for an additional 40 min, LC-MS showed the reaction was complete. The reaction was quenched with water, separated, and the aqueous layer was extracted with dichloromethane (twice). The combined organic layers were washed with 2% sodium hydroxide aqueous solution (twice) and brine (3 times), dried over anhydrous magnesium sulfate. Removal of the solvent in vacuo gave 191 mg of methyl 2-(3-(2-(dimethylamino)ethylcarbamoyl)phenyl)-3,3-dimethyl-1,2,3,4-tetrahydroquinoline-6-carboxylate as a off-white solid, which was washed with hexane and collected by filtration to afford 162 mg product as a white solid. Yield: 89.5%.

A mixture of methyl 2-(3-(2-(dimethylamino)ethylcarbamoyl)phenyl)-3,3-dimethyl-1,2,3,4-tetrahydroquinoline-6-carboxylate (157 mg, 0.38 mmol) in methanol (6.5 mL) and 1M sodium hydroxide aqueous solution (5.1 mL, 5.1 mmol, 13.0 eq.) was heated to reflux for 30 min, LC-MS showed the reaction was complete and only the desired product formed. The solvent was concentrate in vacuo and the residue was dissolved in water and acidified with 1 M hydrochloric acid solution to pH=6. The white precipitated solid was collected by filtration and dried in vacuo to afford 122 mg of 2-(3-(2-(dimethylamino)ethylcarbamoyl)phenyl)-3,3-dimethyl-1,2,3,4-tetrahydroquinoline-6-carboxylic acid as a white solid. Yield: 80.5%. MS (ESI+APCI) M+1=396.2.

Example 204

2-(3-Acetamidophenyl)-3,3-dimethyl-1,2,3,4-tetrahydroquinoline-6-carboxylic acid

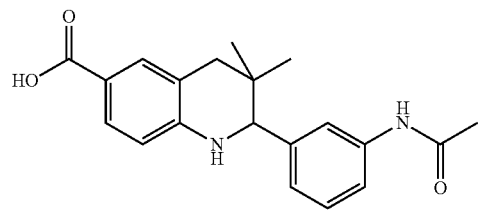 [SMILES: CC(=O)Nc1cccc(C2Nc3ccc(C(=O)O)cc3CC2(C)C)c1]

To a solution of 2-(3-aminophenyl)-3,3-dimethyl-1,2,3,4-tetrahydroquinoline-6-carboxylate (150 mg, 0.48 mmol) and N,N-diisopropylethylamine (0.16 mL, 0.97 mmol) in dichloromethane (10 mL) was added acetyl chloride (0.04 mL, 0.58 mmol) with ice cooling. The resultant mixture was kept 0° C. overnight. Thin layer chromatography (petroleum ether:ethyl acetate=3:1, Rf=0.4) showed the reaction was complete. Solvent was removed in vacuo and the residue was purified by Prep. Thin layer chromatography (petroleum ether:ethyl acetate=3:1) to afford 129 mg of methyl 2-(3-acetamidophenyl)-3,3-dimethyl-1,2,3,4-tetrahydroquinoline-6-carboxylate as a off-white solid. Yield: 71.1%.

To a mixture of methyl 2-(3-acetamidophenyl)-3,3-dimethyl-1,2,3,4-tetrahydroquinoline-6-carboxylate (129 mg, 0.37 mmol) in methanol (10 mL) and water (5 mL) was added with a solution of sodium hydroxide (249 mg, 6.22 mmol) in water (5 mL). The resultant mixture was heated to reflux for 1.5 hours. The methanol was removed under vacuum. The residue was acidified with 2 M hydrochloric acid to pH=5-6. The precipitates were collected by filtration, purified by preparative Thin layer chromatography (silica gel, petroleum ether/ethyl acetate=3:1) to afford 2-(3-acetamidophenyl)-3,3-dimethyl-1,2,3,4-tetrahydroquinoline-6-carboxylic acid as a solid. (41 mg, yield: 33.1%). MS (ES+APCI) M+1=339.1.

Example 205

2-(3-((1-Ethylpyrrolidin-2-yl)methylcarbamoyl)phenyl)-3,3-dimethyl-1,2,3,4-tetrahydroquinoline-6-carboxylic acid

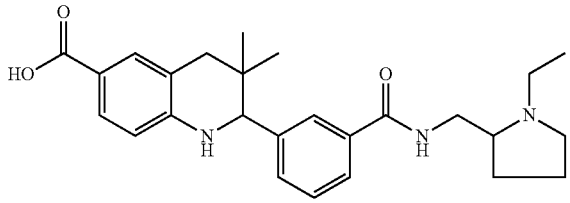 [SMILES: CCN1CCCC1CNC(=O)c1cccc(C2Nc3ccc(C(=O)O)cc3CC2(C)C)c1]

To a suspension of 3-(6-(methoxycarbonyl)-3,3-dimethyl-1,2,3,4-tetrahydroquinolin-2-yl)benzoic acid (100 mg, 0.29 mmol, 1.0 eq.) in dichloromethane (6.7 ml) was added N-hydroxybenzotriazole (59.7 mg, 0.44 mmol, 1.5 eq.) and 1-(3-dimethylaminopropyl)-3-ethylcarbodiimide.hydrochloric acid (169.7 mg, 0.88 mmol, 3.0 eq.), followed by 4-methylmorpholine (89.5 mg, 0.88 mmol) and the resultant mixture was stirred at room temperature for 40 min. Then (1-ethylpyrrolidin-2-yl)methanamine (0.33 mmol, 1.1 eq.) was added to the flask and the reaction mixture was stirred for an additional 30 min, LC-MS showed the reaction was complete. The reaction was quenched with water, separated, and the aqueous layer was extracted with dichloromethane (twice). The combined organic layers were washed with 2% sodium hydroxide aqueous solution (twice) and brine (3 times), dried over anhydrous magnesium sulfate. Removal of the solvent in vacuo gave 160 mg of methyl 2-(3-((1-ethylpyrrolidin-2-yl)methylcarbamoyl)phenyl)-3,3-dimethyl-1,2,3,4-tetrahydroquinoline-6-carboxylate as a yellow oil, which was purified by column chromatography (dichloromethane: methanol=8:1) to afford 45 mg desired product as a yellow powder, yield: 34.0%.

A mixture of methyl 2-(3-((1-ethylpyrrolidin-2-yl)methylcarbamoyl)phenyl)-3,3-dimethyl-1,2,3,4-tetrahydroquinoline-6-carboxylate (44 mg, 0.1 mmol) in methanol (1.6 mL) and 1 M sodium hydroxide aqueous solution (1.27 mL, 1.27 mmol) was heated to reflux for 30 min, LC-MS showed the reaction was complete and only the desired product formed. The solvent was concentrate in vacuo and the residue was dissolved in water and acidified with 1 M hydrochloric acid solution. The off-white precipitated solid was collected by filtration to afford 25 mg of 2-(3-((1-ethylpyrrolidin-2-yl)methylcarbamoyl)phenyl)-3,3-dimethyl-1,2,3,4-tetrahydroquinoline-6-carboxylic acid was a white solid. Yield: 58.7%. MS (ESI+APCI) M+1=436.3.

Example 206

2-(4-Fluoro-3-(3-fluorophenylsulfonamido)phenyl)-3,3-dimethyl-1,2,3,4-tetrahydroquinoline-6-carboxylic acid

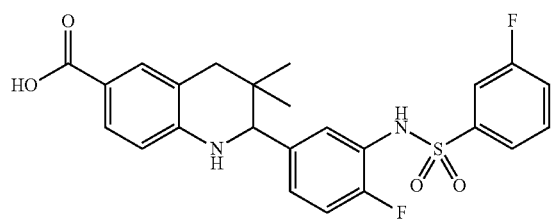 [SMILES: CC1(C)Cc2cc(C(=O)O)ccc2NC1c1ccc(F)c(NS(=O)(=O)c2cccc(F)c2)c1]

To an ice-cold mixture of 2-(3-amino-4-fluorophenyl)-3,3-dimethyl-1,2,3,4-tetrahydroquinoline-6-carboxylic acid (0.19 mmol, 1.0 eq.) in pyridine (5 mL) was added 3-fluorobenzene-1-sulfonyl chloride (0.29 mmol, 1.5 eq.) under nitrogen. Then the reaction mixture was stirred at room temperature for two hours. Thin layer chromatography and LC-MS indicated that the starting material was consumed completely. The reaction was quenched with 20 mL water extracted with ethyl acetate (20 mL×2). The combined organic layers were concentrated and the residue was purified by column chromatography (petroleum ether/ethyl acetate=1:1) to afford 2-(4-fluoro-3-(3-fluorophenylsulfonamido)phenyl)-3,3-dimethyl-1,2,3,4-tetrahydroquinoline-6-carboxylic acid as a pale yellow solid; Yield: 65%; MS (ESI+APCI) M+1=473.

Example 207

2-(3-(1-(Tert-butoxycarbonyl)azetidin-3-ylcarbamoyl)phenyl)-3,3-dimethyl-1,2,3,4-tetrahydroquinoline-6-carboxylic acid

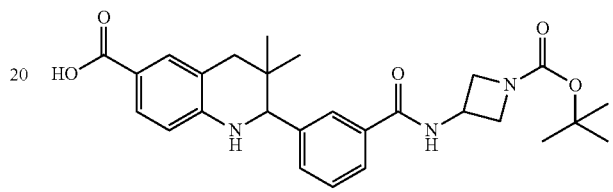

To a suspension of 3-(6-(methoxycarbonyl)-3,3-dimethyl-1,2,3,4-tetrahydroquinolin-2-yl)benzoic acid (150 mg, 0.44 mmol, 1.0 eq.) in dichloromethane (10.0 ml) was added N-hydroxy benzotriazole (89.2 mg, 0.66 mmol, 1.5 eq.) and 1-(3-dimethylaminopropyl)-3-ethylcarbodiimide.hydrochloric acid (253.0 mg, 1.32 mmol, 3.0 eq.), followed by 4-methylmorpholine (133.5 mg, 1.32 mmol) and the resultant mixture was stirred at room temperature for 30 min. Then tert-butyl 3-aminoazetidine-1-carboxylate (90.9 mg, 0.53 mmol, 1.2 eq.) was added to the flask and the reaction mixture was stirred for an additional 30 min. LC-MS showed the reaction was complete. The reaction was quenched with water, separated, and the aqueous layer was extracted with dichloromethane (twice). The combined organic layers were washed with 2% sodium hydroxide aqueous solution (twice) and brine (3 times), dried over anhydrous magnesium sulfate. Removal of the solvent in vacuo gave 234 mg of methyl 2-(3-(1-(tert-butoxycarbonyl) azetidin-3-ylcarbamoyl)phenyl)-3,3-dimethyl-1,2,3,4-tetrahydroquinoline-6-carboxylate as a white solid, which was used in next step without further purification.

A mixture of methyl 2-(3-(1-(tert-butoxycarbonyl)azetidin-3-ylcarbamoyl)phenyl)-3,3-dimethyl-1,2,3,4-tetrahydroquinoline-6-carboxylate (234 mg, 0.44 mmol of theory) in methanol (6.8 mL) and 1 M sodium hydroxide aqueous solution (5.3 mL, 5.3 mmol, 12.0 eq.) was heated to reflux for 60 min, LC-MS showed the reaction was complete and only the desired product formed. The solvent was concentrate in vacuo and the residue was dissolved in water and acidified with 1 M hydrochloric acid solution to pH=6. The white precipitated solid was extracted with tetrahydrofuran (twice). The combined organic layers were washed with brine, dried over anhydrous magnesium sulfate. Removal of the solvent gave 209 mg product as a white solid, which was purified by column chromatography (Pure ethyl acetate) to afford 78 mg of 2-(3-(1-(tert-butoxycarbonyl)azetidin-3-ylcarbamoyl)

phenyl)-3,3-dimethyl-1,2,3,4-tetrahydroquinoline-6-carboxylic acid as a white solid. Yield: 37.2%. MS (ESI+APCI) M+1=480.2.

Example 208

3,3-Dimethyl-2-(3-(1-methylazetidin-3-ylcarbamoyl) phenyl)-1,2,3,4-tetrahydroquinoline-6-carboxylic acid

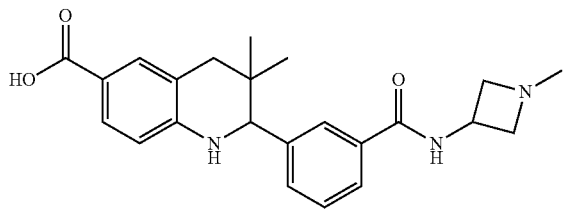 [SMILES: CN1CC(NC(=O)c2cccc(C3Nc4ccc(C(=O)O)cc4CC3(C)C)c2)C1]

To a suspension of 3-(6-(methoxycarbonyl)-3,3-dimethyl-1,2,3,4-tetrahydroquinolin-2-yl)benzoic acid (100 mg, 0.29 mmol) in dichloromethane (6.7 mL) was added N-hydroxybenzotriazole (59.7 mg, 0.44 mmol) and 1-(3-dimethylaminopropyl)-3-ethylcarbodiimide.hydrochloric acid (169.7 mg, 0.88 mmol), followed by 4-methylmorpholine (89.5 mg, 0.88 mmol) and the resultant mixture was stirred at room temperature for 40 min. Then 1-methylazetidin-3-amine (30.5 mg, 0.35 mmol) was added to the flask and the reaction mixture was stirred for an additional 60 min, LC-MS showed the reaction was complete. The reaction was quenched with water, separated, and the aqueous layer was extracted with dichloromethane (twice). The combined organic layers were washed with 2% sodium hydroxide aqueous solution (twice) and brine (3 times), dried over anhydrous magnesium sulfate. Removal of the solvent in vacuo gave 129 mg of methyl 3,3-dimethyl-2-(3-(1-methylazetidin-3-ylcarbamoyl)phenyl)-1,2,3,4-tetrahydroquinoline-6-carboxylate as a white solid, which was washed with ether to afford 103 mg desired product as a white powder, yield: 85.8%.

A mixture of methyl 3,3-dimethyl-2-(3-(1-methylazetidin-3-ylcarbamoyl)phenyl)-1,2,3,4-tetrahydroquinoline-6-carboxylate (100 mg, 0.25 mmol) in methanol (3.75 mL) and 1M sodium hydroxide aqueous solution (2.94 mL, 2.94 mmol) was heated to reflux for 1.5 h, LC-MS showed the reaction was complete and only the desired product formed. The solvent was concentrate in vacuo and the residue was dissolved in water and acidified with 1 M hydrochloric acid solution. The white precipitated solid was collected by filtration to afford 59 mg of 3,3-dimethyl-2-(3-(1-methylazetidin-3-ylcarbamoyl)phenyl)-1,2,3,4-tetrahydroquinoline-6-carboxylic acid was a white solid. Yield: 61.4%. MS (ESI+APCI) M+1=394.2.

Example 209

2-(4-Fluoro-3-(2-fluorophenylsulfonamido)phenyl)-,3-dimethyl-1,2,3,4-tetrahydroquinoline-6-carboxylic acid

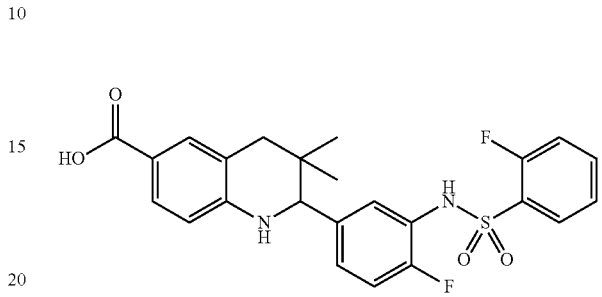

A mixture of 2-(4-fluoro-3-nitrophenyl)-3,3-dimethyl-1,2,3,4-tetrahydroquinoline-6-carboxylate (0.5 g, 0.52 mmol) in methanol (10 mL) and 1 M aqueous sodium hydroxide solution (26 mL, 26 mmol) was heated to reflux for 3 h. LC-MS showed the reaction was complete. The solvent was removed in vacuo and the residue was acidified with 1 M hydrochloric acid solution to pH=6. The precipitated white solid was collected by filtration and washed with water, dried in vacuo to afford 0.48 g of 2-(3-amino-4-fluorophenyl)-3,3-dimethyl-1,2,3,4-tetrahydroquinoline-6-carboxylic acid in quantitative yield.

To an ice-cold mixture of 2-(3-amino-4-fluorophenyl)-3,3-dimethyl-1,2,3,4-tetrahydroquinoline-6-carboxylic acid (0.19 mmol, 1.0 eq.) in pyridine (5 mL) was added 2-fluorobenzene-1-sulfonyl chloride (0.29 mmol, 1.5 eq.) under nitrogen. Then the reaction mixture was stirred at room temperature for two hours. Thin layer chromatography and LC-MS indicated that the starting material was consumed completely. The reaction was quenched with 20 mL water extracted with ethyl acetate (20 mL×2). The combined organic layers were concentrated and the residue was purified by column chromatography (petroleum ether/ethyl acetate=1:1) to afford 2-(4-fluoro-3-(2-fluorophenylsulfonamido)phenyl)-,3-dimethyl-1,2,3,4-tetrahydroquinoline-6-carboxylic acid as a pale yellow solid; Yield: 69%; MS (ESI+ APCI) M+1=473.

Example 210

3,3-Dimethyl-2-(3-(3-phenylpropanamido)phenyl)-1,2,3,4-tetrahydroquinoline-6-carboxylic acid

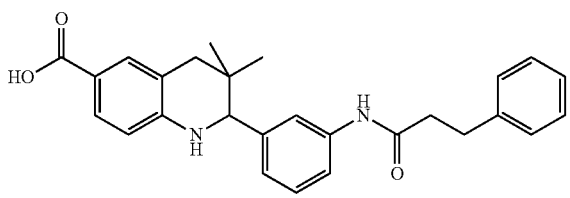 [SMILES: CC1(C)Cc2cc(C(=O)O)ccc2NC1c1cccc(NC(=O)CCc2ccccc2)c1]

To an ice-cold mixture of 2-(3-aminophenyl)-3,3-dimethyl-1,2,3,4-tetrahydroquinoline-6-carboxylate (150 mg, 0.48 mmol), 3-phenylpropanoic acid (95 mg, 0.73 mmol), N,N-diisopropyl ethylamine (0.20 mL, 1.16 mmol) in dichloromethane (10 mL) was added a solution of phosphorus oxychloride (0.06 mL, 0.63 mmol). Then the reaction mixture was stirred at room temperature overnight. LC-MS indicated that the starting material was consumed completely. Solvent was removed in vacuo and the residue was purified by Prep. Thin layer chromatography (petroleum ether/ethyl acetate=2:1) to afford 220 mg of methyl 3,3-dimethyl-2-(3-(3-phenylpropanamido)phenyl)-1,2,3,4-tetrahydroquinoline-6-carboxylate as a pale yellow solid; Yield: 90%.

To a mixture of methyl 3,3-dimethyl-2-(3-(3-phenylpropanamido)phenyl)-1,2,3,4-tetrahydroquinoline-6-carboxylate (222 mg, 0.50 mmol) in methanol (6 mL) and water (3 mL) was added a solution of sodium hydroxide (341 mg, 8.53 mmol) in water (3 mL). The resultant mixture was heated to reflux for 1 hour. The methanol was removed under vacuum. The residue was acidified with 2 M hydrochloric acid to pH=5-6. The precipitates were collected by filtration, purified by preparative Thin layer chromatography (petroleum ether/ethyl acetate=3:1) to afford 3,3-dimethyl-2-(3-(3-phenylpropanamido)phenyl)-1,2,3,4-tetrahydroquinoline-6-carboxylic acid as a solid. (134 mg, yield: 66.1%); MS (ES+APCI) M+1-water=411.1.

Example 211

2-(3-(Cyclohexanecarboxamido)-4-fluorophenyl)-3,3-dimethyl-1,2,3,4-tetrahydroquinoline-6-carboxylic acid

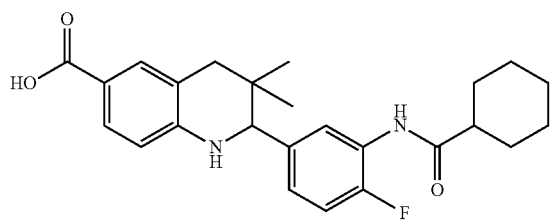 [SMILES: CC1(C)Cc2cc(C(=O)O)ccc2NC1c1ccc(F)c(NC(=O)C2CCCCC2)c1]

To an ice-cold mixture of 2-(4-fluoro-3-nitrophenyl)-3,3-dimethyl-1,2,3,4-tetrahydroquinoline-6-carboxylate (0.3 mmol, 1.0 eq.), cyclohexanecarboxylic acid (0.46 mmol, 1.5 eq.), N,N-diisopropylethylamine (0.6 mmol, 2.0 eq.) in dichloromethane (5 mL) was added a solution of phosphorus oxychloride (0.36 mmol, 1.2 eq.). Then the reaction mixture was stirred at room temperature for 2.5 hours. LC-MS indicated that the starting material was consumed completely. The reaction was quenched by 20 mL water extracted with ethyl acetate (20 mL×2). The combined organic layer was concentrated and the residue was purified by column chromatography (petroleum ether/ethyl acetate=3:1) to afford methyl 2-(3-(cyclohexanecarboxamido)-4-fluorophenyl)-3,3-dimethyl-1,2,3,4-tetrahydroquinoline-6-carboxylate as a pale yellow solid; Yield: 86%; MS (ESI+APCI) M+1=439.

A mixture of methyl 2-(3-(cyclohexanecarboxamido)-4-fluorophenyl)-3,3-dimethyl-1,2,3,4-tetrahydroquinoline-6-carboxylate (0.26 mmol, 1.0 eq.) and 4.5 mL sodium hydroxide (1 mol/L) in 3 mL methanol was stirred at reflux for 1-2 h. LC-MS indicated that the starting material was consumed completely. The methanol was removed by reduced pressure. The residue was acidified pH to 5-6 with 1 M hydrochloric acid. A lot of precipitates were formed and collected by filtration to afford 2-(3-(cyclohexanecarboxamido)-4-fluorophenyl)-3,3-dimethyl-1,2,3,4-tetrahydroquinoline-6-carboxylic acid as a white solid; Yield: 74%; MS (ESI+APCI) M−1=423.

Example 212

2-(4-(3-Fluorophenylsulfonamido)phenyl)-3,3-dimethyl-1,2,3,4-tetrahydroquinoline-6-carboxylic acid

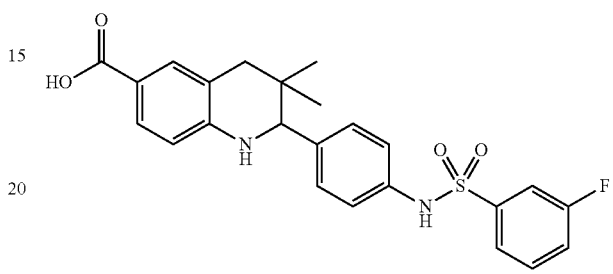

To a solution of 2-(4-aminophenyl)-3,3-dimethyl-1,2,3,4-tetrahydroquinoline-6-carboxylic acid (50 mg, 0.17 mmol) in 5 mL of pyridine was added 3-fluorobenzene-1-sulfonyl chloride (41 mg 0.21 mmol) below 0° C. The mixture was stirred at room temperature under nitrogen overnight. Pyridine was removed in vacuo and the residue was purified by preparative thin layer chromatography to afford 2-(4-(3-fluorophenylsulfonamido)phenyl)-3,3-dimethyl-1,2,3,4-tetrahydroquinoline-6-carboxylic acid as a yellow solid, 43 mg, yield: 62%. MS (ESI+APCI) M+1=455.50.

Example 213

2-(4-(2-Fluorophenylsulfonamido)phenyl)-3,3-dimethyl-1,2,3,4-tetrahydroquinoline-6-carboxylic acid

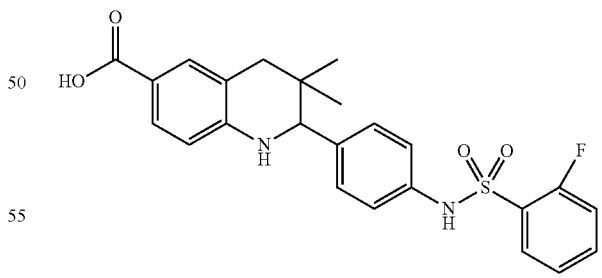

To a solution of 2-(4-aminophenyl)-3,3-dimethyl-1,2,3,4-tetrahydroquinoline-6-carboxylic acid (50 mg, 0.17 mmol) in 5 mL of pyridine was added 2-fluorobenzene-1-sulfonyl chloride (41 mg 0.21 mmol) below 0° C. The mixture was stirred at room temperature under nitrogen overnight. Pyridine was removed in vacuo and the residue was purified by preparative thin layer chromatography to afford 2-(4-(2-fluorophenylsulfonamido)phenyl)-3,3-dimethyl-1,2,3,4-tetrahydroquinoline-6-carboxylic acid as a yellow solid, 43 mg, yield: 62%. MS (ESI+APCI) M+1=455.50.

Example 214

2-(2-(Cyclopropanecarboxamido)phenyl)-3,3-dimethyl-1,2,3,4-tetrahydroquinoline-6-carboxylic acid

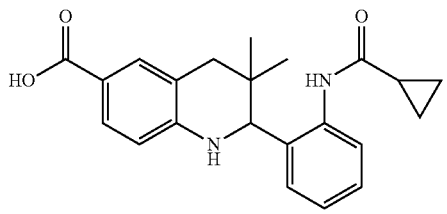 [SMILES: CC1(C)Cc2cc(C(=O)O)ccc2NC1c1ccccc1NC(=O)C1CC1]

A mixture of methyl 4-aminobenzoate (4.0 g, 26.5 mmol) and 2-nitrobenzaldehyde (4.2 g, 27.7 mmol) in toluene (50 mL) was heated to reflux with a Dean-Stark separator overnight. ¹HNMR showed the reaction was complete. The reaction mixture was cooled to room temperature and lots of yellow solid formed, which was collected by filtration to afford 6.3 g of (E)-methyl 4-(2-nitrobenzylideneamino) benzoate. Yield: 84%.

To a mixture of (E)-methyl 4-(2-nitrobenzylideneamino) benzoate (3.26 g, 11.5 mmol) and yttrium(III) trifluoromethanesulfonate (140 mg, 0.27 mmol) in tetrahydrofuran (28 mL) was added isobutylaldehyde (1.9 mL, 20.6 mmol) at room temperature under nitrogen, then the resultant mixture was stirred at room temperature overnight. Thin layer chromatography and LC-MS showed the starting material was completely consumed. The reaction was quenched with water and separated. The aqueous layer was extracted with ethyl acetate twice and the combined organic layers were concentrated in vacuo. The residue was purified by column chromatography (petroleum ether/ethyl acetate=3:1) to afford 1.34 g of methyl 4-hydroxy-3,3-dimethyl-2-(2-nitrophenyl)-1,2,3,4-tetrahydroquinoline-6-carboxylate as a yellow solid. Yield: 32.7%. To an ice-cooled mixture of methyl 4-hydroxy-3,3-dimethyl-2-(2-nitrophenyl)-1,2,3,4-tetrahydroquinoline-6-carboxylate (1.5 g, 4.2 mmol) and triethylsilane (1.48 g, 12.6 mmol) in dichloro methane (150 mL) was added dropwise a solution of trifluoroacetic acid (1.92 g, 16.8 mmol) in dichloromethane (50 mL) over 45 min under nitrogen. The mixture was kept at 0° C. at room temperature for 12 h. Thin layer chromatography and LC-MS showed the starting material was completely consumed. Solid sodium carbonate (2.0 g) was added to the reaction mixture and stirred for 10 min., filtered. The filtrate was concentrated and purified by column chromatography (petroleum ether/ethyl acetate=3:1) to afford 1.26 g of methyl 2-(2-aminophenyl)-3,3-dimethyl-1,2,3,4-tetrahydroquinoline-6-carboxylate as a yellow solid. Yield: 86%.

To a mixture of methyl 2-(2-aminophenyl)-3,3-dimethyl-1,2,3,4-tetrahydroquinoline-6-carboxy late (1.26 g, 3.7 mmol) and iron powder (4.2 g, 74 mmol) in ethanol (30 mL) was added catalytic amount of concentrated hydrochloric acid solution, the resultant mixture was heated to reflux for 3 h. Thin layer chromatography showed the reaction was complete and the reaction mixture was separated by filtration. The filter cake was washed with ethyl acetate and the combined filtrate was concentrated in vacuo. The residue was purified by column chromatography (petroleum ether/ethyl acetate=3:1) to afford 1.04 g of methyl 2-(2-aminophenyl)-3,3-dimethyl-1,2,3,4-tetrahydroquinoline-6-carboxylate as a yellow solid. Yield: 90%.

To an ice-cold mixture of methyl 2-(2-aminophenyl)-3,3-dimethyl-1,2,3,4-tetrahydroquinoline-6-carboxylate (80 mg, 0.26 mmol, 1.0 eq.), cyclopropanecarboxylic acid (33 mg, 0.34 mmol, 1.5 eq.), N,N-diisopropylethylamine (63 mg, 0.51 mmol, 2.0 eq.) in dichloromethane (4 mL) was added a solution of phosphorus oxychloride (45 mg, 0.31 mmol, 1.2 eq.). Then the reaction mixture was stirred at room temperature for 30 min. Thin layer chromatography and LC-MS indicated that the starting material was consumed completely. The reaction was quenched with 20 mL water and extracted with ethyl acetate (20 mL×2). The combined organic layers were concentrated in vacuo and the residue was purified by column chromatography on silica gel (petroleum ether/ethyl acetate=2:1) to afford 57 mg of methyl 2-(2-(cyclopropanecarboxamido)phenyl)-3,3-dimethyl-1,2,3,4-tetrahydroquinoline-6-carboxylate as a pale yellow solid; yield: 58%. MS (ESI+APCI) M+1=379.

A mixture of methyl 2-(2-(cyclopropanecarboxamido)phenyl)-3,3-dimethyl-1,2,3,4-tetrahydroquinoline-6-carboxylate (57 mg, 0.15 mmol, 1.0 eq.) and 1.8 mL aqueous solution of sodium hydroxide (2 M, 3.76 mmol, 25 eq.) in tetrahydrofuran (3 mL) was stirred at reflux for 3 h. Thin layer chromatography indicated that the starting material was consumed completely. The tetrahydrofuran was removed under reduced pressure and the residue was acidified to pH 5-6 with 1 M hydrochloric acid. Then a lot of white precipitates were formed and collected by filtration to afford 47 mg of 2-(2-(cyclopropanecarboxamido)phenyl)-3,3-dimethyl-1,2,3,4-tetrahydroquinoline-6-carboxylic acid as a white solid; yield: 86%. MS (ESI+APCI) M+1=365.

Example 215

2-(4-(Cyclobutanecarboxamido)phenyl)-3,3-dimethyl-1,2,3,4-tetrahydroquinoline-6-carboxylic acid

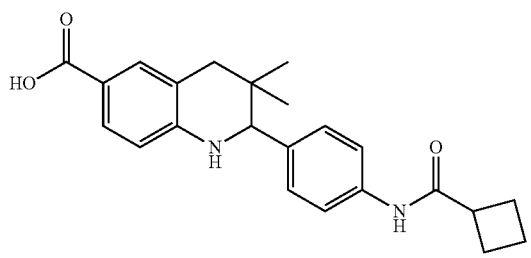 [SMILES: CC1(C)Cc2cc(C(=O)O)ccc2NC1c1ccc(NC(=O)C2CCC2)cc1]

To a solution of methyl 2-(4-aminophenyl)-3,3-dimethyl-1,2,3,4-tetrahydroquinoline-6-carboxylate (50 mg, 0.16 mmol), cyclobutanecarboxylic acid (0.025 mL, 0.24 mmol) and N,N-diisopropylethylamine (0.05 mL, 0.32 mmol) in dichloromethane (5 mL) was added phosphorus oxychloride (0.02 mL, 0.24 mmol) via syringe below 0° C. The mixture was stirred at room temperature for 16 hrs under nitrogen. The solvent was removed and the residue was washed with dichloromethane/petroleum ether, the precipitate was collected to afford methyl 2-(4-(cyclobutane carboxamido)phenyl)-3,3-dimethyl-1,2,3,4-tetrahydroquinoline-6-carboxylate as a yellow solid, 42 mg, yield: 67%.

To a mixture of methyl 2-(4-(cyclobutanecarboxamido)phenyl)-3,3-dimethyl-1,2,3,4-tetrahydroquinoline-6-carboxylate (42 mg, 0.21 mmol) in methanol (3 mL) and water (1.5 mL) was treated with a solution of sodium hydroxide (133 mg, 2.63 mmol) in water (1.5 mL). The resultant mixture was heated to reflux until the completion of the reaction (monitored by thin layer chromatography). The methanol was removed under vacuum. The residue was acidified with 2M hydrochloric acid to pH=1. The precipitates were collected by filtration to afford 30 mg of 2-(4-(cyclobutanecarboxamido)phenyl)-3,3-dimethyl-1,2,3,4-tetrahydroquinoline-6-carboxylic acid as a yellow solid Yield: 84%. MS (ESI+APCI) M+1=379.2.

Example 216

2-(2-(Cyclobutanecarboxamido)phenyl)-3,3-dimethyl-1,2,3,4-tetrahydroquinoline-6-carboxylic acid

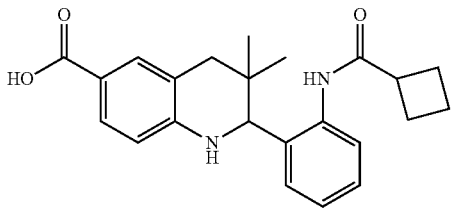 [SMILES: CC1(C)Cc2cc(C(=O)O)ccc2NC1c1ccccc1NC(=O)C1CCC1]

To an ice-cold mixture of methyl 2-(2-aminophenyl)-3,3-dimethyl-1,2,3,4-tetrahydroquinoline-6-carboxylate (80 mg, 0.26 mmol, 1.0 eq.), cyclobutanecarboxylic acid (36 mg, 0.34 mmol, 1.5 eq.), N,N-diisopropylethylamine (63 mg, 0.51 mmol, 2.0 eq.) in dichloromethane (4 mL) was added a solution of phosphorus oxychloride (45 mg, 0.31 mmol, 1.2 eq.). Then the reaction mixture was stirred at room temperature for 30 min. Thin layer chromatography and LC-MS indicated that the starting material was consumed completely. The reaction was quenched with 20 mL water and extracted with ethyl acetate (20 mL×2). The combined organic layers were concentrated in vacuo and the residue was purified by column chromatography on silica gel (petroleum ether/ethyl acetate=2:1) to afford 54 mg of methyl 2-(2-(cyclobutanecarboxamido)phenyl)-3,3-dimethyl-1,2,3,4-tetrahydroquinoline-6-carboxylate as a pale yellow solid; yield: 53%. MS (ESI+APCI) M+1=393.2.

A mixture of methyl 2-(2-(cyclobutanecarboxamido)phenyl)-3,3-dimethyl-1,2,3,4-tetrahydroquinoline-6-carboxylate (54 mg, 0.14 mmol, 1.0 eq.) and 1.8 mL aqueous solution of sodium hydroxide (2 M, 3.57 mmol, 25 eq.) in tetrahydrofuran (3 mL) was stirred at reflux for 3 h. Thin layer chromatography indicated that the starting material was consumed completely. The tetrahydrofuran was removed under reduced pressure and the residue was acidified to pH 5-6 with 1 M hydrochloric acid. Then a lot of white precipitates were formed and collected by filtration to afford 40 mg of 2-(2-(cyclobutanecarboxamido)phenyl)-3,3-dimethyl-1,2,3,4-tetrahydroquinoline-6-carboxylic acid as a white solid; yield: 76%. MS (ESI+APCI) M+1=379.

Example 217

2-(4-(Cyclohex-1-enecarboxamido)phenyl)-3,3-dimethyl-1,2,3,4-tetrahydroquinoline-6-carboxylic acid

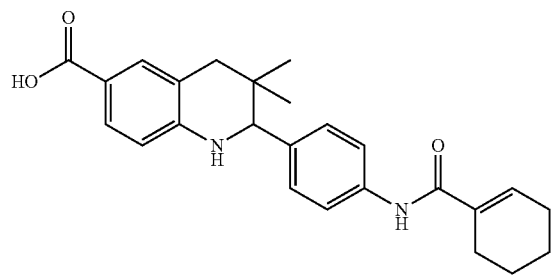 [SMILES: CC1(C)Cc2cc(C(=O)O)ccc2NC1c1ccc(NC(=O)C2=CCCCC2)cc1]

To a solution of methyl 2-(4-aminophenyl)-3,3-dimethyl-1,2,3,4-tetrahydroquinoline-6-carboxylate (150 mg, 0.48 mmol), cyclohex-1-enecarboxylic acid (73 mg, 0.58 mmol) and N,N-diisopropylethylamine (0.2 mL, 1.2 mmol,) in dichloromethane (5 mL) was added phosphorus oxychloride (0.06 mL, 0.58 mmol) via syringe below 0° C. The mixture was stirred at room temperature for 16 hrs under nitrogen. The solvent was removed and the residue was washed with dichloromethane/petroleum ether, the precipitate was collected to afford methyl 2-(4-(cyclohex-1-enecarboxamido)phenyl)-3,3-dimethyl-1,2,3,4-tetrahydroquinoline-6-carboxylate as a yellow solid, 130 mg, yield: 60%.

A mixture of methyl 2-(4-(cyclohex-1-enecarboxamido)phenyl)-3,3-dimethyl-1,2,3,4-tetrahydroquinoline-6-carboxylate (217 mg, 0.52 mmol) in methanol (3 mL) and water (1.5 mL) was treated with a solution of sodium hydroxide (353 mg, 2.63 mmol) in water (1.5 mL) was heated to reflux until the completion of the reaction (monitored by Thin layer chromatography). The methanol was removed under vacuum. The residue was acidified with 2M hydrochloric acid to pH=1. The precipitates were collected by filtration to afford 100 mg of 2-(4-(cyclohex-1-enecarboxamido)phenyl)-3,3-dimethyl-1,2,3,4-tetrahydroquinoline-6-carboxylic acid as a yellow solid Yield: 53%. MS (ESI+APCI) M+1=405.2.

Example 218

2-(2-(4-Fluorophenylsulfonamido)phenyl)-3,3-dimethyl-1,2,3,4-tetrahydroquinoline-6-carboxylic acid

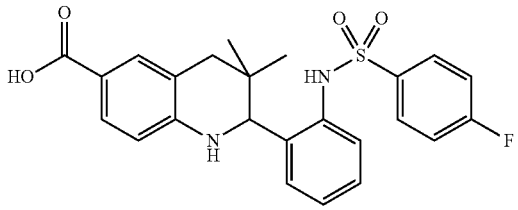 [SMILES: CC1(C)Cc2cc(C(=O)O)ccc2NC1c1ccccc1NS(=O)(=O)c1ccc(F)cc1]

To an ice-cold mixture of methyl 2-(2-aminophenyl)-3,3-dimethyl-1,2,3,4-tetrahydroquinoline-6-carboxylate (60 mg, 0.19 mmol, 1.0 eq.) and pyridine (0.3 mL, 3.8 mmol, 20 eq.) in dichloro methane (5 mL) was added 4-fluorobenzene-1- sulfonyl chloride (51 mg, 0.29 mmol, 1.5 eq.) under nitrogen. Then the reaction mixture was stirred at room temperature for two hours. Thin layer chromatography and LC-MS indicated that the starting material was consumed completely. The reaction was quenched with 20 mL water extracted with ethyl acetate (20 mL×2). The combined organic layers were concentrated and the residue was purified by silica gel (petroleum ether/ethyl acetate=2:1) to afford 66 mg of methyl 24244-fluorophenylsulfonamido)phenyl)-3,3-dimethyl-1,2,3,4-tetrahydroquinoline-6-carboxylate as a pale yellow solid; yield: 74%; MS (ESI+APCI) M+1=469.

A mixture of methyl 2-(2-(4-fluorophenylsulfonamido)phenyl)-3,3-dimethyl-1,2,3,4-tetrahydroquinoline-6-carboxylate (66 mg, 0.14 mmol, 1.0 eq.) and 1.4 mL aqueous solution of sodium hydroxide (2 M, 2.8 mmol, 20 eq.) in tetrahydrofuran (4 mL) was stirred at reflux for 3 h. Thin layer chromatography indicated that the starting material was consumed completely. The tetrahydrofuran was removed under reduced pressure and the residue was acidified to pH 5-6 with 1 M hydrochloric acid. Then a lot of white precipitates were formed and collected by filtration to afford 48 mg of 2-(2-(4-fluorophenylsulfonamido)phenyl)-3,3-dimethyl-1,2,3,4-tetrahydroquinoline-6-carboxylic acid as a white solid; yield: 76%. MS (ESI+APCI) M+1=455.

Example 219

2-(2-(2-Fluorophenylsulfonamido)phenyl)-3,3-dimethyl-1,2,3,4-tetrahydroquinoline-6-carboxylic acid

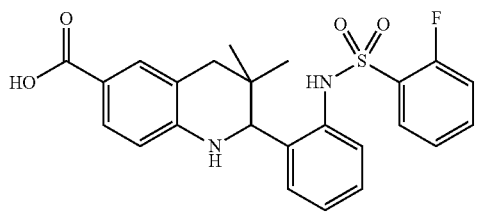

To an ice-cold mixture of methyl 2-(2-aminophenyl)-3,3-dimethyl-1,2,3,4-tetrahydroquinoline-6-carboxylate (60 mg, 0.19 mmol, 1.0 eq.) and pyridine (0.3 mL, 3.8 mmol, 20 eq.) in dichloro methane (5 mL) was added 2-fluorobenzene-1-sulfonyl chloride (51 mg, 0.29 mmol, 1.5 eq.) under nitrogen. Then the reaction mixture was stirred at room temperature for two hours. Thin layer chromatography and LC-MS indicated that the starting material was consumed completely. The reaction was quenched with 20 mL water extracted with ethyl acetate (20 mL×2). The combined organic layers were concentrated and the residue was purified by silica gel (petroleum ether/ethyl acetate=2:1) to afford 62 mg of methyl 24242-fluorophenylsulfonamido)phenyl)-3,3-dimethyl-1,2,3,4-tetrahydroquinoline-6-carboxylate as a pale yellow solid; yield: 70%; MS (ESI+APCI) M+1=469.

A mixture of methyl 2-(2-(2-fluorophenylsulfonamido)phenyl)-3,3-dimethyl-1,2,3,4-tetrahydroquinoline-6-carboxylate (62 mg, 0.13 mmol, 1.0 eq.) and 1.4 mL aqueous solution of sodium hydroxide (2 M, 2.7 mmol, 20 eq.) in tetrahydrofuran (4 mL) was stirred at reflux for 3 h. Thin layer chromatography indicated that the starting material was consumed completely. The tetrahydrofuran was removed under reduced pressure and the residue was acidified to pH 5-6 with 1 M hydrochloric acid. Then a lot of white precipitates were formed and collected by filtration to afford 47 mg of 2-(2-(2-fluorophenylsulfonamido)phenyl)-3,3-dimethyl-1,2,3,4-tetrahydroquinoline-6-carboxylic acid as a white solid; yield: 79%. MS (ESI+APCI) M+1=455.

Example 220

3,3-Dimethyl-2-(2-(phenylsulfonamido)phenyl)-1,2,3,4-tetrahydroquinoline-6-carboxylic acid

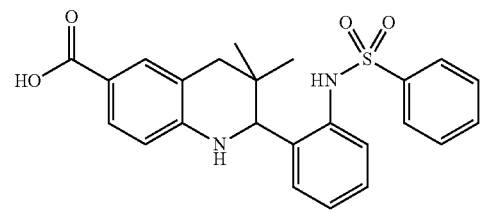 [SMILES: CC1(C)Cc2cc(C(=O)O)ccc2NC1c1ccccc1NS(=O)(=O)c1ccccc1]

To an ice-cold mixture of methyl 2-(2-aminophenyl)-3,3-dimethyl-1,2,3,4-tetrahydroquinoline-6-carboxylate (60 mg, 0.19 mmol, 1.0 eq.) and pyridine (0.3 mL, 3.8 mmol, 20 eq.) in dichloro methane (5 mL) was added benzenesulfonyl chloride (51 mg, 0.29 mmol, 1.5 eq.) under nitrogen. Then the reaction mixture was stirred at room temperature for two hours. Thin layer chromatography and LC-MS indicated that the starting material was consumed completely. The reaction was quenched with 20 mL water extracted with ethyl acetate (20 mL×2). The combined organic layers were concentrated and the residue was purified by silica gel (petroleum ether/ethyl acetate=2:1) to afford 70 mg of methyl 3,3-dimethyl-2-(2-(phenylsulfonamido)phenyl)-1,2,3,4-tetrahydroquinoline-6-carboxylate as a pale yellow solid; yield: 85%; MS (ESI+APCI) M+1=451.

A mixture of methyl 3,3-dimethyl-2-(2-(phenylsulfonamido)phenyl)-1,2,3,4-tetrahydroquinoline-6-carboxylate (70 mg, 0.16 mmol, 1.0 eq.) and 1.6 mL aqueous solution of sodium hydroxide (2 M, 3.3 mmol, 20 eq.) in tetrahydrofuran (4 mL) was stirred at reflux for 3 h. Thin layer chromatography indicated that the starting material was consumed completely. The tetrahydrofuran was removed under reduced pressure and the residue was acidified to pH 5-6 with 1 M hydrochloric acid. Then a lot of white precipitates were formed and collected by filtration to afford 58 mg of 3,3-dimethyl-2-(2-(phenylsulfonamido)phenyl)-1,2,3,4-tetrahydroquinoline-6-carboxylic acid as a white solid; yield: 83%. MS (ESI+APCI) M+1=437.

Example 221

2-(3-(N-isopropylsulfamoyl)phenyl)-3,3-dimethyl-1,2,3,4-tetrahydroquinoline-6-carboxylic acid

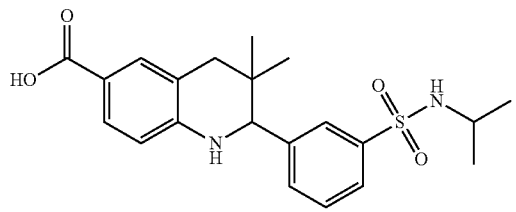 [SMILES: CC(C)NS(=O)(=O)c1cccc(C2Nc3ccc(C(=O)O)cc3CC2(C)C)c1]

To a stirred solution of cuprous chloride (90 mg, 0.91 mmol) in acetic acid (60 mL) was bubbled with sulfur dioxide gas for 6 h at room temperature. A mixture of methyl 2-(3-aminophenyl)-3,3-dimethyl-1,2,3,4-tetrahydroquinoline-6-carboxylate (992 mg, 3.20 mmol) in conc. hydrochloric acid (30 mL) and acetic acid (10 mL) was stirred for 1 hour. After cooling to −10° C., a solution of sodium nitrite (334 mg, 4.84 mmol) in water (7 mL) was added dropwise below −10° C. The resulting mixture was stirred for 1 h at −10° C. The prepared sulfur dioxide-salt solution was added to the solution above at −10° C. After addition, the mixture was stirred for 24 h at room temperature. The reaction mixture was quenched onto 100 g of crushed ice. The mixture was extracted with dichloromethane (40 mL, four times). The combined organic layers were washed with water (40 mL, twice), saturated aqueous Sodium bicarbonate solution (30 mL, twice), and saturated brine (40 mL) and dried over anhydrous magnesium sulfate. Anhydrous magnesium sulfate was removed by filtration, and the organic solvent was evaporated under reduced pressure to afford 1.0 g of methyl 2-(3-(chlorosulfonyl)phenyl)-3,3-dimethyl-3,4-dihydroquinoline-6-carboxylate. MS (ESI+APCI) M+1=394.

To a stirred solution of methyl 2-(3-(chlorosulfonyl)phenyl)-3,3-dimethyl-3,4-dihydroquinoline-6-carboxylate (393 mg, 1.0 mmol) in dichloromethane (4 mL) was added propan-2-amine (60 mg, 1.0 mmol) and N,N-diisopropylethylamine (258 mg, 2.0 mmol). The resultant mixture was stirred overnight. The mixture was purified on preparative Thin layer chromatography to afford 245 mg of methyl 2-(3-(N-isopropylsulfamoyl)phenyl)-3,3-dimethyl-3,4-dihydroquinoline-6-carboxylate, which was used directly.

To a stirred solution of methyl 2-(3-(N-isopropylsulfamoyl)phenyl)-3,3-dimethyl-3,4-dihydroquinoline-6-carboxylate (245 mg, 0.59 mmol) in methanol (5 mL) was added 10% Pd/C (130 mg). The mixture was hydrogenated by a $H_2$ balloon. After filtration, the filtrated was concentrated and purified on preparative Thin layer chromatography to afford 120 mg of methyl 2-(3-(N-isopropylsulfamoyl)phenyl)-3,3-dimethyl-1,2,3,4-tetrahydroquinoline-6-carboxylate as syrup. (Yield: 28%, three steps.)

To a stirred solution of methyl 2-(3-(N-isopropylsulfamoyl)phenyl)-3,3-dimethyl-1,2,3,4-tetrahydroquinoline-6-carboxylate (120 mg, 0.288 mmol) in methanol/tetrahydrofuran (4 mL/4 mL) was added 1N sodium hydroxide (4.32 mL). The resultant mixture was heated to reflux for 1.5 h. Organic solvent was removed and the residue was dissolved in water. The aqueous layer was acidified to pH=4. The precipitates were filtered, and redissolved in tetrahydrofuran, dried over anhydrous magnesium sulfate. anhydrous magnesium sulfate was removed, and after evaporation, the residue was treated with dichloromethane to afford 33 mg of 2-(3-(N-isopropylsulfamoyl)phenyl)-3,3-dimethyl-1,2,3,4-tetrahydroquinoline-6-carboxylic acid (Yield: 28%). MS (ESI+APCI) M+1=403.1.

Example 222

2-(2-(3-Fluorophenylsulfonamido)phenyl)-3,3-dimethyl-1,2,3,4-tetrahydroquinoline-6-carboxylic acid

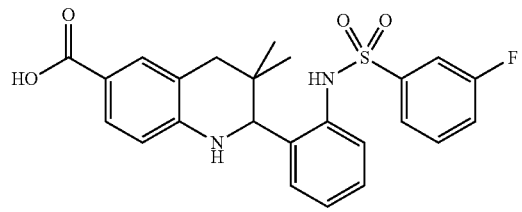 [SMILES: CC1(C)Cc2cc(C(=O)O)ccc2NC1c1ccccc1NS(=O)(=O)c1cccc(F)c1]

To a stirred solution of methyl 2-(2-aminophenyl)-3,3-dimethyl-1,2,3,4-tetrahydroquinoline-6-carboxylate (1.0 g, 3.22 mmol, 1.0 eq.) in pyridine (5 mL) and dichloro methane (20 mL) at 0° C. was dropwise a solution of 3-fluorobenzene-1-sulfonyl chloride (940 mg, 4.83 mmol, 1.5 eq.) in dichloromethane (30 mL). The mixture was stirred at room temperature for 6 h. Thin layer chromatography and LC-MS showed reaction completed. The mixture was quenched with 50 mL water and extracted with ethyl acetate (100 mL×3). The combined organic layers were dried over anhydrous sodium sulfate and evaporated to afford 1.987 g of methyl 2-(2-(3-fluorophenylsulfonamido)phenyl)-3,3-dimethyl-1,2,3,4-tetrahydroquinoline-6-carboxylate (pyridine included) as light yellow solid, which was used in next step without further purification.

To a stirred solution of methyl 2-(2-(3-fluorophenylsulfonamido)phenyl)-3,3-dimethyl-1,2,3,4-tetrahydroquinoline-6-carboxylate (1.99 g, 4.2 mmol, 1.0 eq.) in tetrahydrofuran/methanol (25 mL/25 mL) was added sodium hydroxide (24 mL, 22.63 mmol, 5.4 eq.). The mixture was heated to reflux and stirred for 5 h. LC-MS indicated that 2005467-032-01 was consumed. The mixture was concentrated and the residue was dissolved in water. The aqueous layer was basified to pH=4 by 1M hydrochloric acid. The precipitation was filtered, washed with water and dried to give 1.357 g of 2-(2-(3-fluorophenylsulfonamido)phenyl)-3,3-dimethyl-1,2,3,4-tetrahydroquinoline-6-carboxylic acid as off-white solid. yield: 92.7% (for two steps). MS (ESI+APCI) M+1=455.2.

Example 223

3,3-Dimethyl-2-(2-(methylsulfonamido)phenyl)-1,2,3,4-tetrahydroquinoline-6-carboxylic acid

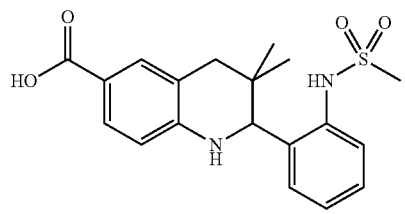 [SMILES: CC1(C)Cc2cc(C(=O)O)ccc2NC1c1ccccc1NS(C)(=O)=O]

To a stirred solution of methyl 2-(2-aminophenyl)-3,3-dimethyl-1,2,3,4-tetrahydroquinoline-6-carboxylate (1.0 g, 3.22 mmol, 1.0 eq.) in pyridine (5 mL, 0.0644 mL, 20.0 eq.) and dichloro methane (20 mL) at 0 C was added dropwise a solution of methanesulfonyl chloride in dichloromethane (30 mL). The mixture was stirred at room temperature for 4 h. Thin layer chromatography and LC-MS showed the reaction was complete. The mixture was quenched with 50 mL water and extracted with ethyl acetate (100 mL×2). The combined organic layers were dried over anhydrous sodium sulfate and evaporated to afford 1.475 g of methyl 3,3-dimethyl-2-(2-(methylsulfonamido)phenyl)-1,2,3,4-tetrahydroquinoline-6-carboxylate (pyridine included) as light yellow solid, which was used in next step without further purification.

To a stirred solution of methyl 3,3-dimethyl-2-(2-(methylsulfonamido)phenyl)-1,2,3,4-tetrahydroquinoline-6-carboxylate (1.475 g, 3.769 mmol) in tetrahydrofuran/methanol (30 mL/30 mL) was added sodium hydroxide (26.5 mL, 53.126 mmol, 14.1 eq.). The mixture was heated to reflux and stirred for 0.5 h. LC-MS indicated that the reaction was completed. The mixture was concentrated and the residue was dissolved in water. The aqueous layer was basified to pH=4 by 1M hydrochloric acid. The precipitation was filtered, washed with water and dried to give 1.45 g of 3,3-dimethyl-2-(2-(methylsulfonamido)phenyl)-1,2,3,4-tetrahydroquinoline-6-carboxylic acid as off-white solid, yield: 86.3% (for two steps). MS (ESI+APCI) M+1=375.1.

Example 224

3,3-Dimethyl-2-(3-(1-methylpyrrolidin-3-ylcarbamoyl)phenyl)-1,2,3,4-tetrahydroquinoline-8-carboxylic acid

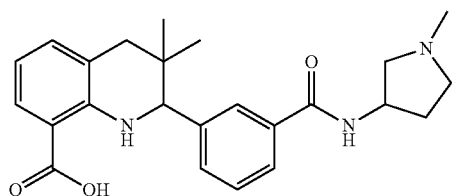 [SMILES: CN1CCC(NC(=O)c2cccc(C3Nc4c(cccc4C(=O)O)CC3(C)C)c2)C1]

To a mixture of methyl 2-aminobenzoate (0.77 g, 5.1 mmol) and benzyl 3-formylbenzoate (1.23 g, 5.1 mmol) in tetrahydrofuran (20.5 mL) was added isobutyl aldehyde (0.48 g, 6.68 mmol), followed by yttrium(III) trifluoromethanesulfonate (159 mg, 0.26 mmol), the reaction mixture was stirred at room temperature under nitrogen atmosphere for 23 h, Thin layer chromatography (petroleum ether: ethyl acetate=10:1) showed the reaction was nearly complete. The reaction was quenched by brine and separated. The aqueous layer was extracted with Ethyl acetate (twice) and the combined organic layers were washed with brine, dried over anhydrous magnesium sulfate. Removal of the solvent in vacuo and the residue was purified by column chromatography (petroleum ether: ethyl acetate=20:1) to afford 0.66 g of methyl 2-(3-(benzyloxycarbonyl)phenyl)-4-hydroxy-3,3-dimethyl-1,2,3,4-tetrahydroquinoline-8-carboxylate as a yellow oil, which was used in next step without further purification.

To a solution of methyl 2-(3-(benzyloxycarbonyl)phenyl)-4-hydroxy-3,3-dimethyl-1,2,3,4-tetrahydroquinoline-8-carboxylate (0.66 g, 1.49 mmol), triethylsilane (0.5 g, 4.3 mmol) in dichloro methane (10 mL) was added a solution of trifluoroacetic acid (0.69 g, 6.1 mmol), which was placed in a drop funnel, under nitrogen with ice cooling. Upon completion of addition, the resulting mixture was allowed to warm back to room temperature naturally overnight. Thin layer chromatography (petroleum ether: ethyl acetate=20:1) showed the reaction was complete. The reaction mixture was basified with solid sodium carbonate to pH=6 and filtered. The filtrate was concentrated in vacuo and the residual was purified by column chromatography (petroleum ether: ethyl acetate=25:1) to give 109 mg of methyl 2-(3-(benzyloxycarbonyl)phenyl)-3,3-dimethyl-1,2,3,4-tetrahydroquinoline-8-carboxylate as a off-yellow solid, yield: 39.6%.

A mixture of methyl 2-(3-(benzyloxycarbonyl)phenyl)-3,3-dimethyl-1,2,3,4-tetrahydroquinoline-8-carboxylate (108 mg, 0.25 mmol), Pd/C (31.6 mg) in methanol/tetrahydrofuran (V/V=1/1, 10 mL) was treated with $H_2$ at room temperature for 19 h Thin layer chromatography (petroleum ether: ethyl acetate=5:1) showed the reaction was complete. The mixture was separated by filtration and the filtrate was concentrated in vacuo to give 73 mg white solid, which was recrystallized from dichloromethane/Hexane to afford 63 mg of 3-(8-(methoxycarbonyl)-3,3-dimethyl-1,2,3,4-tetrahydroquinolin-2-yl)benzoic acid as white powder. Yield: 73.8%.

To a suspension of 3-(8-(methoxycarbonyl)-3,3-dimethyl-1,2,3,4-tetrahydroquinolin-2-yl)benzoic acid (63 mg, 0.19 mmol) in dichloromethane (5.0 mL) was added N-hydroxybenzotriazole (37.6 mg, 0.28 mmol) and 1-(3-dimethylaminopropyl)-3-ethylcarbodiimide.hydrochloric acid (106.7 mg, 0.56 mmol), followed by 4-methylmorpholine (56.3 mg, 0.56 mmol) and the resultant mixture was stirred at room temperature for 1 h., then 1-methylpyrrolidin-3-amine (27.9 mg, 0.28 mmol) was added to the flask and the reaction mixture was stirred for an additional 1 h. LC-MS showed the reaction complete. The reaction was quenched with water and separated. The aqueous layer was extracted with dichloromethane (twice) and the combined organic layers were washed with 5% sodium hydroxide aqueous solution (twice) and water (3 times), dried over anhydrous magnesium sulfate. Removal of the solvent in vacuo gave 76 mg of methyl 3,3-dimethyl-2-(3-(1-methylpyrrolidin-3-ylcarbamoyl)phenyl)-1,2,3,4-tetrahydroquinoline-8-carboxylate as a white solid, which was used in next step without further purification.

A mixture of methyl 3,3-dimethyl-2-(3-(1-methylpyrrolidin-3-ylcarbamoyl)phenyl)-1,2,3,4-tetrahydroquinoline-8-carboxylate (76 mg, 0.18 mmol) in methanol (2.7 mL) and sodium hydroxide aqueous solution (1M, 2.34 mL, 2.34 mmol) was heated to reflux for 1.5 h, LC-MS showed the reaction was complete. The solvent was removed in vacuo and the residue was acidified with 1M hydrochloric acid solution until lots of white solid precipitated, which was collected by filtration and washed with water, dried in vacuo to afford 28 mg of 3,3-dimethyl-2-(3-(1-methylpyrrolidin-3- ylcarbamoyl)phenyl)-1,2,3,4-tetrahydroquinoline-8-carboxylic acid as a white solid. Yield: 38%. MS (ESI+APCI) M+1=408.2.

Example 225

3-(6-Chloro-3,3-dimethyl-1,2,3,4-tetrahydroquinolin-2-yl)-N-(1-methylpyrrolidin-3-yl)benzamide

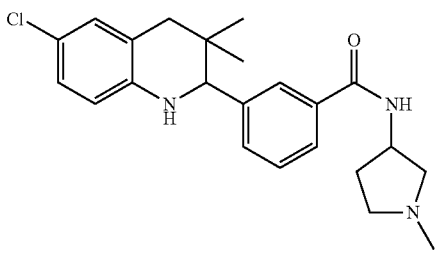 [SMILES: CN1CCC(NC(=O)c2cccc(C3Nc4ccc(Cl)cc4CC3(C)C)c2)C1]

To a solution of 4-chloroaniline (512 mg, 2 mmol) and benzyl 3-formylbenzoate (960 mg, 2 mmol) in dichloromethane (5 ml) was added isobutylaldehyde (158 mg, 2.4 mmol, 1.2 eq.), followed by Boron trifluoride etherate (0.16 mL, 0.2 mmol, 0.1 eq.). The resultant mixture was stirred for 24 hours. The reaction mixture was quenched with water and separated. The organic layer was dried and evaporated under vacuum to give the crude product, which was purified by column chromatography using petroleum ether/ethyl acetate=20:1 as eluant to afford the product 456 mg of benzyl 3-(6-chloro-4-hydroxy-3,3-dimethyl-1,2,3,4-tetrahydroquinolin-2-yl)benzoate (34% yield) as yellow solid. MS (ESI+APCI) M+1=422.4.

To a sealed tube was added benzyl 3-(6-chloro-4-hydroxy-3,3-dimethyl-1,2,3,4-tetrahydroquinolin-2-yl)benzoate (1.98 g, 4.70 mmol), dichloromethane (25 ml) and triethylsilane (1.10 g, 9.40 mmol, 2.0 eq.), followed by the addition of trifluoroacetic acid (1.61 g, 14.11 mmol, 3.0 eq.). The sealed tube was heated at 60 for 16 h and cooled to room temperature. The reaction mixture was washed with saturated Sodium bicarbonate and separated. The organic layer was dried the residue was purified by column chromatography using petroleum ether/ethyl acetate=20:1 to afford benzyl 3-(6-chloro-3,3-dimethyl-1,2,3,4-tetrahydroquinolin-2-yl)benzoate 914 mg (47.9% yield) as a yellow solid. MS (ESI+APCI) M+1=406.2.

A mixture of benzyl 3-(6-chloro-3,3-dimethyl-1,2,3,4-tetrahydroquinolin-2-yl)benzoate (914 mg, 2.25 mmol) in methanol (30 mL) and aqueous sodium hydroxide solution (2 M, 17 mL, 34 mmol) was heated to reflux for 2 h. Solvent was removed under vacuum and the residue was acidified with 2N hydrochloric acid solution to pH=2. The precipitated white solid was collected to afford 539 mg of 3-(6-chloro-3,3-dimethyl-1,2,3,4-tetrahydroquinolin-2-yl)benzoic acid (yield: 76%) as a white powder.

To a suspension of 3-(6-chloro-3,3-dimethyl-1,2,3,4-tetrahydroquinolin-2-yl)benzoic acid (361 mg, 1.07 mmol) in dichloromethane (20 mL) was added N-hydroxybenzotriazole (218 mg, 1.61 mmol, 1.5 eq.), followed by the addition of 1-(3-dimethylaminopropyl)-3-ethylcarbodiimide, hydrochloric acid (616 mg, 3.22 mmol, 3.0 eq.) and 4-methylmorpholine (326 mg, 3.22 mmol, 3.0 eq.). 40 min later, the active intermediate formed was added and stirred for another 2 hrs. Water was added to quench the reaction and the organic layer was washed with 1N sodium hydroxide then brine the separated organic layers was dried and evaporated to afford 398 mg of the mixture 3-(6-chloro-3,3-dimethyl-1,2,3,4-tetrahydroquinolin-2-yl)-N-methylpyrrolidin-3-yl)benzamide (85%) and 3-(6-chloro-3,3-dimethyl-3,4-dihydroquinolin-2-yl)-N-(1-methylpyrrolidin-3-yl)benzamide (15%) which was used for next step without further purification.

To the mixture of 3-(6-chloro-3,3-dimethyl-1,2,3,4-tetrahydroquinolin-2-yl)-N-(1-methylpyrrolidin-3-yl)benzamide (85%) and 3-(6-chloro-3,3-dimethyl-3,4-dihydroquinolin-2-yl)-N-(1-methylpyrrolidin-3-yl)benzamide (15%) (300 mg) in methanol/tetrahydrofuran (7.5 mL/7.5 mL) was added sodium borohydride (0.5 g). The mixture was stirred for 2 hrs and the solvent was removed in vacuo. The residue was dissolved in tetrahydrofuran, washed with brine and separated. The organic layer was dried and concentrated. The residue was purified by preparative Thin layer chromatography using dichloromethane/methanol=10:1 to afford 3-(6-chloro-3,3-dimethyl-1,2,3,4-tetrahydroquinolin-2-yl)-N-(1-methylpyrrolidin-3-yl)benzamide 80 mg (32% yield) as a light-yellow solid. MS (ESI+APCI) M+1=398.2.

Example 226

3,3-Dimethyl-2-(4-(N-methylsulfamoyl)phenyl)-1,2,3,4-tetrahydroquinoline-6-carboxylic acid

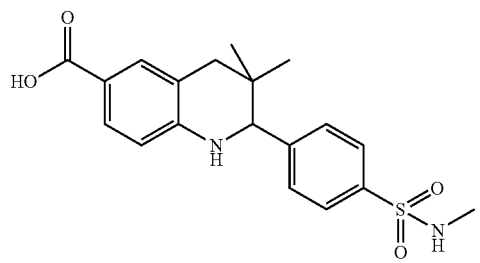 [SMILES: CNS(=O)(=O)c1ccc(C2Nc3ccc(C(=O)O)cc3CC2(C)C)cc1]

The preparation of sulfur dioxide-acetic acid solution cuprous chloride (60 mg, 0.60 mmol) was dissolved in acetic acid (60 mL), then the sulfur dioxide continued to pass into the reaction mixture for above 2 hrs. The color of the reaction mixture turned blue.

The synthesis of Diazonium Salt methyl 2-(4-aminophenyl)-3,3-dimethyl-1,2,3,4-tetrahydroquinoline-6-carboxylate (624 mg, 2.01 mmol) was dissolved in acetic acid (6 mL) and concentrated hydrochloric acid (18 mL) in an ice bath, cooled to −15° C. Then sodium nitrite (208 mg, 3.02 mmol) in water (4 mL) was added dropwise to the reaction mixture. It stirred strongly for above one hour, keeping the temperature below −10° C.

The sulfur dioxide-acetic acid solution was added dropwise to the reaction mixture of the diazonium salt in an ice bath, cooled to −10° C. After addition completely, the reaction mixture was allowed to warm to room temperature for three days. The reaction mixture was added dropwise to a large number of ice water. A lot of yellow solid precipitated. Filtered and the filter cake was washed by ice water. The yellow solid was the desired product methyl 2-(4-(chlorosulfonyl)phenyl)-3,3-dimethyl-3,4-dihydroquinoline-6-carboxylate (603 mg, Yield: 76.6%). MS (ES+APCI) M+1=392.1.

To a round bottom flask, a mixture of methyl 2-(4-(chlorosulfonyl)phenyl)-3,3-dimethyl-3,4-dihydroquinoline-6-carboxylate (396 mg, 1.0 mmol) in dichloromethane (10 mL) was added dropwise to a mixture of methylamine hydrochloride (68 mg, 1.0 mmol) and N,N-diisopropyl ethylamine (0.54 mL, 3.0 mmol) in dichloromethane (10 mL). The resultant mixture was allowed to stir at room temperature for 10 hours. The reaction mixture was washed by water several times, dried over anhydrous magnesium sulfate. Filtered and concentrated to provide methyl 3,3-dimethyl-2-(4-(N-methylsulfamoyl)phenyl)-3,4-dihydroquinoline-6-carboxylate as a yellow oil (190 mg). MS (ES+APCI) M+1=389.1.

To a round bottom flask, Pd/C (100 mg, 40%) was added to a solution of methyl 3,3-dimethyl-2-(4-(N-methylsulfamoyl)phenyl)-3,4-dihydroquinoline-6-carboxylate (230 mg, 0.81 mmol) in tetrahydrofuran (10 mL) and methanol (10 mL). The resultant mixture was allowed to stir at room temperature for 10 hours under $H_2$ pressure. Filtered and concentrated to provide methyl 3,3-dimethyl-2-(4-(N-methylsulfamoyl)phenyl)-1,2,3,4-tetrahydroquinoline-6-carboxylate as a white solid (190 mg). MS (ES+APCI) M+1=389.1.

To a round bottom flask, a mixture of methyl 3,3-dimethyl-2-(4-(N-methylsulfamoyl)phenyl)-1,2,3,4-tetrahydroquinoline-6-carboxylate (190 mg, 0.49 mmol) in methanol (20 mL), and water (2 mL) was treated with a solution of sodium hydroxide (332 mg, 8.3 mmol) in water (3 mL). The resultant mixture was heated for reflux for 1.5 hours. The methanol was removed under vacuum. The residue was acidified with 2M hydrochloric acid to pH=5-6. The precipitates were collected by filtration, purified by preparative Thin layer chromatography (silica gel, petroleum ether/ethyl acetate=1:1) to afford 3,3-dimethyl-2-(4-(N-methylsulfamoyl)phenyl)-1,2,3,4-tetrahydroquinoline-6-carboxylic acid (40 mg, yield: 21.9%). MS (ES+APCI) M+1=375.1.

Example 227

3,3-Dimethyl-2-(3-(pyrrolidin-1-ylsulfonyl)phenyl)-1,2,3,4-tetrahydroquinoline-6-carboxylic acid

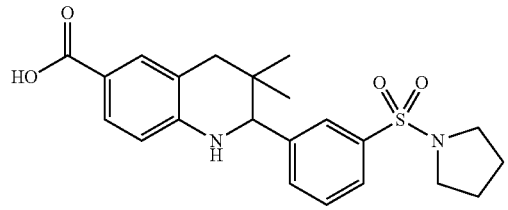 [SMILES: CC1(C)Cc2cc(C(=O)O)ccc2NC1c1cccc(S(=O)(=O)N2CCCC2)c1]

To a stirred solution of pyrrolidine (38 mg, 0.54 mmol) and N,N-diisopropylethylamine (116 mg, 0.90 mmol) in dichloromethane (4 mL) was added methyl 2-(3-(chlorosulfonyl)phenyl)-3,3-dimethyl-3,4-dihydroquinoline-6-carboxylate (175 mg, 0.45 mmol) portionwise. The resultant yellow solution was stirred for 3 h at room temperature. The mixture was purified on preparative Thin layer chromatography to afford 163 mg of methyl 3,3-dimethyl-2-(3-(pyrrolidin-1-ylsulfonyl)phenyl)-3,4-dihydroquinoline-6-carboxylate, which was used directly.

A mixture of methyl 3,3-dimethyl-2-(3-(pyrrolidin-1-ylsulfonyl)phenyl)-3,4-dihydroquinoline-6-carboxylate (140 mg, 0.328 mmol) in methanol/tetrahydrofuran (6 mL/6 mL) was treated with $H_2$ at room temperature overnight. C-MS showed the reaction was complete. The mixture was separated by filtration and the filtrate was concentrate in vacuo and give 110.9 mg of methyl 3,3-dimethyl-2-(3-(pyrrolidin-1-ylsulfonyl)phenyl)-1,2,3,4-tetrahydroquinoline-6-carboxylate, yield: 78.9%.

To a stirred solution of methyl 3,3-dimethyl-2-(3-(pyrrolidin-1-ylsulfonyl)phenyl)-1,2,3,4-tetrahydroquinoline-6-carboxylate (57 mg, 0.133 mmol) in methanol/tetrahydrofuran (2 mL/mL) was added 1M aqueous solution (2.0 mL, 2.0 mmol), LC-MS indicated that 2005467-009-01 was consumed. The mixture was concentrated and the residue was dissolved in water. The aqueous layer was basified to pH=4 with 1M hydrochloric acid solution. The precipitated solid was filtered, and dried to give 35.5 mg of 3,3-dimethyl-2-(3-(pyrrolidin-1-ylsulfonyl)phenyl)-1,2,3,4-tetrahydroquinoline-6-carboxylic acid as a white solid. Yield: 64.4%. MS (ESI+APCI) M+1=415.1.

Example 228

3,3-Dimethyl-2-(3-(N-methylsulfamoyl)phenyl)-1,2,3,4-tetrahydroquinoline-6-carboxylic acid

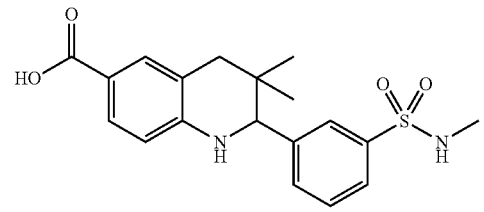 [SMILES: CNS(=O)(=O)c1cccc(C2Nc3ccc(C(=O)O)cc3CC2(C)C)c1]

A mixture of methyl 3,3-dimethyl-2-(3-(N-methylsulfamoyl)phenyl)-3,4-dihydroquinoline-6-carboxylate (175 mg, 0.438 mmol) in methanol/tetrahydrofuran (9.5 mL/9.5 mL) was treated with $H_2$ at room temperature overnight. LC-MS showed the reaction was complete. The mixture was separated by filtration and the filtrate was concentrate in vacuo and the residue was purified by column chromatography (petroleum ether:ethyl acetate=5:1) to give 143.2 mg of methyl 3,3-dimethyl-2-(3-(N-methylsulfamoyl)phenyl)-1,2,3,4-tetrahydroquinoline-6-carboxylate, yield: 81.2%.

To a stirred solution of methyl 3,3-dimethyl-2-(3-(N-methylsulfamoyl)phenyl)-1,2,3,4-tetrahydroquinoline-6-carboxylate (75 mg, 0.19 mmol) in tetrahydrofuran/methanol (2.5 mL/2.5 mL) was added 1M sodium hydroxide aqueous solution (2.89 mL, 2.89 mmol). The mixture was heated to reflux and stirred for 1.5 h. LC-MS indicated that 2005467-012-01 was consumed. The mixture was concentrated and the residue was dissolved in water. The aqueous layer was basified to pH=4 by 1M hydrochloric acid solution. The precipitated solid was filtered, and dried to give 56.7 mg of 3,3-dimethyl-2-(3-(N-methylsulfamoyl)phenyl)-1,2,3,4- tetrahydroquinoline-6-carboxylic acid as a white solid. Yield: 78.5%. MS (ESI+APCI) M+1=375.2.

Example 229

3,3-Dimethyl-2-(3-(N-(1-methylpyrrolidin-3-yl)sulfamoyl)phenyl)-1,2,3,4-tetrahydroquinoline-6-carboxylic acid

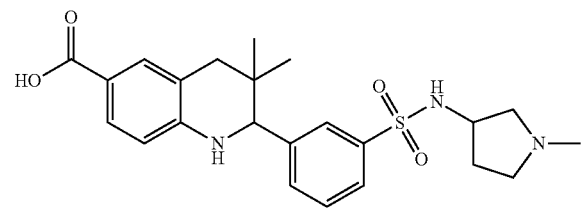 [SMILES: CN1CCC(NS(=O)(=O)c2cccc(C3Nc4ccc(C(=O)O)cc4CC3(C)C)c2)C1]

To a stirred solution of 1-methylpyrrolidin-3-amine (52 mg, 0.52 mmol) and N,N-diisopropylethylamine (112 mg, 0.86 mmol) in dichloromethane (4 mL) was added methyl 2-(3-(chlorosulfonyl)phenyl)-3,3-dimethyl-3,4-dihydroquinoline-6-carboxylate (170 mg, 0.43 mmol) portionwise. The resultant yellow solution was stirred for 3 h at room temperature. The mixture was purified on preparative Thin layer chromatography to afford 152 mg of methyl 3,3-dimethyl-2-(3-(N-(1-methylpyrrolidin-3-yl)sulfamoyl)phenyl)-3,4-dihydroquinoline-6-carboxylate, which was used directly.

A mixture of methyl 3,3-dimethyl-2-(3-(N-(1-methylpyrrolidin-3-yl)sulfamoyl)phenyl)-3,4-dihydroquinoline-6-carboxylate (152 mg, 0.33 mmol) and 10% Pd/C (100 mg) in methanol (3 mL) and tetrahydrofuran (3 mL) was hydrogenated by a H$_2$ balloon at 30° C. After filtration, the filtrated was concentrated and purified on preparative Thin layer chromatography to afford 140 mg of methyl 3,3-dimethyl-2-(3-(N-(1-methylpyrrolidin-3-yl)sulfamoyl)phenyl)-1,2,3,4-tetrahydroquinoline-6-carboxylate as a white solid. (Yield: 92%).

To a stirred solution of methyl 3,3-dimethyl-2-(3-(N-(1-methylpyrrolidin-3-yl)sulfamoyl)phenyl)-1,2,3,4-tetrahydroquinoline-6-carboxylate (140 mg, 0.31 mmol) in methanol/tetrahydrofuran (5 mL/5 mL) was added 1N sodium hydroxide (4.59 mL). The resultant mixture was heated to reflux for 2.5 h. Organic solvent was removed and the residue was dissolved in water. The aqueous layer was acidified to pH=4. The precipitates were filtered, and dissolved in tetrahydrofuran, dried over anhydrous magnesium sulfate. Anhydrous magnesium sulfate was removed, and after evaporation, the residue was treated with ethyl acetate to afford 40 mg of 3,3-dimethyl-2-(3-(N-(1-methylpyrrolidin-3-yl)sulfamoyl)phenyl)-1,2,3,4-tetrahydroquinoline-6-carboxylic acid. (Yield: 29%). MS (ESI+APCI) M+1=444.2.

Example 230

3,3-Dimethyl-2-(3-(N-phenylsulfamoyl)phenyl)-1,2,3,4-tetrahydroquinoline-6-carboxylic acid

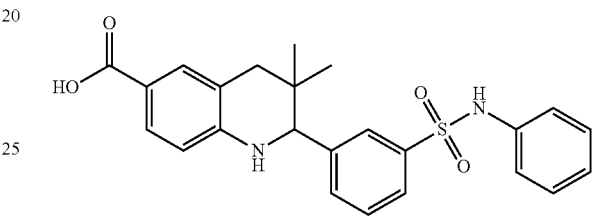

To a stirred solution of aniline (50 mg, 0.52 mmol) and N,N-diisopropylethylamine (122 mg, 0.86 mmol) in dichloromethane (4 mL) was added methyl 2-(3-(chlorosulfonyl)phenyl)-3,3-dimethyl-3,4-dihydroquinoline-6-carboxylate (170 mg, 0.43 mmol) in dichloromethane (2 mL). The mixture was stirred for 18 h at room temperature and purified on preparative Thin layer chromatography to afford 170 mg of methyl 3,3-dimethyl-2-(3-(N-phenylsulfamoyl)phenyl)-3,4-dihydroquinoline-6-carboxylate, which was used directly.

A mixture of methyl 3,3-dimethyl-2-(3-(N-phenylsulfamoyl)phenyl)-3,4-dihydroquinoline-6-carboxylate (170 mg, 0.38 mmol) and 10% Pd/C (150 mg) in methanol (4 mL) and tetrahydrofuran (5 mL) was hydrogenated by a H$_2$ balloon at 30° C. After filtration, the filtrated was concentrated and purified on preparative thin layer chromatography to afford 130 mg of 3,3-Dimethyl-2-(3-phenylsulfamoyl-phenyl)-1,2,3,4-tetrahydro-quinoline-6-carboxylic acid methyl ester.

To a stirred solution of methyl 3,3-dimethyl-2-(3-(N-phenylsulfamoyl)phenyl)-1,2,3,4-tetrahydroquinoline-6-carboxylate (130 mg, 0.29 mmol) in methanol/tetrahydrofuran (5 mL/5 mL) was added 1N sodium hydroxide (4.33 mL). The resultant mixture was heated to reflux for 2.5 h. Organic solvent was removed and the residue was dissolved in water. The aqueous layer was acidified to pH=4. The precipitates were filtered, and dissolved in tetrahydrofuran, dried over anhydrous magnesium sulfate. anhydrous magnesium sulfate was removed, and after evaporation, the residue was purified on preparative Thin layer chromatography to afford 80 mg of crude product, which was recrystallized from dichloromethane and ether to afford 40 mg of 3,3-dimethyl-2-(3-

(N-phenylsulfamoyl)phenyl)-1,2,3,4-tetrahydroquinoline-6-carboxylic acid. (Yield: 32%). MS (ESI+APCI) M+1=437.1.

Example 231

2-(3-(N,N-dimethylsulfamoyl)phenyl)-3,3-dimethyl-1,2,3,4-tetrahydroquinoline-6-carboxylic acid

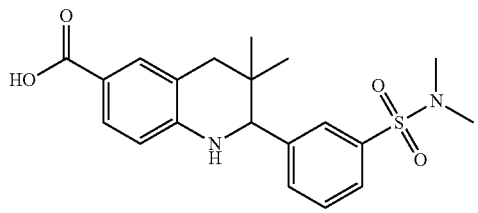 [SMILES: CN(C)S(=O)(=O)c1cccc(C2Nc3ccc(C(=O)O)cc3CC2(C)C)c1]

To a stirred solution of dimethylamine hydrochloride (82 mg, 1.0 mmol) and N,N-diisopropylethyl amine (388 mg, 3.0 mmol) in dichloromethane (4 mL) was added a solution of methyl 2-(3-(chlorosulfonyl)phenyl)-3,3-dimethyl-3,4-dihydroquinoline-6-carboxylate (394 mg, crude product) in dichloromethane (4 mL). The mixture was purified on preparative Thin layer chromatography to afford 100 mg of methyl 2-(3-(N,N-dimethylsulfamoyl)phenyl)-3,3-dimethyl-3,4-dihydroquinoline-6-carboxylate, which was used directly.

A mixture of methyl 2-(3-(N,N-dimethylsulfamoyl)phenyl)-3,3-dimethyl-3,4-dihydroquinoline-6-carboxylate (100 mg, 0.25 mmol) and 10% Pd/C (100 mg) in methanol (3 mL) and tetrahydrofuran (3 mL) was hydrogenated by a H$_2$ balloon at 30° C. After filtration, the filtrated was concentrated and purified on preparative thin layer chromatography to afford 80 mg of methyl 2-(3-(N,N-dimethylsulfamoyl)phenyl)-3,3-dimethyl-1,2,3,4-tetrahydroquinoline-6-carboxylate as a crude product.

To a stirred solution of methyl 2-(3-(N,N-dimethylsulfamoyl)phenyl)-3,3-dimethyl-1,2,3,4-tetrahydroquinoline-6-carboxylate (149 mg, 0.37 mmol) in methanol/tetrahydrofuran (5 mL/5 mL) was added 1N sodium hydroxide (5.6 mL). The resultant mixture was heated to reflux for 2.5 h. Organic solvent was removed and the residue was dissolved in water. The aqueous layer was acidified to pH=4. The precipitates were filtered, and dissolved in tetrahydrofuran, dried over anhydrous magnesium sulfate. Anhydrous magnesium sulfate was removed, and after evaporation, the residue was treated with ethyl acetate to afford 29 mg of 2-(3-(N,N-dimethylsulfamoyl)phenyl)-3,3-dimethyl-1,2,3,4-tetrahydroquinoline-6-carboxylic acid. (Yield: 20%). MS (ESI+APCI) M+1=389.1.

Example 232

3,3-Dimethyl-2-(2-(picolinamido)phenyl)-1,2,3,4-tetrahydroquinoline-6-carboxylic acid

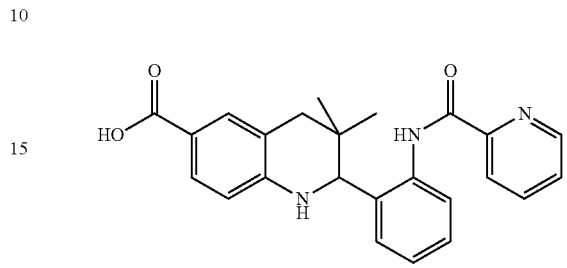

To an ice-cold mixture of methyl 2-(2-aminophenyl)-3,3-dimethyl-1,2,3,4-tetrahydroquinoline-6-carboxylate (60 mg, 0.19 mmol, 1.0 eq.) and N,N-diisopropylethylamine (50 mg, 0.38 mmol, 2.0 eq.) in 4 mL of dichloromethane was added dropwise a solution of picolinoyl chloride (40 mg, 0.29 mmol, 1.5 eq.) in dichloromethane (1 mL). Then the resultant mixture was stirred at room temperature for 30 min. Thin layer chromatography and LC-MS indicated that the starting material was consumed completely. The solvent was removed under reduced pressure and the residue was purified by column chromatography on silica gel (petroleum ether/ethyl acetate=2:1) to afford 44 mg of methyl 3,3-dimethyl-2-(2-(picolinamido)phenyl)-1,2,3,4-tetrahydroquinoline-6-carboxylate as a gray solid; yield: 60%. MS (ESI+APCI) M+1=416.2.

A mixture of methyl 3,3-dimethyl-2-(2-(picolinamido)phenyl)-1,2,3,4-tetrahydroquinoline-6-carboxylate (44 mg, 0.1 mmol, 1.0 eq.) and 1.3 mL aqueous solution of sodium hydroxide (2 M, 2.6 mmol, 25 eq.) in tetrahydrofuran (3 mL) was stirred at reflux for 3 h. Thin layer chromatography indicated that the starting material was consumed completely. The tetrahydrofuran was removed under reduced pressure and the residue was acidified to pH 5-6 with 1 M hydrochloric acid. Then a lot of white precipitates were formed and collected by filtration to afford 30 mg of 3,3-dimethyl-2-(2-(picolinamido)phenyl)-1,2,3,4-tetrahydroquinoline-6-carboxylic acid as a white solid; yield: 65%. MS (ESI+APCI) M+1=402.

Example 233

2-(3-(2-Carboxypropan-2-yloxy)phenyl)-3,3-dimethyl-1,2,3,4-tetrahydroquinoline-6-carboxylic acid

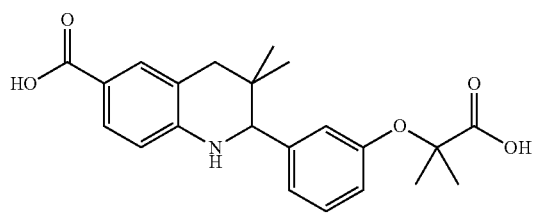 [SMILES: CC(C)(Oc1cccc(C2Nc3ccc(C(=O)O)cc3CC2(C)C)c1)C(=O)O]

To a stirred solution of methyl 4-aminobenzoate (381 mg, 2.5 mmol) and methyl 2-(3-formyl phenoxy)-2-methylpropanoate (555 mg, 2.5 mmol) in toluene (30 mL) was approximate 4A MS, and equipped with a Dean-Stark trap. The mixture was stirred and heated to reflux for 1.5 h. $^1$H NMR indicated the consumption of starting material. The solvent was evaporated, and the residue was used directly in next step.

To a solution of (E)-methyl 4-(3-(1-methoxy-2-methyl-1-oxopropan-2-yloxy)benzylideneamino)benzoate (888 mg, 2.5 mmol) and yttrium(III) trifluoromethanesulfonate (5 mL) in tetrahydrofuran (6 mL) was added a solution of isobutyl aldehyde (216 mg, 3.0 mmol) in tetrahydrofuran (1 mL) under nitrogen. The mixture was stirred at room temperature for 17 h. The mixture was purified by column chromatography to afford 510 mg of methyl 4-hydroxy-2-(3-(1-methoxy-2-methyl-1-oxopropan-2-yloxy)phenyl)-3,3-dimethyl-1,2,3,4-tetrahydroquinoline-6-carboxylate as a white solid. (Yield: 48%, 2 steps).

A mixture of methyl 4-hydroxy-2-(3-(1-methoxy-2-methyl-1-oxopropan-2-yloxy)phenyl)-3,3-dim ethyl-1,2,3,4-tetrahydroquinoline-6-carboxylate (510 mg, 1.19 mmol) and triethylsilane (400 mg, 3.44 mmol) in dichloromethane (6 mL) was stirred and cooled with a ice bath. A solution of trifluoroacetic acid (554 mg, 4.86 mmol) in dichloromethane (6 mL) was added slowly to the mixture. The reaction mixture was treated with sodium carbonate, and stirred for 30 min. The mixture was filtered, and the filtrate was concentrated and purified by column chromatography (silica gel, petroleum ether: ethyl acetate=15:1) to afford 230 mg of methyl 2-(3-(1-methoxy-2-methyl-1-oxopropan-2-yloxy)phenyl)-3,3-dimethyl-1,2,3,4-tetrahydroquinoline-6-carboxylate. (Yield: 47%).

To a solution of methyl 2-(3-(1-methoxy-2-methyl-1-oxopropan-2-yloxy)phenyl)-3,3-dimethyl-3,4-dihydroquinoline-6-carboxylate (230 mg, 0.56 mmol) in methanol (5 mL) and tetrahydrofuran (5 mL) was added 10% Pd/C (100 mg). The mixture was hydrogenated by H$_2$ balloon for 13 h. Pd/C was removed by filtration. The filtrate was concentrated to afford 216 mg of methyl 2-(3-(1-methoxy-2-methyl-1-oxopropan-2-yloxy)phenyl)-3,3-dimethyl-1,2,3,4-tetrahydroquinoline-6-carboxylate as syrup. (Yield: 93%).

To a solution of methyl 2-(3-(1-methoxy-2-methyl-1-oxopropan-2-yloxy)phenyl)-3,3-dimethyl-1,2,3,4-tetrahydroquinoline-6-carboxylate (216 mg, 0.52 mmol) in methanol (8 mL) and tetrahydrofuran (8 mL) was added a 1 M solution of sodium hydroxide (7.87 mL). The mixture was stirred and heated to reflux for 1.5 h. The mixture was concentrated, dissolved in water and acidified to pH=4 with 1M hydrochloric acid. The precipitated solid was filtered and redissolved in tetrahydrofuran, and the organic layers were dried over anhydrous magnesium sulfate. After evaporation of the organic solvent, the residue was treated with dichloromethane to afford 60 mg of 2-(3-(2-carboxypropan-2-yloxy)phenyl)-3,3-dimethyl-1,2,3,4-tetrahydroquinoline-6-carboxylic acid as a white solid. Isolated yield: 30%; MS (ESI+APCI) M+1=384.

Example 234

ADP Quest™ Assay for AMPK Activators

This method evaluates AMP-activated protein kinase (AMPK) activity through detecting the accumulation of ADP product using an ADP Quest kit and determining the $E_{30}$ values of the small molecular AMPK activators. ADP Quest kit (DiscoveRx, Fremont, Calif.) is stored at −20° C. before use. Before an experiment, thaw the kit (include assay buffer, ADP standard solution, reagent A and reagent B) and equilibrate to room temperature. Dispense the ADP Quest reagents into single-use aliquots and store at −20° C. The compound concentrations typically range from 0 μM to 100 μM by 2-fold dilution. AMP concentrations range from 0.98 μM to 1 mM as the reference control. In an assay, thaw and equilibrate the assay buffer, reagent A and reagent B to room temperature for 30 minutes prior to use. Mix ATP, SAMS peptide substrate and compound, and place them into the 384-well assay plate. Add reagent A and B based on the assay kit protocol. Incubate the assay plate at room temperature for 30 minutes after addition the mixture followed by the addition of AMPK protein (Invitrogen, CA) to initiate the AMPK phosphorylation reaction. At the same time, reactions with AMPK activator AMP in the absence of enzyme is included as blank control. The reaction fluorescence signal is monitored and recorded on Envision in kinetic mode with the excitation wavelength of 530 nm and emission wavelength of 590 nm. The $E_{30}$ value, defined as the fold of AMPK activation to phosphorylate SAMS peptide without and with an activator at the concentration of 30 μM, is calculated and analyzed using Prism 5.0.

The compounds of formula (I) have $E_{30}$ values between 1 and 20. Preferred compounds have $E_{30}$ values between 1 and 5; further preferred compounds have $E_{30}$ values between 1.5 and 5; still further preferred compounds have $E_{30}$ values between 2 and 5.

The compounds of examples 1-233 have the following $E_{30}$.

| Example No. | $E_{30}$ |
|---|---|
| Example 1 | 1.43 |
| Example 2 | 1.42 |
| Example 3 | 1.33 |
| Example 4 | 1.33 |
| Example 5 | 1.32 |
| Example 6 | 1.31 |
| Example 7 | 1.31 |
| Example 8 | 1.29 |
| Example 9 | 1.28 |
| Example 10 | 1.27 |
| Example 11 | 1.25 |
| Example 12 | 1.22 |
| Example 13 | 1.21 |
| Example 14 | 1.2 |
| Example 15 | 3.59 |
| Example 16 | 1.59 |
| Example 17 | 1.45 |
| Example 18 | 1.41 |
| Example 19 | 1.38 |
| Example 20 | 1.25 |
| Example 21 | 1.42 |
| Example 22 | 1.39 |
| Example 23 | 1.32 |
| Example 24 | 1.3 |
| Example 25 | 1.29 |
| Example 26 | 1.27 |
| Example 27 | 1.24 |
| Example 28 | 2.5 |
| Example 29 | 1.34 |
| Example 30 | 1.45 |
| Example 31 | 1.33 |
| Example 32 | 1.38 |
| Example 33 | 1.22 |
| Example 34 | 1.15 |
| Example 35 | 1.41 |
| Example 36 | 1.37 |
| Example 37 | 2.19 |
| Example 38 | 2.12 |
| Example 39 | 1.36 |
| Example 40 | 1.35 |
| Example 41 | 1.35 |
| Example 42 | 1.31 |
| Example 43 | 1.29 |

-continued

| Example No. | $E_{30}$ |
|---|---|
| Example 44 | 2.67 |
| Example 45 | 2.41 |
| Example 46 | 1.46 |
| Example 47 | 1.23 |
| Example 48 | 2.62 |
| Example 49 | 2.25 |
| Example 50 | 1.61 |
| Example 51 | 1.42 |
| Example 52 | 1.35 |
| Example 53 | 1.33 |
| Example 54 | 1.28 |
| Example 55 | 1.28 |
| Example 56 | 1.26 |
| Example 57 | 1.25 |
| Example 58 | 1.22 |
| Example 59 | 1.2 |
| Example 60 | 1.2 |
| Example 61 | 1.61 |
| Example 62 | 1.61 |
| Example 63 | 1.56 |
| Example 64 | 1.48 |
| Example 65 | 1.46 |
| Example 66 | 1.42 |
| Example 67 | 1.38 |
| Example 68 | 1.33 |
| Example 69 | 1.28 |
| Example 70 | 1.23 |
| Example 71 | 1.22 |
| Example 72 | 1.21 |
| Example 73 | 1.21 |
| Example 74 | 1.19 |
| Example 75 | 1.19 |
| Example 76 | 1.47 |
| Example 77 | 1.42 |
| Example 78 | 1.79 |
| Example 79 | 1.33 |
| Example 80 | 1.72 |
| Example 81 | 2.85 |
| Example 82 | 1.5 |
| Example 83 | 1.35 |
| Example 84 | 1.25 |
| Example 85 | 1.29 |
| Example 86 | 2.74 |
| Example 87 | 1.3 |
| Example 88 | 1.35 |
| Example 89 | 1.3 |
| Example 90 | 1.44 |
| Example 91 | 1.31 |
| Example 92 | 1.23 |
| Example 93 | 1.32 |
| Example 94 | 1.33 |
| Example 95 | 1.56 |
| Example 96 | 1.5 |
| Example 97 | 1.46 |
| Example 98 | 1.44 |
| Example 99 | 1.42 |
| Example 100 | 1.4 |
| Example 101 | 1.4 |
| Example 102 | 1.4 |
| Example 103 | 1.37 |
| Example 104 | 1.36 |
| Example 105 | 1.35 |
| Example 106 | 1.3 |
| Example 107 | 1.29 |
| Example 108 | 1.29 |
| Example 109 | 1.24 |
| Example 110 | 1.24 |
| Example 111 | 1.24 |
| Example 112 | 1.22 |
| Example 113 | 1.21 |
| Example 114 | 1.21 |
| Example 115 | 1.2 |
| Example 116 | 1.2 |
| Example 117 | 1.7 |
| Example 118 | 1.64 |
| Example 119 | 1.5 |
| Example 120 | 1.5 |
| Example 121 | 1.42 |
| Example 122 | 1.39 |
| Example 123 | 1.36 |
| Example 124 | 1.34 |
| Example 125 | 1.33 |
| Example 126 | 1.28 |
| Example 127 | 1.26 |
| Example 128 | 1.26 |
| Example 129 | 1.25 |
| Example 130 | 1.25 |
| Example 131 | 1.24 |
| Example 132 | 1.23 |
| Example 133 | 1.2 |
| Example 134 | 1.32 |
| Example 135 | 1.31 |
| Example 136 | 1.3 |
| Example 137 | 1.26 |
| Example 138 | 1.21 |
| Example 139 | 1.38 |
| Example 140 | 1.34 |
| Example 141 | 1.3 |
| Example 142 | 1.54 |
| Example 143 | 1.33 |
| Example 144 | 1.25 |
| Example 145 | 1.22 |
| Example 146 | 1.21 |
| Example 147 | 1.35 |
| Example 148 | 1.3 |
| Example 149 | 1.26 |
| Example 150 | 1.22 |
| Example 151 | 1.66 |
| Example 152 | 1.41 |
| Example 153 | 1.27 |
| Example 154 | 1.24 |
| Example 155 | 1.19 |
| Example 156 | 1.66 |
| Example 157 | 1.36 |
| Example 158 | 1.34 |
| Example 159 | 1.31 |
| Example 160 | 1.23 |
| Example 161 | 1.21 |
| Example 162 | 1.2 |
| Example 163 | 3.68 |
| Example 164 | 1.78 |
| Example 165 | 1.53 |
| Example 166 | 1.43 |
| Example 167 | 1.4 |
| Example 168 | 1.39 |
| Example 169 | 1.38 |
| Example 170 | 1.36 |
| Example 171 | 1.36 |
| Example 172 | 1.34 |
| Example 173 | 1.24 |
| Example 174 | 1.54 |
| Example 175 | 1.5 |
| Example 176 | 1.44 |
| Example 177 | 1.4 |
| Example 178 | 1.36 |
| Example 179 | 1.33 |
| Example 180 | 1.32 |
| Example 181 | 1.31 |
| Example 182 | 1.26 |
| Example 183 | 1.25 |
| Example 184 | 1.24 |
| Example 185 | 1.22 |
| Example 186 | 1.21 |
| Example 187 | 1.38 |
| Example 188 | 1.32 |
| Example 189 | 1.31 |
| Example 190 | 1.3 |
| Example 191 | 1.27 |
| Example 192 | 1.27 |
| Example 193 | 1.26 |
| Example 194 | 1.25 |
| Example 195 | 1.25 |
| Example 196 | 1.25 |
| Example 197 | 1.22 |
| Example 198 | 1.2 |
| Example 199 | 1.18 |

-continued

| Example No. | $E_{30}$ |
|---|---|
| Example 200 | 1.58 |
| Example 201 | 1.42 |
| Example 202 | 1.22 |
| Example 203 | 1.53 |
| Example 204 | 1.4 |
| Example 205 | 1.38 |
| Example 206 | 1.33 |
| Example 207 | 1.32 |
| Example 208 | 1.3 |
| Example 209 | 1.28 |
| Example 210 | 1.27 |
| Example 211 | 1.41 |
| Example 212 | 1.28 |
| Example 213 | 1.27 |
| Example 214 | 1.41 |
| Example 215 | 1.38 |
| Example 216 | 1.36 |
| Example 217 | 1.27 |
| Example 218 | 2.53 |
| Example 219 | 2.57 |
| Example 220 | 1.89 |
| Example 221 | 1.33 |
| Example 222 | 2.09 |
| Example 223 | 1.94 |
| Example 224 | 1.43 |
| Example 225 | 1.64 |
| Example 226 | 1.32 |
| Example 227 | 1.2 |
| Example 228 | 1.38 |
| Example 229 | 1.33 |
| Example 230 | 1.27 |
| Example 231 | 1.31 |
| Example 232 | 1.28 |
| Example 233 | 1.29 |

Example A

A compound of formula (I) can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:
1. A compound of formula (I)

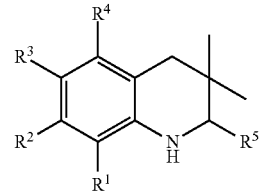

wherein
$R^1$ is selected from the group consisting of: hydrogen, halogen, carboxyl, alkoxycarbonyl, alkylsulfonylaminocarbonyl and cycloalkylsulfonylaminocarbonyl;
$R^2$ is selected from the group consisting of: hydrogen, halogen and carboxyl;
$R^3$ is carboxyl;
$R^4$ is selected from the group consisting of: hydrogen, carboxyl, alkylsulfonylaminocarbonyl and cycloalkylsulfonylaminocarbonyl; and
$R^5$ is selected from the group consisting of: pyridinyl, substituted pyridinyl, morpholinylpyridinyl, phenyl and substituted phenyl wherein substituted pyridinyl and substituted phenyl are pyridinyl and phenyl substituted with one or two substituents independently selected from the group consisting of halogen, halophenyl, alkyl, cycloalkyl, alkoxy, cyano, carboxyl, cycloalkylcarbonylamino, alkylsulfonylamino, phenylsulfonylamino, phenylaminosulfonyl, halophenylsulfonylamino, phenyl, alkylphenyl, alkoxyphenyl, cyanophenyl, alkylaminocarbonylphenyl, alkylsulfonylphenyl, pyrrolidinyl, pyridinylcarbonylamino, morpholinyl, alkylmorpholinyl, piperazinyl, alkylpiperazinyl, alkylcarbonylpiperazinyl, alkylphenylpiperazinyl, halophenylpiperazinyl, oxopyrrolidinyl, dioxoimidazolidinyl, oxoimidazolidinyl, alkyloxoimidazolidinyl, phenyloxoimidazolidinyl, 2-oxo-oxazolidin-3-yl, alkyl-2-oxo-oxazolidin-3-yl, phenylalkyl-2-oxo-oxazolidin-3-yl, dioxopiperazinyl, alkyldioxopiperazinyl, aminocarbonyl, alkylaminocarbonyl, alkoxyalkylaminocarbonyl, alkylaminoalkylaminocarbonyl, cycloalkylaminocarbonyl, alkylpyrrolidinylaminocarbonyl, tetrahydrofuranylaminocarbonyl, alkylpyrrolidinylalkylaminocarbonyl, alkoxycarbonylazetidinylaminocarbonyl, pyrrolidinylcarbonyl, piperidinylcarbonyl, alkylsulfonylaminocarbonyl, cycloaklylsulfonylaminocarbonyl, phenylsulfonylaminocarbonyl, alkylazetidinylaminocarbonyl, haloazetidinyl, alkylpyrrolidinylaminocarbonyl, phenylaminocarbonyl, pyrazinylaminocarbonyl, aminoalkoxyalkyl, aminoalkoxy, carboxylalkoxy, carboxylalkoxyalkyl, alkyltetrazolyl, phenylalkyltetrazolyl, alkylaminosulfonyl, alkylphenylsulfonylamino, alkylcarbonylamino, cycloalkenylcarbonylamino, phenylcarbonylamino, phenylalkylcarbonylamino, alkylaminoalkylamino, 7-benzyl-4-oxo-5,6,7,8-tetrahydro-4H-pyrido[3,4-d] pyrimidin-3-yl, alkylaminophenyl, alkylamino, hydroxyalkylamino, carboxylalkylamino, carboxylcycloalkylamino, alkylaminocarbonylalkylamino, aminocarbonyl(alkyl)amino, morpholinylcarbonylalkylamino, alkylpiperazinylcarbonylalkylamino, alkylaminosulfonylamino, alkylcarbonylaminophenylsulfonylamino, alkylaminocarbonylamino, aminocarbonylamino, morpholinylcarbonylamino, pyrrolidinyl-carbonylamino, piperidinylcarbonylamino, alkylpiperazinylcarbonylamino, phenylalkylaminocarbonylamino, halophenylcarbonylamino, halophenylaminocarbonylamino, pyrazinylcarbonylamino, alkylpiperazinyl, pyrrolidinylsulfonyl and alkylpyrrolidinylaminosulfonyl;

or a pharmaceutically acceptable salt or ester thereof.

2. A compound according to claim 1, wherein $R^1$ is selected from the group consisting of: hydrogen, carboxyl and alkoxycarbonyl.

3. A compound according to claim 1, wherein $R^1$ is selected from the group consisting of: hydrogen, carboxyl and methoxycarbonyl.

4. A compound according to claim 1, wherein $R^2$ is hydrogen.

5. A compound according to claim 1, wherein $R^4$ is selected from the group consisting of: hydrogen, carboxyl, methylsulfonylaminocarbonyl and cyclopropylsulfonylaminocarbonyl.

6. A compound according to claim 1, wherein $R^5$ is substituted phenyl wherein substituted phenyl is phenyl substituted with one or two substituents independently selected from the group consisting of: halogen, alkyl, alkylsulfonylamino, phenylsulfonylamino, halophenylsulfonylamino, alkylphenyl, pyrrolidinyl, morpholinyl, alkylpiperazinyl, alkylphenylpiperazinyl, alkyloxoimidazolidinyl, alkyl-2-oxo-oxazolidin-3-yl, aminocarbonyl, alkylaminoalkylaminocarbonyl, alkylpyrrolidinylaminocarbonyl, phenylsulfonylaminocarbonyl, alkylcarbonylamino, alkylaminoalkylamino, alkylamino, carboxylalkylamino, carboxylcycloalkylamino and alkylaminocarbonylalkylamino.

7. A compound according to claim 1, wherein $R^5$ is substituted phenyl wherein substituted phenyl is phenyl substituted with one or two substituents independently selected from the group consisting of: fluoro, methyl, methylsulfonylamino, phenylsulfonylamino, fluorophenylsulfonylamino, tert-butylphenyl, pyrrolidinyl, morpholinyl, methylpiperazinyl, dimethylphenylpiperazinyl, methylphenylpiperazinyl, methyloxoimidazolidinyl, isoproyl-2-oxo-oxazolidin-3-yl, aminocarbonyl, dimethylaminoethylaminocarbonyl, methylpyrrolidinylaminocarbonyl, phenylsulfonylaminocarbonyl, isopropylcarbonylamino, methylamino(ethyl)(methyl)amino, dimethylamino, carboxylpropylamino, carboxylcyclopropylamino and methylaminocarbonylpropylamino.

8. A pharmaceutical composition comprising a compound according to claim 1 and a therapeutically inert carrier.

9. A compound according to claim 1 selected from the group consisting of:
2-[3-(3-benzyl-ureido)-phenyl]-3,3-dimethyl-1,2,3,4-tetrahydro-quinoline-6-carboxylic acid;
3,3-dimethyl-2-{3-[(pyridine-3-carbonyl)-amino]-phenyl}-1,2,3,4-tetrahydro-quinoline-6-carboxylic acid;
3,3-dimethyl-2-{3-[(pyridine-2-carbonyl)-amino]-phenyl}-1,2,3,4-tetrahydro-quinoline-6-carboxylic acid;
3,3-dimethyl-2-{3-[(pyrazine-2-carbonyl)-amino]-phenyl}-1,2,3,4-tetrahydro-quinoline-6-carboxylic acid;
2-[3-(3-fluoro-benzoylamino)-phenyl]-3,3-dimethyl-1,2,3,4-tetrahydro-quinoline-6-carboxylic acid;
2-(3-carbonyl-phenyl)-3,3-dimethyl-1,2,3,4-tetrahydro-quinoline-6-carboxylic acid;
2-(3-benzoylamino-phenyl)-3,3-dimethyl-1,2,3,4-tetrahydro-quinoline-6-carboxylic acid;
2-{3-[3-(3-fluoro-phenyl)-ureido]-phenyl}-3,3-dimethyl-1,2,3,4-tetrahydro-quinoline-6-carboxylic acid;
3,3-dimethyl-2-(3-phenylcarbamoyl-phenyl)-1,2,3,4-tetrahydro-quinoline-6-carboxylic acid; and
2-[3-(1-carboxy-1-methyl-ethylamino)-phenyl]-3,3-dimethyl-1,2,3,4-tetrahydro-quinoline-6-carboxylic acid.

10. A compound according to claim 1 selected from the group consisting of:
3,3-dimethyl-2-[3-(3-methyl-2-oxo-imidazolidin-1-yl)-phenyl]-1,2,3,4-tetrahydro-quinoline-6-carboxylic acid;
3,3-dimethyl-2-[3-(2-oxo-imidazolidin-1-yl)-phenyl]-1,2,3,4-tetrahydro-quinoline-6-carboxylic acid;
2-[3-(2,5-dioxo-piperazin-1-yl)-phenyl]-3,3-dimethyl-1,2,3,4-tetrahydro-quinoline-6-carboxylic acid;
2-[3-(2,4-dioxo-imidazolidine-1-yl)-phenyl]-3,3-dimethyl-1,2,3,4-tetrahydro-quinoline-6-carboxylic acid;
2-[3-(4-fluoro-benzoylamino)-phenyl]-3,3-dimethyl-1,2,3,4-tetrahydro-quinoline-6-carboxylic acid;
3,3-dimethyl-2-{3-[(morpholine-4-carbonyl)-amino]-phenyl}-1,2,3,4-tetrahydro-quinoline-6-carboxylic acid;
3,3-dimethyl-2-{3-[(piperidine-1-carbonyl)-amino]-phenyl}-1,2,3,4-tetrahydro-quinoline-6-carboxylic acid;
2-(3-(N,N-dimethylsulfamoylamino)phenyl)-3,3-dimethyl-1,2,3,4-tetrahydroquinoline-6-carboxylic acid;
3,3-dimethyl-2-[3-(2-oxo-3-phenyl-imidazolidin-1-yl)-phenyl]-1,2,3,4-tetrahydro-quinoline-6-carboxylic acid; and
3,3-dimethyl-2-{3-[(4-methyl-piperazine-1-carbonyl)-amino]-phenyl}-1,2,3,4-tetrahydro-quinoline-6-carboxylic acid.

11. A compound according to claim 1 selected from the group consisting of:
2-[3-(2-hydroxy-1,1-dimethyl-ethylamino)-phenyl]-3,3-dimethyl-1,2,3,4-tetrahydro-quinoline-6-carboxylic acid;
3,3-dimethyl-2-[3-(trimethyl-ureido)-phenyl]-1,2,3,4-tetrahydro-quinoline-6-carboxylic acid;
3,3-dimethyl-2-[3-(1-methyl-ureido)-phenyl]-1,2,3,4-tetrahydro-quinoline-6-carboxylic acid;
2-[3-(1-isopropyl-ureido)-phenyl]-3,3-dimethyl-1,2,3,4-tetrahydro-quinoline-6-carboxylic acid;
2-[3-(2-amino-1,1-dimethyl-ethoxy)-phenyl]-3,3-dimethyl-1,2,3,4-tetrahydro-quinoline-6-carboxylic acid;
2-[3-(4,4-dimethyl-2-oxo-oxazolidine-3-yl)-phenyl]-3,3-dimethyl-1,2,3,4-tetrahydro-quinoline-6-carboxylic acid;
3,3-dimethyl-2-{3-[(pyrrolidine-1-carbonyl)-amino]-phenyl}-1,2,3,4-tetrahydro-quinoline-6-carboxylic acid;
2-[3-(3,3-diethyl-ureido)-phenyl}-3,3-dimethyl-1,2,3,4-tetrahydro-quinoline-6-carboxylic acid;
2-[3-(1-dimethylcarbamoyl-1-methyl-ethylamino)-phenyl]-3,3-dimethyl-1,2,3,4-tetrahydro-quinoline-6-carboxylic acid; and
2-[3-(1,1-dimethyl-2-morpholin-4-yl-2-oxo-ethylamino)-phenyl]-3,3-dimethyl-1,2,3,4-tetrahydro-quinoline-6-carboxylic acid.

12. A compound according to claim 1 selected from the group consisting of:
2-{3-[1,1-dimethyl-2-(4-methyl-piperazin-1-yl)-2-oxo-ethylamino]-phenyl}-3,3-dimethyl-1,2,3,4-tetrahydro-quinoline-6-carboxylic acid;
2-[3-(1-carboxy-cyclopropylamino)-phenyl]-3,3-dimethyl-1,2,3,4-tetrahydro-quinoline-6-carboxylic acid;
2-[5-(4-tert-butyl-phenyl)-pyridin-3-yl]-3,3-dimethyl-1,2,3,4-tetrahydro-quinoline-6-carboxylic acid;
2-(4'-Cyano-5-fluoro-biphenyl-3-yl)-3,3-dimethyl-1,2,3,4-tetrahydro-quinoline-6-carboxylic acid;

2-(2-Fluoro-5-morpholin-4-yl-phenyl)-3,3-dimethyl-1,2,3,4-tetrahydro-quinoline-6-carboxylic acid;

3,3-Dimethyl-2-(3-methyl-5-morpholin-4-yl-phenyl)-1,2,3,4-tetrahydro-quinoline-6-carboxylic acid;

2-(3-Fluoro-5-piperazin-1-yl-phenyl)-3,3-dimethyl-1,2,3,4-tetrahydro-quinoline-6-carboxylic acid; and 3,3-Dimethyl-2-(4-morpholin-4-yl-phenyl)-1,2,3,4-tetrahydro-quinoline-6-carboxylic acid.

13. A compound according to claim 1 selected from the group consisting of:

2-(4'-Isopropoxy-biphenyl-3-yl)-3,3-dimethyl-1,2,3,4-tetrahydro-quinoline-6-carboxylic acid;

3,3-Dimethyl-2-[3-(4-methyl-piperazin-1-yl)-phenyl]-1,2,3,4-tetrahydro-quinoline-6-carboxylic acid;

3,3-Dimethyl-2-(3-piperazin-1-yl-phenyl)-1,2,3,4-tetrahydro-quinoline-6-carboxylic acid;

2-[3-(2,6-Dimethyl-morpholin-4-yl)-phenyl]-3,3-dimethyl-1,2,3,4-tetrahydro-quinoline-6-carboxylic acid;

3,3-Dimethyl-2-pyridin-3-yl-1,2,3,4-tetrahydro-quinoline-6-carboxylic acid;

2-(4'-Chloro-biphenyl-3-yl)-3,3-dimethyl-1,2,3,4-tetrahydro-quinoline-6-carboxylic acid; and 8-Chloro-3,3-dimethyl-2-(3-morpholin-4-yl-phenyl)-1,2,3,4-tetrahydro-quinoline-6-carboxylic acid.

14. A compound according to claim 1 selected from the group consisting of:

2-(3-Chloro-4-fluoro-phenyl)-3,3-dimethyl-1,2,3,4-tetrahydro-quinoline-6-carboxylic acid;

2-[3-((S)-4-Isopropyl-2-oxo-oxazolidin-3-yl)-phenyl]-3,3-dimethyl-1,2,3,4-tetrahydro-quinoline-6-carboxylic acid;

3,3-Dimethyl-2-{3-[methyl-(2-methylamino-ethyl)-amino]-phenyl}-1,2,3,4-tetrahydro-quinoline-6-carboxylic acid;

2-[3-(R)-4-Isopropyl-2-oxo-oxazolidin-3-yl)-phenyl]-3,3-dimethyl-1,2,3,4-tetrahydro-quinoline-6-carboxylic acid;

2-[3-((S)-4-Benzyl-2-oxo-oxazolidin-3-yl)-phenyl]-3,3-dimethyl-1,2,3,4-tetrahydro-quinoline-6-carboxylic acid;

3,3-Dimethyl-2-[3-(4-methyl-2,3-dioxo-piperazin-1-yl)-phenyl]-1,2,3,4-tetrahydro-quinoline-6-carboxylic acid;

2-[3-((R)-4-Benzyl-2-oxo-oxazolidin-3-yl)-phenyl]-3,3-dimethyl-1,2,3,4-tetrahydro-quinoline-6-carboxylic acid;

2-[3-(7-Benzyl-4-oxo-5,6,7,8-tetrahydro-4H-pyrido[3,4-d]pyrimidin-3-yl)-phenyl]-3,3-dimethyl-1,2,3,4-tetrahydro-quinoline-6-carboxylic acid;

2-[3-(5-Benzyl-tetrazol-1-yl)-phenyl]-3,3-dimethyl-1,2,3,4-tetrahydro-quinoline-6-carboxylic acid; and 2-[3-(5-Ethyl-tetrazol-1-yl)-phenyl]-3,3-dimethyl-1,2,3,4-tetrahydro-quinoline-6-carboxylic acid.

15. A compound according to claim 1 selected from the group consisting of:

3,3-Dimethyl-2-[3-(4-o-tolyl-piperazin-1-yl)-phenyl]-1,2,3,4-tetrahydroquinoline-6-carboxylic acid;

3,3-Dimethyl-2-phenyl-1,2,3,4-tetrahydro-quinoline-6-carboxylic acid;

2-(4'-Isopropylcarbamoyl-biphenyl-3-yl)-3,3-dimethyl-1,2,3,4-tetrahydro-quinoline-6-carboxylic acid;

2-(4'-tert-Butylcarbamoyl-biphenyl-3-yl)-3,3-dimethyl-1,2,3,4-tetrahydro-quinoline-6-carboxylic acid;

2-[2-(1-Carboxy-1-methyl-ethylamino)-phenyl]-3,3-dimethyl-1,2,3,4-tetrahydro-quinoline-6-carboxylic acid;

2-[2-(1-Carboxy-cyclopropylamino)-phenyl]-3,3-dimethyl-1,2,3,4-tetrahydro-quinoline-6-carboxylic acid;

3,3-dimethyl-2-(3-(1-methylethylsulfonamido)phenyl)-1,2,3,4-tetrahydroquinoline-6-carboxylic acid;

3,3-dimethyl-2-(3-(1-methylethylsulfonamido)phenyl)-1,2,3,4-tetrahydroquinoline-6-carboxylic acid;

3,3-dimethyl-2-(3-(tetrahydrofuran-3-ylcarbamoyl)phenyl)-1,2,3,4-tetrahydroquinoline-6-carboxylic acid; and 3,3-dimethyl-2-(4-(phenylsulfonamido)phenyl)-1,2,3,4-tetrahydroquinoline-6-carboxylic acid;

2-(3-(4-acetamidophenylsulfonamido)phenyl)-3,3-dimethyl-1,2,3,4-tetrahydroquinoline-6-carboxylic acid.

16. A compound according to claim 1 selected from the group consisting of:

2-(3-(cyclopropylcarbamoyl)phenyl)-3,3-dimethyl-1,2,3,4-tetrahydroquinoline-6-carboxylic acid;

3,3-dimethyl-2-(3-(pyrrolidine-1-carbonyl)phenyl)-1,2,3,4-tetrahydroquinoline-6-carboxylic acid;

2-(3-(cyclobutylcarbamoyl)phenyl)-3,3-dimethyl-1,2,3,4-tetrahydroquinoline-6-carboxylic acid;

2-(3-(isopropylcarbamoyl)phenyl)-3,3-dimethyl-1,2,3,4-tetrahydroquinoline-6-carboxylic acid;

2-(4-fluoro-3-isobutyramidophenyl)-3,3-dimethyl-1,2,3,4-tetrahydroquinoline-6-carboxylic acid;

3,3-dimethyl-2-(3-(phenylsulfonylcarbamoyl)phenyl)-1,2,3,4-tetrahydroquinoline-6-carboxylic acid;

2-(3-(cyclopropylsulfonylcarbamoyl)-phenyl)-3,3-dimethyl-1,2,3,4-tetrahydroquinoline-6-carboxylic acid;

2-(4-chloro-3-isobutyramidophenyl)-3,3-dimethyl-1,2,3,4-tetrahydroquinoline-6-carboxylic acid;

2-(4-isobutyramidophenyl)-3,3-dimethyl-1,2,3,4-tetrahydroquinoline-6-carboxylic acid; and 3,3-dimethyl-2-(3-(methylsulfonylcarbamoyl)-phenyl)-1,2,3,4-tetrahydroquinoline-6-carboxylic acid.

17. A compound according to claim 1 selected from the group consisting of:

2-(4-fluoro-3-(picolinamido)-phenyl)-3,3-dimethyl-1,2,3,4-tetrahydroquinoline-6-carboxylic acid;

2-(4-(4-fluorophenylsulfonamido)phenyl)-3,3-dimethyl-1,2,3,4-tetrahydroquinoline-6-carboxylic acid;

2-(4-(4-fluorobenzamido)phenyl)-3,3-dimethyl-1,2,3,4-tetrahydroquinoline-6-carboxylic acid;

3,3-dimethyl-2-(4-(4-methylphenylsulfonamido)phenyl)-1,2,3,4-tetrahydroquinoline-6-carboxylic acid;

2-(3-benzamido-4-fluorophenyl)-3,3-dimethyl-1,2,3,4-tetrahydroquinoline-6-carboxylic acid;

2-(4-benzamidophenyl)-3,3-dimethyl-1,2,3,4-tetrahydroquinoline-6-carboxylic acid;

3,3-dimethyl-2-(4-(picolinamido)phenyl)-1,2,3,4-tetrahydroquinoline-6-carboxylic acid;

3,3-dimethyl-2-(3-(methylcarbamoyl)phenyl)-1,2,3,4-tetrahydroquinoline-6-carboxylic acid;

2-(3-(cyclopropanecarboxamido)phenyl)-3,3-dimethyl-1,2,3,4-tetrahydroquinoline-6-carboxylic acid; and 2-(3-(cyclopropanecarboxamido)-4-fluorophenyl)-3,3-dimethyl-1,2,3,4-tetrahydroquinoline-6-carboxylic acid.

18. A compound according to claim 1 selected from the group consisting of:

2-(3-(2-chloro-4-fluorobenzamido)-4-fluorophenyl)-3,3-dimethyl-1,2,3,4-tetrahydroquinoline-6-carboxylic acid;

3,3-dimethyl-2-(3-(piperidine-1-carbonyl)phenyl)-1,2,3,4-tetrahydroquinoline-6-carboxylic acid;

2-(3-(2-methoxyethylcarbamoyl)phenyl)-3,3-dimethyl-1,2,3,4-tetrahydroquinoline-6-carboxylic acid;

3,3-dimethyl-2-(4-(2-phenylacetamido)phenyl)-1,2,3,4-tetrahydroquinoline-6-carboxylic acid;

2-(3-(cyclobutanecarboxamido)-4-fluorophenyl)-3,3-dimethyl-1,2,3,4-tetrahydroquinoline-6-carboxylic acid;

2-(4-chloro-3-(cyclohexanecarboxamido)phenyl)-3,3-dimethyl-1,2,3,4-tetrahydroquinoline-6-carboxylic acid;
2-(3-(cyclopentanecarboxamido)-4-fluorophenyl)-3,3-dimethyl-1,2,3,4-tetrahydroquinoline-6-carboxylic acid;
2-(4-(cyclohexanecarboxamido)phenyl)-3,3-dimethyl-1,2,3,4-tetrahydroquinoline-6-carboxylic acid;
3,3-dimethyl-2-(3-(2-phenylacetamido)phenyl)-1,2,3,4-tetrahydroquinoline-6-carboxylic acid; and
2-(3-carbamoylphenyl)-3,3-dimethyl-1,2,3,4-tetrahydroquinoline-6-carboxylic acid.

19. A compound according to claim 1 selected from the group consisting of:
3,3-dimethyl-2-(3-(methylsulfonamido)phenyl)-1,2,3,4-tetrahydroquinoline-6-carboxylic acid;
2-(3-benzamido-5-chlorophenyl)-3,3-dimethyl-1,2,3,4-tetrahydroquinoline-6-carboxylic acid;
2-(3-(2-(dimethylamino)ethylcarbamoyl)phenyl)-3,3-dimethyl-1,2,3,4-tetrahydroquinoline-6-carboxylic acid;
2-(3-acetamidophenyl)-3,3-dimethyl-1,2,3,4-tetrahydroquinoline-6-carboxylic acid;
2-(3-((1-ethylpyrrolidin-2-yl)methylcarbamoyl)phenyl)-3,3-dimethyl-1,2,3,4-tetrahydroquinoline-6-carboxylic acid;
2-(4-fluoro-3-(3-fluorophenylsulfonamido)phenyl)-3,3-dimethyl-1,2,3,4-tetrahydroquinoline-6-carboxylic acid;
2-(3-(1-(tert-butoxycarbonyl)azetidin-3-ylcarbamoyl)phenyl)-3,3-dimethyl-1,2,3,4-tetrahydroquinoline-6-carboxylic acid;
3,3-dimethyl-2-(3-(1-methylazetidin-3-ylcarbamoyl)phenyl)-1,2,3,4-tetrahydroquinoline-6-carboxylic acid;
2-(4-fluoro-3-(2-fluorophenylsulfonamido)phenyl)-,3-dimethyl-1,2,3,4-tetrahydroquinoline-6-carboxylic acid; and
3,3-dimethyl-2-(3-(3-phenylpropanamido)phenyl)-1,2,3,4-tetrahydroquinoline-6-carboxylic acid.

20. A compound according to claim 1 selected from the group consisting of:
2-(3-(cyclohexanecarboxamido)-4-fluorophenyl)-3,3-dimethyl-1,2,3,4-tetrahydroquinoline-6-carboxylic acid;
2-(4-(3-fluorophenylsulfonamido)phenyl)-3,3-dimethyl-1,2,3,4-tetrahydroquinoline-6-carb oxylic acid;
2-(4-(2-fluorophenylsulfonamido)phenyl)-3,3-dimethyl-1,2,3,4-tetrahydroquinoline-6-carb oxylic acid;
2-(2-(cyclopropanecarboxamido)phenyl)-3,3-dimethyl-1,2,3,4-tetrahydroquinoline-6-carboxylic acid;
2-(4-(cyclobutanecarboxamido)phenyl)-3,3-dimethyl-1,2,3,4-tetrahydroquinoline-6-carboxylic acid;
2-(2-(cyclobutanecarboxamido)phenyl)-3,3-dimethyl-1,2,3,4-tetrahydroquinoline-6-carboxylic acid;
2-(4-(cyclohex-1-enecarboxamido)phenyl)-3,3-dimethyl-1,2,3,4-tetrahydroquinoline-6-carboxylic acid;
2-(2-(4-fluorophenylsulfonamido)phenyl)-3,3-dimethyl-1,2,3,4-tetrahydroquinoline-6-carboxylic acid;
2-(2-(2-fluorophenylsulfonamido)phenyl)-3,3-dimethyl-1,2,3,4-tetrahydroquinoline-6-carboxylic acid; and
3,3-dimethyl-2-(2-(phenylsulfonamido)phenyl)-1,2,3,4-tetrahydroquinoline-6-carboxylic acid.

21. A compound according to claim 1 selected from the group consisting of:
2-(3-(N-isopropylsulfamoyl)phenyl)-3,3-dimethyl-1,2,3,4-tetrahydroquinoline-6-carboxylic acid;
2-(2-(3-fluorophenylsulfonamido)phenyl)-3,3-dimethyl-1,2,3,4-tetrahydroquinoline-6-carboxylic acid;
3,3-dimethyl-2-(2-(methylsulfonamido)phenyl)-1,2,3,4-tetrahydroquinoline-6-carboxylic acid;
3,3-dimethyl-2-(4-(N-methylsulfamoyl)phenyl)-1,2,3,4-tetrahydroquinoline-6-carboxylic acid;
3,3-dimethyl-2-(3-(pyrrolidin-1-ylsulfonyl)phenyl)-1,2,3,4-tetrahydroquinoline-6-carboxylic acid;
3,3-dimethyl-2-(3-(N-methylsulfamoyl)phenyl)-1,2,3,4-tetrahydroquinoline-6-carboxylic acid;
3,3-dimethyl-2-(3-(N-(1-methylpyrrolidin-3-yl)sulfamoyl)phenyl)-1,2,3,4-tetrahydroquinoline-6-carboxylic acid;
3,3-dimethyl-2-(3-(N-phenylsulfamoyl)phenyl)-1,2,3,4-tetrahydroquinoline-6-carboxylic acid;
2-(3-(N,N-dimethylsulfamoyl)phenyl)-3,3-dimethyl-1,2,3,4-tetrahydroquinoline-6-carboxylic acid; and
3,3-dimethyl-2-(2-(picolinamido)phenyl)-1,2,3,4-tetrahydroquinoline-6-carboxylic acid.

22. A compound according to claim 1 selected from the group consisting of:
2-(3-(2-carboxypropan-2-yloxy)phenyl)-3,3-dimethyl-1,2,3,4-tetrahydroquinoline-6-carboxylic acid;
2-[2-(1-Carboxy-1-methyl-ethylamino)-phenyl]-3,3-dimethyl-1,2,3,4-tetrahydro-quinoline-6-carboxylic acid;
2-[3-(1-carboxy-1-methyl-ethylamino)-phenyl]-3,3-dimethyl-1,2,3,4-tetrahydro-quinoline-6-carboxylic acid;
2-[3-(1-carboxy-cyclopropylamino)-phenyl]-3,3-dimethyl-1,2,3,4-tetrahydro-quinoline-6-carboxylic acid;
2-(2-(2-fluorophenylsulfonamido)phenyl)-3,3-dimethyl-1,2,3,4-tetrahydroquinoline-6-carboxylic acid;
2-(2-(4-fluorophenylsulfonamido)phenyl)-3,3-dimethyl-1,2,3,4-tetrahydroquinoline-6-carboxylic acid; and.

23. A compound according to claim 1 selected from the group consisting of:
2-(2-(3-fluorophenylsulfonamido)phenyl)-3,3-dimethyl-1,2,3,4-tetrahydroquinoline-6-carboxylic acid;
3,3-dimethyl-2-(2-(methylsulfonamido)phenyl)-1,2,3,4-tetrahydroquinoline-6-carboxylic acid;
3,3-dimethyl-2-(2-(phenylsulfonamido)phenyl)-1,2,3,4-tetrahydroquinoline-6-carboxylic acid;
2-[2-(1-Carboxy-cyclopropylamino)-phenyl]-3,3-dimethyl-1,2,3,4-tetrahydro-quinoline-6-carboxylic acid; and.

24. A compound according to claim 1 selected from the group consisting of:
3,3-Dimethyl-2-(3-methyl-5-morpholin-4-yl-phenyl)-1,2,3,4-tetrahydro-quinoline-6-carboxylic acid;
2-(4-fluoro-3-isobutyramidophenyl)-3,3-dimethyl-1,2,3,4-tetrahydroquinoline-6-carboxylic acid;
3,3-dimethyl-2-(3-(1-methylethylsulfonamido)phenyl)-1,2,3,4-tetrahydroquinoline-6-carboxylic acid;
2-(3-(2-(dimethylamino)ethylcarbamoyl)phenyl)-3,3-dimethyl-1,2,3,4-tetrahydroquinoline-6-carboxylic acid;
2-[3-((S)-4-Isopropyl-2-oxo-oxazolidin-3-yl)-phenyl]-3,3-dimethyl-1,2,3,4-tetrahydro-quinoline-6-carboxylic acid;
3,3-Dimethyl-2-{3-[methyl-(2-methylamino-ethyl)-amino]-phenyl}-1,2,3,4-tetrahydro-quinoline-6-carboxylic acid;
3,3-dimethyl-2-(3-(phenylsulfonylcarbamoyl)phenyl)-1,2,3,4-tetrahydroquinoline-6-carboxylic acid; and
2-(3-carbamoylphenyl)-3,3-dimethyl-1,2,3,4-tetrahydroquinoline-6-carboxylic acid.

* * * * *

UNITED STATES PATENT AND TRADEMARK OFFICE
CERTIFICATE OF CORRECTION

| | | |
|---|---|---|
| PATENT NO. | : 8,344,137 B2 | Page 1 of 1 |
| APPLICATION NO. | : 13/081527 | |
| DATED | : January 1, 2013 | |
| INVENTOR(S) | : Chen et al. | |

It is certified that error appears in the above-identified patent and that said Letters Patent is hereby corrected as shown below:

Claim 22, column 260, line 29, end of the line, insert -- and --

Claim 22, column 260, line 31, delete "acid; and." and insert -- acid. --

Claim 23, column 260, line 39, end of the line, insert -- and --

Claim 23, column 260, line 41, delete "acid;" and insert -- acid. --

Claim 23, column 260, line 42, delete "and."

Signed and Sealed this
Ninth Day of April, 2013

Teresa Stanek Rea
*Acting Director of the United States Patent and Trademark Office*